United States Patent
Bennett et al.

(10) Patent No.: US 10,202,360 B2
(45) Date of Patent: *Feb. 12, 2019

(54) THERAPEUTIC COMPOUNDS

(71) Applicant: CELGENE QUANTICEL RESEARCH, INC., San Diego, CA (US)

(72) Inventors: Michael John Bennett, San Diego, CA (US); Juan Manuel Betancort, San Diego, CA (US); Amogh Boloor, San Diego, CA (US); Toufike Kanouni, San Diego, CA (US); Jeffrey Alan Stafford, San Diego, CA (US); James Marvin Veal, Apex, NC (US); Michael Brennan Wallace, San Diego, CA (US)

(73) Assignee: CELGENE QUANTICEL RESEARCH, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/488,674

(22) Filed: Apr. 17, 2017

(65) Prior Publication Data
US 2017/0298040 A1 Oct. 19, 2017

Related U.S. Application Data

(60) Provisional application No. 62/324,279, filed on Apr. 18, 2016.

(51) Int. Cl.
*C07D 401/04* (2006.01)
*C07D 401/14* (2006.01)
*C07D 405/14* (2006.01)
*C07D 515/08* (2006.01)

(52) U.S. Cl.
CPC ......... *C07D 401/04* (2013.01); *C07D 401/14* (2013.01); *C07D 405/14* (2013.01); *C07D 515/08* (2013.01)

(58) Field of Classification Search
CPC .. C07D 401/04; C07D 401/14; C07D 405/14; C07D 515/08
See application file for complete search history.

(56) References Cited

U.S. PATENT DOCUMENTS

| 9,034,900 B2 * | 5/2015 | Bennett ................ C07D 498/04 514/309 |
| 9,115,114 B2 * | 8/2015 | Bennett ................ C07D 498/04 |
| 9,598,372 B2 * | 3/2017 | Boloor ................. C07D 498/04 |
| 2014/0179648 A1 | 6/2014 | Liu et al. |
| 2016/0016966 A1 | 1/2016 | Amans et al. |

FOREIGN PATENT DOCUMENTS

| WO | 2014/165143 A1 | 10/2014 |
| WO | 2015/104653 A1 | 7/2015 |

OTHER PUBLICATIONS

Mele et al., "BET bromodomain inhibition suppresses TH17-mediated pathology," J. Exp. Med. 2013, 210 (11):2181-2190.
International Search Report and Written Opinion dated, Jul. 20, 2017, in related International Application No. PCT/US2017/027815, filed Apr. 14, 2017.

* cited by examiner

*Primary Examiner* — Alexander R Pagano
*Assistant Examiner* — Ebenezer O Sackey
(74) *Attorney, Agent, or Firm* — Wiley Rein LLP

(57) ABSTRACT

The present disclosure relates to substituted heterocyclic derivative therapeutic compounds, compositions comprising said compounds, and the use of said compounds and compositions for epigenetic regulation by inhibition of bromodomain-mediated recognition of acetyl lysine regions of proteins, such as histones. Said compositions and methods are useful for the treatment of diseases mediated by aberrant cell signalling, such as inflammatory disorders, cancer and neoplastic disease.

29 Claims, No Drawings

THERAPEUTIC COMPOUNDS

RELATED APPLICATION

This Application claims priority benefit of U.S. application No. 62/324,279 filed Apr. 18, 2016, and incorporated entirely herein for all purposes.

FIELD

The present embodiments relate generally to compounds, pharmaceutical compositions, and methods for epigenetic regulation by inhibition of bromodomain-mediated recognition of acetyl lysine regions of proteins, such as histones.

BACKGROUND

A need exists in the art for an effective treatment of diseases and disorders mediated by aberrant cAMP response element-binding protein activity.

SUMMARY

Provided herein are substituted heterocyclic derivative therapeutic compounds and pharmaceutical compositions comprising said compounds. The subject compounds and compositions are useful for epigenetic regulation by inhibition of bromodomain-mediated recognition of acetyl lysine regions of proteins, such as histones. Furthermore, the subject compounds and compositions are useful for the treatment of diseases mediated by aberrant cell signaling, such as inflammatory disorders, and cancer, such as prostate cancer, breast cancer, bladder cancer, lung cancer and/or melanoma and the like. The substituted heterocyclic derivative compounds described herein are based upon pyridones, and related heterocyclic structures. Said isoquinolinones or pyridones are substituted at the 4-position with a group such as an aryl, a heteroaryl and the like.

A compound, or pharmaceutically acceptable salt thereof, having the structure of Formula (I):

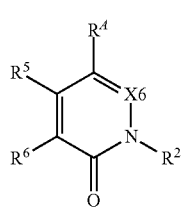

Formula (I)

wherein, $R^2$ is hydrogen, alkyl, aryl, aralkyl, cycloalkyl, cycloalkylalkyl, heterocyclyl, heterocyclylalkyl, heteroaryl, or heteroarylalkyl;

X6 is C—H, C—F, C—Cl, C—Br, or N;

$R^5$ is hydrogen, halogen, —CN, alkyl, cycloalkyl, or alkoxy;

$R^6$ is hydrogen, halogen, —CN, alkyl, cycloalkyl, cycloalkylalkyl, —$OR^{22}$, or —$N(R^{22})_2$;

$R^4$ is

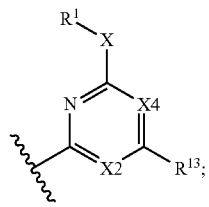

$R^{13}$ is —Y—Z;

Y is selected from a bond, —$CH_2$—, or —$CH(C_1$-$C_4$alkyl)-;

Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$COR^{21}$, —$OC(O)N(R^{22})_2$, —$OSO_2N(R^{22})_2$, —$OSO_2R^{21}$, —$N(R^{22})SO_3R^{21}$, $N(R^{22})_2$, or —CN;

X2 is N, or C—$R^{12}$; wherein $R^{12}$ is hydrogen, halogen, —CN, alkyl, cycloalkyl, or alkoxy;

X4 is N, or C—$R^{14}$; wherein $R^{14}$ is hydrogen, halogen, —CN, alkyl, cycloalkyl, or alkoxy;

X is a bond, —O—, —S—, —$N(R^7)$—, —$CH_2$—, —CF(H)—, —$CF_2$—, or —$CH(C_1$-$C_5$alkyl)-;

$R^7$ is H or $C_1$-$C_6$ alkyl;

$R^1$ is alkyl, aryl, aralkyl, cycloalkyl, cycloalkylalkyl, heterocyclyl, heterocyclylalkyl, heteroaryl, or heteroarylalkyl;

each $R^{21}$ is independently selected from alkyl, cycloalkyl, cycloalkylalkyl, aryl, aralkyl, heterocyclyl, heterocyclylalkyl, heteroaryl, or heteroarylalkyl;

each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl; and provided that the compound of Formula (I) is not N-[2-(2,4-difluorophenoxy)-6-(1,5-dimethyl-6-oxopyridin-3-yl)pyrimidin-4-yl]ethanesulfonamide.

A compound, or pharmaceutically acceptable salt thereof, having the structure of Formula (II):

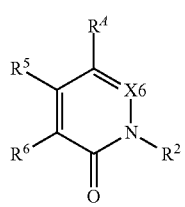

Formula (II)

wherein, $R^2$ is hydrogen, alkyl, aryl, aralkyl, cycloalkyl, cycloalkylalkyl, heterocyclyl, heterocyclylalkyl, heteroaryl, or heteroarylalkyl;

X6 is C—H, C—F, C—Cl, C—Br, or N;

$R^5$ is hydrogen, halogen, —CN, alkyl, cycloalkyl, or alkoxy;

$R^6$ is hydrogen, halogen, —CN, alkyl, cycloalkyl, cycloalkylalkyl, —$OR^{22}$, or —$N(R^{22})_2$;

$R^A$ is a five-membered heteroaryl selected from

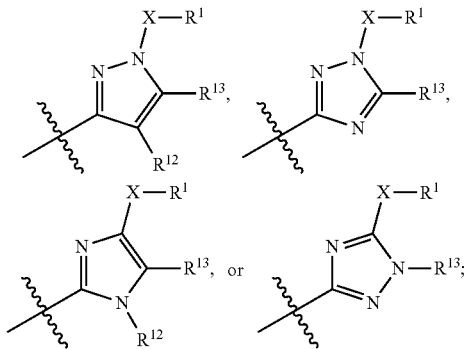

$R^{13}$ is —Y—Z;

Y is selected from a bond, —CH$_2$—, or —CH(C$_1$-C$_4$alkyl)-;

Z is selected from —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —COR$^{21}$, —OC(O)N(R$^{22}$)$_2$, —OSO$_2$N(R$^{22}$)$_2$, —OSO$_2$R$^{21}$, —N(R$^{22}$)SO$_3$R$^{21}$, N(R$^{22}$)$_2$, or —CN R$^{12}$; wherein R$^{12}$ is hydrogen, halogen, —CN, alkyl, cycloalkyl, or alkoxy;

X is a bond, —CH$_2$—, —CF(H)—, —CF$_2$—, —CH(C$_1$-C$_5$alkyl)-, or C$_2$ alkylene;

R$^1$ is alkyl, aryl, aralkyl, cycloalkyl, cycloalkylalkyl, heterocyclyl, heterocyclylalkyl, heteroaryl, or heteroarylalkyl;

each R$^{21}$ is independently selected from alkyl, cycloalkyl, cycloalkylalkyl, aryl, aralkyl, heterocyclyl, heterocyclylalkyl, heteroaryl, or heteroarylalkyl; and each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

A compound, or pharmaceutically acceptable salt thereof, having the structure of Formula (III):

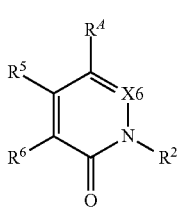

Formula (III)

wherein,

R$^2$ is hydrogen, alkyl, aryl, aralkyl, cycloalkyl, cycloalkylalkyl, heterocyclyl, heterocyclylalkyl, heteroaryl, or heteroarylalkyl;

X6 is C—H, C—F, C—Cl, C—Br, or N;

R$^5$ is hydrogen, halogen, —CN, alkyl, cycloalkyl, or alkoxy;

R$^6$ is hydrogen, halogen, —CN, alkyl, cycloalkyl, cycloalkylalkyl, —OR$^{22}$, or —N(R$^{22}$)$_2$;

$R^A$ is

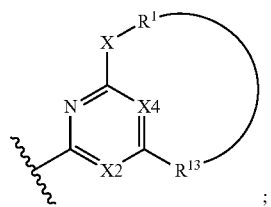

wherein the Z group of R$^{13}$ and R$^1$ join to form a 9- to 19-membered ring;

R$^{13}$ is —Y—Z;

Y is selected from a bond, —CH$_2$—, or —CH(C$_1$-C$_4$alkyl)-;

Z is selected from —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —COR$^{21}$, —OC(O)N(R$^{22}$)$_2$, —OSO$_2$N(R$^{22}$)$_2$, —OSO$_2$R$^{21}$, —N(R$^{22}$)SO$_3$R$^{21}$, or N(R$^{22}$)$_2$;

X2 is N, or C—R$^{12}$; wherein R$^{12}$ is hydrogen, halogen, —CN, alkyl, cycloalkyl, or alkoxy;

X4 is N, or C—R$^{14}$; wherein R$^{14}$ is hydrogen, halogen, —CN, alkyl, cycloalkyl, or alkoxy;

X is a bond, —O—, —S—, —N(R$^7$)—, —CH$_2$—, —CF(H)—, —CF$_2$—, or —CH(C$_1$-C$_5$alkyl)-;

R$^7$ is H or C$_1$-C$_6$ alkyl;

R$^1$ is alkyl, aryl, aralkyl, cycloalkyl, cycloalkylalkyl, heterocyclyl, heterocyclylalkyl, heteroaryl, or heteroarylalkyl;

each R$^{21}$ is independently selected from alkyl, cycloalkyl, cycloalkylalkyl, aryl, aralkyl, heterocyclyl, heterocyclylalkyl, heteroaryl, or heteroarylalkyl; and each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

A compound, or pharmaceutically acceptable salt thereof, having the structure of Formula (IV):

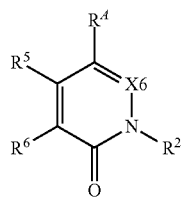

Formula (IV)

wherein,

R$^2$ is hydrogen, alkyl, aryl, aralkyl, cycloalkyl, cycloalkylalkyl, heterocyclyl, heterocyclylalkyl, heteroaryl, or heteroarylalkyl;

X6 is C—H, C—F, C—Cl, C—Br, or N;

R$^5$ is hydrogen, halogen, —CN, alkyl, cycloalkyl, or alkoxy;

R$^6$ is hydrogen, halogen, —CN, alkyl, cycloalkyl, cycloalkylalkyl, —OR$^{22}$, or —N(R$^{22}$)$_2$;

$R^A$ is

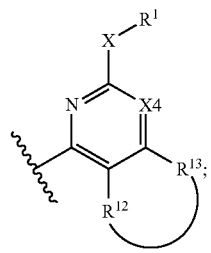

wherein the Z group of $R^{13}$ and $R^{12}$ join to form a 5- to 8-membered ring;
$R^{13}$ is —Y—Z;
Y is selected from a bond, —$CH_2$—, or —$CH(C_1$-$C_4$alkyl)-;
Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$COR^{21}$, —$OC(O)N(R^{22})_2$, —$OSO_2N(R^{22})_2$, —$OSO_2R^{21}$, —$N(R^{22})SO_3R^{21}$, or $N(R^{22})_2$;
$R^{12}$ is alkyl, cycloalkyl, or alkoxy;
X4 is N, or C—$R^{14}$; wherein $R^{14}$ is hydrogen, halogen, —CN, alkyl, cycloalkyl, or alkoxy;
X is a bond, —O—, —S—, —$N(R^7)$—, —$CH_2$—, —$CF(H)$—, —$CF_2$—, or —$CH(C_1$-$C_5$alkyl)-;
$R^7$ is H or $C_1$-$C_6$ alkyl;
$R^1$ is alkyl, aryl, aralkyl, cycloalkyl, cycloalkylalkyl, heterocyclyl, heterocyclylalkyl, heteroaryl, or heteroarylalkyl;
each $R^{21}$ is independently selected from alkyl, cycloalkyl, cycloalkylalkyl, aryl, aralkyl, heterocyclyl, heterocyclylalkyl, heteroaryl, or heteroarylalkyl; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

One embodiment provides a compound of Formula (V), or a pharmaceutically acceptable salt thereof, Formula (V)

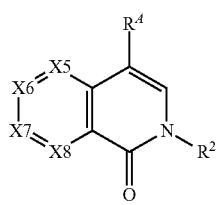

wherein,
$R^2$ is selected from $CH_3$, $CH_2CH_3$, $CH_2CF_3$, $CH_2F$, $CHF_2$, $CF_3$, $CH_2D$, $CHD_2$, or $CD_3$;
X5 is C—$R^5$ or N;
X6 is absent, C—$R^6$ or N;
X7 is C—$R^7$ or N;
X8 is C—$R^8$ or N; wherein no more than two of X5, X6, X7, or X8 may be N;
$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^6$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^7$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;
$R^8$ is hydrogen, halogen, or alkyl;
$R^A$ is

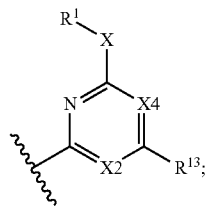

$R^{13}$ is —Y—Z;
Y is selected from a bond, —$CH_2$—, or —$CH(C_1$-$C_4$alkyl)-;
Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$COR^{21}$, —$OC(O)N(R^{22})_2$, —$OSO_2N(R^{22})_2$, —$OSO_2R^{21}$, —$N(R^{22})SO_3R^{21}$, $N(R^{22})_2$, or —CN
X2 is N, or C—$R^{12}$; wherein $R^{12}$ is hydrogen, halogen, —CN, alkyl, cycloalkyl, or alkoxy;
X4 is N, or C—$R^{14}$; wherein $R^{14}$ is hydrogen, halogen, —CN, alkyl, cycloalkyl, or alkoxy;
X is a bond, —O—, —S—, —$N(R^7)$—, —$CH_2$—, —$CF(H)$—, —$CF_2$—, or —$CH(C_1$-$C_5$alkyl)-;
$R^7$ is H or $C_1$-$C_6$ alkyl;
$R^1$ is alkyl, aryl, aralkyl, cycloalkyl, cycloalkylalkyl, heterocyclyl, heterocyclylalkyl, heteroaryl, or heteroarylalkyl;
each $R^{21}$ is independently selected from alkyl, cycloalkyl, cycloalkylalkyl, aryl, aralkyl, heterocyclyl, heterocyclylalkyl, heteroaryl, or heteroarylalkyl; and
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

One embodiment provides a pharmaceutical composition comprising a compound of Formula (I)-(V), or a pharmaceutically acceptable salt thereof, and a pharmaceutically acceptable excipient.

One embodiment provides a method of treating an inflammatory or immune disorder in a patient in need thereof, comprising administering to the patient a compound of Formula (I)-(V), or a pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_8$ alkynylene). In other embodiments, an alkynylene comprises two to five carbon atoms (e.g., $C_2$-$C_5$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^bN(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl, where $R^c$ is an alkynylene chain as defined above. The carbocyclyl part of the carbocyclylalkynyl radical is optionally substituted as described above for a carbocyclyl group. In some embodiments the carbocyclyl group is a cycloalkyl group. The alkynylene chain part of the carbocyclylalkynyl radical is optionally substituted as defined above for an alkynylene chain.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

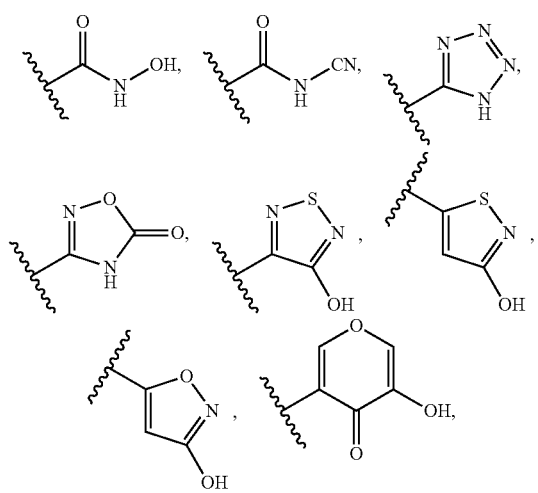

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$C(O)N(R$^a$)$_2$, —R$^b$—N(R$^a$)C(O)OR$^a$, —R$^b$—N(R$^a$)C(O)R$^a$, —R$^b$N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoro-methyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or hetero-arylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-hetero-cyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —R$^c$-heterocyclyl where R$^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—R$^c$-heterocyclyl where R$^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydro-benzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocyclo-octa[d]pyrimidinyl, 5,6,7,8,9,10-hexahydrocycloocta[d]pyridazinyl, 5,6,7,8,9,10-hexahydro-cycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]-pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]-pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]-pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$— heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein may contain one or more asymmetric centers and may thus give rise to enantiomers, diastereomers, and other stereoisomeric forms that may be defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesul-

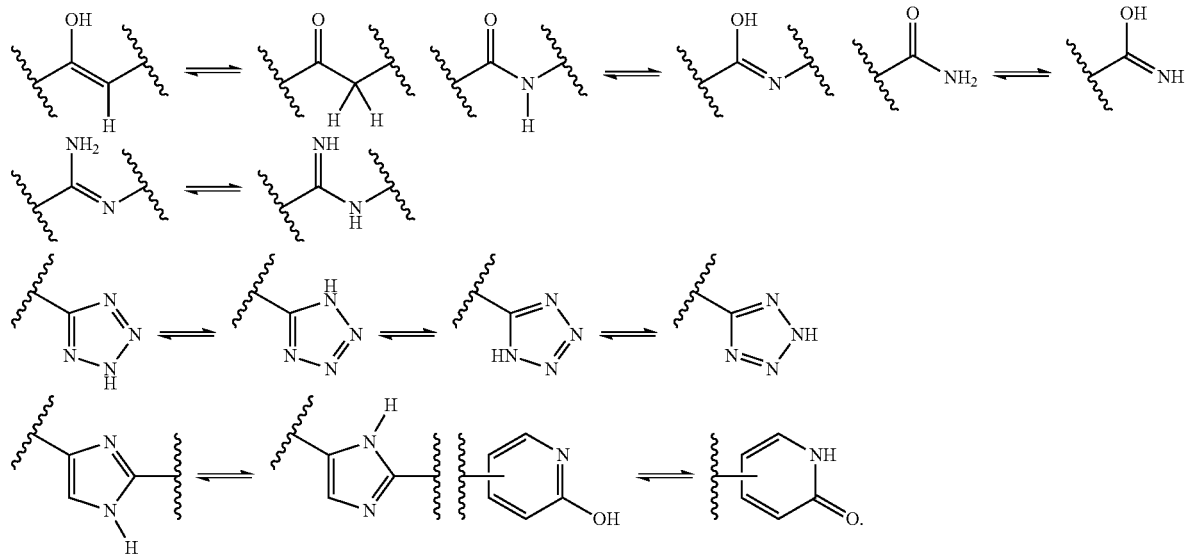

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the substituted heterocyclic derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, fonates, and the like. Also contemplated are salts of amino acids, such as arginates, gluconates, and galacturonates. See, e.g., Berge S. M. et al., *Pharmaceutical Salts*, J. Pharm. Sci. 66:1-19 (1997)). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotophic substitution with $^2H$, $^{11}C$, $^{13}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. All isotopic variations of the compounds of the present embodiments, whether radioactive or not, are encompassed within the scope of the present embodiments.

In certain embodiments, the compounds disclosed herein have some or all of the $^1H$ atoms replaced with $^2H$ atoms. The methods of synthesis for deuterium-containing substituted heterocyclic derivative compounds are known in the art and include, by way of non-limiting example only, the following synthetic methods.

Deuterated starting materials are readily available and are subjected to the synthetic methods described herein to provide for the synthesis of deuterium-containing substituted heterocyclic derivative compounds. Large numbers of deuterium-containing reagents and building blocks are available commerically from chemical vendors, such as Aldrich Chemical Co.

Deuterium-transfer reagents suitable for use in nucleophilic substitution reactions, such as iodomethane-d$_3$ (CD$_3$I), are readily available and may be employed to transfer a deuterium-substituted carbon atom under nucleophilic substitution reaction conditions to the reaction substrate. The use of CD$_3$I is illustrated, by way of example only, in the reaction schemes below.

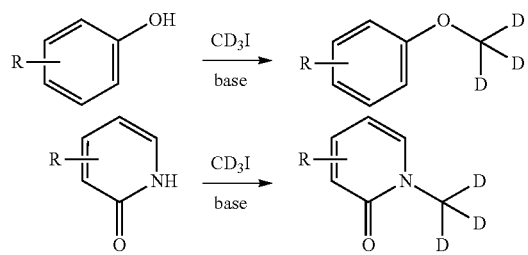

Deuterium-transfer reagents, such as lithium aluminum deuteride (LiAlD$_4$), are employed to transfer deuterium under reducing conditions to the reaction substrate. The use of LiAlD$_4$ is illustrated, by way of example only, in the reaction schemes below.

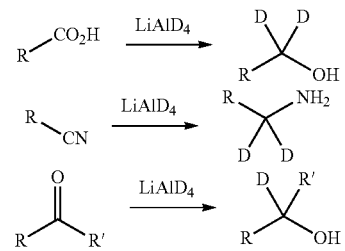

Deuterium gas and palladium catalyst are employed to reduce unsaturated carbon-carbon linkages and to perform a reductive substitution of aryl carbon-halogen bonds as illustrated, by way of example only, in the following reaction schemes:

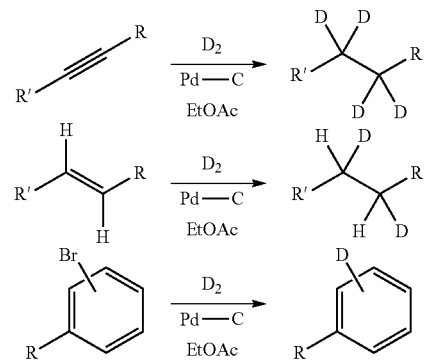

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1$H hydrogen atoms. In one embodiment, the level of deuterium incorporation is determined by synthetic methods in which a deuterated synthetic building block is used as a starting material.

Substituted Heterocyclic Derivative Compounds

Substituted heterocyclic derivative compounds are described herein that are bromodomain inhibitors. These compounds, and compositions comprising these compounds, are useful for the treatment of cancer and neoplastic disease. The compounds described herein may, therefore, be useful for treating NUT midline carcinoma, Burkitts lymphoma, prostate cancer, breast cancer, bladder cancer, lung cancer and/or melanoma and the like.

A compound, or pharmaceutically acceptable salt thereof, having the structure of Formula (I):

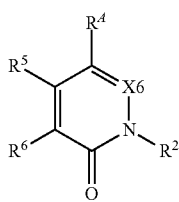

Formula (I)

wherein,

R$^2$ is hydrogen, alkyl, aryl, aralkyl, cycloalkyl, cycloalkylalkyl, heterocyclyl, heterocyclylalkyl, heteroaryl, or heteroarylalkyl;

X6 is C—H, C—F, C—Cl, C—Br, or N;

R$^5$ is hydrogen, halogen, —CN, alkyl, cycloalkyl, or alkoxy;

R$^6$ is hydrogen, halogen, —CN, alkyl, cycloalkyl, cycloalkylalkyl, —OR$^{22}$, or —N(R$^{22}$)$_2$;

R$^4$ is

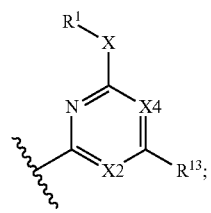

R$^{13}$ is —Y—Z;

Y is selected from a bond, —CH$_2$—, or —CH(C$_1$-C$_4$alkyl)-;

Z is selected from —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —COR$^{21}$, —OC(O)N(R$^{22}$)$_2$, —OSO$_2$N(R$^{22}$)$_2$, —OSO$_2$R$^{21}$, —N(R$^{22}$)SO$_3$R$^{21}$, N(R$^{22}$)$_2$, or —CN;

X2 is N, or C—R$^{12}$; wherein R$^{12}$ is hydrogen, halogen, —CN, alkyl, cycloalkyl, or alkoxy;

X4 is N, or C—R$^{14}$; wherein R$^{14}$ is hydrogen, halogen, —CN, alkyl, cycloalkyl, or alkoxy;

X is a bond, —O—, —S—, —N(R$^7$)—, —CH$_2$—, —CF(H)—, —CF$_2$—, or —CH(C$_1$-C$_5$alkyl)-;

R$^7$ is H or C$_1$-C$_6$ alkyl;

R$^1$ is alkyl, aryl, aralkyl, cycloalkyl, cycloalkylalkyl, heterocyclyl, heterocyclylalkyl, heteroaryl, or heteroarylalkyl;

each R$^{21}$ is independently selected from alkyl, cycloalkyl, cycloalkylalkyl, aryl, aralkyl, heterocyclyl, heterocyclylalkyl, heteroaryl, or heteroarylalkyl;

each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl; and provided that the compound of Formula (I) is not N-[2-(2,4-difluorophenoxy)-6-(1,5-dimethyl-6-oxopyridin-3-yl)pyrimidin-4-yl]ethanesulfonamide.

In some embodiments of a compound of Formula (I), or pharmaceutically acceptable salt thereof, R$^2$ is alkyl, aryl, aralkyl, cycloalkyl, cycloalkylalkyl, heterocyclyl, heterocyclylalkyl, heteroaryl, or heteroarylalkyl. In some embodiments of a compound of Formula (I), or pharmaceutically acceptable salt thereof, R$^2$ is alkyl, cycloalkyl, cycloalkylalkyl, or heterocyclyl. In some embodiments of a compound of Formula (I), or pharmaceutically acceptable salt thereof, R$^2$ is alkyl.

In some embodiments of a compound of Formula (I), or pharmaceutically acceptable salt thereof, X6 is C—H or N.

In some embodiments of a compound of Formula (I), or pharmaceutically acceptable salt thereof, R$^5$ is hydrogen or alkyl. In some embodiments of a compound of Formula (I), or pharmaceutically acceptable salt thereof, R$^5$ is hydrogen.

In some embodiments of a compound of Formula (I), or pharmaceutically acceptable salt thereof, R$^6$ is hydrogen, halogen, alkyl, or —OR$^{22}$; and R$^{22}$ is alkyl. In some embodiments of a compound of Formula (I), or pharmaceutically acceptable salt thereof, R$^6$ is hydrogen, halogen, or alkyl. In some embodiments of a compound of Formula (I), or pharmaceutically acceptable salt thereof, R$^6$ is hydrogen or methyl.

In some embodiments of a compound of Formula (I), or pharmaceutically acceptable salt thereof, Y is selected from a bond or —CH$_2$—. In some embodiments of a compound of Formula (I), or pharmaceutically acceptable salt thereof, Y is a bond.

In some embodiments of a compound of Formula (I), or pharmaceutically acceptable salt thereof, Z is selected from —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —COR$^{21}$, —OC(O)N(R$^{22}$)$_2$, —OSO$_2$N(R$^{22}$)$_2$, or —N(R$^{22}$)SO$_3$R$^{21}$. In some embodiments of a compound of Formula (I), or pharmaceutically acceptable salt thereof, Z is selected from —SO$_2$R$^{21}$, —N(R$^{22}$)SO$_2$R$^{21}$, or —N(R$^{22}$)COR$^{21}$. In some embodiments of a compound of Formula (I), or pharmaceutically acceptable salt thereof, Z is —N(R$^{22}$)SO$_2$R$^{21}$; R$^{21}$ is alkyl, cycloalkyl, or cycloalkylalkyl; and R$^{22}$ is hydrogen or alkyl. In some embodiments of a compound of Formula (I), or pharmaceutically acceptable salt thereof, Z is —SO$_2$R$^{21}$ and R$^{21}$ is alkyl.

In some embodiments of a compound of Formula (I), or pharmaceutically acceptable salt thereof, Z is —N(R$^{22}$)COR$^{21}$; R$^{21}$ is alkyl, cycloalkyl, or cycloalkylalkyl; and R$^{22}$ is hydrogen or alkyl.

In some embodiments of a compound of Formula (I), or pharmaceutically acceptable salt thereof, X2 is N and X4 is C—H. In some embodiments of a compound of Formula (I), or pharmaceutically acceptable salt thereof, X4 is N and X2 is C—H. In some embodiments of a compound of Formula (I), or pharmaceutically acceptable salt thereof, X2 is N and X4 is N.

In some embodiments of a compound of Formula (I), or pharmaceutically acceptable salt thereof, X is —O— or —CH$_2$—. In some embodiments of a compound of Formula (I), or pharmaceutically acceptable salt thereof, X is —O—.

In some embodiments of a compound of Formula (I), or pharmaceutically acceptable salt thereof, R$^1$ is alkyl, aryl, cycloalkyl, heterocyclyl, heteroaryl, or heteroarylalkyl. In some embodiments of a compound of Formula (I), or pharmaceutically acceptable salt thereof, R$^1$ is alkyl, aryl, or heteroaryl.

In some embodiments of a compound of Formula (I), or pharmaceutically acceptable salt thereof, the compound has the structure of Formula (Ia):

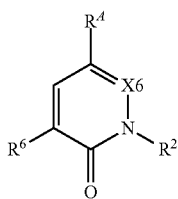

Formula (Ia)

wherein,
R$^2$ is alkyl, aryl, aralkyl, cycloalkyl, cycloalkylalkyl, heterocyclyl, heterocyclylalkyl, heteroaryl, or heteroarylalkyl;
X6 is C—H or N;
R$^6$ is hydrogen, halogen, or C$_1$-C$_3$ alkyl;
R$^A$ is

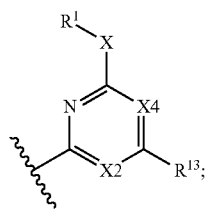

R$^{13}$ is —Y—Z;
Y is selected from a bond, —CH$_2$—, or —CH(C$_1$-C$_4$alkyl)-;
Z is selected from —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —COR$^{21}$, —OC(O)N(R$^{22}$)$_2$, —OSO$_2$N(R$^{22}$)$_2$, or —N(R$^{22}$)SO$_3$R$^{21}$;
X2 is N or C—H;
X4 is N or C—R$^{14}$, wherein R$^{14}$ is hydrogen, halogen, —CN, alkyl, cycloalkyl, or alkoxy;
X is a bond, —O—, —N(R$^7$)—, or —CH(C$_1$-C$_5$alkyl)-;
R$^7$ is H or C$_1$-C$_6$ alkyl;

R$^1$ is alkyl, aryl, aralkyl, cycloalkyl, cycloalkylalkyl, heterocyclyl, heterocyclylalkyl, heteroaryl, or heteroarylalkyl;
each R$^{21}$ is independently selected from alkyl, cycloalkyl, cycloalkylalkyl, aryl, aralkyl, heterocyclyl, heterocyclylalkyl, heteroaryl, or heteroarylalkyl;
each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl; and
provided that the compound of Formula (Ia) is not N-[2-(2,4-difluorophenoxy)-6-(1,5-dimethyl-6-oxopyridin-3-yl)pyrimidin-4-yl]ethanesulfonamide.

A compound, or pharmaceutically acceptable salt thereof, having the structure of Formula (II):

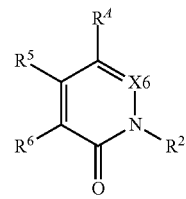

Formula (II)

wherein,
R$^2$ is hydrogen, alkyl, aryl, aralkyl, cycloalkyl, cycloalkylalkyl, heterocyclyl, heterocyclylalkyl, heteroaryl, or heteroarylalkyl;
X6 is C—H, C—F, C—Cl, C—Br, or N;
R$^5$ is hydrogen, halogen, —CN, alkyl, cycloalkyl, or alkoxy;
R$^6$ is hydrogen, halogen, —CN, alkyl, cycloalkyl, cycloalkylalkyl, —OR$^{22}$, or —N(R$^{22}$)$_2$;
R$^A$ is a five-membered heteroaryl selected from

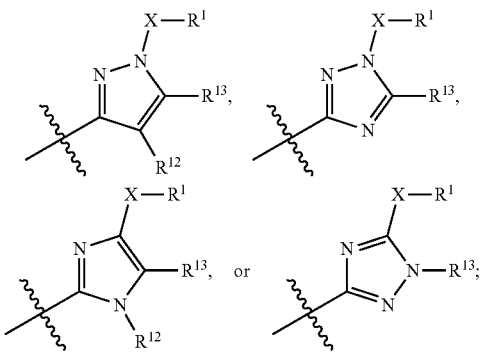

R$^{13}$ is —Y—Z;
Y is selected from a bond, —CH$_2$—, or —CH(C$_1$-C$_4$alkyl)-;
Z is selected from —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —N(R$^{22}$)COR$^{21}$, —COR$^{21}$, —OC(O)N(R$^{22}$)$_2$, —OSO$_2$N(R$^{22}$)$_2$, —OSO$_2$R$^{21}$, —N(R$^{22}$)SO$_3$R$^{21}$, N(R$^{22}$)$_2$, or —CN
R$^{12}$; wherein R$^{12}$ is hydrogen, halogen, —CN, alkyl, cycloalkyl, or alkoxy;
X is a bond, —CH$_2$—, —CF(H)—, —CF$_2$—, —CH(C$_1$-C$_5$alkyl)-, or C2-alkylene;
R$^1$ is alkyl, aryl, aralkyl, cycloalkyl, cycloalkylalkyl, heterocyclyl, heterocyclylalkyl, heteroaryl, or heteroarylalkyl;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

A compound, or pharmaceutically acceptable salt thereof, having the structure of Formula (III):

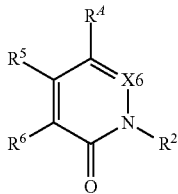

Formula (III)

wherein, $R^2$ is hydrogen, alkyl, aryl, aralkyl, cycloalkyl, cycloalkylalkyl, heterocyclyl, heterocyclylalkyl, heteroaryl, or heteroarylalkyl;

X6 is C—H, C—F, C—Cl, C—Br, or N;

$R^5$ is hydrogen, halogen, —CN, alkyl, cycloalkyl, or alkoxy;

$R^6$ is hydrogen, halogen, —CN, alkyl, cycloalkyl, cycloalkylalkyl, —$OR^{22}$, or —$N(R^{22})_2$;

$R^A$ is

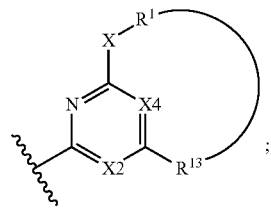

;

wherein the Z group of $R^{13}$ and $R^1$ join to form a 9- to 19-membered ring;

$R^{13}$ is —Y—Z;

Y is selected from a bond, —$CH_2$—, or —$CH(C_1$-$C_4$alkyl)-;

Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$COR^{21}$, —$OC(O)N(R^{22})_2$, —$OSO_2N(R^{22})_2$, —$OSO_2R^{21}$, —$N(R^{22})SO_3R^{21}$, or $N(R^{22})_2$;

X2 is N, or C—$R^{12}$; wherein $R^{12}$ is hydrogen, halogen, —CN, alkyl, cycloalkyl, or alkoxy;

X4 is N, or C—$R^{14}$; wherein $R^{14}$ is hydrogen, halogen, —CN, alkyl, cycloalkyl, or alkoxy;

X is a bond, —O—, —S—, —$N(R^7)$—, —$CH_2$—, —CF(H)—, —$CF_2$—, or —$CH(C_1$-$C_5$alkyl)-;

$R^7$ is H or $C_1$-$C_6$ alkyl;

$R^1$ is alkyl, aryl, aralkyl, cycloalkyl, cycloalkylalkyl, heterocyclyl, heterocyclylalkyl, heteroaryl, or heteroarylalkyl;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

A compound, or pharmaceutically acceptable salt thereof, having the structure of Formula (IV):

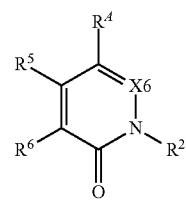

Formula (IV)

wherein, $R^2$ is hydrogen, alkyl, aryl, aralkyl, cycloalkyl, cycloalkylalkyl, heterocyclyl, heterocyclylalkyl, heteroaryl, or heteroarylalkyl;

X6 is C—H, C—F, C—Cl, C—Br, or N;

$R^5$ is hydrogen, halogen, —CN, alkyl, cycloalkyl, or alkoxy;

$R^6$ is hydrogen, halogen, —CN, alkyl, cycloalkyl, cycloalkylalkyl, —$OR^{22}$, or —$N(R^{22})_2$;

$R^A$ is

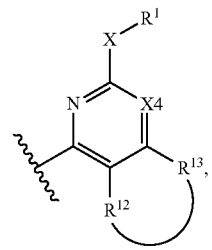

, wherein the Z group of $R^{13}$ and $R^{12}$ join to form a 5- to 8-membered ring;

$R^{13}$ is —Y—Z;

Y is selected from a bond, —$CH_2$—, or —$CH(C_1$-$C_4$alkyl)-;

Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$COR^{21}$, —$OC(O)N(R^{22})_2$, —$OSO_2N(R^{22})_2$, —$OSO_2R^{21}$, —$N(R^{22})SO_3R^{21}$, or $N(R^{22})_2$;

$R^{12}$ is alkyl, cycloalkyl, or alkoxy;

X4 is N, or C—$R^{14}$; wherein $R^{14}$ is hydrogen, halogen, —CN, alkyl, cycloalkyl, or alkoxy;

X is a bond, —O—, —S—, —$N(R^7)$—, —$CH_2$—, —CF(H)—, —$CF_2$—, or —$CH(C_1$-$C_5$alkyl)-;

$R^7$ is H or $C_1$-$C_6$ alkyl;

$R^1$ is alkyl, aryl, aralkyl, cycloalkyl, cycloalkylalkyl, heterocyclyl, heterocyclylalkyl, heteroaryl, or heteroarylalkyl;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

One embodiment provides a compound of Formula (V), or a pharmaceutically acceptable salt thereof,

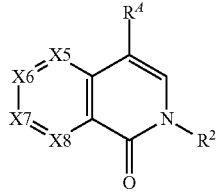

Formula (V)

wherein, $R^2$ is selected from $CH_3$, $CH_2CH_3$, $CH_2CF_3$, $CH_2F$, $CHF_2$, $CF_3$, $CH_2D$, $CHD_2$, or $CD_3$;

X5 is C—$R^5$ or N;

X6 is absent, C—$R^6$ or N;

X7 is C—$R^7$ or N;

X8 is C—$R^8$ or N; wherein no more than two of X5, X6, X7, or X8 may be N;

$R^5$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^6$ is hydrogen, halogen, —OH, —CN, —$OR^{61}$, —$NHR^{61}$—$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^7$ is hydrogen, halogen, —OH, —CN, —$OR^{61}$, —$NHR^{61}$, —$N(R^{61})_2$, alkyl, cycloalkyl, cycloalkylalkyl, aryl, aralkyl, heterocyclyl, heterocyclylalkyl, heteroaryl, or heteroarylalkyl, wherein each $R^{61}$ is independently selected from alkyl, cycloalkyl, cycloalkylalkyl, aryl, aralkyl, heterocyclyl, heterocyclylalkyl, heteroaryl, or heteroarylalkyl;

$R^8$ is hydrogen, halogen, or alkyl;

$R^A$ is

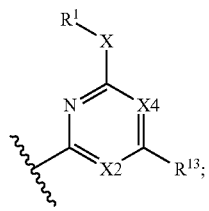

$R^{13}$ is —Y—Z;

Y is selected from a bond, —$CH_2$—, or —$CH(C_1$-$C_4$alkyl)-;

Z is selected from —$SO_2R^{21}$, —$N(R^{22})SO_2R^{21}$, —$SO_2N(R^{22})_2$, —$N(R^{22})SO_2N(R^{22})_2$, —$CON(R^{22})_2$, —$N(R^{22})CO_2R^{21}$, —$N(R^{22})CON(R^{22})_2$, —$N(R^{22})COR^{21}$, —$COR^{21}$, —$OC(O)N(R^{22})_2$, —$OSO_2N(R^{22})_2$, —$OSO_2R^{21}$, —$N(R^{22})SO_3R^{21}$, $N(R^{22})_2$, or —CN X2 is N, or C—$R^{12}$; wherein $R^{12}$ is hydrogen, halogen, —CN, alkyl, cycloalkyl, or alkoxy;

X4 is N, or C—$R^{14}$; wherein $R^{14}$ is hydrogen, halogen, —CN, alkyl, cycloalkyl, or alkoxy;

X is a bond, —O—, —S—, —$N(R^7)$—, —$CH_2$—, —CF(H)—, —$CF_2$—, or —$CH(C_1$-$C_5$alkyl)-;

$R^7$ is H or $C_1$-$C_6$ alkyl;

$R^1$ is alkyl, aryl, aralkyl, cycloalkyl, cycloalkylalkyl, heterocyclyl, heterocyclylalkyl, heteroaryl, or heteroarylalkyl;

each $R^{21}$ is independently selected from alkyl, cycloalkyl, cycloalkylalkyl, aryl, aralkyl, heterocyclyl, heterocyclylalkyl, heteroaryl, or heteroarylalkyl; and each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

A compound, or a pharmaceutically acceptable salt thereof, chosen from:

Butane-1-sulfonic acid [2-(2-chloro-6-methyl-phenoxy)-6-(1,5-dimethyl-6-oxo-1,6-dihydro-pyridin-3-yl)-pyrimidin-4-yl]-amide;

Propane-2-sulfonic acid [2-(2,4-dichloro-6-methyl-phenoxy)-6-(1,5-dimethyl-6-oxo-1,6-dihydro-pyridin-3-yl)-pyrimidin-4-yl]-amide;

Butane-1-sulfonic acid [2-(2-fluoro-6-methyl-phenoxy)-6-(1-methyl-6-oxo-1,6-dihydro-pyridin-3-yl)-pyrimidin-4-yl]-amide;

Butane-1-sulfonic acid [2-(2-fluoro-6-methyl-phenoxy)-6-(1-methyl-6-oxo-1,6-dihydro-pyridin-3-yl)-pyrimidin-4-yl]-amide;

3,3,3-Trifluoro-propane-1-sulfonic acid [2-(2-fluoro-6-methyl-phenoxy)-6-(1-methyl-6-oxo-1,6-dihydro-pyridin-3-yl)-pyrimidin-4-yl]-amide; or 4,4,4-Trifluoro-butane-1-sulfonic acid [2-(2-fluoro-6-methyl-phenoxy)-6-(1-methyl-6-oxo-1,6-dihydro-pyridin-3-yl)-pyrimidin-4-yl]-amide.

In some embodiments, the substituted heterocyclic derivative compound disclosed herein has the structure provided in Table 1.

TABLE 1

| Example | Structure | Name |
|---|---|---|
| 1 | | Propane-2-sulfonic acid [2-(2,5-dichloro-phenoxy)-6-(1,5-dimethyl-6-oxo-1,6-dihydro-pyridin-3-yl)-pyrimidin-4-yl]-amide |
| 2 | | Propane-2-sulfonic acid [6-(1,5-dimethyl-6-oxo-1,6-dihydro-pyridin-3-yl)-2-(2,5-dimethyl-phenoxy)- |

TABLE 1-continued

| Example | Structure | Name |
|---|---|---|
| 3 | | pyrimidin-4-yl]-amide<br>Propane-2-sulfonic acid [2-(2-chloro-6-methyl-phenoxy)-6-(1,5-dimethyl-6-oxo-1,6-dihydro-pyridin-3-yl)-pyrimidin-4-yl]-amide |
| 4 | | Propane-2-sulfonic acid [6-(1,5-dimethyl-6-oxo-1,6-dihydro-pyridin-3-yl)-2-(2-methoxy-5-methyl-phenoxy)-pyrimidin-4-yl]-amide |
| 5 | | Propane-2-sulfonic acid [2-(2-chloro-5-methyl-phenoxy)-6-(1,5-dimethyl-6-oxo-1,6-dihydro-pyridin-3-yl)-pyrimidin-4-yl]-amide |
| 6 | 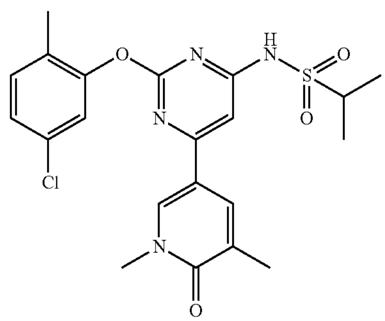 [SMILES: Cc1ccc(Cl)cc1Oc1nc(NS(=O)(=O)C(C)C)cc(-c2cc(C)c(=O)n(C)c2)n1] | Propane-2-sulfonic acid [2-(5-chloro-2-methyl-phenoxy)-6-(1,5-dimethyl-6-oxo-1,6-dihydro-pyridin-3-yl)-pyrimidin-4-yl]-amide |
| 7 | 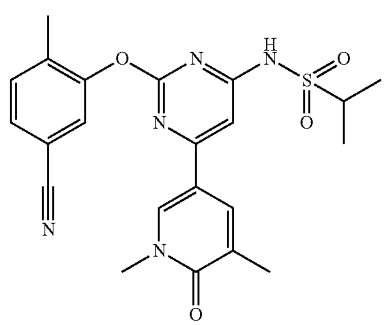 [SMILES: Cc1ccc(C#N)cc1Oc1nc(NS(=O)(=O)C(C)C)cc(-c2cc(C)c(=O)n(C)c2)n1] | Propane-2-sulfonic acid [2-(5-cyano-2-methyl-phenoxy)-6-(1,5-dimethyl-6-oxo-1,6-dihydro-pyridin-3-yl)-pyrimidin-4-yl]-amide |
| 8 | 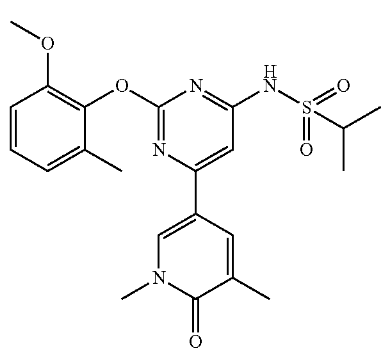 [SMILES: COc1cccc(C)c1Oc1nc(NS(=O)(=O)C(C)C)cc(-c2cc(C)c(=O)n(C)c2)n1] | Propane-2-sulfonic acid [6-(1,5-dimethyl-6-oxo-1,6-dihydro-pyridin-3-yl)-2-(2-methoxy-6-methyl-phenoxy)-pyrimidin-4-yl]-amide |

TABLE 1-continued

| Example | Structure | Name |
|---|---|---|
| 9 | 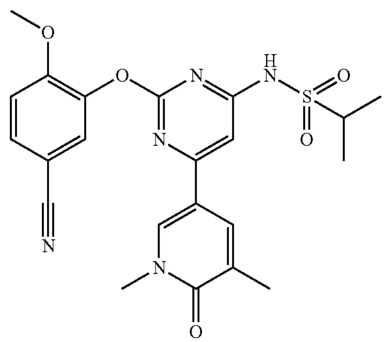 [SMILES: COc1ccc(C#N)cc1Oc1nc(NS(=O)(=O)C(C)C)cc(-c2cc(C)c(=O)n(C)c2)n1] | Propane-2-sulfonic acid [2-(5-cyano-2-methoxy-phenoxy)-6-(1,5-dimethyl-6-oxo-1,6-dihydro-pyridin-3-yl)-pyrimidin-4-yl]-amide |
| 10 | 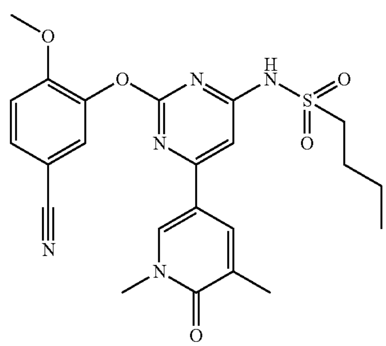 [SMILES: CCCCS(=O)(=O)Nc1cc(-c2cc(C)c(=O)n(C)c2)nc(Oc2cc(C#N)ccc2OC)n1] | Butane-1-sulfonic acid [2-(5-cyano-2-methoxy-phenoxy)-6-(1,5-dimethyl-6-oxo-1,6-dihydro-pyridin-3-yl)-pyrimidin-4-yl]-amide |
| 11 | 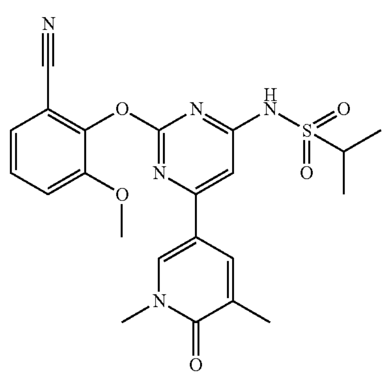 [SMILES: COc1cccc(C#N)c1Oc1nc(NS(=O)(=O)C(C)C)cc(-c2cc(C)c(=O)n(C)c2)n1] | Propane-2-sulfonic acid [2-(2-cyano-6-methoxy-phenoxy)-6-(1,5-dimethyl-6-oxo-1,6-dihydro-pyridin-3-yl)-pyrimidin-4-yl]-amide |
| 12 | 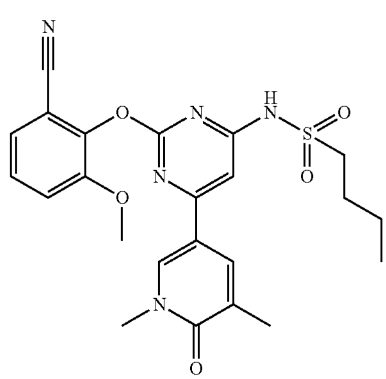 [SMILES: CCCCS(=O)(=O)Nc1cc(-c2cc(C)c(=O)n(C)c2)nc(Oc2c(C#N)cccc2OC)n1] | Butane-1-sulfonic acid [2-(2-cyano-6-methoxy-phenoxy)-6-(1,5-dimethyl-6-oxo-1,6-dihydro-pyridin-3-yl)-pyrimidin-4-yl]-amide |

TABLE 1-continued

| Example | Structure | Name |
|---|---|---|
| 13 | 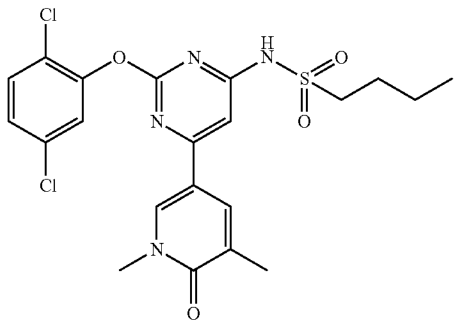 | Butane-1-sulfonic acid [2-(2,5-dichloro-phenoxy)-6-(1,5-dimethyl-6-oxo-1,6-dihydro-pyridin-3-yl)-pyrimidin-4-yl]-amide |
| 14 | 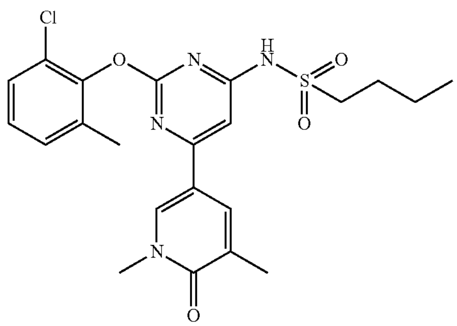 [SMILES: CCCCS(=O)(=O)Nc1cc(-c2cc(C)c(=O)n(C)c2)nc(Oc2c(C)cccc2Cl)n1] | Butane-1-sulfonic acid [2-(2-chloro-6-methyl-phenoxy)-6-(1,5-dimethyl-6-oxo-1,6-dihydro-pyridin-3-yl)-pyrimidin-4-yl]-amide |
| 15 | 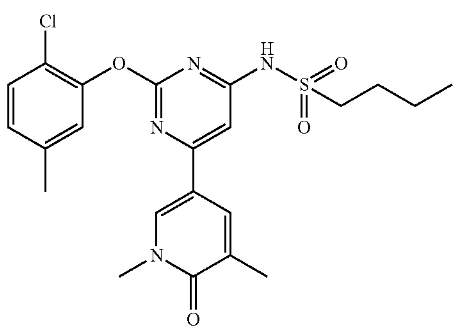 [SMILES: CCCCS(=O)(=O)Nc1cc(-c2cc(C)c(=O)n(C)c2)nc(Oc2cc(C)ccc2Cl)n1] | Butane-1-sulfonic acid [2-(2-chloro-5-methyl-phenoxy)-6-(1,5-dimethyl-6-oxo-1,6-dihydro-pyridin-3-yl)-pyrimidin-4-yl]-amide |
| 16 | 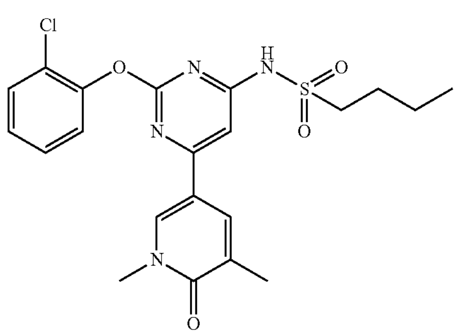 [SMILES: CCCCS(=O)(=O)Nc1cc(-c2cc(C)c(=O)n(C)c2)nc(Oc2ccccc2Cl)n1] | Butane-1-sulfonic acid [2-(2-chloro-phenoxy)-6-(1,5-dimethyl-6-oxo-1,6-dihydro-pyridin-3-yl)-pyrimidin-4-yl]-amide |

TABLE 1-continued

| Example | Structure | Name |
|---|---|---|
| 17 | 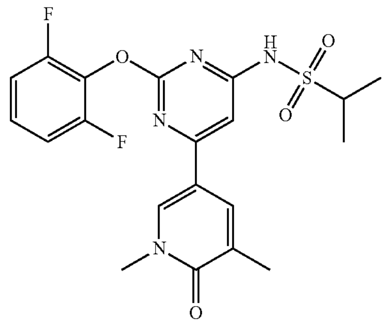 [SMILES: Cc1cc(-c2cc(NS(=O)(=O)C(C)C)nc(Oc3c(F)cccc3F)n2)cn(C)c1=O] | Propane-2-sulfonic acid [2-(2,6-difluoro-phenoxy)-6-(1,5-dimethyl-6-oxo-1,6-dihydro-pyridin-3-yl)-pyrimidin-4-yl]-amide |
| 18 | 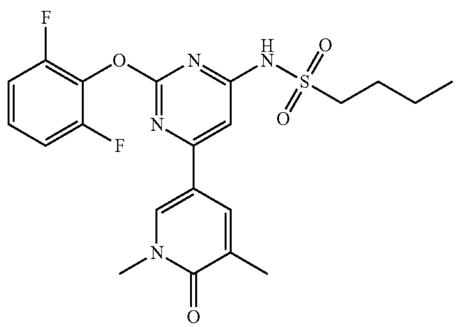 | Butane-1-sulfonic acid [2-(2,6-difluoro-phenoxy)-6-(1,5-dimethyl-6-oxo-1,6-dihydro-pyridin-3-yl)-pyrimidin-4-yl]-amide |
| 19 | 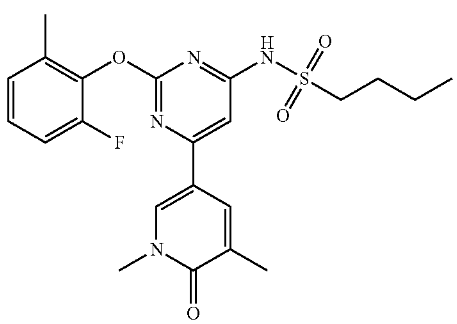 [SMILES: CCCCS(=O)(=O)Nc1cc(-c2cc(C)c(=O)n(C)c2)nc(Oc2c(C)cccc2F)n1] | Butane-1-sulfonic acid [6-(1,5-dimethyl-6-oxo-1,6-dihydro-pyridin-3-yl)-2-(2-fluoro-6-methyl-phenoxy)-pyrimidin-4-yl]-amide |
| 20 | 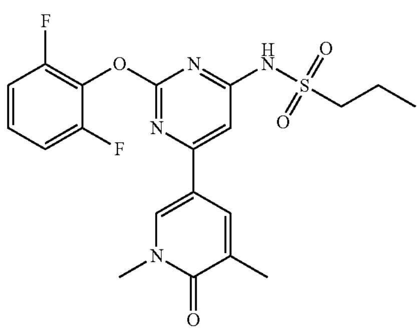 [SMILES: CCCS(=O)(=O)Nc1cc(-c2cc(C)c(=O)n(C)c2)nc(Oc2c(F)cccc2F)n1] | Propane-1-sulfonic acid [2-(2,6-difluoro-phenoxy)-6-(1,5-dimethyl-6-oxo-1,6-dihydro-pyridin-3-yl)-pyrimidin-4-yl]-amide |

TABLE 1-continued

| Example | Structure | Name |
|---|---|---|
| 21 | 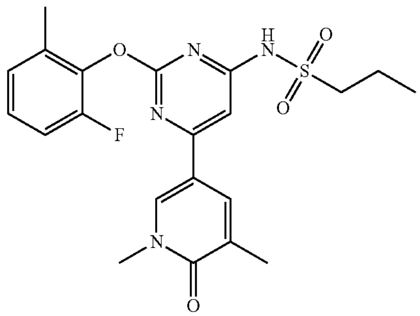 [SMILES: CCCS(=O)(=O)Nc1cc(-c2cc(C)c(=O)n(C)c2)nc(Oc2c(C)cccc2F)n1] | Propane-1-sulfonic acid [6-(1,5-dimethyl-6-oxo-1,6-dihydro-pyridin-3-yl)-2-(2-fluoro-6-methyl-phenoxy)-pyrimidin-4-yl]-amide |
| 22 | 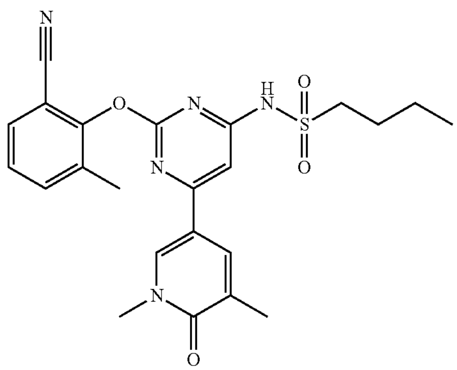 [SMILES: CCCCS(=O)(=O)Nc1cc(-c2cc(C)c(=O)n(C)c2)nc(Oc2c(C)cccc2C#N)n1] | Butane-1-sulfonic acid [2-(2-cyano-6-methyl-phenoxy)-6-(1,5-dimethyl-6-oxo-1,6-dihydro-pyridin-3-yl)-pyrimidin-4-yl]-amide |
| 23 | 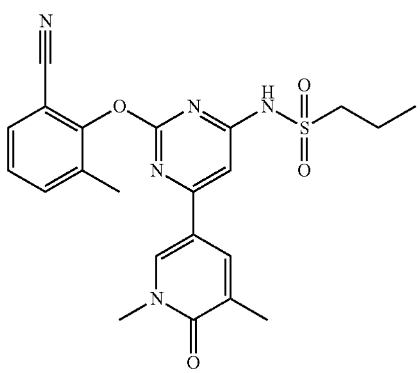 [SMILES: CCCS(=O)(=O)Nc1cc(-c2cc(C)c(=O)n(C)c2)nc(Oc2c(C)cccc2C#N)n1] | Propane-1-sulfonic acid [2-(2-cyano-6-methyl-phenoxy)-6-(1,5-dimethyl-6-oxo-1,6-dihydro-pyridin-3-yl)-pyrimidin-4-yl]-amide |
| 24 | 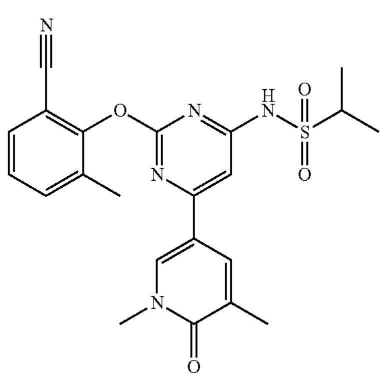 [SMILES: Cc1cccc(C#N)c1Oc1nc(NS(=O)(=O)C(C)C)cc(-c2cc(C)c(=O)n(C)c2)n1] | Propane-2-sulfonic acid [2-(2-cyano-6-methyl-phenoxy)-6-(1,5-dimethyl-6-oxo-1,6-dihydro-pyridin-3-yl)-pyrimidin-4-yl]-amide |

TABLE 1-continued

| Example | Structure | Name |
|---|---|---|
| 25 | 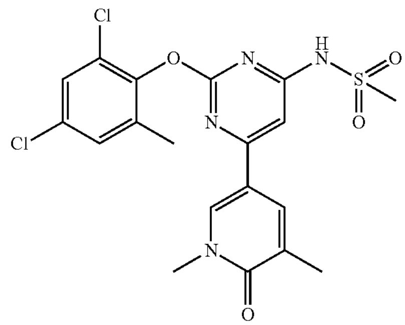 [SMILES: Cc1cc(Cl)cc(Cl)c1Oc1nc(NS(C)(=O)=O)cc(-c2cc(C)c(=O)n(C)c2)n1] | N-[2-(2,4-Dichloro-6-methyl-phenoxy)-6-(1,5-dimethyl-6-oxo-1,6-dihydro-pyridin-3-yl)-pyrimidin-4-yl]-methanesulfonamide |
| 26 | 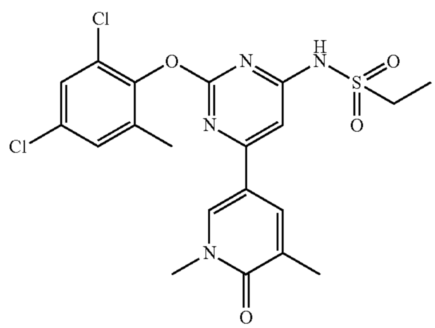 [SMILES: CCS(=O)(=O)Nc1cc(-c2cc(C)c(=O)n(C)c2)nc(Oc2c(C)cc(Cl)cc2Cl)n1] | Ethanesulfonic acid [2-(2,4-dichloro-6-methyl-phenoxy)-6-(1,5-dimethyl-6-oxo-1,6-dihydro-pyridin-3-yl)-pyrimidin-4-yl]-amide |
| 27 | 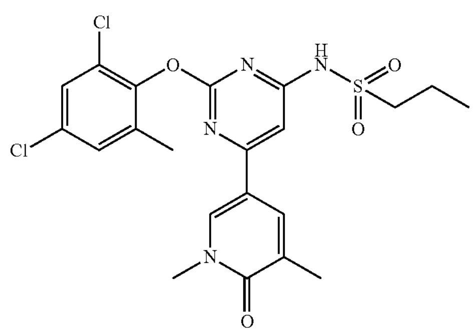 [SMILES: CCCS(=O)(=O)Nc1cc(-c2cc(C)c(=O)n(C)c2)nc(Oc2c(C)cc(Cl)cc2Cl)n1] | Propane-1-sulfonic acid [2-(2,4-dichloro-6-methyl-phenoxy)-6-(1,5-dimethyl-6-oxo-1,6-dihydro-pyridin-3-yl)-pyrimidin-4-yl]-amide |
| 28 | 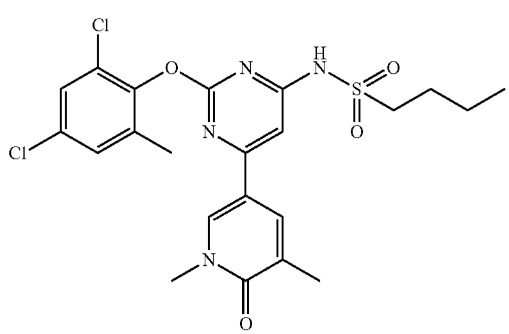 [SMILES: CCCCS(=O)(=O)Nc1cc(-c2cc(C)c(=O)n(C)c2)nc(Oc2c(C)cc(Cl)cc2Cl)n1] | Butane-1-sulfonic acid [2-(2,4-dichloro-6-methyl-phenoxy)-6-(1,5-dimethyl-6-oxo-1,6-dihydro-pyridin-3-yl)-pyrimidin-4-yl]-amide |

TABLE 1-continued

| Example | Structure | Name |
|---|---|---|
| 29 | 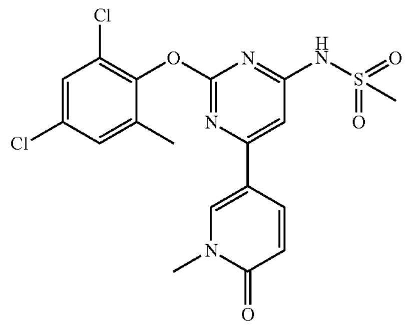 [SMILES: Cc1cc(Cl)cc(Cl)c1Oc1nc(NS(C)(=O)=O)cc(-c2ccc(=O)n(C)c2)n1] | N-[2-(2,4-Dichloro-6-methyl-phenoxy)-6-(1-methyl-6-oxo-1,6-dihydro-pyridin-3-yl)-pyrimidin-4-yl]-methanesulfonamide |
| 30 | 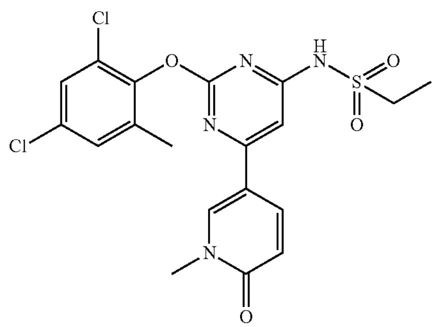 [SMILES: CCS(=O)(=O)Nc1cc(-c2ccc(=O)n(C)c2)nc(Oc2c(C)cc(Cl)cc2Cl)n1] | Ethanesulfonic acid [2-(2,4-dichloro-6-methyl-phenoxy)-6-(1-methyl-6-oxo-1,6-dihydro-pyridin-3-yl)-pyrimidin-4-yl]-amide |
| 31 | 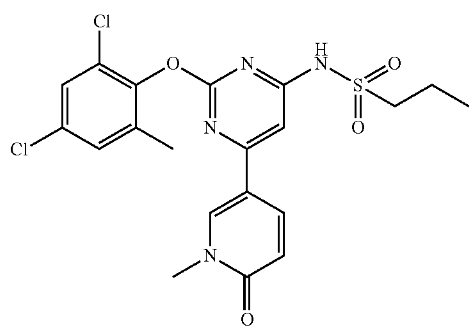 [SMILES: CCCS(=O)(=O)Nc1cc(-c2ccc(=O)n(C)c2)nc(Oc2c(C)cc(Cl)cc2Cl)n1] | Propane-1-sulfonic acid [2-(2,4-dichloro-6-methyl-phenoxy)-6-(1-methyl-6-oxo-1,6-dihydro-pyridin-3-yl)-pyrimidin-4-yl]-amide |
| 32 | 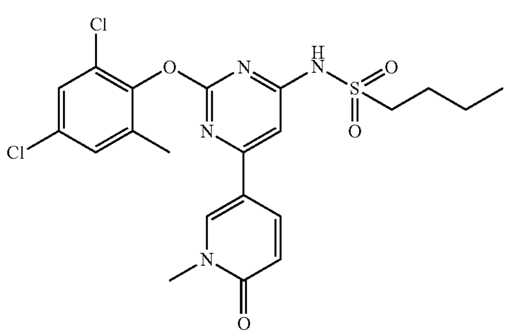 [SMILES: CCCCS(=O)(=O)Nc1cc(-c2ccc(=O)n(C)c2)nc(Oc2c(C)cc(Cl)cc2Cl)n1] | Butane-1-sulfonic acid [2-(2,4-dichloro-6-methyl-phenoxy)-6-(1-methyl-6-oxo-1,6-dihydro-pyridin-3-yl)-pyrimidin-4-yl]-amide |

TABLE 1-continued

| Example | Structure | Name |
|---|---|---|
| 33 | 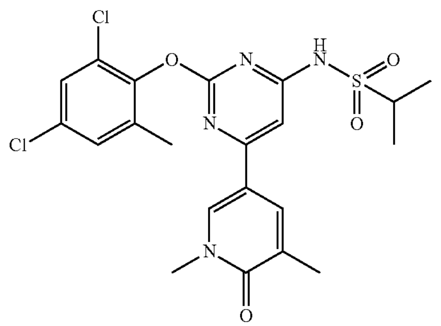 [SMILES: Cc1cc(Cl)cc(Cl)c1Oc1nc(NS(=O)(=O)C(C)C)cc(-c2cc(C)c(=O)n(C)c2)n1] | Propane-2-sulfonic acid [2-(2,4-dichloro-6-methyl-phenoxy)-6-(1,5-dimethyl-6-oxo-1,6-dihydro-pyridin-3-yl)-pyrimidin-4-yl]-amide |
| 34 | 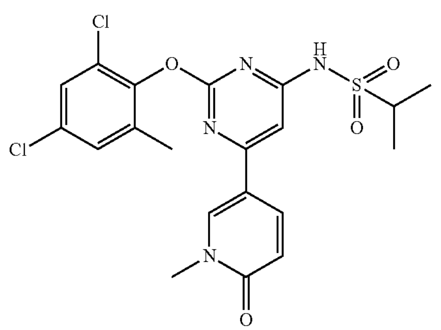 [SMILES: Cc1cc(Cl)cc(Cl)c1Oc1nc(NS(=O)(=O)C(C)C)cc(-c2ccc(=O)n(C)c2)n1] | Propane-2-sulfonic acid [2-(2,4-dichloro-6-methyl-phenoxy)-6-(1-methyl-6-oxo-1,6-dihydro-pyridin-3-yl)-pyrimidin-4-yl]-amide |
| 35 | 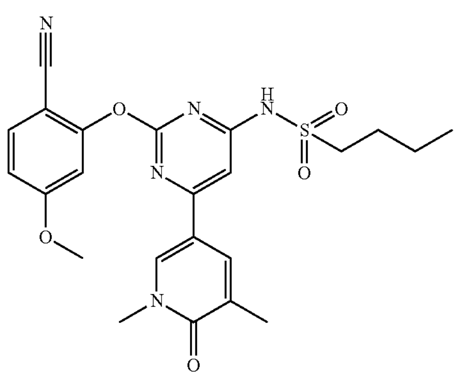 [SMILES: CCCCS(=O)(=O)Nc1cc(-c2cc(C)c(=O)n(C)c2)nc(Oc2cc(OC)ccc2C#N)n1] | Butane-1-sulfonic acid [2-(2-cyano-5-methoxy-phenoxy)-6-(1,5-dimethyl-6-oxo-1,6-dihydro-pyridin-3-yl)-pyrimidin-4-yl]-amide |
| 36 | 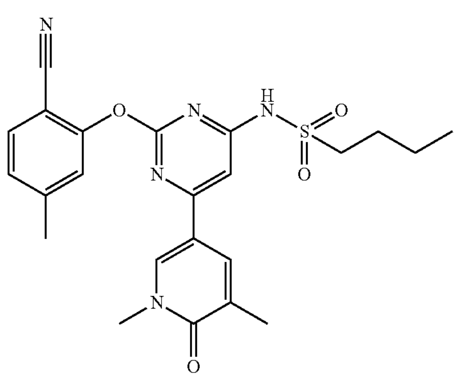 [SMILES: CCCCS(=O)(=O)Nc1cc(-c2cc(C)c(=O)n(C)c2)nc(Oc2cc(C)ccc2C#N)n1] | Butane-1-sulfonic acid [2-(2-cyano-5-methyl-phenoxy)-6-(1,5-dimethyl-6-oxo-1,6-dihydro-pyridin-3-yl)-pyrimidin-4-yl]-amide |

TABLE 1-continued

| Example | Structure | Name |
|---|---|---|
| 37 | 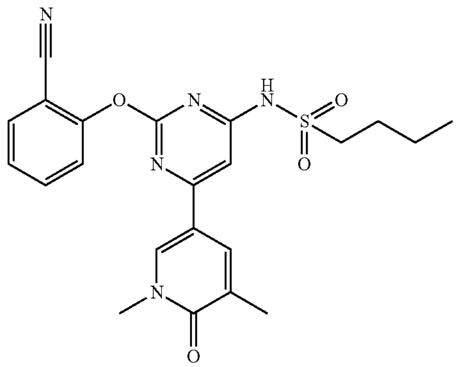 [SMILES: CCCCS(=O)(=O)Nc1cc(-c2cc(C)c(=O)n(C)c2)nc(Oc2ccccc2C#N)n1] | Butane-1-sulfonic acid [2-(2-cyano-phenoxy)-6-(1,5-dimethyl-6-oxo-1,6-dihydro-pyridin-3-yl)-pyrimidin-4-yl]-amide |
| 38 | 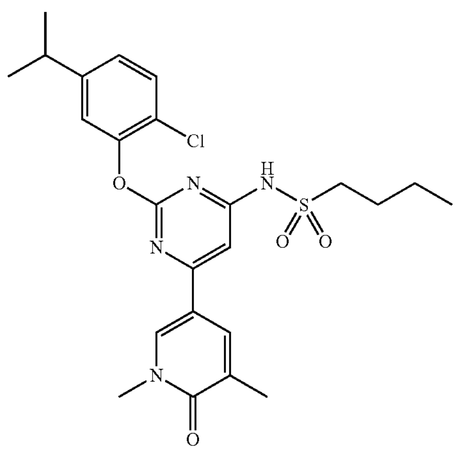 [SMILES: CCCCS(=O)(=O)Nc1cc(-c2cc(C)c(=O)n(C)c2)nc(Oc2cc(C(C)C)ccc2Cl)n1] | Butane-1-sulfonic acid [2-(2-chloro-5-isopropyl-phenoxy)-6-(1,5-dimethyl-6-oxo-1,6-dihydro-pyridin-3-yl)-pyrimidin-4-yl]-amide |
| 39 | 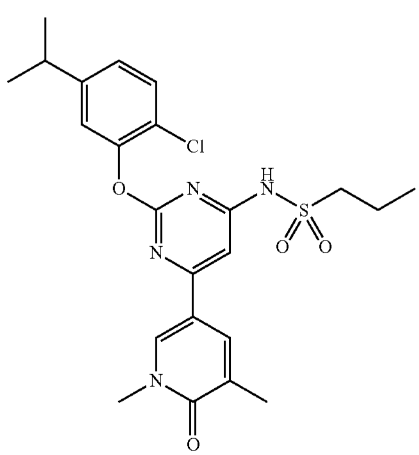 [SMILES: CCCS(=O)(=O)Nc1cc(-c2cc(C)c(=O)n(C)c2)nc(Oc2cc(C(C)C)ccc2Cl)n1] | Propane-1-sulfonic acid [2-(2-chloro-5-isopropyl-phenoxy)-6-(1,5-dimethyl-6-oxo-1,6-dihydro-pyridin-3-yl)-pyrimidin-4-yl]-amide |

TABLE 1-continued

| Example | Structure | Name |
|---|---|---|
| 40 | 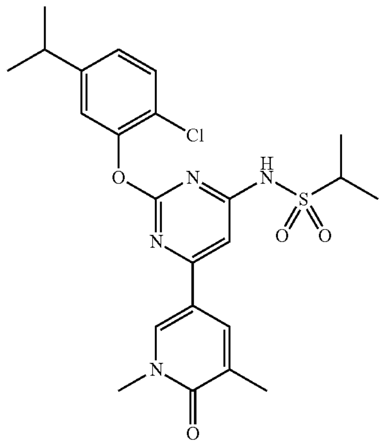 [SMILES: Cc1cc(-c2cc(NS(=O)(=O)C(C)C)nc(Oc3cc(C(C)C)ccc3Cl)n2)cn(C)c1=O] | Propane-2-sulfonic acid [2-(2-chloro-5-isopropyl-phenoxy)-6-(1,5-dimethyl-6-oxo-1,6-dihydro-pyridin-3-yl)-pyrimidin-4-yl]-amide |
| 41 | 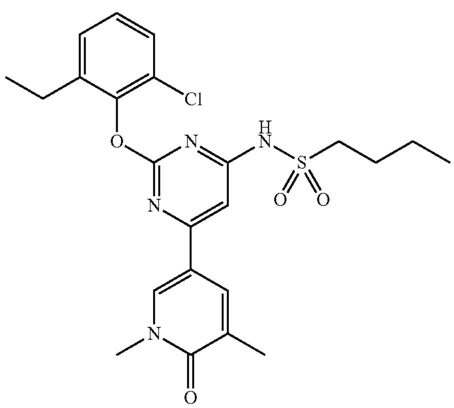 [SMILES: CCCCS(=O)(=O)Nc1cc(-c2cc(C)c(=O)n(C)c2)nc(Oc2c(Cl)cccc2CC)n1] | Butane-1-sulfonic acid [2-(2-chloro-6-ethyl-phenoxy)-6-(1,5-dimethyl-6-oxo-1,6-dihydro-pyridin-3-yl)-pyrimidin-4-yl]-amide |
| 42 | 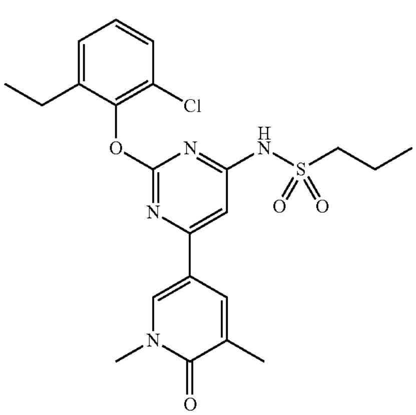 [SMILES: CCCS(=O)(=O)Nc1cc(-c2cc(C)c(=O)n(C)c2)nc(Oc2c(Cl)cccc2CC)n1] | Propane-1-sulfonic acid [2-(2-chloro-6-ethyl-phenoxy)-6-(1,5-dimethyl-6-oxo-1,6-dihydro-pyridin-3-yl)-pyrimidin-4-yl]-amide |

TABLE 1-continued

| Example | Structure | Name |
|---|---|---|
| 43 | 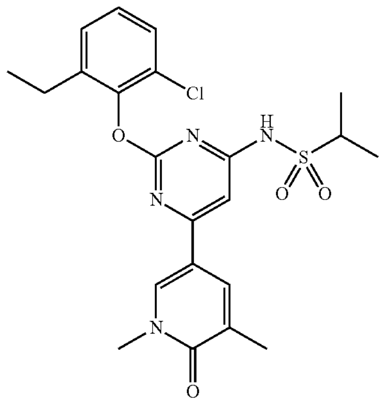 [SMILES: CCc1cccc(Cl)c1Oc1nc(NS(=O)(=O)C(C)C)cc(-c2cc(C)c(=O)n(C)c2)n1] | Propane-2-sulfonic acid [2-(2-chloro-6-ethyl-phenoxy)-6-(1,5-dimethyl-6-oxo-1,6-dihydro-pyridin-3-yl)-pyrimidin-4-yl]-amide |
| 44 | 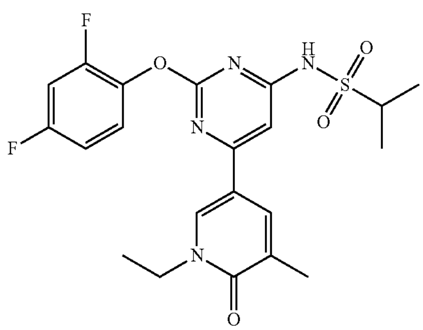 [SMILES: CCn1cc(-c2cc(NS(=O)(=O)C(C)C)nc(Oc3ccc(F)cc3F)n2)cc(C)c1=O] | Propane-2-sulfonic acid [2-(2,4-difluoro-phenoxy)-6-(1-ethyl-5-methyl-6-oxo-1,6-dihydro-pyridin-3-yl)-pyrimidin-4-yl]-amide |
| 45 | 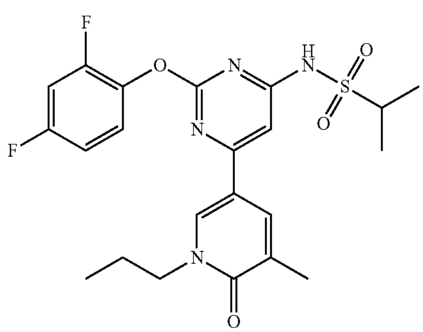 [SMILES: CCCn1cc(-c2cc(NS(=O)(=O)C(C)C)nc(Oc3ccc(F)cc3F)n2)cc(C)c1=O] | Propane-2-sulfonic acid [2-(2,4-difluoro-phenoxy)-6-(5-methyl-6-oxo-1-propyl-1,6-dihydro-pyridin-3-yl)-pyrimidin-4-yl]-amide |
| 46 | 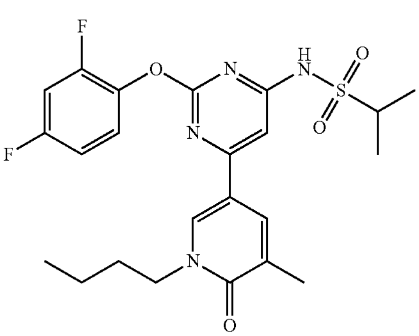 [SMILES: CCCCn1cc(-c2cc(NS(=O)(=O)C(C)C)nc(Oc3ccc(F)cc3F)n2)cc(C)c1=O] | Propane-2-sulfonic acid [6-(1-butyl-5-methyl-6-oxo-1,6-dihydro-pyridin-3-yl)-2-(2,4-difluoro-phenoxy)-pyrimidin-4-yl]-amide |

TABLE 1-continued

| Example | Structure | Name |
|---|---|---|
| 47 | 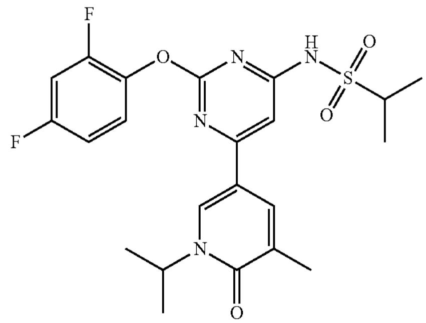 [SMILES: Cc1cc(-c2cc(NS(=O)(=O)C(C)C)nc(Oc3ccc(F)cc3F)n2)cn(C(C)C)c1=O] | Propane-2-sulfonic acid [2-(2,4-difluoro-phenoxy)-6-(1-isopropyl-5-methyl-6-oxo-1,6-dihydro-pyridin-3-yl)-pyrimidin-4-yl]-amide |
| 48 | 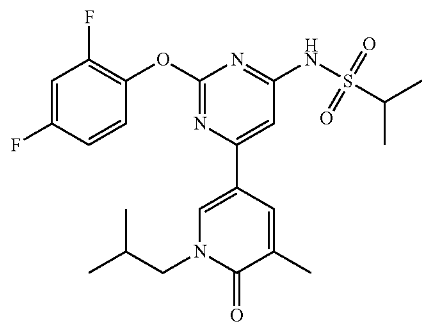 [SMILES: Cc1cc(-c2cc(NS(=O)(=O)C(C)C)nc(Oc3ccc(F)cc3F)n2)cn(CC(C)C)c1=O] | Propane-2-sulfonic acid [2-(2,4-difluoro-phenoxy)-6-(1-isobutyl-5-methyl-6-oxo-1,6-dihydro-pyridin-3-yl)-pyrimidin-4-yl]-amide |
| 49 | 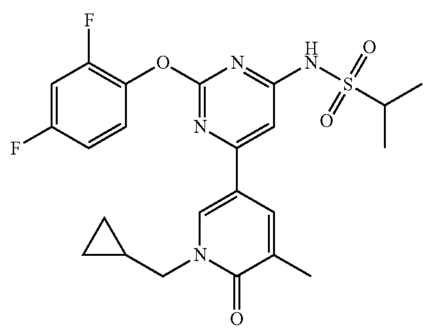 [SMILES: Cc1cc(-c2cc(NS(=O)(=O)C(C)C)nc(Oc3ccc(F)cc3F)n2)cn(CC2CC2)c1=O] | Propane-2-sulfonic acid [6-(1-cyclopropylmethyl-5-methyl-6-oxo-1,6-dihydro-pyridin-3-yl)-2-(2,4-difluoro-phenoxy)-pyrimidin-4-yl]-amide |
| 50 | 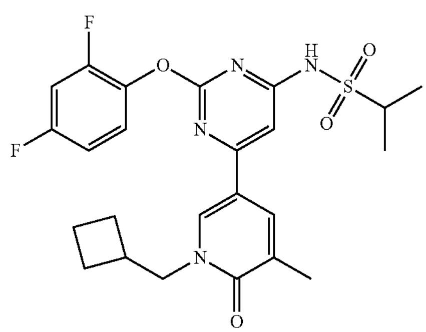 [SMILES: Cc1cc(-c2cc(NS(=O)(=O)C(C)C)nc(Oc3ccc(F)cc3F)n2)cn(CC2CCC2)c1=O] | Propane-2-sulfonic acid [6-(1-cyclobutylmethyl-5-methyl-6-oxo-1,6-dihydro-pyridin-3-yl)-2-(2,4-difluoro-phenoxy)-pyrimidin-4-yl]-amide |

TABLE 1-continued

| Example | Structure | Name |
|---|---|---|
| 51 | 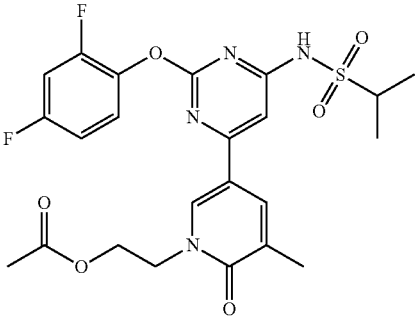 [SMILES: CC(=O)OCCn1cc(-c2cc(NS(=O)(=O)C(C)C)nc(Oc3ccc(F)cc3F)n2)cc(C)c1=O] | Acetic acid 2-{5-[2-(2,4-difluoro-phenoxy)-6-(propane-2-sulfonylamino)-pyrimidin-4-yl]-3-methyl-2-oxo-2H-pyridin-1-yl}-ethyl ester |
| 52 | 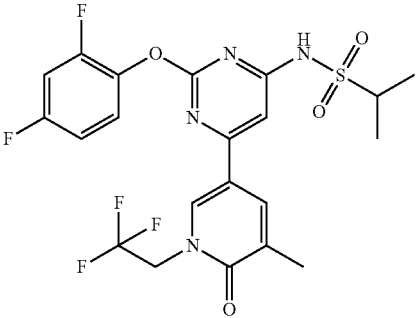 [SMILES: Cc1cc(-c2cc(NS(=O)(=O)C(C)C)nc(Oc3ccc(F)cc3F)n2)cn(CC(F)(F)F)c1=O] | Propane-2-sulfonic acid {2-(2,4-difluoro-phenoxy)-6-[5-methyl-6-oxo-1-(2,2,2-trifluoro-ethyl)-1,6-dihydro-pyridin-3-yl]-pyrimidin-4-yl}-amide |
| 53 | 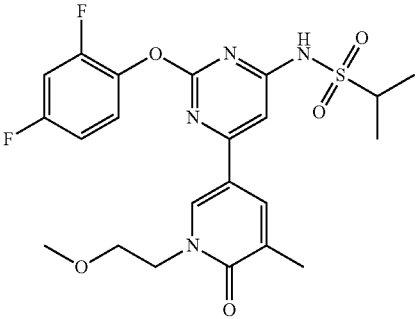 | Propane-2-sulfonic acid {2-(2,4-difluoro-phenoxy)-6-[1-(2-methoxy-ethyl)-5-methyl-6-oxo-1,6-dihydro-pyridin-3-yl]-pyrimidin-4-yl}-amide |
| 54 | 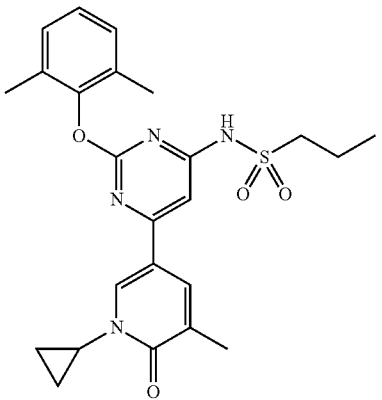 [SMILES: CCCS(=O)(=O)Nc1cc(-c2cc(C)c(=O)n(C3CC3)c2)nc(Oc2c(C)cccc2C)n1] | Propane-1-sulfonic acid [6-(1-cyclopropyl-5-methyl-6-oxo-1,6-dihydro-pyridin-3-yl)-2-(2,6-dimethyl-phenoxy)-pyrimidin-4-yl]-amide |

TABLE 1-continued

| Example | Structure | Name |
|---|---|---|
| 55 | 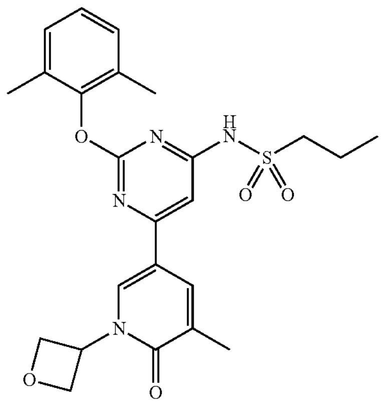 [SMILES: CCCS(=O)(=O)Nc1cc(-c2cc(C)c(=O)n(C3COC3)c2)nc(Oc2c(C)cccc2C)n1] | Propane-1-sulfonic acid [2-(2,6-dimethyl-phenoxy)-6-(5-methyl-1-oxetan-3-yl-6-oxo-1,6-dihydro-pyridin-3-yl)-pyrimidin-4-yl]-amide |
| 56 | 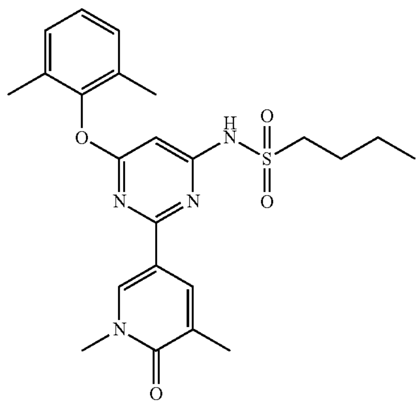 [SMILES: CCCCS(=O)(=O)Nc1cc(Oc2c(C)cccc2C)nc(-c2cc(C)c(=O)n(C)c2)n1] | Butane-1-sulfonic acid [2-(1,5-dimethyl-6-oxo-1,6-dihydro-pyridin-3-yl)-6-(2,6-dimethyl-phenoxy)-pyrimidin-4-yl]-amide |
| 57 | 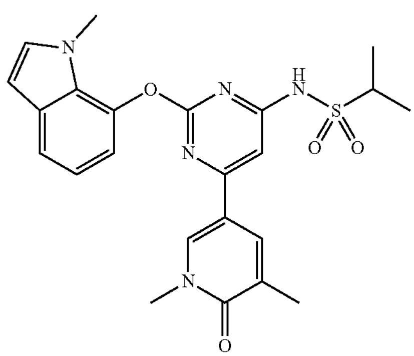 [SMILES: Cc1cc(-c2cc(NS(=O)(=O)C(C)C)nc(Oc3cccc4ccn(C)c34)n2)cn(C)c1=O] | Propane-2-sulfonic acid [6-(1,5-dimethyl-6-oxo-1,6-dihydro-pyridin-3-yl)-2-(1-methyl-1H-indol-7-yloxy)-pyrimidin-4-yl]-amide |
| 58 | 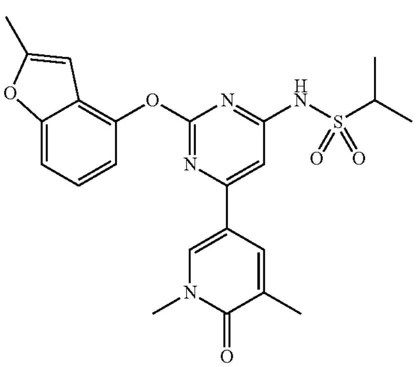 [SMILES: Cc1cc2c(Oc3nc(NS(=O)(=O)C(C)C)cc(-c4cc(C)c(=O)n(C)c4)n3)cccc2o1] | N-(6-(1,5-dimethyl-6-oxo-1,6-dihydropyridin-3-yl)-2-((2-methylbenzofuran-4-yl)oxy)pyrimidin-4-yl)propane-2-sulfonamide |

TABLE 1-continued

| Example | Structure | Name |
|---|---|---|
| 59 | 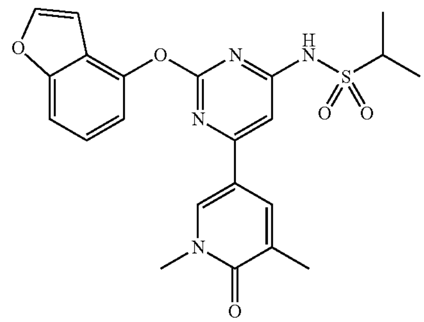 [SMILES: Cc1cc(-c2cc(NS(=O)(=O)C(C)C)nc(Oc3cccc4occc34)n2)cn(C)c1=O] | N-(2-(benzofuran-4-yloxy)-6-(1,5-dimethyl-6-oxo-1,6-dihydropyridin-3-yl)pyrimidin-4-yl)propane-2-sulfonamide |
| 60 | 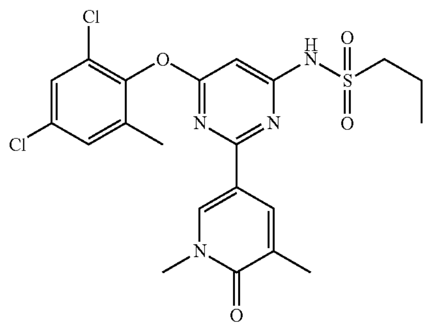 [SMILES: CCCS(=O)(=O)Nc1cc(Oc2c(C)cc(Cl)cc2Cl)nc(-c2cc(C)c(=O)n(C)c2)n1] | Propane-1-sulfonic acid [6-(2,4-dichloro-6-methyl-phenoxy)-2-(1,5-dimethyl-6-oxo-1,6-dihydro-pyridin-3-yl)-pyrimidin-4-yl]-amide |
| 61 | 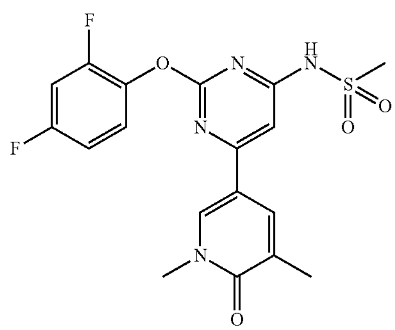 [SMILES: Cc1cc(-c2cc(NS(C)(=O)=O)nc(Oc3ccc(F)cc3F)n2)cn(C)c1=O] | N-(2-(2,4-difluorophenoxy)-6-(1,5-dimethyl-6-oxo-1,6-dihydropyridin-3-yl)pyrimidin-4-yl)methanesulfonamide |
| 62 | 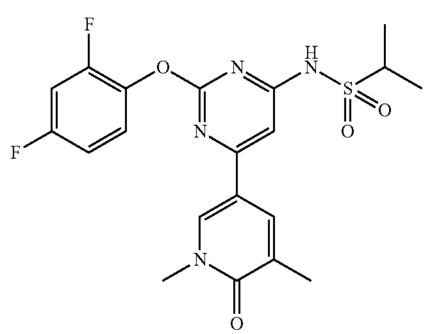 [SMILES: Cc1cc(-c2cc(NS(=O)(=O)C(C)C)nc(Oc3ccc(F)cc3F)n2)cn(C)c1=O] | N-(2-(2,4-difluorophenoxy)-6-(1,5-dimethyl-6-oxo-1,6-dihydropyridin-3-yl)pyrimidin-4-yl)propane-2-sulfonamide |

TABLE 1-continued

| Example | Structure | Name |
|---|---|---|
| 63 | 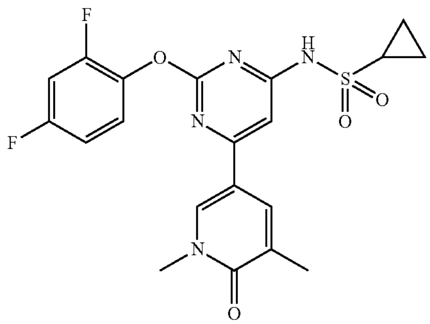 [SMILES: Cc1cc(-c2cc(NS(=O)(=O)C3CC3)nc(Oc3ccc(F)cc3F)n2)cn(C)c1=O] | N-(2-(2,4-difluorophenoxy)-6-(1,5-dimethyl-6-oxo-1,6-dihydropyridin-3-yl)pyrimidin-4-yl)cyclopropanesulfonamide |
| 64 | 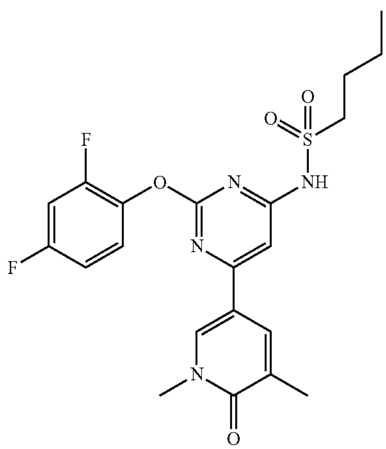 [SMILES: CCCCS(=O)(=O)Nc1cc(-c2cc(C)c(=O)n(C)c2)nc(Oc2ccc(F)cc2F)n1] | N-(2-(2,4-difluorophenoxy)-6-(1,5-dimethyl-6-oxo-1,6-dihydropyridin-3-yl)pyrimidin-4-yl)butane-1-sulfonamide |
| 65 | 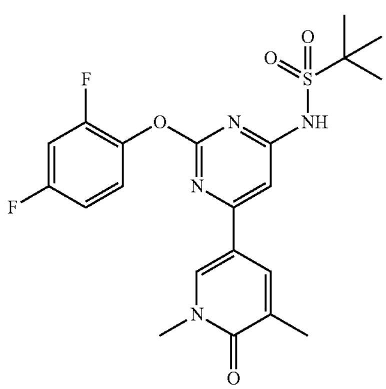 [SMILES: Cc1cc(-c2cc(NS(=O)(=O)C(C)(C)C)nc(Oc3ccc(F)cc3F)n2)cn(C)c1=O] | N-(2-(2,4-difluorophenoxy)-6-(1,5-dimethyl-6-oxo-1,6-dihydropyridin-3-yl)pyrimidin-4-yl)-2-methylpropane-2-sulfonamide |
| 66 | 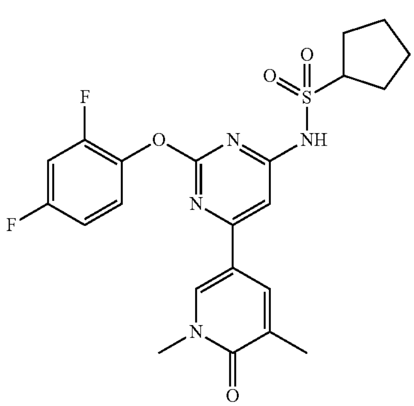 [SMILES: Cc1cc(-c2cc(NS(=O)(=O)C3CCCC3)nc(Oc3ccc(F)cc3F)n2)cn(C)c1=O] | N-(2-(2,4-difluorophenoxy)-6-(1,5-dimethyl-6-oxo-1,6-dihydropyridin-3-yl)pyrimidin-4-yl)cyclopentanesulfonamide |

TABLE 1-continued

| Example | Structure | Name |
|---|---|---|
| 67 | 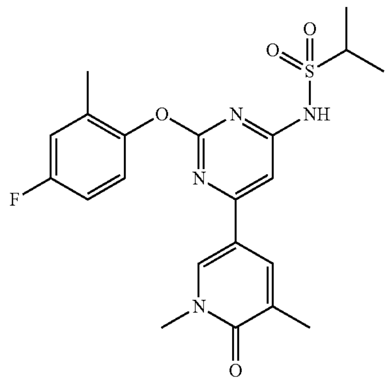 | N-(6-(1,5-dimethyl-6-oxo-1,6-dihydropyridin-3-yl)-2-(4-fluoro-2-methylphenoxy)pyrimidin-4-yl)propane-2-sulfonamide |
| 68 | 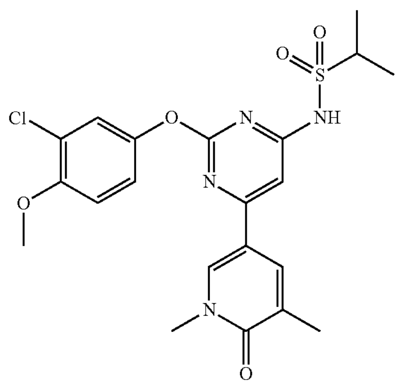 [SMILES: COc1ccc(Oc2nc(NS(=O)(=O)C(C)C)cc(-c3cc(C)c(=O)n(C)c3)n2)cc1Cl] | N-(2-(3-chloro-4-methoxyphenoxy)-6-(1,5-dimethyl-6-oxo-1,6-dihydropyridin-3-yl)pyrimidin-4-yl)propane-2-sulfonamide |
| 69 | 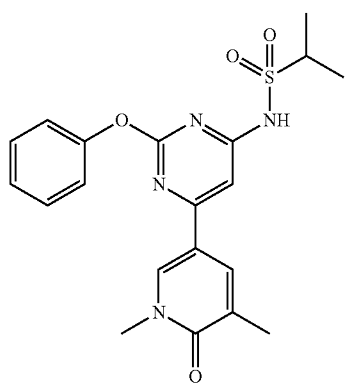 [SMILES: Cc1cc(-c2cc(NS(=O)(=O)C(C)C)nc(Oc3ccccc3)n2)cn(C)c1=O] | N-(6-(1,5-dimethyl-6-oxo 1,6-dihydropyridin-3-yl)-2-phenoxypyrimidin-4-yl)propane-2-sulfonamide |
| 70 | 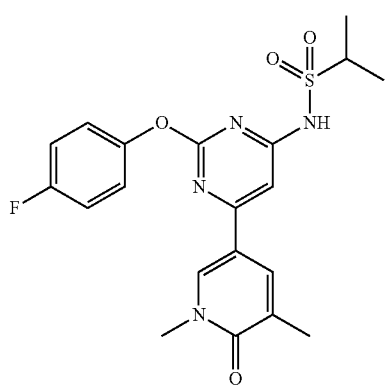 [SMILES: Cc1cc(-c2cc(NS(=O)(=O)C(C)C)nc(Oc3ccc(F)cc3)n2)cn(C)c1=O] | N-(6-(1,5-dimethyl-6-oxo-1,6-dihydropyridin-3-yl)-2-(4-fluorophenoxy)pyrimidin-4-yl)propane-2-sulfonamide |

TABLE 1-continued

| Example | Structure | Name |
|---|---|---|
| 71 | 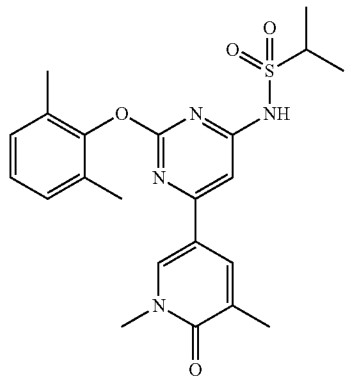 [SMILES: Cc1cccc(C)c1Oc1nc(NS(=O)(=O)C(C)C)cc(-c2cc(C)c(=O)n(C)c2)n1] | N-(6-(1,5-dimethyl-6-oxo-1,6-dihydropyridin-3-yl)-2-(2,6-dimethylphenoxy)pyrimidin-4-yl)propane-2-sulfonamide |
| 72 | 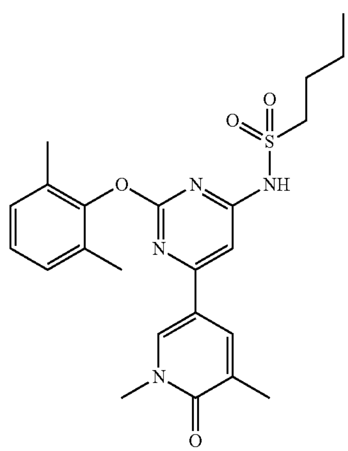 [SMILES: CCCCS(=O)(=O)Nc1cc(-c2cc(C)c(=O)n(C)c2)nc(Oc2c(C)cccc2C)n1] | N-(6-(1,5-dimethyl-6-oxo-1,6-dihydropyridin-3-yl)-2-(2,6-dimethylphenoxy)pyrimidin-4-yl)butane-1-sulfonamide |
| 73 | 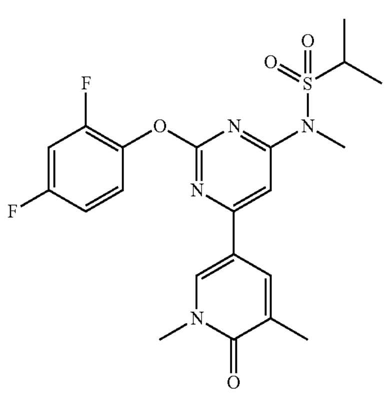 [SMILES: Cc1cc(-c2cc(N(C)S(=O)(=O)C(C)C)nc(Oc3ccc(F)cc3F)n2)cn(C)c1=O] | N-(2-(2,4-difluorophenoxy)-6-(1,5-dimethyl-6-oxo-1,6-dihydropyridin-3-yl)pyrimidin-4-yl)-N-methylpropane-2-sulfonamide |

TABLE 1-continued

| Example | Structure | Name |
|---|---|---|
| 74 | 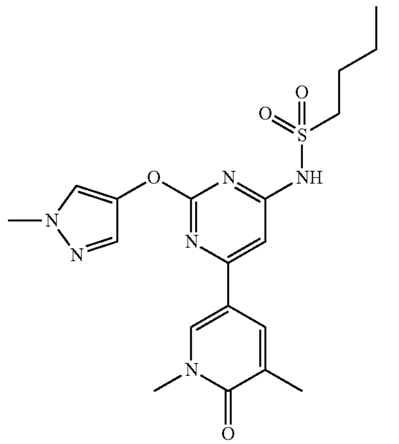 [SMILES: CCCCS(=O)(=O)Nc1cc(-c2cc(C)c(=O)n(C)c2)nc(Oc2cnn(C)c2)n1] | N-(6-(1,5-dimethyl-6-oxo-1,6-dihydropyridin-3-yl)-2-((1-methyl-1H-pyrazol-4-yl)oxy)pyrimidin-4-yl)butane-1-sulfonamide |
| 75 | 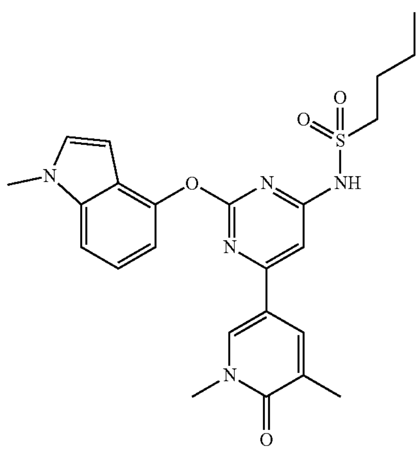 [SMILES: CCCCS(=O)(=O)Nc1cc(-c2cc(C)c(=O)n(C)c2)nc(Oc2cccc3c2ccn3C)n1] | N-(6-(1,5-dimethyl-6-oxo-1,6-dihydropyridin-3-yl)-2-((1-methyl-1H-indol-4-yl)oxy)pyrimidin-4-yl)butane-1-sulfonamide |
| 76 | 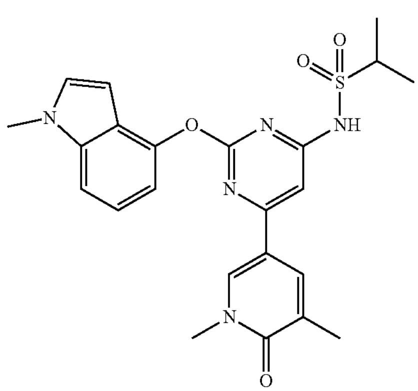 [SMILES: Cc1cc(-c2cc(NS(=O)(=O)C(C)C)nc(Oc3cccc4c3ccn4C)n2)cn(C)c1=O] | N-(6-(1,5-dimethyl-6-oxo-1,6-dihydropyridin-3-yl)-2-((1-methyl-1H-indol-4-yl)oxy)pyrimidin-4-yl)propane-2-sulfonamide |

TABLE 1-continued

| Example | Structure | Name |
|---|---|---|
| 77 | 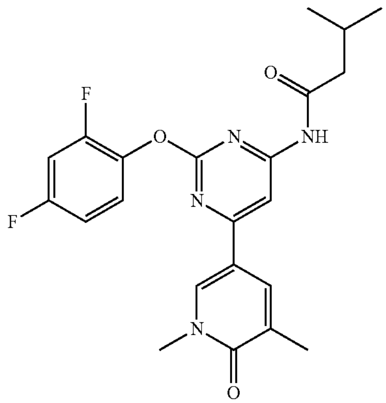 [SMILES: Cc1cc(-c2cc(NC(=O)CC(C)C)nc(Oc3ccc(F)cc3F)n2)cn(C)c1=O] | N-(2-(2,4-difluorophenoxy)-6-(1,5-dimethyl-6-oxo-1,6-dihydropyridin-3-yl)pyrimidin-4-yl)-3-methylbutanamide |
| 78 | 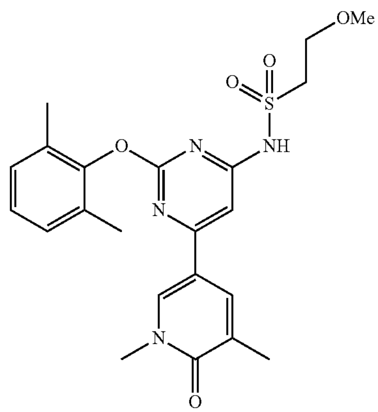 [SMILES: COCCS(=O)(=O)Nc1cc(-c2cc(C)c(=O)n(C)c2)nc(Oc2c(C)cccc2C)n1] | N-(6-(1,5-dimethyl-6-oxo-1,6-dihydropyridin-3-yl)-2-(2,6-dimethylphenoxy)pyrimidin-4-yl)-2-methoxyethane-1-sulfonamide |
| 79 | 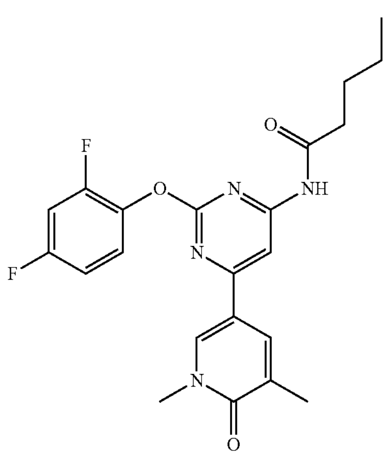 [SMILES: CCCCC(=O)Nc1cc(-c2cc(C)c(=O)n(C)c2)nc(Oc2ccc(F)cc2F)n1] | N-(2-(2,4-difluorophenoxy)-6-(1,5-dimethyl-6-oxo-1,6-dihydropyridin-3-yl)pyrimidin-4-yl)pentanamide |

TABLE 1-continued

| Example | Structure | Name |
|---|---|---|
| 80 | 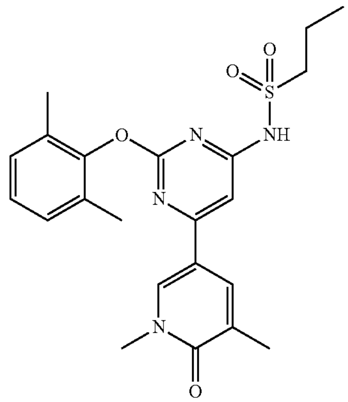 | N-(6-(1,5-dimethyl-6-oxo-1,6-dihydropyridin-3-yl)-2-(2,6-dimethylphenoxy)pyrimidin-4-yl)propane-1-sulfonamide |
| 81 | 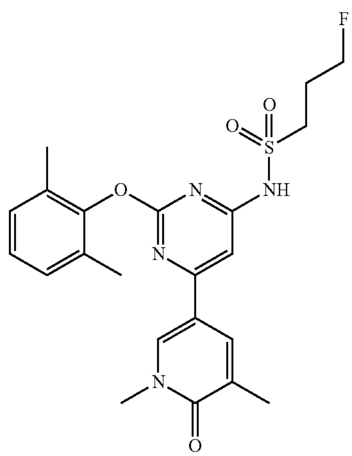 [SMILES: Cc1cccc(C)c1Oc1nc(NS(=O)(=O)CCCF)cc(-c2cc(C)c(=O)n(C)c2)n1] | N-(6-(1,5-dimethyl-6-oxo-1,6-dihydropyridin-3-yl)-2-(2,6-dimethylphenoxy)pyrimidin-4-yl)-3-fluoropropane-1-sulfonamide |
| 82 | 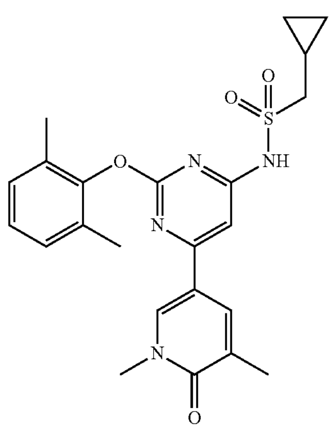 [SMILES: Cc1cccc(C)c1Oc1nc(NS(=O)(=O)CC2CC2)cc(-c2cc(C)c(=O)n(C)c2)n1] | 1-cyclopropyl-N-(6-(1,5-dimethyl-6-oxo-1,6-dihydropyridin-3-yl)-2-(2,6-dimethylphenoxy)pyrimidin-4-yl)methanesulfonamide |

TABLE 1-continued

| Example | Structure | Name |
|---|---|---|
| 83 | 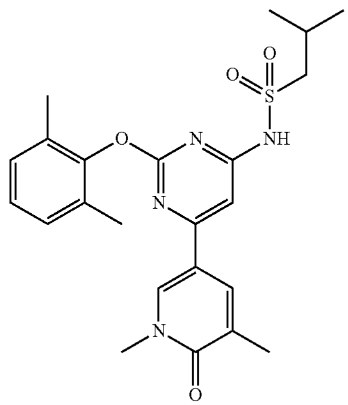 [SMILES: Cc1cccc(C)c1Oc1nc(NS(=O)(=O)CC(C)C)cc(-c2cc(C)c(=O)n(C)c2)n1] | N-(6-(1,5-dimethyl-6-oxo-1,6-dihydropyridin-3-yl)-2-(2,6-dimethylphenoxy)pyrimidin-4-yl)-2-methylpropane-1-sulfonamide |
| 84 | 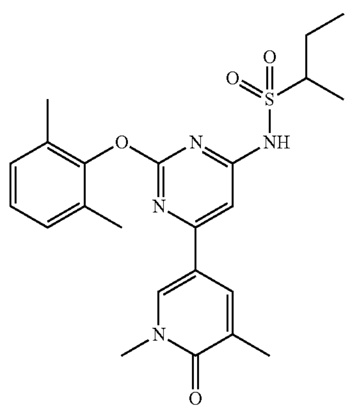 [SMILES: CCC(C)S(=O)(=O)Nc1cc(-c2cc(C)c(=O)n(C)c2)nc(Oc2c(C)cccc2C)n1] | N-(6-(1,5-dimethyl-6-oxo-1,6-dihydropyridin-3-yl)-2-(2,6-dimethylphenoxy)pyrimidin-4-yl)butane-2-sulfonamide |
| 85 | 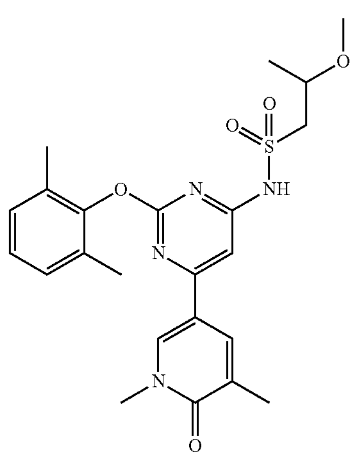 [SMILES: COC(C)CS(=O)(=O)Nc1cc(-c2cc(C)c(=O)n(C)c2)nc(Oc2c(C)cccc2C)n1] | N-(6-(1,5-dimethyl-6-oxo-1,6-dihydropyridin-3-yl)-2-(2,6-dimethylphenoxy)pyrimidin-4-yl)-2-methoxypropane-1-sulfonamide |

TABLE 1-continued

| Example | Structure | Name |
|---|---|---|
| 86 | 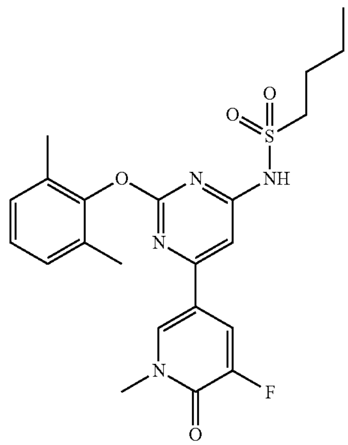 [SMILES: CCCCS(=O)(=O)Nc1cc(-c2cc(F)c(=O)n(C)c2)nc(Oc2c(C)cccc2C)n1] | N-(2-(2,6-dimethylphenoxy)-6-(5-fluoro-1-methyl-6-oxo-1,6-dihydropyridin-3-yl)pyrimidin-4-yl)butane-1-sulfonamide |
| 87 | 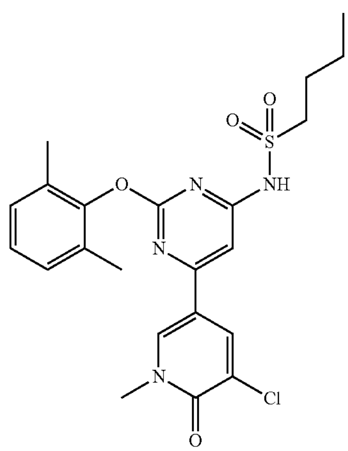 [SMILES: CCCCS(=O)(=O)Nc1cc(-c2cc(Cl)c(=O)n(C)c2)nc(Oc2c(C)cccc2C)n1] | N-(6-(5-chloro-1-methyl-6-oxo-1,6-dihydropyridin-3-yl)-2-(2,6-dimethylphenoxy)pyrimidin-4-yl)butane-1-sulfonamide |
| 88 | 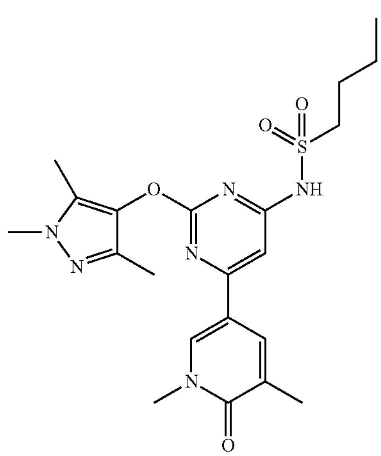 [SMILES: CCCCS(=O)(=O)Nc1cc(-c2cc(C)c(=O)n(C)c2)nc(Oc2c(C)nn(C)c2C)n1] | N-(6-(1,5-dimethyl-6-oxo-1,6-dihydropyridin-3-yl)-2-(((1,3,5-trimethyl-1H-pyrazol-4-yl)oxy)pyrimidin-4-yl)butane-1-sulfonamide |

TABLE 1-continued

| Example | Structure | Name |
|---|---|---|
| 89 | 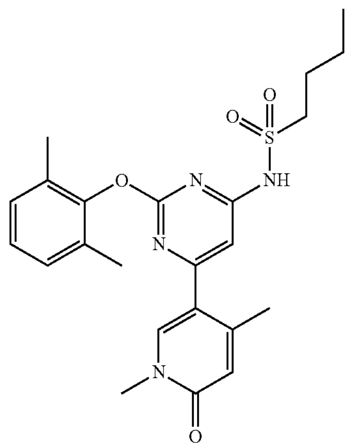 [SMILES: CCCCS(=O)(=O)Nc1cc(-c2cn(C)c(=O)cc2C)nc(Oc2c(C)cccc2C)n1] | N-(6-(1,4-dimethyl-6-oxo-1,6-dihydropyridin-3-yl)-2-(2,6-dimethylphenoxy)pyrimidin-4-yl)butane-1-sulfonamide |
| 90 | 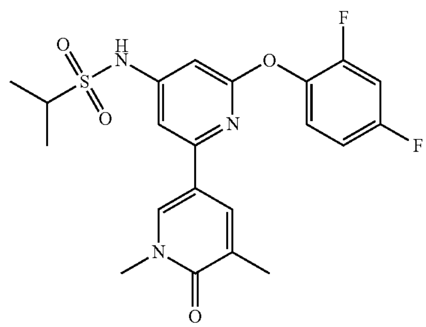 [SMILES: Cc1cc(-c2cc(NS(=O)(=O)C(C)C)cc(Oc3ccc(F)cc3F)n2)cn(C)c1=O] | N-(6-(2,4-difluorophenoxy)-1',5'-dimethyl-6'-oxo-1',6'-dihydro-[2,3'-bipyridin]-4-yl)propane-2-sulfonamide |
| 91 | 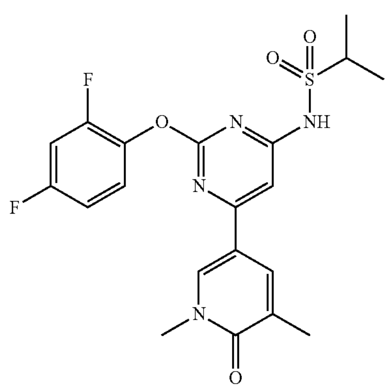 | N-(2-((2,4-difluorophenyl)amino)-6-(1,5-dimethyl-6-oxo-1,6-dihydropyridin-3-yl)pyrimidin-4-yl)propane-2-sulfonamide |
| 92 | 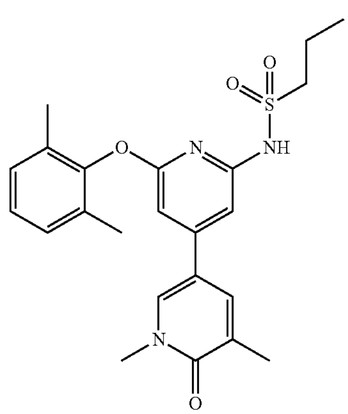 [SMILES: CCCS(=O)(=O)Nc1cc(-c2cc(C)c(=O)n(C)c2)cc(Oc2c(C)cccc2C)n1] | N-(6'-(2,6-dimethylphenoxy)-1,5-dimethyl-6-oxo-1,6-dihydro-[3,4'-bipyridin]-2'-yl)propane-1-sulfonamide |

TABLE 1-continued

| Example | Structure | Name |
|---|---|---|
| 93 | 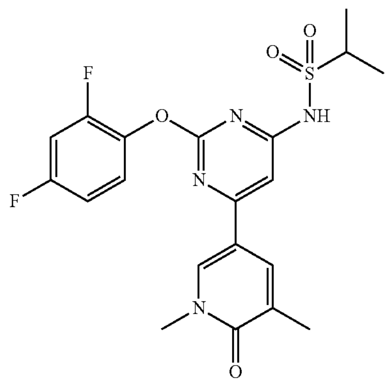 | Propane-2-sulfonic acid [2-(2,4-difluoro-benzyl)-6-(1,5-dimethyl-6-oxo-1,6-dihydro-pyridin-3-yl)-pyrimidin-4-yl]-amide |
| 94 | 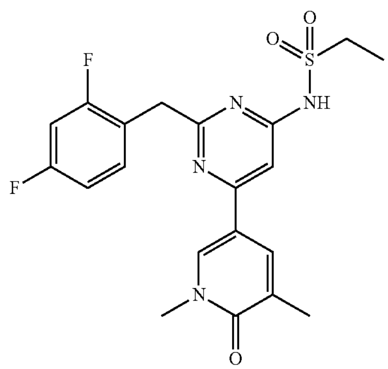 [SMILES: CCS(=O)(=O)Nc1cc(-c2cc(C)c(=O)n(C)c2)nc(Cc2ccc(F)cc2F)n1] | Ethanesulfonic acid [2-(2,4-difluoro-benzyl)-6-(1,5-dimethyl-6-oxo-1,6-dihydro-pyridin-3-yl)-pyrimidin-4-yl]-amide |
| 95 | 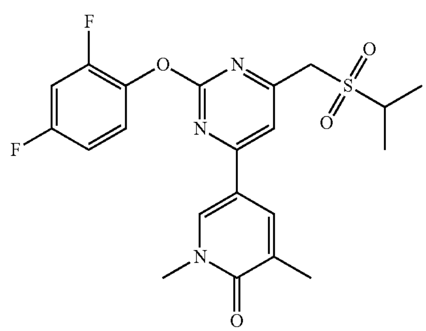 [SMILES: Cc1cc(-c2cc(CS(=O)(=O)C(C)C)nc(Oc3ccc(F)cc3F)n2)cn(C)c1=O] | 5-[2-(2,4-Difluoro-phenoxy)-6-(propane-2-sulfonylmethyl)-pyrimidin-4-yl]-1,3-dimethyl-1H-pyridin-2-one |
| 96 | 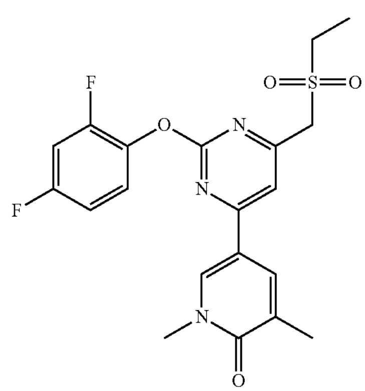 [SMILES: CCS(=O)(=O)Cc1cc(-c2cc(C)c(=O)n(C)c2)nc(Oc2ccc(F)cc2F)n1] | 5-[2-(2,4-Difluoro-phenoxy)-6-ethanesulfonylmethyl-pyrimidin-4-yl]-1,3-dimethyl-1H-pyridin-2-one |

TABLE 1-continued

| Example | Structure | Name |
|---|---|---|
| 97 | 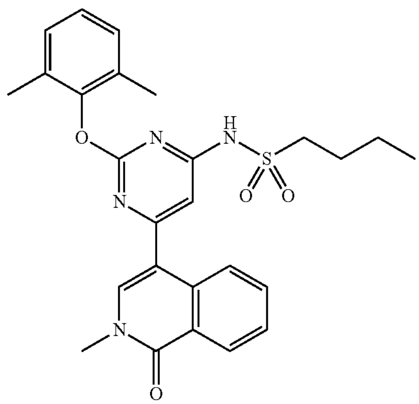 [SMILES: CCCCS(=O)(=O)Nc1cc(-c2cn(C)c(=O)c3ccccc23)nc(Oc2c(C)cccc2C)n1] | Butane-1-sulfonic acid [2-(2,6-dimethyl-phenoxy)-6-(2-methyl-1-oxo-1,2-dihydro-isoquinolin-4-yl)-pyrimidin-4-yl]-amide |
| 98 | 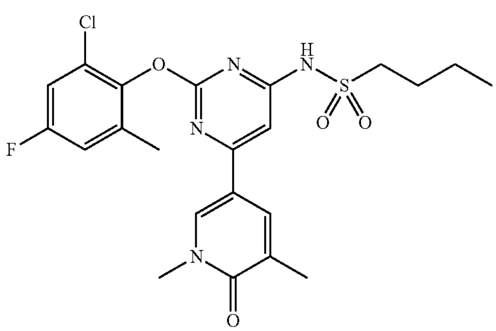 [SMILES: CCCCS(=O)(=O)Nc1cc(-c2cc(C)c(=O)n(C)c2)nc(Oc2c(C)cc(F)cc2Cl)n1] | Butane-1-sulfonic acid [2-(2-chloro-4-fluoro-6-methyl-phenoxy)-6-(1,5-dimethyl-6-oxo-1,6-dihydro-pyridin-3-yl)-pyrimidin-4-yl]-amide |
| 99 | 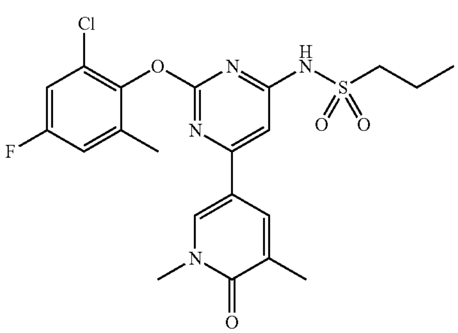 [SMILES: CCCS(=O)(=O)Nc1cc(-c2cc(C)c(=O)n(C)c2)nc(Oc2c(C)cc(F)cc2Cl)n1] | Propane-1-sulfonic acid [2-(2-chloro-4-fluoro-6-methyl-phenoxy)-6-(1,5-dimethyl-6-oxo-1,6-dihydro-pyridin-3-yl)-pyrimidin-4-yl]-amide |
| 100 | 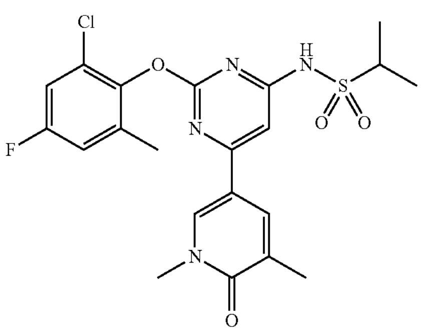 [SMILES: Cc1cc(F)cc(Cl)c1Oc1nc(NS(=O)(=O)C(C)C)cc(-c2cc(C)c(=O)n(C)c2)n1] | Propane-2-sulfonic acid [2-(2-chloro-4-fluoro-6-methyl-phenoxy)-6-(1,5-dimethyl-6-oxo-1,6-dihydro-pyridin-3-yl)-pyrimidin-4-yl]-amide |

TABLE 1-continued

| Example | Structure | Name |
|---|---|---|
| 101 | 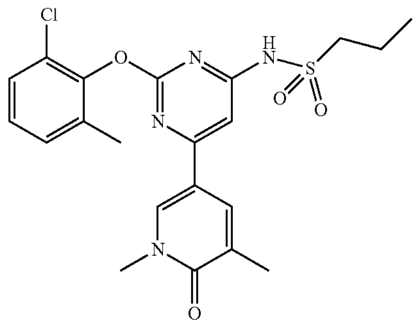 [SMILES: CCCS(=O)(=O)Nc1cc(-c2cc(C)c(=O)n(C)c2)nc(Oc2c(C)cccc2Cl)n1] | Propane-1-sulfonic acid [2-(2-chloro-6-methyl-phenoxy)-6-(1,5-dimethyl-6-oxo-1,6-dihydro-pyridin-3-yl)-pyrimidin-4-yl]-amide |
| 102 | 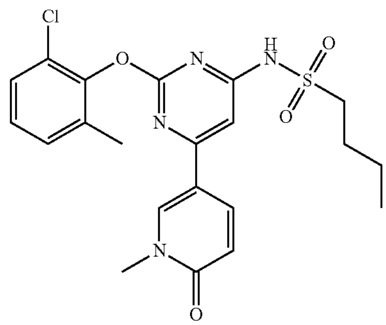 [SMILES: CCCCS(=O)(=O)Nc1cc(-c2ccc(=O)n(C)c2)nc(Oc2c(C)cccc2Cl)n1] | Butane-1-sulfonic acid [2-(2-chloro-6-methyl-phenoxy)-6-(1-methyl-6-oxo-1,6-dihydro-pyridin-3-yl)-pyrimidin-4-yl]-amide |
| 103 | 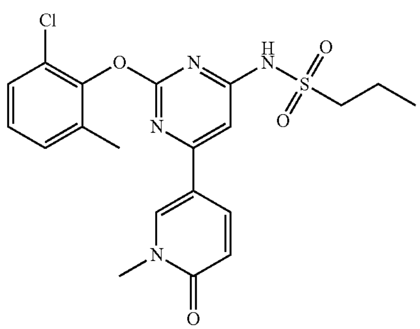 [SMILES: CCCS(=O)(=O)Nc1cc(-c2ccc(=O)n(C)c2)nc(Oc2c(C)cccc2Cl)n1] | Propane-1-sulfonic acid [2-(2-chloro-6-methyl-phenoxy)-6-(1-methyl-6-oxo-1,6-dihydro-pyridin-3-yl)-pyrimidin-4-yl]-amide |
| 104 | 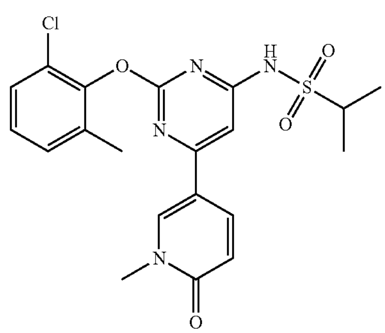 [SMILES: Cc1cccc(Cl)c1Oc1nc(NS(=O)(=O)C(C)C)cc(-c2ccc(=O)n(C)c2)n1] | Propane-2-sulfonic acid [2-(2-chloro-6-methyl-phenoxy)-6-(1-methyl-6-oxo-1,6-dihydro-pyridin-3-yl)-pyrimidin-4-yl]-amide |

TABLE 1-continued

| Example | Structure | Name |
|---|---|---|
| 105 | 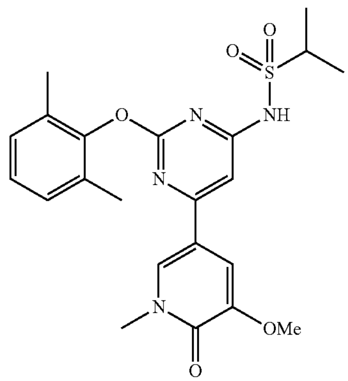 [SMILES: COc1cc(-c2cc(NS(=O)(=O)C(C)C)nc(Oc3c(C)cccc3C)n2)cn(C)c1=O] | N-(2-(2,6-dimethylphenoxy)-6-(5-methoxy-1-methyl-6-oxo-1,6-dihydropyridin-3-yl)pyrimidin-4-yl)propane-2-sulfonamide |
| 106 | 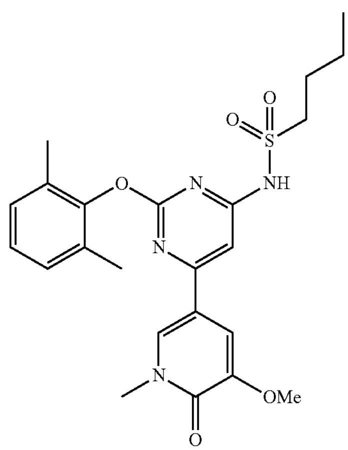 [SMILES: CCCCS(=O)(=O)Nc1cc(-c2cc(OC)c(=O)n(C)c2)nc(Oc2c(C)cccc2C)n1] | N-(2-(2,6-dimethylphenoxy)-6-(5-methoxy-1-methyl-6-oxo-1,6-dihydropyridin-3-yl)pyrimidin-4-yl)butane-1-sulfonamide |
| 107 | 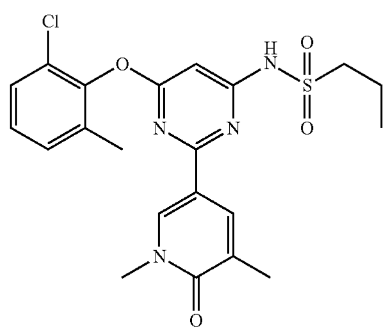 [SMILES: CCCS(=O)(=O)Nc1cc(Oc2c(C)cccc2Cl)nc(-c2cc(C)c(=O)n(C)c2)n1] | Propane-1-sulfonic acid [6-(2-chloro-6-methyl-phenoxy)-2-(1,5-dimethyl-6-oxo-1,6-dihydro-pyridin-3-yl)-pyrimidin-4-yl]-amide |
| 108 | 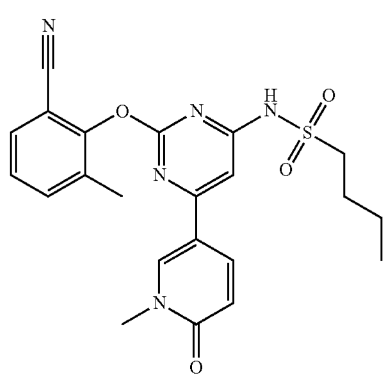 [SMILES: CCCCS(=O)(=O)Nc1cc(-c2ccc(=O)n(C)c2)nc(Oc2c(C)cccc2C#N)n1] | Butane-1-sulfonic acid [2-(2-cyano-6-methyl-phenoxy)-6-(1-methyl-6-oxo-1,6-dihydro-pyridin-3-yl)-pyrimidin-4-yl]-amide |

TABLE 1-continued

| Example | Structure | Name |
|---|---|---|
| 109 | 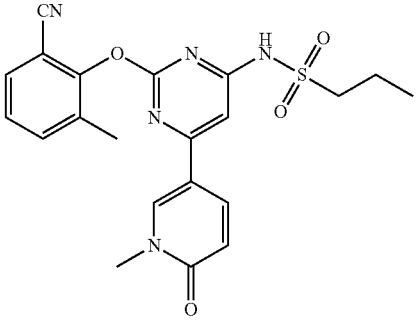 [SMILES: CCCS(=O)(=O)Nc1cc(-c2ccc(=O)n(C)c2)nc(Oc2c(C)cccc2C#N)n1] | Propane-1-sulfonic acid [2-(2-cyano-6-methyl-phenoxy)-6-(1-methyl-6-oxo-1,6-dihydro-pyridin-3-yl)-pyrimidin-4-yl]-amide |
| 110 | 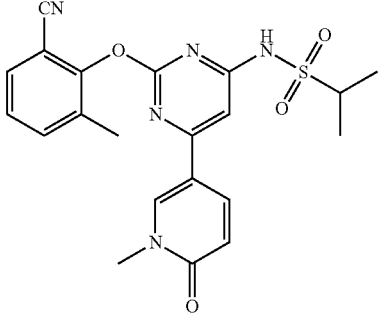 [SMILES: Cc1cccc(C#N)c1Oc1nc(NS(=O)(=O)C(C)C)cc(-c2ccc(=O)n(C)c2)n1] | Propane-2-sulfonic acid [2-(2-cyano-6-methyl-phenoxy)-6-(1-methyl-6-oxo-1,6-dihydro-pyridin-3-yl)-pyrimidin-4-yl]-amide |
| 111 | 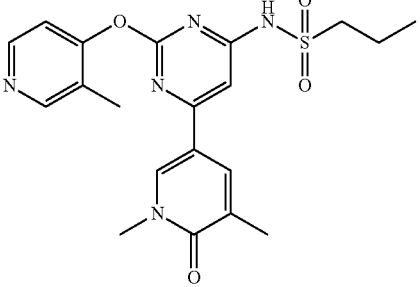 | Propane-1-sulfonic acid [6-(1,5-dimethyl-6-oxo-1,6-dihydro-pyridin-3-yl)-2-(3-methyl-pyridin-4-yloxy)-pyrimidin-4-yl]-amide |
| 112 | 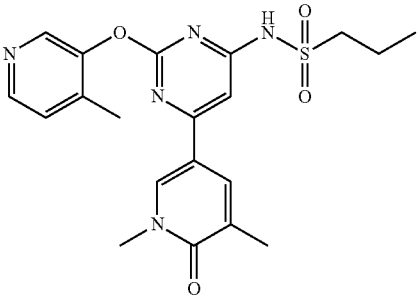 [SMILES: CCCS(=O)(=O)Nc1cc(-c2cc(C)c(=O)n(C)c2)nc(Oc2cnccc2C)n1] | Propane-1-sulfonic acid [6-(1,5-dimethyl-6-oxo-1,6-dihydro-pyridin-3-yl)-2-(4-methyl-pyridin-3-yloxy)-pyrimidin-4-yl]-amide |
| 113 | 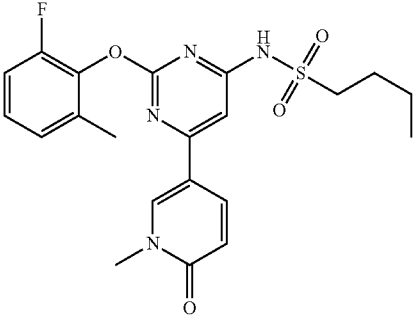 [SMILES: CCCCS(=O)(=O)Nc1cc(-c2ccc(=O)n(C)c2)nc(Oc2c(C)cccc2F)n1] | Butane-1-sulfonic acid [2-(2-fluoro-6-methyl-phenoxy)-6-(1-methyl-6-oxo-1,6-dihydro-pyridin-3-yl)-pyrimidin-4-yl]-amide |

TABLE 1-continued

| Example | Structure | Name |
|---|---|---|
| 114 | 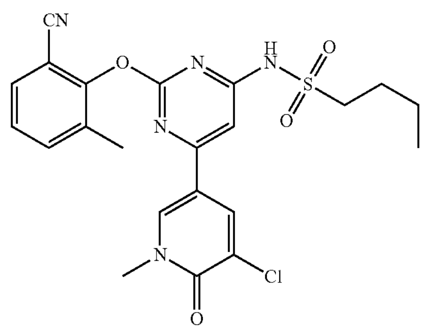 [SMILES: CCCCS(=O)(=O)Nc1cc(-c2cc(Cl)c(=O)n(C)c2)nc(Oc2c(C)cccc2C#N)n1] | Butane-1-sulfonic acid [6-(5-chloro-1-methyl-6-oxo-1,6-dihydro-pyridin-3-yl)-2-(2-cyano-6-methyl-phenoxy)-pyrimidin-4-yl]-amide |
| 115 | 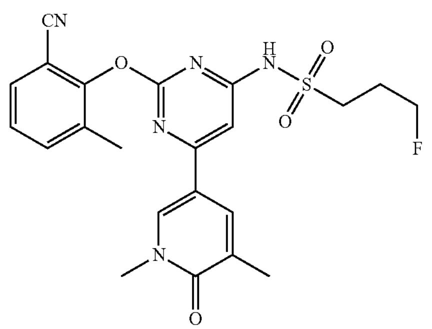 [SMILES: Cc1cccc(C#N)c1Oc1nc(NS(=O)(=O)CCCF)cc(-c2cc(C)c(=O)n(C)c2)n1] | 3-Fluoro-propane-1-sulfonic acid [2-(2-cyano-6-methyl-phenoxy)-6-(1,5-dimethyl-6-oxo-1,6-dihydro-pyridin-3-yl)-pyrimidin-4-yl]-amide |
| 116 | 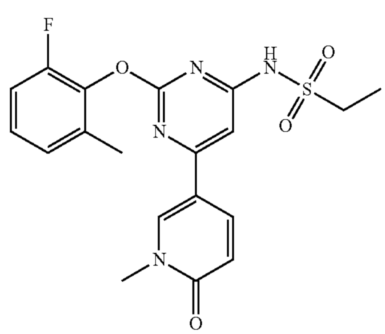 [SMILES: CCS(=O)(=O)Nc1cc(-c2ccc(=O)n(C)c2)nc(Oc2c(C)cccc2F)n1] | Ethanesulfonic acid [2-(2-fluoro-6-methyl-phenoxy)-6-(1-methyl-6-oxo-1,6-dihydro-pyridin-3-yl)-pyrimidin-4-yl]-amide |
| 117 | 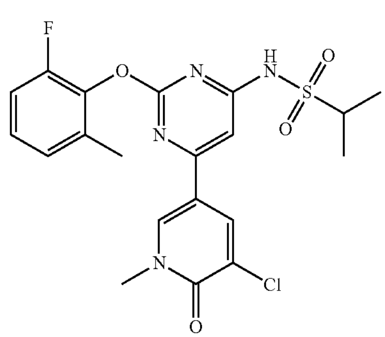 [SMILES: Cc1cccc(F)c1Oc1nc(NS(=O)(=O)C(C)C)cc(-c2cc(Cl)c(=O)n(C)c2)n1] | Propane-2-sulfonic acid [6-(5-chloro-1-methyl-6-oxo-1,6-dihydro-pyridin-3-yl)-2-(2-fluoro-6-methyl-phenoxy)-pyrimidin-4-yl]-amide |

TABLE 1-continued

| Example | Structure | Name |
|---|---|---|
| 118 | 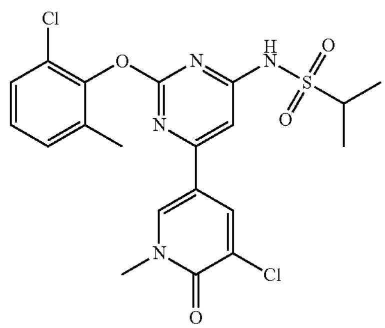 | Propane-2-sulfonic acid [6-(5-chloro-1-methyl-6-oxo-1,6-dihydro-pyridin-3-yl)-2-(2-chloro-6-methyl-phenoxy)-pyrimidin-4-yl]-amide |
| 119 | 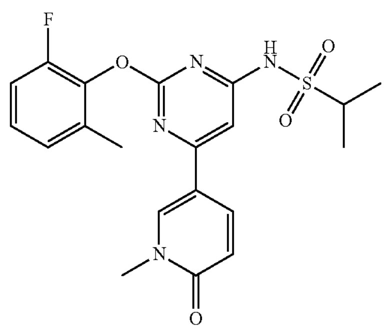 [SMILES: Cc1cccc(F)c1Oc1nc(NS(=O)(=O)C(C)C)cc(-c2ccc(=O)n(C)c2)n1] | Propane-2-sulfonic acid [2-(2-fluoro-6-methyl-phenoxy)-6-(1-methyl-6-oxo-1,6-dihydro-pyridin-3-yl)-pyrimidin-4-yl]-amide |
| 120 | 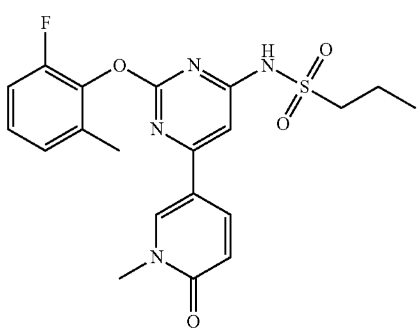 [SMILES: CCCS(=O)(=O)Nc1cc(-c2ccc(=O)n(C)c2)nc(Oc2c(C)cccc2F)n1] | Propane-1-sulfonic acid [2-(2-fluoro-6-methyl-phenoxy)-6-(1-methyl-6-oxo-1,6-dihydro-pyridin-3-yl)-pyrimidin-4-yl]-amide |
| 121 | 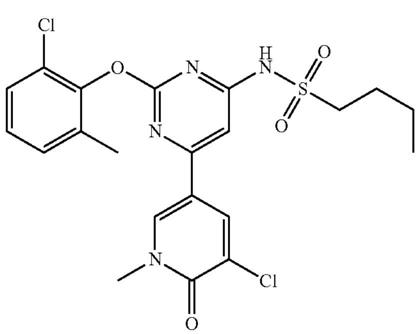 | Butane-1-sulfonic acid [6-(5-chloro-1-methyl-6-oxo-1,6-dihydro-pyridin-3-yl)-2-(2-chloro-6-methyl-phenoxy)-pyrimidin-4-yl]-amide |

TABLE 1-continued

| Example | Structure | Name |
|---|---|---|
| 122 | 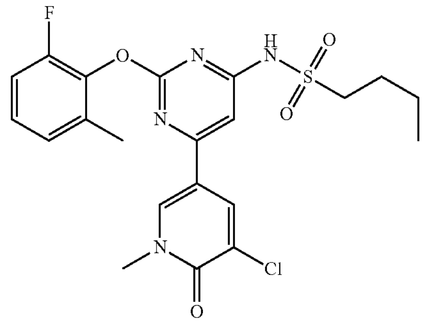 [SMILES: CCCCS(=O)(=O)Nc1cc(-c2cc(Cl)c(=O)n(C)c2)nc(Oc2c(C)cccc2F)n1] | Butane-1-sulfonic acid [6-(5-chloro-1-methyl-6-oxo-1,6-dihydro-pyridin-3-yl)-2-(2-fluoro-6-methyl-phenoxy)-pyrimidin-4-yl]-amide |
| 123 | 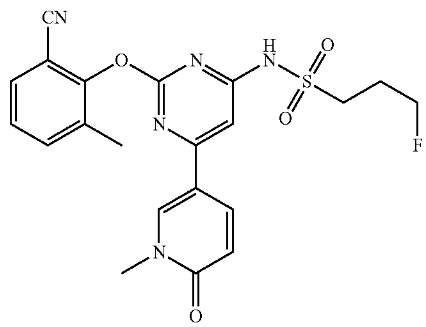 [SMILES: Cc1cccc(C#N)c1Oc1nc(NS(=O)(=O)CCCF)cc(-c2ccc(=O)n(C)c2)n1] | 3-Fluoro-propane-1-sulfonic acid [2-(2-cyano-6-methyl-phenoxy)-6-(1-methyl-6-oxo-1,6-dihydro-pyridin-3-yl)-pyrimidin-4-yl]-amide |
| 124 | 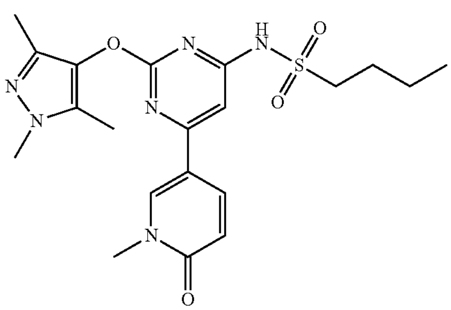 [SMILES: CCCCS(=O)(=O)Nc1cc(-c2ccc(=O)n(C)c2)nc(Oc2c(C)nn(C)c2C)n1] | Butane-1-sulfonic acid [6-(1-methyl-6-oxo-1,6-dihydro-pyridin-3-yl)-2-(1,3,5-trimethyl-1H-pyrazol-4-yloxy)-pyrimidin-4-yl]-amide |
| 125 | 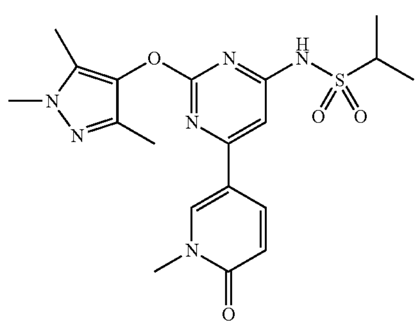 [SMILES: Cc1nn(C)c(C)c1Oc1nc(NS(=O)(=O)C(C)C)cc(-c2ccc(=O)n(C)c2)n1] | Propane-2-sulfonic acid [6-(1-methyl-6-oxo-1,6-dihydro-pyridin-3-yl)-2-(1,3,5-trimethyl-1H-pyrazol-4-yloxy)-pyrimidin-4-yl]-amide |
| 126 | 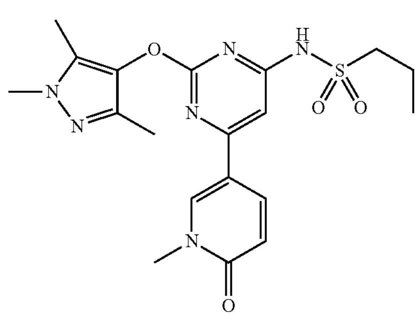 [SMILES: CCCS(=O)(=O)Nc1cc(-c2ccc(=O)n(C)c2)nc(Oc2c(C)nn(C)c2C)n1] | Propane-1-sulfonic acid [6-(1-methyl-6-oxo-1,6-dihydro-pyridin-3-yl)-2-(1,3,5-trimethyl-1H-pyrazol-4-yloxy)-pyrimidin-4-yl]-amide |

TABLE 1-continued

| Example | Structure | Name |
|---|---|---|
| 127 | 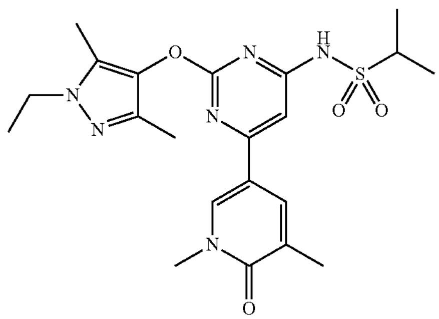 [SMILES: CCn1nc(C)c(Oc2nc(NS(=O)(=O)C(C)C)cc(-c3cc(C)c(=O)n(C)c3)n2)c1C] | Propane-2-sulfonic acid [6-(1,5-dimethyl-6-oxo-1,6-dihydro-pyridin-3-yl)-2-(1-ethyl-3,5-dimethyl-1H-pyrazol-4-yloxy)-pyrimidin-4-yl]-amide |
| 128 | 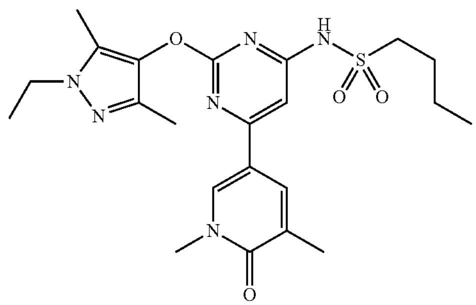 [SMILES: CCCCS(=O)(=O)Nc1cc(-c2cc(C)c(=O)n(C)c2)nc(Oc2c(C)nn(CC)c2C)n1] | Butane-1-sulfonic acid [6-(1,5-dimethyl-6-oxo-1,6-dihydro-pyridin-3-yl)-2-(1-ethyl-3,5-dimethyl-1H-pyrazol-4-yloxy)-pyrimidin-4-yl]-amide |
| 129 | 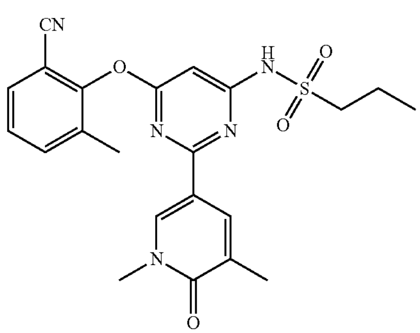 [SMILES: CCCS(=O)(=O)Nc1cc(Oc2c(C)cccc2C#N)nc(-c2cc(C)c(=O)n(C)c2)n1] | Propane-1-sulfonic acid [6-(2-cyano-6-methyl-phenoxy)-2-(1,5-dimethyl-6-oxo-1,6-dihydro-pyridin-3-yl)-pyrimidin-4-yl]-amide |
| 130 | 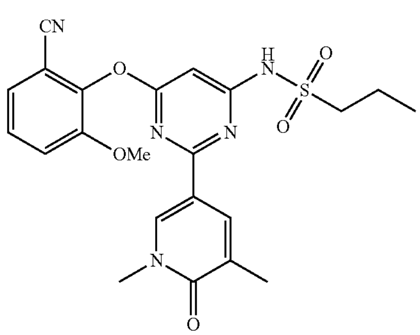 [SMILES: CCCS(=O)(=O)Nc1cc(Oc2c(C#N)cccc2OC)nc(-c2cc(C)c(=O)n(C)c2)n1] | Propane-1-sulfonic acid [6-(2-cyano-6-methoxy-phenoxy)-2-(1,5-dimethyl-6-oxo-1,6-dihydro-pyridin-3-yl)-pyrimidin-4-yl]-amide |

TABLE 1-continued

| Example | Structure | Name |
|---|---|---|
| 131 | 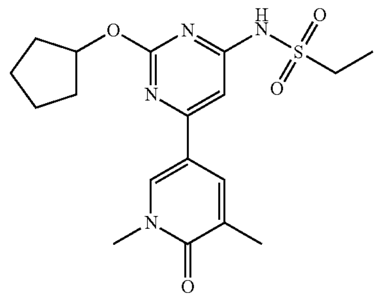 [SMILES: CCS(=O)(=O)Nc1cc(-c2cc(C)c(=O)n(C)c2)nc(OC2CCCC2)n1] | Ethanesulfonic acid [2-cyclopentyloxy-6-(1,5-dimethyl-6-oxo-1,6-dihydro-pyridin-3-yl)-pyrimidin-4-yl]-amide |
| 132 | 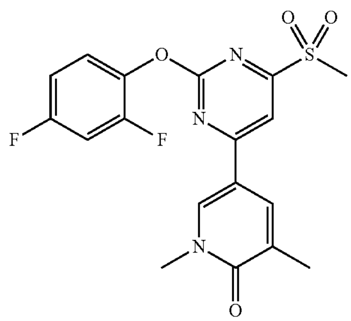 [SMILES: Cc1cc(-c2cc(S(C)(=O)=O)nc(Oc3ccc(F)cc3F)n2)cn(C)c1=O] | 5-[2-(2,4-Difluoro-phenoxy)-6-methanesulfonyl-pyrimidin-4-yl]-1,3-dimethyl-1H-pyridin-2-one |
| 133 | 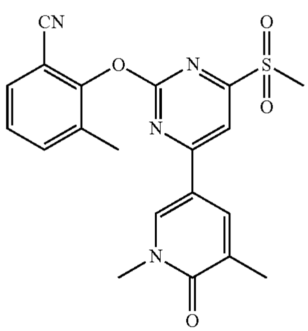 [SMILES: Cc1cccc(C#N)c1Oc1nc(-c2cc(C)c(=O)n(C)c2)cc(S(C)(=O)=O)n1] | 5-[2-(2-Chloro-6-methyl-phenoxy)-6-methanesulfonyl-pyrimidin-4-yl]-1,3-dimethyl-1H-pyridin-2-one |
| 134 | 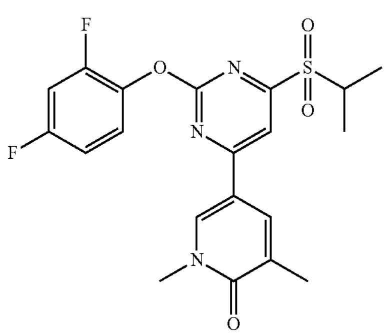 [SMILES: Cc1cc(-c2cc(S(=O)(=O)C(C)C)nc(Oc3ccc(F)cc3F)n2)cn(C)c1=O] | 5-[2-(2,4-Difluoro-phenoxy)-6-(propane-2-sulfonyl)-pyrimidin-4-yl]-1,3-dimethyl-1H-pyridin-2-one |

| Example | Structure | Name |
|---|---|---|
| 135 | 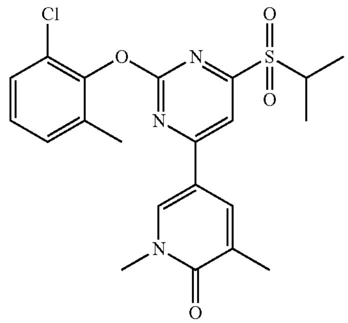 [SMILES: Cc1cccc(Cl)c1Oc1nc(-c2cc(C)c(=O)n(C)c2)cc(S(=O)(=O)C(C)C)n1] | 5-[2-(2-Chloro-6-methyl-phenoxy)-6-(propane-2-sulfonyl)-pyrimidin-4-yl]-1,3-dimethyl-1H-pyridin-2-one |
| 136 | 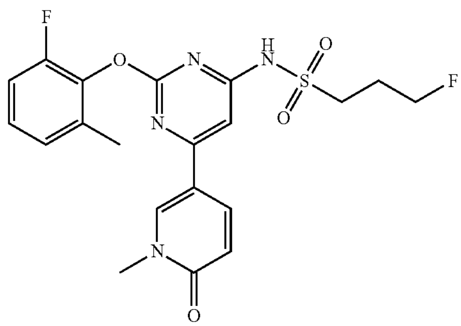 [SMILES: Cc1cccc(F)c1Oc1nc(NS(=O)(=O)CCCF)cc(-c2ccc(=O)n(C)c2)n1] | 3-Fluoro-propane-1-sulfonic acid [2-(2-fluoro-6-methyl-phenoxy)-6-(1-methyl-6-oxo-1,6-dihydro-pyridin-3-yl)-pyrimidin-4-yl]-amide |
| 137 | 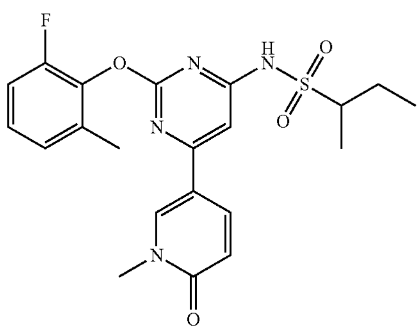 [SMILES: CCC(C)S(=O)(=O)Nc1cc(-c2ccc(=O)n(C)c2)nc(Oc2c(C)cccc2F)n1] | Butane-2-sulfonic acid [2-(2-fluoro-6-methyl-phenoxy)-6-(1-methyl-6-oxo-1,6-dihydro-pyridin-3-yl)-pyrimidin-4-yl]-amide |
| 138 | 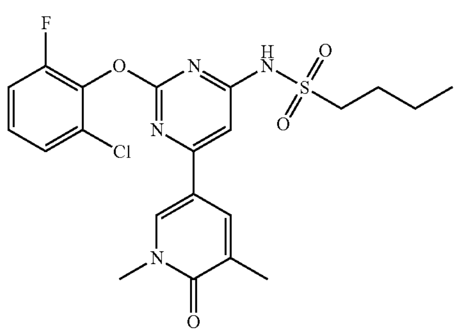 | Butane-1-sulfonic acid [2-(2-chloro-6-fluoro-phenoxy)-6-(1,5-dimethyl-6-oxo-1,6-dihydro-pyridin-3-yl)-pyrimidin-4-yl]-amide |

TABLE 1-continued

| Example | Structure | Name |
|---|---|---|
| 139 | 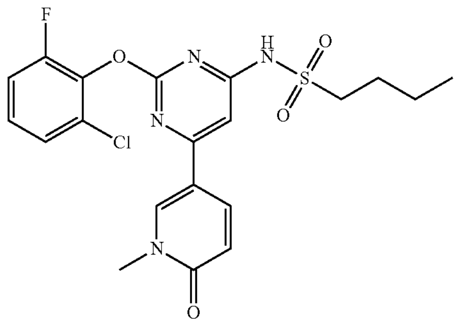 [SMILES: CCCCS(=O)(=O)Nc1cc(-c2ccc(=O)n(C)c2)nc(Oc2c(F)cccc2Cl)n1] | Butane-1-sulfonic acid [2-(2-chloro-6-fluoro-phenoxy)-6-(1-methyl-6-oxo-1,6-dihydro-pyridin-3-yl)-pyrimidin-4-yl]-amide |
| 140 | 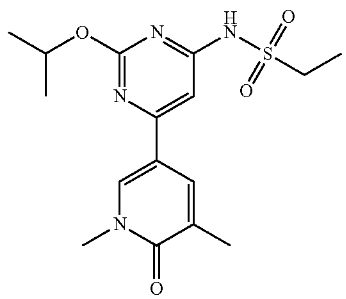 [SMILES: CCS(=O)(=O)Nc1cc(-c2cc(C)c(=O)n(C)c2)nc(OC(C)C)n1] | Ethanesulfonic acid [6-(1,5-dimethyl-6-oxo-1,6-dihydro-pyridin-3-yl)-2-isopropoxy-pyrimidin-4-yl]-amide |
| 141 | 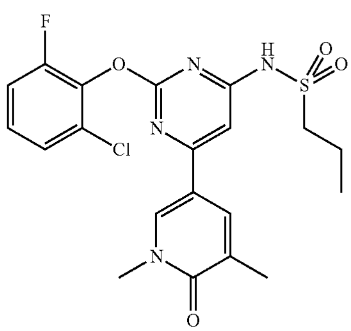 [SMILES: CCCS(=O)(=O)Nc1cc(-c2cc(C)c(=O)n(C)c2)nc(Oc2c(F)cccc2Cl)n1] | Propane-1-sulfonic acid [2-(2-chloro-6-fluoro-phenoxy)-6-(1,5-dimethyl-6-oxo-1,6-dihydro-pyridin-3-yl)-pyrimidin-4-yl]-amide |
| 142 | 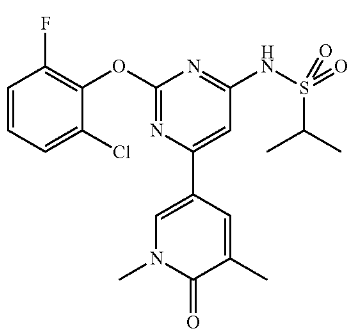 [SMILES: Cc1cc(-c2cc(NS(=O)(=O)C(C)C)nc(Oc3c(F)cccc3Cl)n2)cn(C)c1=O] | Propane-2-sulfonic acid [2-(2-chloro-6-fluoro-phenoxy)-6-(1,5-dimethyl-6-oxo-1,6-dihydro-pyridin-3-yl)-pyrimidin-4-yl]-amide |

TABLE 1-continued

| Example | Structure | Name |
|---|---|---|
| 143 | 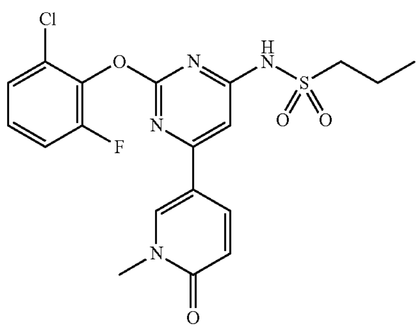 [SMILES: CCCS(=O)(=O)Nc1cc(-c2ccc(=O)n(C)c2)nc(Oc2c(F)cccc2Cl)n1] | Propane-1-sulfonic acid [2-(2-chloro-6-fluoro-phenoxy)-6-(1-methyl-6-oxo-1,6-dihydro-pyridin-3-yl)-pyrimidin-4-yl]-amide |
| 144 | 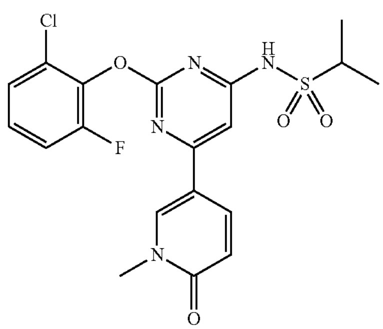 [SMILES: CC(C)S(=O)(=O)Nc1cc(-c2ccc(=O)n(C)c2)nc(Oc2c(F)cccc2Cl)n1] | Propane-2-sulfonic acid [2-(2-chloro-6-fluoro-phenoxy)-6-(1-methyl-6-oxo-1,6-dihydro-pyridin-3-yl)-pyrimidin-4-yl]-amide |
| 145 | 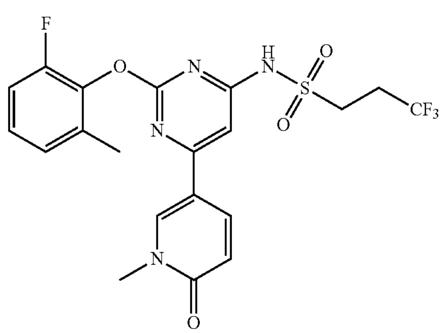 [SMILES: Cc1cccc(F)c1Oc1nc(NS(=O)(=O)CCC(F)(F)F)cc(-c2ccc(=O)n(C)c2)n1] | 3,3,3-Trifluoro-propane-1-sulfonic acid [2-(2-fluoro-6-methyl-phenoxy)-6-(1-methyl-6-oxo-1,6-dihydro-pyridin-3-yl)-pyrimidin-4-yl]-amide |
| 146 | 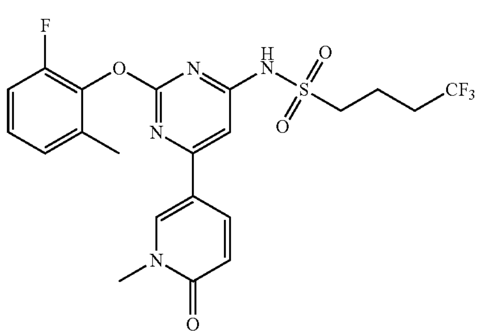 [SMILES: Cc1cccc(F)c1Oc1nc(NS(=O)(=O)CCCC(F)(F)F)cc(-c2ccc(=O)n(C)c2)n1] | 4,4,4-Trifluoro-butane-1-sulfonic acid [2-(2-fluoro-6-methyl-phenoxy)-6-(1-methyl-6-oxo-1,6-dihydro-pyridin-3-yl)-pyrimidin-4-yl]-amide |

TABLE 1-continued

| Example | Structure | Name |
|---|---|---|
| 147 | 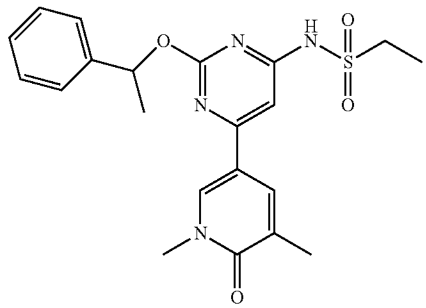 [SMILES: CCS(=O)(=O)Nc1cc(-c2cc(C)c(=O)n(C)c2)nc(OC(C)c2ccccc2)n1] | Ethanesulfonic acid [6-(1,5-dimethyl-6-oxo-1,6-dihydro-pyridin-3-yl)-2-(1-phenyl-ethoxy)-pyrimidin-4-yl]-amide |
| 148 | 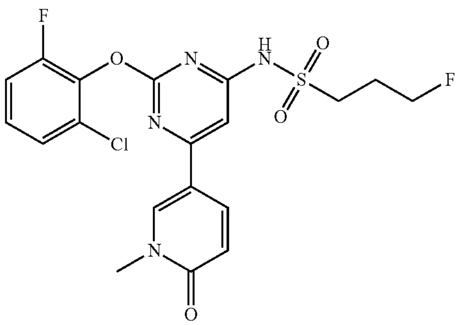 [SMILES: Cn1cc(-c2cc(NS(=O)(=O)CCCF)nc(Oc3c(F)cccc3Cl)n2)ccc1=O] | N-(2-(2-chloro-6-fluorophenoxy)-6-(1-methyl-6-oxo-1,6-dihydropyridin-3-yl)pyrimidin-4-yl)-3-fluoropropane-1-sulfonamide |
| 149 | 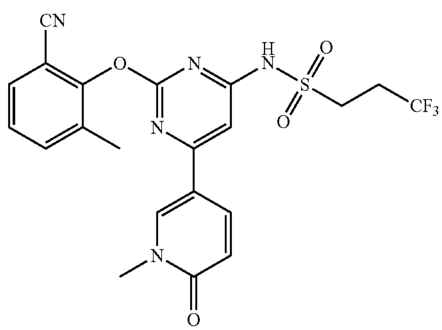 [SMILES: Cc1cccc(C#N)c1Oc1nc(NS(=O)(=O)CCC(F)(F)F)cc(-c2ccc(=O)n(C)c2)n1] | N-(2-(2-cyano-6-methylphenoxy)-6-(1-methyl-6-oxo-1,6-dihydropyridin-3-yl)pyrimidin-4-yl)-3,3,3-trifluoropropane-1-sulfonamide |
| 150 | 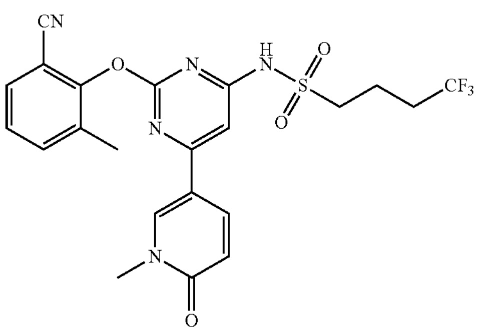 [SMILES: Cc1cccc(C#N)c1Oc1nc(NS(=O)(=O)CCCC(F)(F)F)cc(-c2ccc(=O)n(C)c2)n1] | N-(2-(2-cyano-6-methylphenoxy)-6-(1-methyl-6-oxo-1,6-dihydropyridin-3-yl)pyrimidin-4-yl)-4,4,4-trifluorobutane-1-sulfonamide |
| 151 | 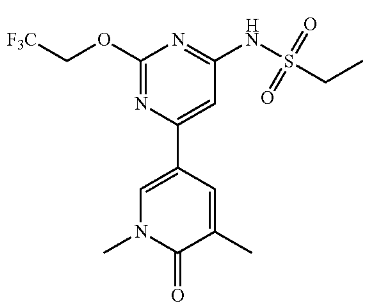 | N-(6-(1,5-dimethyl-6-oxo-1,6-dihydropyridin-3-yl)-2-(2,2,2-trifluoroethoxy)pyrimidin-4-yl)ethanesulfonamide |

TABLE 1-continued

| Example | Structure | Name |
|---|---|---|
| 152 | 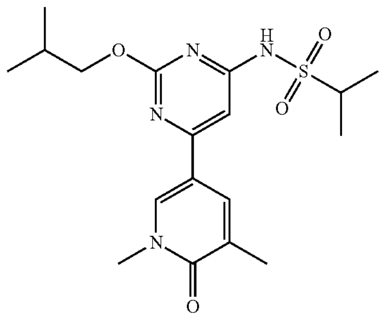 [SMILES: Cc1cc(-c2cc(NS(=O)(=O)C(C)C)nc(OCC(C)C)n2)cn(C)c1=O] | N-(6-(1,5-dimethyl-6-oxo-1,6-dihydropyridin-3-yl)-2-isobutoxypyrimidin-4-yl)propane-2-sulfonamide |
| 153 | 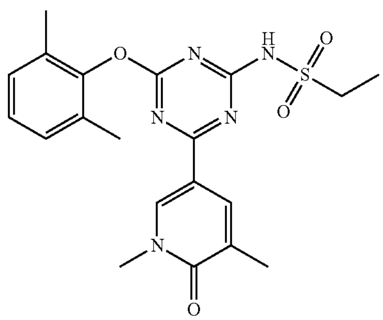 [SMILES: CCS(=O)(=O)Nc1nc(Oc2c(C)cccc2C)nc(-c2cc(C)c(=O)n(C)c2)n1] | Ethanesulfonic acid [4-(1,5-dimethyl-6-oxo-1,6-dihydro-pyridin-3-yl)-6-(2,6-dimethyl-phenoxy)-[1,3,5]triazin-2-yl]-amide |
| 154 | 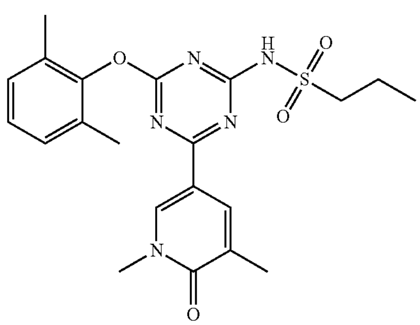 [SMILES: CCCS(=O)(=O)Nc1nc(Oc2c(C)cccc2C)nc(-c2cc(C)c(=O)n(C)c2)n1] | Propane-1-sulfonic acid [4-(1,5-dimethyl-6-oxo-1,6-dihydro-pyridin-3-yl)-6-(2,6-dimethyl-phenoxy)-[1,3,5]triazin-2-yl]-amide |
| 155 | 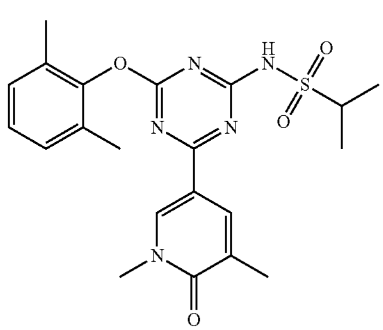 [SMILES: Cc1cccc(C)c1Oc1nc(NS(=O)(=O)C(C)C)nc(-c2cc(C)c(=O)n(C)c2)n1] | Propane-2-sulfonic acid [4-(1,5-dimethyl-6-oxo-1,6-dihydro-pyridin-3-yl)-6-(2,6-dimethyl-phenoxy)-[1,3,5]triazin-2-yl]-amide |

TABLE 1-continued

| Example | Structure | Name |
|---|---|---|
| 156 | 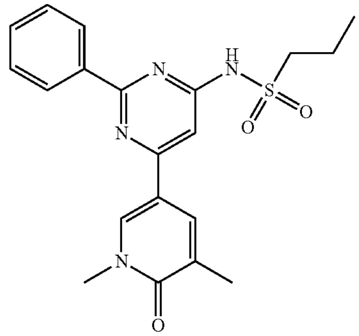 [SMILES: CCCS(=O)(=O)Nc1cc(-c2cc(C)c(=O)n(C)c2)nc(-c2ccccc2)n1] | N-(6-(1,5-dimethyl-6-oxo-1,6-dihydropyridin-3-yl)-2-phenylpyrimidin-4-yl)propane-1-sulfonamide |
| 157 | 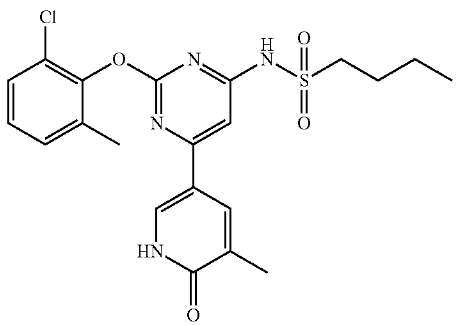 [SMILES: CCCCS(=O)(=O)Nc1cc(-c2c[nH]c(=O)c(C)c2)nc(Oc2c(C)cccc2Cl)n1] | Butane-1-sulfonic acid [2-(2-chloro-6-methyl-phenoxy)-6-(5-methyl-6-oxo-1,6-dihydro-pyridin-3-yl)-pyrimidin-4-yl]-amide |
| 158 | 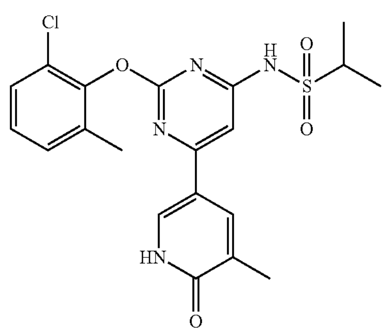 [SMILES: Cc1cccc(Cl)c1Oc1nc(NS(=O)(=O)C(C)C)cc(-c2c[nH]c(=O)c(C)c2)n1] | Propane-2-sulfonic acid [2-(2-chloro-6-methyl-phenoxy)-6-(5-methyl-6-oxo-1,6-dihydro-pyridin-3-yl)-pyrimidin-4-yl]-amide |
| 159 | 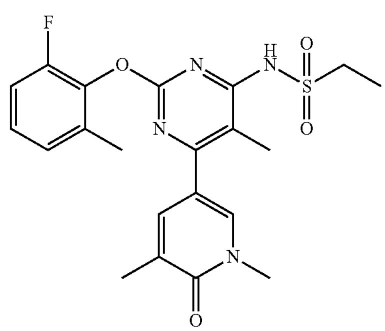 [SMILES: CCS(=O)(=O)Nc1nc(Oc2c(C)cccc2F)nc(-c2cc(C)c(=O)n(C)c2)c1C] | Ethane-2-sulfonic acid [6-(1,5-dimethyl-6-oxo-1,6-dihydro-pyridin-3-yl)-2-(2-fluoro-6-methyl-phenoxy)-5-methyl-pyrimidin-4-yl]-amide |

TABLE 1-continued

| Example | Structure | Name |
|---|---|---|
| 160 | 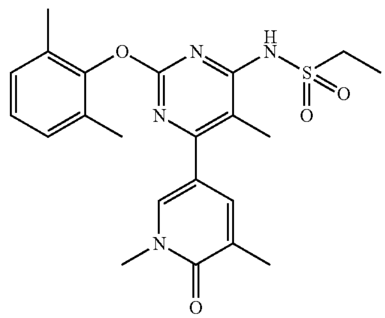 [SMILES: CCS(=O)(=O)Nc1nc(Oc2c(C)cccc2C)nc(-c2cc(C)c(=O)n(C)c2)c1C] | Ethanesulfonic acid [6-(1,5-dimethyl-6-oxo-1,6-dihydro-pyridin-3-yl)-2-(2,6-dimethyl-phenoxy)-5-methyl-pyrimidin-4-yl]-amide |
| 161 | 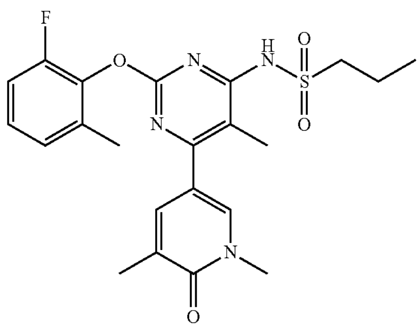 [SMILES: CCCS(=O)(=O)Nc1nc(Oc2c(C)cccc2F)nc(-c2cc(C)c(=O)n(C)c2)c1C] | Propane-1-sulfonic acid [6-(1,5-dimethyl-6-oxo-1,6-dihydro-pyridin-3-yl)-2-(2-fluoro-6-methyl-phenoxy)-5-methyl-pyrimidin-4-yl]-amide |
| 162 | 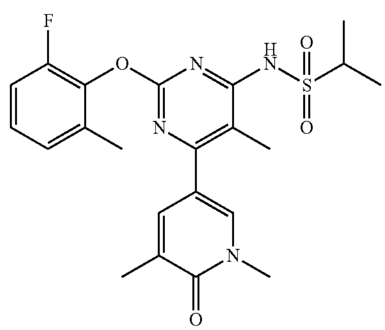 [SMILES: Cc1cccc(F)c1Oc1nc(NS(=O)(=O)C(C)C)c(C)c(-c2cc(C)c(=O)n(C)c2)n1] | Propane-2-sulfonic acid [6-(1,5-dimethyl-6-oxo-1,6-dihydro-pyridin-3-yl)-2-(2-fluoro-6-methyl-phenoxy)-5-methyl-pyrimidin-4-yl]-amide |
| 163 | 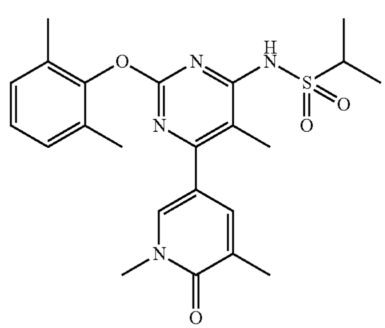 [SMILES: Cc1cccc(C)c1Oc1nc(NS(=O)(=O)C(C)C)c(C)c(-c2cc(C)c(=O)n(C)c2)n1] | Propane-2-sulfonic acid [6-(1,5-dimethyl-6-oxo-1,6-dihydro-pyridin-3-yl)-2-(2,6-dimethyl-phenoxy)-5-methyl-pyrimidin-4-yl]-amide |

TABLE 1-continued

| Example | Structure | Name |
|---|---|---|
| 164 | 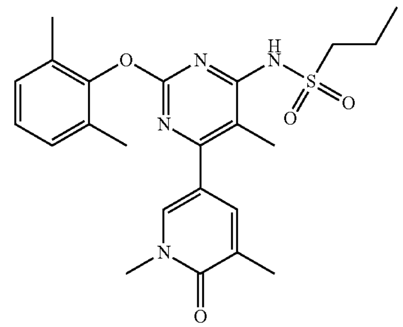 [SMILES: CCCS(=O)(=O)Nc1nc(Oc2c(C)cccc2C)nc(-c2cc(C)c(=O)n(C)c2)c1C] | Propane-1-sulfonic acid [6-(1,5-dimethyl-6-oxo-1,6-dihydro-pyridin-3-yl)-2-(2,6-dimethyl-phenoxy)-5-methyl-pyrimidin-4-yl]-amide |
| 165 | 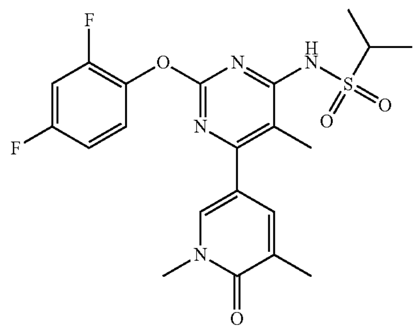 [SMILES: Cc1c(NS(=O)(=O)C(C)C)nc(Oc2ccc(F)cc2F)nc1-c1cc(C)c(=O)n(C)c1] | Propane-2-sulfonic acid [2-(2,4-difluoro-phenoxy)-6-(1,5-dimethyl-6-oxo-1,6-dihydro-pyridin-3-yl)-5-methyl-pyrimidin-4-yl]-amide |
| 166 | 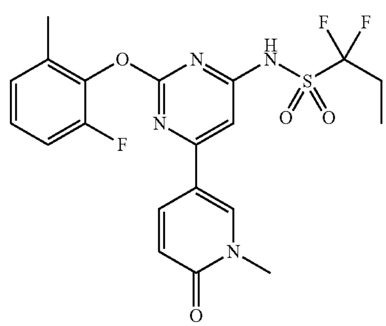 [SMILES: CCC(F)(F)S(=O)(=O)Nc1cc(-c2ccc(=O)n(C)c2)nc(Oc2c(C)cccc2F)n1] | 1,1-Difluoro-propane-1-sulfonic acid [2-(2-fluoro-6-methyl-phenoxy)-6-(1-methyl-6-oxo-1,6-dihydro-pyridin-3-yl)-pyrimidin-4-yl]-amide |
| 167 | 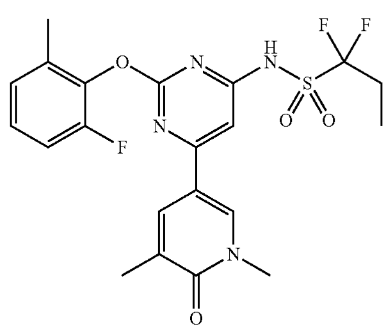 [SMILES: CCC(F)(F)S(=O)(=O)Nc1cc(-c2cc(C)c(=O)n(C)c2)nc(Oc2c(C)cccc2F)n1] | 1,1-Difluoro-propane-1-sulfonic acid [6-(1,5-dimethyl-6-oxo-1,6-dihydro-pyridin-3-yl)-2-(2-fluoro-6-methyl-phenoxy)-pyrimidin-4-yl]-amide |

TABLE 1-continued

| Example | Structure | Name |
|---|---|---|
| 168 | 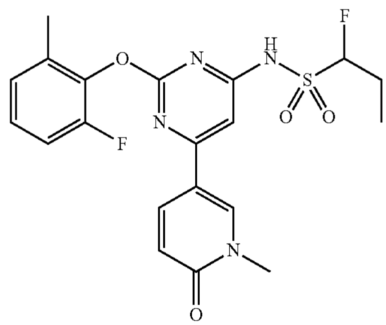 [SMILES: CCC(F)S(=O)(=O)Nc1cc(-c2ccc(=O)n(C)c2)nc(Oc2c(C)cccc2F)n1] | 1-Fluoro-propane-1-sulfonic acid [2-(2-fluoro-6-methyl-phenoxy)-6-(1-methyl-6-oxo-1,6-dihydro-pyridin-3-yl)-pyrimidin-4-yl]-amide |
| 169 | 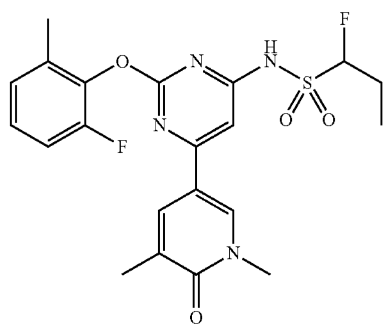 [SMILES: CCC(F)S(=O)(=O)Nc1cc(-c2cc(C)c(=O)n(C)c2)nc(Oc2c(C)cccc2F)n1] | 1-Fluoro-propane-1-sulfonic acid [6-(1,5-dimethyl-6-oxo-1,6-dihydro-pyridin-3-yl)-2-(2-fluoro-6-methyl-phenoxy)-pyrimidin-4-yl]-amide |
| 170 | 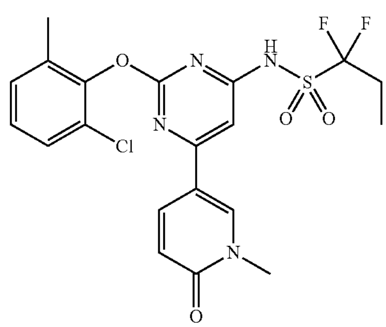 [SMILES: CCC(F)(F)S(=O)(=O)Nc1cc(-c2ccc(=O)n(C)c2)nc(Oc2c(C)cccc2Cl)n1] | 1,1-Difluoro-propane-1-sulfonic acid [2-(2-chloro-6-methyl-phenoxy)-6-(1-methyl-6-oxo-1,6-dihydro-pyridin-3-yl)-pyrimidin-4-yl]-amide |
| 171 | 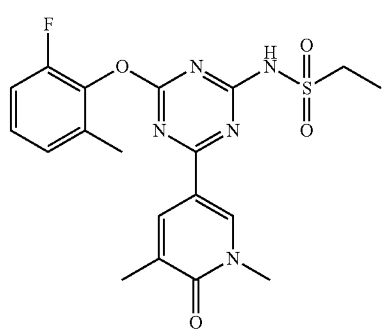 [SMILES: CCS(=O)(=O)Nc1nc(Oc2c(C)cccc2F)nc(-c2cc(C)c(=O)n(C)c2)n1] | Ethanesulfonic acid [4-(1,5-dimethyl-6-oxo-1,6-dihydro-pyridin-3-yl)-6-(2-fluoro-6-methyl-phenoxy)-[1,3,5]triazin-2-yl]-amide |

TABLE 1-continued

| Example | Structure | Name |
|---|---|---|
| 172 | 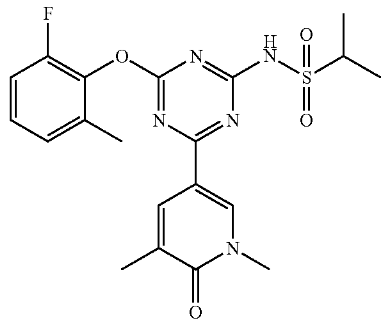 [SMILES: Cc1cccc(F)c1Oc1nc(NS(=O)(=O)C(C)C)nc(-c2cc(C)c(=O)n(C)c2)n1] | Propane-2-sulfonic acid [4-(1,5-dimethyl-6-oxo-1,6-dihydro-pyridin-3-yl)-6-(2-fluoro-6-methyl-phenoxy)-[1,3,5]triazin-2-yl]-amide |
| 173 | 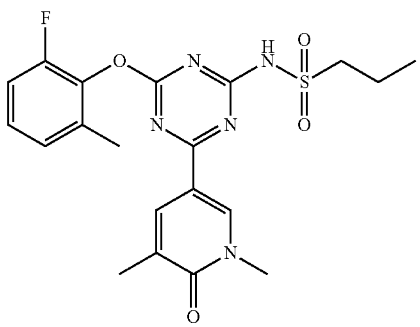 [SMILES: CCCS(=O)(=O)Nc1nc(Oc2c(C)cccc2F)nc(-c2cc(C)c(=O)n(C)c2)n1] | Propane-1-sulfonic acid [4-(1,5-dimethyl-6-oxo-1,6-dihydro-pyridin-3-yl)-6-(2-fluoro-6-methyl-phenoxy)-[1,3,5]triazin-2-yl]-amide |
| 174 | 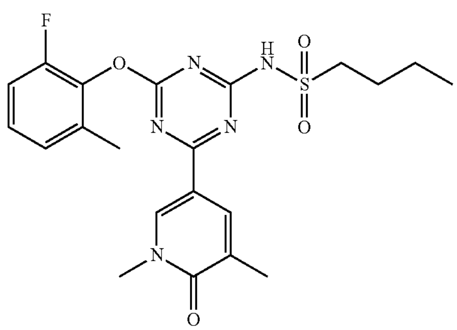 [SMILES: CCCCS(=O)(=O)Nc1nc(Oc2c(C)cccc2F)nc(-c2cc(C)c(=O)n(C)c2)n1] | Butane-1-sulfonic acid [4-(1,5-dimethyl-6-oxo-1,6-dihydro-pyridin-3-yl)-6-(2-fluoro-6-methyl-phenoxy)-[1,3,5]triazin-2-yl]-amide |
| 175 | 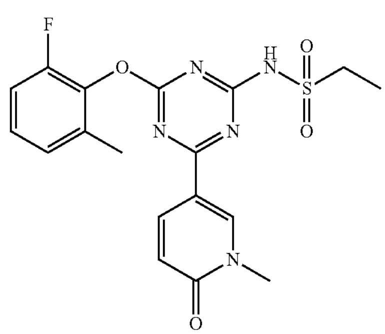 [SMILES: CCS(=O)(=O)Nc1nc(Oc2c(C)cccc2F)nc(-c2ccc(=O)n(C)c2)n1] | Ethanesulfonic acid [4-(2-fluoro-6-methyl-phenoxy)-6-(1-methyl-6-oxo-1,6-dihydro-pyridin-3-yl)-[1,3,5]triazin-2-yl]-amide |

TABLE 1-continued

| Example | Structure | Name |
|---|---|---|
| 176 | 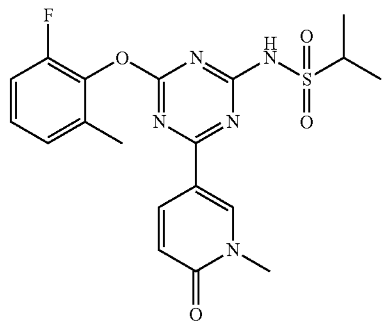 [SMILES: Cc1cccc(F)c1Oc1nc(NS(=O)(=O)C(C)C)nc(-c2ccc(=O)n(C)c2)n1] | Propane-2-sulfonic acid [4-(2-fluoro-6-methyl-phenoxy)-6-(1-methyl-6-oxo-1,6-dihydro-pyridin-3-yl)-[1,3,5]triazin-2-yl]-amide |
| 177 | 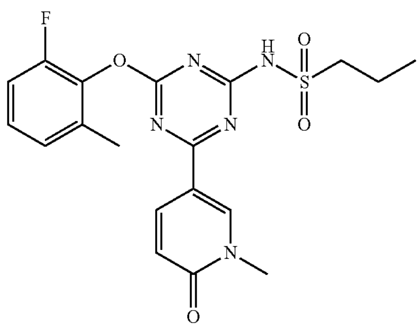 [SMILES: CCCS(=O)(=O)Nc1nc(Oc2c(C)cccc2F)nc(-c2ccc(=O)n(C)c2)n1] | Propane-1-sulfonic acid [4-(2-fluoro-6-methyl-phenoxy)-6-(1-methyl-6-oxo-1,6-dihydro-pyridin-3-yl)-[1,3,5]triazin-2-yl]-amide |
| 178 | 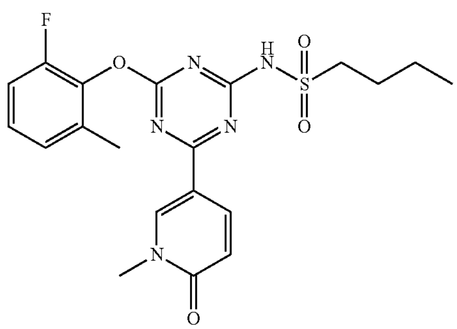 [SMILES: CCCCS(=O)(=O)Nc1nc(Oc2c(C)cccc2F)nc(-c2ccc(=O)n(C)c2)n1] | Butane-1-sulfonic acid [4-(2-fluoro-6-methyl-phenoxy)-6-(1-methyl-6-oxo-1,6-dihydro-pyridin-3-yl)-[1,3,5]triazin-2-yl]-amide |
| 179 | 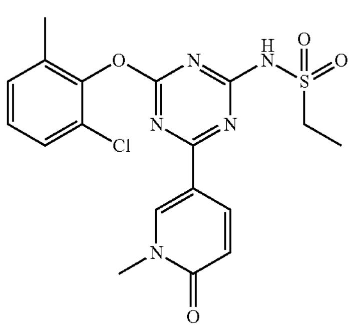 [SMILES: CCS(=O)(=O)Nc1nc(Oc2c(C)cccc2Cl)nc(-c2ccc(=O)n(C)c2)n1] | Ethanesulfonic acid [4-(2-chloro-6-methyl-phenoxy)-6-(1-methyl-6-oxo-1,6-dihydro-pyridin-3-yl)-[1,3,5]triazin-2-yl]-amide |

TABLE 1-continued

| Example | Structure | Name |
|---|---|---|
| 180 | 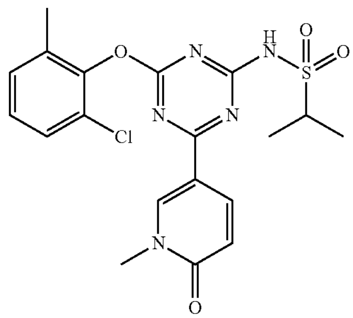 [SMILES: Cc1cccc(Cl)c1Oc1nc(NS(=O)(=O)C(C)C)nc(-c2ccc(=O)n(C)c2)n1] | Propane-2-sulfonic acid [4-(2-chloro-6-methyl-phenoxy)-6-(1-methyl-6-oxo-1,6-dihydro-pyridin-3-yl)-[1,3,5]triazin-2-yl]-amide |
| 181 | 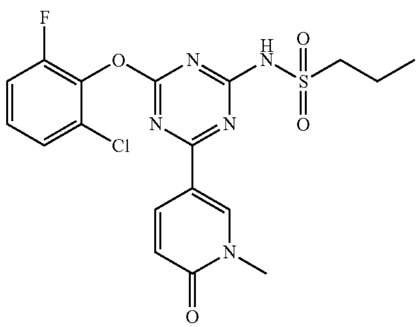 | Propane-1-sulfonic acid [4-(2-chloro-6-fluoro-phenoxy)-6-(1-methyl-6-oxo-1,6-dihydro-pyridin-3-yl)-[1,3,5]triazin-2-yl]-amide |
| 182 | 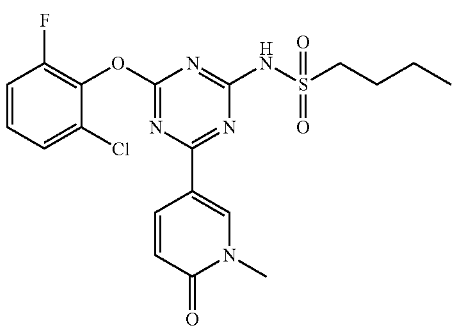 [SMILES: CCCCS(=O)(=O)Nc1nc(Oc2c(F)cccc2Cl)nc(-c2ccc(=O)n(C)c2)n1] | Butane-1-sulfonic acid [4-(2-chloro-6-fluoro-phenoxy)-6-(1-methyl-6-oxo-1,6-dihydro-pyridin-3-yl)-[1,3,5]triazin-2-yl]-amide |
| 183 | 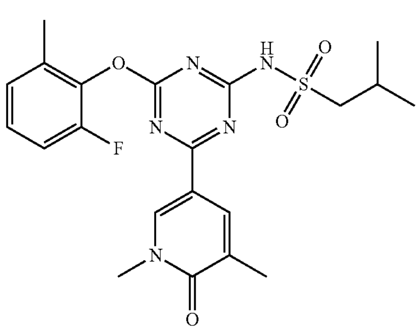 [SMILES: Cc1cccc(F)c1Oc1nc(NS(=O)(=O)CC(C)C)nc(-c2cc(C)c(=O)n(C)c2)n1] | 2-Methyl-propane-1-sulfonic acid [4-(1,5-dimethyl-6-oxo-1,6-dihydro-pyridin-3-yl)-6-(2-fluoro-6-methyl-phenoxy)-[1,3,5]triazin-2-yl]-amide |

TABLE 1-continued

| Example | Structure | Name |
|---|---|---|
| 184 | 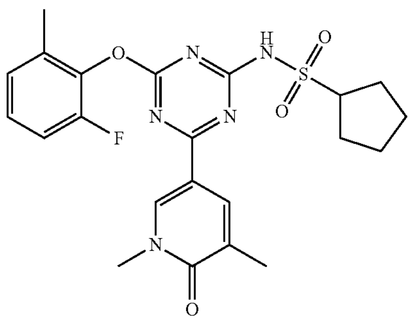 [SMILES: Cc1cccc(F)c1Oc1nc(NS(=O)(=O)C2CCCC2)nc(-c2cc(C)c(=O)n(C)c2)n1] | Cyclopentanesulfonic acid [4-(1,5-dimethyl-6-oxo-1,6-dihydro-pyridin-3-yl)-6-(2-fluoro-6-methyl-phenoxy)-[1,3,5]triazin-2-yl]-amide |
| 185 | 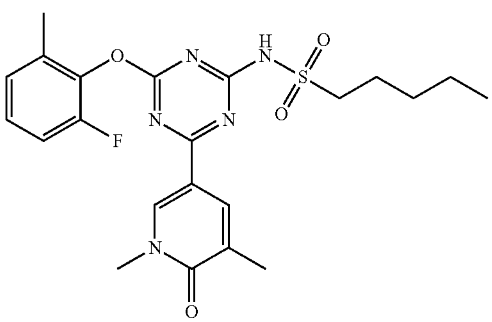 | Pentane-1-sulfonic acid [4-(1,5-dimethyl-6-oxo-1,6-dihydro-pyridin-3-yl)-6-(2-fluoro-6-methyl-phenoxy)-[1,3,5]triazin-2-yl]-amide |
| 186 | 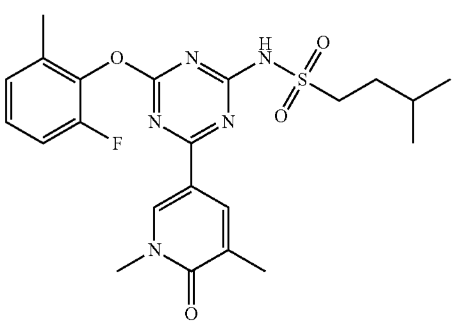 [SMILES: Cc1cccc(F)c1Oc1nc(NS(=O)(=O)CCC(C)C)nc(-c2cc(C)c(=O)n(C)c2)n1] | 3-Methyl-butane-1-sulfonic acid [4-(1,5-dimethyl-6-oxo-1,6-dihydro-pyridin-3-yl)-6-(2-fluoro-6-methyl-phenoxy)-[1,3,5]triazin-2-yl]-amide |
| 187 | 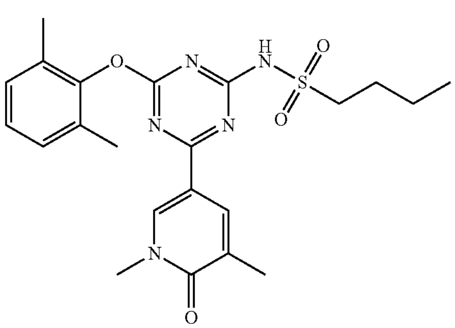 [SMILES: CCCCS(=O)(=O)Nc1nc(Oc2c(C)cccc2C)nc(-c2cc(C)c(=O)n(C)c2)n1] | Butane-1-sulfonic acid [4-(1,5-dimethyl-6-oxo-1,6-dihydro-pyridin-3-yl)-6-(2,6-dimethyl-phenoxy)-[1,3,5]triazin-2-yl]-amide |

TABLE 1-continued

| Example | Structure | Name |
|---|---|---|
| 188 | 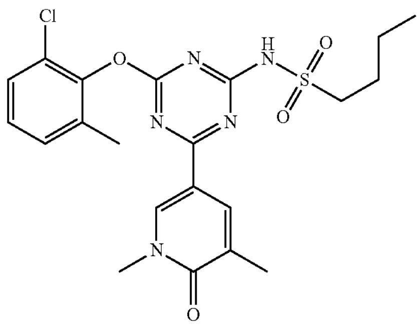 | Butane-1-sulfonic acid [4-(2-chloro-6-methyl-phenoxy)-6-(1,5-dimethyl-6-oxo-1,6-dihydro-pyridin-3-yl)-[1,3,5]triazin-2-yl]-amide |
| 189 | 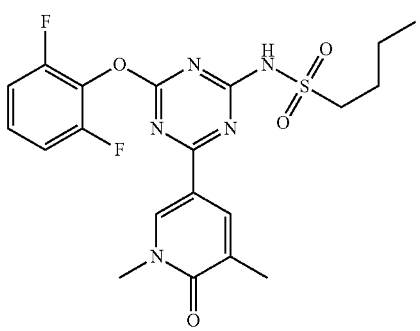 [SMILES: CCCCS(=O)(=O)Nc1nc(Oc2c(F)cccc2F)nc(-c2cc(C)c(=O)n(C)c2)n1] | Butane-1-sulfonic acid [4-(2,6-difluoro-phenoxy)-6-(1,5-dimethyl-6-oxo-1,6-dihydro-pyridin-3-yl)-[1,3,5]triazin-2-yl]-amide |
| 190 | 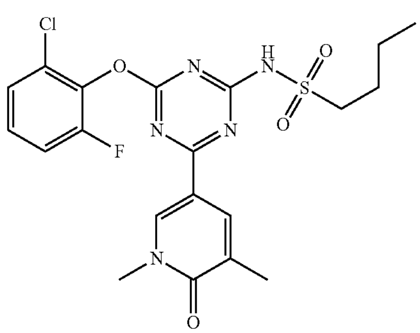 [SMILES: CCCCS(=O)(=O)Nc1nc(Oc2c(F)cccc2Cl)nc(-c2cc(C)c(=O)n(C)c2)n1] | Butane-1-sulfonic acid [4-(2-chloro-6-fluoro-phenoxy)-6-(1,5-dimethyl-6-oxo-1,6-dihydro-pyridin-3-yl)-[1,3,5]triazin-2-yl]-amide |
| 191 | 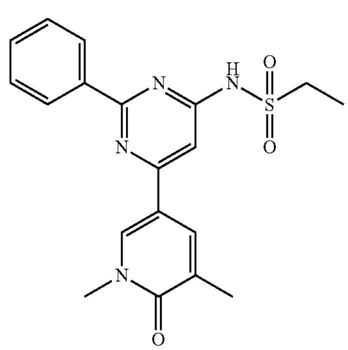 [SMILES: CCS(=O)(=O)Nc1cc(-c2cc(C)c(=O)n(C)c2)nc(-c2ccccc2)n1] | Ethanesulfonic acid [6-(1,5-dimethyl-6-oxo-1,6-dihydro-pyridin-3-yl)-2-phenyl-pyrimidin-4-yl]-amide |

TABLE 1-continued

| Example | Structure | Name |
|---|---|---|
| 192 | 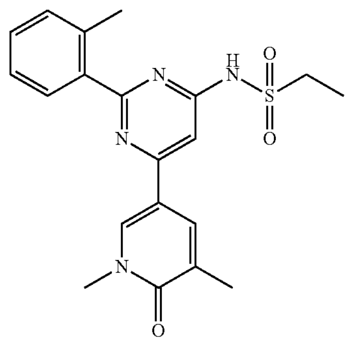 [SMILES: CCS(=O)(=O)Nc1cc(-c2cc(C)c(=O)n(C)c2)nc(-c2ccccc2C)n1] | Ethanesulfonic acid [6-(1,5-dimethyl-6-oxo-1,6-dihydro-pyridin-3-yl)-2-o-tolyl-pyrimidin-4-yl]-amide |
| 193 | 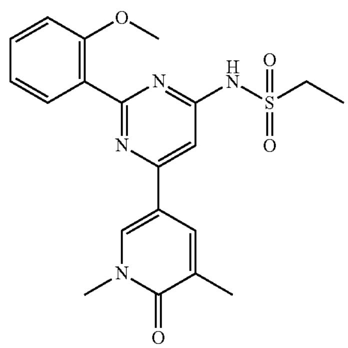 [SMILES: CCS(=O)(=O)Nc1cc(-c2cc(C)c(=O)n(C)c2)nc(-c2ccccc2OC)n1] | Ethanesulfonic acid [6-(1,5-dimethyl-6-oxo-1,6-dihydro-pyridin-3-yl)-2-(2-methoxy-phenyl)-pyrimidin-4-yl]-amide |
| 194 | 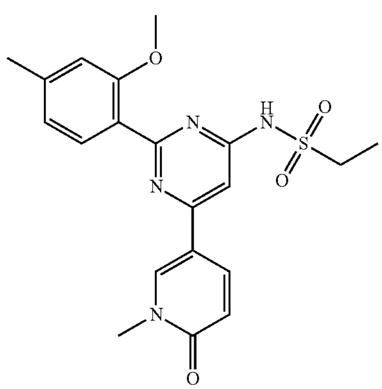 [SMILES: CCS(=O)(=O)Nc1cc(-c2ccc(=O)n(C)c2)nc(-c2ccc(C)cc2OC)n1] | Ethanesulfonic acid [2-(2-methoxy-4-methyl-phenyl)-6-(1-methyl-6-oxo-1,6-dihydro-pyridin-3-yl)-pyrimidin-4-yl]-amide |
| 195 | 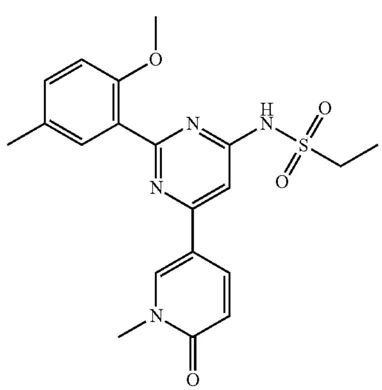 [SMILES: CCS(=O)(=O)Nc1cc(-c2ccc(=O)n(C)c2)nc(-c2cc(C)ccc2OC)n1] | Ethanesulfonic acid [2-(2-methoxy-5-methyl-phenyl)-6-(1-methyl-6-oxo-1,6-dihydro-pyridin-3-yl)-pyrimidin-4-yl]-amide |

TABLE 1-continued

| Example | Structure | Name |
|---|---|---|
| 196 | 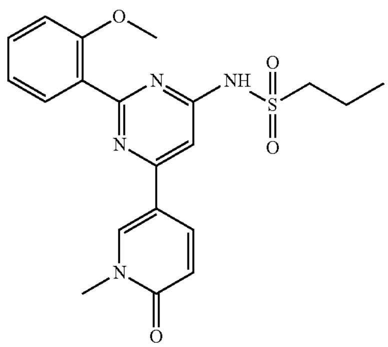 [SMILES: CCCS(=O)(=O)Nc1cc(-c2ccc(=O)n(C)c2)nc(-c2ccccc2OC)n1] | Propane-1-sulfonic acid [2-(2-methoxy-phenyl)-6-(1-methyl-6-oxo-1,6-dihydro-pyridin-3-yl)-pyrimidin-4-yl]-amide |
| 197 | 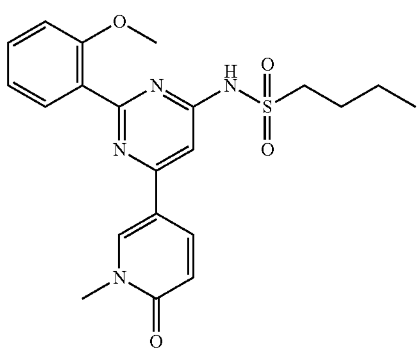 [SMILES: CCCCS(=O)(=O)Nc1cc(-c2ccc(=O)n(C)c2)nc(-c2ccccc2OC)n1] | Butane-1-sulfonic acid [2-(2-methoxy-phenyl)-6-(1-methyl-6-oxo-1,6-dihydro-pyridin-3-yl)-pyrimidin-4-yl]-amide |
| 198 | 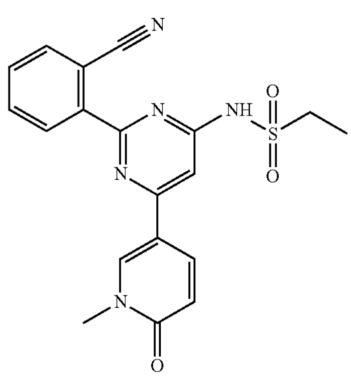 [SMILES: CCS(=O)(=O)Nc1cc(-c2ccc(=O)n(C)c2)nc(-c2ccccc2C#N)n1] | Ethanesulfonic acid [2-(2-cyano-phenyl)-6-(1-methyl-6-oxo-1,6-dihydro-pyridin-3-yl)-pyrimidin-4-yl]-amide |
| 199 | 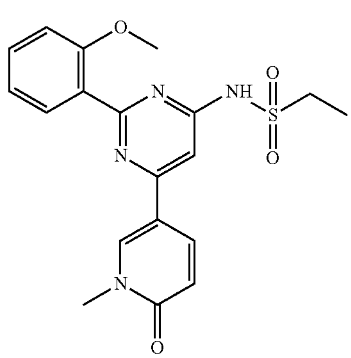 [SMILES: CCS(=O)(=O)Nc1cc(-c2ccc(=O)n(C)c2)nc(-c2ccccc2OC)n1] | Ethanesulfonic acid [2-(2-methoxy-phenyl)-6-(1-methyl-6-oxo-1,6-dihydro-pyridin-3-yl)-pyrimidin-4-yl]-amide |

TABLE 1-continued

| Example | Structure | Name |
|---|---|---|
| 200 | 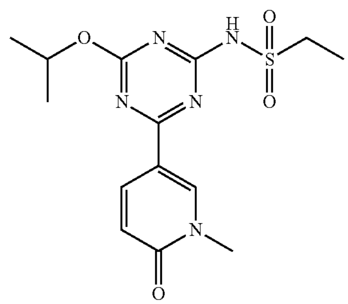 [SMILES: CCS(=O)(=O)Nc1nc(OC(C)C)nc(-c2ccc(=O)n(C)c2)n1] | Ethanesulfonic acid [4-isopropoxy-6-(1-methyl-6-oxo-1,6-dihydro-pyridin-3-yl)-[1,3,5]triazin-2-yl]-amide |
| 201 | 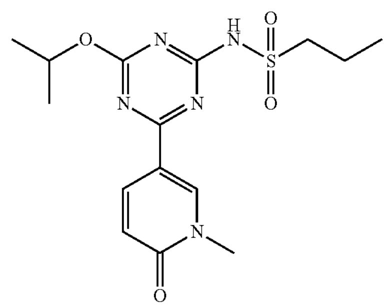 [SMILES: CCCS(=O)(=O)Nc1nc(OC(C)C)nc(-c2ccc(=O)n(C)c2)n1] | Propane-1-sulfonic acid [4-isopropoxy-6-(1-methyl-6-oxo-1,6-dihydro-pyridin-3-yl)-[1,3,5]triazin-2-yl]-amide |
| 202 | 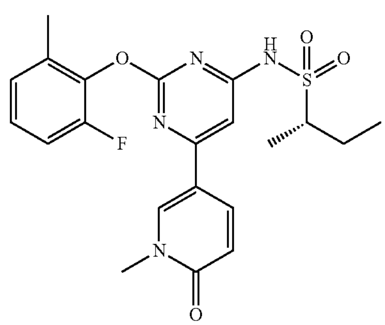 [SMILES: CC[C@H](C)S(=O)(=O)Nc1cc(-c2ccc(=O)n(C)c2)nc(Oc2c(C)cccc2F)n1] | (S)-N-(2-(2-fluoro-6-methylphenoxy)-6-(1-methyl-6-oxo-1,6-dihydropyridin-3-yl)pyrimidin-4-yl)butane-2-sulfonamide |
| 203 | 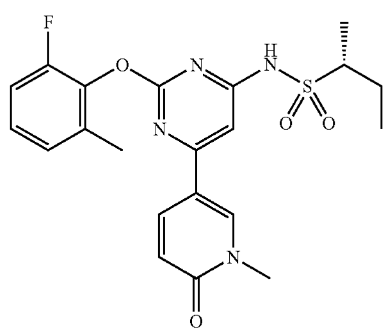 [SMILES: CC[C@@H](C)S(=O)(=O)Nc1cc(-c2ccc(=O)n(C)c2)nc(Oc2c(C)cccc2F)n1] | (R)-N-(2-(2-fluoro-6-methylphenoxy)-6-(1-methyl-6-oxo-1,6-dihydropyridin-3-yl)pyrimidin-4-yl)butane-2-sulfonamide |
| 204 | 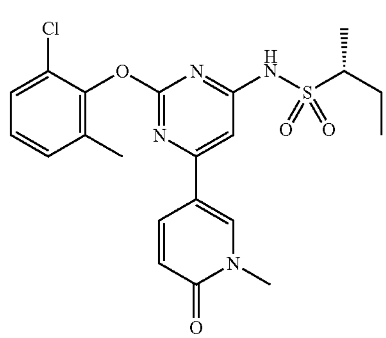 [SMILES: CC[C@@H](C)S(=O)(=O)Nc1cc(-c2ccc(=O)n(C)c2)nc(Oc2c(C)cccc2Cl)n1] | Butane-(2R)-sulfonic acid [2-(2-chloro-6-methyl-phenoxy)-6-(1-methyl-6-oxo-1,6-dihydro-pyridin-3-yl)-pyrimidin-4-yl]-amide |

TABLE 1-continued

| Example | Structure | Name |
|---|---|---|
| 205 | 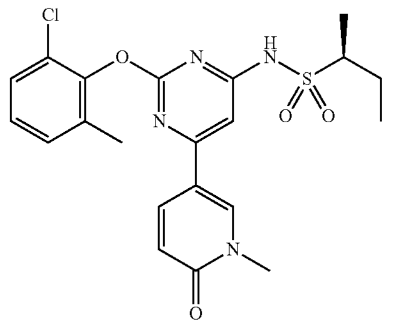 [SMILES: CC[C@H](C)S(=O)(=O)Nc1cc(-c2ccc(=O)n(C)c2)nc(Oc2c(C)cccc2Cl)n1] | Butane-(2S)-sulfonic acid [2-(2-chloro-6-methyl-phenoxy)-6-(1-methyl-6-oxo-1,6-dihydro-pyridin-3-yl)-pyrimidin-4-yl]-amide |
| 206 | 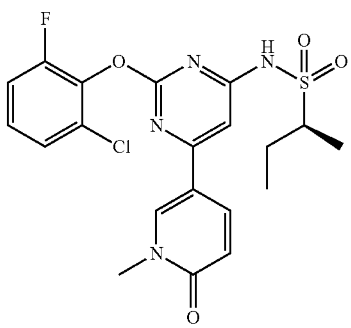 [SMILES: CC[C@H](C)S(=O)(=O)Nc1cc(-c2ccc(=O)n(C)c2)nc(Oc2c(F)cccc2Cl)n1] | Butane-(2S)-sulfonic acid [2-(2-chloro-6-fluoro-phenoxy)-6-(1-methyl-6-oxo-1,6-dihydro-pyridin-3-yl)-pyrimidin-4-yl]-amide |
| 207 | 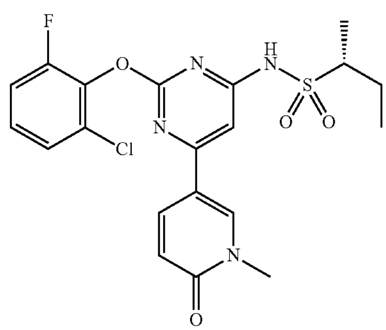 [SMILES: CC[C@@H](C)S(=O)(=O)Nc1cc(-c2ccc(=O)n(C)c2)nc(Oc2c(F)cccc2Cl)n1] | Butane-(2R)-sulfonic acid [2-(2-chloro-6-fluoro-phenoxy)-6-(1-methyl-6-oxo-1,6-dihydro-pyridin-3-yl)-pyrimidin-4-yl]-amide |
| 208 | 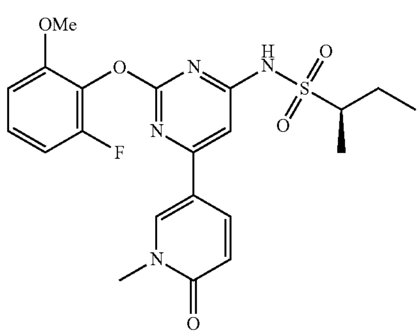 [SMILES: CC[C@@H](C)S(=O)(=O)Nc1cc(-c2ccc(=O)n(C)c2)nc(Oc2c(F)cccc2OC)n1] | Butane-(2R)-sulfonic acid [2-(2-fluoro-6-methoxy-phenoxy)-6-(1-methyl-6-oxo-1,6-dihydro-pyridin-3-yl)-pyrimidin-4-yl]-amide |

TABLE 1-continued

| Example | Structure | Name |
|---|---|---|
| 209 | 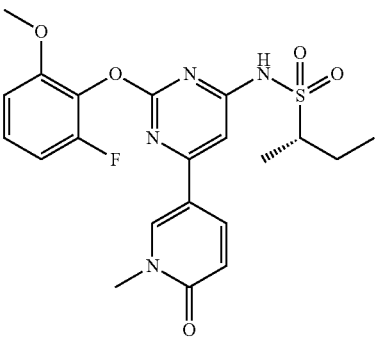 [SMILES: CC[C@H](C)S(=O)(=O)Nc1cc(-c2ccc(=O)n(C)c2)nc(Oc2c(F)cccc2OC)n1] | Butane-(2S)-sulfonic acid [2-(2-fluoro-6-methoxy-phenoxy)-6-(1-methyl-6-oxo-1,6-dihydro-pyridin-3-yl)-pyrimidin-4-yl]-amide |
| 210 | 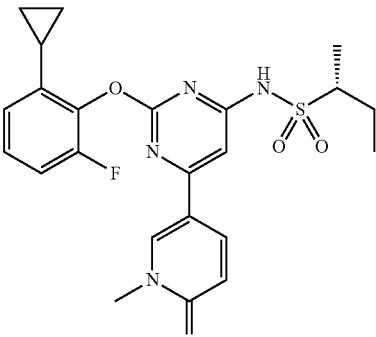 | Butane-(2R)-sulfonic acid [2-(2-cyclopropyl-6-fluoro-phenoxy)-6-(1-methyl-6-oxo-1,6-dihydro-pyridin-3-yl)-pyrimidin-4-yl]-amide |
| 211 | 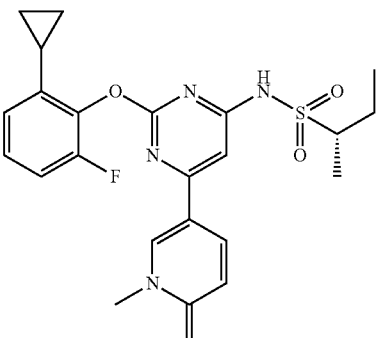 | Butane-(2S)-sulfonic acid [2-(2-cyclopropyl-6-methyl-phenoxy)-6-(1-methyl-6-oxo-1,6-dihydro-pyridin-3-yl)-pyrimidin-4-yl]-amide |
| 212 | 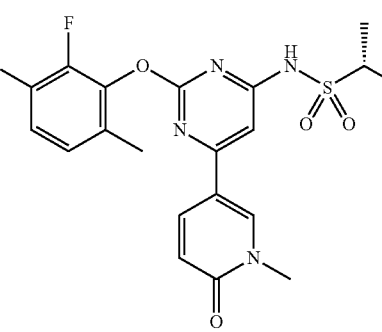 | (2R)-Butane-2-sulfonic acid [2-(2,3-difluoro-6-methyl-phenoxy)-6-(1-methyl-6-oxo-1,6-dihydro-pyridin-3-yl)-pyrimidin-4-yl]-amide |

TABLE 1-continued

| Example | Structure | Name |
|---|---|---|
| 213 | 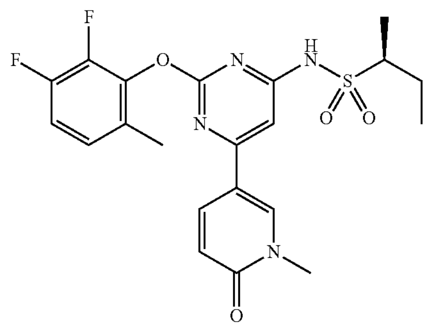 [SMILES: CC[C@H](C)S(=O)(=O)Nc1cc(-c2ccc(=O)n(C)c2)nc(Oc2c(C)ccc(F)c2F)n1] | (2S)-Butane-2-sulfonic acid [2-(2,3-difluoro-6-methyl-phenoxy)-6-(1-methyl-6-oxo-1,6-dihydro-pyridin-3-yl)-pyrimidin-4-yl]-amide |
| 214 | 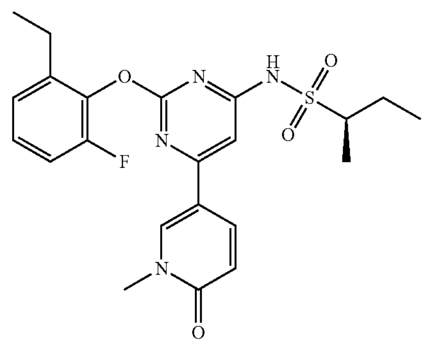 [SMILES: CCc1cccc(F)c1Oc1nc(NS(=O)(=O)[C@H](C)CC)cc(-c2ccc(=O)n(C)c2)n1] | (2R)-Butane-2-sulfonic acid [2-(2-ethyl-6-fluoro-phenoxy)-6-(1-methyl-6-oxo-1,6-dihydro-pyridin-3-yl)-pyrimidin-4-yl]-amide |
| 215 | 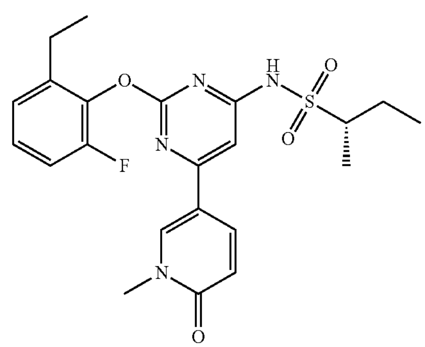 [SMILES: CCc1cccc(F)c1Oc1nc(NS(=O)(=O)[C@@H](C)CC)cc(-c2ccc(=O)n(C)c2)n1] | (2S)-Butane-2-sulfonic acid [2-(2-ethyl-6-fluoro-phenoxy)-6-(1-methyl-6-oxo-1,6-dihydro-pyridin-3-yl)-pyrimidin-4-yl]-amide |
| 216 | 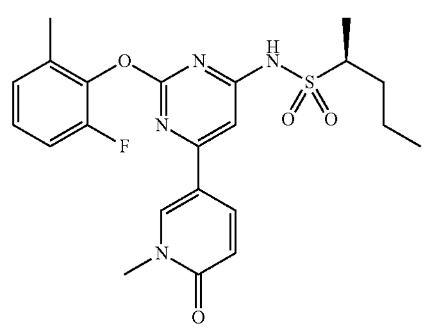 [SMILES: CCC[C@H](C)S(=O)(=O)Nc1cc(-c2ccc(=O)n(C)c2)nc(Oc2c(C)cccc2F)n1] | (2S)-Pentane-2-sulfonic acid [2-(2-fluoro-6-methyl-phenoxy)-6-(1-methyl-6-oxo-1,6-dihydro-pyridin-3-yl)-pyrimidin-4-yl]-amide |

TABLE 1-continued

| Example | Structure | Name |
|---|---|---|
| 217 | 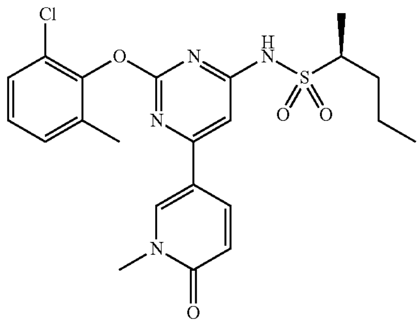 | (2S)-Pentane-2-sulfonic acid [2-(2-chloro-6-methyl-phenoxy)-6-(1-methyl-6-oxo-1,6-dihydro-pyridin-3-yl)-pyrimidin-4-yl]-amide |
| 218 | 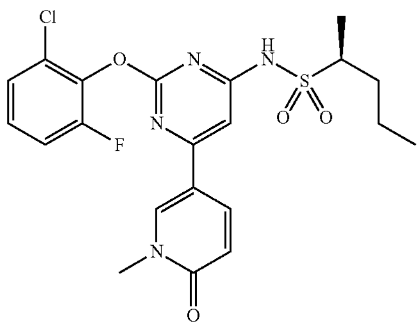 [SMILES: CCC[C@H](C)S(=O)(=O)Nc1cc(-c2ccc(=O)n(C)c2)nc(Oc2c(F)cccc2Cl)n1] | (2S)-Pentane-2-sulfonic acid [2-(2-chloro-6-fluoro-phenoxy)-6-(1-methyl-6-oxo-1,6-dihydro-pyridin-3-yl)-pyrimidin-4-yl]-amide |
| 219 | 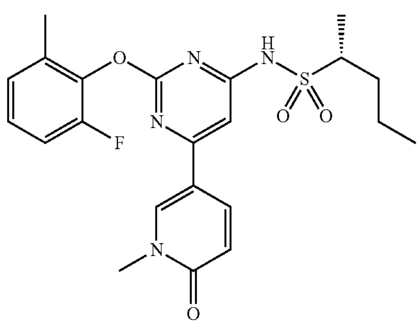 [SMILES: CCC[C@@H](C)S(=O)(=O)Nc1cc(-c2ccc(=O)n(C)c2)nc(Oc2c(C)cccc2F)n1] | (2R)-Pentane-2-sulfonic acid [2-(2-fluoro-6-methyl-phenoxy)-6-(1-methyl-6-oxo-1,6-dihydro-pyridin-3-yl)-pyrimidin-4-yl]-amide |
| 220 | 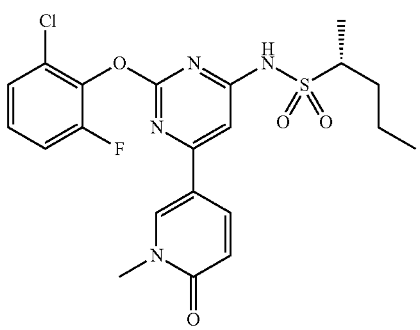 | (2R)-Pentane-2-sulfonic acid [2-(2-chloro-6-fluoro-phenoxy)-6-(1-methyl-6-oxo-1,6-dihydro-pyridin-3-yl)-pyrimidin-4-yl]-amide |

TABLE 1-continued

| Example | Structure | Name |
|---|---|---|
| 221 | 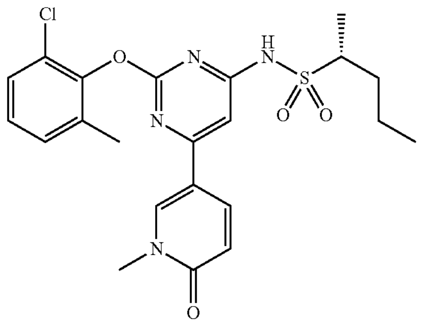 [SMILES: CCC[C@@H](C)S(=O)(=O)Nc1cc(-c2ccc(=O)n(C)c2)nc(Oc2c(C)cccc2Cl)n1] | (2R)-Pentane-2-sulfonic acid [2-(2-chloro-6-methyl-phenoxy)-6-(1-methyl-6-oxo-1,6-dihydro-pyridin-3-yl)-pyrimidin-4-yl]-amide |
| 222 | 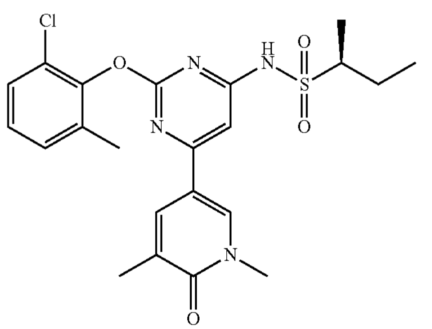 [SMILES: CC[C@H](C)S(=O)(=O)Nc1cc(-c2cc(C)c(=O)n(C)c2)nc(Oc2c(C)cccc2Cl)n1] | (S)-N-(2-(2-chloro-6-methylphenoxy)-6-(1,5-dimethyl-6-oxo-1,6-dihydropyridin-3-yl)pyrimidin-4-yl)butane-2-sulfonamide |
| 223 | 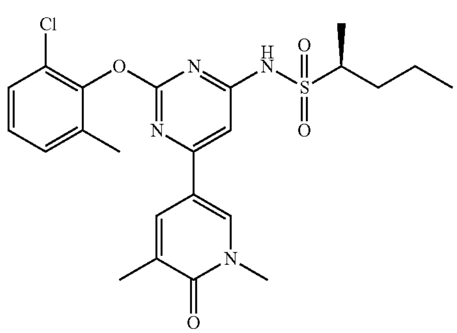 [SMILES: CCC[C@H](C)S(=O)(=O)Nc1cc(-c2cc(C)c(=O)n(C)c2)nc(Oc2c(C)cccc2Cl)n1] | (S)-N-(2-(2-chloro-6-methylphenoxy)-6-(1,5-dimethyl-6-oxo-1,6-dihydropyridin-3-yl)pyrimidin-4-yl)pentane-2-sulfonamide |
| 224 | 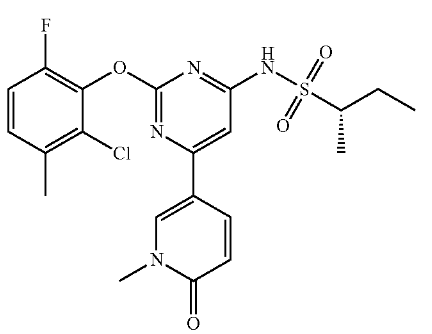 [SMILES: CC[C@H](C)S(=O)(=O)Nc1cc(-c2ccc(=O)n(C)c2)nc(Oc2c(F)ccc(C)c2Cl)n1] | (2S)-Butane-2-sulfonic acid [2-(2-chloro-6-fluoro-3-methyl-phenoxy)-6-(1-methyl-6-oxo-1,6-dihydro-pyridin-3-yl)-pyrimidin-4-yl]-amide |

TABLE 1-continued

| Example | Structure | Name |
|---|---|---|
| 225 | 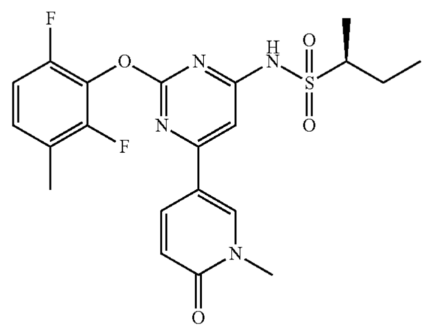 [SMILES: CC[C@H](C)S(=O)(=O)Nc1cc(-c2ccc(=O)n(C)c2)nc(Oc2c(F)ccc(C)c2F)n1] | (S)-N-(2-(2,6-difluoro-3-methylphenoxy)-6-(1-methyl-6-oxo-1,6-dihydropyridin-3-yl)pyrimidin-4-yl)butane-2-sulfonamide |
| 226 | 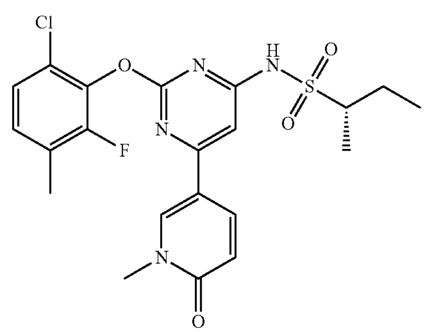 [SMILES: CC[C@H](C)S(=O)(=O)Nc1cc(-c2ccc(=O)n(C)c2)nc(Oc2c(Cl)ccc(C)c2F)n1] | (S)-Butane-2-sulfonic acid [2-(6-chloro-2-fluoro-3-methyl-phenoxy)-6-(1-methyl-6-oxo-1,6-dihydro-pyridin-3-yl)-pyrimidin-4-yl]-amide |
| 227 | 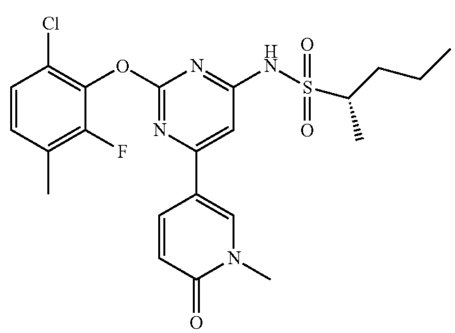 [SMILES: CCC[C@H](C)S(=O)(=O)Nc1cc(-c2ccc(=O)n(C)c2)nc(Oc2c(Cl)ccc(C)c2F)n1] | (2S)-Pentane-2-sulfonic acid [2-(6-chloro-2-fluoro-3-methyl-phenoxy)-6-(1-methyl-6-oxo-1,6-dihydro-pyridin-3-yl)-pyrimidin-4-yl]-amide |
| 228 | 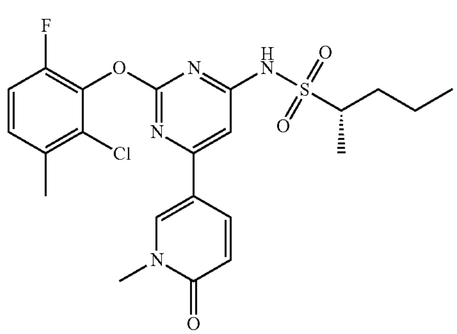 [SMILES: CCC[C@H](C)S(=O)(=O)Nc1cc(-c2ccc(=O)n(C)c2)nc(Oc2c(F)ccc(C)c2Cl)n1] | (2S)-Pentane-2-sulfonic acid [2-(2-chloro-6-fluoro-3-methyl-phenoxy)-6-(1-methyl-6-oxo-1,6-dihydro-pyridin-3-yl)-pyrimidin-4-yl]-amide |

TABLE 1-continued

| Example | Structure | Name |
|---|---|---|
| 229 | 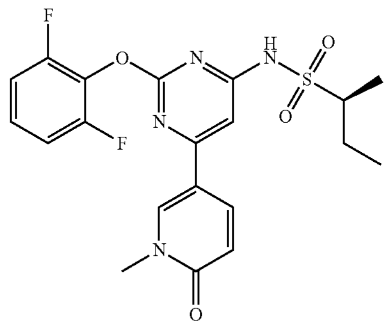 [SMILES: CC[C@H](C)S(=O)(=O)Nc1cc(-c2ccc(=O)n(C)c2)nc(Oc2c(F)cccc2F)n1] | (S)-N-(2-(2,6-difluorophenoxy)-6-(1-methyl-6-oxo-1,6-dihydropyridin-3-yl)pyrimidin-4-yl)butane-2-sulfonamide |
| 230 | 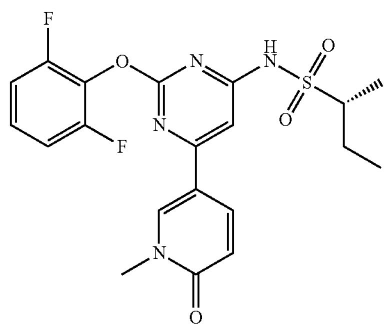 [SMILES: CC[C@@H](C)S(=O)(=O)Nc1cc(-c2ccc(=O)n(C)c2)nc(Oc2c(F)cccc2F)n1] | (R)-N-(2-(2,6-difluorophenoxy)-6-(1-methyl-6-oxo-1,6-dihydropyridin-3-yl)pyrimidin-4-yl)butane-2-sulfonamide |
| 231 | 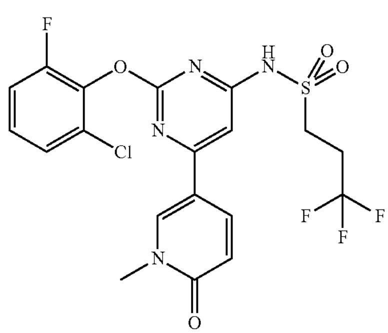 [SMILES: Cn1cc(-c2cc(NS(=O)(=O)CCC(F)(F)F)nc(Oc3c(F)cccc3Cl)n2)ccc1=O] | 3,3,3-Trifluoro-propane-1-sulfonic acid [2-(2-chloro-6-fluoro-phenoxy)-6-(1-methyl-6-oxo-1,6-dihydro-pyridin-3-yl)-pyrimidin-4-yl]-amide |
| 232 | 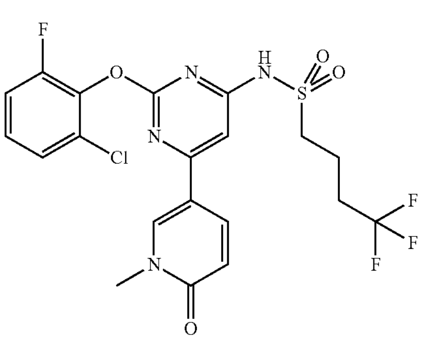 [SMILES: Cn1cc(-c2cc(NS(=O)(=O)CCCC(F)(F)F)nc(Oc3c(F)cccc3Cl)n2)ccc1=O] | 4,4,4-Trifluoro-butane-1-sulfonic acid [2-(2-chloro-6-fluoro-phenoxy)-6-(1-methyl-6-oxo-1,6-dihydro-pyridin-3-yl)-pyrimidin-4-yl]-amide |

TABLE 1-continued

| Example | Structure | Name |
|---|---|---|
| 233 | 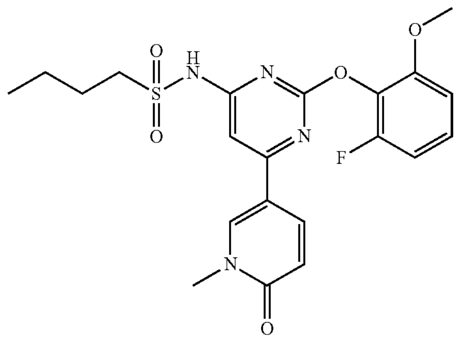 [SMILES: CCCCS(=O)(=O)Nc1cc(-c2ccc(=O)n(C)c2)nc(Oc2c(F)cccc2OC)n1] | Butane-1-sulfonic acid [2-(2-fluoro-6-methoxy-phenoxy)-6-(1-methyl-6-oxo-1,6-dihydro-pyridin-3-yl)-pyrimidin-4-yl]-amide |
| 234 | 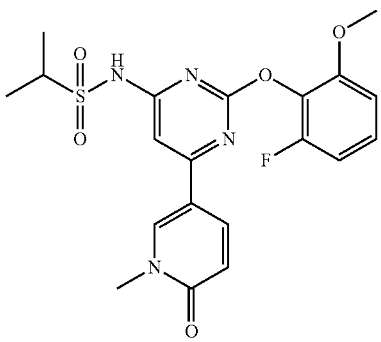 [SMILES: COc1cccc(F)c1Oc1nc(NS(=O)(=O)C(C)C)cc(-c2ccc(=O)n(C)c2)n1] | Propane-2-sulfonic acid [2-(2-fluoro-6-methoxy-phenoxy)-6-(1-methyl-6-oxo-1,6-dihydro-pyridin-3-yl)-pyrimidin-4-yl]-amide |
| 235 | 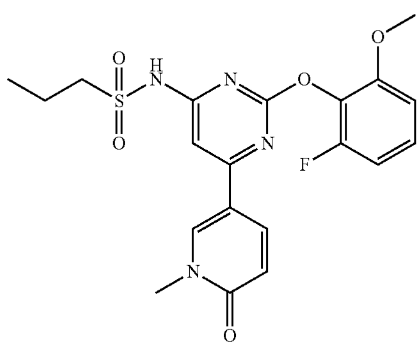 [SMILES: CCCS(=O)(=O)Nc1cc(-c2ccc(=O)n(C)c2)nc(Oc2c(F)cccc2OC)n1] | Propane-1-sulfonic acid [2-(2-fluoro-6-methoxy-phenoxy)-6-(1-methyl-6-oxo-1,6-dihydro-pyridin-3-yl)-pyrimidin-4-yl]-amide |
| 236 | 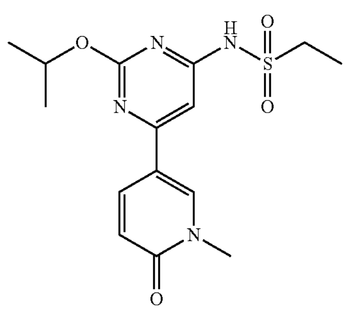 | Ethanesulfonic acid [2-isopropoxy-6-(1-methyl-6-oxo-1,6-dihydro-pyridin-3-yl)-pyrimidin-4-yl]-amide |

TABLE 1-continued

| Example | Structure | Name |
|---|---|---|
| 237 | 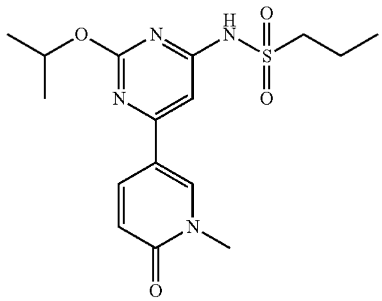 [SMILES: CCCS(=O)(=O)Nc1cc(-c2ccc(=O)n(C)c2)nc(OC(C)C)n1] | Propane-1-sulfonic acid [2-isopropoxy-6-(1-methyl-6-oxo-1,6-dihydro-pyridin-3-yl)-pyrimidin-4-yl]-amide |
| 238 | 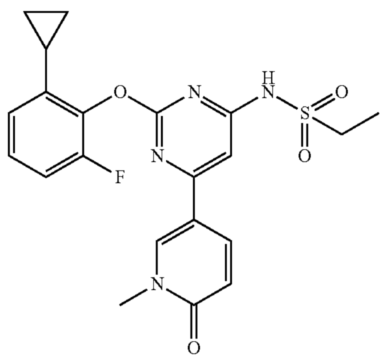 [SMILES: CCS(=O)(=O)Nc1cc(-c2ccc(=O)n(C)c2)nc(Oc2c(F)cccc2C2CC2)n1] | Ethanesulfonic acid [2-(2-cyclopropyl-6-fluoro-phenoxy)-6-(1-methyl-6-oxo-1,6-dihydro-pyridin-3-yl)-pyrimidin-4-yl]-amide |
| 239 | 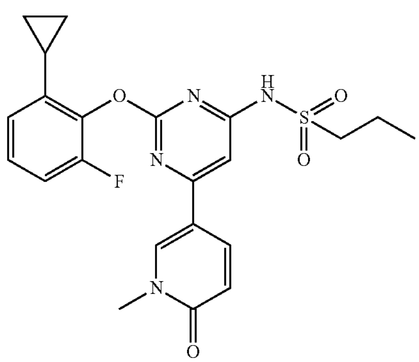 [SMILES: CCCS(=O)(=O)Nc1cc(-c2ccc(=O)n(C)c2)nc(Oc2c(F)cccc2C2CC2)n1] | Propane-1-sulfonic acid [2-(2-cyclopropyl-6-fluoro-phenoxy)-6-(1-methyl-6-oxo-1,6-dihydro-pyridin-3-yl)-pyrimidin-4-yl]-amide |
| 240 | 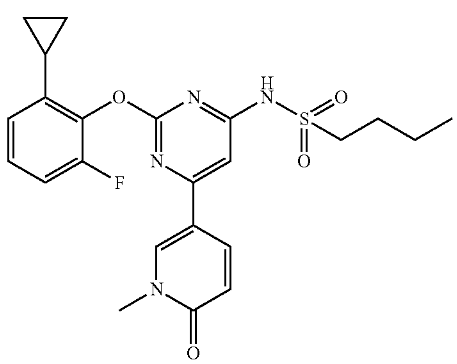 [SMILES: CCCCS(=O)(=O)Nc1cc(-c2ccc(=O)n(C)c2)nc(Oc2c(F)cccc2C2CC2)n1] | Butane-1-sulfonic acid [2-(2-cyclopropyl-6-fluoro-phenoxy)-6-(1-methyl-6-oxo-1,6-dihydro-pyridin-3-yl)-pyrimidin-4-yl]-amide |

TABLE 1-continued

| Example | Structure | Name |
|---|---|---|
| 241 | 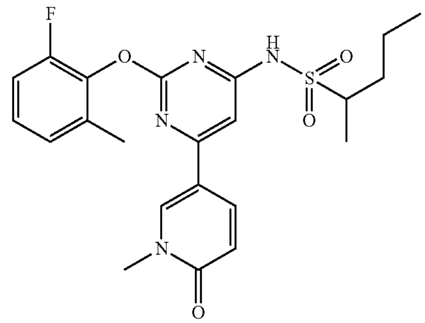 | Pentane-2-sulfonic acid [2-(2-fluoro-6-methyl-phenoxy)-6-(1-methyl-6-oxo-1,6-dihydro-pyridin-3-yl)-pyrimidin-4-yl]-amide |
| 242 | 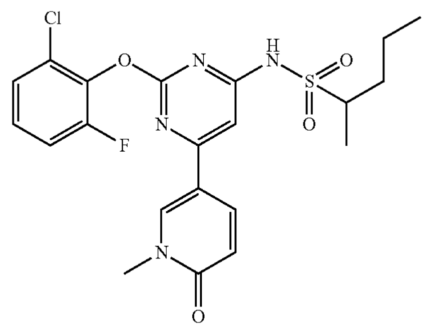 [SMILES: CCCC(C)S(=O)(=O)Nc1cc(-c2ccc(=O)n(C)c2)nc(Oc2c(C)cccc2F)n1] | Pentane-2-sulfonic acid [2-(2-chloro-6-fluoro-phenoxy)-6-(1-methyl-6-oxo-1,6-dihydro-pyridin-3-yl)-pyrimidin-4-yl]-amide |
| 243 | 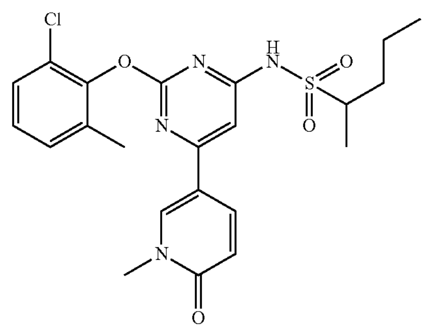 | Pentane-2-sulfonic acid [2-(2-chloro-6-methyl-phenoxy)-6-(1-methyl-6-oxo-1,6-dihydro-pyridin-3-yl)-pyrimidin-4-yl]-amide |
| 244 | 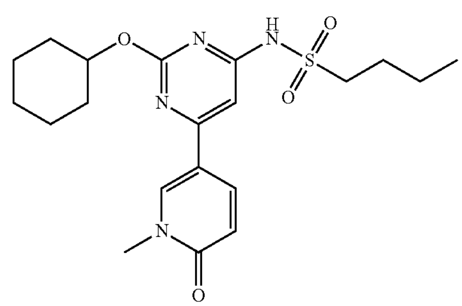 [SMILES: CCCCS(=O)(=O)Nc1cc(-c2ccc(=O)n(C)c2)nc(OC2CCCCC2)n1] | Butane-1-sulfonic acid [2-cyclohexyloxy-6-(1-methyl-6-oxo-1,6-dihydro-pyridin-3-yl)-pyrimidin-4-yl]-amide |
| 245 | 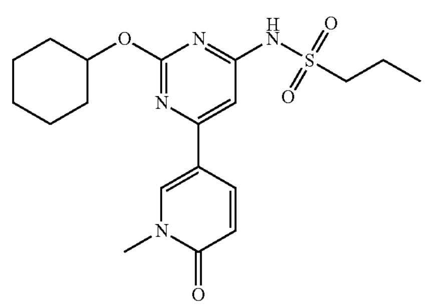 [SMILES: CCCS(=O)(=O)Nc1cc(-c2ccc(=O)n(C)c2)nc(OC2CCCCC2)n1] | Propane-1-sulfonic acid [2-cyclohexyloxy-6-(1-methyl-6-oxo-1,6-dihydro-pyridin-3-yl)-pyrimidin-4-yl]-amide |

TABLE 1-continued

| Example | Structure | Name |
|---|---|---|
| 246 | 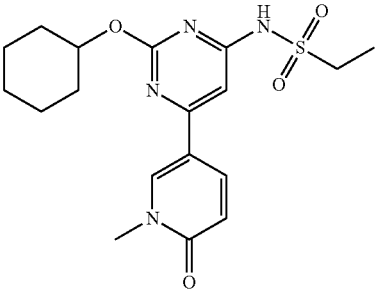 [SMILES: CCS(=O)(=O)Nc1cc(-c2ccc(=O)n(C)c2)nc(OC2CCCCC2)n1] | Ethanesulfonic acid [2-cyclohexyloxy-6-(1-methyl-6-oxo-1,6-dihydro-pyridin-3-yl)-pyrimidin-4-yl]-amide |
| 247 | 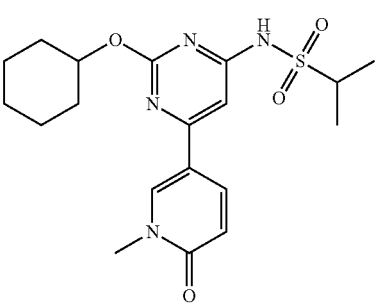 [SMILES: CC(C)S(=O)(=O)Nc1cc(-c2ccc(=O)n(C)c2)nc(OC2CCCCC2)n1] | Propane-2-sulfonic acid [2-cyclohexyloxy-6-(1-methyl-6-oxo-1,6-dihydro-pyridin-3-yl)-pyrimidin-4-yl]-amide |
| 248 | 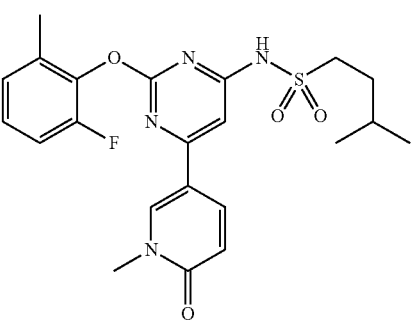 [SMILES: Cc1cccc(F)c1Oc1nc(NS(=O)(=O)CCC(C)C)cc(-c2ccc(=O)n(C)c2)n1] | 3-Methyl-butane-1-sulfonic acid [2-(2-fluoro-6-methyl-phenoxy)-6-(1-methyl-6-oxo-1,6-dihydro-pyridin-3-yl)-pyrimidin-4-yl]-amide |
| 249 | 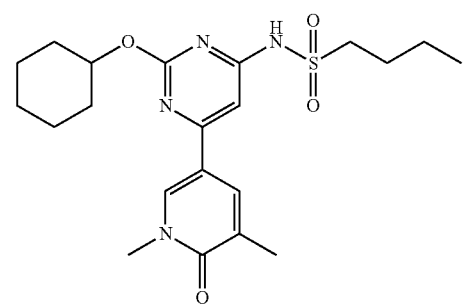 [SMILES: CCCCS(=O)(=O)Nc1cc(-c2cc(C)c(=O)n(C)c2)nc(OC2CCCCC2)n1] | Butane-1-sulfonic acid [2-cyclohexyloxy-6-(1,5-dimethyl-6-oxo-1,6-dihydro-pyridin-3-yl)-pyrimidin-4-yl]-amide |
| 250 | 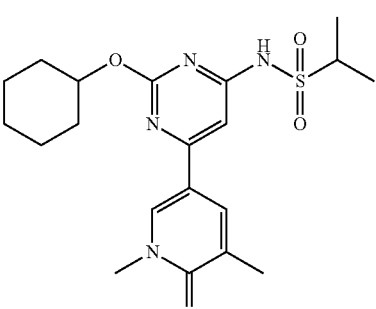 | Propane-2-sulfonic acid [2-cyclohexyloxy-6-(1,5-dimethyl-6-oxo-1,6-dihydro-pyridin-3-yl)-pyrimidin-4-yl]-amide |

TABLE 1-continued

| Example | Structure | Name |
|---|---|---|
| 251 | 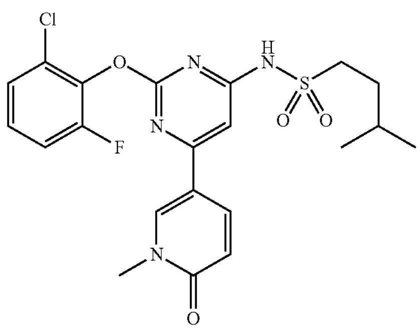 [SMILES: CC(C)CCS(=O)(=O)Nc1cc(-c2ccc(=O)n(C)c2)nc(Oc2c(F)cccc2Cl)n1] | 3-Methyl-butane-1-sulfonic acid [2-(2-chloro-6-fluoro-phenoxy)-6-(1-methyl-6-oxo-1,6-dihydro-pyridin-3-yl)-pyrimidin-4-yl]-amide |
| 252 | 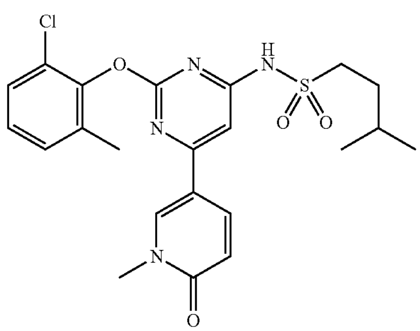 [SMILES: Cc1cccc(Cl)c1Oc1nc(NS(=O)(=O)CCC(C)C)cc(-c2ccc(=O)n(C)c2)n1] | 3-Methyl-butane-1-sulfonic acid [2-(2-chloro-6-methyl-phenoxy)-6-(1-methyl-6-oxo-1,6-dihydro-pyridin-3-yl)-pyrimidin-4-yl]-amide |
| 253 | 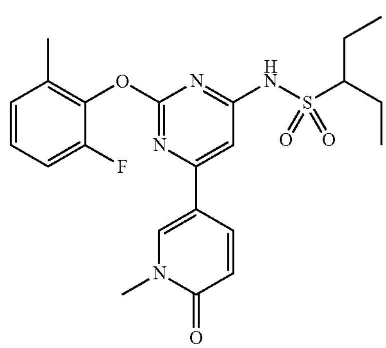 [SMILES: CCC(CC)S(=O)(=O)Nc1cc(-c2ccc(=O)n(C)c2)nc(Oc2c(C)cccc2F)n1] | Pentane-3-sulfonic acid [2-(2-fluoro-6-methyl-phenoxy)-6-(1-methyl-6-oxo-1,6-dihydro-pyridin-3-yl)-pyrimidin-4-yl]-amide |
| 254 | 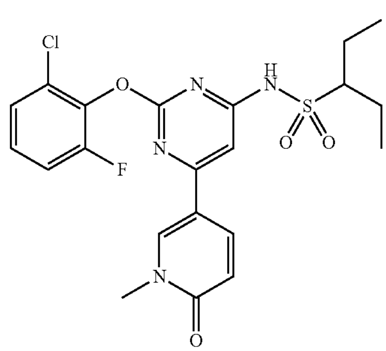 [SMILES: CCC(CC)S(=O)(=O)Nc1cc(-c2ccc(=O)n(C)c2)nc(Oc2c(F)cccc2Cl)n1] | Pentane-3-sulfonic acid [2-(2-chloro-6-fluoro-phenoxy)-6-(1-methyl-6-oxo-1,6-dihydro-pyridin-3-yl)-pyrimidin-4-yl]-amide |

TABLE 1-continued

| Example | Structure | Name |
|---|---|---|
| 255 | 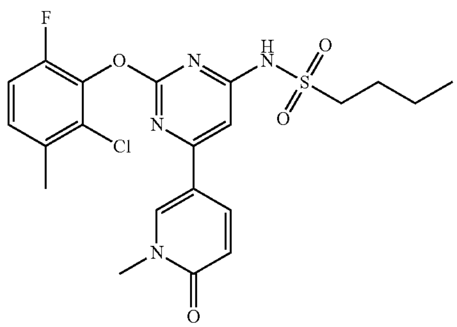 [SMILES: CCCCS(=O)(=O)Nc1cc(-c2ccc(=O)n(C)c2)nc(Oc2c(F)ccc(C)c2Cl)n1] | Butane-1-sulfonic acid [2-(2-chloro-6-fluoro-3-methyl-phenoxy)-6-(1-methyl-6-oxo-1,6-dihydro-pyridin-3-yl)-pyrimidin-4-yl]-amide |
| 256 | 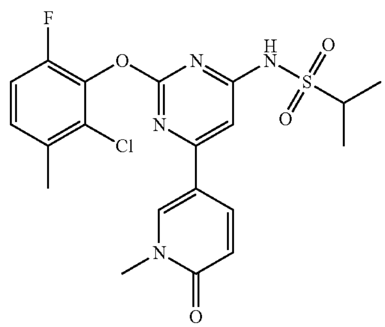 [SMILES: Cc1ccc(F)c(Oc2nc(NS(=O)(=O)C(C)C)cc(-c3ccc(=O)n(C)c3)n2)c1Cl] | Propane-2-sulfonic acid [2-(2-chloro-6-fluoro-3-methyl-phenoxy)-6-(1-methyl-6-oxo-1,6-dihydro-pyridin-3-yl)-pyrimidin-4-yl]-amide |
| 257 | 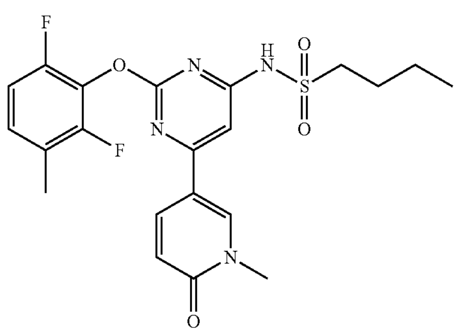 [SMILES: CCCCS(=O)(=O)Nc1cc(-c2ccc(=O)n(C)c2)nc(Oc2c(F)ccc(C)c2F)n1] | Butane-1-sulfonic acid [2-(2,6-difluoro-3-methyl-phenoxy)-6-(1-methyl-6-oxo-1,6-dihydro-pyridin-3-yl)-pyrimidin-4-yl]-amide |
| 258 | 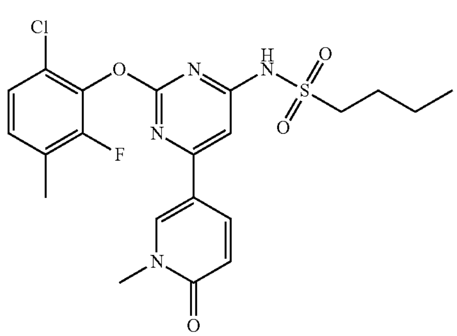 [SMILES: CCCCS(=O)(=O)Nc1cc(-c2ccc(=O)n(C)c2)nc(Oc2c(Cl)ccc(C)c2F)n1] | Butane-1-sulfonic acid [2-(6-chloro-2-fluoro-3-methyl-phenoxy)-6-(1-methyl-6-oxo-1,6-dihydro-pyridin-3-yl)-pyrimidin-4-yl]-amide |

TABLE 1-continued

| Example | Structure | Name |
|---|---|---|
| 259 | 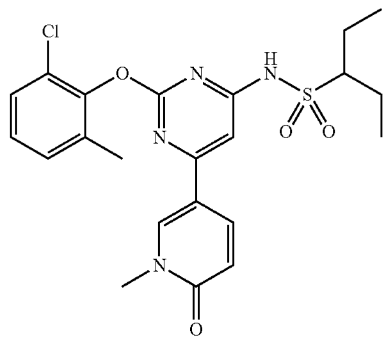 [SMILES: CCC(CC)S(=O)(=O)Nc1cc(-c2ccc(=O)n(C)c2)nc(Oc2c(C)cccc2Cl)n1] | Pentane-3-sulfonic acid [2-(2-chloro-6-methyl-phenoxy)-6-(1-methyl-6-oxo-1,6-dihydro-pyridin-3-yl)-pyrimidin-4-yl]-amide |
| 260 | 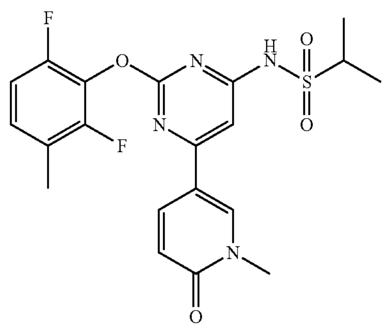 [SMILES: Cc1ccc(F)c(Oc2nc(NS(=O)(=O)C(C)C)cc(-c3ccc(=O)n(C)c3)n2)c1F] | Propane-2-sulfonic acid [2-(2,6-difluoro-3-methyl-phenoxy)-6-(1-methyl-6-oxo-1,6-dihydro-pyridin-3-yl)-pyrimidin-4-yl]-amide |
| 261 | 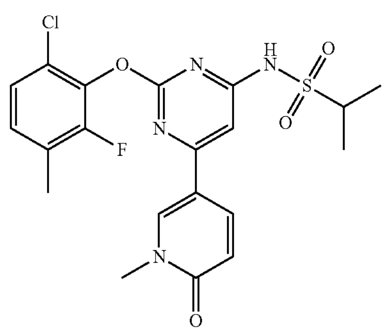 [SMILES: Cc1ccc(Cl)c(Oc2nc(NS(=O)(=O)C(C)C)cc(-c3ccc(=O)n(C)c3)n2)c1F] | Propane-2-sulfonic acid [2-(6-chloro-2-fluoro-3-methyl-phenoxy)-6-(1-methyl-6-oxo-1,6-dihydro-pyridin-3-yl)-pyrimidin-4-yl]-amide |
| 262 | 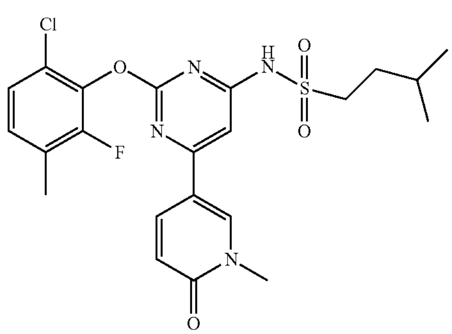 [SMILES: Cc1ccc(Cl)c(Oc2nc(NS(=O)(=O)CCC(C)C)cc(-c3ccc(=O)n(C)c3)n2)c1F] | 3-Methyl-butane-1-sulfonic acid [2-(6-chloro-2-fluoro-3-methyl-phenoxy)-6-(1-methyl-6-oxo-1,6-dihydro-pyridin-3-yl)-pyrimidin-4-yl]-amide |

TABLE 1-continued

| Example | Structure | Name |
|---|---|---|
| 263 | 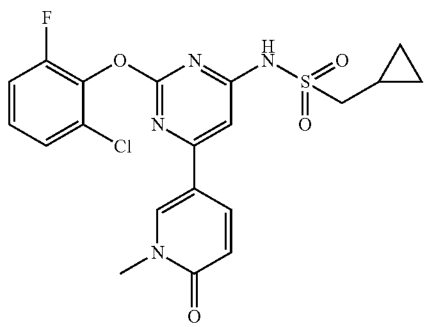 [SMILES: Cn1cc(-c2cc(NS(=O)(=O)CC3CC3)nc(Oc3c(F)cccc3Cl)n2)ccc1=O] | N-[2-(2-Chloro-6-fluoro-phenoxy)-6-(1-methyl-6-oxo-1,6-dihydro-pyridin-3-yl)-pyrimidin-4-yl]-C-cyclopropyl-methanesulfonamide |
| 264 | 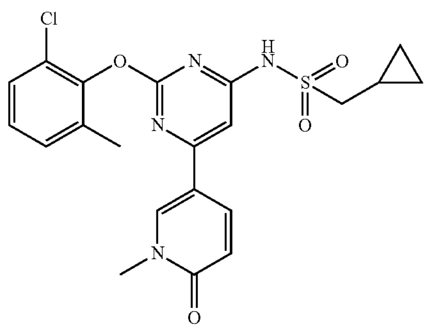 [SMILES: Cc1cccc(Cl)c1Oc1nc(NS(=O)(=O)CC2CC2)cc(-c2ccc(=O)n(C)c2)n1] | N-[2-(2-Chloro-6-methyl-phenoxy)-6-(1-methyl-6-oxo-1,6-dihydro-pyridin-3-yl)-pyrimidin-4-yl]-C-cyclopropyl-methanesulfonamide |
| 265 | 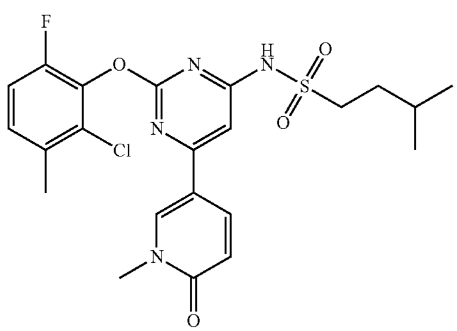 [SMILES: Cc1ccc(F)c(Oc2nc(NS(=O)(=O)CCC(C)C)cc(-c3ccc(=O)n(C)c3)n2)c1Cl] | 3-Methyl-butane-1-sulfonic acid [2-(2-chloro-6-fluoro-3-methyl-phenoxy)-6-(1-methyl-6-oxo-1,6-dihydro-pyridin-3-yl)-pyrimidin-4-yl]-amide |
| 266 | 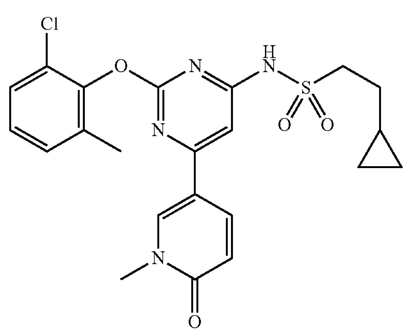 [SMILES: Cc1cccc(Cl)c1Oc1nc(NS(=O)(=O)CCC2CC2)cc(-c2ccc(=O)n(C)c2)n1] | 2-Cyclopropyl-ethanesulfonic acid [2-(2-chloro-6-methyl-phenoxy)-6-(1-methyl-6-oxo-1,6-dihydro-pyridin-3-yl)-pyrimidin-4-yl]-amide |

TABLE 1-continued

| Example | Structure | Name |
|---|---|---|
| 267 | 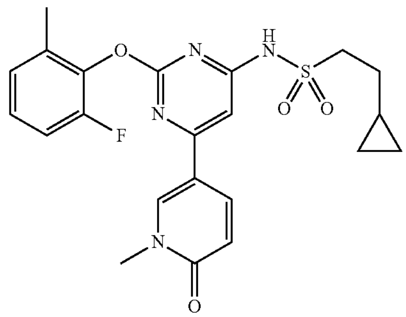 [SMILES: Cc1cccc(F)c1Oc1nc(NS(=O)(=O)CCC2CC2)cc(-c2ccc(=O)n(C)c2)n1] | 2-Cyclopropyl-ethanesulfonic acid [2-(2-fluoro-6-methyl-phenoxy)-6-(1-methyl-6-oxo-1,6-dihydro-pyridin-3-yl)-pyrimidin-4-yl]-amide |
| 268 | 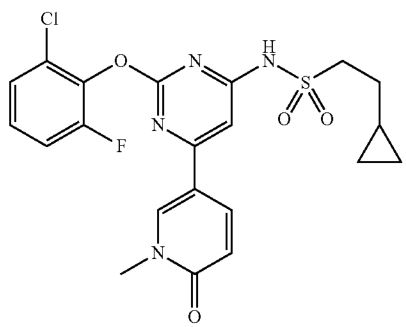 [SMILES: Cn1cc(-c2cc(NS(=O)(=O)CCC3CC3)nc(Oc3c(F)cccc3Cl)n2)ccc1=O] | 2-Cyclopropyl-ethanesulfonic acid [2-(2-chloro-6-fluoro-phenoxy)-6-(1-methyl-6-oxo-1,6-dihydro-pyridin-3-yl)-pyrimidin-4-yl]-amide |
| 269 | 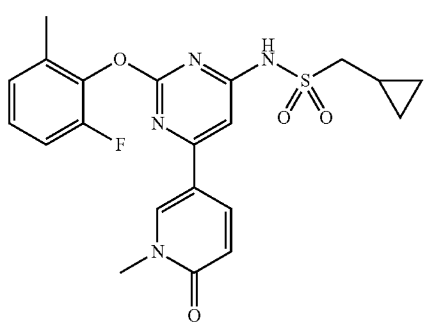 [SMILES: Cc1cccc(F)c1Oc1nc(NS(=O)(=O)CC2CC2)cc(-c2ccc(=O)n(C)c2)n1] | 1-Cyclopropyl-N-[2-(2-fluoro-6-methyl-phenoxy)-6-(1-methyl-6-oxo-1,6-dihydro-pyridin-3-yl)-pyrimidin-4-yl]-methanesulfonamide |
| 270 | 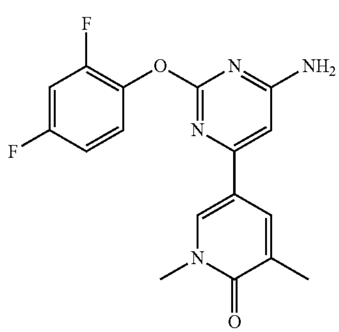 [SMILES: Cc1cc(-c2cc(N)nc(Oc3ccc(F)cc3F)n2)cn(C)c1=O] | 5-(6-amino-2-(2,4-difluorophenoxy)pyrimidin-4-yl)-1,3-dimethylpyridin-2(1H)-one |

TABLE 1-continued
| Example | Structure | Name |
|---|---|---|
| 271 | 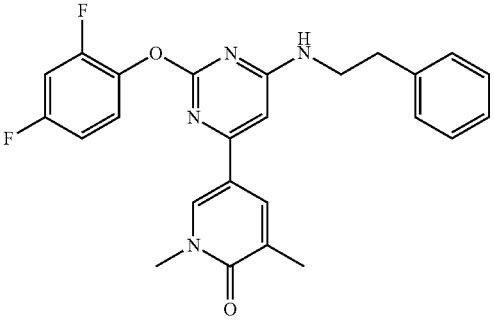 [SMILES: Cc1cc(-c2cc(NCCc3ccccc3)nc(Oc3ccc(F)cc3F)n2)cn(C)c1=O] | 5-(2-(2,4-difluorophenoxy)-6-(phenethylamino)pyrimidin-4-yl)-1,3-dimethylpyridin-2(1H)-one |
| 272 | 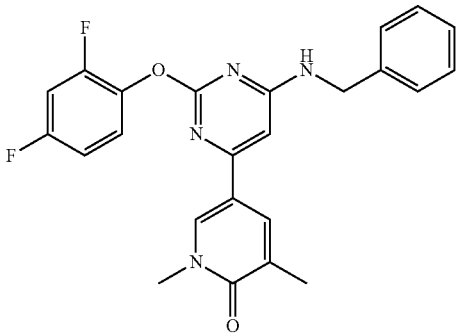 [SMILES: Cc1cc(-c2cc(NCc3ccccc3)nc(Oc3ccc(F)cc3F)n2)cn(C)c1=O] | 5-(6-(benzylamino)-2-(2,4-difluorophenoxy)pyrimidin-4-yl)-1,3-dimethylpyridin-2(1H)-one |
| 273 | 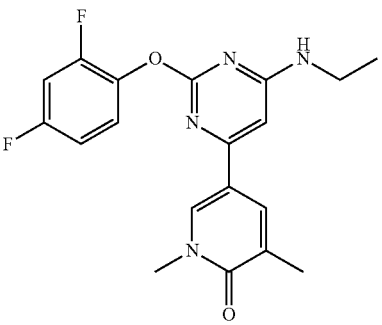 [SMILES: CCNc1cc(-c2cc(C)c(=O)n(C)c2)nc(Oc2ccc(F)cc2F)n1] | 5-(2-(2,4-difluorophenoxy)-6-(ethylamino)pyrimidin-4-yl)-1,3-dimethylpyridin-2(1H)-one |
| 274 | 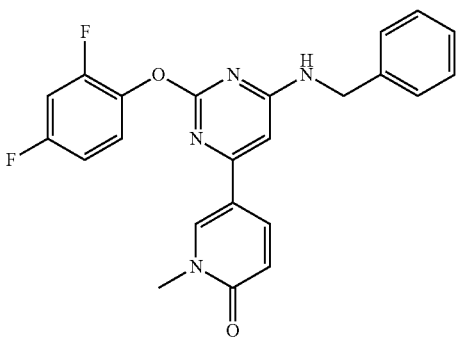 [SMILES: Cn1cc(-c2cc(NCc3ccccc3)nc(Oc3ccc(F)cc3F)n2)ccc1=O] | 5-(6-(benzylamino)-2-(2,4-difluorophenoxy)pyrimidin-4-yl)-1-methylpyridin-2(1H)-one |

TABLE 1-continued

| Example | Structure | Name |
|---|---|---|
| 275 | 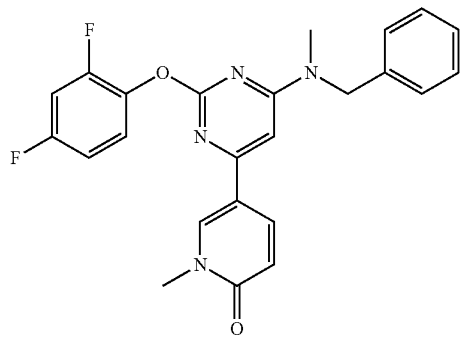 [SMILES: CN(Cc1ccccc1)c1cc(-c2ccc(=O)n(C)c2)nc(Oc2ccc(F)cc2F)n1] | 5-(6-(benzyl(methyl)amino)-2-(2,4-difluorophenoxy)pyrimidin-4-yl)-1-methylpyridin-2(1H)-one |
| 276 | 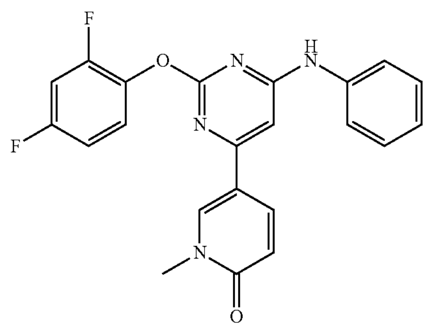 [SMILES: Cn1cc(-c2cc(Nc3ccccc3)nc(Oc3ccc(F)cc3F)n2)ccc1=O] | 5-(2-(2,4-difluorophenoxy)-6-(phenylamino)pyrimidin-4-yl)-1-methylpyridin-2(1H)-one |
| 277 | 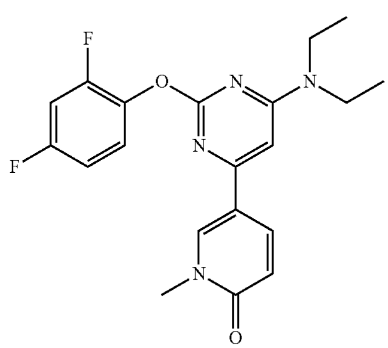 [SMILES: CCN(CC)c1cc(-c2ccc(=O)n(C)c2)nc(Oc2ccc(F)cc2F)n1] | 5-(6-(diethylamino)-2-(2,4-difluorophenoxy)pyrimidin-4-yl)-1-methylpyridin-2(1H)-one |
| 278 | 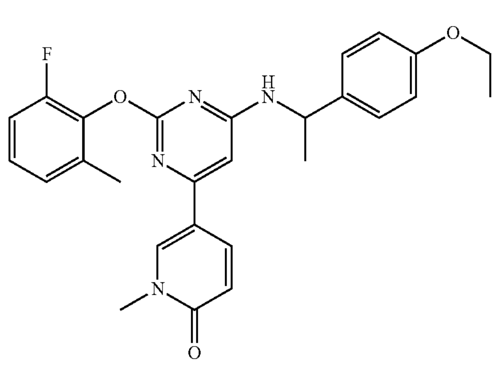 [SMILES: CCOc1ccc(C(C)Nc2cc(-c3ccc(=O)n(C)c3)nc(Oc3c(C)cccc3F)n2)cc1] | 5-(6-((1-(4-ethoxyphenyl)ethyl)amino)-2-(2-fluoro-6-methylphenoxy)pyrimidin-4-yl)-1-methylpyridin-2(1H)-one |

TABLE 1-continued

| Example | Structure | Name |
|---|---|---|
| 279 | 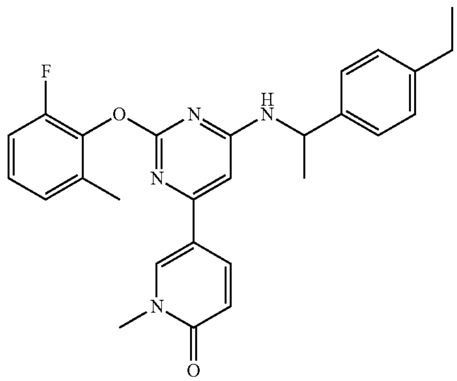 [SMILES: CCc1ccc(C(C)Nc2cc(-c3ccc(=O)n(C)c3)nc(Oc3c(C)cccc3F)n2)cc1] | 5-(6-((1-(4-ethylphenyl)ethyl)amino)-2-(2-fluoro-6-methylphenoxy)pyrimidin-4-yl)-1-methylpyridin-2(1H)-one |
| 280 | 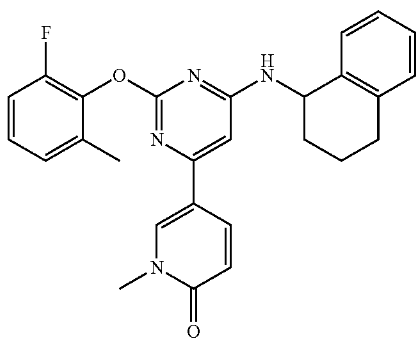 [SMILES: Cc1cccc(F)c1Oc1nc(NC2CCCc3ccccc32)cc(-c2ccc(=O)n(C)c2)n1] | 5-(2-(2-fluoro-6-methylphenoxy)-6-((1,2,3,4-tetrahydronaphthalen-1-yl)amino)pyrimidin-4-yl)-1-methylpyridin-2(1H)-one |
| 281 | 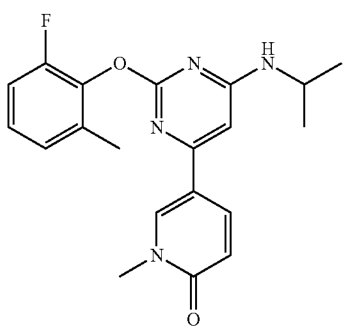 [SMILES: Cc1cccc(F)c1Oc1nc(NC(C)C)cc(-c2ccc(=O)n(C)c2)n1] | 5-(2-(2-fluoro-6-methylphenoxy)-6-(isopropylamino)pyrimidin-4-yl)-1-methylpyridin-2(1H)-one |
| 282 | 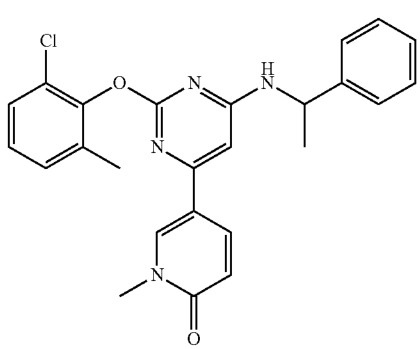 [SMILES: Cc1cccc(Cl)c1Oc1nc(NC(C)c2ccccc2)cc(-c2ccc(=O)n(C)c2)n1] | 5-(2-(2-chloro-6-methylphenoxy)-6-((1-phenylethyl)amino)pyrimidin-4-yl)-1-methylpyridin-2(1H)-one |

TABLE 1-continued

| Example | Structure | Name |
|---|---|---|
| 283 | 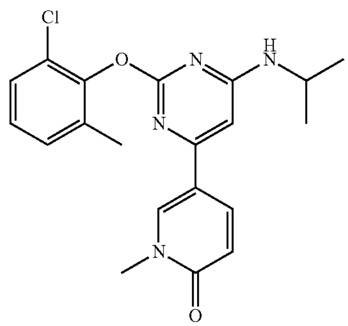 | 5-(2-(2-chloro-6-methylphenoxy)-6-(isopropylamino)pyrimidin-4-yl)-1-methylpyridin-2(1H)-one |
| 284 | 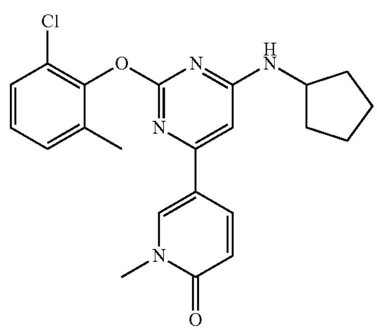 [SMILES: Cc1cccc(Cl)c1Oc1nc(NC2CCCC2)cc(-c2ccc(=O)n(C)c2)n1] | 5-(2-(2-chloro-6-methylphenoxy)-6-(cyclopentylamino)pyrimidin-4-yl)-1-methylpyridin-2(1H)-one |
| 285 | 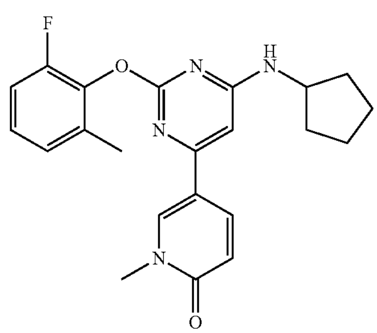 [SMILES: Cc1cccc(F)c1Oc1nc(NC2CCCC2)cc(-c2ccc(=O)n(C)c2)n1] | 5-(6-(cyclopentylamino)-2-(2-fluoro-6-methylphenoxy)pyrimidin-4-yl)-1-methylpyridin-2(1H)-one |
| 286 | 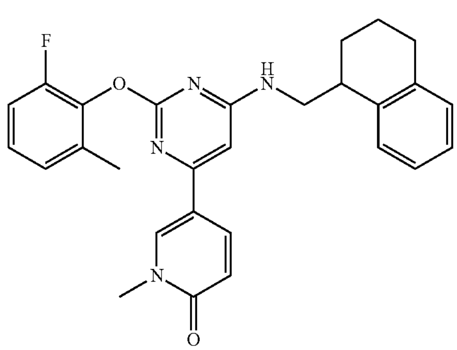 [SMILES: Cc1cccc(F)c1Oc1nc(NCC2CCCc3ccccc32)cc(-c2ccc(=O)n(C)c2)n1] | 5-(2-(2-fluoro-6-methylphenoxy)-6-(((1,2,3,4-tetrahydronaphthalen-1-yl)methyl)amino)pyrimidin-4-yl)-1-methylpyridin-2(1H)-one |

TABLE 1-continued

| Example | Structure | Name |
|---|---|---|
| 287 | 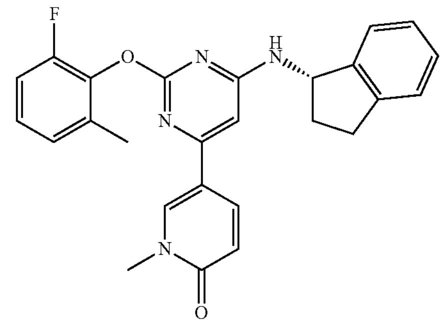 [SMILES: Cc1cccc(F)c1Oc1nc(N[C@H]2CCc3ccccc32)cc(-c2ccc(=O)n(C)c2)n1] | (S)-5-(6-((2,3-dihydro-1H-inden-1-yl)amino)-2-(2-fluoro-6-methylphenoxy)pyrimidin-4-yl)-1-methylpyridin-2(1H)-one |
| 288 | 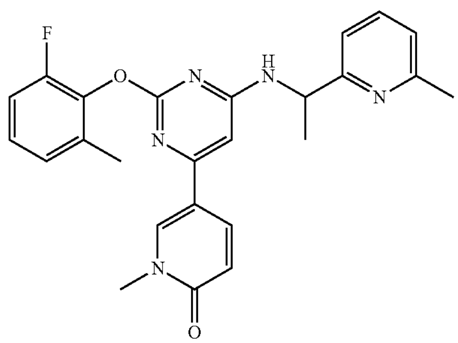 | 5-(2-(2-fluoro-6-methylphenoxy)-6-((1-(6-methylpyridin-2-yl)ethyl)amino)pyrimidin-4-yl)-1-methylpyridin-2(1H)-one |
| 289 | 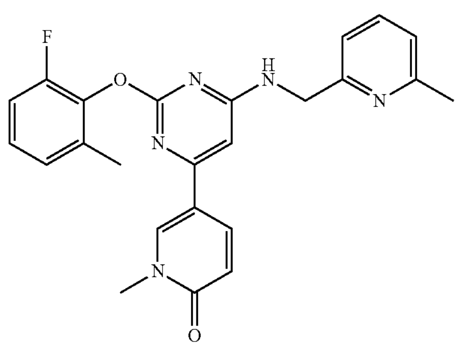 | 5-(2-(2-fluoro-6-methylphenoxy)-6-(((6-methylpyridin-2-yl)methyl)amino)pyrimidin-4-yl)-1-methylpyridin-2(1H)-one |
| 290 | 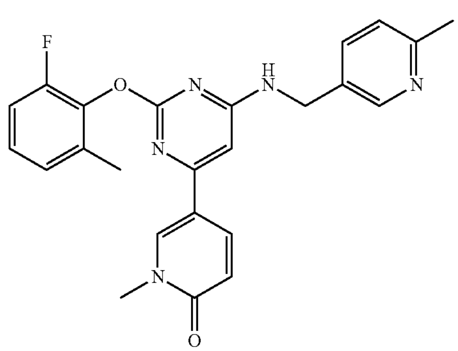 [SMILES: Cc1ccc(CNc2cc(-c3ccc(=O)n(C)c3)nc(Oc3c(C)cccc3F)n2)cn1] | 5-(2-(2-fluoro-6-methylphenoxy)-6-(((6-methylpyridin-3-yl)methyl)amino)pyrimidin-4-yl)-1-methylpyridin-2(1H)-one |

TABLE 1-continued

| Example | Structure | Name |
|---|---|---|
| 291 | 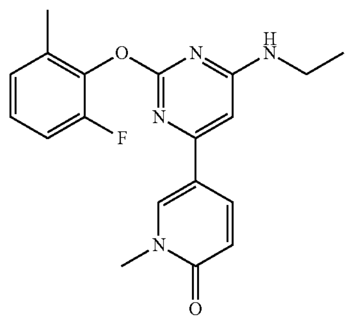 [SMILES: CCNc1cc(-c2ccc(=O)n(C)c2)nc(Oc2c(C)cccc2F)n1] | 5-[6-Ethylamino-2-(2-fluoro-6-methyl-phenoxy)-pyrimidin-4-yl]-1-methyl-1H-pyridin-2-one |
| 292 | 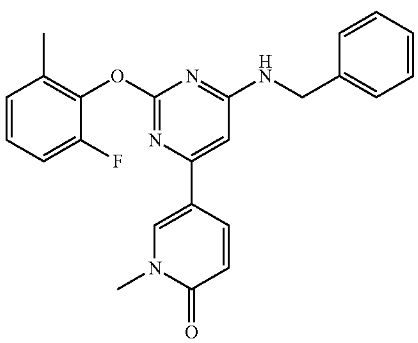 | 5-[6-Benzylamino-2-(2-fluoro-6-methyl-phenoxy)-pyrimidin-4-yl]-1-methyl-1H-pyridin-2-one |
| 293 | 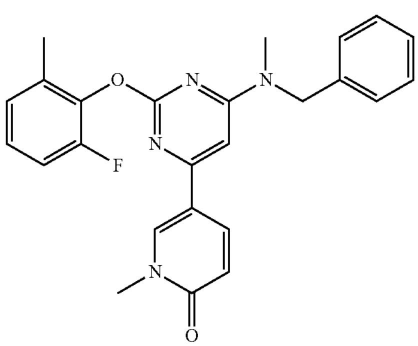 [SMILES: Cc1cccc(F)c1Oc1nc(-c2ccc(=O)n(C)c2)cc(N(C)Cc2ccccc2)n1] | 5-[6-(Benzyl-methyl-amino)-2-(2-fluoro-6-methyl-phenoxy)-pyrimidin-4-yl]-1-methyl-1H-pyridin-2-one |
| 294 | 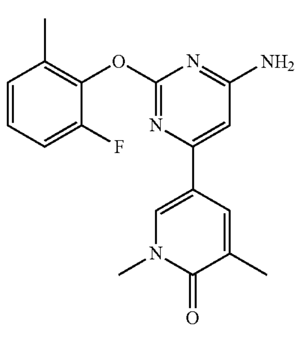 [SMILES: Cc1cccc(F)c1Oc1nc(N)cc(-c2cc(C)c(=O)n(C)c2)n1] | 5-[6-Amino-2-(2-fluoro-6-methyl-phenoxy)-pyrimidin-4-yl]-1,3-dimethyl-1H-pyridin-2-one |

TABLE 1-continued

| Example | Structure | Name |
|---|---|---|
| 295 | 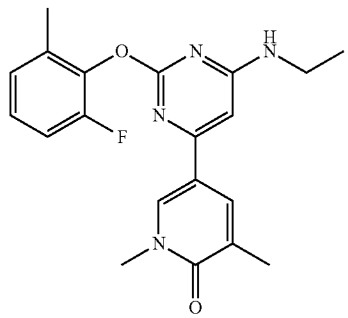 [SMILES: CCNc1cc(-c2cc(C)c(=O)n(C)c2)nc(Oc2c(C)cccc2F)n1] | 5-[6-Ethylamino-2-(2-fluoro-6-methyl-phenoxy)-pyrimidin-4-yl]-1,3-dimethyl-1H-pyridin-2-one |
| 296 | 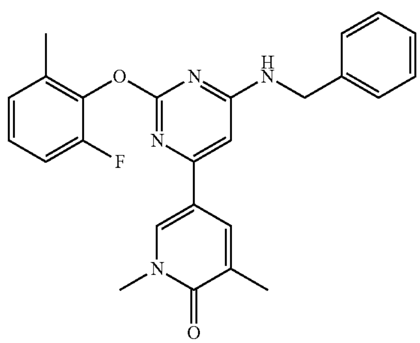 | 5-[6-Benzylamino-2-(2-fluoro-6-methyl-phenoxy)-pyrimidin-4-yl]-1,3-dimethyl-1H-pyridin-2-one |
| 297 | 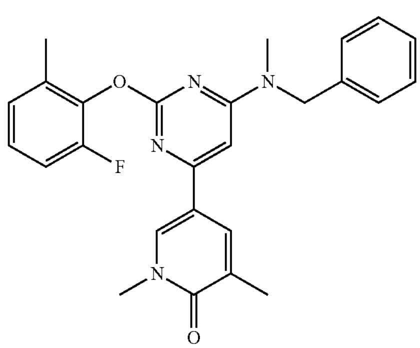 | 5-[6-(Benzyl-methyl-amino)-2-(2-fluoro-6-methyl-phenoxy)-pyrimidin-4-yl]-1,3-dimethyl-1H-pyridin-2-one |
| 298 | 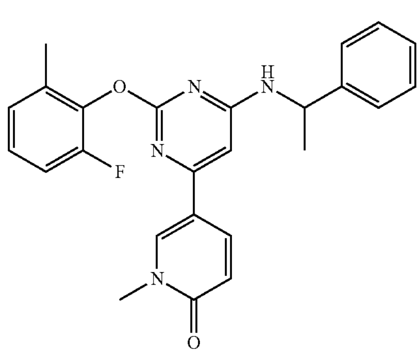 | 5-[2-(2-Fluoro-6-methyl-phenoxy)-6-(1-phenyl-ethylamino)-pyrimidin-4-yl]-1-methyl-1H-pyridin-2-one |

TABLE 1-continued

| Example | Structure | Name |
|---|---|---|
| 299 | 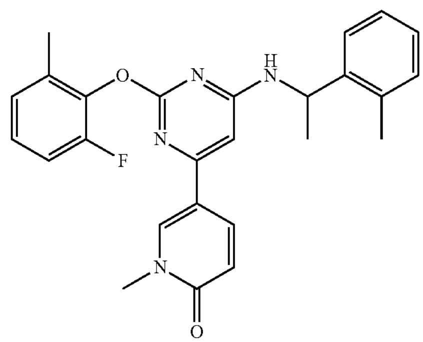 [SMILES: Cc1ccccc1C(C)Nc1cc(-c2ccc(=O)n(C)c2)nc(Oc2c(C)cccc2F)n1] | 5-[2-(2-Fluoro-6-methyl-phenoxy)-6-(1-o-tolyl-ethylamino)-pyrimidin-4-yl]-1-methyl-1H-pyridin-2-one |
| 300 | 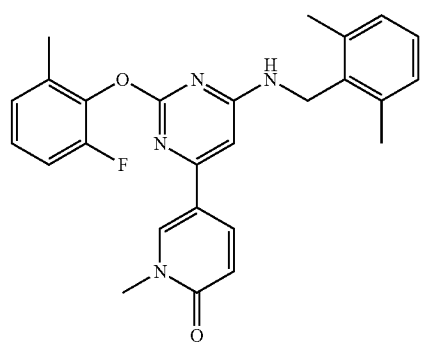 [SMILES: Cc1cccc(C)c1CNc1cc(-c2ccc(=O)n(C)c2)nc(Oc2c(C)cccc2F)n1] | 5-[6-(2,6-Dimethyl-benzylamino)-2-(2-fluoro-6-methyl-phenoxy)-pyrimidin-4-yl]-1-methyl-1H-pyridin-2-one |
| 301 | 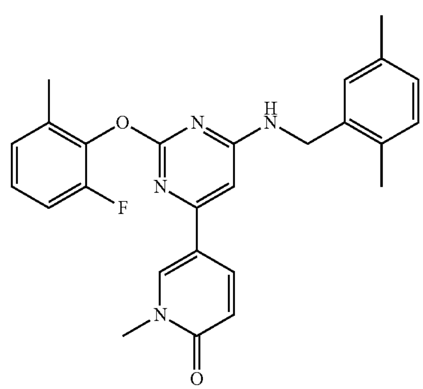 [SMILES: Cc1ccc(C)c(CNc2cc(-c3ccc(=O)n(C)c3)nc(Oc3c(C)cccc3F)n2)c1] | 5-[6-(2,5-Dimethyl-benzylamino)-2-(2-fluoro-6-methyl-phenoxy)-pyrimidin-4-yl]-1-methyl-1H-pyridin-2-one |
| 302 | 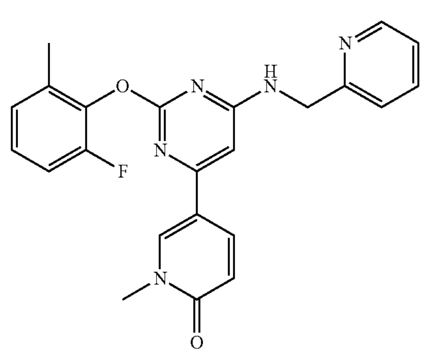 | 5-{2-(2-Fluoro-6-methyl-phenoxy)-6-[(pyridin-2-ylmethyl)-amino]-pyrimidin-4-yl}-1-methyl-1H-pyridin-2-one |

TABLE 1-continued

| Example | Structure | Name |
|---|---|---|
| 303 | 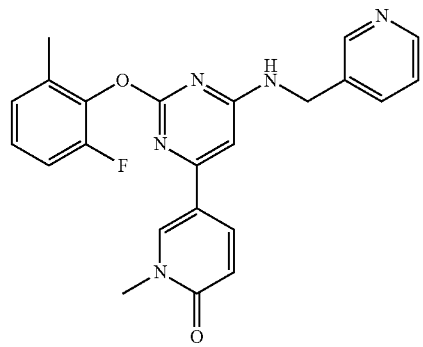 [SMILES: Cc1cccc(F)c1Oc1nc(NCc2cccnc2)cc(-c2ccc(=O)n(C)c2)n1] | 5-{2-(2-Fluoro-6-methyl-phenoxy)-6-[(pyridin-3-ylmethyl)-amino]-pyrimidin-4-yl}-1-methyl-1H-pyridin-2-one |
| 304 | 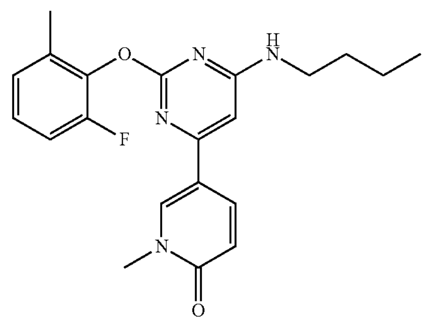 | 5-[6-Butylamino-2-(2-fluoro-6-methyl-phenoxy)-pyrimidin-4-yl]-1-methyl-1H-pyridin-2-one |
| 305 | 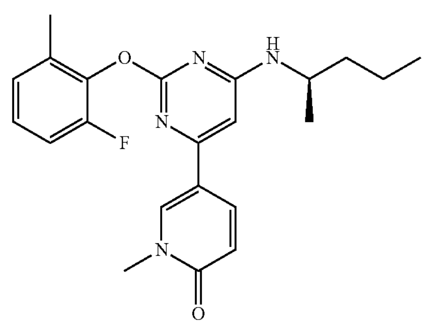 [SMILES: CCC[C@@H](C)Nc1cc(-c2ccc(=O)n(C)c2)nc(Oc2c(C)cccc2F)n1] | (R)-5-[2-(2-Fluoro-6-methyl-phenoxy)-6-(1-methyl-butylamino)-pyrimidin-4-yl]-1-methyl-1H-pyridin-2-one |
| 306 | 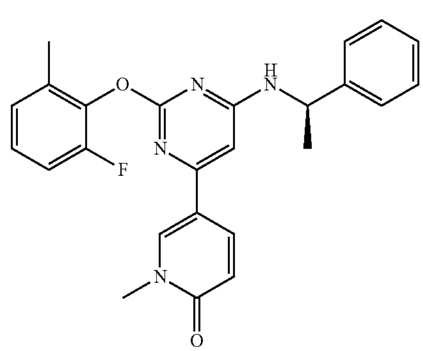 | (R)-5-[2-(2-Fluoro-6-methyl-phenoxy)-6-(1-phenyl-ethylamino)-pyrimidin-4-yl]-1-methyl-1H-pyridin-2-one |

TABLE 1-continued

| Example | Structure | Name |
|---|---|---|
| 307 | 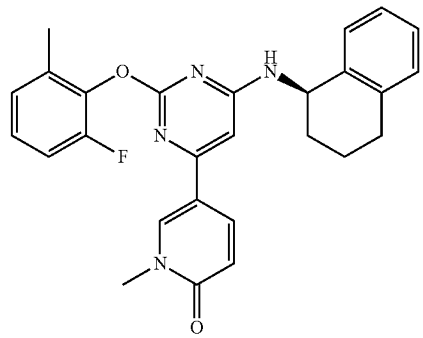 [SMILES: Cc1cccc(F)c1Oc1nc(N[C@@H]2CCCc3ccccc32)cc(-c2ccc(=O)n(C)c2)n1] | (R)-5-[2-(2-Fluoro-6-methyl-phenoxy)-6-(1,2,3,4-tetrahydro-naphthalen-1-ylamino)-pyrimidin-4-yl]-1-methyl-1H-pyridin-2-one |
| 308 | 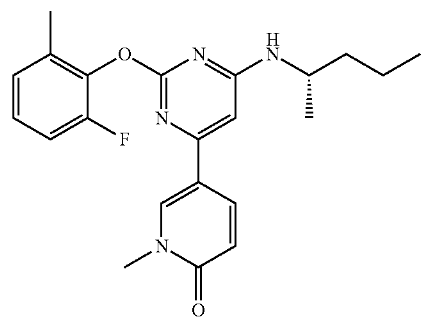 [SMILES: CCC[C@H](C)Nc1cc(-c2ccc(=O)n(C)c2)nc(Oc2c(C)cccc2F)n1] | (S)-5-[2-(2-Fluoro-6-methyl-phenoxy)-6-(1,2,3,4-tetrahydro-naphthalen-1-ylamino)-pyrimidin-4-yl]-1-methyl-1H-pyridin-2-one |
| 309 | 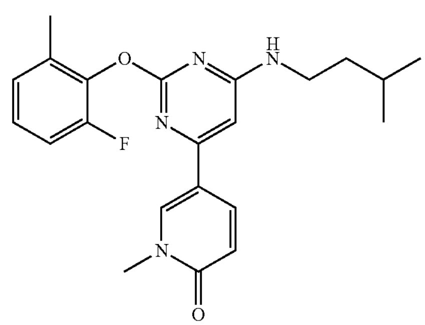 [SMILES: Cc1cccc(F)c1Oc1nc(NCCC(C)C)cc(-c2ccc(=O)n(C)c2)n1] | 5-[2-(2-Fluoro-6-methyl-phenoxy)-6-(3-methyl-butylamino)-pyrimidin-4-yl]-1-methyl-1H-pyridin-2-one |
| 310 | 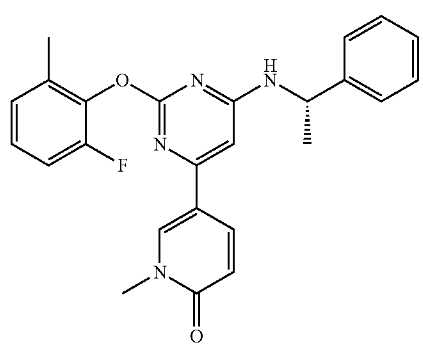 [SMILES: Cc1cccc(F)c1Oc1nc(N[C@@H](C)c2ccccc2)cc(-c2ccc(=O)n(C)c2)n1] | (S)-5-[2-(2-Fluoro-6-methyl-phenoxy)-6-(1-phenyl-ethylamino)-pyrimidin-4-yl]-1-methyl-1H-pyridin-2-one |

TABLE 1-continued

| Example | Structure | Name |
|---|---|---|
| 311 | 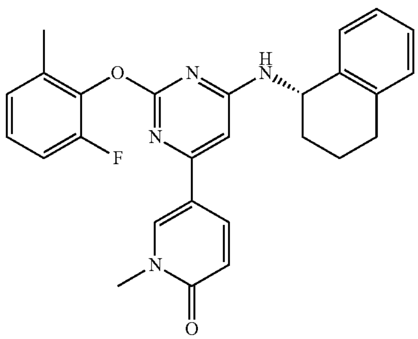 | (S)-5-[2-(2-Fluoro-6-methyl-phenoxy)-6-(1,2,3,4-tetrahydro-naphthalen-1-ylamino)-pyrimidin-4-yl]-1-methyl-1H-pyridin-2-one |
| 312 | 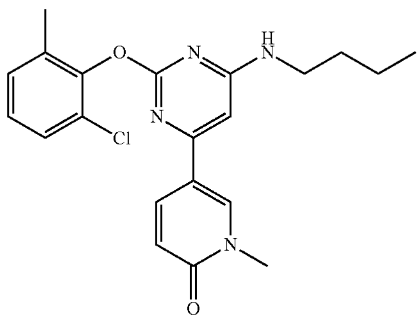 [SMILES: CCCCNc1cc(-c2ccc(=O)n(C)c2)nc(Oc2c(C)cccc2Cl)n1] | 5-[6-Butylamino-2-(2-chloro-6-methyl-phenoxy)-pyrimidin-4-yl]-1-methyl-1H-pyridin-2-one |
| 313 | 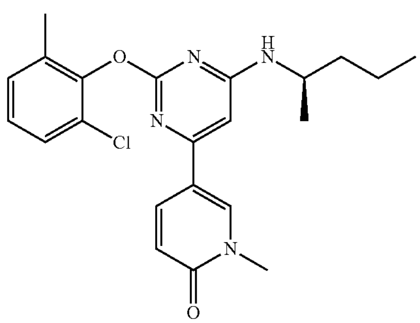 | (R)-5-[2-(2-Chloro-6-methyl-phenoxy)-6-(1-methyl-butylamino)-pyrimidin-4-yl]-1-methyl-1H-pyridin-2-one |
| 314 | 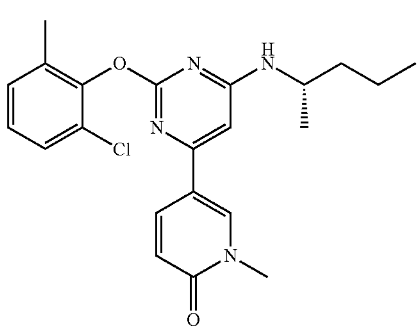 [SMILES: CCC[C@H](C)Nc1cc(-c2ccc(=O)n(C)c2)nc(Oc2c(C)cccc2Cl)n1] | (S)-5-[2-(2-Chloro-6-methyl-phenoxy)-6-(1-methyl-butylamino)-pyrimidin-4-yl]-1-methyl-1H-pyridin-2-one |

TABLE 1-continued

| Example | Structure | Name |
|---|---|---|
| 315 | 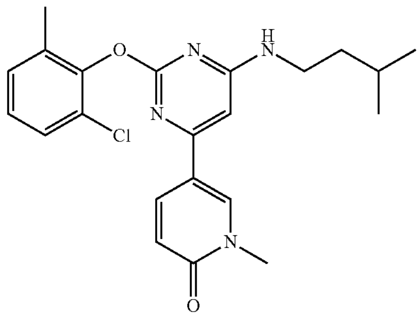 [SMILES: Cc1cccc(Cl)c1Oc1nc(NCCC(C)C)cc(-c2ccc(=O)n(C)c2)n1] | 5-[2-(2-Chloro-6-methyl-phenoxy)-6-(3-methyl-butylamino)-pyrimidin-4-yl]-1-methyl-1H-pyridin-2-one |
| 316 | 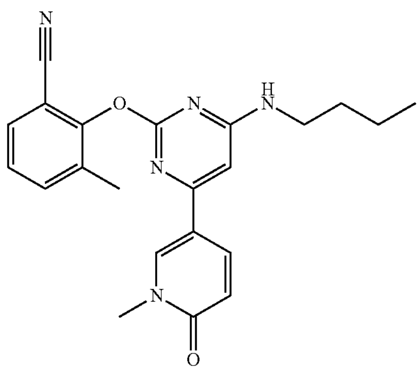 [SMILES: CCCCNc1cc(-c2ccc(=O)n(C)c2)nc(Oc2c(C)cccc2C#N)n1] | 2-[4-Butylamino-6-(1-methyl-6-oxo-1,6-dihydro-pyridin-3-yl)-pyrimidin-2-yloxy]-3-methyl-benzonitrile |
| 317 | 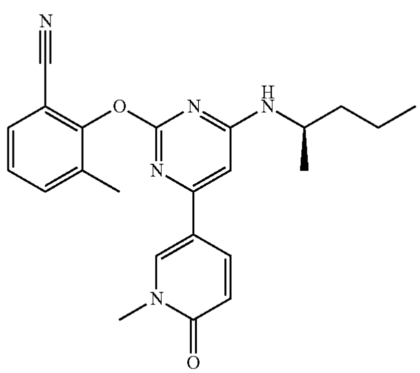 [SMILES: CCC[C@@H](C)Nc1cc(-c2ccc(=O)n(C)c2)nc(Oc2c(C)cccc2C#N)n1] | (R)-3-Methyl-2-[4-(1-methyl-butylamino)-6-(1-methyl-6-oxo-1,6-dihydro-pyridin-3-yl)-pyrimidin-2-yloxy]-benzonitrile |
| 318 | 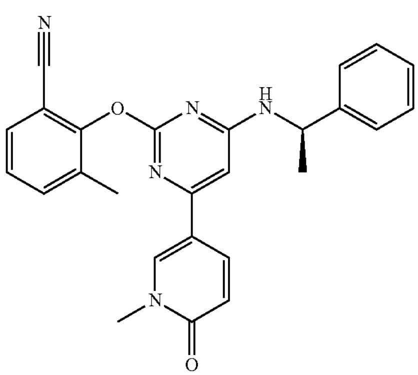 | (R)-3-Methyl-2-[4-(1-methyl-6-oxo-1,6-dihydro-pyridin-3-yl)-6-(1-phenyl-ethylamino)-pyrimidin-2-yloxy]-benzonitrile |

TABLE 1-continued

| Example | Structure | Name |
|---|---|---|
| 319 | 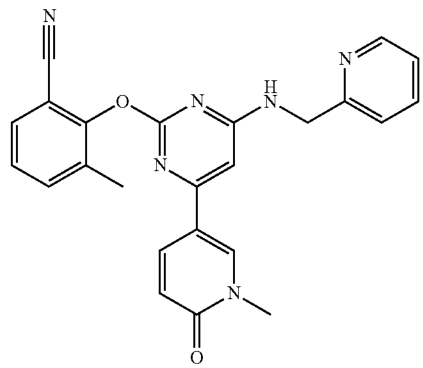 [SMILES: Cc1cccc(C#N)c1Oc1nc(NCc2ccccn2)cc(-c2ccc(=O)n(C)c2)n1] | 3-Methyl-2-{4-(1-methyl-6-oxo-1,6-dihydro-pyridin-3-yl)-6-[(pyridin-2-ylmethyl)-amino]-pyrimidin-2-yloxy}-benzonitrile |
| 320 | 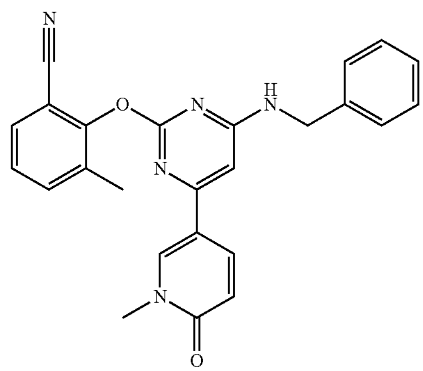 | 2-[4-Benzylamino-6-(1-methyl-6-oxo-1,6-dihydro-pyridin-3-yl)-pyrimidin-2-yloxy]-3-methyl-benzonitrile |
| 321 | 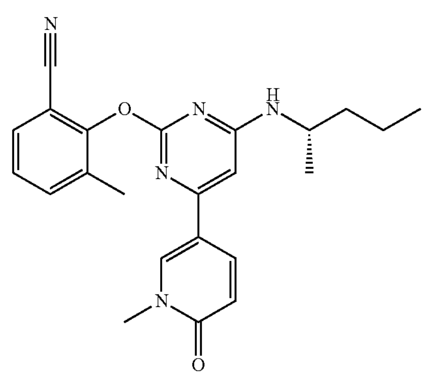 [SMILES: CCC[C@H](C)Nc1cc(-c2ccc(=O)n(C)c2)nc(Oc2c(C)cccc2C#N)n1] | (S)-3-Methyl-2-[4-(1-methyl-butylamino)-6-(1-methyl-6-oxo-1,6-dihydro-pyridin-3-yl)-pyrimidin-2-yloxy]-benzonitrile |
| 322 | 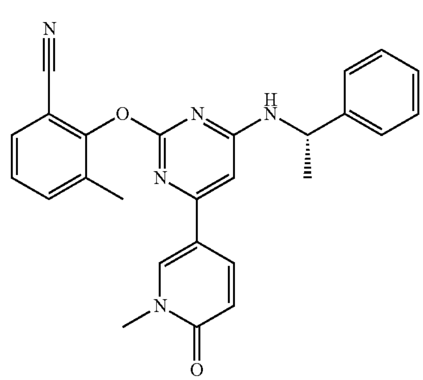 | (S)-3-Methyl-2-[4-(1-methyl-6-oxo-1,6-dihydro-pyridin-3-yl)-6-(1-phenyl-ethylamino)-pyrimidin-2-yloxy]-benzonitrile |

TABLE 1-continued

| Example | Structure | Name |
|---|---|---|
| 323 | 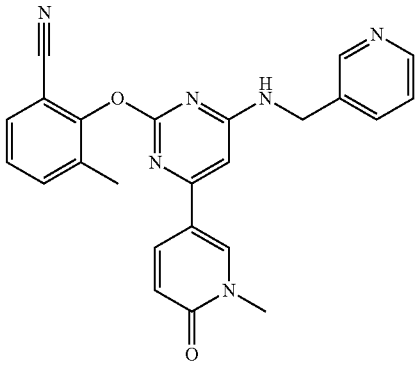 | 3-Methyl-2-{4-(1-methyl-6-oxo-1,6-dihydro-pyridin-3-yl)-6-[(pyridin-3-ylmethyl)-amino]-pyrimidin-2-yloxy}-benzonitrile |
| 324 | 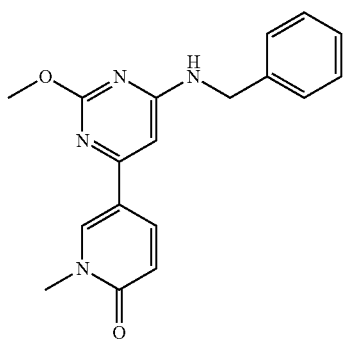 [SMILES: COc1nc(NCc2ccccc2)cc(-c2ccc(=O)n(C)c2)n1] | 5-(6-Benzylamino-2-methoxy-pyrimidin-4-yl)-1-methyl-1H-pyridin-2-one |
| 325 | 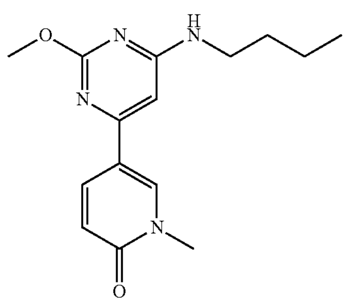 [SMILES: CCCCNc1cc(-c2ccc(=O)n(C)c2)nc(OC)n1] | 5-(6-Butylamino-2-methoxy-pyrimidin-4-yl)-1-methyl-1H-pyridin-2-one |
| 326 | 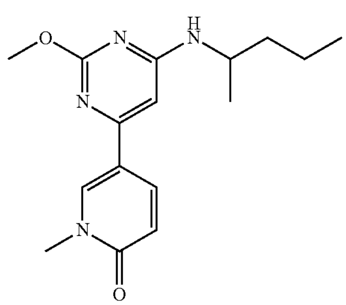 [SMILES: CCCC(C)Nc1cc(-c2ccc(=O)n(C)c2)nc(OC)n1] | 5-[2-Methoxy-6-(1-methyl-butylamino)-pyrimidin-4-yl]-1-methyl-1H-pyridin-2-one |

TABLE 1-continued

| Example | Structure | Name |
|---|---|---|
| 327 | 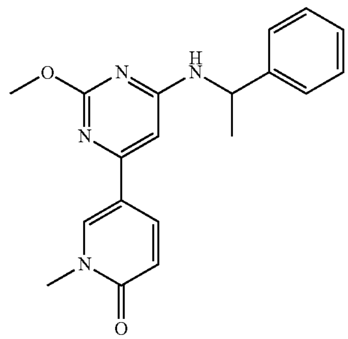 [SMILES: COc1nc(NC(C)c2ccccc2)cc(-c2ccc(=O)n(C)c2)n1] | 5-[2-Methoxy-6-(1-phenyl-ethylamino)-pyrimidin-4-yl]-1-methyl-1H-pyridin-2-one |
| 328 | 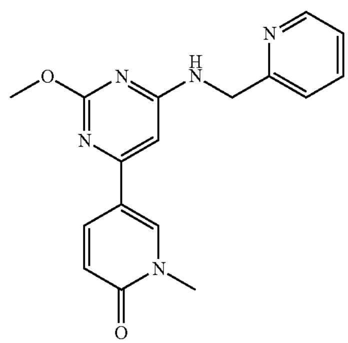 [SMILES: COc1nc(NCc2ccccn2)cc(-c2ccc(=O)n(C)c2)n1] | 5-{2-Methoxy-6-[(pyridin-2-ylmethyl)-amino]-pyrimidin-4-yl}-1-methyl-1H-pyridin-2-one |
| 329 | 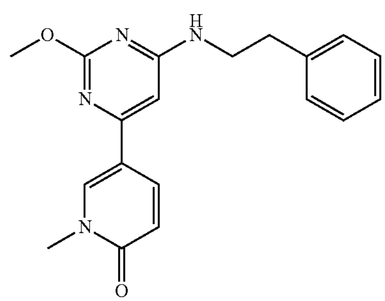 [SMILES: COc1nc(NCCc2ccccc2)cc(-c2ccc(=O)n(C)c2)n1] | 5-(2-Methoxy-6-phenethylamino-pyrimidin-4-yl)-1-methyl-1H-pyridin-2-one |
| 330 | 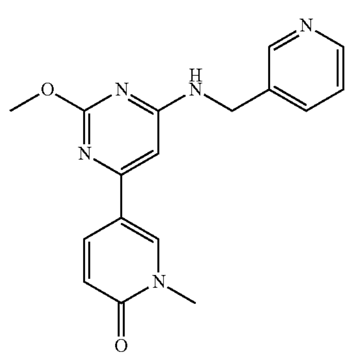 [SMILES: COc1nc(NCc2cccnc2)cc(-c2ccc(=O)n(C)c2)n1] | 5-{2-Methoxy-6-[(pyridin-3-ylmethyl)-amino]-pyrimidin-4-yl}-1-methyl-1H-pyridin-2-one |

TABLE 1-continued

| Example | Structure | Name |
|---|---|---|
| 331 | 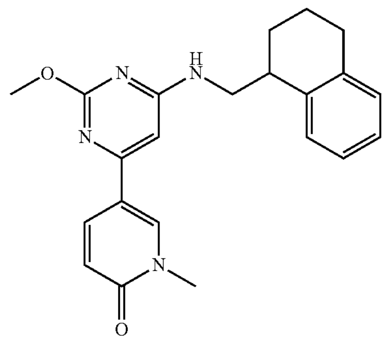 [SMILES: COc1nc(NCC2CCCc3ccccc32)cc(-c2ccc(=O)n(C)c2)n1] | 5-{2-Methoxy-6-[(1,2,3,4-tetrahydro-naphthalen-1-ylmethyl)-amino]-pyrimidin-4-yl}-1-methyl-1H-pyridin-2-one |
| 332 | 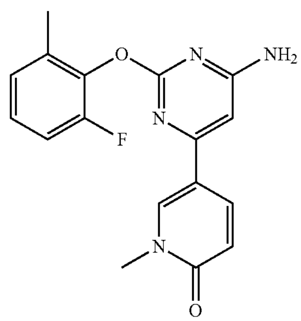 [SMILES: Cc1cccc(F)c1Oc1nc(N)cc(-c2ccc(=O)n(C)c2)n1] | 5-[6-Amino-2-(2-fluoro-6-methyl-phenoxy)-pyrimidin-4-yl]-1-methyl-1H-pyridin-2-one |
| 333 | 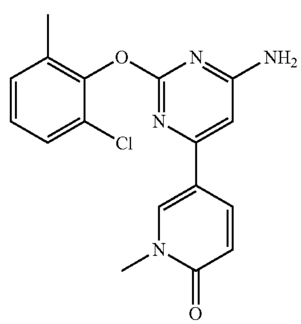 [SMILES: Cc1cccc(Cl)c1Oc1nc(N)cc(-c2ccc(=O)n(C)c2)n1] | 5-[6-Amino-2-(2-chloro-6-methyl-phenoxy)-pyrimidin-4-yl]-1-methyl-1H-pyridin-2-one |
| 334 | 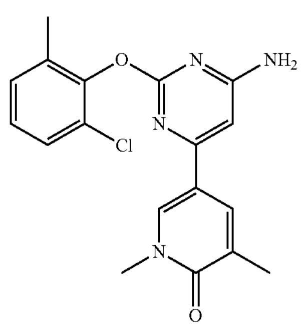 [SMILES: Cc1cccc(Cl)c1Oc1nc(N)cc(-c2cc(C)c(=O)n(C)c2)n1] | 5-[6-Amino-2-(2-chloro-6-methyl-phenoxy)-pyrimidin-4-yl]-1,3-dimethyl-1H-pyridin-2-one |

TABLE 1-continued

| Example | Structure | Name |
|---|---|---|
| 335 | 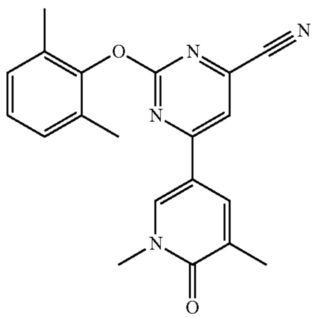 | 6-(1,5-dimethyl-6-oxo(3-hydropyridyl))-2-(2,6-dimethylphenoxy)pyrimidine-4-carbonitrile |
| 336 | 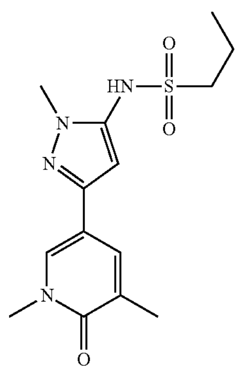 [SMILES: CCCS(=O)(=O)Nc1cc(-c2cc(C)c(=O)n(C)c2)nn1C] | Propane-1-sulfonic acid [5-(1,5-dimethyl-6-oxo-1,6-dihydro-pyridin-3-yl)-2-methyl-2H-pyrazol-3-yl]-amide |
| 337 | 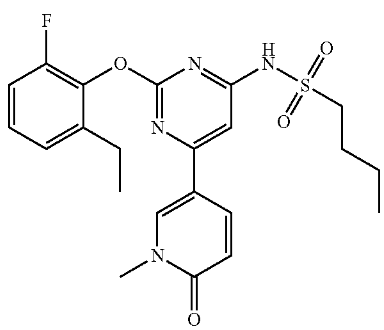 [SMILES: CCCCS(=O)(=O)Nc1cc(-c2ccc(=O)n(C)c2)nc(Oc2c(F)cccc2CC)n1] | N-(2-(2-ethyl-6-fluorophenoxy)-6-(1-methyl-6-oxo-1,6-dihydropyridin-3-yl)pyrimidin-4-yl)butane-1-sulfonamide |
| 338 | 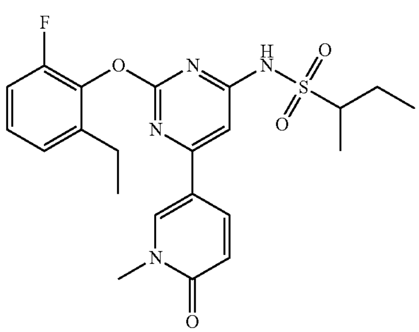 [SMILES: CCc1cccc(F)c1Oc1nc(NS(=O)(=O)C(C)CC)cc(-c2ccc(=O)n(C)c2)n1] | N-(2-(2-ethyl-6-fluorophenoxy)-6-(1-methyl-6-oxo-1,6-dihydropyridin-3-yl)pyrimidin-4-yl)butane-2-sulfonamide |

TABLE 1-continued

| Example | Structure | Name |
|---|---|---|
| 339 | 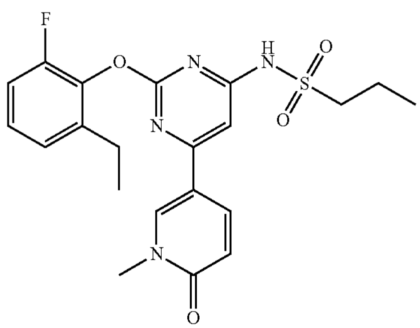 [SMILES: CCCS(=O)(=O)Nc1cc(-c2ccc(=O)n(C)c2)nc(Oc2c(F)cccc2CC)n1] | N-(2-(2-ethyl-6-fluorophenoxy)-6-(1-methyl-6-oxo-1,6-dihydropyridin-3-yl)pyrimidin-4-yl)propane-1-sulfonamide |
| 340 | 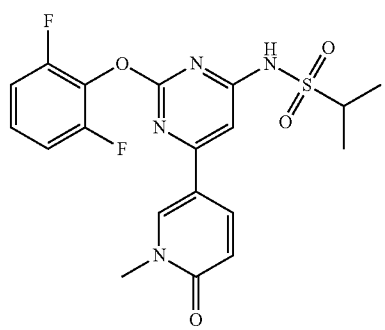 | N-(2-(2,6-difluorophenoxy)-6-(1-methyl-6-oxo-1,6-dihydropyridin-3-yl)pyrimidin-4-yl)propane-2-sulfonamide |
| 341 | 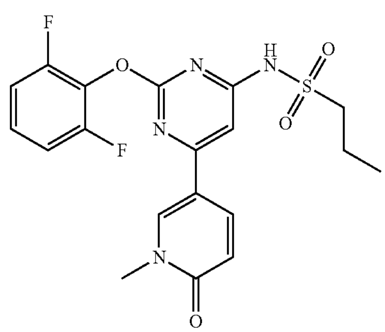 [SMILES: CCCS(=O)(=O)Nc1cc(-c2ccc(=O)n(C)c2)nc(Oc2c(F)cccc2F)n1] | N-(2-(2,6-difluorophenoxy)-6-(1-methyl-6-oxo-1,6-dihydropyridin-3-yl)pyrimidin-4-yl)propane-1-sulfonamide |
| 342 | 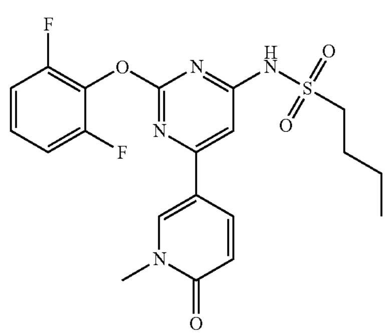 [SMILES: CCCCS(=O)(=O)Nc1cc(-c2ccc(=O)n(C)c2)nc(Oc2c(F)cccc2F)n1] | N-(2-(2,6-difluorophenoxy)-6-(1-methyl-6-oxo-1,6-dihydropyridin-3-yl)pyrimidin-4-yl)butane-1-sulfonamide |

TABLE 1-continued

| Example | Structure | Name |
|---|---|---|
| 343 | 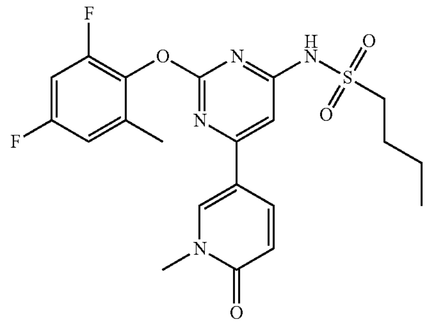 [SMILES: CCCCS(=O)(=O)Nc1cc(-c2ccc(=O)n(C)c2)nc(Oc2c(C)cc(F)cc2F)n1] | N-(2-(2,4-difluoro-6-methylphenoxy)-6-(1-methyl-6-oxo-1,6-dihydropyridin-3-yl)pyrimidin-4-yl)butane-1-sulfonamide |
| 344 | 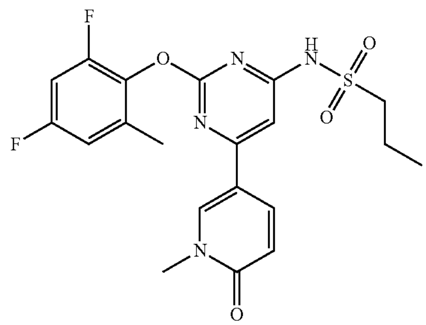 [SMILES: CCCS(=O)(=O)Nc1cc(-c2ccc(=O)n(C)c2)nc(Oc2c(C)cc(F)cc2F)n1] | N-(2-(2,4-difluoro-6-methylphenoxy)-6-(1-methyl-6-oxo-1,6-dihydropyridin-3-yl)pyrimidin-4-yl)propane-1-sulfonamide |
| 345 | 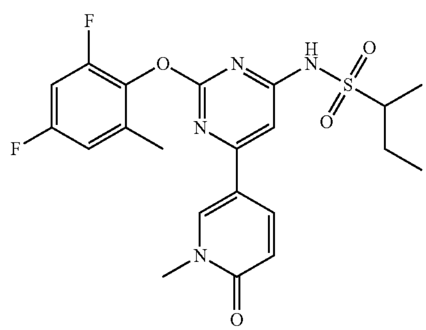 [SMILES: CCC(C)S(=O)(=O)Nc1cc(-c2ccc(=O)n(C)c2)nc(Oc2c(C)cc(F)cc2F)n1] | N-(2-(2,4-difluoro-6-methylphenoxy)-6-(1-methyl-6-oxo-1,6-dihydropyridin-3-yl)pyrimidin-4-yl)butane-2-sulfonamide |
| 346 | 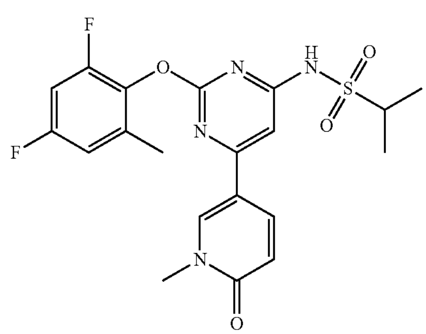 [SMILES: Cc1cc(F)cc(F)c1Oc1nc(NS(=O)(=O)C(C)C)cc(-c2ccc(=O)n(C)c2)n1] | N-(2-(2,4-difluoro-6-methylphenoxy)-6-(1-methyl-6-oxo-1,6-dihydropyridin-3-yl)pyrimidin-4-yl)propane-2-sulfonamide |

TABLE 1-continued

| Example | Structure | Name |
|---|---|---|
| 347 | 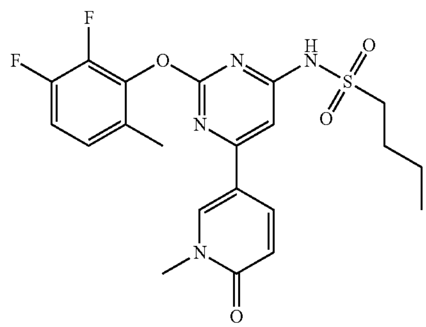 [SMILES: CCCCS(=O)(=O)Nc1cc(-c2ccc(=O)n(C)c2)nc(Oc2c(C)ccc(F)c2F)n1] | N-(2-(2,3-difluoro-6-methylphenoxy)-6-(1-methyl-6-oxo-1,6-dihydropyridin-3-yl)pyrimidin-4-yl)butane-1-sulfonamide |
| 348 | 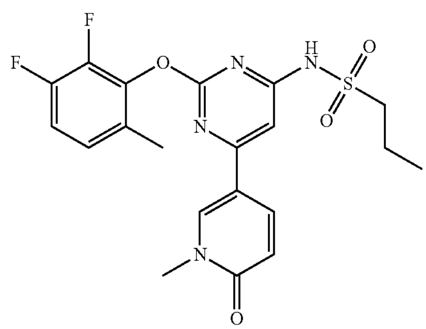 [SMILES: CCCS(=O)(=O)Nc1cc(-c2ccc(=O)n(C)c2)nc(Oc2c(C)ccc(F)c2F)n1] | N-(2-(2,3-difluoro-6-methylphenoxy)-6-(1-methyl-6-oxo-1,6-dihydropyridin-3-yl)pyrimidin-4-yl)propane-1-sulfonamide |
| 349 | 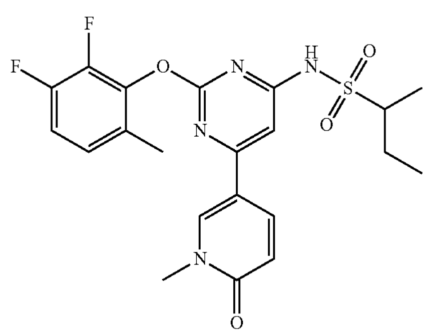 [SMILES: CCC(C)S(=O)(=O)Nc1cc(-c2ccc(=O)n(C)c2)nc(Oc2c(C)ccc(F)c2F)n1] | N-(2-(2,3-difluoro-6-methylphenoxy)-6-(1-methyl-6-oxo-1,6-dihydropyridin-3-yl)pyrimidin-4-yl)butane-2-sulfonamide |
| 350 | 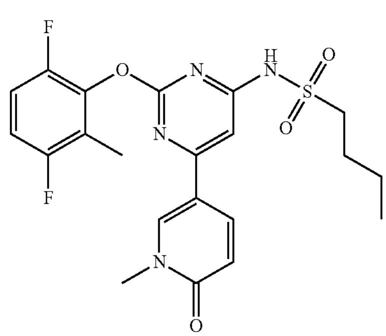 [SMILES: CCCCS(=O)(=O)Nc1cc(-c2ccc(=O)n(C)c2)nc(Oc2c(F)ccc(F)c2C)n1] | N-(2-(3,6-difluoro-2-methylphenoxy)-6-(1-methyl-6-oxo-1,6-dihydropyridin-3-yl)pyrimidin-4-yl)butane-1-sulfonamide |

TABLE 1-continued

| Example | Structure | Name |
|---|---|---|
| 351 | 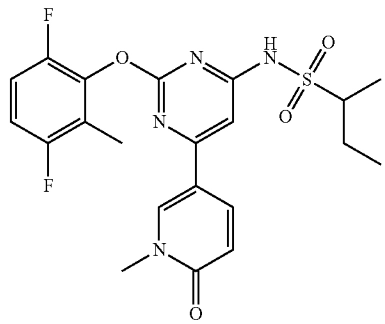 [SMILES: CCC(C)S(=O)(=O)Nc1cc(-c2ccc(=O)n(C)c2)nc(Oc2c(F)ccc(F)c2C)n1] | N-(2-(3,6-difluoro-2-methylphenoxy)-6-(1-methyl-6-oxo-1,6-dihydropyridin-3-yl)pyrimidin-4-yl)butane-2-sulfonamide |
| 352 | 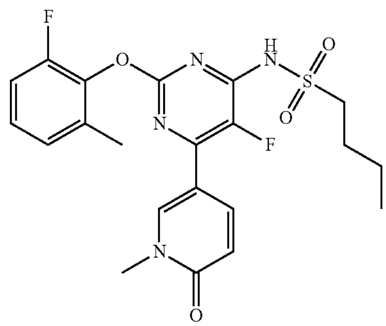 [SMILES: CCCCS(=O)(=O)Nc1nc(Oc2c(C)cccc2F)nc(-c2ccc(=O)n(C)c2)c1F] | N-(5-fluoro-2-(2-fluoro-6-methylphenoxy)-6-(1-methyl-6-oxo-1,6-dihydropyridin-3-yl)pyrimidin-4-yl)butane-1-sulfonamide |
| 353 | 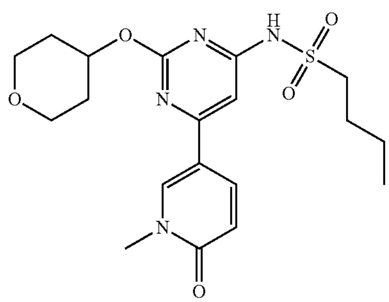 [SMILES: CCCCS(=O)(=O)Nc1cc(-c2ccc(=O)n(C)c2)nc(OC2CCOCC2)n1] | N-(6-(1-methyl-6-oxo-1,6-dihydropyridin-3-yl)-2-((tetrahydro-2H-pyran-4-yl)oxy)pyrimidin-4-yl)butane-1-sulfonamide |
| 354 | 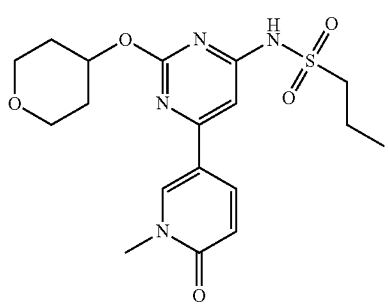 [SMILES: CCCS(=O)(=O)Nc1cc(-c2ccc(=O)n(C)c2)nc(OC2CCOCC2)n1] | N-(6-(1-methyl-6-oxo-1,6-dihydropyridin-3-yl)-2-((tetrahydro-2H-pyran-4-yl)oxy)pyrimidin-4-yl)propane-1-sulfonamide |
| 355 | 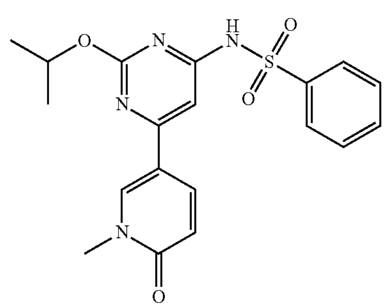 [SMILES: CC(C)Oc1nc(NS(=O)(=O)c2ccccc2)cc(-c2ccc(=O)n(C)c2)n1] | N-(2-isopropoxy-6-(1-methyl-6-oxo-1,6-dihydropyridin-3-yl)pyrimidin-4-yl)benzenesulfonamide |

TABLE 1-continued

| Example | Structure | Name |
|---|---|---|
| 356 | 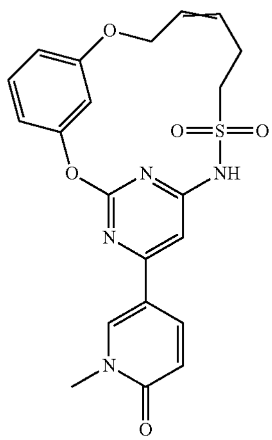 [SMILES: Cn1cc(-c2cc3nc(n2)Oc2cccc(c2)OCC=CCCS(=O)(=O)N3)ccc1=O] | 5-(10,10-dioxido-2,4-dioxa-10-thia-11-aza-1(2,4)-pyrimidina-3(1,3)-benzenacycloundecaphan-6-en-1⁶-yl)-1-methylpyridin-2(1H)-one |
| 357 | 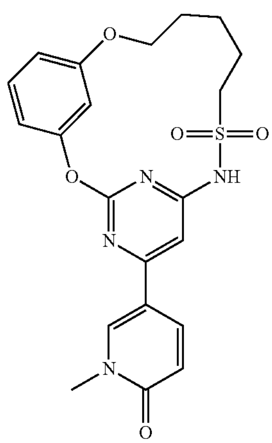 [SMILES: Cn1cc(-c2cc3nc(n2)Oc2cccc(c2)OCCCCCS(=O)(=O)N3)ccc1=O] | 5-(10,10-dioxido-2,4-dioxa-10-thia-11-aza-1(2,4)-pyrimidina-3(1,3)-benzenacycloundecaphane-1⁶-yl)-1-methylpyridin-2(1H)-one |
| 358 | 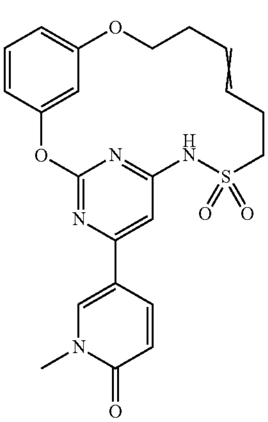 [SMILES: Cn1cc(-c2cc3nc(n2)Oc2cccc(c2)OCCC=CCCS(=O)(=O)N3)ccc1=O] | 5-(11,11-dioxido-2,4-dioxa-11-thia-12-aza-1(2,4)-pyrimidina-3(1,3)-benzenacyclododecaphan-7-en-1⁶-yl)-1-methylpyridin-2(1H)-one |

TABLE 1-continued

| Example | Structure | Name |
|---|---|---|
| 359 | 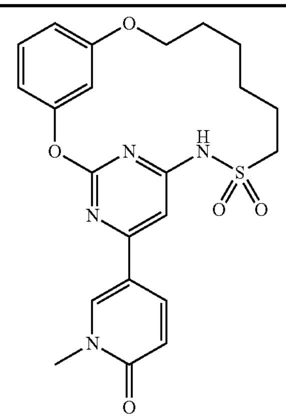 | 5-(11,11-dioxido-2,4-dioxa-11-thia-12-aza-1(2,4)-pyrimidina-3(1,3)-benzenacyclododecaphane-1⁶-yl)-1-methylpyridin-2(1H)-one |
| 360 | | 5-(36-chloro-10,10-dioxido-2,4-dioxa-10-thia-11-aza-1(2,4)-pyrimidina-3(1,3)-benzenacycloundecaphan-6-en-1⁶-yl)-1-methylpyridin-2(1H)-one |
| 361 | | 5-(36-chloro-11,11-dioxido-2,4-dioxa-11-thia-12-aza-1(2,4)-pyrimidina-3(1,3)-benzenacyclododecaphan-6-en-1⁶-yl)-1-methylpyridin-2(1H)-one |
| 362 | | 5-(36-fluoro-11,11-dioxido-2,4-dioxa-11-thia-12-aza-1(2,4)-pyrimidina-3(1,3)-benzenacyclododecaphan-6-en-1⁶-yl)-1-methylpyridin-2(1H)-one |

In some embodiments, the substituted heterocyclic derivative compound disclosed herein has the structure provided in Table 2.

TABLE 2-continued
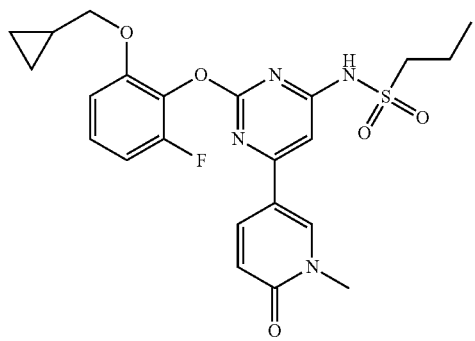 [SMILES: CCCS(=O)(=O)Nc1cc(-c2ccc(=O)n(C)c2)nc(Oc2c(F)cccc2OCC2CC2)n1]
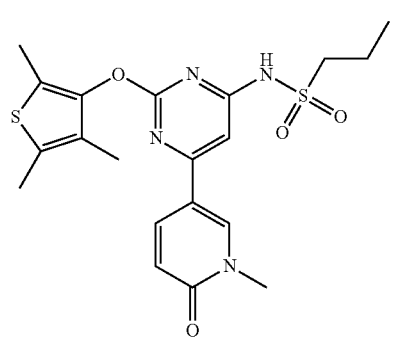 [SMILES: CCCS(=O)(=O)Nc1cc(-c2ccc(=O)n(C)c2)nc(Oc2c(C)sc(C)c2C)n1]
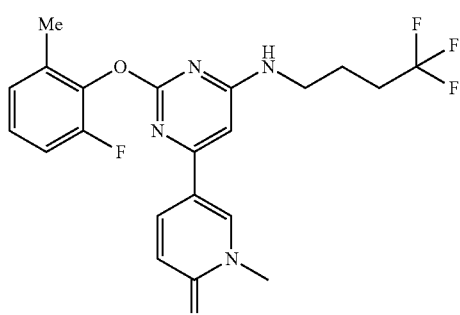
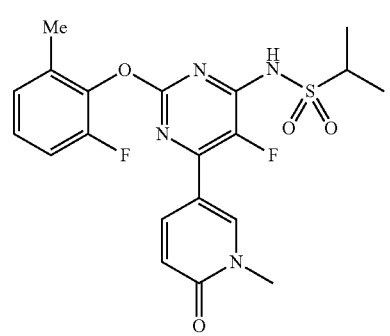 [SMILES: Cc1cccc(F)c1Oc1nc(NS(=O)(=O)C(C)C)c(F)c(-c2ccc(=O)n(C)c2)n1]
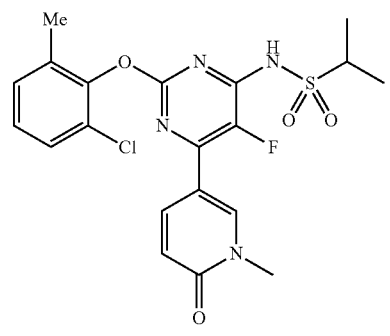 [SMILES: Cc1cccc(Cl)c1Oc1nc(NS(=O)(=O)C(C)C)c(F)c(-c2ccc(=O)n(C)c2)n1]
TABLE 2-continued
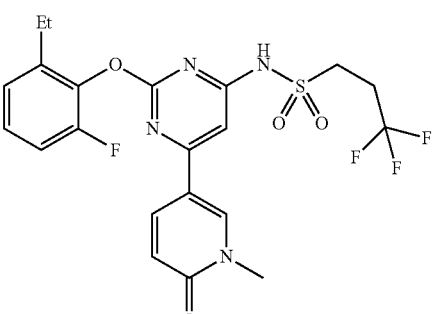
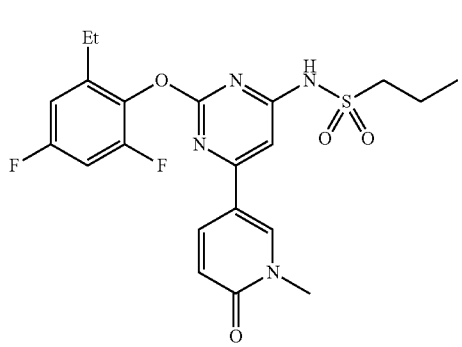 [SMILES: CCCS(=O)(=O)Nc1cc(-c2ccc(=O)n(C)c2)nc(Oc2c(F)cc(F)cc2CC)n1]
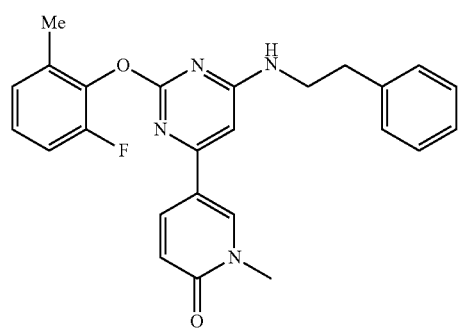 [SMILES: Cc1cccc(F)c1Oc1nc(NCCc2ccccc2)cc(-c2ccc(=O)n(C)c2)n1]
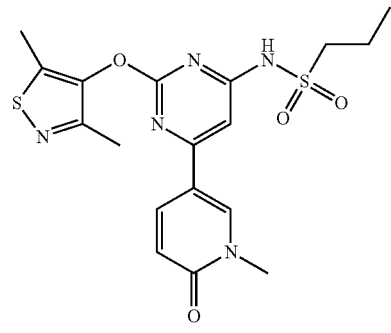 [SMILES: CCCS(=O)(=O)Nc1cc(-c2ccc(=O)n(C)c2)nc(Oc2c(C)nsc2C)n1]

TABLE 2-continued
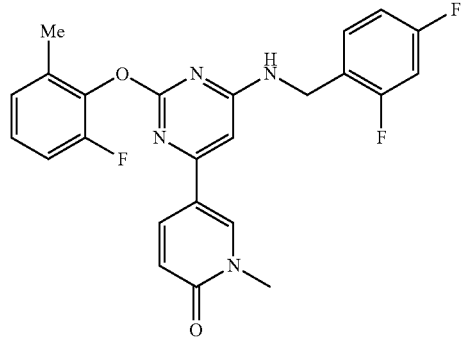 [SMILES: Cc1cccc(F)c1Oc1nc(NCc2ccc(F)cc2F)cc(-c2ccc(=O)n(C)c2)n1]
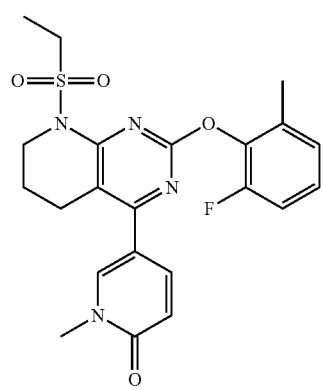 [SMILES: CCS(=O)(=O)N1CCCc2c(-c3ccc(=O)n(C)c3)nc(Oc3c(C)cccc3F)nc21]
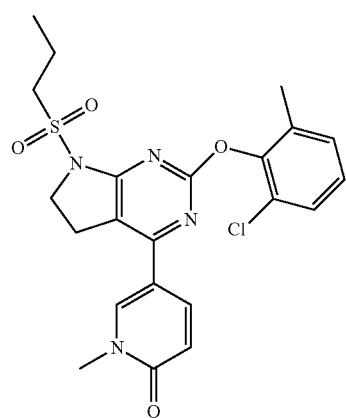 [SMILES: CCCS(=O)(=O)N1CCc2c(-c3ccc(=O)n(C)c3)nc(Oc3c(C)cccc3Cl)nc21]
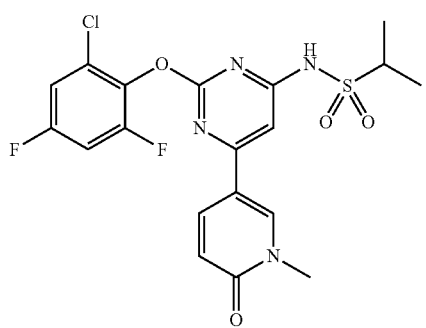 [SMILES: CC(C)S(=O)(=O)Nc1cc(-c2ccc(=O)n(C)c2)nc(Oc2c(F)cc(F)cc2Cl)n1]
TABLE 2-continued
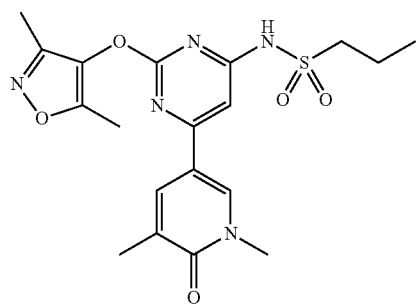 [SMILES: CCCS(=O)(=O)Nc1cc(-c2cc(C)c(=O)n(C)c2)nc(Oc2c(C)noc2C)n1]
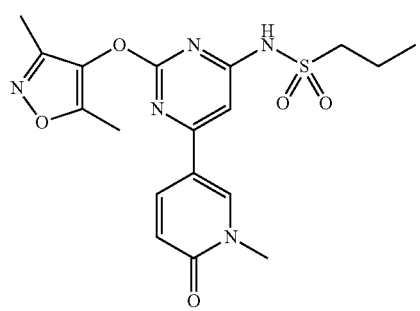 [SMILES: CCCS(=O)(=O)Nc1cc(-c2ccc(=O)n(C)c2)nc(Oc2c(C)noc2C)n1]
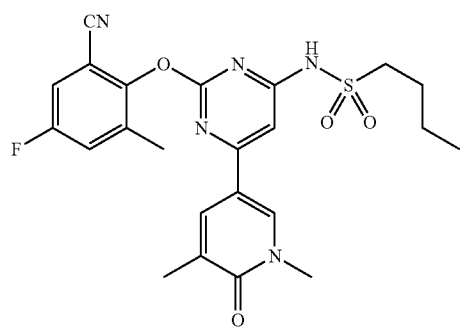 [SMILES: CCCCS(=O)(=O)Nc1cc(-c2cc(C)c(=O)n(C)c2)nc(Oc2c(C)cc(F)cc2C#N)n1]
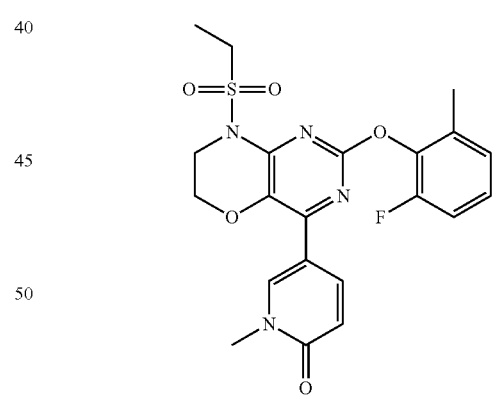
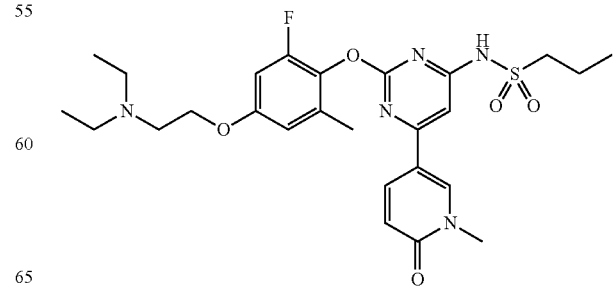

TABLE 2-continued
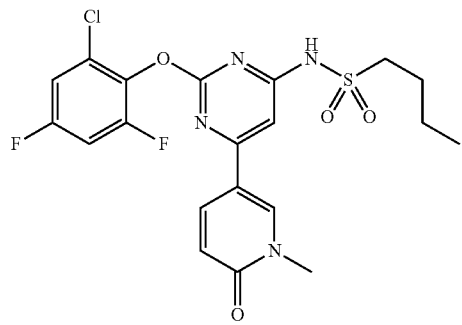
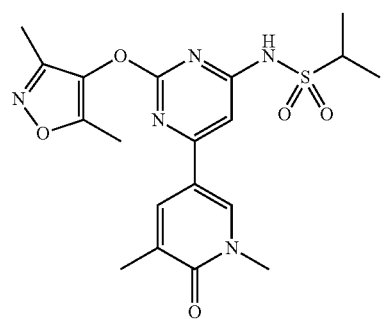 [SMILES: Cc1noc(C)c1Oc1nc(NS(=O)(=O)C(C)C)cc(-c2cc(C)c(=O)n(C)c2)n1]
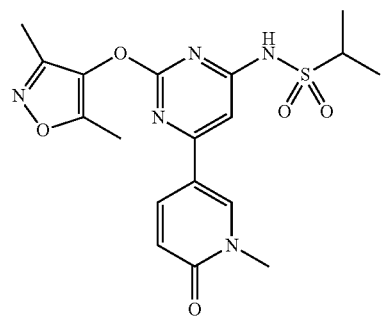 [SMILES: Cc1noc(C)c1Oc1nc(NS(=O)(=O)C(C)C)cc(-c2ccc(=O)n(C)c2)n1]
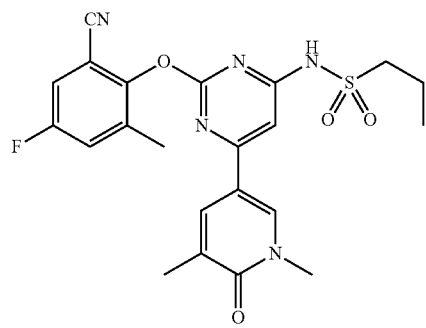 [SMILES: CCCS(=O)(=O)Nc1cc(-c2cc(C)c(=O)n(C)c2)nc(Oc2c(C)cc(F)cc2C#N)n1]
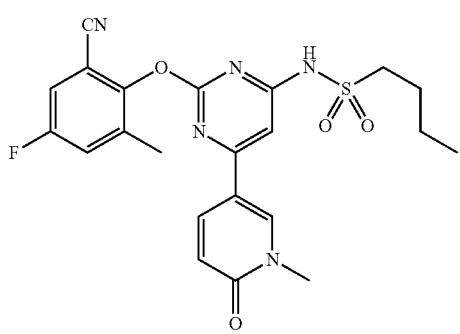 [SMILES: CCCCS(=O)(=O)Nc1cc(-c2ccc(=O)n(C)c2)nc(Oc2c(C)cc(F)cc2C#N)n1]
TABLE 2-continued
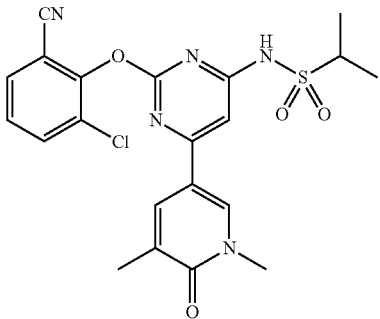 [SMILES: Cc1cc(-c2cc(NS(=O)(=O)C(C)C)nc(Oc3c(Cl)cccc3C#N)n2)cn(C)c1=O]
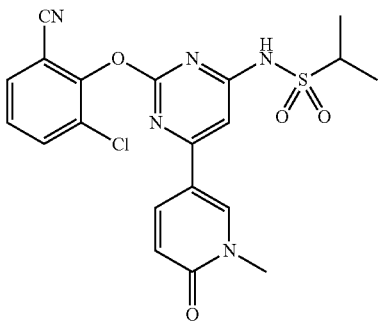 [SMILES: CC(C)S(=O)(=O)Nc1cc(-c2ccc(=O)n(C)c2)nc(Oc2c(Cl)cccc2C#N)n1]
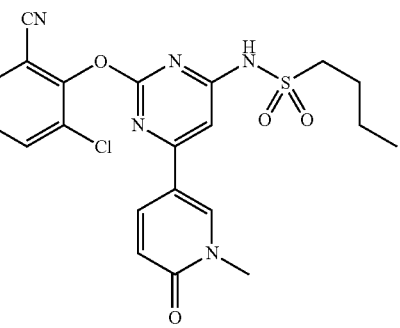
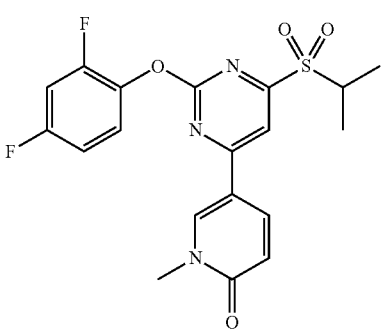 [SMILES: CC(C)S(=O)(=O)c1cc(-c2ccc(=O)n(C)c2)nc(Oc2ccc(F)cc2F)n1]
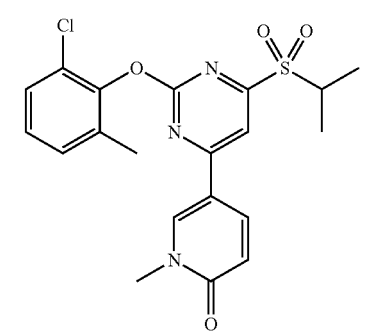 [SMILES: Cc1cccc(Cl)c1Oc1nc(-c2ccc(=O)n(C)c2)cc(S(=O)(=O)C(C)C)n1]

TABLE 2-continued
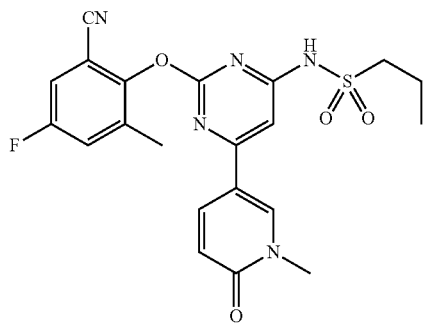 [SMILES: CCCS(=O)(=O)Nc1cc(-c2ccc(=O)n(C)c2)nc(Oc2c(C)cc(F)cc2C#N)n1]
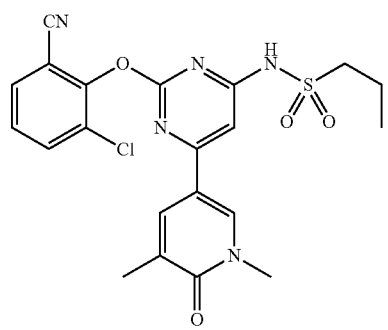 [SMILES: CCCS(=O)(=O)Nc1cc(-c2cc(C)c(=O)n(C)c2)nc(Oc2c(Cl)cccc2C#N)n1]
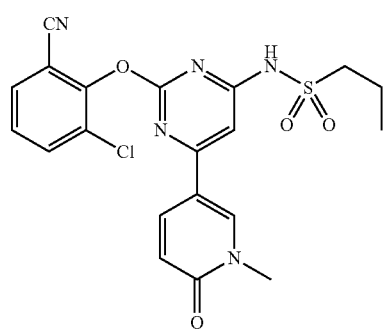 [SMILES: CCCS(=O)(=O)Nc1cc(-c2ccc(=O)n(C)c2)nc(Oc2c(Cl)cccc2C#N)n1]
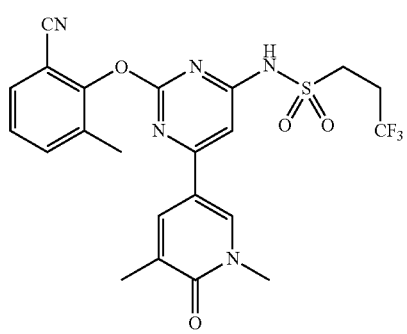 [SMILES: Cc1cccc(C#N)c1Oc1nc(NS(=O)(=O)CCC(F)(F)F)cc(-c2cc(C)c(=O)n(C)c2)n1]
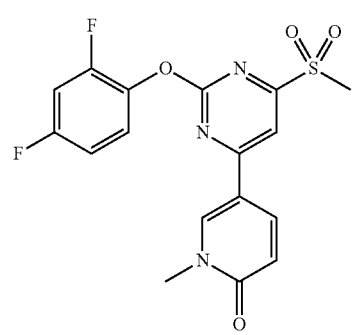 [SMILES: Cn1cc(-c2cc(S(C)(=O)=O)nc(Oc3ccc(F)cc3F)n2)ccc1=O]
TABLE 2-continued
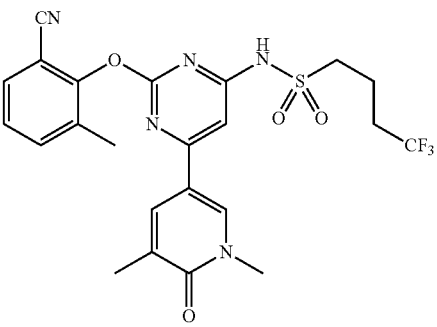 [SMILES: Cc1cccc(C#N)c1Oc1nc(NS(=O)(=O)CCCC(F)(F)F)cc(-c2cc(C)c(=O)n(C)c2)n1]
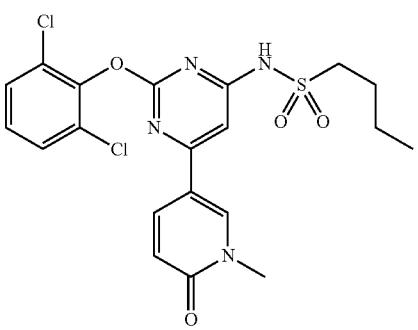
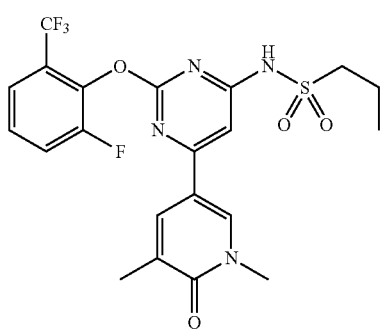 [SMILES: CCCS(=O)(=O)Nc1cc(-c2cc(C)c(=O)n(C)c2)nc(Oc2c(F)cccc2C(F)(F)F)n1]
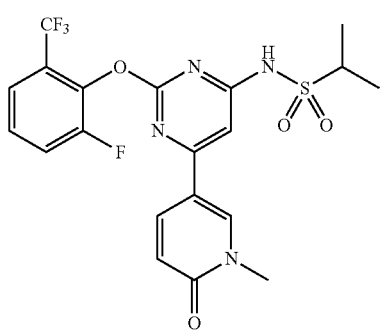 [SMILES: CC(C)S(=O)(=O)Nc1cc(-c2ccc(=O)n(C)c2)nc(Oc2c(F)cccc2C(F)(F)F)n1]
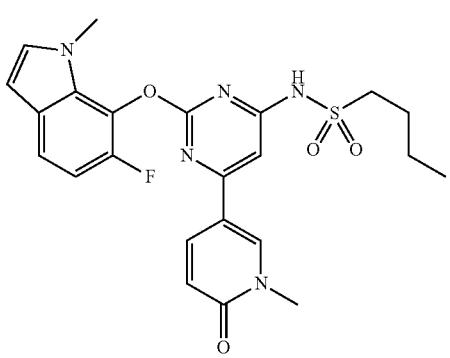 [SMILES: CCCCS(=O)(=O)Nc1cc(-c2ccc(=O)n(C)c2)nc(Oc2c(F)ccc3ccn(C)c23)n1]

TABLE 2-continued
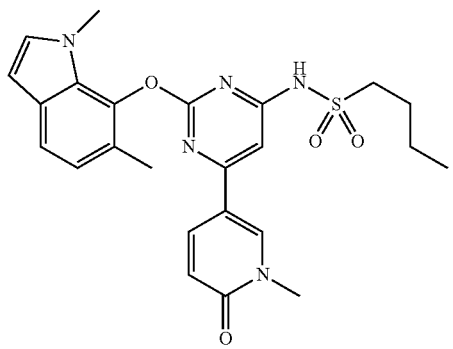 [SMILES: CCCCS(=O)(=O)Nc1cc(-c2ccc(=O)n(C)c2)nc(Oc2c(C)ccc3ccn(C)c23)n1]
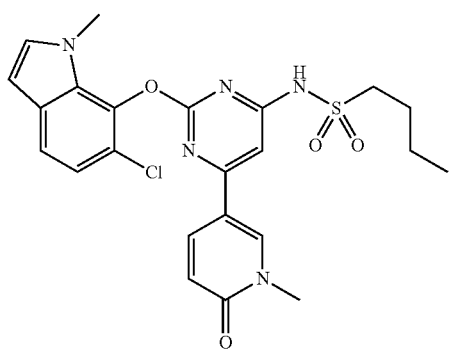 [SMILES: CCCCS(=O)(=O)Nc1cc(-c2ccc(=O)n(C)c2)nc(Oc2c(Cl)ccc3ccn(C)c23)n1]
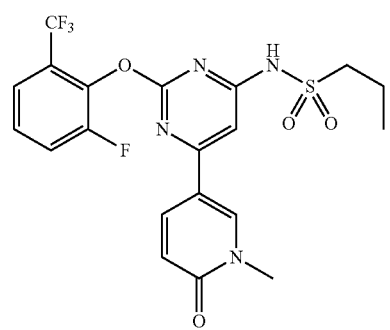 [SMILES: CCCS(=O)(=O)Nc1cc(-c2ccc(=O)n(C)c2)nc(Oc2c(F)cccc2C(F)(F)F)n1]
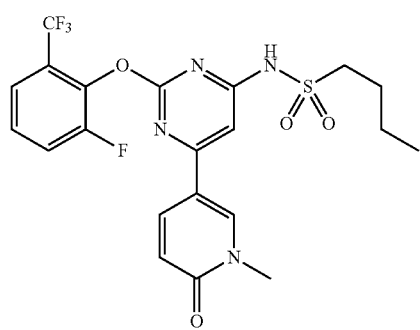 [SMILES: CCCCS(=O)(=O)Nc1cc(-c2ccc(=O)n(C)c2)nc(Oc2c(F)cccc2C(F)(F)F)n1]
TABLE 2-continued
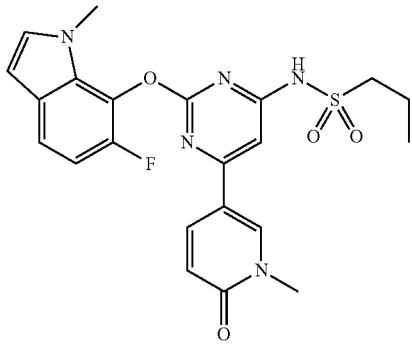 [SMILES: CCCS(=O)(=O)Nc1cc(-c2ccc(=O)n(C)c2)nc(Oc2c(F)ccc3ccn(C)c23)n1]
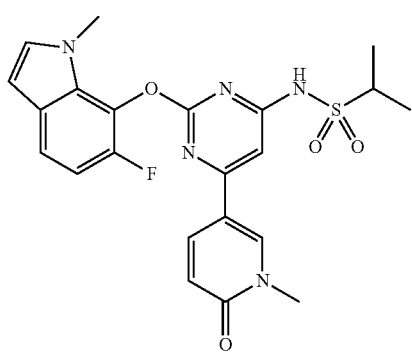 [SMILES: CC(C)S(=O)(=O)Nc1cc(-c2ccc(=O)n(C)c2)nc(Oc2c(F)ccc3ccn(C)c23)n1]
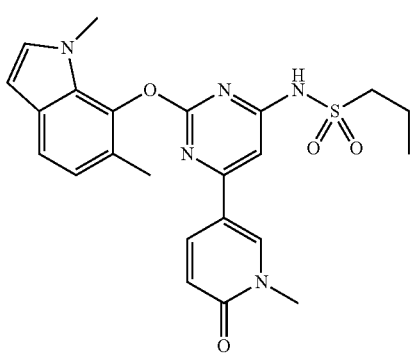 [SMILES: CCCS(=O)(=O)Nc1cc(-c2ccc(=O)n(C)c2)nc(Oc2c(C)ccc3ccn(C)c23)n1]
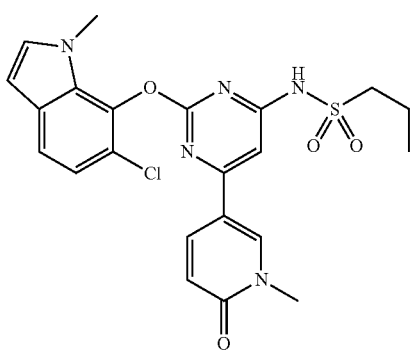 [SMILES: CCCS(=O)(=O)Nc1cc(-c2ccc(=O)n(C)c2)nc(Oc2c(Cl)ccc3ccn(C)c23)n1]

TABLE 2-continued
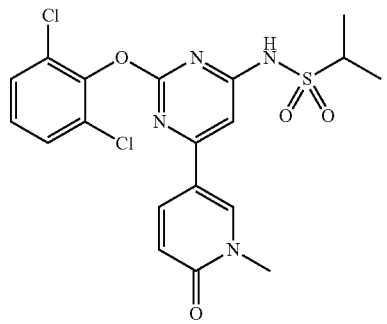
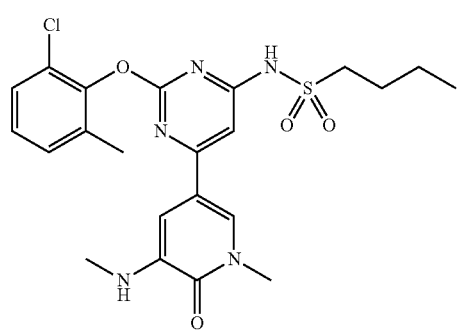 [SMILES: CCCCS(=O)(=O)Nc1cc(-c2cc(NC)c(=O)n(C)c2)nc(Oc2c(C)cccc2Cl)n1]
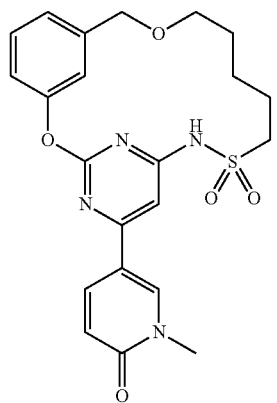 [SMILES: Cn1cc(-c2cc3nc(n2)Oc2cccc(c2)COCCCCCS(=O)(=O)N3)ccc1=O]
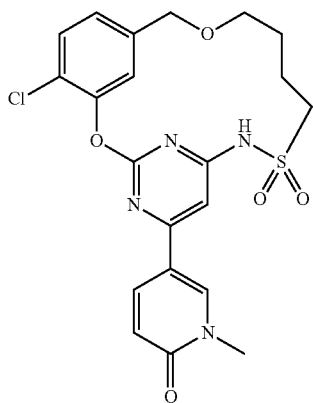 [SMILES: Cn1cc(-c2cc3nc(n2)Oc2cc(ccc2Cl)COCCCCS(=O)(=O)N3)ccc1=O]
TABLE 2-continued
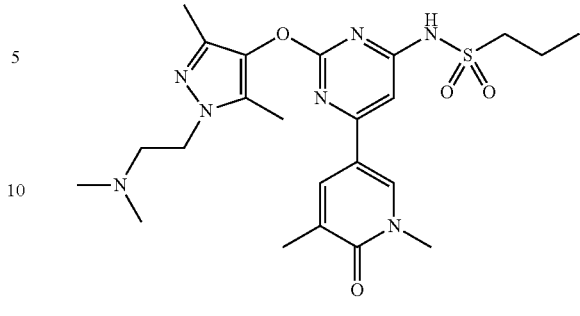
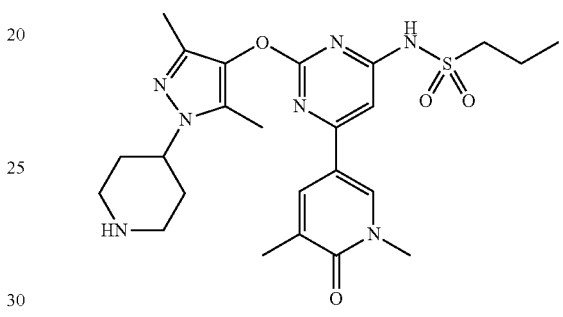
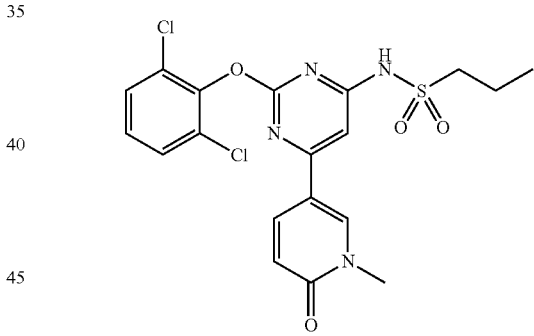
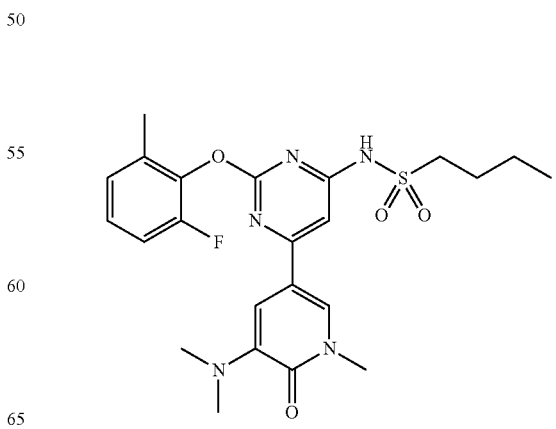

TABLE 2-continued
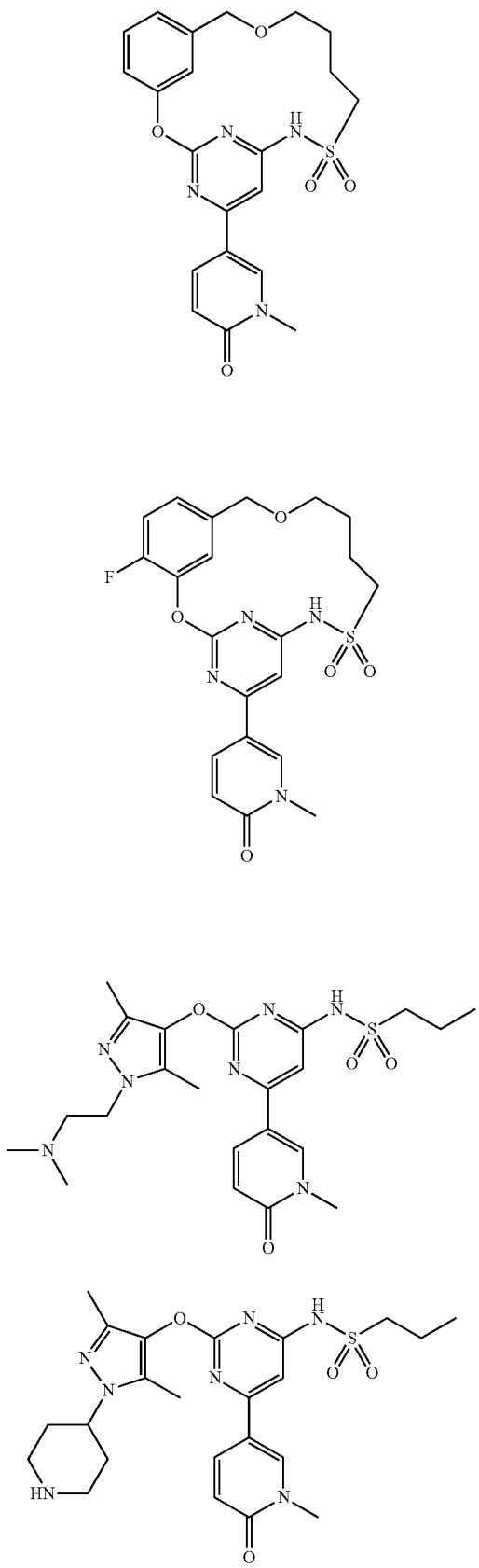
TABLE 2-continued
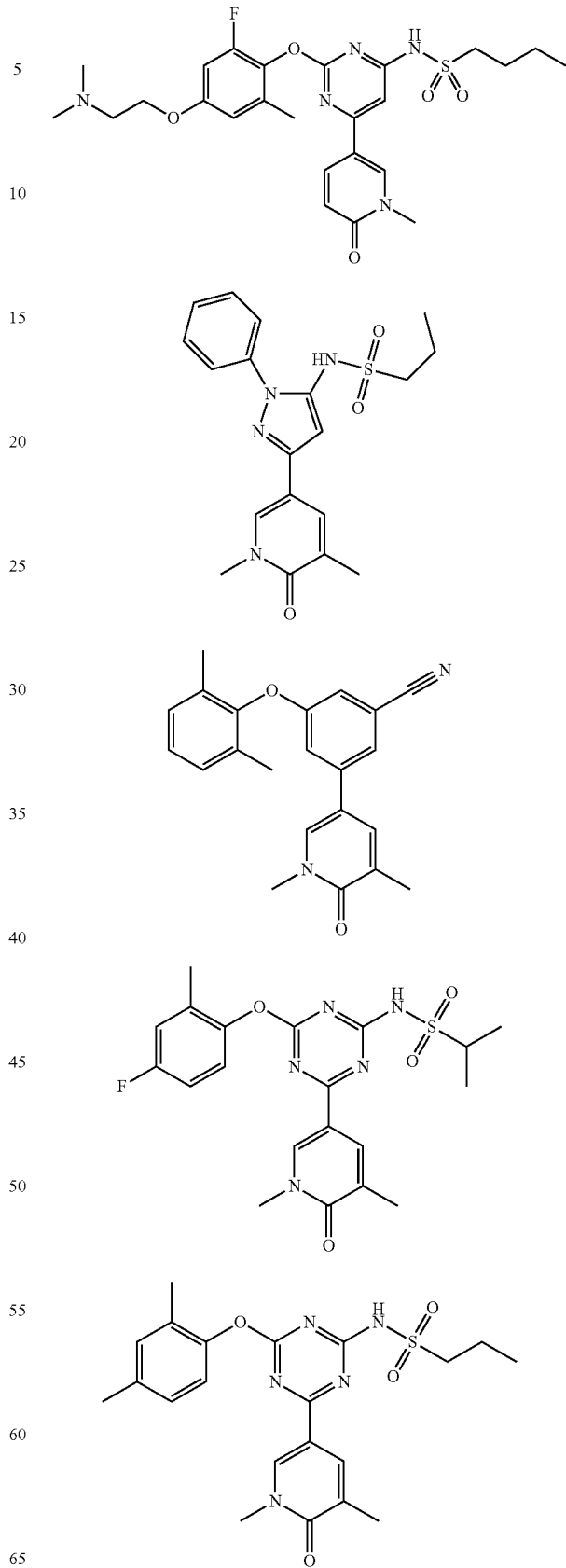

TABLE 2-continued
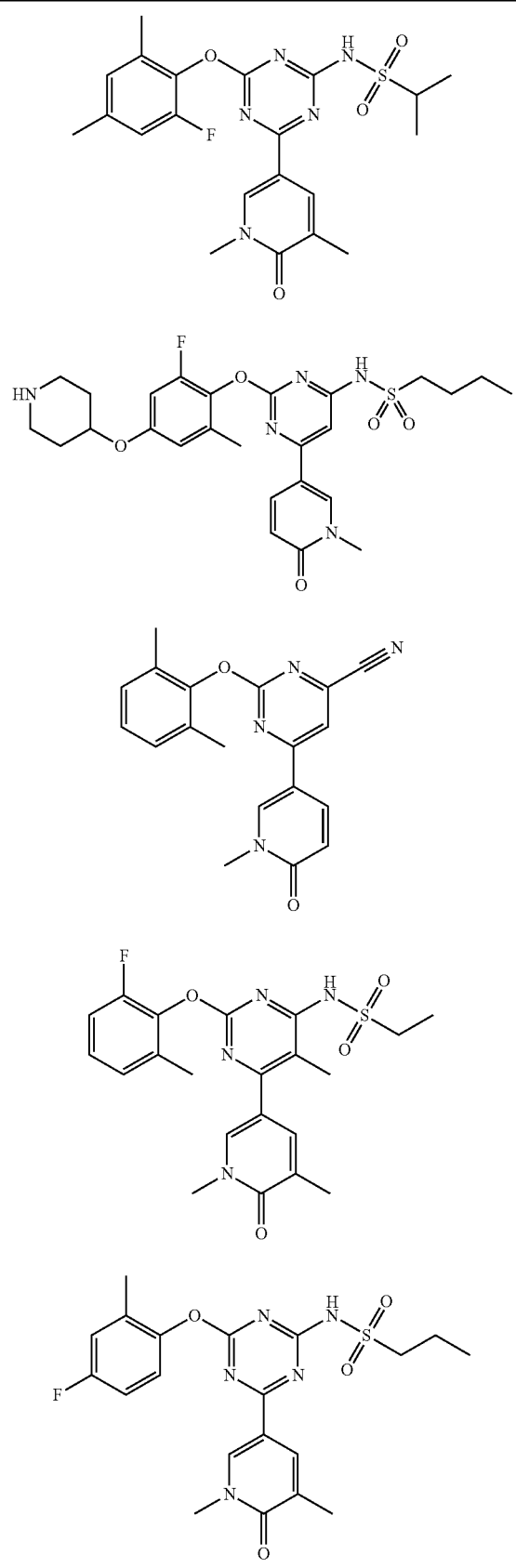
TABLE 2-continued
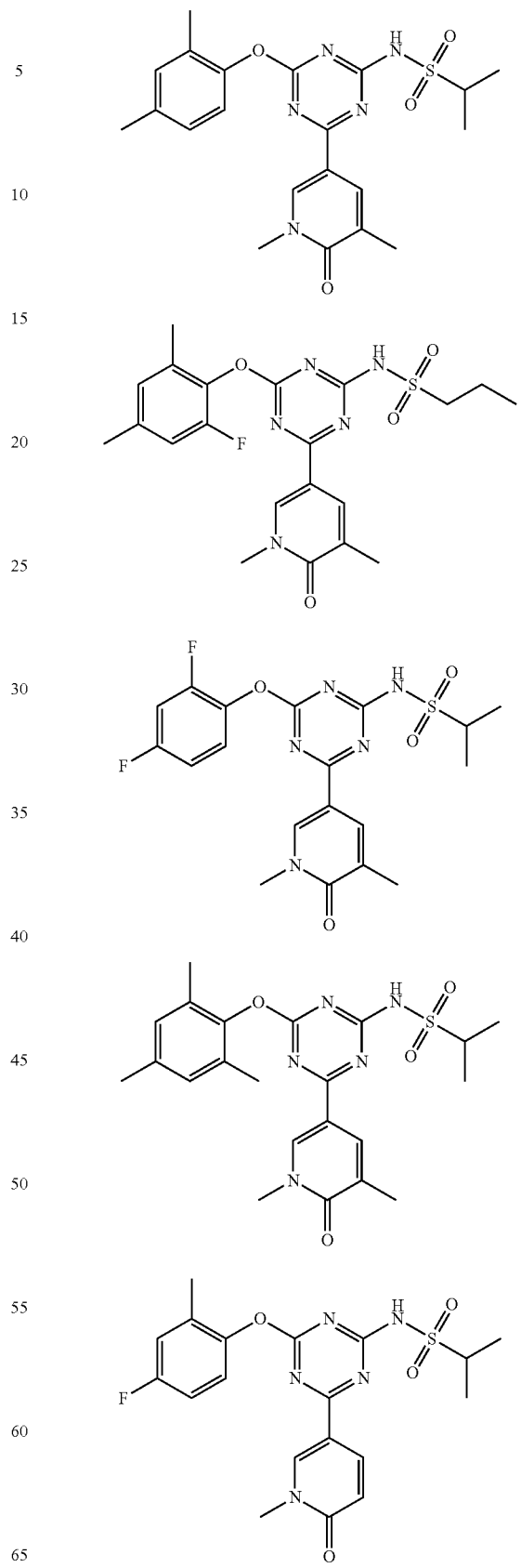

TABLE 2-continued
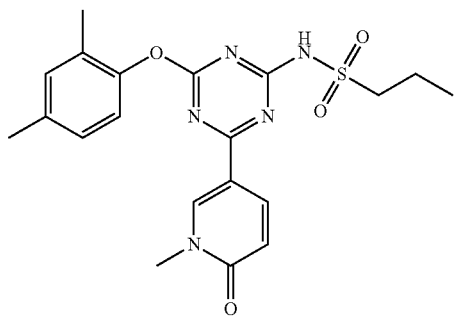 [SMILES: CCCS(=O)(=O)Nc1nc(Oc2ccc(C)cc2C)nc(-c2ccc(=O)n(C)c2)n1]
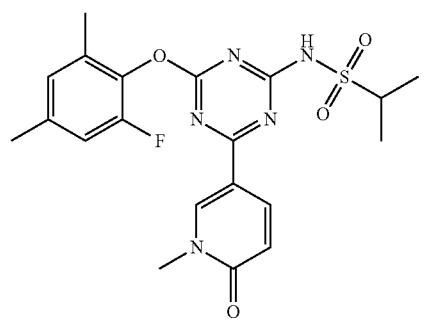 [SMILES: Cc1cc(C)c(Oc2nc(NS(=O)(=O)C(C)C)nc(-c3ccc(=O)n(C)c3)n2)c(F)c1]
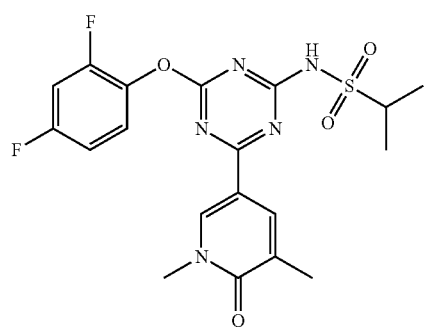 [SMILES: Cc1cc(-c2nc(NS(=O)(=O)C(C)C)nc(Oc3ccc(F)cc3F)n2)cn(C)c1=O]
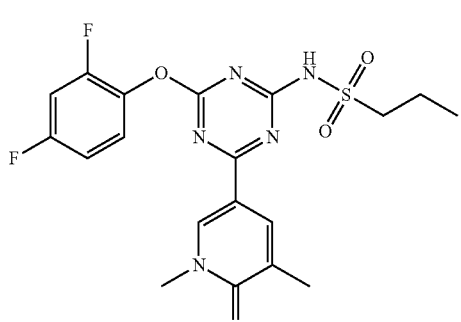
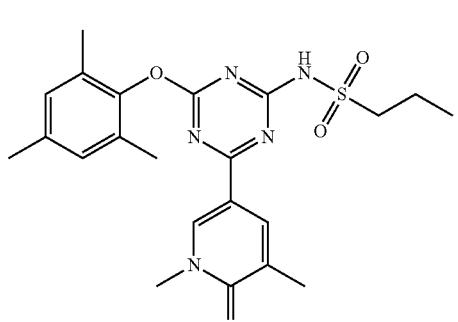
TABLE 2-continued
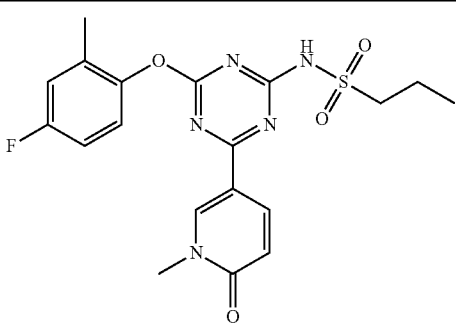
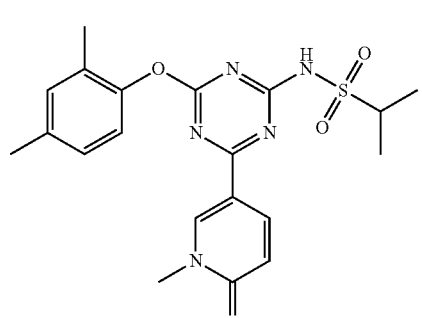
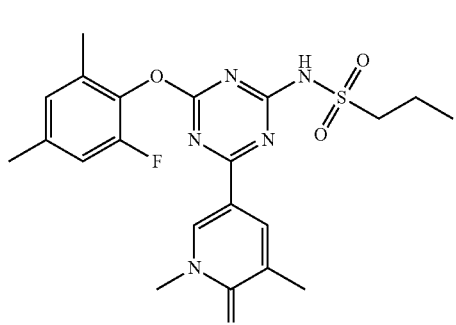
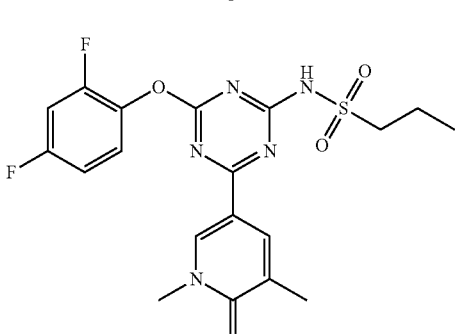
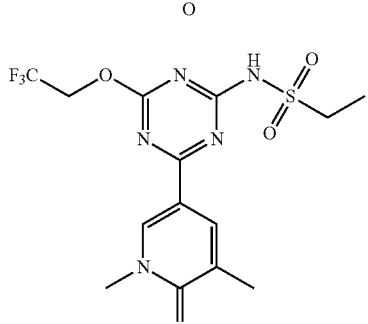

TABLE 2-continued
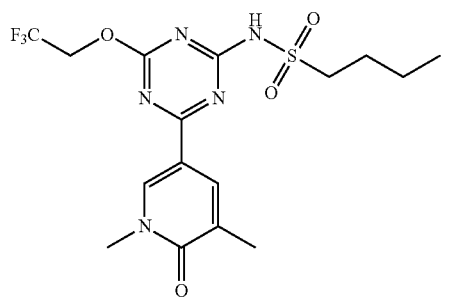 [SMILES: CCCCS(=O)(=O)Nc1nc(OCC(F)(F)F)nc(-c2cc(C)c(=O)n(C)c2)n1]
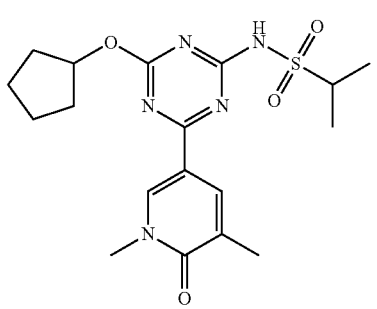 [SMILES: Cc1cc(-c2nc(NS(=O)(=O)C(C)C)nc(OC3CCCC3)n2)cn(C)c1=O]
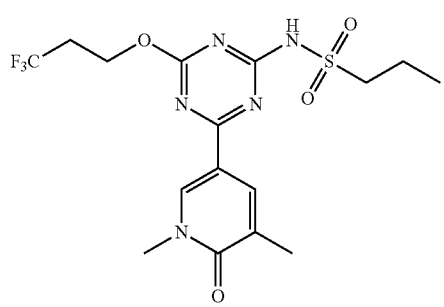 [SMILES: CCCS(=O)(=O)Nc1nc(OCCC(F)(F)F)nc(-c2cc(C)c(=O)n(C)c2)n1]
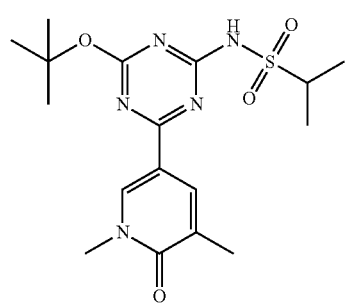 [SMILES: Cc1cc(-c2nc(NS(=O)(=O)C(C)C)nc(OC(C)(C)C)n2)cn(C)c1=O]
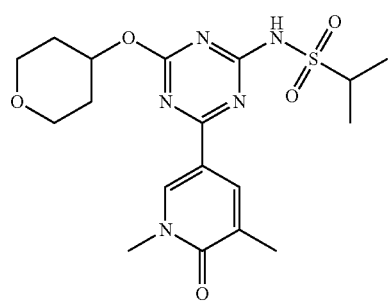 [SMILES: Cc1cc(-c2nc(NS(=O)(=O)C(C)C)nc(OC3CCOCC3)n2)cn(C)c1=O]
TABLE 2-continued
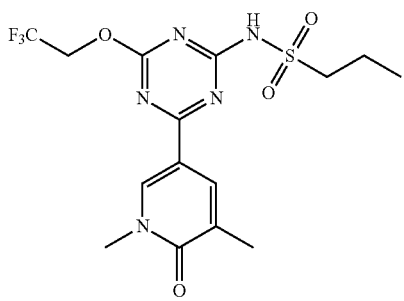 [SMILES: CCCS(=O)(=O)Nc1nc(OCC(F)(F)F)nc(-c2cc(C)c(=O)n(C)c2)n1]
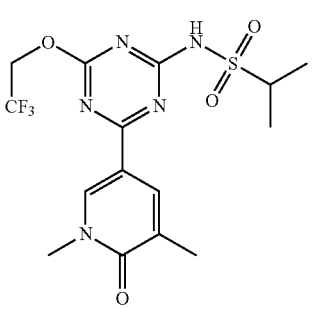 [SMILES: Cc1cc(-c2nc(NS(=O)(=O)C(C)C)nc(OCC(F)(F)F)n2)cn(C)c1=O]
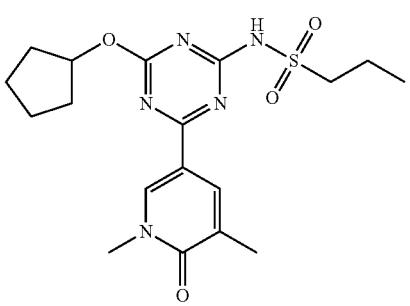 [SMILES: CCCS(=O)(=O)Nc1nc(OC2CCCC2)nc(-c2cc(C)c(=O)n(C)c2)n1]
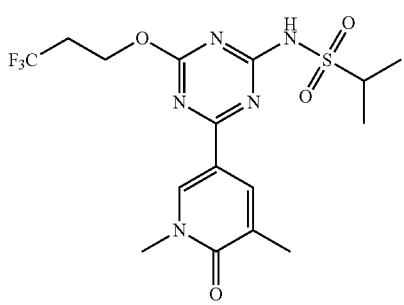 [SMILES: Cc1cc(-c2nc(NS(=O)(=O)C(C)C)nc(OCCC(F)(F)F)n2)cn(C)c1=O]
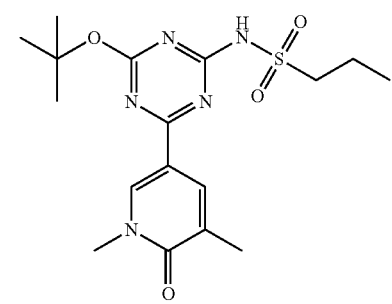 [SMILES: CCCS(=O)(=O)Nc1nc(OC(C)(C)C)nc(-c2cc(C)c(=O)n(C)c2)n1]

TABLE 2-continued
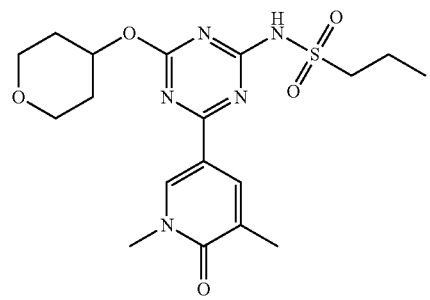 [SMILES: CCCS(=O)(=O)Nc1nc(OC2CCOCC2)nc(-c2cc(C)c(=O)n(C)c2)n1]
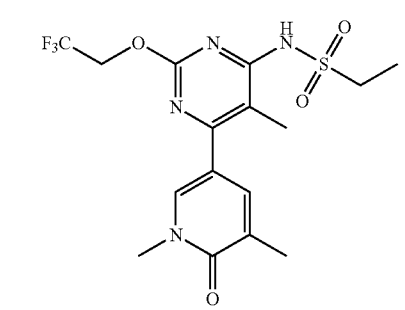 [SMILES: CCS(=O)(=O)Nc1nc(OCC(F)(F)F)nc(-c2cc(C)c(=O)n(C)c2)c1C]
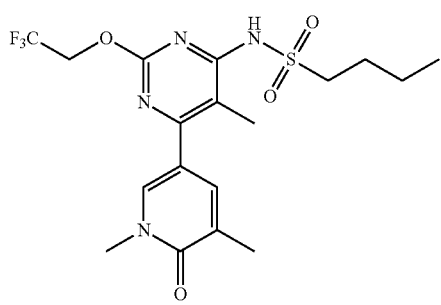 [SMILES: CCCCS(=O)(=O)Nc1nc(OCC(F)(F)F)nc(-c2cc(C)c(=O)n(C)c2)c1C]
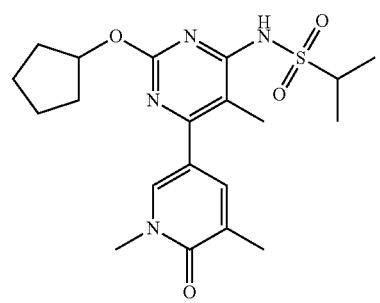 [SMILES: Cc1c(NS(=O)(=O)C(C)C)nc(OC2CCCC2)nc1-c1cc(C)c(=O)n(C)c1]
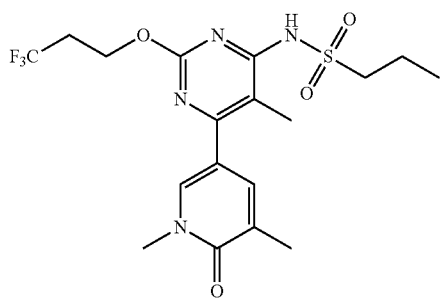 [SMILES: CCCS(=O)(=O)Nc1nc(OCCC(F)(F)F)nc(-c2cc(C)c(=O)n(C)c2)c1C]
TABLE 2-continued
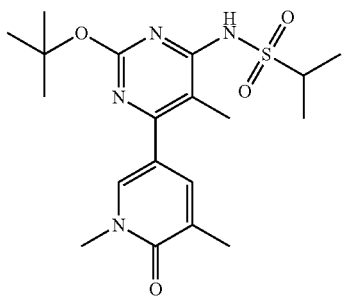 [SMILES: Cc1c(NS(=O)(=O)C(C)C)nc(OC(C)(C)C)nc1-c1cc(C)c(=O)n(C)c1]
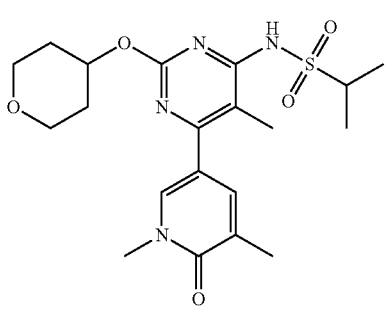 [SMILES: Cc1c(NS(=O)(=O)C(C)C)nc(OC2CCOCC2)nc1-c1cc(C)c(=O)n(C)c1]
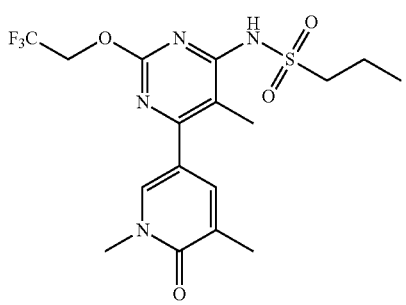 [SMILES: CCCS(=O)(=O)Nc1nc(OCC(F)(F)F)nc(-c2cc(C)c(=O)n(C)c2)c1C]
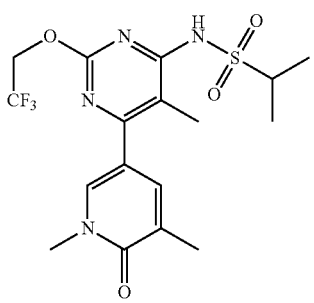 [SMILES: Cc1c(NS(=O)(=O)C(C)C)nc(OCC(F)(F)F)nc1-c1cc(C)c(=O)n(C)c1]
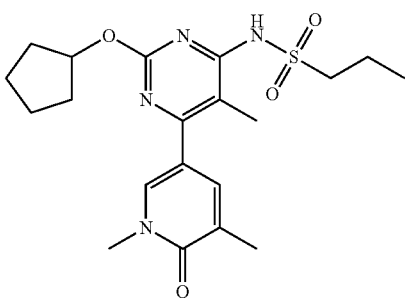 [SMILES: CCCS(=O)(=O)Nc1nc(OC2CCCC2)nc(-c2cc(C)c(=O)n(C)c2)c1C]

TABLE 2-continued
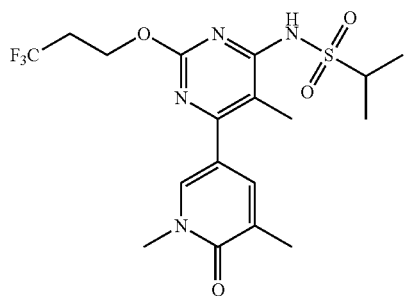 [SMILES: Cc1c(NS(=O)(=O)C(C)C)nc(OCCC(F)(F)F)nc1-c1cc(C)c(=O)n(C)c1]
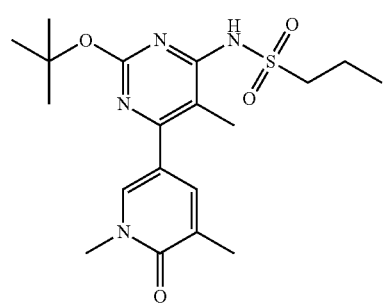 [SMILES: CCCS(=O)(=O)Nc1nc(OC(C)(C)C)nc(-c2cc(C)c(=O)n(C)c2)c1C]
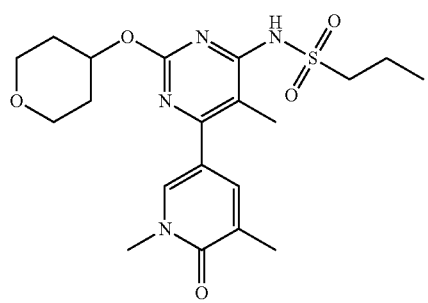 [SMILES: CCCS(=O)(=O)Nc1nc(OC2CCOCC2)nc(-c2cc(C)c(=O)n(C)c2)c1C]
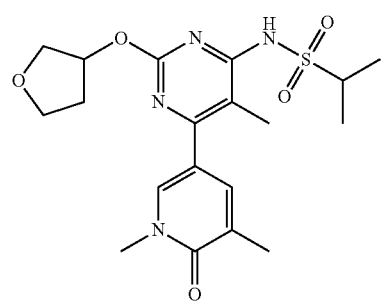 [SMILES: Cc1c(NS(=O)(=O)C(C)C)nc(OC2CCOC2)nc1-c1cc(C)c(=O)n(C)c1]
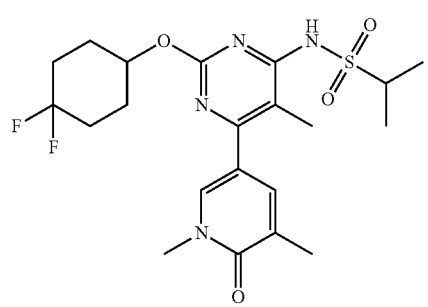 [SMILES: Cc1c(NS(=O)(=O)C(C)C)nc(OC2CCC(F)(F)CC2)nc1-c1cc(C)c(=O)n(C)c1]
TABLE 2-continued
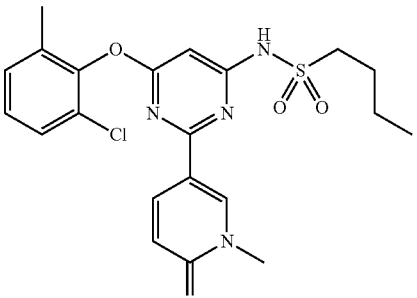
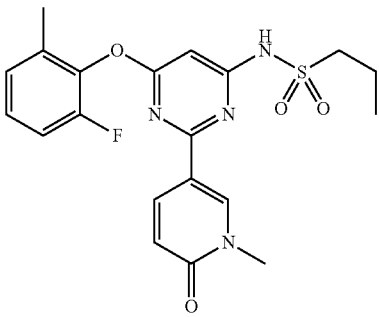 [SMILES: CCCS(=O)(=O)Nc1cc(Oc2c(C)cccc2F)nc(-c2ccc(=O)n(C)c2)n1]
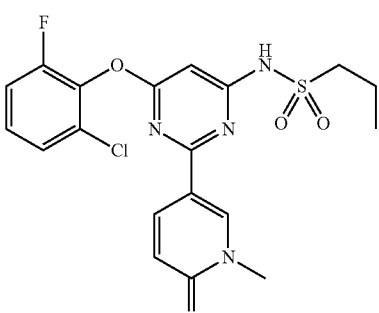
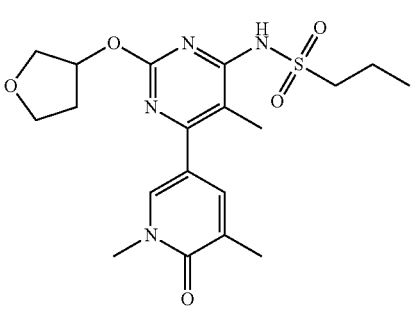 [SMILES: CCCS(=O)(=O)Nc1nc(OC2CCOC2)nc(-c2cc(C)c(=O)n(C)c2)c1C]
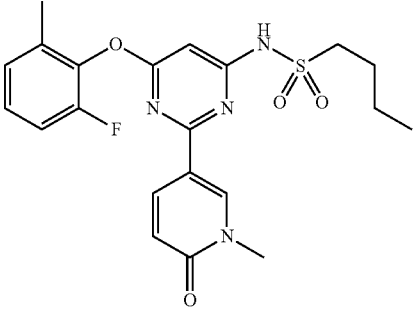 [SMILES: CCCCS(=O)(=O)Nc1cc(Oc2c(C)cccc2F)nc(-c2ccc(=O)n(C)c2)n1]

TABLE 2-continued
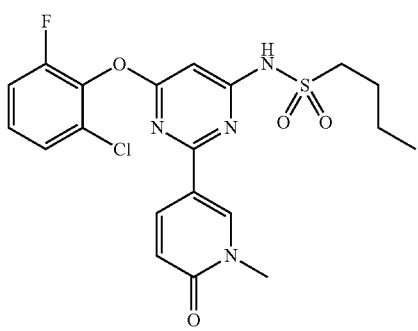 [SMILES: CCCCS(=O)(=O)Nc1cc(Oc2c(F)cccc2Cl)nc(-c2ccc(=O)n(C)c2)n1]
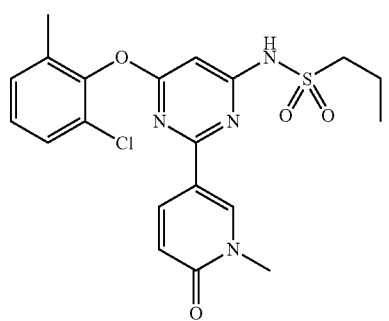 [SMILES: CCCS(=O)(=O)Nc1cc(Oc2c(C)cccc2Cl)nc(-c2ccc(=O)n(C)c2)n1]
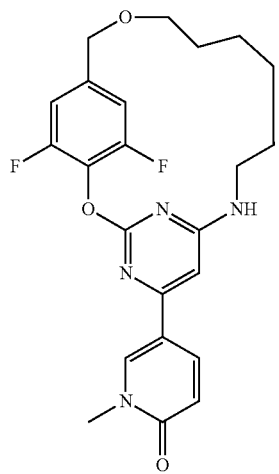 [SMILES: Cn1cc(-c2cc3nc(n2)Oc2c(F)cc(cc2F)COCCCCCCN3)ccc1=O]
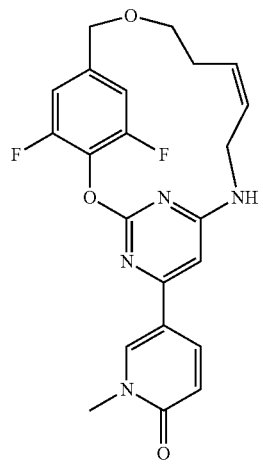 [SMILES: Cn1cc(-c2cc3nc(n2)Oc2c(F)cc(cc2F)COCC/C=C\CN3)ccc1=O]
TABLE 2-continued
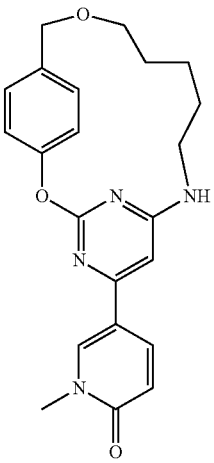 [SMILES: Cn1cc(-c2cc3nc(n2)Oc2ccc(cc2)COCCCCCN3)ccc1=O]
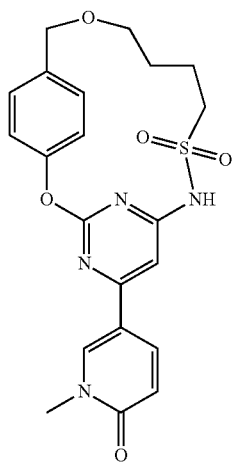 [SMILES: Cn1cc(-c2cc3nc(n2)Oc2ccc(cc2)COCCCCS(=O)(=O)N3)ccc1=O]
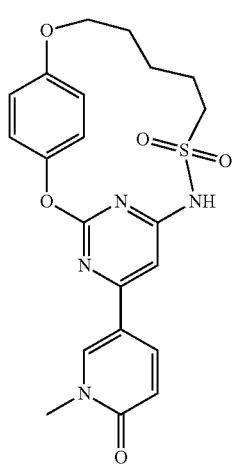 [SMILES: Cn1cc(-c2cc3nc(n2)Oc2ccc(cc2)OCCCCCS(=O)(=O)N3)ccc1=O]

TABLE 2-continued

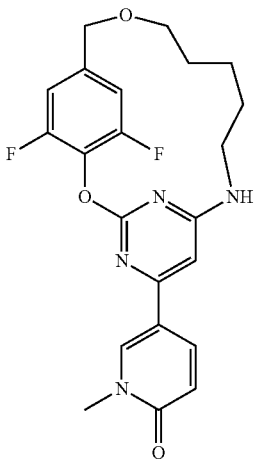 [SMILES: Cn1cc(-c2cc3nc(n2)Oc2c(F)cc(cc2F)COCCCCCN3)ccc1=O]

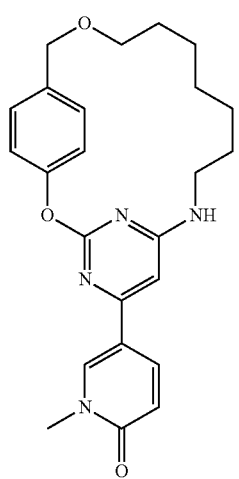 [SMILES: Cn1cc(-c2cc3nc(n2)Oc2ccc(cc2)COCCCCCCCN3)ccc1=O]

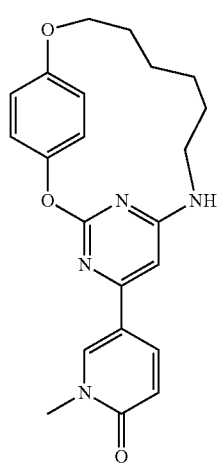

TABLE 2-continued

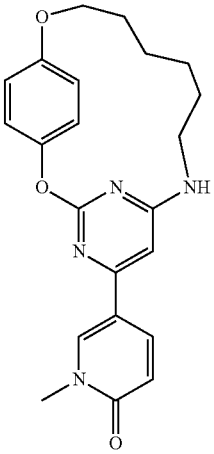 [SMILES: Cn1cc(-c2cc3nc(n2)Oc2ccc(cc2)OCCCCCCN3)ccc1=O]

Preparation of the Substituted Heterocyclic Derivative Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted heterocyclic derivative compounds described herein is P. H. Stahl & C. G. Wermuth "Handbook of Pharmaceutical Salts", Verlag Helvetica Chimica Acta, Zurich, 2002.

General methods for the synthesis of substituted heterocyclic derivatives are provided in, but not limited to, the following references: WO 2009/158396; WO 2005/63768; WO 2006/112666; Briet et. al., Tetrahedron (2002), 58(29), 5761-5766; WO 2008/77550; WO 2008/77551; WO 2008/77556; WO 2007/12421; WO 2007/12422; US 2007/99911; WO 2008/77550; Havera et al., J. Med. Chem. (1999), 42, 3860-3873; WO 2004/29051; and US 2009/0054434. Additional examples of the synthesis of substituted heterocyclic derivatives are found in the following references: WO 2012/171337; WO 2011/044157; WO 2009/097567; WO 2005/030791; EP 203216; Becknell et al., Bioorganic & Medicinal Chemistry Letters (2011), 21(23), 7076-7080; Svechkarev et al., Visnik Kharkivs'kogo Natsional'nogo Universitetu im. V. N. Karazina (2007), 770, 201-207; Coskun et al., Synthetic Communications (2005), 35(18), 2435-2443; Alvarez et al., Science of Synthesis (2005), 15, 839-906; Kihara et al., Heterocycles (2000), 53(2), 359-372; Couture et al., Journal of the Chemical Society, Perkin Transactions 1: Organic and Bio-Organic Chemistry (1999), (7), 789-794; Kihara et al., Heterocycles (1998), 48(12), 2473-2476; Couture et al., Tetrahedron (1996), 52(12), 4433-48; Couturre et al., Tetrahedron Letters (1996), 37(21), 3697-3700; Natsugari et al., Journal of Medicinal Chemistry (1995), 38(16), 3106-20; Moehrle et al., Archiv der Pharmazie (Weinheim, Germany) (1988), 321(10), 759-64; Gore et al., Journal of the Chemical Society, Perkin Transactions 1: Organic and Bio-Organic Chemistry (1972-1999) (1988), (3), 481-3; Narasimhan et al., Journal of the Chemical Society, Chemical Communications (1987), (3), 191-2; Henry et al., Journal of Organic Chemistry (1975), 40(12), 1760-6; Berti, Gazzetta Chimica Italiana (1960), 90, 559-72; Berti et al., Annali di Chimica (Rome, Italy) (1959), 49, 2110-23; Berti et al., Annali di Chimica (Rome, Italy) (1959), 49, 1253-68; WO 2012/000595; Couture et al., Tetrahedron (1996), 52(12), 4433-48; WO 2010/069504; WO 2010/069504; WO 2006/030032; WO 2005/095384; US 2005/0222159; WO 2013/064984; Mishra et al., European Journal of Organic Chemistry (2013), 2013(4), 693-700; Vachhani et al., Tetrahedron (2013), 69(1), 359-365; Xie et al., European Journal of Medicinal Chemistry (2010), 45(1), 210-218; Mukaiyama et al., Bioorganic & Medicinal Chemistry (2007), 15(2), 868-885; JP 2005/089352; Wang et al., Molecules (2004), 9(7), 574-582; WO 2000/023487; US 2006/0287341; CN 103183675; Hares et al., Egyptian Journal of Pharmaceutical Sciences (1991), 32(1-2), 303-14; DE 2356005; DE 2133898; DE 2133998; U.S. Pat. No. 3,816,422; DE 2011970; and Staehle et al., Justus Liebigs Annalen der Chemie (1973), (8), 1275-81.

In some embodiments, the substituted heterocyclic derivative compounds disclosed herein are prepared by the general synthetic routes described below in Schemes 1-6. These schemes are intended to exemplary to one of skill in the art and are not limiting. Additional methods for the synthesis of the substituted heterocyclic derivative compounds disclosed herein are readily available to one of skill in the art.

Scheme 1

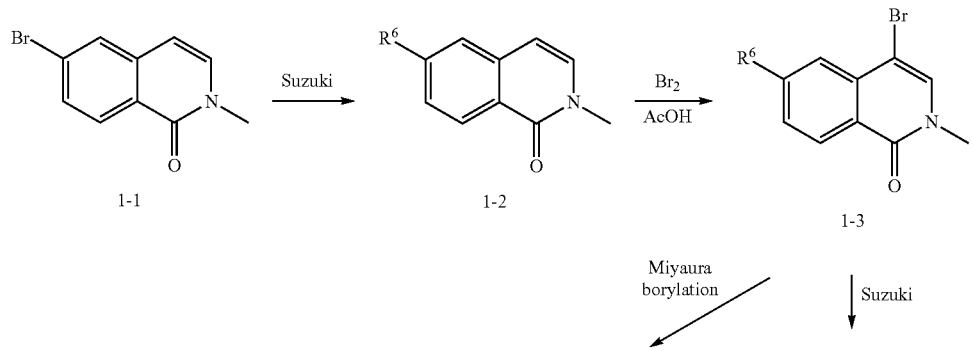

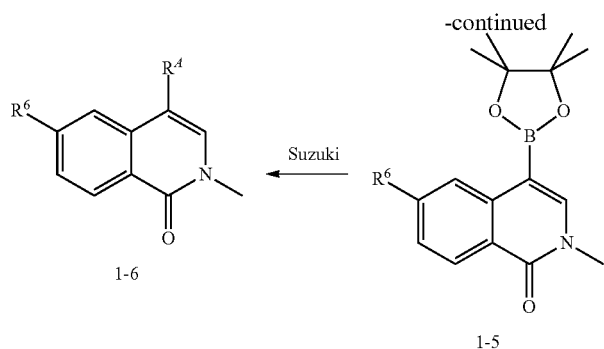
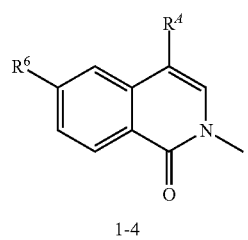

A method for preparing some of the substituted heterocyclic derivative compounds described herein is provided in Scheme 1, above. 6-Bromo-2-methylisoquinolin-1(2H)-one (1-1) is subjected to a palladium-catalyzed cross coupling reaction to provide isoquinolinone 1-2. Bromination under acidic conditions provides compound 1-3. Further palladium-catalyzed cross coupling reaction with a boronic acid, or ester, provides the isoquinolinone 1-4. Alternatively, palladium-catalyzed cross coupling of compound 1-3 with 4,4,5,5-tetramethyl-2-(tetramethyl-1,3,2-dioxaborolan-2-yl)-1,3,2-dioxaborolane under the conditions described by Miyaura (Ishiyama et al., J. Org. Chem. 1995, 60, 7508-7510) provides the boron ester 1-5. Further palladium-catalyzed cross coupling reaction of compound 1-5 with a suitable halide provides the isoquinolinone 1-6.

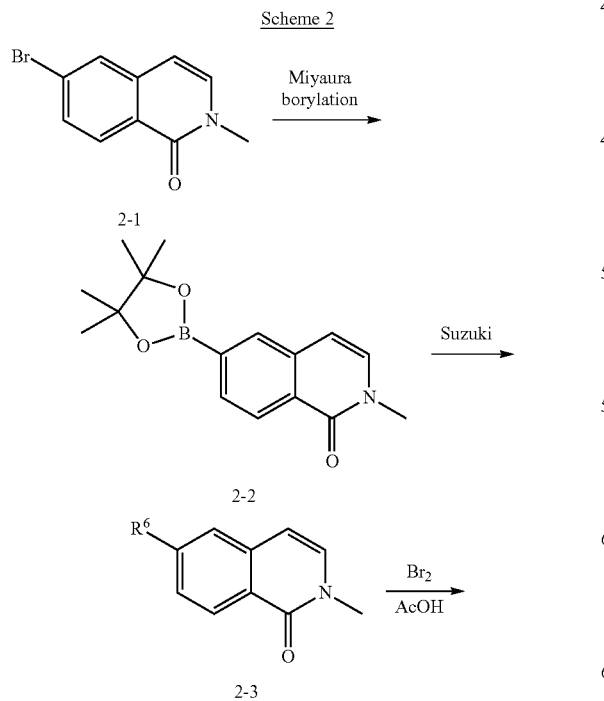

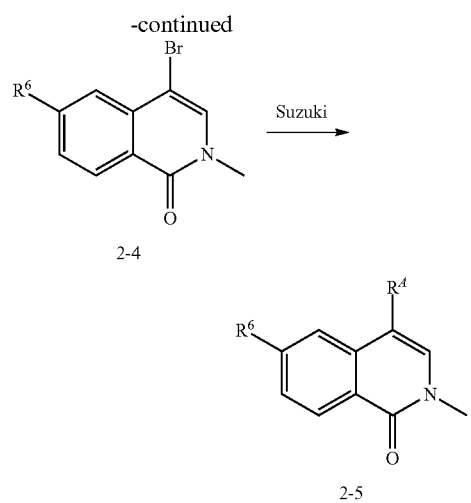

A method for preparing some of the substituted heterocyclic derivative compounds described herein is provided in Scheme 2. 6-Bromo-2-methylisoquinolin-1(2H)-one (2-1) is subjected to a palladium-catalyzed cross coupling reaction with 4,4,5,5-tetramethyl-2-(tetramethyl-1,3,2-dioxaborolan-2-yl)-1,3,2-dioxaborolane to provide boron ester 2-2. Further palladium-catalyzed cross coupling reaction of compound 2-2 with a suitable halide provides compound 2-3. Bromination under acidic conditions provides compound 2-4. Further palladium-catalyzed cross coupling reaction with a boronic acid, or ester, provides the isoquinolinone 2-5.

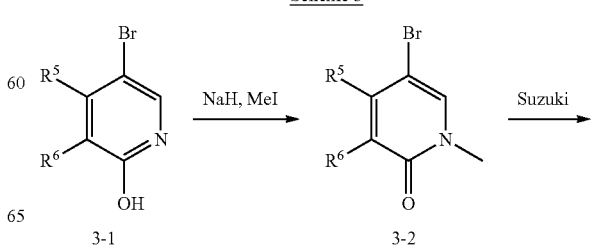

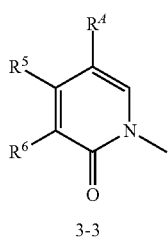

3-3

A method for preparing some of the substituted heterocyclic derivative compounds described herein is provided is provided in Scheme 3, above. 5-Bromopyridin-2-ol derivative (3-1) is subjected to alkylation with methyl iodide under basic conditions to provide the related 5-bromo-1-methylpyridin-2(1H)-one derivative (3-2). Further palladium-catalyzed cross coupling reaction of compound 3-2 with a suitable halide provides compound 3-3.

A method for preparing some of the substituted heterocyclic derivative compounds described herein is provided is provided in Scheme 4. 3-Amino-5-bromo-1-methylpyridin-2(1H)-one derivative 4-1 is used as a starting material for several routes. In one route, compound 4-1 is directly subjected to a palladium-catalyzed cross coupling reaction to provide pyridone 4-3. The amino group of compound 4-3 is subjected to a reductive amination with an aldehyde and a reducing agent, such as sodium cyanoborohydride, to provide the substituted amino derivative compound 4-7. A second route involving selective alkylation of the amino group of compound 4-1 begins with protection of the amino group as the BOC carbamate. Alkylation of the carbamate under basic conditions followed by removal of the BOC carbamate under acidic conditions provides the secondary amine compound 4-5. Treatment of 4-5 with a suitable halide under palladium-catalyzed cross coupling conditions affords compound 4-6.

Scheme 4

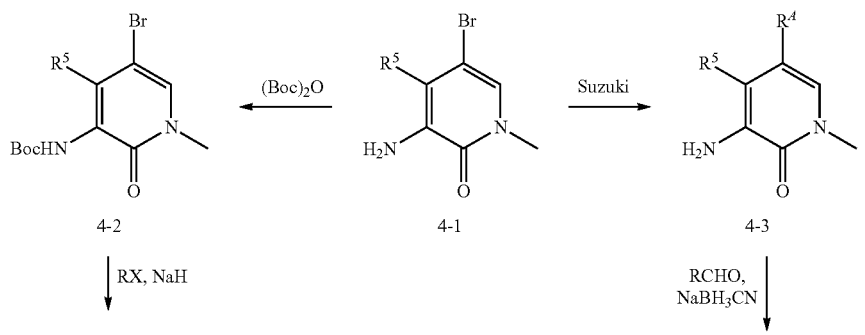

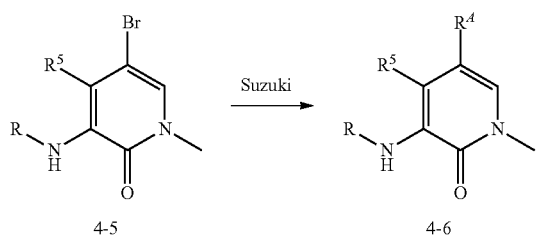

Scheme 5

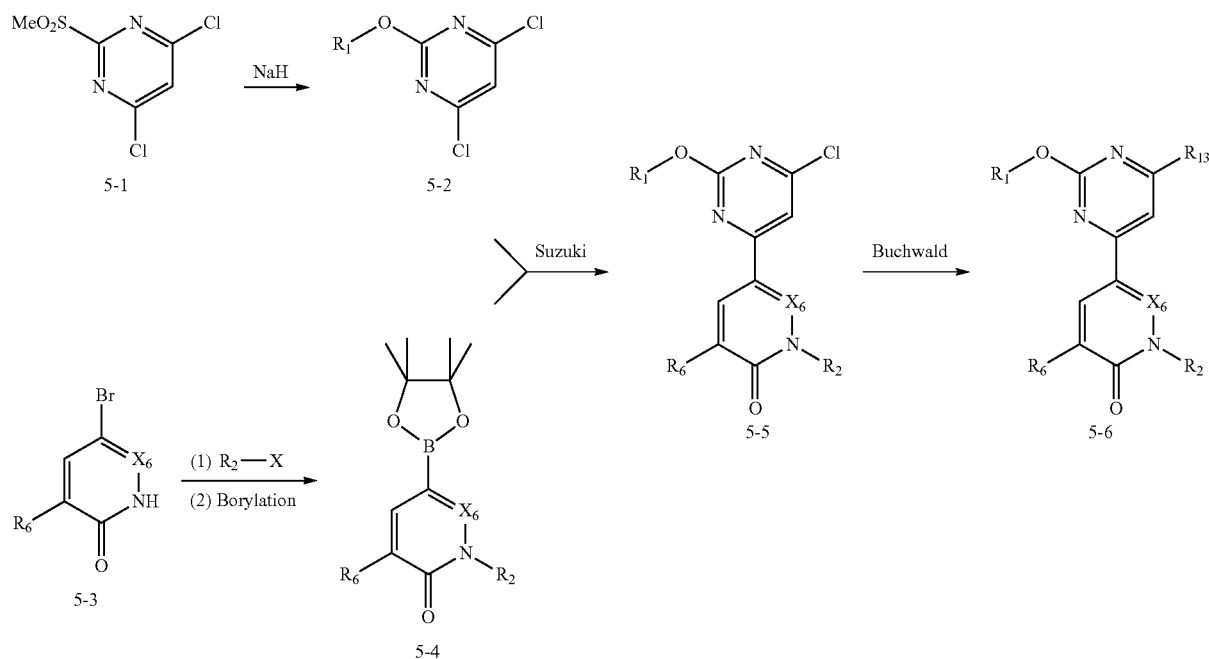

A method for preparing some of the substituted heterocyclic derivative compounds described herein is provided is provided in Scheme 5, above. Dichloropyrimidine 5-1 is consensed with an alcohol under basic conditions. Separately, halide 5-3 is substituted with boronate ester under palladium catalyst. Palladium-catalyzed cross coupling of pyrimidine 5-2 and boronate ester 5-4 affords the linked heterocyclic derivative 5-5. Substitution of the chloropyrimidine yields pyrimidine 5-6.

Scheme 6

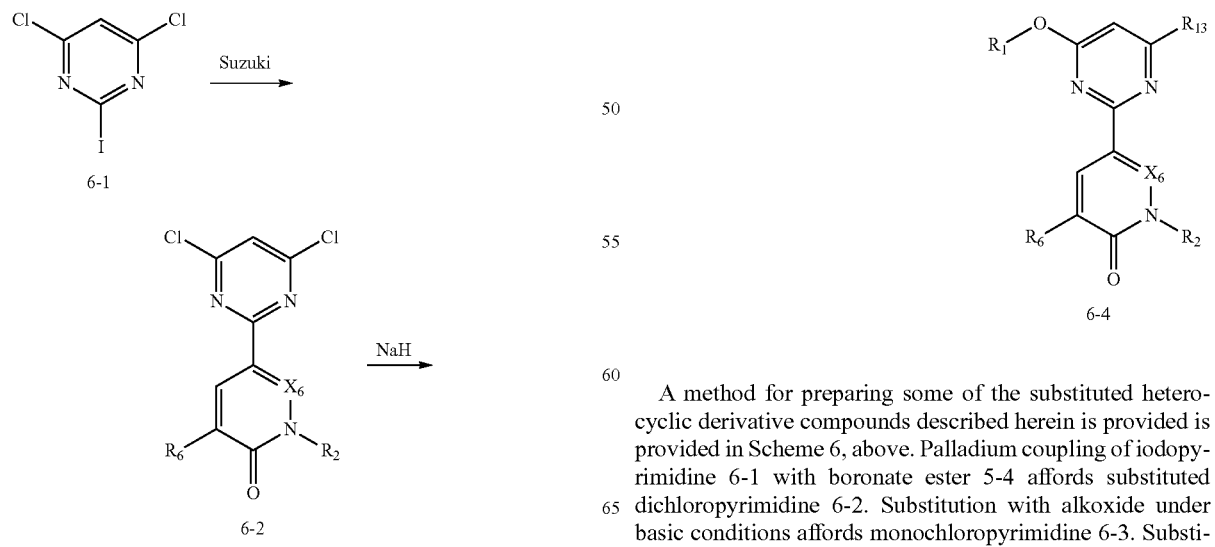

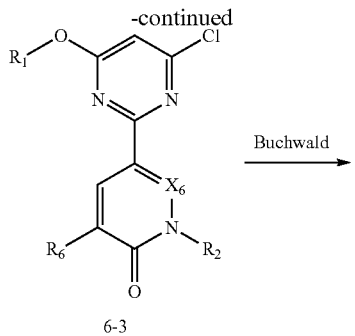

A method for preparing some of the substituted heterocyclic derivative compounds described herein is provided is provided in Scheme 6, above. Palladium coupling of iodopyrimidine 6-1 with boronate ester 5-4 affords substituted dichloropyrimidine 6-2. Substitution with alkoxide under basic conditions affords monochloropyrimidine 6-3. Substitution of the chloropyrimidine yields pyrimidine 6-4.

Scheme 7

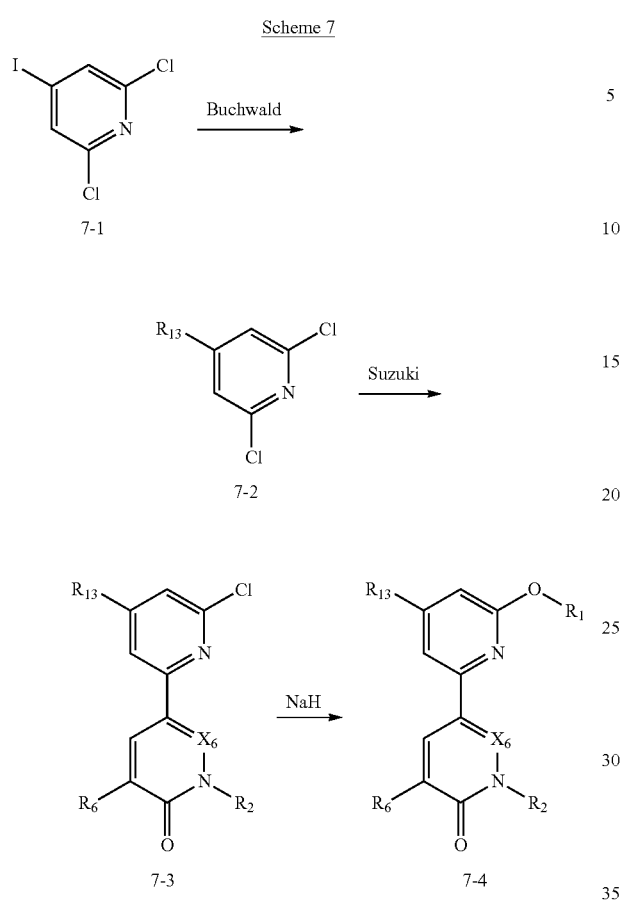

A method for preparing some of the substituted heterocyclic derivative compounds described herein is provided is provided in Scheme 7. Substitution of 2,6-dichloro-4-iodopyrimidine (7-1) under Buchwald conditions yields substituted dichloropyrimide 7-2. Palladium-catalyzed cross coupling with boronate ester 5-4 affords substituted monochloropyrimidine 7-3. Substitution with alkoxide under basic conditions affords pyrimidine 7-4.

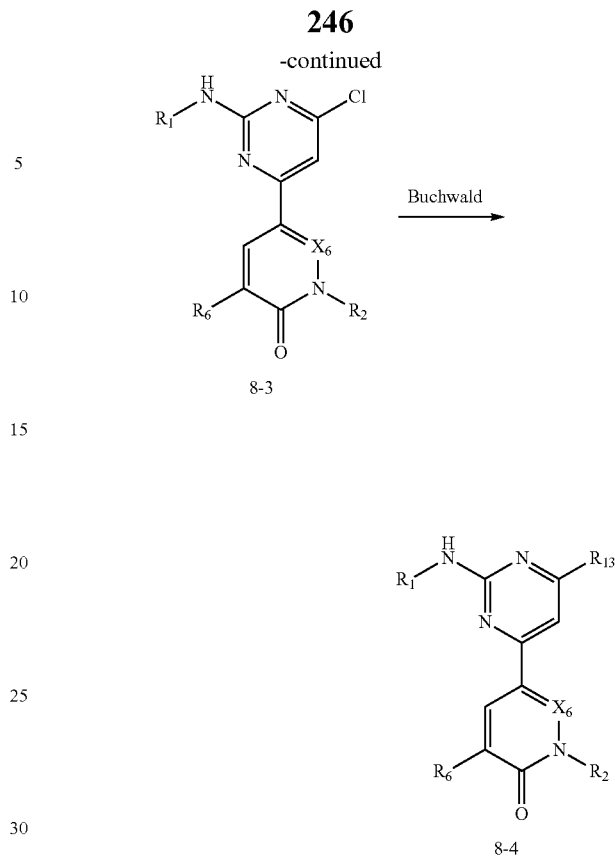

A method for preparing some of the substituted heterocyclic derivative compounds described herein is provided is provided in Scheme 8. Dichloropyrimidine 8-1 is consensed with an amine under basic conditions. Palladium-catalyzed cross coupling of pyrimidine 8-2 and boronate ester 5-4 affords the linked heterocyclic derivative 8-3. Substitution of the chloropyrimidine yields pyrimidine 5-6.

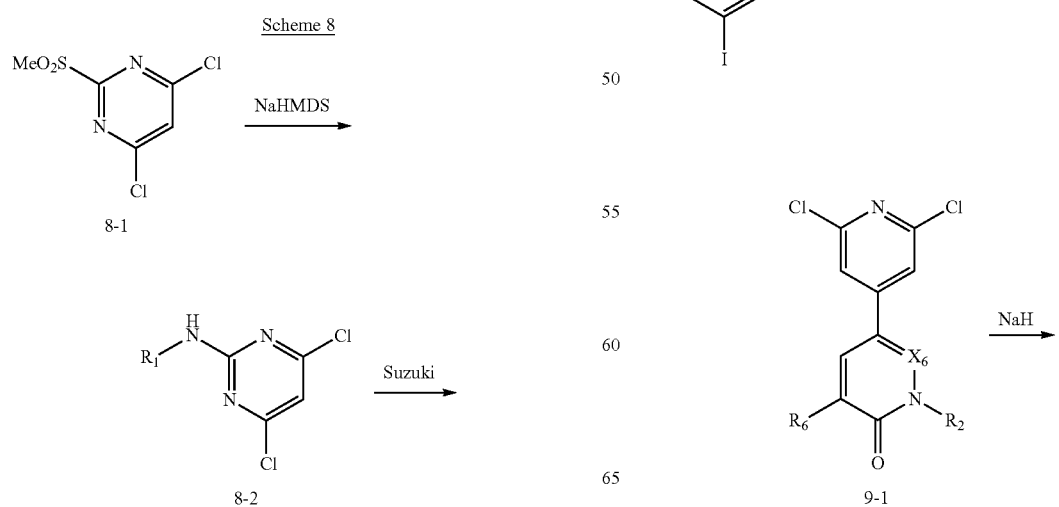

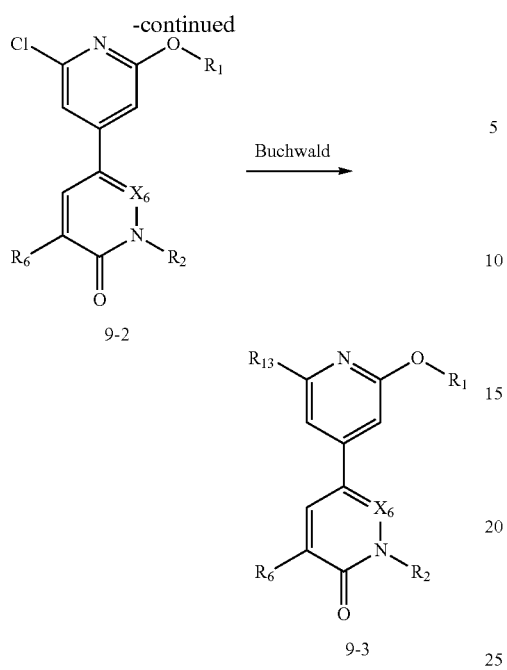

A method for preparing some of the substituted heterocyclic derivative compounds described herein is provided is provided in Scheme 9, above. Palladium coupling of 2,6-dichloro-4-iodopyrimidine with boronate ester 5-4 affords substituted 2,6-dichloropyrimidine 9-1. Substitution with alkoxide under basic conditions affords monochloropyrimidine 9-2. Substitution of the monochloropyrimidine yields pyrimidine 9-3.

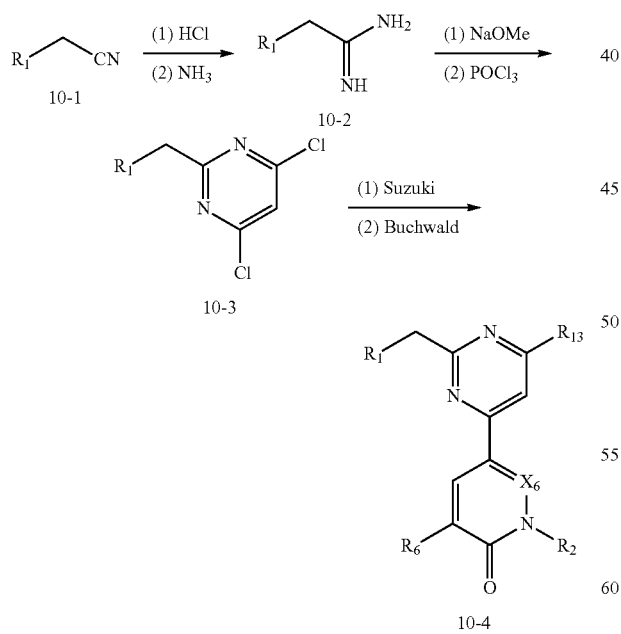

A method for preparing some of the substituted heterocyclic derivative compounds described herein is provided is provided in Scheme 10, above. Aminolysis of nitrile 10-1 affords carboximidamide 10-2. Condensation with a malonic acid derivative under basic conditions, followed by chlorination provides dichloropyrimidine 10-3. Palladium-catalyzed cross coupling with boronate ester 5-4 followed by substitution under Buchwald conditions affords pyrimidine 10-4.

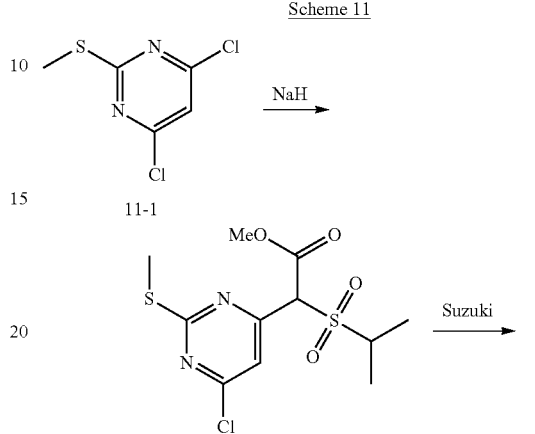

A method for preparing some of the substituted heterocyclic derivative compounds described herein is provided is provided in Scheme 11, above. Nucleophilic substitution of dichloropyrimidine 11-1 provides pyrimidine 11-2. Palladium-catalyzed cross coupling with boronate ester 5-4 yields compound 11-3. Decarboxylation followed by oxidation of the sulfide affords sulfone 11-4. Substitution under bacis conditions with an alcohol gives th final product 11-5.

In each of the above reaction procedures or schemes, the various substituents may be selected from among the various substituents otherwise taught herein.

Pharmaceutical Compositions

In certain embodiments, the substituted heterocyclic derivative compound as described herein is administered as a pure chemical. In other embodiments, the substituted heterocyclic derivative compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Accordingly, provided herein is a pharmaceutical composition comprising at least one substituted heterocyclic derivative compound, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a compound of Formula (I)-(V), or a pharmaceutically acceptable salt thereof, and a pharmaceutically acceptable excipient. In certain embodiments, the substituted heterocyclic derivative compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. Suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

The dose of the composition comprising at least one substituted heterocyclic derivative compound as described herein may differ, depending upon the patient's (e.g., human) condition, that is, stage of the disease, general health status, age, and other factors that a person skilled in the medical art will use to determine dose.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient.

Oral doses typically range from about 1.0 mg to about 1000 mg, one to four times, or more, per day.

Bromodomain Inhibition and cAMP Response Element-Binding Protein

Histone acetylation is generally associated with the activation of gene transcription, as the modification is known to loosen the interaction of the DNA and the histone octamer by changing the electrostatics. In addition to this physical change, specific proteins are known to bind to acetylated lysine residues within histones in order to read the epigenetic code. Bromodomains are small (110 amino acid) distinct domains within proteins that are known to bind to acetylated lysine resides commonly, but not exclusively, in the context of histones. Around 50 proteins are known to contain bromodomains, and they have a range of functions within the cell, including bromodomain and extra-terminal (BET) family of proteins and cAMP response element-binding protein (CREB)-binding protein (CBP).

CBP and its paralog p300 are highly homologous, ubiquitous, versatile transcriptional coactivator proteins that are essential for development and many other physiological processes. In addition to involvement in transcriptional events, the coactivator proteins are known to contribute to other processes such DNA repair, RNA splicing. (R. Janknecht, The versatile functions of the transcriptional coactivators p300 and CBP and their roles in disease, Histology and Histopathology, 2002, 17: 657-668).

The human CBP protein contains 2442 amino acids. Several structural and functional domains have been identified in CBP, including the bromodomain (BRD), three cysteine-histidine rich regions (CH1, CH2 and CH3), and the histone acetyltransferase (HAT) domain. The bromodomain, which is found in many chromatin associated proteins, is thought to function as a histone binding motif. The three cysteine/histidine-rich domains are known to serve as docking modules for numerous transcriptional regulators. The $CH_2$ domain is partly located within the HAT domain. Based on sequence homology data, part of the $CH_2$ region has been classified as a plant homeodomain (PHD) type zinc finger which is found predominantly in proteins that function at the chromatin level. (Kalkhoven et al., The PHD Type Zinc Finger Is an Integral Part of the CBP Acetyltransferase Domain, Molecular and Cellular Biology, 2002, Vol. 22, No. 7: 1961-1970).

Bromodomains are made up of about 110 amino acids arranged in a characteristic structure made up of four α-helices (αZ, αA, αB, αC) connected by interhelical loops, termed the BRD fold. Bromodomains are known to bind specifically to acetylated lysine. (Hay et al., Discovery and Optimization of Small-Molecule Ligands for the CBP/p300 Bromodomains, Journal of The American Chemical Society, 2014, 136: 9308-9319). The human bromodomain family consists of 61 members, of which there are two distinct subgroups representing the histone acetyltransferase transcriptional co-activators, such as CBP/p300 which contains a single bromodomain, and the BET family proteins that usually contain two tandem bromodomains, such as BRD4.

The bromodomains of BRD4 and CBP are also known to function differently as a transcriptional co-activator and a chromatin organizer, respectively. (Plotnikov et al., Structural Insights into Acetylated-Histone H4 Recognistion by the Bromodomain-PHD Finger Module of Human Transcriptional Co-Activator CBP, Structure, 2014, 22(2): 353-360).

Recent studies have elucidated the structure of the bromodomain-PHD tandem module of human CBP protein bound lysine-acetylated histone H4 peptides. Two different histone H4 peptides were used in the study, containing the same H4 residues 5-25, but carrying distinct lysine acetylation sites, i.e. lysine residue 20 was acetylated in case of H4K20ac and lysine residues 12 and 16 were acetylated in case of H4K12ac/K16ac. The structural analysis revealed various distinctions between the bromodomains of BRD4 and that of CBP. For example, it was observed that unlike the BRD4 bromodomains, which prefer di-acetylated histone H4 sequences, the CBP bromodomain demonstrated a clear preference of a singly-acetylated H4 sequence motif. The study further provided insights into distinct modes of singly and di-acetylated histone H4 recognition by the bromodomains of CBP and BRD4. (Plotnikov et al., Structural Insights into Acetylated-Histone H4 Recognition by the Bromodomain-PHD Finger Module of Human Transcriptional Co-Activator CBP, Structure, 2014, 22(2): 353-360). Without being bound by any specific theory, it is hypothesized that the differences between the bromodomains of CBP and BRD4 will facilitate the identification of inhibitors that selectively target the bromodomain of CBP.

The CBP proteins have been associated with various clinical conditions. Haploinsufficiency of CBP in humans leads to Rubinstein-Taybi syndrome, characterized by mental retardation, craniofacial abnormalities, and broad thumbs and big toes. Heterozygous deletion of CBP in mice has been shown to cause defects in multiple tissues including the hematopoietic system. Altered function of CBP, resulting from chromosomal translocations, also contributes to the formation of leukemias. (Gerd A. Blobel, CBP and p300: versatile coregulators with important roles in hematopoietic gene expression, Journal of Leukocyte Biology, 2002, Vol. 71: 545-556). The CBP protein has also been implicated to play a role in human cancers characterized by p53 mutations. In response to cellular stress, p53 undergoes post-translational modification of the C and N-terminal regions, including acetylation at the C-terminal region (e.g., lysine acetylation at K382 pf p53), which results in recruitment of CBP via its bromodomain. The CBP-p53 acetylated lysine interaction in turn is crucial for p53-induced p21 mediated G1 cell cycle arrest. Thus, it is hypothesized that inhibition of the CBP bromodomain, and thereby p53-mediated p21 activation, has important clinical applications in cancer and other diseases wherein hyperactive p53 is known to play a role, such as Alzheimer's disease, Parkinson's disease, Huntington's disease spinal cord diseases, multiple sclerosis, ischemic brain injury, infectious and auto-immune diseases, and myocardial ischemia. (Hay et al., Discovery and Optimization of Small-Molecule Ligands for the CBP/p300 Bromodomains, Journal of The American Chemical Society, 2014, 136: 9308-9319). Furthermore, studies have suggested that sequenstration of CBP is one of the underlying cause of neurodegenerative diseases caused by expanded polyglutamine repeats, such as Huntington's disease, Dentatorubral pallioluysian atrophy, spinal bulbar muscular atrophy and spinocerebellar ataxia type 1, 2,3,6,7 and 12 (Janknecht, *The versatile functions of the transcriptional coactivators p300 and CBP and their roles in disease*, Histol. Histopathol. 17:657-668 (2002)).

Therapeutic targeting of bromodomains has recently been recognized as an important potential therapeutic modality in human malignant and inflammatory diseases (Muller et al., 2011, Expert Rev Mol Med 13:e29; Filippakopoulos and Knapp, 2014, Nat Rev Drug Discov 13(5):337-356). Inhibitors of bromodomains exhibit anti-inflammatory activity by inhibiting expression of anti-inflammatory genes. Th17 cells are a subset of T helper cells which produce IL-17A, IL17F, IL-21, IL-22, and GM-CSF. Th17 cells have been implicated as key effectors of autoimmune diseases such as ankylosing spondylitis (AS), psoriasis and psoriatic arthritis (PSA), rheumatoid arthritis, Crohn's disease, and multiple sclerosis (MS). JQ1, a bromo and extraterminal domain (BET) bromodomain inhibitor, was shown to reduce collagen-induced arthritis and experimental autoimmune encephalomyelitis, two other human inflammatory diseases in which Th17 is implicated (Belkina et al., 2013, J Immunology 190(7): 3670-3678). Secukinumab, an anti-IL-17A antibody, was shown to ameliorate ankylosing spondylitis (Baeten et al., 2013, Lancet 382(9906):1705-1713). In addition to supporting the importance of TH17 cells in such inflammatory diseases, this finding has intensified the search for new drugs capable of targeting TH17 cytokine production.

Th17 cells serve an important role in host immune responses by mediating the recruitment of neutrophils and macrophages in infected areas. Aberrant regulation of Th17 cells has been suggested to be a component in the pathogeneis of multiple inflammatory and autoimmune disorders. While Th17 cells have been understood to play a role in autoimmune and inflammatory processes, more recently Th17 cells have received new attention for their role in tumor immunology (Zou and Restifo, 2010, Nat Rev Immuno 10, 248-256; Coffelt et al., 2015, Nature 522, 345-348).

Regulatory T cells (Tregs) are often recruited to and accumulate within tumors, which lead to immune evasion by cancer cells. These intra-tumoral regulatory T cells decrease the response of effector T cells, which is a major roadblock to clearance of tumor cells by the immune system. One approach to strengthening the immune response to tumors is to specifically inhibit regulatory T cell recruitment or accumulation within tumors, an approach referred to as cancer immunotherapy (Dougan and Dranoff, 2009, Ann. Rev Immuno 27, 83-117; Mellman et al., 2011, Nature 480, 480-489; Curiel, 2007, J Clinical Inv 117, 1167-1174; Nishikawa and Sakaguchi, 2014, Cur Op Imm 27, 1-7).

CBP has been shown to be a critical component in regulatory T cell biology and suggested to be required for differentiation of Tregs from naïve T cells. Specifically, deletion of CBP in mouse regulatory T cells led to impaired Treg suppressive function and reduced tumor growth in murine cancer models. Liu et al., Nat. Med. 19:1173 (2013); Liu et al., Mol. Cel. Biol. 34:3993 (2014). The CBP bromodomain comprises a hydrophobic pocket well suited to binding inhibitors, while the diversity of the surface and loop residues across the bromodomain allows for selective targeting by pharmacological agents. (Muller et al., 2011, Exp Rev Mol Med 13, e29; Hay et al., 2014, J Am Chem Soc, 136, 9308-9313). These characteristics make CBP an ideal target for immunotherapy. In support of this approach, Th17 cytokine production is disrupted by CBP bromodomain inhibition (Ghosh et al., J. Biol. Chem. (2016); Hammitzsch et al., PNAS 112:10768-10773 (2015)).

The activity of CBP inhibitors could result in impaired Treg differentiation and function, thus releasing suppression of effector responses in cancer and possibly reinitiate antitumor immunity. Therefore, these inhibitors, either alone or in conjunction with complementary cancer immunotherapies, could potentiate tumor eradication, such as through the reversal of cytotoxic CD8+ T cell exhaustion by antibody-mediated checkpoint inhibition (Brahmer et al., NEJM 366: 2455 (2012); Topalian et al., 2012, NEJM 366, 2443-2454; Hodi et al., NEJM 363:711-723 (2010)). Other CBP inhibitors have been studied in the context of leukemia therapy (Picaud et al., Cancer Res. 75(23):1-14 (2015).

In some embodiments, the compounds disclosed herein are capable of inhibiting activity of CBP protein, or a mutant thereof, in a biological sample is useful for a variety of purposes that are known to one of skill in the art. Examples of such purposes include, but are not limited to, blood transfusion, organ-transplantation, biological specimen storage, and biological assays.

In some embodiments, the compounds disclosed herein are capable of inhibiting activity of CBP protein, or a mutant thereof, in a patient comprising the step of administering to said patient a provided compound, or a composition comprising said compound.

Some embodiments relate to a method of inhibiting CBP protein, or a mutant thereof, in a biological sample comprising the step of contacting said biological sample with a compound as disclosed herein. Some embodiments provide a method for treating a disorder mediated by CBP protein, such as a BET protein, or a mutant thereof, in a patient in need thereof, comprising the step of administering to said patient a compound as disclosed herein.

Diseases and conditions treatable according to the disclosed methods include, but are not limited to, cancer and other proliferative disorders, Alzheimer's disease, Parkinson's disease, Huntington's disease spinal cord diseases, multiple sclerosis, ischemic brain injury, infectious and auto-immune diseases, Dentatorubral pallioluysian atrophy, spinal bulbar muscular atrophy and spinocerebellar ataxia type 1,2,3,6,7 and 12, viral infections, and myocardial ischemia. Thus one aspect is a method of treating a subject having a disease, disorder, or symptom thereof the method including administration of a compound or composition herein to the subject. In one embodiment, a human patient is treated with a disclosed compound and a pharmaceutically acceptable carrier, adjuvant, or vehicle, wherein said compound is present in an amount to measurably inhibit CBP protein activity in the patient.

The disclosure further provides a method of treating a subject, such as a human, suffering from one of the conditions, illnesses, disorders or diseases disclosed herein. The method comprises administering a therapeutically effective amount of one or more provided compounds, which function by inhibiting CBP protein and, in general, by modulating gene expression, to induce various cellular effects, in particular induction or repression of gene expression, arresting cell proliferation, inducing cell differentiation and/or inducing apoptosis, to a subject in need of such treatment.

The disclosure further provides a therapeutic method of modulating protein methylation, gene expression, cell proliferation, cell differentiation and/or apoptosis in vivo in conditions, illnesses, disorders or diseases disclosed herein, in particular cancer, inflammatory disease, and/or viral disease comprising administering to a subject in need of such therapy a pharmacologically active and therapeutically effective amount of one or more compounds disclosed herein.

In certain embodiments, the compounds disclosed herein treat or ameliorate inflammatory or autoimmune disorders. In some aspects the inflammatory or autoimmune disorders include, but are not limited to, ankylosing spondylitis (AS), psoriasis and psoriatic arthritis (PSA), rheumatoid arthritis, Crohn's disease, and multiple sclerosis (MS).

In some embodiments, the compounds disclosed herein inhibit Th17 cell function. In some aspects, the embodiment inhibits cytokine secretion, such as, but not limited to, IL-17A secretion.

In some embodiments, the compounds disclosed herein are used in immune-oncology therapies. In some aspects, the disclosed compounds impair regulatory T cell differentiation and function. In some aspects, use of the disclosed compounds decreased recruitment or accumulation of regulatory T cells in tumors. In some aspects, use of the disclosed compounds reduces suppression of effector cells in cancer contexts.

The disclosure further relates to a method for treating or ameliorating cancer or another proliferative disorder by administration of an effective amount of a compound, as disclosed herein, to a mammal, in particular a human in need of such treatment. In some embodiments, the disease to be treated by the disclosed methods is cancer.

In certain embodiments, the cancer is adult T-cell leukemia/lymphoma, breast cancer, brain cancer, or lung cancer.

In some embodiments, the compounds disclosed herein treat or prevent viral infections such as herpes virus, human papilloma virus, adenovirus, poxvirus and other DNA viruses.

One embodiment provides a method of regulating gene transcription in a cell comprising exposing a bromodomain containing protein to a compound of Formula (I). One embodiment provides a method of inhibiting bromodomain-mediated recognition of an acetyl lysine region of a protein comprising exposing the bromodomain to a compound of Formula (I).

Methods of Treatment

One embodiment provides a method of treating cancer in a patient in need thereof, comprising administering to the patient a compound of Formula (I), or a pharmaceutically acceptable salt thereof.

Other embodiments and uses will be apparent to one skilled in the art in light of the present disclosures. The following examples are provided merely as illustrative of various embodiments and shall not be construed to limit the disclosure in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling Example 1: Propane-2-sulfonic acid [2-(2,5-dichloro-phenoxy)-6-(1,5-dimethyl-6-oxo-1,6-dihydro-pyridin-3-yl)-pyrimidin-4-yl]-amide Step 1: 4,6-Dichloro-2-(2,5-dichloro-phenoxy)-pyrimidine

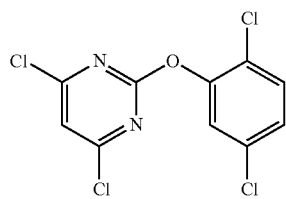 [SMILES: Clc1ccc(Cl)c(Oc2nc(Cl)cc(Cl)n2)c1]

A solution of 2,5-dichlorophenol (300 mg, 1.8 mmol) in THF (20 mL) stirred at −50° C. under $N_2$ was treated with NaH (81 mg, 2.0 mmol). Stirred at −50° C. for 20 min, the reaction mixture was treated with 4,6-dichloro-2-methanesulfonyl-pyrimidine (418 mg, 1.8 mmol). The mixture stirred at −50° C. under $N_2$ for 2 h. LC-MS showed the reaction was complete. The reaction mixture was quenched with water and extracted with EtOAc (25 mL*2). The combined organic layer was washed with brine, dried over $Na_2SO_4$, filtered, and concentrated under vacuum. The residue was purified by column chromatography on silica gel eluting with PE/EtOAc (10:1) to give the title compound (552 mg, 1.8 mmol) as a white solid in 97% yield. $^1$H NMR (300 MHz, $CDCl_3$): δ 7.43-7.40 (m, 1H), 7.26-7.22 (m, 2H), 7.17 (s, 1H). LCMS (M+H)$^+$ 309.

Step 2: 5-[6-Chloro-2-(2,5-dichloro-phenoxy)-pyrimidin-4-yl]-1,3-dimethyl-1H-pyridin-2-one

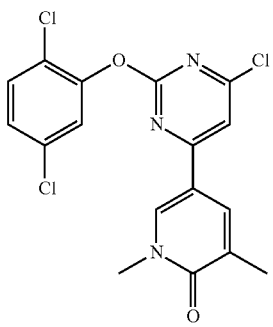 [SMILES: Cc1cc(-c2cc(Cl)nc(Oc3cc(Cl)ccc3Cl)n2)cn(C)c1=O]

A solution of the title compound of step 1 (425 mg, 1.4 mmol), 1,3-dimethyl-5-(4,4,5,5-tetramethyl-[1,3,2]dioxaborolan-2-yl)-1H-pyridin-2-one (309 mg, 1.2 mmol), Pd(dppf)Cl$_2$ (101 mg, 0.14 mmol), $K_3PO_4$ (0.92 mL, 3.8 mol/L) in dioxane (5 mL) was bubbled with $N_2$ for 5 min. The mixture was stirred at 75° C. for 2 h. LC-MS showed the reaction was complete. After water addition, the mixture was extracted with EtOAc (30 mL*2), and the combined organic layer was washed with brine, dried over $Na_2SO_4$, filtered, and the filtrate was concentrated under vacuum. The residue was purified by column chromatography on silica gel eluting with PE/EtOAc (2:1) to give the title compound (327 mg, 0.82 mmol) as a white solid in 67% yield. $^1$H NMR (400 MHz, $CDCl_3$): δ 8.17 (d, J=2.4 Hz, 1H), 7.68 (s, 1H), 7.44 (d, J=8.7 Hz, 1H). 7.31 (d, J=2.1 Hz, 1H), 7.26-7.23 (m, 2H), 3.62 (s, 3H), 2.21 (s, 3H). LCMS (M+H)$^+$ 396.

Step 3: Propane-2-sulfonic acid [2-(2,5-dichloro-phenoxy)-6-(1,5-dimethyl-6-oxo-1,6-dihydro-pyridin-3-yl)-pyrimidin-4-yl]-amide

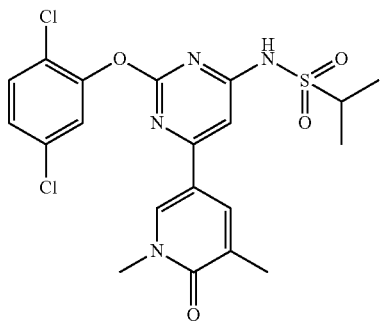 [SMILES: Cc1cc(-c2cc(NS(=O)(=O)C(C)C)nc(Oc3cc(Cl)ccc3Cl)n2)cn(C)c1=O]

A mixture of the title compound of step 2 (100 mg, 0.25 mmol), propane-2-sulfonic acid amide (78 mg, 0.63 mmol), Pd$_2$(dba)$_3$ (12 mg, 0.01 mmol), X-phos (18 mg, 0.04 mmol) and $Cs_2CO_3$ (116 mg, 0.35 mmol) in dioxane (5 mL) was placed in a seal tube and purged with $N_2$ for 5 min. The sealed tube was stirred at 90° C. for 4 h. LC-MS showed the reaction was complete. The mixture was poured into saturated $NH_4Cl$ solution (45 mL) and adjusted pH to 5 with aqueous 2M HCl, extracted with EtOAc (30 mL), and the organic layer was washed with brine, dried over $Na_2SO_4$, filtered and concentrated under vacuum. The residue was purified by column chromatography on silica gel eluting with PE/EtOAc (1:1) to give the title compound (45 mg, 0.09 mmol) as a white solid in 37% yield. $^1$H NMR (400 MHz, $CD_3OD$): δ 8.41 (s, 1H), 7.96 (s, 1H), 7.55 (d, J=8.7 Hz, 1H), 7.44 (s, 1H), 7.35-7.33 (m, 1H), 6.88 (s, 1H), 3.66 (s, 3H), 3.44-3.39 (m, 1H), 2.18 (s, 3H), 1.22 (d, J=6.6 Hz, 6H). LCMS (M+H)$^+$ 483.

Examples 2-43 in Table 3 were prepared using the appropriate phenol and sulfonamide in a similar multi-step manner as Example 1.

TABLE 3

| Example | Structure | IUPAC Name | ¹H NMR ppm (δ) | MS (M + H) |
|---|---|---|---|---|
| 2 | | Propane-2-sulfonic acid [6-(1,5-dimethyl-6-oxo-1,6-dihydro-pyridin-3-yl)-2-(2,5-dimethyl-phenoxy)-pyrimidin-4-yl]-amide | (CD$_3$OD, 300 MHz) δ 8.41 (d, J = 2.7 Hz, 1H), 7.98 (s, 1H), 7.18 (d, J = 7.8 Hz, 1H), 7.01 (d, J = 7.8 Hz, 1H), 6.91 (s, 1H), 6.79 (s, 1H), 3.67 (s, 3H), 3.27-3.23 (m, 1H), 2.33 (s, 3H), 2.19 (s, 3H), 2.10 (s, 3H), 1.13 (d, J = 6.9 Hz, 6H) | 443 |
| 3 | | Propane-2-sulfonic acid [2-(2-chloro-6-methyl-phenoxy)-6-(1,5-dimethyl-6-oxo-1,6-dihydro-pyridin-3-yl)-pyrimidin-4-yl]-amide | (CD$_3$OD, 300 MHz) δ 8.44 (d, J = 2.1 Hz, 1H), 7.98 (s, 1H), 7.35 (d, J = 8.4 Hz, 1H), 7.28 (d, J = 6.9 Hz, 1H), 7.21-7.16 (m, 1H), 6.84 (s, 1H), 3.67 (s, 3H), 3.25-3.20 (m, 1H), 2.21 (s, 3H), 2.20 (s, 3H), 1.14 (d, J = 6.9 Hz, 6H) | 463 |
| 4 | | Propane-2-sulfonic acid [6-(1,5-dimethyl-6-oxo-1,6-dihydro-pyridin-3-yl)-2-(2-methoxy-5-methyl-phenoxy)-pyrimidin-4-yl]-amide | (CD$_3$OD, 300 MHz) δ 8.40 (d, J = 2.1 Hz, 1H), 7.97 (s, 1H), 7.07-7.05 (m, 1H), 6.99 (d, J = 8.1 Hz, 2H), 6.78 (s, 1H), 3.72 (s, 3H), 3.66 (s, 3H), 3.34-3.32 (m, 1H), 2.31 (s, 3H), 2.19 (s, 3H), 1.14 (d, J = 6.6 Hz, 6H) | 459 |
| 5 | | Propane-2-sulfonic acid [2-(2-chloro-5-methyl-phenoxy)-6-(1,5-dimethyl-6-oxo-1,6-dihydro-pyridin-3-yl)-pyrimidin-4-yl]-amide | (CD$_3$OD, 300 MHz) δ 8.40 (d, J = 2.1 Hz, 1H), 7.97 (d, J = 1.2 Hz, 1H), 7.39 (d, J = 8.1 Hz, 1H), 7.15-7.10 (m, 2H), 6.84 (s, 1H), 3.66 (s, 3H), 3.50-3.37 (m, 1H), 2.38 (s, 3H), 2.19 (s, 3H), 1.18 (d, J = 6.9 Hz, 6H) | 463 |
| 6 | 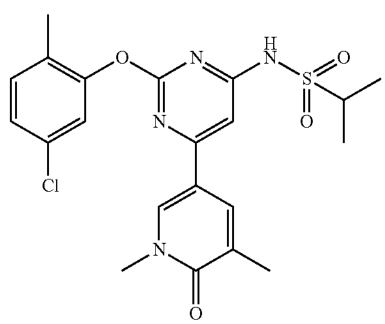 [SMILES: Cc1ccc(Cl)cc1Oc1nc(NS(=O)(=O)C(C)C)cc(-c2cc(C)c(=O)n(C)c2)n1] | Propane-2-sulfonic acid [2-(5-chloro-2-methyl-phenoxy)-6-(1,5-dimethyl-6-oxo-1,6-dihydro-pyridin-3-yl)-pyrimidin-4-yl]-amide | (CD$_3$OD, 300 MHz) δ 8.41 (s, 1H), 7.98 (s, 1H), 7.31 (d, J = 8.1 Hz, 1H), 7.22-7.18 (m, 2H), 6.81 (s, 1H), 3.66 (s, 3H), 3.36-3.33 (m, 1H), 2.19 (s, 3H), 2.14 (s, 3H), 1.17 (d, J = 6.6 Hz, 6H) | 463 |
| 7 | 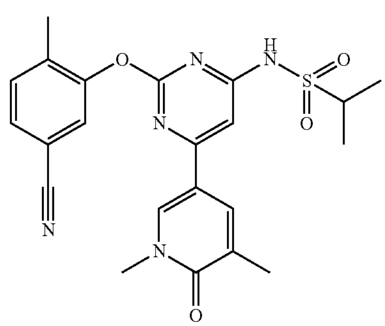 [SMILES: Cc1ccc(C#N)cc1Oc1nc(NS(=O)(=O)C(C)C)cc(-c2cc(C)c(=O)n(C)c2)n1] | Propane-2-sulfonic acid [2-(5-cyano-2-methyl-phenoxy)-6-(1,5-dimethyl-6-oxo-1,6-dihydro-pyridin-3-yl)-pyrimidin-4-yl]-amide | (CD$_3$OD, 300 MHz) δ 8.41 (d, J = 2.1 Hz, 1H), 7.97 (s, 1H), 7.59-7.56 (m, 2H), 7.52 (d, J = 8.4 Hz, 1H), 6.85 (s, 1H), 3.66 (s, 3H), 3.26 (m, 1H), 2.26 (s, 3H), 2.19 (s, 3H), 1.19 (d, J = 6.9 Hz, 6H) | 454 |

TABLE 3-continued

| Example | Structure | IUPAC Name | ¹H NMR ppm (δ) | MS (M + H) |
|---|---|---|---|---|
| 8 | 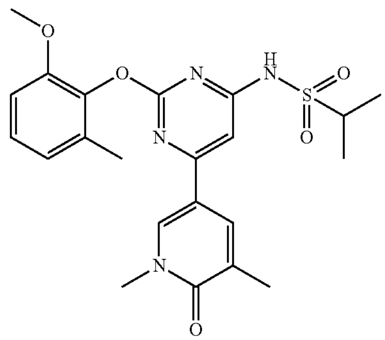 [SMILES: COc1cccc(C)c1Oc1nc(NS(=O)(=O)C(C)C)cc(-c2cc(C)c(=O)n(C)c2)n1] | Propane-2-sulfonic acid [6-(1,5-dimethyl-6-oxo-1,6-dihydro-pyridin-3-yl)-2-(2-methoxy-6-methyl-phenoxy)-pyrimidin-4-yl]-amide | (CD$_3$OD, 300 MHz) δ 8.42 (d, J = 1.8 Hz, 1H), 7.99 (d, J = 2.4 Hz, 1H), 7.14 (t, J = 8.1 Hz, 1H), 6.94 (d, J = 8.1 Hz, 1H), 6.88 (d, J = 7.2 Hz, 1H), 6.77 (s, 1H), 3.73 (s, 3H), 3.67 (s, 3H), 3.21-3.16 (m, 1H), 2.20 (s, 3H), 2.17 (s, 3H), 1.10 (d, J = 6.9 Hz, 6H) | 459 |
| 9 | 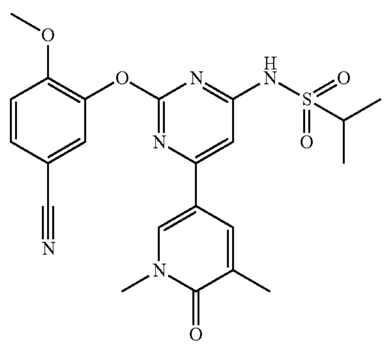 [SMILES: COc1ccc(C#N)cc1Oc1nc(NS(=O)(=O)C(C)C)cc(-c2cc(C)c(=O)n(C)c2)n1] | Propane-2-sulfonic acid [2-(5-cyano-2-methoxy-phenoxy)-6-(1,5-dimethyl-6-oxo-1,6-dihydro-pyridin-3-yl)-pyrimidin-4-yl]-amide | (CD$_3$OD, 300 MHz) δ 8.40 (d, J = 2.4 Hz, 1H), 7.96 (d, J = 1.5 Hz, 1H), 7.69 (dd, J = 1.8 Hz, 8.4 Hz, 1H), 7.59 (d, J = 2.1 Hz, 1H), 7.29 (d, J = 8.7 Hz, 1H), 6.83 (s, 1H), 3.85 (s, 3H), 3.66 (s, 3H), 3.27 (m, 1H), 2.19 (s, 3H), 1.18 (d, J = 7.2 Hz, 6H) | 470 |
| 10 | 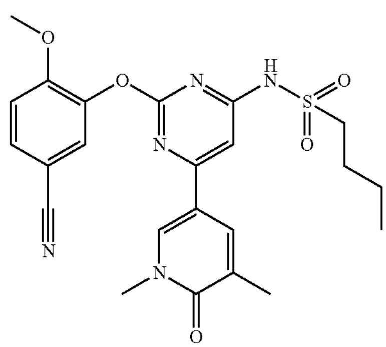 [SMILES: CCCCS(=O)(=O)Nc1cc(-c2cc(C)c(=O)n(C)c2)nc(Oc2cc(C#N)ccc2OC)n1] | Butane-1-sulfonic acid [2-(5-cyano-2-methoxy-phenoxy)-6-(1,5-dimethyl-6-oxo-1,6-dihydro-pyridin-3-yl)-pyrimidin-4-yl]-amide | (CD$_3$OD, 300 MHz) δ 8.41 (d, J = 2.4 Hz, 1H), 7.97 (s, 1H), 7.68 (dd, J = 2.4 Hz, 9.0 Hz, 1H), 7.59 (d, J = 1.5 Hz, 1H), 7.29 (d, J = 8.7 Hz, 1H), 6.79 (s, 1H), 3.85 (s, 3H), 3.66 (s, 3H), 3.06-3.01 (m, 2H), 2.19 (s, 3H), 1.59-1.53 (m, 2H), 1.35-1.27 (m, 2H), 0.89 (t, J = 7.2 Hz, 3H) | 484 |
| 11 | 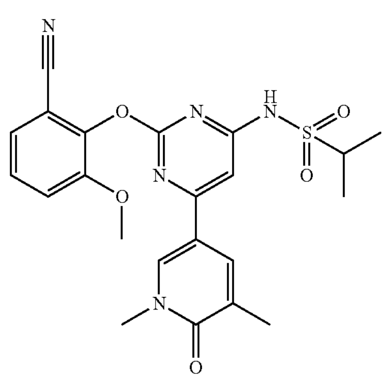 [SMILES: COc1cccc(C#N)c1Oc1nc(NS(=O)(=O)C(C)C)cc(-c2cc(C)c(=O)n(C)c2)n1] | Propane-2-sulfonic acid [2-(2-cyano-6-methoxy-phenoxy)-6-(1,5-dimethyl-6-oxo-1,6-dihydro-pyridin-3-yl)-pyrimidin-4-yl]-amide | (CD$_3$OD, 300 MHz) δ 8.44 (s, 1H), 7.98 (s, 1H), 7.46-7.36 (m, 3H), 6.87 (s, 1H), 3.81 (s, 3H), 3.67 (s, 3H), 3.25-3.24 (m, 1H), 2.19 (s, 3H), 1.17 (d, J = 7.2 Hz, 6H) | 470 |

TABLE 3-continued

| Example | Structure | IUPAC Name | ¹H NMR ppm (δ) | MS (M + H) |
|---|---|---|---|---|
| 12 | 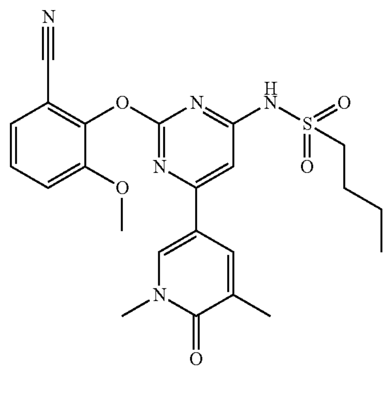 [SMILES: CCCCS(=O)(=O)Nc1cc(-c2cc(C)c(=O)n(C)c2)nc(Oc2c(C#N)cccc2OC)n1] | Butane-1-sulfonic acid [2-(2-cyano-6-methoxy-phenoxy)-6-(1,5-dimethyl-6-oxo-1,6-dihydro-pyridin-3-yl)-pyrimidin-4-yl]-amide | (CD₃OD, 300 MHz) δ 8.45 (d, J = 2.1 Hz, 1H), 7.98 (s, 1H), 7.46-7.33 (m, 3H), 6.84 (s, 1H), 3.81 (s, 3H), 3.67 (s, 3H), 3.04-2.99 (m, 2H), 2.19 (s, 3H), 1.59-1.53 (m, 2H), 1.36-1.28 (m, 2H), 0.89 (t, J = 7.2 Hz, 3H) | 484 |
| 13 | 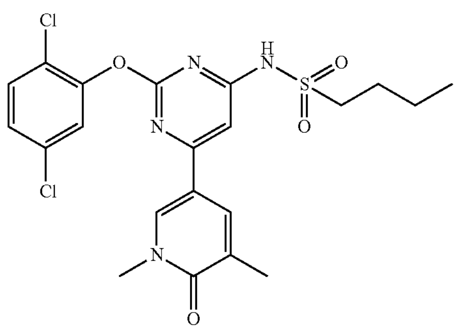 | Butane-1-sulfonic acid [2-(2,5-dichloro-phenoxy)-6-(1,5-dimethyl-6-oxo-1,6-dihydro-pyridin-3-yl)-pyrimidin-4-yl]-amide | (CD₃OD, 300 MHz) δ 8.42 (d, J = 2.4 Hz, 1H), 7.97 (s, 1H), 7.54 (d, J = 8.7 Hz, 1H), 7.45 (d, J = 2.1 Hz, 1H), 7.36-7.32 (m, 1H), 6.86 (s, 1H), 3.66 (s, 3H), 3.16 (t, J = 7.8 Hz, 2H), 2.19 (s, 3H), 1.65-1.58 (m, 2H), 1.40-1.33 (m, 2H), 0.91 (t, J = 7.5 Hz, 3H) | 497 |
| 14 | 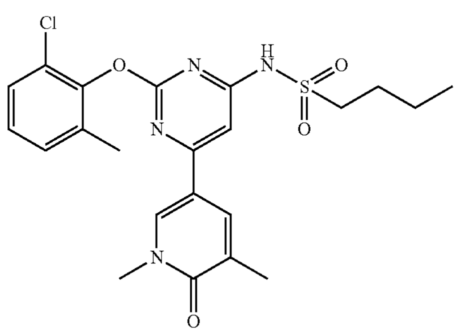 [SMILES: CCCCS(=O)(=O)Nc1cc(-c2cc(C)c(=O)n(C)c2)nc(Oc2c(C)cccc2Cl)n1] | Butane-1-sulfonic acid [2-(2-chloro-6-methyl-phenoxy)-6-(1,5-dimethyl-6-oxo-1,6-dihydro-pyridin-3-yl)-pyrimidin-4-yl]-amide | (CD₃OD, 300 MHz) δ 8.45 (d, J = 2.1 Hz, 1H), 7.99 (s, 1H), 7.34 (d, J = 8.4 Hz, 1H), 7.28 (d, J = 6.6 Hz, 1H), 7.21-7.16 (m, 1H), 6.82 (s, 1H), 3.37 (s, 3H), 2.98 (t, J = 8.1 Hz, 2H), 2.22 (s, 3H), 2.19 (s, 3H), 1.57-1.49 (m, 2H), 1.34-1.27 (m, 2H), 0.89 (t, J = 7.2 Hz, 3H) | 477 |
| 15 | 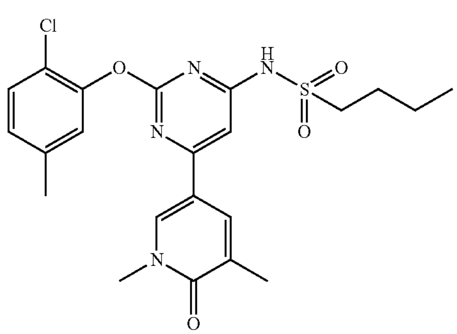 [SMILES: CCCCS(=O)(=O)Nc1cc(-c2cc(C)c(=O)n(C)c2)nc(Oc2cc(C)ccc2Cl)n1] | Butane-1-sulfonic acid [2-(2-chloro-5-methyl-phenoxy)-6-(1,5-dimethyl-6-oxo-1,6-dihydro-pyridin-3-yl)-pyrimidin-4-yl]-amide | (CD₃OD, 300 MHz) δ 8.42 (d, J = 1.8 Hz, 1H), 7.98 (s, 1H), 7.38 (d, J = 8.1 Hz, 1H), 7.16-7.10 (m, 2H), 6.82 (s, 1H), 3.66 (s, 3H), 3.12-3.06 (m, 2H), 2.37 (s, 3H), 2.19 (s, 3H), 1.61-1.53 (m, 2H), 1.36-1.29 (m, 2H), 0.89 (t, J = 7.2 Hz, 3H) | 477 |

TABLE 3-continued

| Example | Structure | IUPAC Name | ¹H NMR ppm (δ) | MS (M + H) |
|---|---|---|---|---|
| 16 | 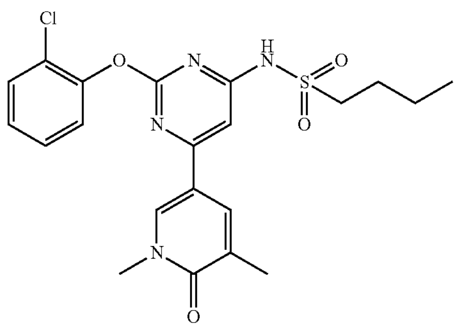 [SMILES: CCCCS(=O)(=O)Nc1cc(-c2cc(C)c(=O)n(C)c2)nc(Oc2ccccc2Cl)n1] | Butane-1-sulfonic acid [2-(2-chloro-phenoxy)-6-(1,5-dimethyl-6-oxo-1,6-dihydro-pyridin-3-yl)-pyrimidin-4-yl]-amide | (CD$_3$OD, 300 MHz) δ 8.41 (d, J = 1.5 Hz, 1H), 7.97 (s, 1H), 7.53 (d, J = 8.7 Hz, 1H), 7.42-7.39 (m, 1H), 7.34-7.27 (m, 2H), 6.84 (s, 1H), 3.66 (s, 3H), 3.12-3.06 (m, 2H), 2.18 (s, 3H), 1.62-1.53 (m, 2H), 1.38-1.30 (m, 2H), 0.89 (t, J = 6.9 Hz, 3H) | 463 |
| 17 | 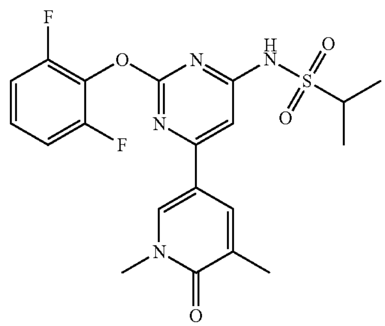 [SMILES: Cc1cc(-c2cc(NS(=O)(=O)C(C)C)nc(Oc3c(F)cccc3F)n2)cn(C)c1=O] | Propane-2-sulfonic acid [2-(2,6-difluoro-phenoxy)-6-(1,5-dimethyl-6-oxo-1,6-dihydro-pyridin-3-yl)-pyrimidin-4-yl]-amide | (DMSO-d$_6$, δ 300 MHz) δ 11.3 (s, 1H), 8.44 (s, 1H), 7.80 (s, 1H), 7.40-7.29 (m, 3H), 6.91 (s, 1H), 3.56 (s, 3H), 3.29-3.27 (m, 1H), 2.08 (s, 3H), 1.12 (d, J = 6.9 Hz, 6H) | 451 |
| 18 | 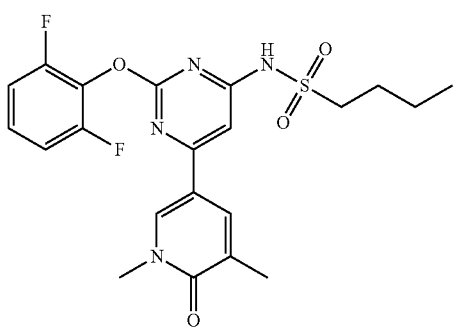 [SMILES: CCCCS(=O)(=O)Nc1cc(-c2cc(C)c(=O)n(C)c2)nc(Oc2c(F)cccc2F)n1] | Butane-1-sulfonic acid [2-(2,6-difluoro-phenoxy)-6-(1,5-dimethyl-6-oxo-1,6-dihydro-pyridin-3-yl)-pyrimidin-4-yl]-amide | (CD$_3$OD, 300 MHz) δ 8.40 (s, 1H), 7.96 (s, 1H), 7.33-7.30 (m, 1H), 7.17-7.11 (m, 2H), 6.88 (s, 1H), 3.65 (s, 3H), 3.18-3.13 (m, 2H), 2.18 (s, 3H), 1.65-1.60 (m, 2H), 1.40-1.32 (m, 2H), 0.90 (t, J = 7.2 Hz, 3H) | 465 |
| 19 | 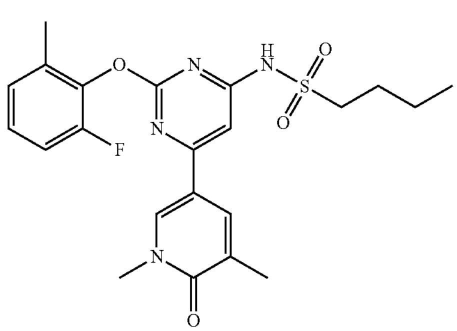 [SMILES: CCCCS(=O)(=O)Nc1cc(-c2cc(C)c(=O)n(C)c2)nc(Oc2c(C)cccc2F)n1] | Butane-1-sulfonic acid [6-(1,5-dimethyl-6-oxo-1,6-dihydro-pyridin-3-yl)-2-(2-fluoro-6-methyl-phenoxy)-pyrimidin-4-yl]-amide | (CD$_3$OD, 300 MHz) δ 8.41 (s, 1H), 7.97 (s, 1H), 7.19-7.07 (m, 3H), 6.82 (s, 1H), 3.66 (s, 3H), 3.06-3.01 (m, 2H), 2.22 (s, 3H), 2.18 (s, 3H), 1.59-1.54 (m, 2H), 1.34-1.27 (m, 2H), 0.88 (t, J = 7.2 Hz, 3H) | 461 |

TABLE 3-continued

| Example | Structure | IUPAC Name | ¹H NMR ppm (δ) | MS (M + H) |
|---|---|---|---|---|
| 20 | 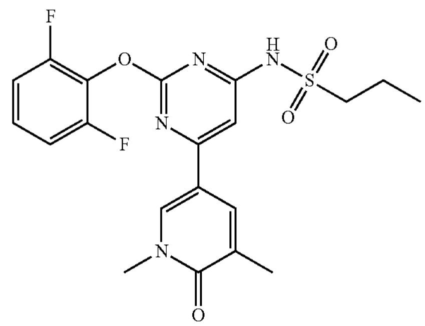 [SMILES: CCCS(=O)(=O)Nc1cc(-c2cc(C)c(=O)n(C)c2)nc(Oc2c(F)cccc2F)n1] | Propane-1-sulfonic acid [2-(2,6-difluoro-phenoxy)-6-(1,5-dimethyl-6-oxo-1,6-dihydro-pyridin-3-yl)-pyrimidin-4-yl]-amide | (CD$_3$OD, 300 MHz) δ 8.39 (s, 1H), 7.96 (s, 1H), 7.35-7.31 (m, 1H), 7.17-7.11 (m, 2H), 6.87 (s, 1H), 3.65 (s, 3H), 3.14-3.09 (m, 2H), 2.18 (s, 3H), 1.71-1.63 (m, 2H), 0.96 (t, J = 7.5 Hz, 3H) | 451 |
| 21 | 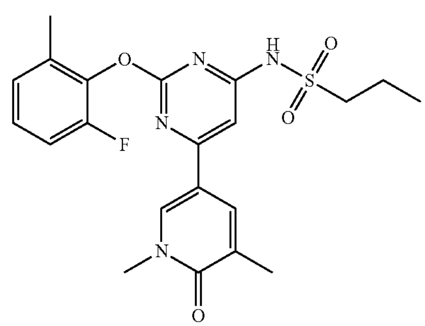 [SMILES: CCCS(=O)(=O)Nc1cc(-c2cc(C)c(=O)n(C)c2)nc(Oc2c(C)cccc2F)n1] | Propane-1-sulfonic acid [6-(1,5-dimethyl-6-oxo-1,6-dihydro-pyridin-3-yl)-2-(2-fluoro-6-methyl-phenoxy)-pyrimidin-4-yl]-amide | (CD$_3$OD, 300 MHz) δ 8.38 (s, 1H), 7.98 (s, 1H), 7.19-7.07 (m, 3H), 6.77 (s, 1H), 3.66 (s, 3H), 2.98-2.92 (m, 2H), 2.23 (s, 3H), 2.19 (s, 3H), 1.63-1.56 (m, 2H), 0.89 (t, J = 7.2 Hz, 3H) | 447 |
| 22 | 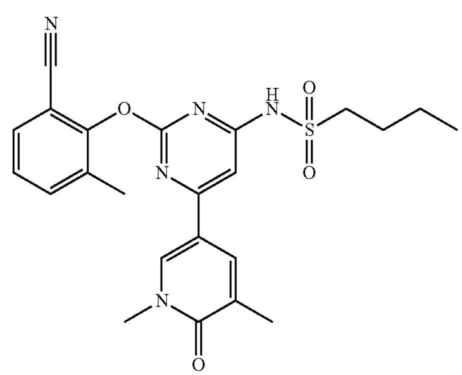 [SMILES: CCCCS(=O)(=O)Nc1cc(-c2cc(C)c(=O)n(C)c2)nc(Oc2c(C)cccc2C#N)n1] | Butane-1-sulfonic acid [2-(2-cyano-6-methyl-phenoxy)-6-(1,5-dimethyl-6-oxo-1,6-dihydro-pyridin-3-yl)-pyrimidin-4-yl]-amide | (CD$_3$OD, 400 MHz) δ 8.45 (d, J = 2.4 Hz, 1H), 7.98 (s, 1H), 7.67-7.64 (m, 2H), 7.74 (t, J = 7.6 Hz, 1H), 6.86 (s, 1H), 3.66 (s, 3H), 3.00 (t, J = 7.6 Hz, 2H), 2.23 (s, 3H), 2.19 (s, 3H), 1.61-1.53 (m, 2H), 1.36-1.27 (m, 2H), 0.89 (t, J = 6.8 Hz, 3H) | 468 |
| 23 | 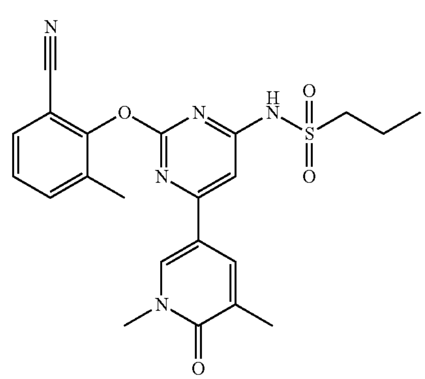 [SMILES: CCCS(=O)(=O)Nc1cc(-c2cc(C)c(=O)n(C)c2)nc(Oc2c(C)cccc2C#N)n1] | Propane-1-sulfonic acid [2-(2-cyano-6-methyl-phenoxy)-6-(1,5-dimethyl-6-oxo-1,6-dihydro-pyridin-3-yl)-pyrimidin-4-yl]-amide | (CD$_3$OD, 400 MHz) δ 8.45 (d, J = 2.4 Hz, 1H), 7.99-7.98 (m, 1H), 7.68-7.65 (m, 2H), 7.38 (t, J = 7.6 Hz, 1H), 6.86 (s, 1H), 3.67 (s, 3H), 2.99-2.95 (m, 2H), 2.23 (s, 3H), 2.19 (s, 3H), 1.67-1.57 (m, 2H), 0.92 (t, J = 7.6 Hz, 3H) | 454 |

TABLE 3-continued

| Example | Structure | IUPAC Name | ¹H NMR ppm (δ) | MS (M + H) |
|---|---|---|---|---|
| 24 | 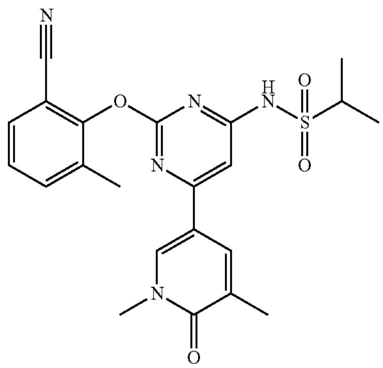 [SMILES: Cc1cccc(C#N)c1Oc1nc(NS(=O)(=O)C(C)C)cc(-c2cc(C)c(=O)n(C)c2)n1] | Propane-2-sulfonic acid [2-(2-cyano-6-methyl-phenoxy)-6-(1,5-dimethyl-6-oxo-1,6-dihydro-pyridin-3-yl)-pyrimidin-4-yl]-amide | (CD$_3$OD, 400 MHz) δ 8.41 (d, J = 2.4 Hz, 1H), 7.99-7.98 (m, 1H), 7.65 (d, J = 7.6 Hz, 2H), 7.37 (t, J = 7.6 Hz, 1H), 6.83 (s, 1H), 3.66 (s, 3H), 3.23-3.14 (m, 1H), 2.22 (s, 3H), 2.19 (s, 3H), 1.14 (d, J = 6.8 Hz, 6H) | 454 |
| 25 | 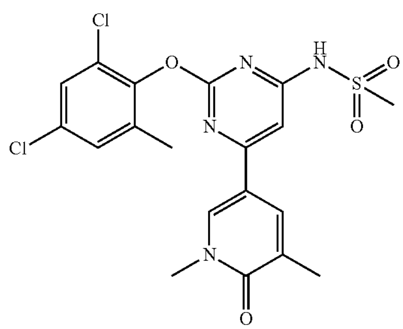 [SMILES: Cc1cc(Cl)cc(Cl)c1Oc1nc(NS(C)(=O)=O)cc(-c2cc(C)c(=O)n(C)c2)n1] | N-[2-(2,4-Dichloro-6-methyl-phenoxy)-6-(1,5-dimethyl-6-oxo-1,6-dihydro-pyridin-3-yl)-pyrimidin-4-yl]-methanesulfonamide | (CD$_3$OD, 300 MHz) δ 8.42 (s, 1H), 7.97 (s, 1H), 7.43 (d, J = 2.1 Hz, 1H, 7.34 (s, 1H), 6.87 (s, 1H), 3.66 (s, 3H), 3.01 (s, 3H), 2.21 (s, 3H), 2.19 (s, 3H). | 469 |
| 26 | 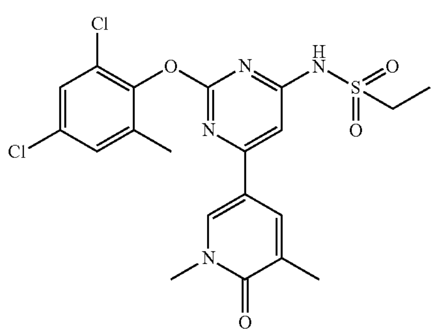 [SMILES: CCS(=O)(=O)Nc1cc(-c2cc(C)c(=O)n(C)c2)nc(Oc2c(C)cc(Cl)cc2Cl)n1] | Ethanesulfonic acid [2-(2,4-dichloro-6-methyl-phenoxy)-6-(1,5-dimethyl-6-oxo-1,6-dihydro-pyridin-3-yl)-pyrimidin-4-yl]-amide | (CD$_3$OD, 300 MHz) δ 8.43 (d, J = 1.2 Hz, 1H), 7.98 (s, 1H), 7.43 (d, J = 1.8 Hz, 1H), 7.34 (s, 1H), 6.85 (s, 1H), 3.67 (s, 3H), 3.08 (q, J = 7.2 Hz, 2H), 2.21 (s, 3H), 2.19 (s, 3H), 1.17 (t, J = 7.5 Hz, 3H) | 483 |
| 27 | 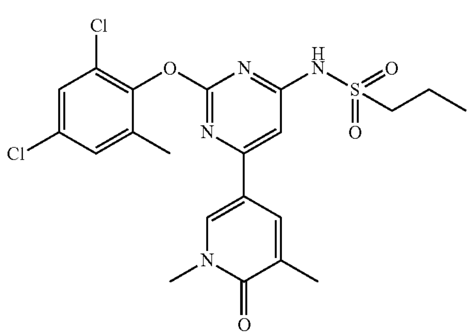 [SMILES: CCCS(=O)(=O)Nc1cc(-c2cc(C)c(=O)n(C)c2)nc(Oc2c(C)cc(Cl)cc2Cl)n1] | Propane-1-sulfonic acid [2-(2,4-dichloro-6-methyl-phenoxy)-6-(1,5-dimethyl-6-oxo-1,6-dihydro-pyridin-3-yl)-pyrimidin-4-yl]-amide | (CD$_3$OD, 300 MHz) δ 8.46 (s, 1H), 7.99 (s, 1H), 7.44 (d, J = 1.2 Hz, 1H), 7.35 (d, J = 1.5 Hz, 1H), 6.83 (s, 1H), 3.67 (s, 3H), 3.04-2.99 (m, 2H), 2.21 (s, 3H), 2.20 (s, 3H), 1.66-1.59 (m, 2H), 0.95 (t, J = 7.5 Hz, 3H) | 497 |

TABLE 3-continued

| Example | Structure | IUPAC Name | ¹H NMR ppm (δ) | MS (M + H) |
|---|---|---|---|---|
| 28 | 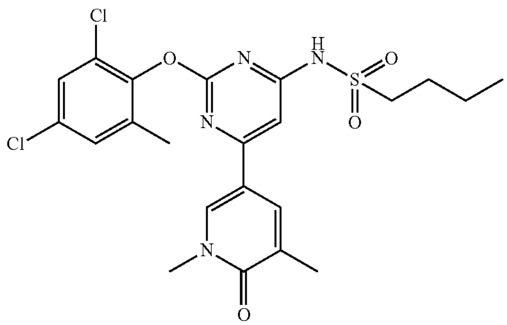 [SMILES: CCCCS(=O)(=O)Nc1cc(-c2cc(C)c(=O)n(C)c2)nc(Oc2c(C)cc(Cl)cc2Cl)n1] | Butane-1-sulfonic acid [2-(2,4-dichloro-6-methyl-phenoxy)-6-(1,5-dimethyl-6-oxo-1,6-dihydro-pyridin-3-yl)-pyrimidin-4-yl]-amide | (CD₃OD, 400 MHz) δ 8.45 (s, 1H), 7.99 (s, 1H), 7.42 (d, J = 1.2 Hz, 1H), 7.34 (s, 1H), 6.82 (s, 1H), 3.67 (s, 3H), 3.06-3.01 (m, 2H), 2.21 (s, 3H), 2.19 (s, 3H), 1.57-1.55 (m, 2H), 1.34-1.32 (m, 2H), 0.91 (t, J = 7.2 Hz, 3H) | 511 |
| 29 | 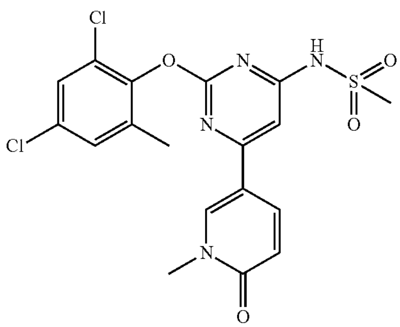 [SMILES: Cc1cc(Cl)cc(Cl)c1Oc1nc(NS(C)(=O)=O)cc(-c2ccc(=O)n(C)c2)n1] | N-[2-(2,4-Dichloro-6-methyl-phenoxy)-6-(1-methyl-6-oxo-1,6-dihydro-pyridin-3-yl)-pyrimidin-4-yl]-methanesulfonamide | (CD₃OD, 300 MHz) δ 8.55 (d, J = 2.7 Hz, 1H), 8.09 (dd, J = 9.3 Hz, 2.1 Hz, 1H), 7.42 (d, J = 1.8 Hz, 1H), 7.34 (d, J = 1.5 Hz, 1H), 6.89 (s, 1H), 6.62 (d, J = 9.6 Hz, 1H), 3.66 (s, 3H), 3.02 (s, 3H), 2.21 (s, 3H) | 455 |
| 30 | 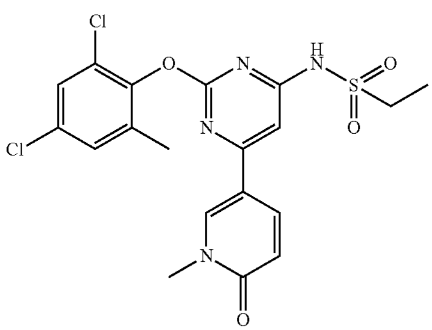 [SMILES: CCS(=O)(=O)Nc1cc(-c2ccc(=O)n(C)c2)nc(Oc2c(C)cc(Cl)cc2Cl)n1] | Ethanesulfonic acid [2-(2,4-dichloro-6-methyl-phenoxy)-6-(1-methyl-6-oxo-1,6-dihydro-pyridin-3-yl)-pyrimidin-4-yl]-amide | (CD₃OD, 300 MHz) δ 8.57 (d, J = 2.7 Hz, 1H), 8.11 (dd, J = 9.9 Hz, 2.7 Hz, 1H), 7.43 (d, J = 2.4 Hz, 1H), 7.34 (d, J = 1.5 Hz, 1H), 6.88 (s, 1H), 6.63 (d, J = 9.6 Hz, 1H), 3.66 (s, 3H), 3.09 (q, J = 7.5 Hz, 2H), 2.20 (s, 3H), 1.18 (t, J = 7.5 Hz, 3H) | 469 |
| 31 | 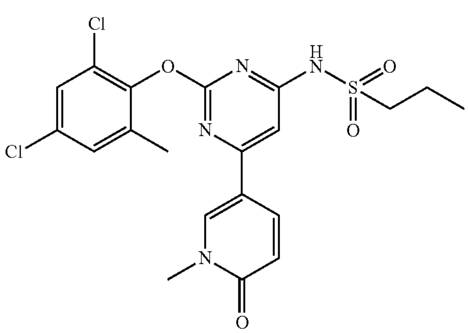 [SMILES: CCCS(=O)(=O)Nc1cc(-c2ccc(=O)n(C)c2)nc(Oc2c(C)cc(Cl)cc2Cl)n1] | Propane-1-sulfonic acid [2-(2,4-dichloro-6-methyl-phenoxy)-6-(1-methyl-6-oxo-1,6-dihydro-pyridin-3-yl)-pyrimidin-4-yl]-amide | (CD₃OD, 300 MHz) δ 8.59 (d, J = 2.7 Hz, 1H), 8.11 (dd, J = 9.6 Hz, 2.7 Hz, 1H), 7.43 (d, J = 2.7 Hz, 1H), 7.35 (s, 1H), 6.85 (s, 1H), 6.64 (d, J = 9.6 Hz, 1H), 3.67 (s, 3H), 3.05-3.00 (m, 2H), 2.21 (s, 3H), 1.67-1.59 (m, 2H), 0.95 (t, J = 7.5 Hz, 3H) | 483 |

TABLE 3-continued

| Example | Structure | IUPAC Name | ¹H NMR ppm (δ) | MS (M + H) |
|---|---|---|---|---|
| 32 | 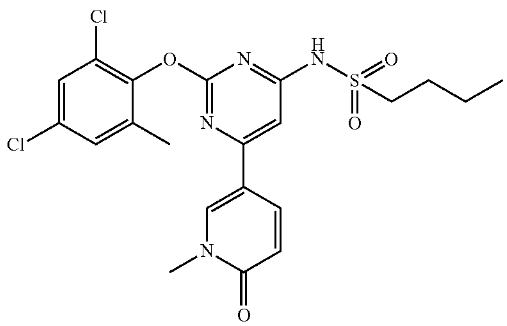 [SMILES: CCCCS(=O)(=O)Nc1cc(-c2ccc(=O)n(C)c2)nc(Oc2c(C)cc(Cl)cc2Cl)n1] | Butane-1-sulfonic acid [2-(2,4-dichloro-6-methyl-phenoxy)-6-(1-methyl-6-oxo-1,6-dihydro-pyridin-3-yl)-pyrimidin-4-yl]-amide | (CD$_3$OD, 300 MHz) δ 8.59 (d, J = 2.4 Hz, 1H), 8.11 (dd, J = 9.9 Hz, 3.0 Hz, 1H), 7.42 (d, J = 2.1 Hz, 1H), 7.34(d J = 1.8 Hz, 1H), 6.85 (s, 1H), 6.64 (d, J = 9.6 Hz, 1H), 3.67 (s, 3H), 3.08-3.03 (m, 2H), 2.21 (s, 3H), 1.61-1.55 (m, 2H), 1.37-1.30 (m, 2H), 0.91 (t, J = 7.5 Hz, 3H) | 497 |
| 33 | 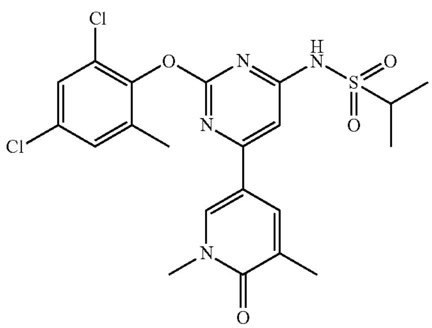 [SMILES: Cc1cc(Cl)cc(Cl)c1Oc1nc(NS(=O)(=O)C(C)C)cc(-c2cc(C)c(=O)n(C)c2)n1] | Propane-2-sulfonic acid [2-(2,4-dichloro-6-methyl-phenoxy)-6-(1,5-dimethyl-6-oxo-1,6-dihydro-pyridin-3-yl)-pyrimidin-4-yl]-amide | (CD$_3$OD, 400 MHz) δ 8.45 (d, J = 2.4 Hz, 1H), 7.99 (s, 1H), 7.44 (d, J = 2.0 Hz, 1H), 7.35 (d, J = 2.4 Hz, 1H), 6.84 (s, 1H), 3.67 (s, 3H), 3.27-3.20 (m, 1H), 2.20 (s, 3H), 2.19 (s, 3H), 1.17 (d, J = 6.8 Hz, 6H) | 497 |
| 34 | 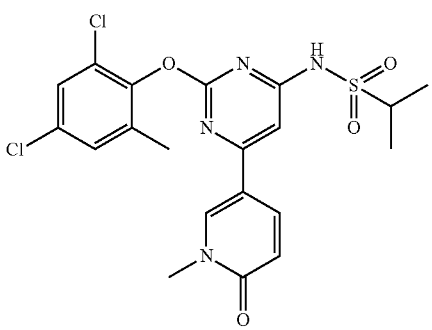 [SMILES: Cc1cc(Cl)cc(Cl)c1Oc1nc(NS(=O)(=O)C(C)C)cc(-c2ccc(=O)n(C)c2)n1] | Propane-2-sulfonic acid [2-(2,4-dichloro-6-methyl-phenoxy)-6-(1-methyl-6-oxo-1,6-dihydro-pyridin-3-yl)-pyrimidin-4-yl]-amide | (CD$_3$OD, 400 MHz) δ 8.59 (d, J = 2.8 Hz, 1H), 8.11 (dd, J = 9.6 Hz, 2.8 Hz 1H), 7.44 (d, J = 2.4 Hz, 1H), 7.34 (d, J = 1.6 Hz, 1H), 6.86 (s, 1H), 6.64 (d, J = 9.2 Hz, 1H), 3.67 (s, 3H), 3.26-3.23 (m, 1H), 2.21 (s, 3H), 1.18 (d, J = 7.2 Hz, 6H) | 483 |
| 35 | 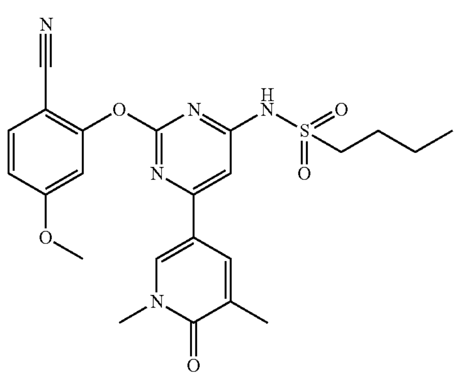 [SMILES: CCCCS(=O)(=O)Nc1cc(-c2cc(C)c(=O)n(C)c2)nc(Oc2cc(OC)ccc2C#N)n1] | Butane-1-sulfonic acid [2-(2-cyano-5-methoxy-phenoxy)-6-(1,5-dimethyl-6-oxo-1,6-dihydro-pyridin-3-yl)-pyrimidin-4-yl]-amide | (CD$_3$OD, 400 MHz) δ 8.43 (d, J = 2.4 Hz, 1H), 7.98 (s, 1H), 7.71 (d, J = 8.8 Hz, 1H), 7.04-6.98 (m, 2H), 6.87 (s, 1H), 3.90 (s, 3H), 3.66 (s, 3H), 3.17-3.13 (m, 2H), 2.19 (s, 3H), 1.64-1.60 (m, 2H), 1.36-1.30 (m, 2H), 0.88 (t, J = 7.6 Hz, 3H) | 484 |

TABLE 3-continued

| Example | Structure | IUPAC Name | ¹H NMR ppm (δ) | MS (M + H) |
|---|---|---|---|---|
| 36 | 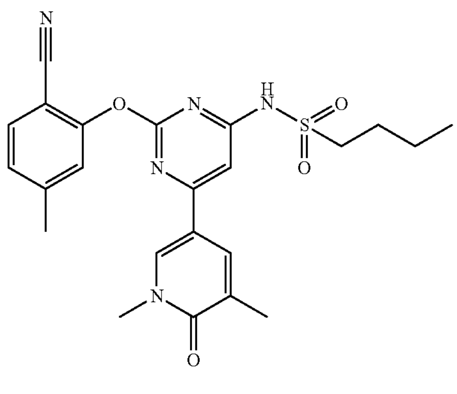 [SMILES: CCCCS(=O)(=O)Nc1cc(-c2cc(C)c(=O)n(C)c2)nc(Oc2cc(C)ccc2C#N)n1] | Butane-1-sulfonic acid [2-(2-cyano-5-methyl-phenoxy)-6-(1,5-dimethyl-6-oxo-1,6-dihydro-pyridin-3-yl)-pyrimidin-4-yl]-amide | (CD$_3$OD, 400 MHz) δ 8.43 (d, J = 2.4 Hz, 1H), 7.97 (d, J = 1.2 Hz, 1H), 7.68 (d, J = 7.6 Hz, 1H), 7.30-7.27 (m, 2H), 6.88 (s, 1H), 3.66 (s, 3H), 3.15-3.11 (m, 2H), 2.47 (s, 3H), 2.19 (s, 3H), 1.63-1.59 (m, 2H), 1.36-1.30 (m, 2H), 0.88 (t, J = 7.2 Hz, 3H) | 468 |
| 37 | 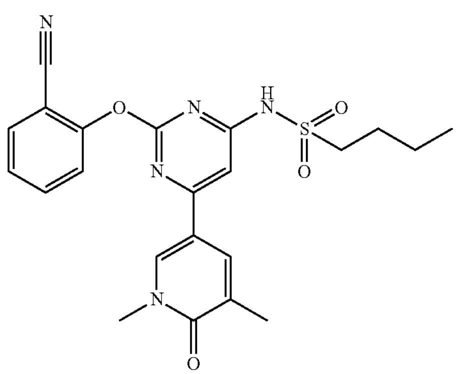 [SMILES: CCCCS(=O)(=O)Nc1cc(-c2cc(C)c(=O)n(C)c2)nc(Oc2ccccc2C#N)n1] | Butane-1-sulfonic acid [2-(2-cyano-phenoxy)-6-(1,5-dimethyl-6-oxo-1,6-dihydro-pyridin-3-yl)-pyrimidin-4-yl]-amide | (CD$_3$OD, 400 MHz) δ 8.41 (d, J = 2.0 Hz, 1H), 7.97 (s, 1H), 7.84-7.76 (m, 2H), 7.48-7.45 (m, 2H), 6.90 (s, 1H), 3.65 (s, 3H), 3.17-3.13 (m, 2H), 2.18 (s, 3H), 1.64-1.60 (m, 2H), 1.38-1.32 (m, 2H), 0.89 (t, J = 7.2 Hz, 3H) | 454 |
| 38 | 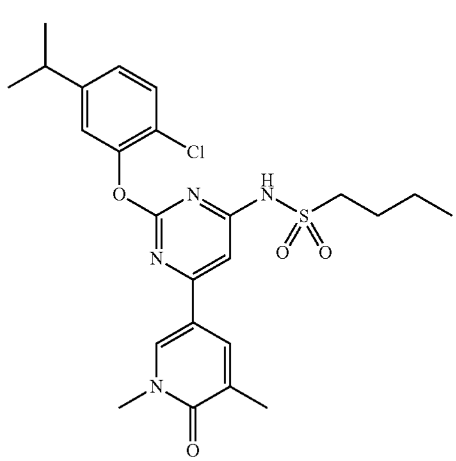 [SMILES: CCCCS(=O)(=O)Nc1cc(-c2cc(C)c(=O)n(C)c2)nc(Oc2cc(C(C)C)ccc2Cl)n1] | Butane-1-sulfonic acid [2-(2-chloro-5-isopropyl-phenoxy)-6-(1,5-dimethyl-6-oxo-1,6-dihydro-pyridin-3-yl)-pyrimidin-4-yl]-amide | (400 MHz, CD$_3$OD) δ 8.40 (d, J = 2.0 Hz, 1H), 7.97 (d, J = 1.2 Hz, 1H), 7.40 (d, J = 8.0 Hz, 1H), 7.20-7.16 (m, 2H), 6.79 (s, 1H), 3.66 (s, 3H), 3.04-3.02 (m, 2H), 3.00-2.95 (m, 1H), 2.19 (s, 3H), 1.56 (m, 2H), 1.32-1.27 (m, 8H), 0.88 (t, J = 6.8 Hz, 3H) | 505 |

| Example | Structure | IUPAC Name | ¹H NMR ppm (δ) | MS (M + H) |
|---|---|---|---|---|
| 39 | 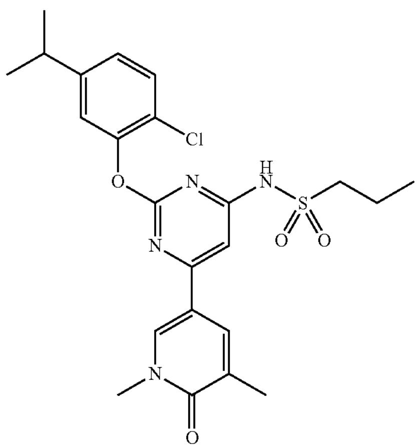 [SMILES: CCCS(=O)(=O)Nc1cc(-c2cc(C)c(=O)n(C)c2)nc(Oc2cc(C(C)C)ccc2Cl)n1] | Propane-1-sunnic acid [2-(2-chloro-5-isopropyl-phenoxy)-6-(1,5-dimethyl-6-oxo-1,6-dihydro-pyridin-3-yl)-pyrimidin-4-yl]-amide | (400 MHz, CD₃OD) δ 8.39 (d, J = 2.4 Hz, 1H), 7.97 (d, J = 0.8 Hz, 1H), 7.42 (d, J = 8.4 Hz, 1H), 7.20-7.16 (m, 2H), 6.77 (s, 1H), 3.66 (s, 3H), 3.00-2.94 (m, 3H), 2.19 (s, 3H), 1.64-1.58 (m, 2H), 1.28-1.27 (d, J = 6.8 Hz, 6H), 0.92 (t, J = 7.2 Hz, 3H) | 491 |
| 40 | 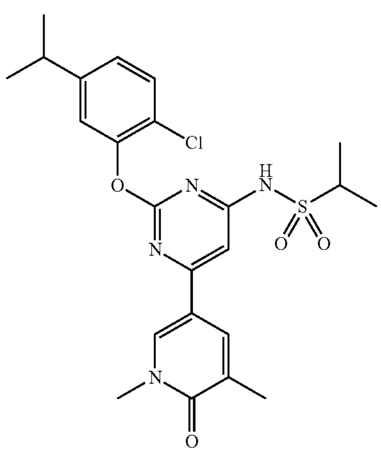 [SMILES: Cc1cc(-c2cc(NS(=O)(=O)C(C)C)nc(Oc3cc(C(C)C)ccc3Cl)n2)cn(C)c1=O] | Propane-2-sulfonic acid [2-(2-chloro-5-isopropyl-phenoxy)-6-(1,5-dimethyl-6-oxo-1,6-dihydro-pyridin-3-yl)-pyrimidin-4-yl]-amide | (400 MHz, CD₃OD) δ 8.42 (d, J = 2.4 Hz, 1H), 7.98 (d, J = 1.2 Hz, 1H), 7.43 (m, 1H), 7.20-7.17 (m, 2H), 6.84 (s, 1H), 3.66 (s, 3H), 3.29-3.25 (m, 1H), 2.98-2.94 (m, 1H), 2.19 (s, 3H), 1.28 (d, J = 7.2 Hz, 6H), 1.16 (d, J = 6.8 Hz, 6H) | 491 |
| 41 | 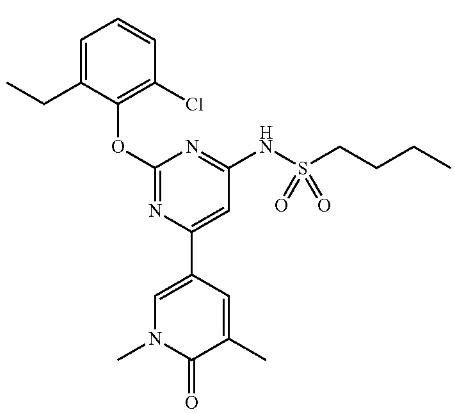 [SMILES: CCCCS(=O)(=O)Nc1cc(-c2cc(C)c(=O)n(C)c2)nc(Oc2c(Cl)cccc2CC)n1] | Butane-1-sulfonic acid [2-(2-chloro-6-ethyl-phenoxy)-6-(1,5-dimethyl-6-oxo-1,6-dihydro-pyridin-3-yl)-pyrimidin-4-yl]-amide | (300 MHz, CD₃OD) δ 8.44 (s, 1H), 7.99 (s, 1H), 7.36-7.30 (m, 2H), 7.25-7.23 (m, 1H), 6.82 (s, 1H), 3.66 (s, 3H), 3.03-2.98 (m, 2H), 2.61 (q, J = 7.5 Hz, 2H), 2.19 (s, 3H), 1.58-1.52 (m, 2H), 1.35-1.15 (m, 2H), 1.18 (t, J = 7.5 Hz, 3H), 0.89 (t, J = 7.5 Hz, 3H) | 491 |
| 42 | | Propane-1-sulfonic acid [2-(2-chloro-6-ethyl-phenoxy)-6-(1,5-dimethyl-6-oxo-1,6-dihydro-pyridin-3-yl)-pyrimidin-4-yl]-amide | (300 MHz, CD₃OD) δ 8.45 (s, 1H), 7.99 (s, 1H), 7.37-7.30 (m, 2H), 7.26-7.23 (m, 1H), 6.82 (s, 1H), 3.67 (s, 3H), 2.99-2.94 (m, 2H), 2.61 (q, J = 7.5 Hz, 2H), 2.19 (s, 3H), 1.64-1.56 (m, 2H), 1.18 (t, J = 7.2 Hz, 3H), 0.92 (t, J = 7.2 Hz, 3H) | 477 |

TABLE 3-continued

| Example | Structure | IUPAC Name | $^1$H NMR ppm (δ) | MS (M + H) |
|---|---|---|---|---|
| 43 | | Propane-2-sulfonic acid [2-(2-chloro-6-ethyl-phenoxy)-6-(1,5-dimethyl-6-oxo-1,6-dihydro-pyridin-3-yl)-pyrimidin-4-yl]-amide | (300 MHz, CD$_3$OD) δ 8.45 (s, 1H), 7.99 (s, 1H), 7.38-7.30 (m, 2H), 7.25-7.23 (m, 1H), 6.84 (s, 1H), 3.67 (s, 3H), 3.28-3.22 (m, 1H), 2.61 (q, J = 7.5 Hz, 2H), 2.20 (s, 3H), 1.20-1.12 (m, 9H) | 477 |

Example 44: Propane-2-sulfonic acid [2-(2,4-difluoro-phenoxy)-6-(1-ethyl-5-methyl-6-oxo-1,6-dihydro-pyridin-3-yl)-pyrimidin-4-yl]-amide Step 1: 5-Bromo-1-ethyl-3-methyl-1H-pyridin-2-one

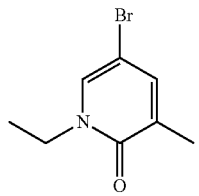

NaH (255 mg, 6.4 mmol, 60% in mineral oil) was added to solution of 5-bromo-3-methyl-1H-pyridin-2-one (1.0 g, 5.3 mmol) in DMF (12 mL) in an ice-water bath which was warmed to rt slowly and then stirred for 30 min. Iodo-ethane (995 mg, 6.4 mmol) was then added dropwise. The mixture was stirred for 3 h, quenched with ice-water, and extracted with DCM (×5). Dried over Na$_2$SO$_4$, filtered, and concentrated under vacuum, the residue was purified by silica gel chromatography eluting with PE/EtOAc (1:1) to give the title compound (621 mg, 2.9 mmol) as a white solid in 54% yield. $^1$H NMR (400 MHz, CDCl$_3$) δ 7.29-7.28 (m, 1H), 7.24-7.23 (m, 1H), 3.97 (q, J=7.2 Hz, 2H), 2.15 (s, 3H), 1.35 (t, J=7.2 Hz, 3H). LCMS (M+H)$^+$ 216, 218.

Step 2: 1-Ethyl-3-methyl-5-(4,4,5,5-tetramethyl-[1,3,2]dioxaborolan-2-yl)-1H-pyridin-2-one

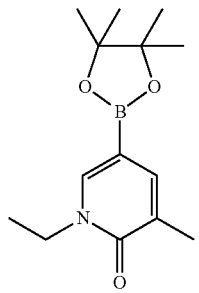 [SMILES: CCn1cc(B2OC(C)(C)C(C)(C)O2)cc(C)c1=O]

A suspension of the title compound of step 1 (553 mg, 2.6 mmol), 4,4,5,5-tetramethyl-2-(tetramethyl-1,3,2-dioxaborolan-2-yl)-1,3,2-dioxaborolane (130 mg, 5.1 mmol), KOAc (753 mg, 7.7 mmol), X-phos (110 mg, 0.23 mmol), and Pd$_2$(dba)$_3$ (70 mg, 0.08 mmol) in dioxane (10 mL) was stirred at 70° C. for 3 h. After cooling to rt, the reaction mixture was filtered through a short plug of celite which was rinsed with DCM and the combined filtrates were washed with brine, dried over sodium sulfate, filtered and concentrated in vacuo. The residue was purified by silica gel chromatography on PE/EA (1:1) to give the title compound (500 mg, crude) as a yellow oil. $^1$H NMR (300 MHz, CDCl$_3$) δ 7.64 (s, 1H), 7.47 (s, 1H), 4.00 (q, J=6.9 Hz, 2H), 2.12 (s, 3H), 1.35 (t, J=7.2 Hz, 3H), 1.31 (s, 12H). LCMS (M+H)$^+$ 264.

Step 3: Propane-2-sulfonic acid [2-(2,4-difluoro-phenoxy)-6-(1-ethyl-5-methyl-6-oxo-1,6-dihydro-pyridin-3-yl)-pyrimidin-4-yl]-amide

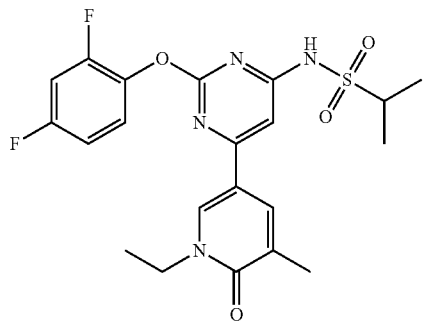

4,6-dichloro-2-(2,4-difluorophenoxy)pyrimidine was prepared from 2,4-difluorophenol and 4,6-dichloro-2-methanesulfonyl-pyrimidine in a manner similar to Example 1, step 1 which was then coupled to the title compound of step 2 in a manner similar to Example 1, step 2 to give 5-(6-chloro-2-(2,4-difluorophenoxy)pyrimidin-4-yl)-1-ethyl-3-methyl-pyridin-2(1H)-one which was then reacted with propane-2-sulfonic acid amide in a manner similar to Example 1, step 3 to give the title compound. $^1$H NMR (CD$_3$OD, 300 MHz) δ 8.39 (d, J=2.1 Hz, 1H), 7.94 (s, 1H), 7.39-7.31 (m, 1H), 7.21-7.14 (m, 1H), 7.08-7.02 (m, 1H), 6.89 (s, 1H), 4.12 (q, J=7.2 Hz, 2H), 3.51-3.42 (m, 1H), 2.18 (s, 3H), 1.38 (t, J=7.2 Hz, 3H), 1.24 (d, J=6.9 Hz, 6H). LCMS (M+H)$^+$ 465.

Examples 45-55 (Table 4) were prepared using standard N-alkylating agents and elaborated in a similar multi-step manner as Example 44.

TABLE 4

| Example | Structure | IUPAC Name | ¹H NMR ppm (δ) | MS (M + H) |
|---|---|---|---|---|
| 45 | | Propane-2-sulfonic acid [2-(2,4-difluoro-phenoxy)-6-(5-methyl-6-oxo-1-propyl-1,6-dihydro-pyridin-3-yl)-pyrimidin-4-yl]-amide | (CD$_3$OD, 300 MHz) δ 8.35 (d, J = 2.1 Hz, 1H), 7.93 (s, 1H), 7.39-7.31 (m, 1H), 7.21-7.14 (m, 1H), 7.08-7.02 (m, 1H), 6.89 (s, 1H), 4.04 (t, J = 7.2 Hz, 2H), 3.53-3.44 (m, 1H), 2.18 (s, 3H), 1.84-1.77 (m, 2H), 1.24 (d, J = 6.9 Hz, 6H), 0.97 (t, J = 7.2 Hz, 3H) | 479 |
| 46 | | Propane-2-sulfonic acid [6-(1-butyl-5-methyl-6-oxo-1,6-dihydro-pyridin-3-yl)-2-(2,4-difluoro-phenoxy)-pyrimidin-4-yl]-amide | (CD$_3$OD, 300 MHz) δ 8.33 (d, J = 2.4 Hz, 1H), 7.92 (s, 1H), 7.39-7.31 (m, 1H), 7.21-7.13 (m, 1H), 7.08-7.02 (m, 1H), 6.89 (s, 1H), 4.07 (t, J = 7.2 Hz, 2H), 3.54-3.44 (m, 1H), 2.17 (s, 3H), 1.80-1.70 (m, 2H), 1.45-1.32 (m, 2H), 1.25 (d, J = 6.9 Hz, 6H), 0.98 (t, J = 7.2 Hz, 3H). | 493 |
| 47 | | Propane-2-sulfonic acid [2-(2,4-difluoro-phenoxy)-6-(1-isopropyl-5-methyl-6-oxo-1,6-dihydro-pyridin-3-yl)-pyrimidin-4-yl]-amide | (CD$_3$OD, 300 MHz) δ 8.35 (bs, 1H), 7.89 (s, 1H), 7.41-7.33 (m, 1H), 7.23-7.15 (m, 1H), 7.09-7.03 (m, 1H), 6.90 (s, 1H), 5.28-5.18 (m, 1H), 3.59-3.50 (m, 1H), 2.19 (s, 3H), 1.40 (d, J = 6.6 Hz, 6H), 1.27 (d, J = 6.9 Hz, 6H) | 479 |
| 48 | | Propane-2-sulfonic acid [2-(2,4-difluoro-phenoxy)-6-(1-isobutyl-5-methyl-6-oxo-1,6-dihydro-pyridin-3-yl)-pyrimidin-4-yl]-amide | (CD$_3$OD, 300 MHz) δ 8.28 (d, J = 1.8 Hz, 1H), 7.93 (s, 1H), 7.39-7.32 (m, 1H), 7.21-7.13 (m, 1H), 7.07-7.02 (m, 1H), 6.88 (s, 1H), 3.88 (d, J = 7.5 Hz, 2H), 3.54-3.45 (m, 1H), 2.21-2.12 (m, 4H), 1.25 (d, J = 6.9 Hz, 6H), 0.95 (d, J = 6.6 Hz, 6H) | 493 |
| 49 | 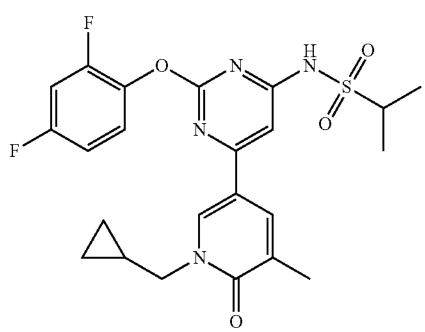 [SMILES: Cc1cc(-c2cc(NS(=O)(=O)C(C)C)nc(Oc3ccc(F)cc3F)n2)cn(CC2CC2)c1=O] | Propane-2-sulfonic acid [6-(1-cyclopropylmethyl-5-methyl-6-oxo-1,6-dihydro-pyridin-3-yl)-2-(2,4-difluoro-phenoxy)-pyrimidin-4-yl]-amide | (CD$_3$OD, 300 MHz) δ 8.40 (d, J = 2.4 Hz, 1H), 7.94 (s, 1H), 7.39-7.31 (m, 1H), 7.21-7.14 (m, 1H), 7.07-7.02 (m, 1H), 6.88 (s, 1H), 3.92 (d, J = 7.5 Hz, 2H), 3.53-3.46 (m, 1H), 3.19 (s, 3H), 1.35-1.34 (m, 1H), 1.25 (d, J = 6.9 Hz, 6H), 0.63-0.56 (m, 2H), 0.46-0.41 (m, 2H) | 491 |
| 50 | 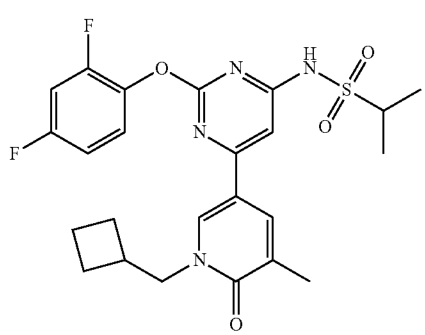 [SMILES: Cc1cc(-c2cc(NS(=O)(=O)C(C)C)nc(Oc3ccc(F)cc3F)n2)cn(CC2CCC2)c1=O] | Propane-2-sulfonic acid [6-(1-cyclobutylmethyl-5-methyl-6-oxo-1,6-dihydro-pyridin-3-yl)-2-(2,4-difluoro-phenoxy)-pyrimidin-4-yl]-amide | (CD$_3$OD, 300 MHz) δ 8.29 (d, J = 1.8 Hz, 1H), 7.91 (s, 1H), 7.37-7.31 (m, 1H), 7.21-7.14 (m, 1H), 7.08-7.03 (m, 1H), 6.89 (s, 1H), 4.08 (d, J = 7.5 Hz, 2H), 3.55-3.51 (m, 1H), 2.82-2.77 (m, 1H), 2.17 (s, 3H), 2.03-1.80 (m, 6H), 1.26 (d, J = 6.6 Hz, 6H) | 505 |

TABLE 4-continued

| Example | Structure | IUPAC Name | ¹H NMR ppm (δ) | MS (M + H) |
|---|---|---|---|---|
| 51 | 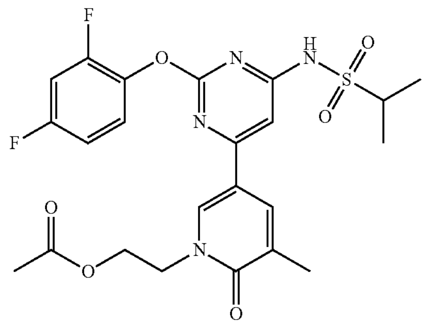 [SMILES: CC(=O)OCCn1cc(-c2cc(NS(=O)(=O)C(C)C)nc(Oc3ccc(F)cc3F)n2)cc(C)c1=O] | Acetic acid 2-{5-[2-(2,4-difluoro-phenoxy)-6-(propane-2-sulfonylamino)-pyrimidin-4-yl]-3-methyl-2-oxo-2H-pyridin-1-yl}-ethyl ester | (CD₃OD, 300 MHz) δ 8.10 (d, J = 1.8 Hz, 1H), 7.70 (s, 1H), 7.29-7.21 (m, 1H), 7.07 (s, 1H), 7.09-6.91 (m, 2H), 4.42-4.39 (m, 2H), 4.26-4.23 (m, 2H), 3.52-3.42 (m, 1H), 2.21 (s, 3H), 2.01 (s, 3H), 1.40-1.38 (d, J = 6.9 Hz, 6H) | 523 |
| 52 | 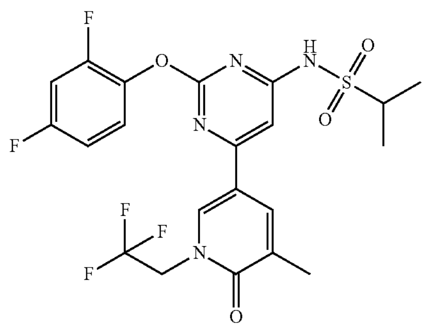 [SMILES: Cc1cc(-c2cc(NS(=O)(=O)C(C)C)nc(Oc3ccc(F)cc3F)n2)cn(CC(F)(F)F)c1=O] | Propane-2-sulfonic acid {2-(2,4-difluoro-phenoxy)-6-[5-methyl-6-oxo-1-(2,2,2-trifluoro-ethyl)-1,6-dihydro-pyridin-3-yl]-pyrimidin-4-yl}-amide | (CD₃OD, 300 MHz) δ 8.45 (s, 1H), 7.97 (s, 1H), 7.39-7.31 (m, 1H), 7.20-7.13 (m, 1H), 7.07-7.00 (m, 1H), 6.88 (s, 1H), 4.95-4.86 (m, 2H), 3.52-3.43 (m, 1H), 2.20 (s, 3H), 1.24 (d, J = 6.9 Hz, 6H) | 519 |
| 53 | 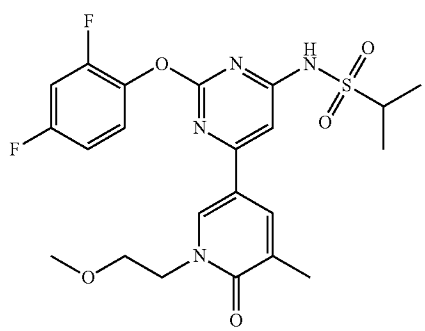 | Propane-2-sulfonic acid {2-(2,4-difluoro-phenoxy)-6-[1-(2-methoxy-ethyl)-5-methyl-6-oxo-1,6-dihydro-pyridin-3-yl]-pyrimidin-4-yl}-amide | (CD₃OD, 300 MHz) δ 8.29 (d, J = 2.4 Hz, 1H), 7.94 (s, 1H), 7.38-7.30 (m, 1H), 7.20-7.12 (m, 1H), 7.07-7.01 (m, 1H), 6.85 (s, 1H), 4.24 (t, J = 5.0 Hz, 2H), 3.69 (t, J = 5.0 Hz, 2H), 3.50-3.43 (m, 1H), 3.32 (s, 3H), 2.18 (s, 3H), 1.23 (d, J = 6.9 Hz, 6H) | 495 |
| 54 | | Propane-1-sulfonic acid [6-(1-cyclopropyl-5-methyl-6-oxo-1,6-dihydro-pyridin-3-yl)-2-(2,6-dimethyl-phenoxy)-pyrimidin-4-yl]-amide | (CD₃OD, 400 MHz) δ 8.32 (s, 1H), 7.94 (s, 1H), 7.15-7.07 (m, 3H), 6.77 (s, 1H), 3.46-3.34 (m, 1H), 2.92-2.88 (m, 2H), 2.20 (s, 3H), 2.14 (s, 6H), 1.59-1.53 (m, 2H), 1.20-1.14 (m, 2H), 1.00-0.96 (m, 2H), 0.87 (t, J = 7.6 Hz, 3H) | 469 |
| 55 | | Propane-1-sulfonic acid [2-(2,6-dimethyl-phenoxy)-6-(5-methyl-1-oxetan-3-yl-6-oxo-1,6-dihydro-pyridin-3-yl)-pyrimidin-4-yl]-amide | (CD₃OD, 400 MHz) δ 8.44 (d, J = 2.0 Hz, 1H), 7.99-7.98 (m, 1H), 7.14-7.08 (m, 3H), 6.80 (s, 1H), 5.69-5.42 (m, 1H), 5.06 (t, J = 7.4 Hz, 2H), 4.93 (t, J = 7.2 Hz, 2H), 2.92-2.89 (m, 2H), 2.18 (s, 3H), 2.14 (s, 6H), 1.59-1.53 (m, 2H), 0.87 (t, J = 7.6 Hz, 3H) | 485 |

Example 56: Butane-1-sulfonic acid [2-(1,5-dimethyl-6-oxo-1,6-dihydro-pyridin-3-yl)-6-(2,6-dimethyl-phenoxy)-pyrimidin-4-yl]-amide Step 1: 4,6-Dichloro-2-iodo-pyrimidine

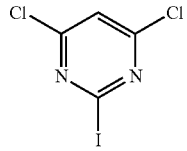

t-BuONO (2,944 mg, 28.1 mmol) was added to a solution of 4,6-dichloro-pyrimidin-2-ylamine (1,013 mg, 6.1 mmol) and $CH_2I_2$ (25.3 mL) in anhydrous $CH_3CN$ (6.0 mL) under nitrogen. The reaction mixture was heated in an oil bath at 80° C. for 3.5 h, then cooled to rt and concentrated under vacuum. The residue was directly chromatographed on silica gel (PE/EA=15:1) to give the title compound (933 mg, 56%) as a yellow solid. $^1$H NMR (300 MHz, $CDCl_3$): δ 7.40 (s, 1H). LCMS (M+H)$^+$ 275.

Step 2: 5-(4,6-Dichloro-pyrimidin-2-yl)-1,3-dimethyl-1H-pyridin-2-one

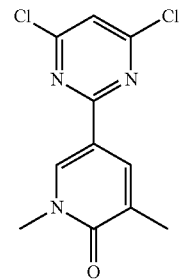 [SMILES: Cc1cc(-c2nc(Cl)cc(Cl)n2)cn(C)c1=O]

A mixture of the title compound of step 1 (746 mg, 2.7 mmol), 1,3-dimethyl-5-(4,4,5,5-tetramethyl-[1,3,2]dioxaborolan-2-yl)-1H-pyridin-2-one (609 mg, 2.4 mmol), Pd(dppf)Cl$_2$ (198 mg, 0.27 mmol), $K_3PO_4$ (1.81 mL, 6.8 mmol, 3.75 M) in dioxane (10 mL) was bubbled with $N_2$ for 5 min and then capped and stirred at 30° C. for 5 h. The reaction mixture was extracted with DCM, and the combined organic layer was washed with brine, dried over $Na_2SO_4$, filtered, and the filtrate was concentrated under vacuum, the residue was purified by silica gel chromatography eluting with PE/EtOAc (1:1 to 0:1) to give the title compound as a brown solid in 32% yield. $^1$H NMR (300 MHz, $CDCl_3$): δ 8.50 (d, J=2.1 Hz, 1H), 8.17 (s, 1H), 7.17 (s, 1H), 3.67 (s, 3H), 2.23 (s, 3H). LCMS (M+H)$^+$ 270, 272.

Step 3: 5-[4-Chloro-6-(2,6-dimethyl-phenoxy)-pyrimidin-2-yl]-1,3-dimethyl-1H-pyridin-2-one

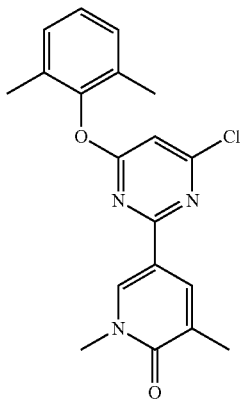

Sodium hydride (9 mg, 0.22 mmol, 60% in mineral oil) was added to a solution of 2,6-dimethyl-phenol (25 mg, 0.20 mmol) in DMF (20 mL) in ice-water bath, then stirred for 45 min at the same temperature. The title compound of step 2 (995 mg, 6.4 mmol) was added and stirred for 2 h. The reaction mixture was quenched with ice-water, extracted with DCM for 5 times, dried over $Na_2SO_4$, filtered and then reduced under vacuum. The residue was purified by preparative-TLC (PE/EtOAc 1:1) to give the title compound (50 mg, 0.14 mmol) as a white solid in 70% yield. $^1$H NMR (300 MHz, $CDCl_3$): δ 8.30 (d, J=1.8 Hz, 1H), 8.03 (s, 1H), 7.15 (s, 3H), 6.44 (s, 1H), 3.61 (s, 3H), 2.18 (s, 3H), 2.15 (s, 6H). LCMS (M+H)$^+$ 356.

Step 4: Butane-1-sulfonic acid [2-(1,5-dimethyl-6-oxo-1,6-dihydro-pyridin-3-yl)-6-(2,6-dimethyl-phenoxy)-pyrimidin-4-yl]-amide

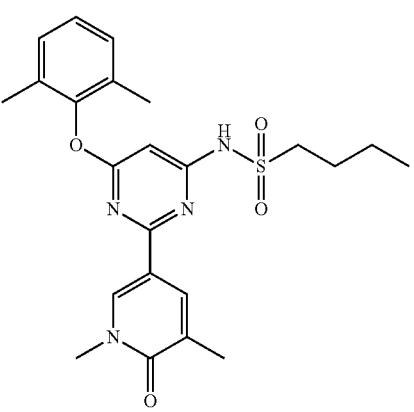 [SMILES: CCCCS(=O)(=O)Nc1cc(Oc2c(C)cccc2C)nc(-c2cc(C)c(=O)n(C)c2)n1]

A mixture of the title compound of step 3 (50 mg, 0.14 mmol), butane-1-sulfonic acid amide (48 mg, 0.35 mmol), Pd$_2$(dba)$_3$ (7 mg, 0.01 mmol), X-phos (10 mg, 0.02 mmol) and $Cs_2CO_3$ (68 mg, 0.21 mmol) in dioxane (3 mL) was placed in a sealed tube, then the mixture was purged with $N_2$ for 5 min. The sealed tube was stirred at 90° C. for 3 h, LC-MS showed the reaction was complete. The mixture was poured into saturated $NH_4Cl$ solution (45 mL) and adjusted pH to 5 with aqueous 2M HCl, extracted with EtOAc (30 mL), and the organic layer was washed with brine, dried over Na$_2$SO$_4$, filtered, and concentrated under vacuum. The residue was purified by preparative HPLC (15-80% CH$_3$CN in H$_2$O containing 0.1% NH$_4$HCO$_3$) to give the title compound (45 mg, 0.10 mmol) as a white solid in 70% yield. $^1$H NMR (300 MHz, CD$_3$OD) δ 8.36 (d, J=1.8 Hz, 1H), 8.08 (s, 1H), 7.17-7.14 (m, 3H), 6.12 (s, 1H), 3.60 (s, 3H), 3.50 (t, J=7.8 Hz, 2H), 2.13 (s, 9H), 1.83-1.77 (m, 2H), 1.52-1.44 (m, 2H), 0.93 (t, J=7.4 Hz, 3H). LCMS (M+H)$^+$ 457.

Example 57: Propane-2-sulfonic acid [6-(1,5-dimethyl-6-oxo-1,6-dihydro-pyridin-3-yl)-2-(1-methyl-1H-indol-7-yloxy)-pyrimidin-4-yl]-amide Step 1: 7-Benzyloxy-1-methyl-1H-indole

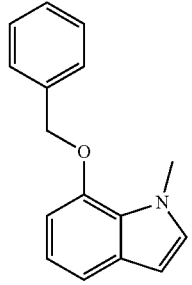 [SMILES: Cn1ccc2cccc(OCc3ccccc3)c21]

A solution of 7-benzyloxy-1H-indole (1.0 g, 4.5 mmol) in DMF (30 mL) stirred at 0° C. under N$_2$ was treated with NaH (215 mg, 5.4 mmol). After 30 min, CH$_3$I (1.3 g, 9.0 mmol) was added. The reaction was warmed up to RT and stirred for 1 hour. The reaction mixture was quenched with water and extracted with DCM (25 mL*2). The combined organic layers were washed with brine, dried over Na$_2$SO$_4$, filtered and concentrated under reduced pressure. The residue was purified by silica gel column chromatography (eluting with PE) to give the title compound as a colorless oil in 94% yield. $^1$H NMR (300 MHz, CDCl$_3$): δ 7.42-7.40 (m, 2H), 7.36-7.29 (m, 3H), 7.09 (d, J=8.1 Hz, 1H), 6.90 (d, J=2.7 Hz, 1H), 6.86 (t, J=7.8 Hz, 1H), 6.62 (d, J=7.5 Hz, 1H), 6.32 (d, J=3.0 Hz, 1H), 5.06 (s, 2H), 3.92 (s, 3H). LCMS (M+H)$^+$ 238.

Step 2: 1-Methyl-1H-indol-7-ol

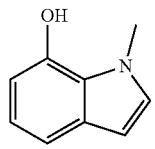

To a solution of 7-benzyloxy-1-methyl-1H-indole (1.1 g, 4.64 mmol) in ethanol (20 mL) was added Pd/C (150 mg). The mixture was stirred at RT under H$_2$ for 5 hours. The reaction mixture was filtered and concentrated under reduced pressure to give the title compound (680 mg, 4.6 mmol) as a black oil in 99% yield. $^1$H NMR (300 MHz, CDCl$_3$): δ 7.20 (dd, J=0.9 Hz, 8.1 Hz, 1H), 6.96 (d, J=3.0 Hz, 1H), 6.88 (t, J=7.8 Hz, 1H), 6.48 (d, J=7.2 Hz, 1H), 6.43 (d, J=3.0 Hz, 1H), 4.09 (s, 3H). LCMS (M+H)$^+$ 148.

Step 3: Propane-2-sulfonic acid [6-(1,5-dimethyl-6-oxo-1,6-dihydro-pyridin-3-yl)-2-(1-methyl-1H-indol-7-yloxy)-pyrimidin-4-yl]-amide

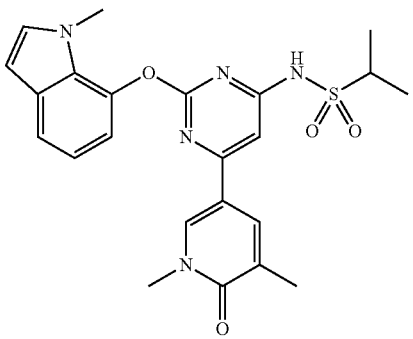 [SMILES: Cc1cc(-c2cc(NS(=O)(=O)C(C)C)nc(Oc3cccc4ccn(C)c34)n2)cn(C)c1=O]

The title compound was prepared in a manner similar to Example 1 by substituting the title compound from step 2 for 2,5-dichlorophenol in step 1. $^1$H NMR (CDCl$_3$, 300 MHz): δ 8.20 (s, 1H), 7.70 (s, 1H), 7.51 (d, J=7.8 Hz, 1H), 7.07 (t, J=7.8 Hz, 1H), 6.98 (d, J=3.0 Hz, 1H), 6.95-6.93 (m, 2H), 6.51 (d, J=3.0 Hz, 1H), 3.81 (s, 3H), 3.62 (s, 3H), 3.13-3.08 (m, 1H), 2.23 (s, 3H), 1.23 (d, J=6.6 Hz, 6H). LCMS (M+H)$^+$ 468.

Example 58: N-(6-(1,5-dimethyl-6-oxo-1,6-dihydropyridin-3-yl)-2-((2-methylbenzofuran-4-yl)oxy)pyrimidin-4-yl)propane-2-sulfonamide Step 1: (Benzofuran-4-yloxy)-tert-butyl-dimethyl-silane

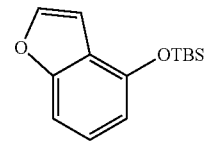 [SMILES: CC(C)(C)[Si](C)(C)Oc1cccc2occc12]

To a solution of benzofuran-4-ol (600 mg, 4.5 mmol) in DCM (15 mL) was added TBSCl (811 mg, 5.4 mmol), DMAP (55 mg, 0.5 mmol) and Et$_3$N (1.3 g, 12.5 mmol). The mixture was stirred at RT for 3 hours. The reaction mixture was quenched with water and extracted with DCM (25 mL*2). The combined organic layers were washed with brine, dried over Na$_2$SO$_4$, filtered and concentrated under reduced pressure. The residue was purified by silica gel column chromatography (eluting with PE) to give the title compound (850 mg, 3.4 mmol) as a colorless oil in 77% yield. $^1$H NMR (300 MHz, CDCl$_3$): δ 7.53 (d, J=2.1 Hz, 1H), 7.15-7.14 (m, 2H), 6.80 (d, J=2.1 Hz, 1H), 6.67-6.64 (m, 1H), 1.05 (s, 9H), 0.24 (s, 6H).

Step 2: tert-Butyl-dimethyl-(2-methyl-benzofuran-4-yloxy)-silane

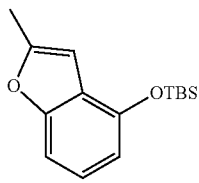 [SMILES: Cc1cc2c(O[Si](C)(C)C(C)(C)C)cccc2o1]

A solution of (benzofuran-4-yloxy)-tert-butyl-dimethyl-silane (650 mg, 2.6 mmol) in THF (15 mL) under $N_2$ at −78° C. was treated with n-BuLi (1.4 mL, 2.9 mmol). The mixture was stirred at −78° C. for 30 min followed by dropwise addition of $CH_3I$ (0.8 mL, 13.1 mmol) at that temperature. The reaction was allowed to slowly warm up to RT over 36 hours. The mixture was further stirred at 30° C. for 12 hours. It was poured over $NH_4Cl$ and extracted with DCM (30 mL*2). The combined organic layers were dried over $Na_2SO_4$, filtered and concentrated under reduced pressure. The residue was purified by silica gel column chromatography (eluting with PE) to give the title compound (430 mg, 1.6 mmol) as a colorless oil in 63% yield.

Step 3: 2-Methyl-benzofuran-4-ol

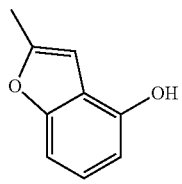

To a solution of tert-butyl-dimethyl-(2-methyl-benzofuran-4-yloxy)-silane (430 mg, 1.6 mmol) in THF (15 mL) at RT was added TBAF (1.3 g, 4.9 mmol). After stirring for 2 hr, the reaction mixture was treated with water and extracted with DCM (25 mL*2). The combined organic layers were washed with brine, dried over $Na_2SO_4$, filtered and concentrated under reduced pressure. The residue was purified by silica gel column chromatography (eluting with a 1:1 PE/EtOAc mixture) to give the crude title compound (240 mg, 1.6 mmol) as a colorless oil in 99% yield. LCMS (M−H)$^+$ 147.

Step 4: N-(6-(1,5-dimethyl-6-oxo-1,6-dihydropyridin-3-yl)-2-((2-methylbenzofuran-4-yl)oxy)pyrimidin-4-yl)propane-2-sulfonamide

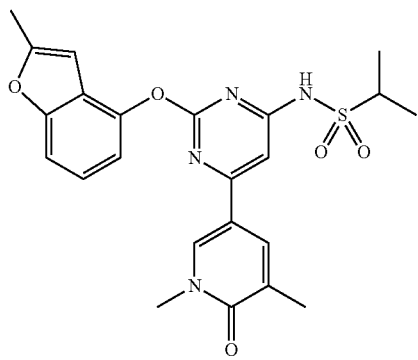 [SMILES: Cc1cc2c(Oc3nc(NS(=O)(=O)C(C)C)cc(-c4cc(C)c(=O)n(C)c4)n3)cccc2o1]

The title compound was prepared in a manner similar to Example 1 by substituting the title compound from step 3 for 2,5-dichlorophenol in step 1. $^1$H NMR (CD$_3$OD, 300 MHz): δ 8.40 (d, J=2.1 Hz, 1H), 7.97 (s, 1H), 7.35 (d, J=8.1 Hz, 1H), 7.27 (t, J=7.8 Hz, 1H), 7.03 (d, J=7.8 Hz, 1H), 6.84 (s, 1H), 6.25 (s, 1H), 3.65 (s, 3H), 3.20-3.15 (m, 1H), 2.42 (s, 3H), 2.19 (s, 3H), 1.06 (d, J=7.2 Hz, 6H). LCMS (M+H)$^+$ 469.

Example 59: N-(2-(benzofuran-4-yloxy)-6-(1,5-dimethyl-6-oxo-1,6-dihydropyridin-3-yl)pyrimidin-4-yl)propane-2-sulfonamide

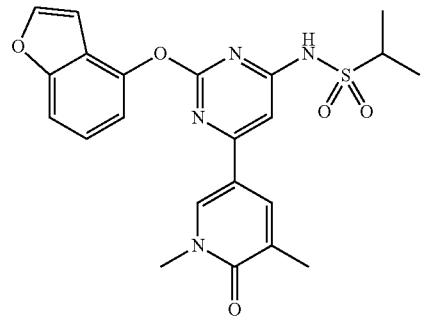 [SMILES: Cc1cc(-c2cc(NS(=O)(=O)C(C)C)nc(Oc3cccc4occc34)n2)cn(C)c1=O]

The title compound was prepared in a manner similar to Example 1 by substituting benzofuran-4-ol for 2,5-dichlorophenol in step 1. $^1$H NMR (CD$_3$OD, 300 MHz): δ 8.39 (s, 1H), 7.97 (s, 1H), 7.76 (d, J=1.5 Hz, 1H), 7.48 (d, J=7.8 Hz, 1H), 7.37 (t, J=7.8 Hz, 1H), 7.10 (d, J=7.8 Hz, 1H), 6.85 (s, 1H), 6.67 (s, 1H), 3.65 (s, 3H), 3.19-3.15 (m, 1H), 2.18 (s, 3H), 1.06 (d, J=6.9 Hz, 6H). LCMS (M+H)$^+$ 455.

Example 60: Propane-1-sulfonic acid [6-(2,4-dichloro-6-methyl-phenoxy)-2-(1,5-dimethyl-6-oxo-1,6-dihydro-pyridin-3-yl)-pyrimidin-4-yl]-amide

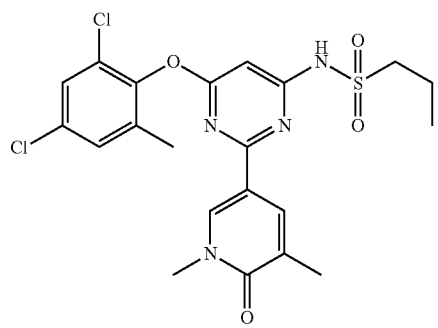 [SMILES: CCCS(=O)(=O)Nc1cc(Oc2c(C)cc(Cl)cc2Cl)nc(-c2cc(C)c(=O)n(C)c2)n1]

The title compound was prepared in a manner similar to Example 56 by substituting 2,4-dichloro-6-methylphenol for 2,6-dimethylphenol in Step 3 and propane-1-sulfonamide for butane-1-sulfonamide in Step 4. $^1$H NMR (CDCl$_3$, 300 MHz) δ 8.11 (s, 1H), 7.92 (s, 1H), 7.37 (d, J=2.4 Hz, 1H), 7.24-7.23 (m, 1H), 6.52 (s, 1H), 3.61 (s, 3H), 3.40 (t, J=7.8 Hz, 2H), 2.21 (s, 3H), 2.18 (s, 3H), 2.01-1.93 (m, 2H), 1.13 (t, J=7.5 Hz, 3H) LCMS (M+H)$^+$ 497

Examples 61-89 in Table 5 were prepared in a similar multi-step a manner as Example 1.

TABLE 5

| Example | Structure | IUPAC Name | ¹H NMR ppm (δ) | MS (M + H) |
|---|---|---|---|---|
| 61 | | N-(2-(2,4-difluorophenoxy)-6-(1,5-dimethyl-6-oxo-1,6-dihydropyridin-3-yl)pyrimidin-4-yl)methanesulfonamide | (400 MHz, DMSO-d6) δ ppm 2.07 (s, 3H) 3.07 (s, 3H) 3.54 (s, 3H) 6.85 (s, 1H) 7.13-7.20 (m, 1H) 7.43-7.51 (m, 2H) 7.78 (s, 1H) 8.38 (s, 1H) 11.43 (br s, 1H) | 423 |
| 62 | | N-(2-(2,4-difluorophenoxy)-6-(1,5-dimethyl-6-oxo-1,6-dihydropyridin-3-yl)pyrimidin-4-yl)propane-2-sulfonamide | (400 MHz, DMSO-d6) δ ppm 1.14 (m, 6H) 2.08 (s, 3H) 3.38 (m, 1H) 3.55 (s, 3H) 6.86 (s, 1H) 7.18 (m, 1H) 7.43-7.54 (m, 2H) 7.80 (s, 1H) 8.41 (s, 1H) 11.28 (br s, 1H) | 451 |
| 63 | | N-(2-(2,4-difluorophenoxy)-6-(1,5-dimethyl-6-oxo-1,6-dihydropyridin-3-yl)pyrimidin-4-yl)cyclopropanesulfonamide | (400 MHz, DMSO-d6) δ ppm 0.90-1.02 (m, 4H) 2.07 (s, 3H) 2.79 (s, 1H) 3.54 (s, 3H) 6.94 (s, 1H) 7.17 (m, 1H) 7.44-7.52 (m, 2H) 7.78 (s, 1H) 8.38 (s, 1H) 11.40 (br s, 1H) | 449 |
| 64 | 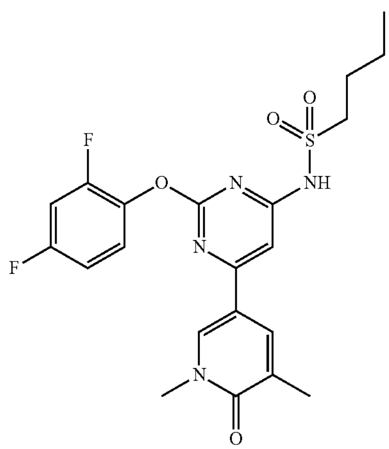 [SMILES: CCCCS(=O)(=O)Nc1cc(-c2cc(C)c(=O)n(C)c2)nc(Oc2ccc(F)cc2F)n1] | N-(2-(2,4-difluorophenoxy)-6-(1,5-dimethyl-6-oxo-1,6-dihydropyridin-3-yl)pyrimidin-4-yl)butane-1-sulfonamide | (400 MHz, DMSO-d6) δ ppm 0.78-0.92 (m, 3H) 1.20-1.36 (m, 2H) 1.42-1.56 (m, 2H) 2.00-2.16 (m, 3H) 3.09-3.20 (m, 2H) 3.49-3.61 (s, 3H) 6.74-6.94 (m, 1H) 7.10-7.30 (s, 1H) 7.42-7.56 (m, 2H) 7.70-7.92 (m, 1H) 8.36-8.51 (s, 1H) 11.16-11.51 (br s, 1H) | 465 |
| 65 | 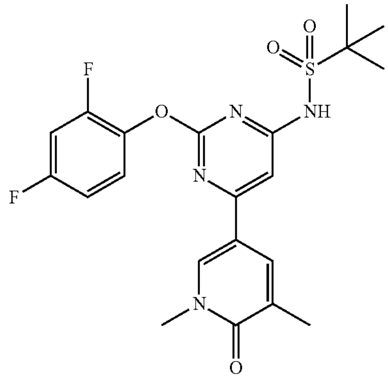 [SMILES: Cc1cc(-c2cc(NS(=O)(=O)C(C)(C)C)nc(Oc3ccc(F)cc3F)n2)cn(C)c1=O] | N-(2-(2,4-difluorophenoxy)-6-(1,5-dimethyl-6-oxo-1,6-dihydropyridin-3-yl)pyrimidin-4-yl)-2-methylpropane-2-sulfonamide | (400 MHz, DMSO-d6) δ ppm 1.30 (s, 9H) 2.03-2.11 (m, 3H) 3.50-3.58 (m, 3H) 7.11-7.20 (m, 1H) 7.20-7.25 (m, 1H) 7.42-7.56 (m, 2H) 7.67-7.80 (m, 1H) 8.29-8.40 (m, 1H) 10.92-11.08 (br s, 1H) | 465 |

TABLE 5-continued

| Example | Structure | IUPAC Name | ¹H NMR ppm (δ) | MS (M + H) |
|---|---|---|---|---|
| 66 | 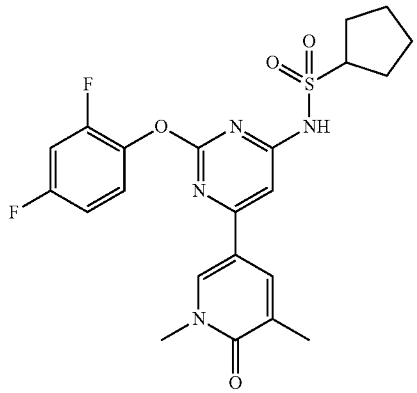 [SMILES: Cc1cc(-c2cc(NS(=O)(=O)C3CCCC3)nc(Oc3ccc(F)cc3F)n2)cn(C)c1=O] | N-(2-(2,4-difluorophenoxy)-6-(1,5-dimethyl-6-oxo-1,6-dihydropyridin-3-yl)pyrimidin-4-yl)cyclopentanesulfonamide | (400 MHz, DMSO-d6) δ ppm 1.48-1.87 (m, 8H) 2.08 (s, 3H) 3.51-3.59 (s, 3H) 3.59-3.70 (m, 1H) 6.81-6.92 (s, 1H) 7.12-7.25 (m, 1H) 7.40-7.61 (m, 2H) 7.74-7.87 (s, 1H) 8.36-8.48 (s, 1H) 11.11-11.58 (br s, 1H) | 477 |
| 67 | 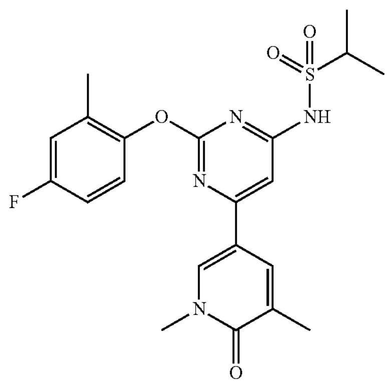 | N-(6-(1,5-dimethyl-6-oxo-1,6-dihydropyridin-3-yl)-2-(4-fluoro-2-methylphenoxy)pyrimidin-4-yl)propane-2-sulfonamide | (400 MHz, DMSO-d6) δ ppm 1.02-1.15 (m, 6H) 2.09 (m, 6H) 3.12-3.21 (m, 1H) 3.49-3.63 (s, 3H) 6.76-6.85 (m, 1H) 7.03-7.27 (m, 3H) 7.78-7.87 (m, 1H) 8.38-8.48 (m, 1H) 11.10-11.25 (br s, 1H) | 447 |
| 68 | 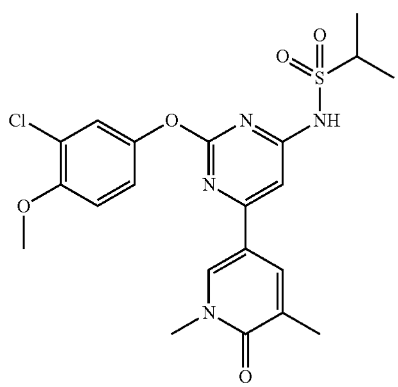 [SMILES: COc1ccc(Oc2nc(NS(=O)(=O)C(C)C)cc(-c3cc(C)c(=O)n(C)c3)n2)cc1Cl] | N-(2-(3-chloro-4-methoxyphenoxy)-6-(1,5-dimethyl-6-oxo-1,6-dihydropyridin-3-yl)pyrimidin-4-yl)propane-2-sulfonamide | (400 MHz, DMSO-d6) δ ppm 1.07-1.20 (m, 6H) 2.01-2.13 (s, 3H) 3.39-3.51 (s, 1H) 3.51-3.60 (s, 3H) 3.82-3.91 (s, 3H) 6.75-6.93 (s, 1H) 7.16-7.30 (m, 2H) 7.36-7.49 (ms, 1H) 7.75-7.88 (s, 1H) 8.34-8.49 (s, 1H) 11.10-11.25 (br s, 1H) | 479 |
| 69 | 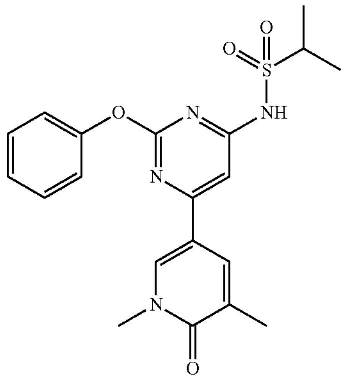 [SMILES: Cc1cc(-c2cc(NS(=O)(=O)C(C)C)nc(Oc3ccccc3)n2)cn(C)c1=O] | N-(6-(1,5-dimethyl-6-oxo 1,6-dihydropyridin-3-yl)-2-phenoxypyrimidin-4-yl)propane-2-sulfonamide | (400 MHz, DMSO-d6) δ ppm 1.04-1.19 (m, 6H) 2.03-2.12 (s, 3H) 3.37-3.48 (m, 1H) 3.51-3.60 (s, 3H) 6.74-6.90 (m, 1H) 7.13-7.34 (m, 3H) 7.39-7.53 (m, 2H) 7.75-7.88 (s, 1H) 8.34-8.48 (s, 1H) 11.02-11.28 (br s, 1H) | 415 |

TABLE 5-continued

| Example | Structure | IUPAC Name | ¹H NMR ppm (δ) | MS (M + H) |
|---|---|---|---|---|
| 70 | 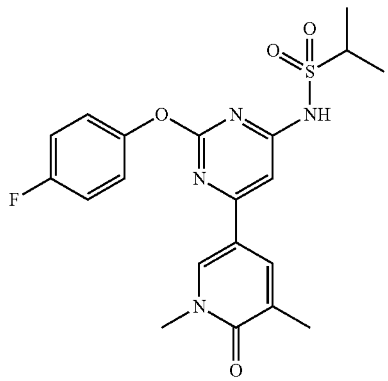 [SMILES: Cc1cc(-c2cc(NS(=O)(=O)C(C)C)nc(Oc3ccc(F)cc3)n2)cn(C)c1=O] | N-(6-(1,5-dimethyl-6-oxo-1,6-dihydropyridin-3-yl)-2-(4-fluorophenoxy)pyrimidin-4-yl)propane-2-sulfonamide | (400 MHz, DMSO-d6) δ ppm 1.05-1.22 (m, 6H) 2.03-2.13 (s, 3H) 3.37-3.49 (m, 1H) 3.51-3.60 (s, 3H) 6.78-6.92 (s, 1H) 7.21-7.36 (m, 4H) 7.67-7.89 (s, 1H) 8.31-8.46 (s, 1H) 11.06-11.32 (br s, 1H) | 433 |
| 71 | 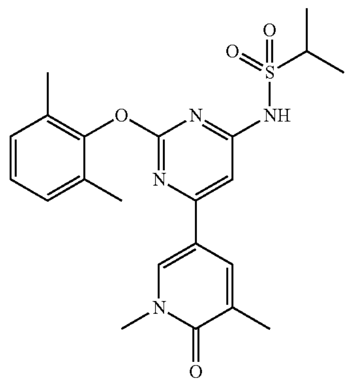 [SMILES: Cc1cccc(C)c1Oc1nc(NS(=O)(=O)C(C)C)cc(-c2cc(C)c(=O)n(C)c2)n1] | N-(6-(1,5-dimethyl-6-oxo-1,6-dihydropyridin-3-yl)-2-(2,6-dimethylphenoxy)pyrimidin-4-yl)propane-2-sulfonamide | (400 MHz, DMSO-d6) δ ppm 0.97 (m, 6H) 2.05 (s, 6H) 2.08-2.12 (m, 3H) 2.98 (m, 1H) 3.53-3.62 (m, 3H) 6.78 (s, 1H) 7.06-7.17 (m, 3H) 7.85 (s, 1H) 8.47 (s, 1H) 11.12 (br s, 1H) | 443 |
| 72 | 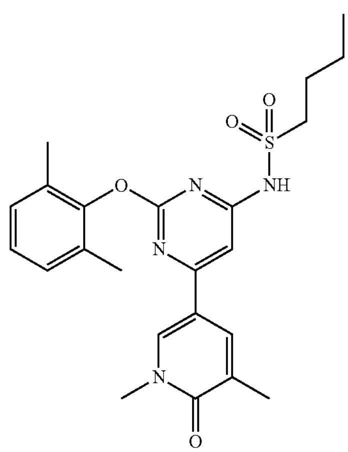 [SMILES: CCCCS(=O)(=O)Nc1cc(-c2cc(C)c(=O)n(C)c2)nc(Oc2c(C)cccc2C)n1] | N-(6-(1,5-dimethyl-6-oxo-1,6-dihydropyridin-3-yl)-2-(2,6-dimethylphenoxy)pyrimidin-4-yl)butane-1-sulfonamide | (400 MHz, DMSO-d6) δ ppm 0.73-0.84 (m, 3H) 1.09-1.21 (m, 2H) 1.28-1.43 (m, 2H) 2.03-2.14 (m, 9H) 2.77-2.90 (m, 2H) 3.52-3.62 (s, 3H) 6.73-6.81 (s, 1H) 7.02-7.19 (m, 3H) 7.78-7.88 (s, 1H) 8.43-8.51 (s, 1H) 11.06-11.31 (br s, 1H) | 457 |
| 73 | 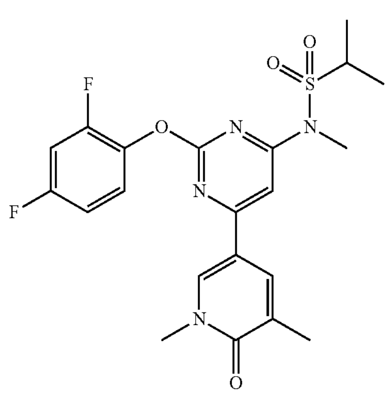 [SMILES: Cc1cc(-c2cc(N(C)S(=O)(=O)C(C)C)nc(Oc3ccc(F)cc3F)n2)cn(C)c1=O] | N-(2-(2,4-difluorophenoxy)-6-(1,5-dimethyl-6-oxo-1,6-dihydropyridin-3-yl)pyrimidin-4-yl)-N-methylpropane-2-sulfonamide | (400 MHz, DMSO-d6) δ ppm 1.03-1.14 (m, 6H) 2.10 (s, 3H) 3.35 (s, 3H) 3.40-3.47 (m, 1H) 3.58 (s, 3H) 7.16-7.24 (m, 1H) 7.24-7.29 (m, 1H) 7.44-7.55 (m, 2H) 8.06-8.13 (m, 1H) 8.63 (s, 1H) 11.06-11.31 (br s, 1H) | 465 |

TABLE 5-continued

| Example | Structure | IUPAC Name | ¹H NMR ppm (δ) | MS (M + H) |
|---------|-----------|------------|----------------|------------|
| 74 | 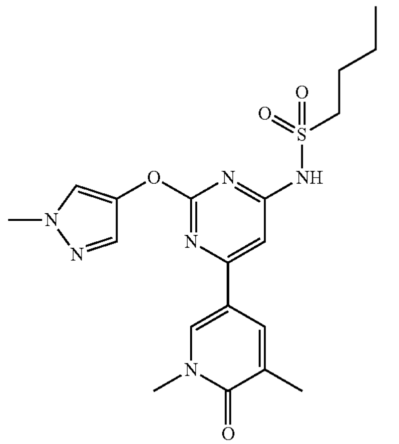 [SMILES: CCCCS(=O)(=O)Nc1cc(-c2cc(C)c(=O)n(C)c2)nc(Oc2cnn(C)c2)n1] | N-(6-(1,5-dimethyl-6-oxo-1,6-dihydropyridin-3-yl)-2-((1-methyl-1H-pyrazol-4-yl)oxy)pyrimidin-4-yl)butane-1-sulfonamide | (400 MHz, DMSO-d6) δ ppm 0.80-0.84 (m, 3H) 1.30-1.35 (m, 2H) 1.60-1.65 (m, 2H) 2.09-2.10 (s, 3H) 3.39-3.31 (m, 2H) 3.56-3.59 (s, 3H) 3.83-3.81 (s, 3H) 6.83-6.85 (s, 1H) 7.54-7.56 (s, 1H) 7.96-7.94 (s, 1H) 8.41-8.44 (s, 1H) 11.34-11.37 (br s, 1H) | 433 |
| 75 | 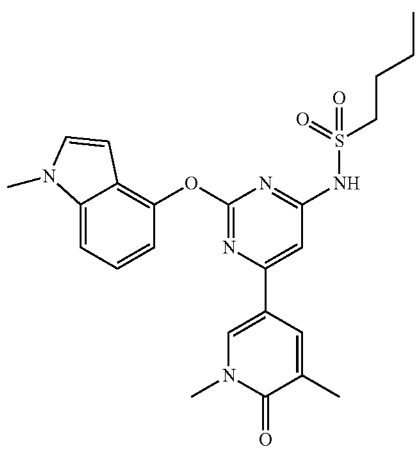 [SMILES: CCCCS(=O)(=O)Nc1cc(-c2cc(C)c(=O)n(C)c2)nc(Oc2cccc3c2ccn3C)n1] | N-(6-(1,5-dimethyl-6-oxo-1,6-dihydropyridin-3-yl)-2-((1-methyl-1H-indol-4-yl)oxy)pyrimidin-4-yl)butane-1-sulfonamide | (400 MHz, DMSO-d6) δ ppm 0.69-0.77 (m, 3H) 0.93-1.04 (m, 2H) 1.22-1.34 (m, 2H) 2.08 (s, 3H) 2.80-2.88 (m, 2H) 3.53-3.60 (m, 3H) 3.81 (s, 3H) 6.15 (s, 1H) 6.80-6.90 (m, 2H) 7.15-7.22 (m, 1H) 7.27-7.38 (m, 2H) 7.82 (s, 1H) 8.43 (s, 1H) 11.13 (br s, 1H) | 482 |
| 76 | 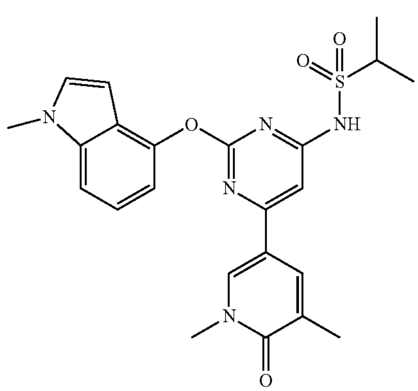 [SMILES: Cc1cc(-c2cc(NS(=O)(=O)C(C)C)nc(Oc3cccc4c3ccn4C)n2)cn(C)c1=O] | N-(6-(1,5-dimethyl-6-oxo-1,6-dihydropyridin-3-yl)-2-((1-methyl-1H-indol-4-yl)oxy)pyrimidin-4-yl)propane-2-sulfonamide | (400 MHz, DMSO-d6) δ ppm 0.81-0.93 (m, 6H) 2.08 (s, 3H) 2.86-2.99 (m, 1H) 3.56 (s, 3H) 3.82 (s, 3H) 6.10 (s, 1H) 6.81 (s, 1H) 6.84-6.94 (m, 1H) 7.16-7.25 (m, 1H) 7.30 (s, 1H) 7.32-7.42 (m, 1H) 7.83 (s, 1H) 8.44 (s, 1H) 11.04 (br s, 1H) | 468 |

TABLE 5-continued

| Example | Structure | IUPAC Name | ¹H NMR ppm (δ) | MS (M + H) |
|---|---|---|---|---|
| 77 | 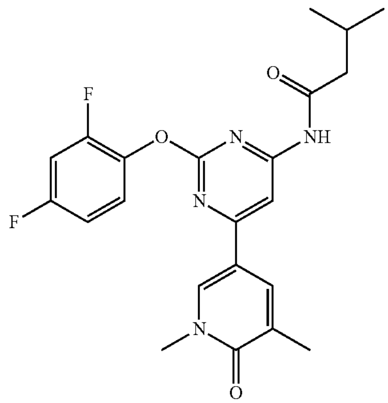 [SMILES: Cc1cc(-c2cc(NC(=O)CC(C)C)nc(Oc3ccc(F)cc3F)n2)cn(C)c1=O] | N-(2-(2,4-difluorophenoxy)-6-(1,5-dimethyl-6-oxo-1,6-dihydropyridin-3-yl)pyrimidin-4-yl)-3-methylbutanamide | (400 MHz, DMSO-d6) δ ppm 0.87-0.96 (m, 6H) 2.07 (m, 4H) 2.27-2.35 (m, 2H) 3.56 (s, 3H) 7.18 (s, 1H) 7.49 (s, 2H) 7.80 (s, 1H) 8.17 (s, 1H) 8.40 (s, 1H) 10.74 (br s, 1H) | 429 |
| 78 | 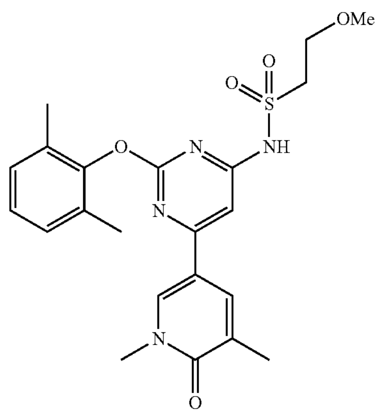 [SMILES: COCCS(=O)(=O)Nc1cc(-c2cc(C)c(=O)n(C)c2)nc(Oc2c(C)cccc2C)n1] | N-(6-(1,5-dimethyl-6-oxo-1,6-dihydropyridin-3-yl)-2-(2,6-dimethylphenoxy)pyrimidin-4-yl)-2-methoxyethane-1-sulfonamide | (400 MHz, DMSO-d6) δ ppm 2.03-2.11 (m, 8H) 3.11 (s, 3H) 3.17 (m, 3H) 3.35-3.42 (m, 2H) 3.57 (s, 3H) 6.78 (s, 1H) 7.06-7.15 (m, 3H) 7.83 (s, 1H) 8.44 (s, 1H) 11.30 (br s, 1H) | 459 |
| 79 | 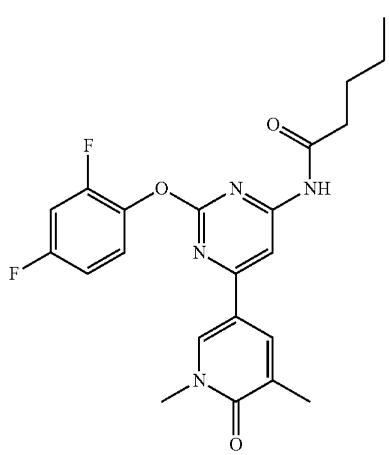 [SMILES: CCCCC(=O)Nc1cc(-c2cc(C)c(=O)n(C)c2)nc(Oc2ccc(F)cc2F)n1] | N-(2-(2,4-difluorophenoxy)-6-(1,5-dimethyl-6-oxo-1,6-dihydropyridin-3-yl)pyrimidin-4-yl)pentanamide | (400 MHz, DMSO-d6) δ ppm 0.85-0.91 (m, 3H) 1.23-1.35 (m, 2H) 1.50-1.59 (m, 2H) 2.07 (s, 3H) 2.39-2.47 (m, 2H) 3.55 (s, 3H) 7.17 (s, 1H) 7.49 (s, 2H) 7.80 (s, 1H) 8.16 (s, 1H) 8.40 (s, 1H) 10.75 (br s, 1H) | 429 |

TABLE 5-continued

| Example | Structure | IUPAC Name | ¹H NMR ppm (δ) | MS (M + H) |
|---|---|---|---|---|
| 80 | 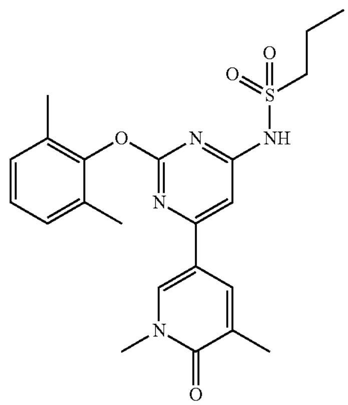 | N-(6-(1,5-dimethyl-6-oxo-1,6-dihydropyridin-3-yl)-2-(2,6-dimethylphenoxy)pyrimidin-4-yl)propane-1-sulfonamide | (400 MHz, DMSO-d6) δ ppm 0.74-0.81 (m, 3H) 1.36-1.46 (m, 2H) 2.03-2.13 (m, 9H) 2.76-2.84 (m, 2H) 3.58 (s, 3H) 6.78 (s, 1H) 7.06-7.17 (m, 3H) 7.84 (s, 1H) 8.47 (s, 1H) 11.19 (br s, 1H) | 443 |
| 81 | 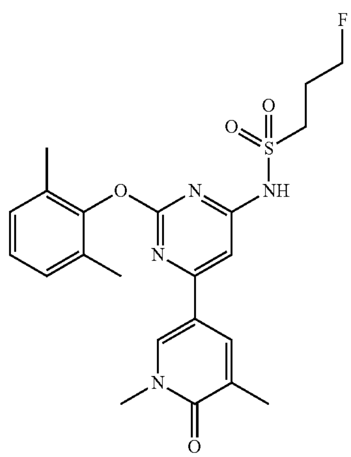 [SMILES: Cc1cccc(C)c1Oc1nc(NS(=O)(=O)CCCF)cc(-c2cc(C)c(=O)n(C)c2)n1] | N-(6-(1,5-dimethyl-6-oxo-1,6-dihydropyridin-3-yl)-2-(2,6-dimethylphenoxy)pyrimidin-4-yl)-3-fluoropropane-1-sulfonamide | (400 MHz, DMSO-d6) δ ppm 1.71-1.88 (m, 2H) 2.02-2.13 (m, 9H) 2.89-3.01 (m, 2H) 3.57 (s, 3H) 4.22-4.29 (m, 1H) 4.33-4.41 (m, 1H) 6.79 (s, 1H) 7.05-7.17 (m, 3H) 7.84 (s, 1H) 8.46 (s, 1H) 11.12-11.56 (br s, 1H) | 461 |
| 82 | 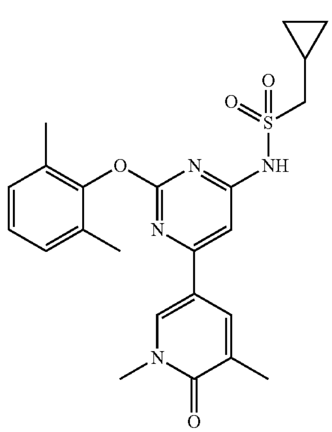 [SMILES: Cc1cccc(C)c1Oc1nc(NS(=O)(=O)CC2CC2)cc(-c2cc(C)c(=O)n(C)c2)n1] | 1-cyclopropyl-N-(6-(1,5-dimethyl-6-oxo-1,6-dihydropyridin-3-yl)-2-(2,6-dimethylphenoxy)pyrimidin-4-yl)methanesulfonamide | (400 MHz, DMSO-d6) δ ppm 0.40-0.49 (m, 2H) 0.74-0.87 (m, 1H) 1.72-1.79 (m, 2H) 2.04-2.15 (m, 9H) 2.70-2.78 (m, 2H) 3.58 (s, 3H) 6.78 (s, 1H) 7.01-7.19 (m, 3H) 7.85 (s, 1H) 8.48 (s, 1H) 11.22 (br s, 1H) | 455 |

TABLE 5-continued

| Example | Structure | IUPAC Name | ¹H NMR ppm (δ) | MS (M + H) |
|---|---|---|---|---|
| 83 | 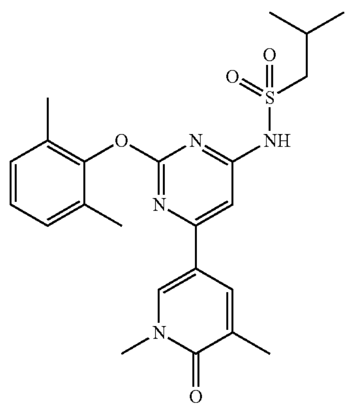 [SMILES: Cc1cccc(C)c1Oc1nc(NS(=O)(=O)CC(C)C)cc(-c2cc(C)c(=O)n(C)c2)n1] | N-(6-(1,5-dimethyl-6-oxo-1,6-dihydropyridin-3-yl)-2-(2,6-dimethylphenoxy)pyrimidin-4-yl)-2-methylpropane-1-sulfonamide | (400 MHz, DMSO-d6) δ ppm 0.76-0.83 (m, 6H) 1.78-1.88 (m, 1H) 2.04-2.13 (m, 9H) 2.73-2.79 (m, 2H) 3.57 (s, 3H) 6.76 (s, 1H) 7.05-7.16 (m, 3H) 7.84 (s, 1H) 8.47 (s, 1H) 11.24 (br s, 1H) | 457 |
| 84 | 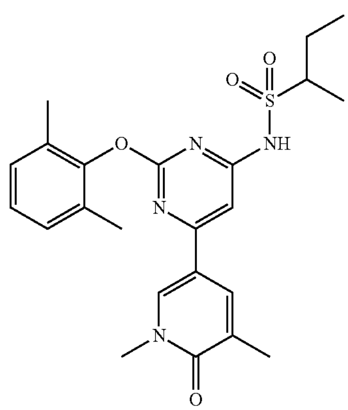 [SMILES: CCC(C)S(=O)(=O)Nc1cc(-c2cc(C)c(=O)n(C)c2)nc(Oc2c(C)cccc2C)n1] | N-(6-(1,5-dimethyl-6-oxo-1,6-dihydropyridin-3-yl)-2-(2,6-dimethylphenoxy)pyrimidin-4-yl)butane-2-sulfonamide | (400 MHz, DMSO-d6) δ ppm 0.68-0.79 (m, 3H) 0.90-0.99 (m, 3H) 1.18-1.33 (m, 1H) 1.49-1.64 (m, 1H) 2.02-2.15 (m, 9H) 2.71-2.84 (m, 1H) 3.56 (s, 3H) 6.74 (s, 1H) 7.02-7.25 (m, 3H) 7.83 (s, 1H) 8.48 (s, 1H) 11.13 (br s, 1H) | 457 |
| 85 | 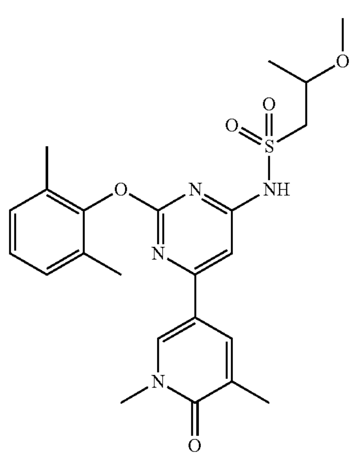 [SMILES: COC(C)CS(=O)(=O)Nc1cc(-c2cc(C)c(=O)n(C)c2)nc(Oc2c(C)cccc2C)n1] | N-(6-(1,5-dimethyl-6-oxo-1,6-dihydropyridin-3-yl)-2-(2,6-dimethylphenoxy)pyrimidin-4-yl)-2-methoxypropane-1-sulfonamide | (400 MHz, DMSO-d6) δ ppm 0.95-1.01 (m, 3H) 2.04-2.12 (m, 9H) 2.91-2.99 (m, 1H) 3.07 (s, 3H) 3.11-3.25 (m, 1H) 3.48 (m, 1H) 3.57 (s, 3H) 6.79 (s, 1H) 7.05-7.17 (m, 3H) 7.82 (s, 1H) 8.44 (s, 1H) 11.29 (br s, 1H) | 473 |

TABLE 5-continued

| Example | Structure | IUPAC Name | ¹H NMR ppm (δ) | MS (M + H) |
|---|---|---|---|---|
| 86 | 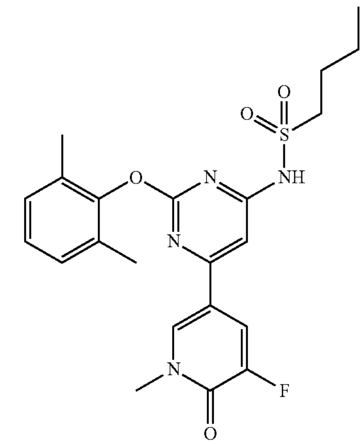 [SMILES: CCCCS(=O)(=O)Nc1cc(-c2cc(F)c(=O)n(C)c2)nc(Oc2c(C)cccc2C)n1] | N-(2-(2,6-dimethylphenoxy)-6-(5-fluoro-1-methyl-6-oxo-1,6-dihydropyridin-3-yl)pyrimidin-4-yl)butane-1-sulfonamide | (400 MHz, DMSO-d6) δ ppm 0.75-0.83 (m, 3H) 1.10-1.25 (m, 2H) 1.32-1.42 (m, 2H) 2.06 (br s, 6H) 2.80-2.89 (m, 2H) 3.64 (s, 3H) 6.78 (s, 1H) 7.05-7.16 (m, 3H) 7.86 (m, 1H) 8.49 (s, 1H) 11.32 (br s, 1H) | 461 |
| 87 | 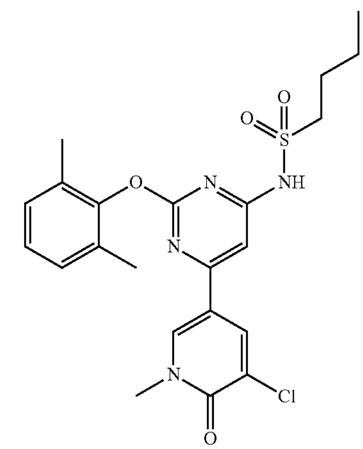 | N-(6-(5-chloro-1-methyl-6-oxo-1,6-dihydropyridin-3-yl)-2-(2,6-dimethylphenoxy)pyrimidin-4-yl)butane-1-sulfonamide | (400 MHz, DMSO-d6) δ ppm 0.75-0.85 (m, 3H) 1.12-1.21 (m, 2H) 1.30-1.43 (m, 2H) 2.09 (s, 6H) 2.74-2.85 (m, 2H) 3.65 (s, 3H) 6.76 (s, 1H) 7.03-7.24 (m, 3H) 8.22 (s, 1H) 8.61 (s, 1H) 11.37 (br s, 1H) | 477 |
| 88 | 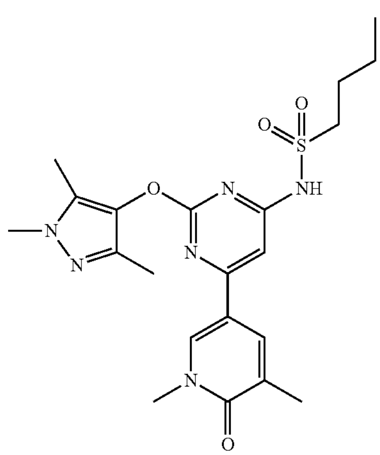 [SMILES: CCCCS(=O)(=O)Nc1cc(-c2cc(C)c(=O)n(C)c2)nc(Oc2c(C)nn(C)c2C)n1] | N-(6-(1,5-dimethyl-6-oxo-1,6-dihydropyridin-3-yl)-2-((1,3,5-trimethyl-1H-pyrazol-4-yl)oxy)pyrimidin-4-yl)butane-1-sulfonamide | (400 MHz, DMSO-d6) δ ppm 0.73-0.85 (m, 3H) 1.15-1.30 (m, 2H) 1.40-1.54 (m, 2H) 1.95 (s, 3H) 2.00-2.13 (m, 6H) 3.14 (br s, 2H) 3.56 (s, 3H) 3.64 (s, 3H) 6.78 (s, 1H) 7.84 (s, 1H) 8.43 (s, 1H) 11.23 (br s, 1H) | 461 |

| Example | Structure | IUPAC Name | $^1$H NMR ppm (δ) | MS (M + H) |
|---|---|---|---|---|
| 89 | 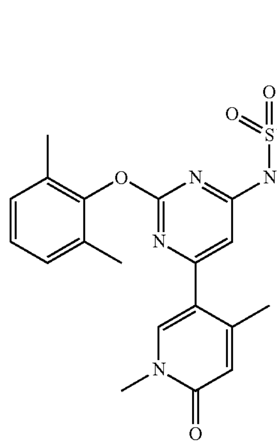 | N-(6-(1,4-dimethyl-6-oxo-1,6-dihydropyridin-3-yl)-2-(2,6-dimethylphenoxy)pyrimidin-4-yl)butane-1-sulfonamide | (400 MHz, DMSO-d6) δ ppm 0.77-0.87 (m, 3H) 1.18-1.30 (m, 2H) 1.42-1.53 (m, 2H) 2.01-2.14 (m, 9H) 3.08 (br s, 2H) 3.45 (s, 3H) 6.29 (s, 1H) 6.65 (s, 1H) 7.04-7.15 (m, 3H) 8.01 (s, 1H) 11.26 (br s, 1H) | 457 |

Example 90: N-(6-(2,4-difluorophenoxy)-1',5'-dimethyl-6'-oxo-1',6'-dihydro-[2,3'-bipyridin]-4-yl)propane-2-sulfonamide Step 1: N-(2,6-dichloropyridin-4-yl)propane-2-sulfonamide

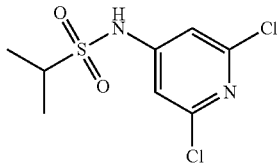

A mixture of 2,6-dichloro-4-iodopyridine (274 mg, 1 mmol), propane-2-sulfonamide (135 mg, 1.1 mmol), Pd(OAc)$_2$ (11 mg, 5%), Xantphos (58 mg, 10%), and Cs$_2$CO$_3$ (650 mg, 2 mmol) in 1,4 dioxane (3.3 mL) was bubbled with nitrogen for 5 min. The reaction vial was sealed and was heated at 90° C. for 90 min. After cooling, the mixture was evaporated to dryness. The resulting residue was purified by flash column chromatography eluting with a gradient of MeOH [0 to 6%] in DCM. The fractions were collected and concentrated under reduced pressure to afford the title compound (168 mg, 61%) as a white solid. LCMS (M+H)$^+$ 270.

Step 2: N-(6-chloro-1',5'-dimethyl-6'-oxo-1',6'-dihydro-[2,3'-bipyridin]-4-yl) propane-2-sulfonamide

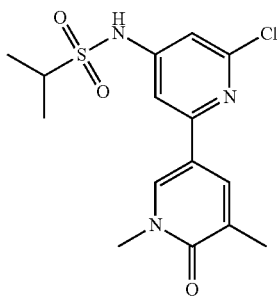 [SMILES: Cc1cc(-c2cc(NS(=O)(=O)C(C)C)cc(Cl)n2)cn(C)c1=O]

A mixture of N-(2,6-dichloropyridin-4-yl)propane-2-sulfonamide (165 mg, 0.61 mmol), 1,3-dimethyl-5-(4,4,5,5-tetramethyl-1,3,2-dioxaborolan-2-yl)pyridin-2-one (162 mg, 0.61 mmol), and Pd(dppf)Cl$_2$ (44 mg, 10%) was diluted with 1,4 dioxane (4 mL) and 3.75M aqueous K$_3$PO$_4$ (400 μL, 1.5 mmol). After the mixture was bubbled with nitrogen for 5 min, the sealed vial was stirred at 75° C. for 4 h. After cooling, the mixture was evaporated to dryness. The resulting residue was purified by flash column chromatography eluting with a gradient of MeOH [0 to 2% (20 min), 2% to 10% (10 min), and 10% (10 min)] in DCM. The fractions were collected and concentrated under reduced pressure to afford the title compound (30 mg, 14%) as a tan solid.
LCMS (M+H)$^+$ 356

Step 3: N-(6-(2,4-difluorophenoxy)-1',5'-dimethyl-6'-oxo-1',6'-dihydro-[2,3'-bipyridin]-4-yl)propane-2-sulfonamide

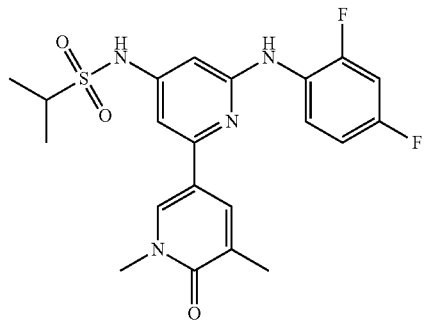 [SMILES: Cc1cc(-c2cc(NS(=O)(=O)C(C)C)cc(Nc3ccc(F)cc3F)n2)cn(C)c1=O]

A mixture of N-(6-chloro-1',5'-dimethyl-6'-oxo-1',6'-dihydro-[2,3'-bipyridin]-4-yl)-propane-2-sulfonamide (30 mg, 0.08 mmol), 2,4-difluorophenol (16 μL, 0.16 mmol), Pd(OAc)$_2$ (2 mg, 5%), Xantphos (10 mg, 10%) and Cs$_2$CO$_3$ (82 mg, 0.24 mmol) was diluted with 1,4 dioxane (840 After the mixture was bubbled with nitrogen for 5 min, it was sealed and heated to 120° C. for 2 hr. The resulting residue was purified by flash column chromatography eluting with a gradient of MeOH [0 to 3%] in DCM. The fractions were collected and concentrated under reduced pressure to afford the title compound (34 mg, 90%) as a tan solid. ¹H NMR (400 MHz, DMSO-d₆) δ 1.30 (m, 6H) 2.01 (s, 3H) 3.46 (s, 3H) 3.49-3.60 (m, 1H) 6.65 (s, 1H) 7.17 (s, 2H) 7.40-7.59 (m, 3H) 7.94 (s, 1H) 10.59 (br s, 1H). LCMS (M+H)⁺ 450.

Example 91: N-(2-((2,4-difluorophenyl)amino)-6-(1,5-dimethyl-6-oxo-1,6-dihydropyridin-3-yl)pyrimidin-4-yl)propane-2-sulfonamide Step 1: 4,6-dichloro-N-(2,4-difluorophenyl)pyrimidin-2-amine

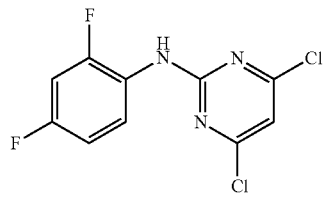 [SMILES: Fc1ccc(Nc2nc(Cl)cc(Cl)n2)c(F)c1]

A 0.25M solution of 2,4-difluoroaniline (129 mg, 1 mmol) in THF stirred under nitrogen at −70° C. was treated with a 0.6M solution of NaHMDS in toluene (1.1 mmol). After 15 min, the mixture was treated with 4,6-dichloro-2-(methylsulfonyl)pyrimidine. After stirring at −70° C. for 2 h, the reaction mixture was quenched with AcOH, partitioned between brine and EtOAc, and separated. The combined organic layers were washed with brine, dried over MgSO₄, filtered and concentrated under reduced pressure. The resulting residue was purified by flash column chromatography eluting with a gradient of EtOAc (0 to 60%) in DCM to afford the title compound (172 mg, 71%) as a white solid. LCMS (M+H)⁺ 277

Step 2: 5-(6-chloro-2-((2,4-difluorophenyl)amino)pyrimidin-4-yl)-1,3-dimethylpyridin-2(1H)-one

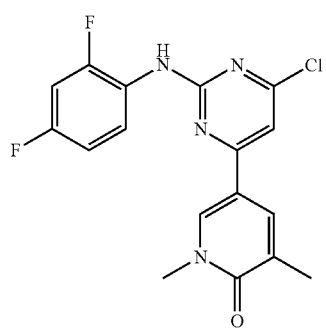 [SMILES: Cc1cc(-c2cc(Cl)nc(Nc3ccc(F)cc3F)n2)cn(C)c1=O]

A mixture of 4,6-dichloro-N-(2,4-difluorophenyl)pyrimidin-2-amine (171 mg, 0.62 mmol), 1,3-dimethyl-5-(4,4,5,5-tetramethyl-1,3,2-dioxaborolan-2-yl)pyridin-2-one (153 mg, 0.62 mmol), and Pd(dppf)Cl₂ (44 mg, 10%) in 1,4 dioxane (4 mL) and 3.75M aqueous K₃PO₄ (400 μL, 1.5 mmol) was purged with nitrogen for 5 min. The sealed vial was stirred at 75° C. for 4 h. After cooling, the mixture was evaporated to dryness. The resulting residue was purified by flash column chromatography eluting with a gradient of EtOAc [0 to 30%] in DCM. The fractions were collected and concentrated under reduced pressure to afford the title compound (77 mg, 34%) as a tan solid. LCMS (M+H)⁺ 363

Step 3: N-(2-((2,4-difluorophenyl)amino)-6-(1,5-dimethyl-6-oxo-1,6-dihydropyridin-3-yl)pyrimidin-4-yl)propane-2-sulfonamide

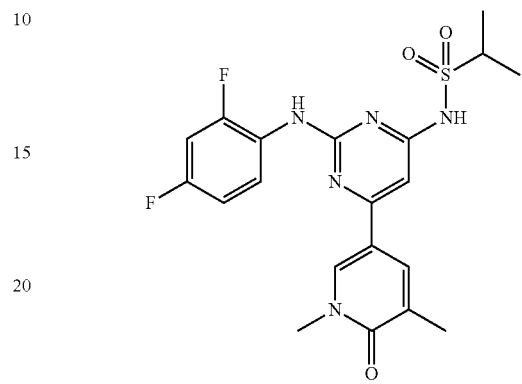

A mixture of 5-(6-chloro-2-((2,4-difluorophenyl)amino)pyrimidin-4-yl)-1,3-dimethylpyridin-2(1H)-one (77 mg, 0.21 mmol), propane-2-sulfonamide (65 mg, 0.52 mmol), Pd₂(dba)₃ (10 mg, 5%), X-Phos (15 mg, 15%) and Cs₂CO₃ (96 mg, 0.29 mmol) in 1,4 dioxane (2 mL) was purged with nitrogen for 5 min, sealed, and heated to 90° C. for 2 h. The cooled mixture was poured into H₂O and extracted with EtOAc; the combined organic layers were washed with brine, dried over Na₂SO₄, filtered and concentrated under reduced pressure. The resulting residue was purified by prep-HPLC (10 min_10-95% ACN_0.1% formic acid, @ 20 ml/min) to afford the title compound (61 mg, 65%) as an off-white solid. ¹H NMR (400 MHz, DMSO-d₆) δ 1.23 (m, 6H) 2.08 (s, 3H) 3.54 (s, 3H) 3.82 (s, 1H) 6.54 (s, 1H) 7.07 (s, 1H) 7.27-7.34 (m, 1H) 7.81-7.92 (m, 2H) 8.29 (s, 1H) 8.97 (s, 1H) 10.87 (br s, 1H). LCMS (M+H)⁺ 450

Example 92: N-(6'-(2,6-dimethylphenoxy)-1,5-dimethyl-6-oxo-1,6-dihydro-[3,4'-bipyridin]-2'-yl)propane-1-sulfonamide Step 1: 2',6'-dichloro-1,5-dimethyl-[3,4'-bipyridin]-6(1H)-one

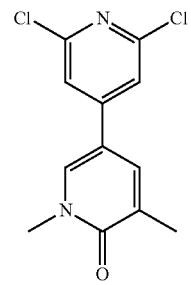 [SMILES: Cc1cc(-c2cc(Cl)nc(Cl)c2)cn(C)c1=O]

A mixture of 2,6-dichloro-4-iodopyridine (400 mg, 1.45 mmol), 1,3-dimethyl-5-(4,4,5,5-tetramethyl-1,3,2-dioxaborolan-2-yl)pyridin-2-one (364 mg, 1.45 mmol) and Pd(dppf)Cl₂ (106 mg, 10%) in 1,4 dioxane (10 mL) and 3.75M aqueous K₃PO₄ (973 µL, 3.6 mmol) was bubbled with nitrogen for 5 min. The sealed vial was stirred at 55° C. for 2 h. After cooling, the mixture was evaporated to dryness. The resulting residue was purified by flash column chromatography eluting with a gradient of EtOAc [0 to 20% (15 min), 20 to 100% (3 min)] in DCM. The fractions were collected and concentrated under reduced pressure to afford the title compound (255 mg, 65%) as an orange solid. LCMS (M+H)⁺ 270

Step 2: 2'-chloro-6'-(2,6-dimethylphenoxy)-1,5-dimethyl-[3,4'-bipyridin]-6(1H)-one

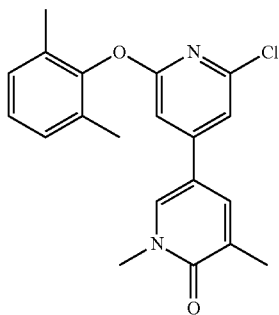 [SMILES: Cc1cccc(C)c1Oc1cc(-c2cc(C)c(=O)n(C)c2)cc(Cl)n1]

A 0.2M solution of 2',6'-dichloro-1,5-dimethyl[3,4'-bipyridin]-6(1H)-one (60 mg, 0.22 mmol) in THF was treated with 2,6-dimethylphenol (27 mg, 0.22 mmol) and Cs₂CO₃ (93 mg, 0.29 mmol). The mixture was heated to 70° C. for 90 min. LCMS analysis showed no evidence of the desired product; the mixture was heated to 90° C. overnight. LCMS analysis showed evidence of the desired product along with unreacted starting material. The reaction mixture was diluted with water and extracted with EtOAc. The combined organic layers were washed with brine, dried over MgSO₄, filtered and concentrated under reduced pressure. The resulting residue was purified by flash column chromatography eluting with a gradient of EtOAc (0 to 20%) in DCM to afford the title compound (55 mg, 71%) as a white solid. LCMS (M+H)⁺ 355

Step 3: N-(6'-(2,6-dimethylphenoxy)-1,5-dimethyl-6-oxo-1,6-dihydro-[3,4'-bipyridin]-2'-yl)propane-1-sulfonamide

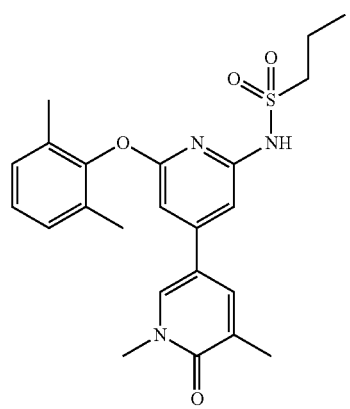 [SMILES: CCCS(=O)(=O)Nc1cc(-c2cc(C)c(=O)n(C)c2)cc(Oc2c(C)cccc2C)n1]

A mixture of 2'-chloro-6'-(2,6-dimethylphenoxy)-1,5-dimethyl-[3,4'-bipyridin]-6(1H)-one (52 mg, 0.15 mmol), propane-1-sulfonamide (46 mg, 0.37 mmol), Pd₂(dba)₃ (7 mg, 5%), X-Phos (11 mg, 15%) and Cs₂CO₃ (68 mg, 0.21 mmol) was diluted with 1,4 dioxane (1 mL). After the mixture was purged with nitrogen for 5 min, it was sealed and heated to 90° C. for 3 hr. The cooled mixture was poured into H₂O and extracted with EtOAc. The combined organic layers were washed with brine, dried over Na₂SO₄, filtered and concentrated under reduced pressure. The resulting residue was purified by prep-HPLC (10 min_10-95% ACN_0.1% formic acid, 20 ml/min) to afford the title compound (36 mg, 55%) as a tan solid. ¹H NMR (400 MHz, DMSO-d6) δ 0.69-0.76 (m, 3H) 1.32-1.43 (m, 2H) 2.03-2.12 (m, 9H) 2.62-2.71 (m, 2H) 3.54 (s, 3H) 6.62 (s, 1H) 6.98 (s, 1H) 7.03-7.15 (m, 3H) 7.72 (s, 1H) 8.22 (s, 1H) 10.36 (br s, 1H). LCMS (M+H)⁺ 442.

Example 93: Propane-2-sulfonic acid [2-(2,4-difluoro-benzyl)-6-(1,5-dimethyl-6-oxo-1,6-dihydro-pyridin-3-yl)-pyrimidin-4-yl]-amide Step 1: 2-(2,4-Difluoro-phenyl)-acetamidine hydrochloride

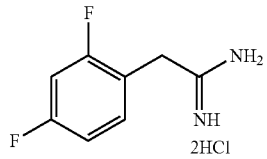 [SMILES: N=C(N)Cc1ccc(F)cc1F]

(2,4-Difluoro-phenyl)-acetonitrile (9.0 g, 59 mmol) was added to a 13.5M solution of HCl in EtOH (5.5 mL) stirred at 0° C. under nitrogen; after the mixture was allowed to stir for 6 hr at 0° C. it was warmed to room temperature and stir overnight. The mixture was diluted with EtOH (30 mL) and a 4.3M solution of ammonia in EtOH (18 mL) and was stirred for another 3 h. The mixture was concentrated under reduced pressure to give the title compound (11.5 g, 95%) as white solid. ¹H NMR (300 MHz, DMSO-d₆) δ 9.17 (br s, 2H), 9.05 (br s, 2H), 7.56-7.48 (m, 1H), 7.32-7.25 (m, 1H), 7.14-7.08 (m, 1H), 3.83 (s, 2H). LCMS (M+H)⁺ 171

Step 2: 2-(2,4-Difluoro-benzyl)-pyrimidine-4,6-diol

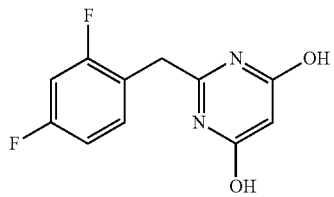 [SMILES: Oc1cc(O)nc(Cc2ccc(F)cc2F)n1]

A 0.67M solution of sodium methylate (6.6 g, 122 mmol) in anhydrous EtOH stirred at 0° C. was treated with 2-(2,4-Difluoro-phenyl)-acetamidine hydrochloride (10 g, 49 mmol). After 10 min, the mixture was treated with malonic acid diethyl ester (7.8 g, 49 mmol) and was heated to 95° C. for 6 hr. After the mixture was cooled and concentrated, H₂O (50 mL) was added and the mixture was adjusted pH 2 with concentrated HCl. The resulting precipitate was filtered, and the cake was dried under reduced pressure to give the title compound (9.0 g, 77%) as a white solid. $^1$H NMR (400 MHz, DMSO-d$_6$) δ 11.7 (br s, 2H), 7.44-7.38 (m, 1H), 7.25-7.20 (m, 1H), 7.09-7.04 (m, 1H), 5.15 (s, 1H), 3.88 (s, 2H). LCMS (M+H)$^+$ 239.

Step 3:
4,6-Dichloro-2-(2,4-difluoro-benzyl)-pyrimidine

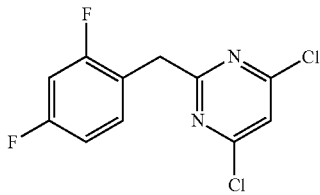 [SMILES: Fc1ccc(Cc2nc(Cl)cc(Cl)n2)c(F)c1]

A mixture of 2-(2,4-Difluoro-benzyl)-pyrimidine-4,6-diol (5.0 g, 21 mmol) in POCl$_3$ (100 mL) was heated to 105° C. for 15 h. After cooling to room temperature, the mixture was concentrated under reduced pressure. The resulting residue was purified by flash column chromatography eluting with PE/EtOAc (50:1) to give the title compound (4.0 g, 69%) as a yellow solid. $^1$H NMR (300 MHz, DMSO-d$_6$) δ 7.90 (s, 1H), 7.46-7.38 (m, 1H), 7.25-7.18 (m, 1H), 7.09-7.02 (m, 1H), 4.25 (s, 2H). LCMS (M+H)$^+$ 276.

Step 4: 5-[6-Chloro-2-(2,4-difluoro-benzyl)-pyrimidin-4-yl]-1,3-dimethyl-1H-pyridin-2-one

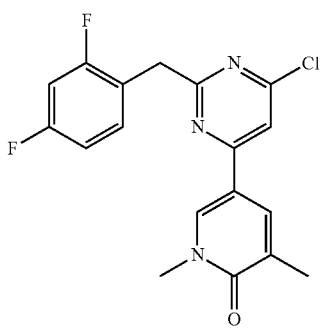

A mixture of 4,6-Dichloro-2-(2,4-difluoro-benzyl)-pyrimidine (900 mg, 3.3 mmol), 1,3-Dimethyl-5-(4,4,5,5-tetramethyl-[1,3,2]dioxaborolan-2-yl)-1H-pyridin-2-one (815 mg, 3.3 mmol), and Pd(dppf)Cl$_2$ (240 mg, 0.33 mmol) was diluted with 1,4 dioxane (10 mL) and 3.75M aqueous K$_3$PO$_4$ (2.2 mL, 8.3 mmol). The mixture was purged with nitrogen for 3 min, sealed and heated to 75° C. for 90 min. After cooling to room temperature, the mixture was poured into H$_2$O and extracted with EtOAc. The combined organic layers were washed with brine, dried over Na$_2$SO$_4$, filtered and concentrated under reduced pressure. The residue was diluted with Et$_2$O (10 mL); the resulting suspension was filtered. The filter cake was dried to give the title compound (700 mg, 54%) as a yellow solid. $^1$H NMR (300 MHz, CDCl$_3$) δ 8.20 (s, 1H), 7.71 (s, 1H), 7.33-7.23 (m, 2H), 6.87-6.79 (m, 2H), 4.25 (s, 2H), 3.64 (s, 3H), 2.22 (s, 3H). LCMS (M+H)$^+$ 362

Step 5: Propane-2-sulfonic acid [2-(2,4-difluoro-benzyl)-6-(1,5-dimethyl-6-oxo-1,6-dihydro-pyridin-3-yl)-pyrimidin-4-yl]-amide

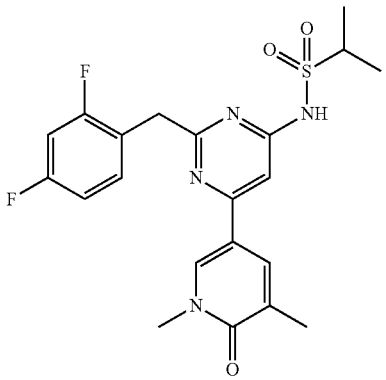

A mixture of 5-[6-Chloro-2-(2,4-difluoro-benzyl)-pyrimidin-4-yl]-1,3-dimethyl-1H-pyridin-2-one (200 mg, 0.55 mmol), propane-2-sulfonamide (170 mg, 1.4 mmol), Pd$_2$(dba)$_3$ (25 mg, 0.03 mmol), X-Phos (40 mg, 0.08 mmol) and Cs$_2$CO$_3$ (252 mg, 0.77 mmol) was diluted with 1,4 dioxane (8 mL). The mixture was purged with nitrogen for 3 min, sealed and heated to 90° C. for 4 h. After the mixture was cooled to room temperature, it was poured into H$_2$O (50 mL), adjusted to pH 5 with 2M HCl, and extracted with EtOAc. The combined organic layers were washed with brine, dried over Na$_2$SO$_4$, filtered and concentrated under reduced pressure. The resulting residue was purified by flash column chromatography eluting with PE/EtOAc (1:1) to give the title compound (110 mg, 44%) as a light yellow solid. $^1$H NMR (300 MHz, CD$_3$OD) δ 8.39 (s, 1H), 7.97 (s, 1H), 7.41-7.39 (m, 1H), 7.00-6.92 (m, 3H), 4.19 (s, 2H), 3.65 (s, 3H), 3.54-3.52 (s, 1H), 2.18 (s, 3H), 1.26 (m, 6H). LCMS (M+H)$^+$ 449.

Example 94: Ethanesulfonic acid [2-(2,4-difluoro-benzyl)-6-(1,5-dimethyl-6-oxo-1,6-dihydro-pyridin-3-yl)-pyrimidin-4-yl]-amide

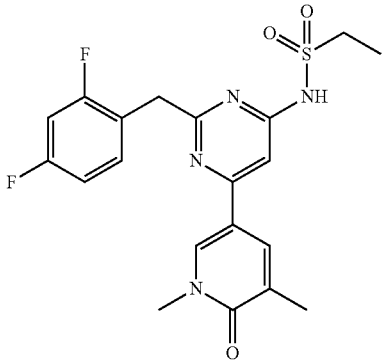 [SMILES: CCS(=O)(=O)Nc1cc(-c2cc(C)c(=O)n(C)c2)nc(Cc2ccc(F)cc2F)n1]

Example 94 was prepared in a manner similar procedure to Example 93, specifically replacing propane-2-sulfonamide in step 5 with ethanesulfonamide. $^1$H NMR (CD$_3$OD, 300 MHz) δ 8.39 (s, 1H), 7.98 (s, 1H), 7.42-7.39 (m, 1H), 6.99-6.91 (m, 3H), 4.19 (s, 2H), 3.65 (s, 3H), 3.34-3.27 (m, 2H), 2.18 (s, 3H), 1.24 (m, 3H). LCMS (M+H)$^+$ 435.

Example 95: 5-[2-(2,4-Difluoro-phenoxy)-6-(propane-2-sulfonylmethyl)-pyrimidin-4-yl]-1,3-dimethyl-1H-pyridin-2-one

Step 1: (Propane-2-sulfonyl)-acetic acid methyl ester

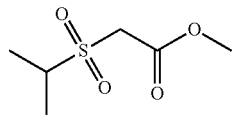

A 0.59 M solution of isopropylsulfanyl-acetic acid methyl ester (1.3 g, 8.8 mmol) stirred in DCM was treated with m-CPBA (2.9 g, 17 mmol). The mixture was filtered after stirring for 48 h; the filtrate was washed with saturated NaHCO₃ solution (30 mL*3), dried over Na₂SO₄, filtered and concentrated to give the title compound (1.1 g, 68%) as a tan oil. The material was used in the next step without any further purification. ¹H NMR (300 MHz, CDCl₃) δ 3.97 (s, 2H), 3.82 (s, 3H), 3.58-3.53 (m, 1H), 1.43 (m, 6H).

Step 2: (6-Chloro-2-methyl sulfanyl-pyrimidin-4-yl)-(propane-2-sulfonyl)-acetic acid methyl ester

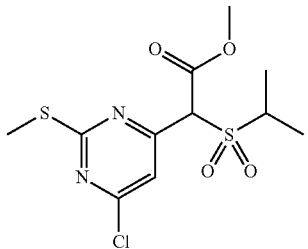 [SMILES: COC(=O)C(c1cc(Cl)nc(SC)n1)S(=O)(=O)C(C)C]

A 0.40 M solution of (Propane-2-sulfonyl)-acetic acid methyl ester (1.1 g, 6.1 mmol) stirred in DMF at room temperature was treated with NaH (440 mg, 11 mmol, 60% in mineral oil). After stirring for 15 min, the mixture was treated with 4,6-Dichloro-2-methylsulfanyl-pyrimidine (1.1 g, 5.6 mmol). After 10 h at room temperature, the mixture was warmed to 40° C. for another 14 h. The mixture was poured into saturated NH₄Cl solution (aq) (50 mL), adjusted to pH 4 with HCl (2.0 M), and extracted with EtOAc (40 mL*2). The combined organic layers were dried over Na₂SO₄, filtered, and concentrated under reduced pressure. The resulting residue was purified by column chromatography on silica gel eluting with PE/EtOAc (3:1) to give the title compound (900 mg, 42%) as a yellow solid. ¹H NMR (300 MHz, CDCl₃) δ 7.65 (s, 1H), 5.31 (s, 1H), 3.88 (s, 3H), 3.50-3.41 (m, 1H), 2.55 (s, 3H), 1.43 (m, 6H). LCMS (M–H)⁻ 337.

Step 3: [6-(1,5-Dimethyl-6-oxo-1,6-dihydro-pyridin-3-yl)-2-methylsulfanyl-pyrimidin-4-yl]-(propane-2-sulfonyl)-acetic acid methyl ester

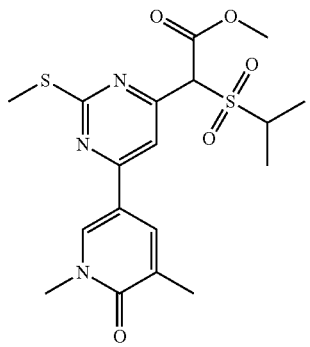 [SMILES: COC(=O)C(c1cc(-c2cc(C)c(=O)n(C)c2)nc(SC)n1)S(=O)(=O)C(C)C]

A mixture of (6-Chloro-2-methyl sulfanyl-pyrimidin-4-yl)-(propane-2-sulfonyl)-acetic acid methyl ester (900 mg, 2.7 mmol), 1,3-Dimethyl-5-(4,4,5,5-tetramethyl-[1,3,2]dioxaborolan-2-yl)-1H-pyridin-2-one (663 mg, 2.7 mmol), and Pd(dppf)Cl₂ (195 mg, 0.03 mmol) was diluted with 1,4 dioxane (12 mL) and 3.75 M K₃PO₄ aqueous solution (1.8 mL, 6.8 mmol). The resulting suspension was purged with N₂ for 3 min, sealed and heated to 75° C. for 2 hr. After cooling to room temperature, the mixture was poured into H₂O (50 mL) and extracted with DCM (50 mL*2). The combined organic layers were washed with brine (50 mL), dried over Na₂SO₄, filtered and concentrated under reduced pressure. The resulting residue was triturated with Et₂O (20 mL) and filtered. The filter cake was dried and collected to give the title compound (1.0 g, 91%) as a yellow solid. ¹H NMR (300 MHz, CDCl₃) δ 8.26 (s, 1H), 7.89 (s, 1H), 7.76 (s, 1H), 5.34 (s, 1H), 3.88 (s, 3H), 3.66 (s, 3H), 3.45-3.40 (m, 1H), 2.58 (s, 3H), 2.23 (s, 3H), 1.45-1.41 (m, 6H). LCMS (M–H)⁻ 424

Step 4: 1,3-Dimethyl-5-[2-methylsulfanyl-6-(propane-2-sulfonylmethyl)-pyrimidin-4-yl]-1H-pyridin-2-one

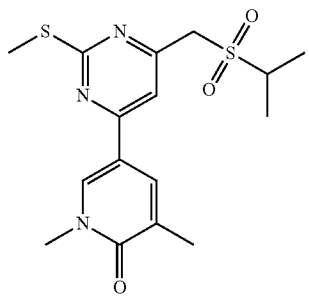 [SMILES: CSc1nc(CS(=O)(=O)C(C)C)cc(-c2cc(C)c(=O)n(C)c2)n1]

A stirred suspension of [6-(1,5-Dimethyl-6-oxo-1,6-dihydro-pyridin-3-yl)-2-methyl-sulfanyl-pyrimidin-4-yl]-(propane-2-sulfonyl)-acetic acid methyl ester (1.0 g, 2.4 mmol) in MeOH (16 mL) and H₂O (4 mL) was treated with NaOH (282 mg, 7.1 mmol). The mixture was heated to 65° C. for 4 h. After cooling to room temperature, the mixture was poured into saturated NH₄Cl solution (50 mL) and extracted with DCM (50 mL*2). The combined organic layers were washed with brine (45 mL), dried over $Na_2SO_4$, filtered and concentrated under reduced pressure. The resulting residue was triturated with $Et_2O$ (15 mL) and then filtered. The resulting filter cake was dried and collected to give the title compound (800 mg, 92%) as a yellow solid. $^1H$ NMR (300 MHz, $CDCl_3$) δ 8.26 (s, 1H), 7.84 (s, 1H), 7.32 (m, 1H), 4.31 (s, 2H), 3.65 (s, 3H), 3.26-3.17 (m, 1H), 2.59 (s, 3H), 2.22 (s, 3H), 1.44 (m, 6H). LCMS (M+H)$^+$ 368.

Step 5: 5-[2-Methanesulfonyl-6-(propane-2-sulfonylmethyl)-pyrimidin-4-yl]-1,3-dimethyl-1H-pyridin-2-one

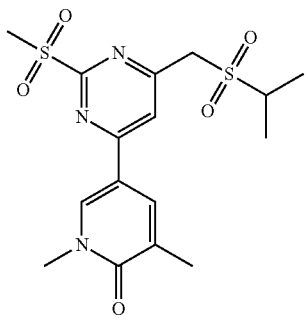 [SMILES: Cc1cc(-c2cc(CS(=O)(=O)C(C)C)nc(S(C)(=O)=O)n2)cn(C)c1=O]

A 0.15 M solution of 1,3-Dimethyl-5-[2-methylsulfanyl-6-(propane-2-sulfonylmethyl)-pyrimidin-4-yl]-1H-pyridin-2-one (800 mg, 2.2 mmol) stirred in DCM at 0° C. was treated with mCPBA (940 mg, 5.4 mmol). After stirring at room temperature for 30 h, the mixture was diluted with DCM (25 mL) and washed with saturated $NaHCO_3$ solution (40 mL) and $Na_2S_2SO_3$ solution (40 mL); the combined organic layers were washed with brine (60 mL), dried over $Na_2SO_4$, filtered, and concentrated under reduced pressure. The resulting residue was purified by column chromatography on silica gel eluting with PE/EtOAc (1:1) to give the title compound (300 mg, 34%) as a yellow solid. $^1H$ NMR (300 MHz, $CD_3OD$) δ 8.47 (s, 1H), 7.87-7.83 (m, 2H), 4.48 (s, 2H), 3.70 (s, 3H), 3.39 (s, 3H), 3.25-3.16 (m, 1H), 2.25 (s, 3H), 1.47 (m, 6H). LCMS (M+H)$^+$ 400

Step 6: 5-[2-(2,4-Difluoro-phenoxy)-6-(propane-2-sulfonylmethyl)-pyrimidin-4-yl]-1,3-dimethyl-1H-pyridin-2-one

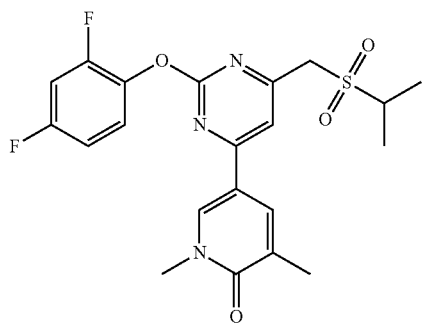 [SMILES: Cc1cc(-c2cc(CS(=O)(=O)C(C)C)nc(Oc3ccc(F)cc3F)n2)cn(C)c1=O]

A 0.075 M solution of 2,4-Difluoro-phenol (78 mg, 0.60 mmol) stirred at −30° C. in DMF was treated with NaH (26 mg, 0.65 mmol, 60% in mineral oil). After 30 min. the mixture was treated with 5-[2-Methanesulfonyl-6-(propane-2-sulfonylmethyl)-pyrimidin-4-yl]-1,3-dimethyl-1H-pyridin-2-one (200 mg, 0.50 mmol); the cooling bath was removed and the mixture was stirred at room temperature for 5 h. The mixture was poured into saturated $NH_4Cl$ solution and extracted with DCM. The combined organic layers were washed with brine, dried over $Na_2SO_4$, filtered, and concentrated under reduced pressure. The resulting residue was purified by prep-HPLC to give the title compound (30 mg, 13%) as a white solid. $^1H$ NMR (300 MHz, DMSO-$d_6$) δ 8.63 (s, 1H), 7.98 (s, 1H), 7.79 (s, 1H), 7.57-7.49 (m, 2H), 7.22-7.18 (m, 1H), 4.47 (s, 2H), 3.55 (s, 3H), 3.22-3.15 (m, 1H), 2.07 (s, 3H), 1.11 (m, 6H). LCMS (M+H)$^+$ 450

Example 96: 5-[2-(2,4-Difluoro-phenoxy)-6-ethanesulfonylmethyl-pyrimidin-4-yl]-1,3-dimethyl-1H-pyridin-2-one

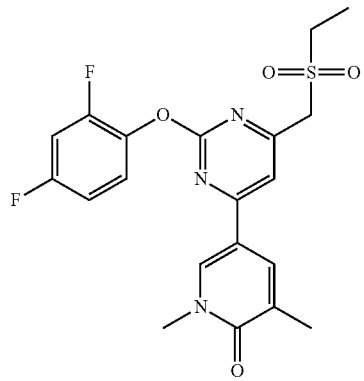 [SMILES: CCS(=O)(=O)Cc1cc(-c2cc(C)c(=O)n(C)c2)nc(Oc2ccc(F)cc2F)n1]

Example 96 was prepared in a manner similar procedure to Example 95, specifically replacing isopropylsulfanyl-acetic acid methyl ester in step 1 with methyl 2-(ethylsulfonyl)acetate. $^1H$ NMR (300 MHz, DMSO-$d_6$) δ 8.51 (s, 1H), 8.07 (s, 1H), 7.67 (s, 1H), 7.40-7.34 (m, 1H), 7.23-7.18 (m, 1H), 7.09-7.05 (m, 1H), 4.85 (s, 2H), 3.66 (s, 3H), 3.06 (q, J=7.2 Hz, 2H), 2.18 (s, 3H), 1.25 (t, J=7.2 Hz, 3H). LCMS (M+H)$^+$ 436

Example 97: Butane-1-sulfonic acid [2-(2,6-dimethyl-phenoxy)-6-(2-methyl-1-oxo-1,2-dihydro-isoquinolin-4-yl)-pyrimidin-4-yl]-amide

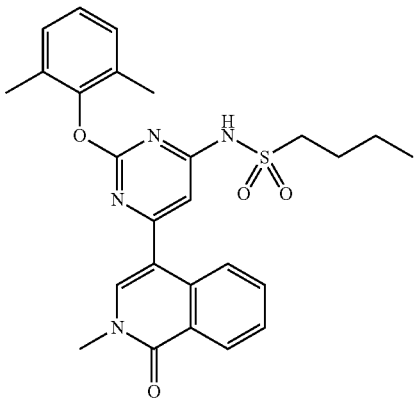 [SMILES: CCCCS(=O)(=O)Nc1cc(-c2cn(C)c(=O)c3ccccc23)nc(Oc2c(C)cccc2C)n1]

The title compound was prepared in a similar multi-step manner as Example 1 by employing 2,6-dimethylphenol, n-butyl sulfonamide and 2-methyl-4-(4,4,5,5-tetramethyl-1,3,2-dioxaborolan-2-yl)isoquinolin-1-one. $^1$H NMR (CD$_3$OD, 300 MHz) 8.42 (d, J=7.5 Hz, 1H), 8.06 (d, J=8.4 Hz, 1H), 7.79-7.72 (m, 2H), 7.62-7.60 (m, 1H), 7.14-7.08 (m, 3H), 6.69-6.68 (m, 1H), 3.69 (s, 3H), 2.93-2.88 (m, 2H), 2.19 (s, 6H), 1.55-1.48 (m, 2H), 1.30-1.22 (m, 2H), 0.87 (t, J=7.5 Hz, 3H). LCMS (M+H)$^+$ 493

Examples 98-100 (Table 6) were prepared from 2-chloro-4-fluoro-6-methyl-phenol (synthesis shown below) and the appropriate sulfonamide in a similar multi-step manner as Example 1.

2-Chloro-4-fluoro-6-methyl-phenol

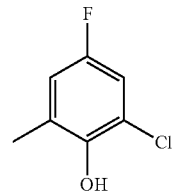

A three-necked flask (25 mL) charged with a solution of 4-Fluoro-2-methyl-phenol (100 mg, 0.79 mmol) and NCS (111 mg, 0.83 mmol) in acetonitrile (3 mL) was placed in a pre-heated oil bath (90° C.), then the reaction mixture was stirred for 1 hour at the same temperature, cooled to rt. The mixture was concentrated at 35° C. in vacuum and the residue was purified by column chromatography on silica gel eluting with PE/EtOAc (100:1) to give the compound 2-Chloro-4-fluoro-6-methyl-phenol (73 mg, 0.46 mmol) as a white solid in 57% yield. $^1$H NMR (400 MHz, CDCl$_3$): δ 6.91 (dd, J=8.0 Hz, 2.8 Hz, 1H), 6.79 (dd, J=8.8 Hz, 2.8 Hz, 1H), 5.39 (s, 1H), 2.27 (s, 3H).

TABLE 6

| Example | Structure | IUPAC Name | $^1$H NMR ppm (δ) | MS (M + H) |
|---|---|---|---|---|
| 98 | | Butane-1-sulfonic acid [2-(2-chloro-4-fluoro-6-methyl-phenoxy)-6-(1,5-dimethyl-6-oxo-1,6-dihydro-pyridin-3-yl)-pyrimidin-4-yl]-amide | (DMSO-d$_6$, 300 MHz) 11.36 (s, 1H), 8.48 (s, 1H), 7.83 (s, 1H), 7.47-7.42 (m, 1H), 7.30-7.26 (m, 1H), 6.82 (s, 1H), 3.63 (s, 3H), 3.01-2.95 (m, 2H), 2.14 (s, 3H), 2.09 (s, 3H), 1.45-1.38 (m, 2H), 1.25-1.18 (m, 2H), 0.81 (t, J = 7.2 Hz, 3H) | 495 |
| 99 | | Propane-1-sulfonic acid [2-(2-chloro-4-fluoro-6-methyl-phenoxy)-6-(1,5-dimethyl-6-oxo-1,6-dihydro-pyridin-3-yl)-pyrimidin-4-yl]-amide | (DMSO-d$_6$, 400 MHz) 11.35 (s, 1H), 8.48 (d, J = 2.4 Hz, 1H), 7.83 (s, 1H), 7.46 (dd, J = 8.4 Hz, 2.8 Hz, 1H), 7.28 (dd, J = 9.2 Hz, 2.8 Hz, 1H), 6.82 (s, 1H), 3.57 (s, 3H), 2.97-2.93 (m, 2H), 2.15 (s, 3H), 2.09 (s, 3H), 1.53-1.43 (m, 2H), 0.84 (t, J = 7.2 Hz, 3H) | 481 |
| 100 | | Propane-2-sulfonic acid [2-(2-chloro-4-fluoro-6-methyl-phenoxy)-6-(1,5-dimethyl-6-oxo-1,6-dihydro-pyridin-3-yl)-pyrimidin-4-yl]-amide | (DMSO-d$_6$, 400 MHz) 11.28 (s, 1H), 8.48 (d, J = 2.8 Hz, 1H), 7.84 (s, 1H), 7.47 (dd, J = 8.4 Hz, 2.8 Hz, 1H), 7.29 (dd, J = 9.2 Hz, 2.4 Hz, 1H), 6.84 (s, 1H), 3.57 (s, 3H), 3.16-3.09 (m, 1H), 2.14 (s, 3H), 2.09 (s, 3H), 1.07 (d, J = 6.8 Hz, 6H) | 481 |

Examples 101-104 (Table 7) were prepared from 2-chloro-6-methyl-phenol, the appropriate sulfonamide and either 1,3-dimethyl-5-(4,4,5,5-tetramethyl-[1,3,2]dioxaborolan-2-yl)-1H-pyridin-2-one (Example 101) or 1-methyl-5-(4,4,5,5-tetramethyl-1,3,2-dioxaborolan-2-yl) pyridin-2(1H)-one (Examples 102-104) in a similar multi-step manner as Example 1.

TABLE 7

| Example | Structure | IUPAC Name | $^1$H NMR ppm (δ) | MS (M + H) |
|---|---|---|---|---|
| 101 | | Propane-1-sulfonic acid [2-(2-chloro-6-methyl-phenoxy)-6-(1,5-dimethyl-6-oxo-1,6-dihydro-pyridin-3-yl)-pyrimidin-4-yl]-amide | (DMSO-d$_6$, 400 MHz) 11.33 (s, 1H), 8.49 (d, J = 2.4 Hz, 1H), 7.84 (s, 1H), 7.42 (d, J = 8.0 Hz, 1H), 7.33 (d, J = 8.0 Hz, 1H), 7.24-7.21 (m, 1H), 6.82 (s, 1H), 3.57 (s, 3H), 2.89-2.85 (m, 2H), 2.15 (s, 3H), 2.09 (s, 3H), 1.47-1.41 (m, 2H), 0.81 (t, J = 6.8 Hz, 3H) | 463 |
| 102 | | Butane-1-sulfonic acid [2-(2-chloro-6-methyl-phenoxy)-6-(1-methyl-6-oxo-1,6-dihydro-pyridin-3-yl)-pyrimidin-4-yl]-amide | (DMSO-d$_6$, 400 MHz) 11.35 (s, 1H), 8.59 (s, 1H), 7.91-7.89 (m, 1H), 7.41 (d, J = 6.8 Hz, 1H), 7.32 (d, J = 6.8 Hz, 1H), 7.24-7.20 (m, 1H), 6.82 (s, 1H), 6.52 (d, J = 9.2 Hz, 1H), 3.56 (s, 3H), 2.94-2.91 (m, 2H), 2.14 (s, 3H), 1.41-1.39 (m, 2H), 1.23-1.17 (m, 2H), 0.81 (t, J = 7.2 Hz, 3H) | 463 |
| 103 | | Propane-1-sulfonic acid [2-(2-chloro-6-methyl-phenoxy)-6-(1-methyl-6-oxo-1,6-dihydro-pyridin-3-yl)-pyrimidin-4-yl]-amide | (CDCl$_3$, 400 MHz) 8.40 (s, 1H), 7.80 (d, J = 9.6 Hz, 1H), 7.42 (s, 1H), 7.31 (d, J = 7.6 Hz, 1H), 7.21 (d, J = 7.2 Hz, 1H), 7.16-7.12 (m, 1H), 6.90 (s, 1H), 6.64 (d, J = 10.0 Hz, 1H), 3.63 (s, 3H), 3.09-3.05 (m, 2H), 2.24 (s, 3H), 1.78-1.73 (m, 2H), 0.98 (t, J = 7.2 Hz, 3H). | 449 |
| 104 | | Propane-2-sulfonic acid [2-(2-chloro-6-methyl-phenoxy)-6-(1-methyl-6-oxo-1,6-dihydro-pyridin-3-yl)-pyrimidin-4-yl]-amide | (CDCl$_3$, 400 MHz) 8.36 (s, 1H), 7.80 (d, J = 8.8 Hz, 1H), 7.31-7.28 (m, 2H), 7.21 (d, J = 7.6 Hz 1H), 7.15-7.12 (m, 1H), 6.99 (s, 1H), 6.63 (d, J = 9.2 Hz, 1H), 3.62 (s, 3H), 3.33-3.30 (m, 1H), 2.24 (s, 3H), 1.33 (d, J = 6.8 Hz, 6H) | 449 |

Examples 105-106 (Table 8) were prepared in a manner similar procedure to Example 1 using the appropriate phenol and sulfonamide. 1,3-dimethyl-5-(4,4,5,5-tetramethyl-[1,3,2]dioxaborolan-2-yl)-1H-pyridin-2-one was replaced with 3-methoxy-1-methyl-5-(4,4,5,5-tetramethyl-1,3,2-dioxaborolan-2-yl)pyridin-2(1H)-one in step 2.

TABLE 8

| Example | Structure | IUPAC Name | $^1$H NMR ppm (δ) | MS (M + H) |
|---|---|---|---|---|
| 105 | | N-(2-(2,6-dimethylphenoxy)-6-(5-methoxy-1-methyl-6-oxo-1,6-dihydropyridin-3-yl)pyrimidin-4-yl)propane-2-sulfonamide | (400 MHz, DMSO-d6) δ ppm 0.99 (m, 6H) 2.06 (m, 6H) 3.01 (m, 1H) 3.58 (s, 3H) 3.78 (s, 3H) 6.84 (s, 1H) 7.08-7.16 (3H) 7.25 (s, 1H) 8.21 (s, 1H) 11.09 (br s, 1H) | 459 |
| 106 | | N-(2-(2,6-dimethylphenoxy)-6-(5- | (400 MHz, DMSO-d6) δ ppm 0.79 (m, 3H) | 473 |

TABLE 8-continued

| Example | Structure | IUPAC Name | $^1$H NMR ppm (δ) | MS (M + H) |
|---|---|---|---|---|
| | | methoxy-1-methyl-6-oxo-1,6-dihydropyridin-3-yl)pyrimidin-4-yl)butane-1-sulfonamide | 1.18 (m, 2H) 1.38 (m, 2H) 2.07 (m, 6H) 2.86 (m, 2H) 3.57 (s, 3H) 3.79 (s, 3H) 6.83 (s, 1H) 7.05-7.16 (3H) 7.24 (s, 1H) 8.21 (s, 1H) 11.19 (br s, 1H) | |

Example 107: Propane-1-sulfonic acid [6-(2-chloro-6-methyl-phenoxy)-2-(1,5-dimethyl-6-oxo-1,6-dihydro-pyridin-3-yl)-pyrimidin-4-yl]-amide

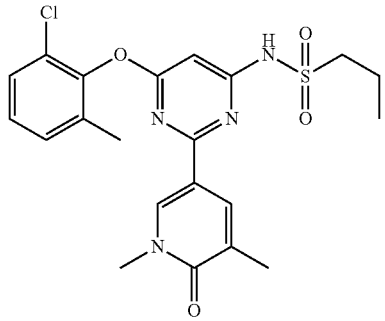 [SMILES: CCCS(=O)(=O)Nc1cc(Oc2c(C)cccc2Cl)nc(-c2cc(C)c(=O)n(C)c2)n1]

The title compound was prepared in a manner similar to Example 56 by substituting 2-chloro-6-methylphenol for 2,6-dimethylphenol in Step 3 and propane-1-sulfonamide for butane-1-sulfonamide in Step 4. $^1$H NMR (CDCl$_3$, 400 MHz) δ 8.12 (d, J=2.4 Hz, 1H), 7.92 (s, 1H), 7.33 (dd, J=8.0 Hz, 1.2 Hz, 1H), 7.23-7.15 (m, 2H), 6.42 (s, 1H), 3.57 (s, 3H), 3.41-3.37 (m, 2H), 2.21 (s, 3H), 2.15 (s, 3H), 1.97-1.91 (m, 2H), 1.10 (t, J=7.6 Hz, 3H). LCMS (M+H)$^+$ 463

Example 108: Butane-1-sulfonic acid [2-(2-cyano-6-methyl-phenoxy)-6-(1-methyl-6-oxo-1,6-dihydro-pyridin-3-yl)-pyrimidin-4-yl]-amide

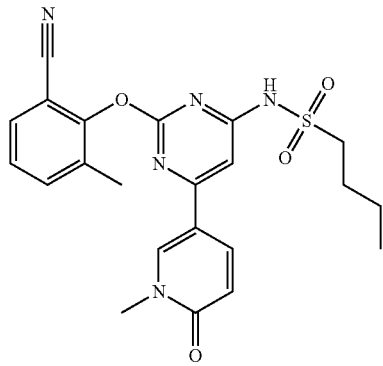 [SMILES: CCCCS(=O)(=O)Nc1cc(-c2ccc(=O)n(C)c2)nc(Oc2c(C)cccc2C#N)n1]

The title compound was prepared in a manner similar to Example 1 by substituting 2-hydroxy-3-methylbenzonitrile for 2,5-dichlorophenol in Step 1, 1-methyl-5-(4,4,5,5-tetramethyl-1,3,2-dioxaborolan-2-yl)pyridin-2(1H)-one for 1,3-dimethyl-5-(4,4,5,5-tetramethyl-[1,3,2]dioxaborolan-2-yl)-1H-pyridin-2-one in Step 2 and butane-1-sulfonamide for propane-2-sulfonamide in Step 3. $^1$H NMR (CD$_3$OD, 400 MHz) δ 8.58 (d, J=2.4 Hz, 1H), 8.10 (dd, J=9.6 Hz, 3.2 Hz, 1H), 7.67-7.64 (m, 2H), 7.38 (d, J=7.6 Hz, 1H), 6.88 (s, 1H), 6.63 (d, J=9.6 Hz, 1H), 3.66 (s, 3H), 3.03-2.99 (m, 2H), 2.23 (s, 3H), 1.59-1.55 (m, 2H), 1.34-1.29 (m, 2H), 0.89 (t, J=7.6 Hz, 3H). LCMS (M+H)$^+$ 454

Examples 109-126 (Table 9) were prepared in a similar multi-step a manner as Example 1.

TABLE 9

| Example | Structure | IUPAC Name | $^1$H NMR ppm (δ) | MS (M + H) |
|---|---|---|---|---|
| 109 | | Propane-1-sulfonic acid [2-(2-cyano-6-methyl-phenoxy)-6-(1-methyl-6-oxo-1,6-dihydro-pyridin-3-yl)-pyrimidin-4-yl]-amide | (CDCl$_3$, 300 MHz) 8.37 (d, J = 2.1 Hz, 1H), 7.82 (dd, J = 9.6 Hz, 2.4 Hz, 1H), 7.59-7.57 (m, 2H), 7.35-7.30 (m, 2H), 6.99 (s, 1H), 6.66 (d, J = 9.6 Hz, 1H), 3.65 (s, 3H), 3.15-3.10 (m, 2H), 2.27 (s, 3H), 1.84-1.77 (m, 2H), 1.01 (t, J = 7.5 Hz, 3H) | 440 |

TABLE 9-continued

| Example | Structure | IUPAC Name | $^1$H NMR ppm ($\delta$) | MS (M + H) |
|---|---|---|---|---|
| 110 | 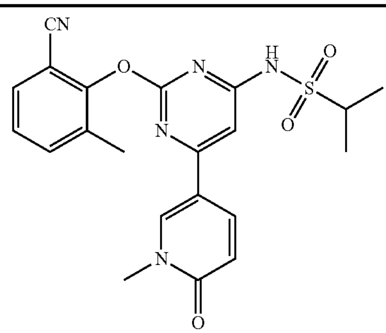 | Propane-2-sulfonic acid [2-(2-cyano-6-methyl-phenoxy)-6-(1-methyl-6-oxo-1,6-dihydro-pyridin-3-yl)-pyrimidin-4-yl]-amide | (CDCl$_3$, 400 MHz) 8.32 (s, 1H), 7.80 (d, J = 9.6 Hz, 1H), 7.58-7.55 (m, 2H), 7.32-7.29 (m, 2H), 7.08 (s, 1H), 6.64 (d, J = 9.6 Hz, 1H), 3.63 (s, 3H), 3.38-3.34 (m, 1H), 2.25 (s, 3H), 1.37 (d, J = 6.4 Hz, 6H) | 440 |
| 111 | 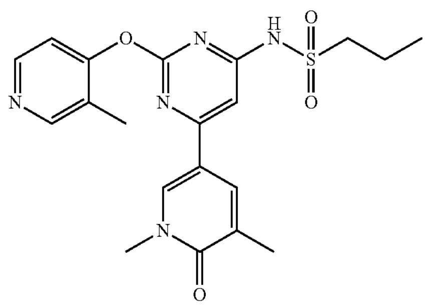 [SMILES: CCCS(=O)(=O)Nc1cc(-c2cc(C)c(=O)n(C)c2)nc(Oc2ccncc2C)n1] | Propane-1-sulfonic acid [6-(1,5-dimethyl-6-oxo-1,6-dihydro-pyridin-3-yl)-2-(3-methyl-pyridin-4-yloxy)-pyrimidin-4-yl]-amide | (CD$_3$OD, 400 MHz) 9.08 (dd, J = 8.0 Hz, 2.4 Hz, 1H), 9.01 (s, 1H), 8.66 (d, J = 2.0 Hz, 1H), 8.07 (s, 1H), 7.09 (s, 1H), 6.50 (d, J = 7.6 Hz, 1H), 3.72 (s, 3H), 3.54-3.50 (m, 2H), 2.22 (s, 3H), 2.13 (s, 3H), 1.92-1.87 (m, 2H), 1.08 (t, J = 7.2 Hz, 3H) | 430 |
| 112 | 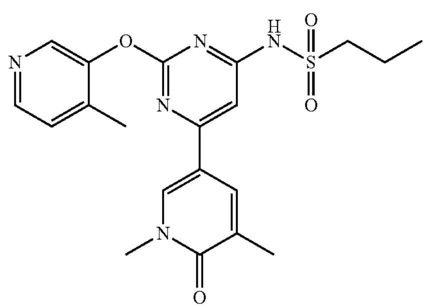 | Propane-1-sulfonic acid [6-(1,5-dimethyl-6-oxo-1,6-dihydro-pyridin-3-yl)-2-(4-methyl-pyridin-3-yloxy)-pyrimidin-4-yl]-amide | (CD$_3$OD, 400 MHz) 8.41 (d, J = 2.4 Hz, 1H), 8.35-8.34 (m, 2H), 7.97 (s, 1H), 7.45 (d, J = 7.6 Hz, 1H), 6.83 (s, 1H), 3.65 (s, 3H), 3.03-2.99 (m, 2H), 2.26 (s, 3H), 2.18 (s, 3H), 1.63-1.61 (m, 2H), 0.92-0.88 (t, J = 7.2 Hz, 3H) | 430 |
| 113 | 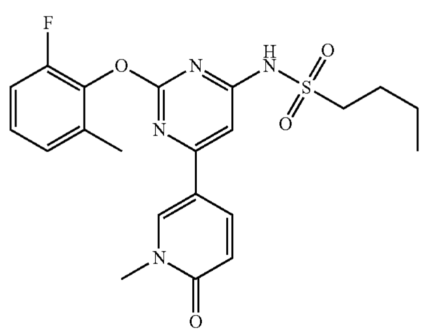 [SMILES: CCCCS(=O)(=O)Nc1cc(-c2ccc(=O)n(C)c2)nc(Oc2c(C)cccc2F)n1] | Butane-1-sulfonic acid [2-(2-fluoro-6-methyl-phenoxy)-6-(1-methyl-6-oxo-1,6-dihydro-pyridin-3-yl)-pyrimidin-4-yl]-amide | (CDCl$_3$, 400 MHz) 8.36 (d, J = 2.0 Hz, 1H), 7.81 (dd, J = 9.6 Hz, 2.8 Hz, 1H), 7.30 (br, 1H), 7.17-7.12 (m, 1H), 7.07-6.99 (m, 2H), 6.95 (s, 1H), 6.63 (d, J = 9.2 Hz, 1H), 3.70 (s, 3H), 3.16-3.13 (m, 2H), 2.26 (s, 3H), 1.77-1.69 (m, 2H), 1.42-1.33 (m, 2H), 0.91 (t, J = 7.2 Hz, 3H) | 447 |
| 114 | 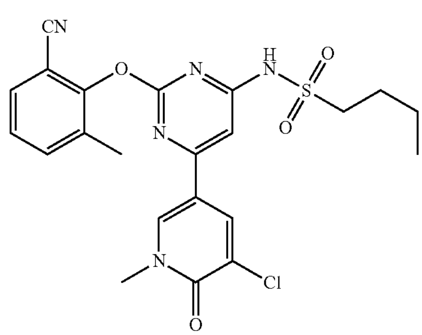 [SMILES: CCCCS(=O)(=O)Nc1cc(-c2cc(Cl)c(=O)n(C)c2)nc(Oc2c(C)cccc2C#N)n1] | Butane-1-sulfonic acid [6-(5-chloro-1-methyl-6-oxo-1,6-dihydro-pyridin-3-yl)-2-(2-cyano-6-methyl-phenoxy)-pyrimidin-4-yl]-amide | (DMSO-d$_6$, 400 MHz) 11.5 (s, 1H), 8.66 (d, J = 2.8 Hz, 1H), 8.20 (d, J = 2.4 Hz, 1H), 7.80 (d, J = 7.6 Hz, 1H), 7.73 (d, J = 7.6 Hz, 1H), 7.43 (t, J = 7.6 Hz, 1H), 6.91 (s, 1H), 3.65 (s, 3H), 2.95 (t, J = 7.6 Hz, 2H), 2.15 (s, 3H), 1.44-1.40 (m, 2H), 1.24-1.19 (m, 2H), 0.81 (t, J = 7.2 Hz, 3H) | 488 |

TABLE 9-continued

| Example | Structure | IUPAC Name | ¹H NMR ppm (δ) | MS (M + H) |
|---|---|---|---|---|
| 115 | 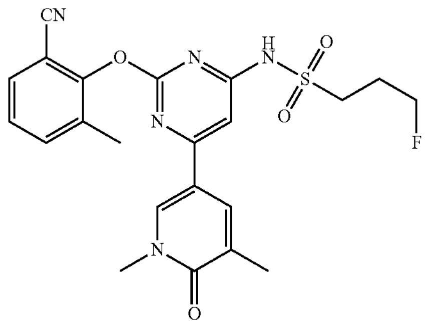 [SMILES: Cc1cccc(C#N)c1Oc1nc(NS(=O)(=O)CCCF)cc(-c2cc(C)c(=O)n(C)c2)n1] | 3-Fluoro-propane-1-sulfonic acid [2-(2-cyano-6-methyl-phenoxy)-6-(1,5-dimethyl-6-oxo-1,6-dihydro-pyridin-3-yl)-pyrimidin-4-yl]-amide | (CD$_3$OD, 300 MHz) 8.47 (s, 1H), 8.00 (s, 1H), 7.68-7.66 (m, 2H), 7.39 (m, 1H), 6.88 (s, 1H), 4.51-4.48 (m, 1H), 4.36-4.32 (m, 1H), 3.68 (s, 3H), 3.17-3.12 (m, 2H), 2.24 (s, 3H), 2.21 (s, 3H), 2.03-1.94 (m, 2H) | 472 |
| 116 | 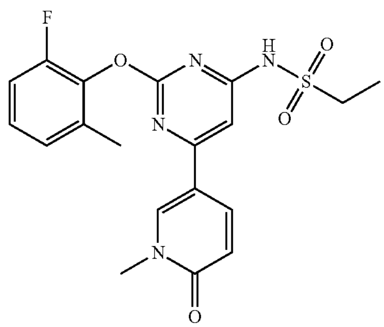 [SMILES: CCS(=O)(=O)Nc1cc(-c2ccc(=O)n(C)c2)nc(Oc2c(C)cccc2F)n1] | Ethanesulfonic acid [2-(2-fluoro-6-methyl-phenoxy)-6-(1-methyl-6-oxo-1,6-dihydro-pyridin-3-yl)-pyrimidin-4-yl]-amide | (CDCl$_3$, 300 MHz) 8.36 (d, J = 1.2 Hz, 1H), 7.84-7.80 (m, 1H), 7.59 (br, 1H), 7.17-7.07 (m, 1H), 7.03-6.76 (m, 3H), 6.64 (d, J = 9.3 Hz, 1H), 3.64 (s, 3H), 3.24-3.16 (m, 2H), 2.27 (s, 3H), 1.34 (t, J = 7.5 Hz, 3H) | 419 |
| 117 | 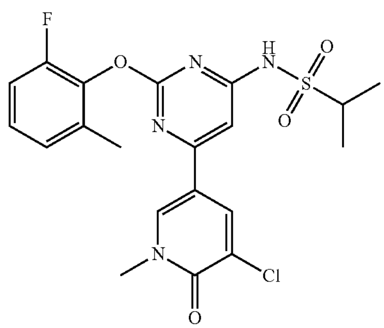 [SMILES: Cc1cccc(F)c1Oc1nc(NS(=O)(=O)C(C)C)cc(-c2cc(Cl)c(=O)n(C)c2)n1] | Propane-2-sulfonic acid [6-(5-chloro-1-methyl-6-oxo-1,6-dihydro-pyridin-3-yl)-2-(2-fluoro-6-methyl-phenoxy)-pyrimidin-4-yl]-amide | (CDCl$_3$, 400 MHz) 8.28 (s, 1H), 8.05 (d, J = 1.6 Hz, 1H), 7.17-7.13 (m, 1H), 7.08-7.01 (m, 3H), 3.70 (s, 3H), 3.39-3.35 (m, 1H), 2.26 (s, 3H), 1.36 (d, J = 6.8 Hz, 6H) | 467 |
| 118 | 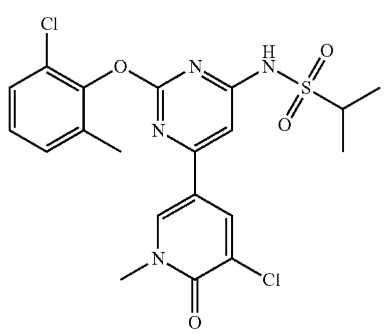 | Propane-2-sulfonic acid [6-(5-chloro-1-methyl-6-oxo-1,6-dihydro-pyridin-3-yl)-2-(2-chloro-6-methyl-phenoxy)-pyrimidin-4-yl]-amide | (CDCl$_3$, 300 MHz) 8.32 (s, 1H), 8.06 (s, 1H), 7.34-7.30 (m, 1H), 7.26-7.13 (m, 2H), 7.01 (s, 1H), 3.71 (s, 3H), 3.35-3.30 (m, 1H), 2.24 (s, 3H), 1.34 (d, J = 6.9 Hz, 6H) | 484 |

TABLE 9-continued

| Example | Structure | IUPAC Name | $^1$H NMR ppm ($\delta$) | MS (M + H) |
|---|---|---|---|---|
| 119 | 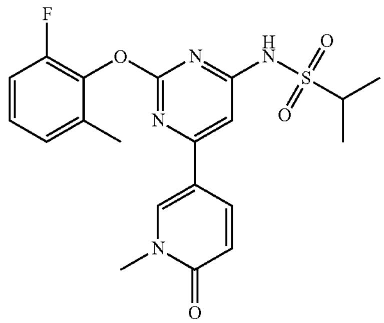 [SMILES: Cc1cccc(F)c1Oc1nc(NS(=O)(=O)C(C)C)cc(-c2ccc(=O)n(C)c2)n1] | Propane-2-sulfonic acid [2-(2-fluoro-6-methyl-phenoxy)-6-(1-methyl-6-oxo-1,6-dihydro-pyridin-3-yl)-pyrimidin-4-yl]-amide | (CDCl$_3$, 300 MHz) 8.34 (d, J = 1.5 Hz, 1H), 7.82 (dd, J = 9.6 Hz, 2.4 Hz, 1H), 7.41 (br, 1H), 7.17-7.12 (m, 1H), 7.09-7.02 (m, 3H), 6.64 (d, J = 9.9 Hz, 1H), 3.63 (s, 3H), 3.40-3.35 (m, 1H), 2.27 (s, 3H), 1.37 (d, J = 6.9 Hz, 6H) | 433 |
| 120 | 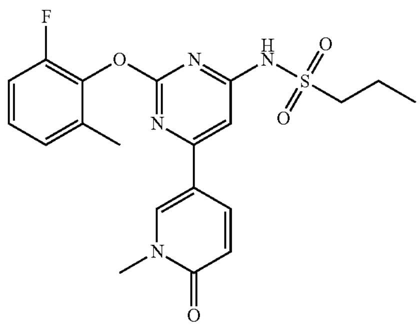 [SMILES: CCCS(=O)(=O)Nc1cc(-c2ccc(=O)n(C)c2)nc(Oc2c(C)cccc2F)n1] | Propane-1-sulfonic acid [2-(2-fluoro-6-methyl-phenoxy)-6-(1-methyl-6-oxo-1,6-dihydro-pyridin-3-yl)-pyrimidin-4-yl]-amide | (CD$_3$OD, 300 MHz) 8.58 (d, J = 2.4 Hz, 1H), 8.13 (dd, J = 9.0 Hz, 2.1 Hz, 1H), 7.21-7.09 (m, 3H), 6.86 (s, 1H), 6.64 (d, J = 9.3 Hz, 1H), 3.67 (s, 3H), 3.05-3.00 (m, 2H), 2.24 (s, 3H), 1.67-1.59 (m, 2H), 0.93 (t, J = 7.5 Hz, 3H). | 433 |
| 121 | 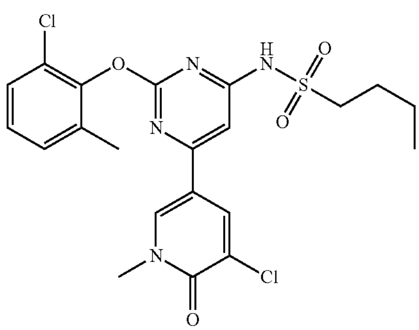 [SMILES: CCCCS(=O)(=O)Nc1cc(-c2cc(Cl)c(=O)n(C)c2)nc(Oc2c(C)cccc2Cl)n1] | Butane-1-sulfonic acid [6-(5-chloro-1-methyl-6-oxo-1,6-dihydro-pyridin-3-yl)-2-(2-chloro-6-methyl-phenoxy)-pyrimidin-4-yl]-amide | (DMSO-d$_6$, 400 MHz) 11.4 (s, 1H), 8.63 (d, J = 2.4 Hz, 1H), 8.19 (d, J = 2.1 Hz, 1H), 7.41 (dd, J = 8.0 Hz, 1.2 Hz, 1H), 7.32 (d, J = 6.8 Hz, 1H), 7.23 (t, J = 7.6 Hz, 1H), 6.86 (s, 1H), 3.65 (s, 3H), 2.95-2.91 (m, 2H), 2.14 (s, 3H), 1.43-1.37 (m, 2H), 1.24-1.18 (m, 2H), 0.81 (t, J = 7.2 Hz, 3H) | 498 |
| 122 | 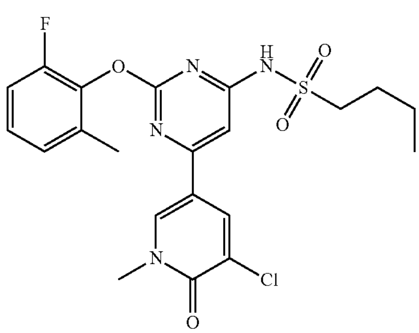 [SMILES: CCCCS(=O)(=O)Nc1cc(-c2cc(Cl)c(=O)n(C)c2)nc(Oc2c(C)cccc2F)n1] | Butane-1-sulfonic acid [6-(5-chloro-1-methyl-6-oxo-1,6-dihydro-pyridin-3-yl)-2-(2-fluoro-6-methyl-phenoxy)-pyrimidin-4-yl]-amide | (CDCl$_3$, 300 MHz) 8.32 (d, J = 1.8 Hz, 1H), 8.07 (d, J = 1.8 Hz, 1H), 7.18-6.98 (m, 4H), 3.72 (s, 3H), 3.20-3.15 (m, 2H), 2.28 (s, 3H), 1.80-1.70 (m, 2H), 1.44-1.37 (m, 2H), 0.94 (t, J = 7.2 Hz, 3H) | 481 |

TABLE 9-continued

| Example | Structure | IUPAC Name | ¹H NMR ppm (δ) | MS (M + H) |
|---|---|---|---|---|
| 123 | 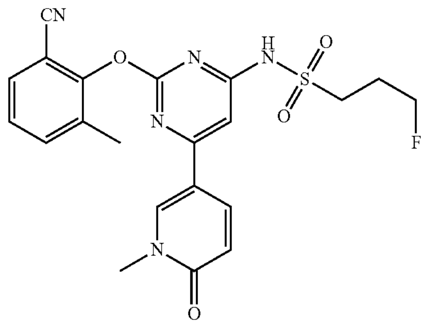 [SMILES: Cc1cccc(C#N)c1Oc1nc(NS(=O)(=O)CCCF)cc(-c2ccc(=O)n(C)c2)n1] | 3-Fluoro-propane-1-sulfonic acid [2-(2-cyano-6-methyl-phenoxy)-6-(1-methyl-6-oxo-1,6-dihydro-pyridin-3-yl)-pyrimidin-4-yl]-amide | (CD$_3$OD, 300 MHz) 8.60 (d, J = 2.4 Hz, 1H), 8.12 (dd, J = 9.3 Hz, 2.4 Hz, 1H), 7.67 (d, J = 7.8 Hz, 2H), 7.39 (t, J = 7.8 Hz, 1H), 6.90 (s, 1H), 6.65 (d, J = 9.3 Hz, 1H), 4.50 (t, J = 5.7 Hz, 1H), 4.34 (t, J = 5.7 Hz, 1H), 3.68 (s, 3H), 3.18-3.13 (m, 2H), 2.24 (s, 3H), 2.05-1.92 (m, 2H) | 458 |
| 124 | 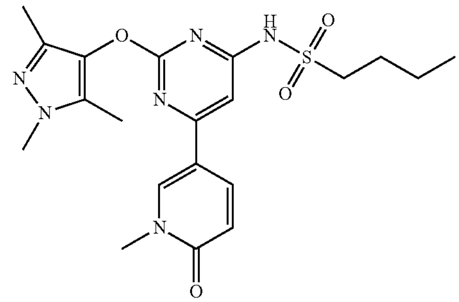 [SMILES: CCCCS(=O)(=O)Nc1cc(-c2ccc(=O)n(C)c2)nc(Oc2c(C)nn(C)c2C)n1] | Butane-1-sulfonic acid [6-(1-methyl-6-oxo-1,6-dihydro-pyridin-3-yl)-2-(1,3,5-trimethyl-1H-pyrazol-4-yloxy)-pyrimidin-4-yl]-amide | (CDCl$_3$, 300 MHz) 8.39 (d, J = 2.4 Hz, 1H), 7.84 (dd, J = 9.9, 2.7 Hz, 1H), 6.97 (s, 1H), 6.65 (d, J = 9.9 Hz, 1H), 3.76 (s, 3H), 3.67 (s, 3H), 3.28-3.22 (m, 2H), 2.15 (s, 3H), 2.12 (s, 3H), 1.81-1.76 (m, 2H), 1.47-1.39 (m, 2H), 0.94 (t, J = 7.4 Hz, 3H) | 447 |
| 125 | 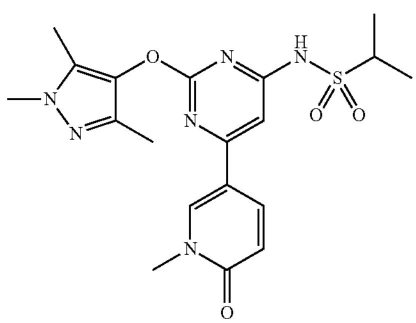 [SMILES: Cc1nn(C)c(C)c1Oc1nc(NS(=O)(=O)C(C)C)cc(-c2ccc(=O)n(C)c2)n1] | Propane-2-sulfonic acid [6-(1-methyl-6-oxo-1,6-dihydro-pyridin-3-yl)-2-(1,3,5-trimethyl-1H-pyrazol-4-yloxy)-pyrimidin-4-yl]-amide | (CD$_3$OD, 300 MHz) 8.57 (d, J = 2.4 Hz, 1H), 8.13 (dd, J = 9.6 Hz, 2.7 Hz, 1H), 6.86 (s, 1H), 6.65 (d, J = 9.6 Hz, 1H), 3.75 (s, 3H), 3.68 (s, 3H), 3.51-3.47 (m, 1H), 2.14 (s, 3H), 2.06 (s, 3H), 1.27 (d, J = 6.9 Hz, 6H) | 433 |
| 126 | 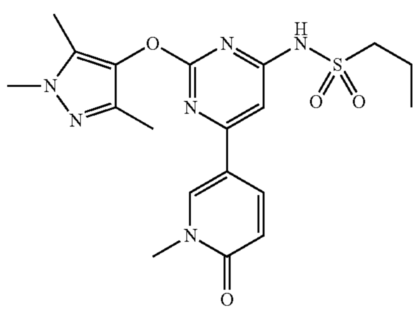 [SMILES: CCCS(=O)(=O)Nc1cc(-c2ccc(=O)n(C)c2)nc(Oc2c(C)nn(C)c2C)n1] | Propane-1-sulfonic acid [6-(1-methyl-6-oxo-1,6-dihydro-pyridin-3-yl)-2-(1,3,5-trimethyl-1H-pyrazol-4-yloxy)-pyrimidin-4-yl]-amide | (CD$_3$OD, 300 MHz) 8.58 (d, J = 2.4 Hz, 1H), 8.13 (dd, J = 9.6 Hz, 2.4 Hz, 1H), 6.83 (s, 1H), 6.65 (d, J = 9.6 Hz, 1H), 3.75 (s, 3H), 3.68 (s, 3H), 3.21-3.15 (m, 2H), 2.15 (s, 3H), 2.08 (s, 3H), 1.83-1.66 (m, 2H), 0.97 (t, J = 7.5 Hz, 3H) | 433 |

Example 127: Propane-2-sulfonic acid [6-(1,5-dimethyl-6-oxo-1,6-dihydro-pyridin-3-yl)-2-(1-ethyl-3,5-dimethyl-1H-pyrazol-4-yloxy)-pyrimidin-4-yl]-amide Step 1: Benzoic acid 1-acetyl-2-oxo-propyl ester

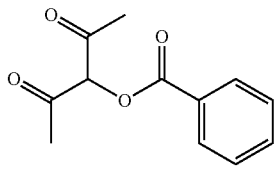 [SMILES: CC(=O)C(OC(=O)c1ccccc1)C(C)=O]

A suspension of benzoic acid (2.0 g, 16 mmol) and KOH (918 mg, 16 mmol) in DMF (25 mL) was heated to 50° C. for 1 hour, then cooled to rt. 3-Chloro-pentane-2,4-dione (2.2 g, 16 mmol) was added by syringe, and the mixture was heated to 50° C. overnight. It was then cooled to rt, diluted with H$_2$O (50 mL), and extracted with ether (45 mL*2). The combined organic layers were washed with brine, dried over Na$_2$SO$_4$, filtered and concentrated under vacuum to give the title compound (3.0 g, 14 mmol) as a colorless oil in 83% yield. It was used in the next step LCMS (M+H)$^+$ 221.

Step 2: Benzoic acid 1-ethyl-3,5-dimethyl-1H-pyrazol-4-yl ester

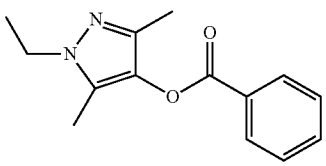 [SMILES: CCn1nc(C)c(OC(=O)c2ccccc2)c1C]

Benzoic acid 1-acetyl-2-oxo-propyl ester (3.0 g, 14 mmol) was dissolved in EtOH (50 mL); ethylhydrazine oxalate (4.0 g, 27 mmol) and K$_2$CO$_3$ (4.7 g, 34 mmol) were added. The reaction mixture was stirred at 20° C. for 6 hours. It was then diluted with H$_2$O (80 mL) and extracted with DCM (50 mL*2). The combined organic layers were washed with brine, dried over Na$_2$SO$_4$, filtered and concentrated under vacuum. The residue was purified by column chromatography on silica gel eluting with PE/EtOAc (6:1) to give the title compound (2.0 g, 8.2 mmol) as a yellow solid in 58% yield. $^1$H NMR (300 MHz, CDCl$_3$): δ 8.20 (d, J=7.2 Hz, 2H), 7.64 (t, J=7.5 Hz, 1H), 7.51 (t, J=7.5 Hz, 2H), 4.03 (q, J=7.2 Hz, 2H), 2.14 (s, 6H), 1.40 (t, J=7.2 Hz, 3H). LCMS (M+H)$^+$ 245

Step 3: 1-Ethyl-3,5-dimethyl-1H-pyrazol-4-ol

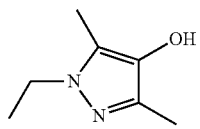

Benzoic acid 1-ethyl-3,5-dimethyl-1H-pyrazol-4-yl ester (1.8 g, 7.4 mmol) was dissolved in EtOH (30 mL) and NaOH solution (3.7 mL, 3.0 mol/L). After stirring at rt for 2 hours, the reaction mixture was concentrated and to the residue was added DCM (100 mL) and EtOH (20 mL). The mixture was stirred for 5 min and then filtered. The cake was washed with DCM/EtOH (5:1, 20 mL*5). The combined layers were concentrated under vacuum to give the crude title compound (950 mg, 6.8 mmol) as a white solid in 92% yield. It was used in the next step directly without further purification. LCMS (M+H)$^+$ 141.

Step 4: Propane-2-sulfonic acid [6-(1,5-dimethyl-6-oxo-1,6-dihydro-pyridin-3-yl)-2-(1-ethyl-3,5-dimethyl-1H-pyrazol-4-yloxy)-pyrimidin-4-yl]-amide

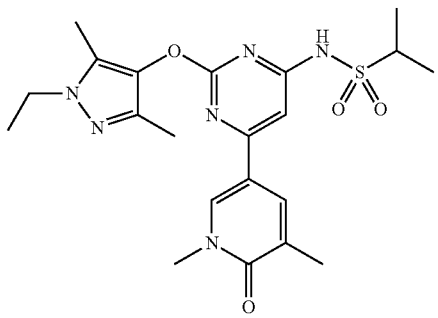 [SMILES: CCn1nc(C)c(Oc2nc(NS(=O)(=O)C(C)C)cc(-c3cc(C)c(=O)n(C)c3)n2)c1C]

The title compound was prepared in a manner similar to Example 1 by substituting 1-ethyl-3,5-dimethyl-1H-pyrazol-4-ol for 2,5-dichlorophenol in step 1. $^1$H NMR (CDCl$_3$, 400 MHz) δ 8.23 (s, 1H), 7.71 (s, 1H), 7.45 (br, 1H), 7.02 (s, 1H), 4.04 (q, J=7.2 Hz, 2H), 3.64 (s, 3H), 3.50-3.43 (m, 1H), 2.22 (s, 3H), 2.13 (s, 3H), 2.10 (s, 3H), 1.45-1.36 (m, 9H). LCMS (M+H)$^+$ 461.

Example 128: Butane-1-sulfonic acid [6-(1,5-dimethyl-6-oxo-1,6-dihydro-pyridin-3-yl)-2-(1-ethyl-3,5-dimethyl-1H-pyrazol-4-yloxy)-pyrimidin-4-yl]-amide

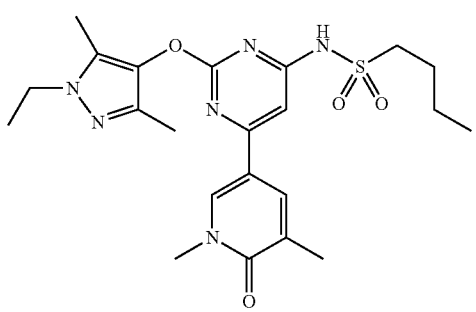 [SMILES: CCCCS(=O)(=O)Nc1cc(-c2cc(C)c(=O)n(C)c2)nc(Oc2c(C)nn(CC)c2C)n1]

The title compound was prepared in a manner similar to Example 127 by substituting butane-1-sulfonamide for propane-2-sulfonic acid amide in Step 4. $^1$H NMR (CDCl$_3$, 400 MHz) δ 8.26 (s, 1H), 7.94 (br, 1H), 7.72 (s, 1H), 6.92 (s, 1H), 4.04 (q, J=7.2 Hz, 2H), 3.64 (s, 3H), 3.24-3.20 (m, 2H), 2.22 (s, 3H), 2.13 (s, 3H), 2.11 (s, 3H), 1.78-1.71 (m, 2H), 1.45-1.37 (m, 5H), 0.91 (t, J=7.2 Hz, 3H). LCMS (M+H)$^+$ 475

Examples 129-130 (Table 10) were prepared using the appropriate phenol and sulfonamide in a similar multi-step manner as Example 56.

TABLE 10

| Example | Structure | IUPAC Name | $^1$H NMR ppm (δ) | MS (M + H) |
|---|---|---|---|---|
| 129 | | Propane-1-sulfonic acid [6-(2-cyano-6-methyl-phenoxy)-2-(1,5-dimethyl-6-oxo-1,6-dihydro-pyridin-3-yl)-pyrimidin-4-yl]-amide | (CDCl$_3$, 400 MHz) δ 8.06 (d, J = 2.0 Hz, 1H), 7.80 (s, 1H), 7.60-7.56 (m, 2H), 7.34 (t, J = 8.0 Hz, 1H), 6.65 (s, 1H), 3.56 (s, 3H), 3.43-3.39 (m, 2H), 2.22 (s 3H), 2.13 (s, 3H), 1.99-1.94 (m, 2H), 1.12 (t, J = 7.4 Hz, 3H) | 454 |
| 130 | | Propane-1-sulfonic acid [6-(2-cyano-6-methoxy-phenoxy)-2-(1,5-dimethyl-6-oxo-1,6-dihydro-pyridin-3-yl)-pyrimidin-4-yl]-amide | (CDCl$_3$, 300 MHz) δ 8.05 (d, J = 2.1 Hz, 1H), 7.80 (s, 1H), 7.42-7.27 (m, 3H), 6.62 (s, 1H), 3.80 (s, 3H), 3.55 (s, 3H), 3.43-3.37 (m, 2H), 2.13 (s, 3H), 2.00-1.92 (m, 2H), 1.11 (t, J = 7.4 Hz, 3H) | 470 |

Example 131: Ethanesulfonic acid [2-cyclopentyloxy-6-(1,5-dimethyl-6-oxo-1,6-dihydro-pyridin-3-yl)-pyrimidin-4-yl]-amide

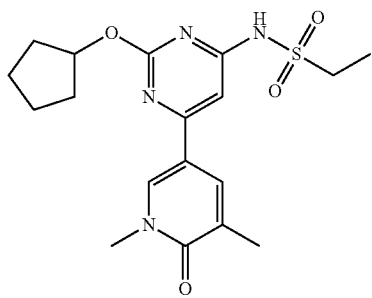 [SMILES: CCS(=O)(=O)Nc1cc(-c2cc(C)c(=O)n(C)c2)nc(OC2CCCC2)n1]

The title compound was prepared in a manner similar to Example 1 by substituting cyclopentanol for 2,5-dichlorophenol in Step 1 and ethanesulfonamide for propane-2-sulfonic acid amide in Step 3. $^1$H NMR (CDCl$_3$, 400 MHz) δ 8.22 (s, 1H), 7.74 (s, 1H), 6.88 (s, 1H), 5.43 (m, 1H), 3.66 (s, 3H), 3.40-3.38 (m, 2H), 2.23 (s, 3H), 2.05-1.66 (m, 8H), 1.45 (t, J=7.6 Hz, 3H). LCMS (M+H)$^+$ 393

Example 132: 5-[2-(2,4-Difluoro-phenoxy)-6-methanesulfonyl-pyrimidin-4-yl]-1,3-dimethyl-1H-pyridin-2-one Step 1: 5-(2-(2,4-difluorophenoxy)-6-(methylthio)pyrimidin-4-yl)-1,3-dimethylpyridin-2(1H)-one

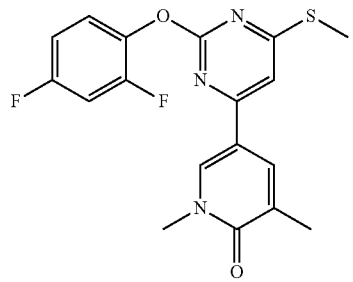 [SMILES: CSc1cc(-c2cc(C)c(=O)n(C)c2)nc(Oc2ccc(F)cc2F)n1]

Sodium thiomethoxide (42 mg, 0.60 mmol) was added to a solution of 5-(6-chloro-2-(2,4-difluorophenoxy)pyrimidin-4-yl)-1,3-dimethylpyridin-2(1H)-one (prepared in a manner similar to Example 1, steps 1 and 2, by substituting 2,4-difluorophenol for 2,5-dichlorophenol) (122 mg, 0.34 mmol) in anhydrous THF (20 mL) under nitrogen and stirred at rt overnight. The mixture was poured into saturated NH$_4$Cl solution (50 mL) and extracted with EtOAc (2×20 mL). The combined organic layers were washed with brine, dried over Na$_2$SO$_4$, filtered and concentrated under reduced pressure to give the product (115 mg, 0.31 mmol) as a yellow solid in 91% yield. $^1$H NMR (300 MHz, CDCl$_3$): δ 8.17 (d, J=1.8 Hz, 1H), 7.70 (s, 1H), 7.30-7.23 (m, 1H), 7.10 (s, 1H), 7.01-6.93 (m, 2H), 3.63 (s, 3H), 2.39 (s, 3H), 2.22 (s, 3H). LCMS (M+H)$^+$ 376

Step 2: 5-[2-(2,4-Difluoro-phenoxy)-6-methanesulfonyl-pyrimidin-4-yl]-1,3-dimethyl-1H-pyridin-2-one

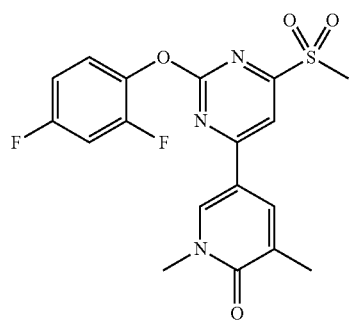 [SMILES: Cc1cc(-c2cc(S(C)(=O)=O)nc(Oc3ccc(F)cc3F)n2)cn(C)c1=O]

A solution of the title compound from Step 1 (115 mg, 0.31 mmol) and mCPBA (146 mg, 0.85 mmol) in DCM (12 mL) was stirred at rt for 18 hours. The reaction mixture was quenched with saturated NaHCO$_3$ solution (25 mL) and extracted with DCM (30 mL*). The combined organic layers were washed with saturated a Na$_2$S$_2$O$_3$ solution (2×25 mL), dried over Na$_2$SO$_4$, filtered and concentrated under vacuum. The residue was slurried in PE/EtOAc (2:1, 5 mL) and filtered. The cake was washed with Et$_2$O (2×3 mL) and dried to give the product (73 mg, 0.18 mmol) as a yellow solid in 58% yield. $^1$H NMR (DMSO-d$_6$, 400 MHz) δ 8.90 (d, J=2.4 Hz, 1H), 8.23 (s, 1H), 7.98 (s, 1H), 7.60-7.56 (m, 2H), 7.24 (m, 1H), 3.56 (s, 3H), 3.26 (s, 3H), 2.05 (s, 3H). LCMS (M+H)$^+$ 408.

Examples 133-135 (Table 11) were prepared using the appropriate phenol and thiol in a similar multi-step manner as Example 132.

TABLE 11

| Example | Structure | IUPAC Name | $^1$H NMR ppm (δ) | MS (M + H) |
|---|---|---|---|---|
| 133 | | 5-[2-(2-Chloro-6-methyl-phenoxy)-6-methanesulfonyl-pyrimidin-4-yl]-1,3-dimethyl-1H-pyridin-2-one | (DMSO-d$_6$, 400 MHz) 8.91 (d, J = 2.0 Hz, 1H), 8.22 (s, 1H), 7.97 (s, 1H), 7.48 (d, J = 8.0 Hz, 1H), 7.38 (d, J = 8.0 Hz, 1H), 7.29 (t, J = 7.8 Hz, 1H), 3.56 (s, 3H), 3.21 (s, 3H), 2.19 (s, 3H), 2.04 (s, 3H) | 420 |
| 134 | | 5-[2-(2,4-Difluoro-phenoxy)-6-(propane-2-sulfonyl)-pyrimidin-4-yl]-1,3-dimethyl-1H-pyridin-2-one | (CDCl$_3$, 400 MHz) 8.30 (d, J = 2.4 Hz, 1H), 7.88 (s, 1H), 7.84 (bs, 1H), 7.31-7.26 (m, 1H), 7.02-6.94 (m, 2H), 3.69-3.62 (m, 4H), 2.30 (s, 3H), 1.33 (d, J = 6.8 Hz, 6H) | 436 |
| 135 | | 5-[2-(2-Chloro-6-methyl-phenoxy)-6-(propane-2-sulfonyl)-pyrimidin-4-yl]-1,3-dimethyl-1H-pyridin-2-one | (CDCl$_3$, 400 MHz) 8.33 (s, 1H), 7.85 (s, 2H), 7.31 (d, J = 7.6 Hz, 1H), 7.22 (d, J = 7.2 Hz, 1H), 7.15 (t, J = 7.8 Hz, 1H), 3.66 (s, 3H), 3.61-3.55 (m, 1H), 2.26 (s, 3H), 2.23 (s, 3H), 1.28 (d, J = 6.8 Hz, 6H) | 448 |

Examples 136-154 (Table 12) were prepared in a similar multi-step a manner as Example 1.

TABLE 12

| Example | Structure | IUPAC Name | $^1$H NMR ppm (δ) | MS (M + H) |
|---|---|---|---|---|
| 136 | | 3-Fluoro-propane-1-sulfonic acid [2-(2-fluoro-6-methyl-phenoxy)-6-(1-methyl-6-oxo-1,6-dihydro-pyridin-3-yl)-pyrimidin-4-yl]-amide | (CD$_3$OD, 400 MHz) 8.55 (d, J = 2.4 Hz, 1H), 8.10 (dd, J = 9.6, 2.8 Hz, 1H), 7.19-7.07 (m, 3H), 6.85 (s, 1H), 6.62 (d, J = 9.6 Hz, 1H), 4.39 (dt, J = 47.2, 5.6 Hz, 2H), 3.66 (s, 3H), 3.19-3.15 (m, 2H), 2.22 (s, 3H), 2.02-1.92 (m, 2H) | 451 |
| 137 | 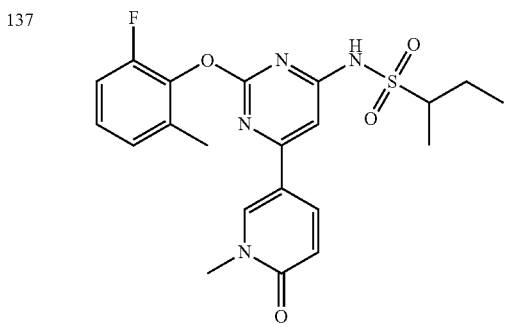 | Butane-2-sulfonic acid [2-(2-fluoro-6-methyl-phenoxy)-6-(1-methyl-6-oxo-1,6-dihydro-pyridin-3-yl)-pyrimidin-4-yl]-amide | (CD$_3$OD, 400 MHz) 8.54 (d, J = 2.8 Hz, 1H), 8.10 (dd, J = 9.6, 2.4 Hz, 1H), 7.20-7.04 (m, 3H), 6.81 (s, 1H), 6.62 (d, J = 9.6 Hz, 1H), 3.66 (s, 3H), 3.10-3.05 (m, 1H), 2.22 (s, 3H), 1.81-1.75 (m, 1H), 1.45-1.38 (m, 1H), 1.12 (d, J = 6.8 Hz, 3H), 0.87 (t, J = 7.6 Hz, 3H) | 447 |

TABLE 12-continued

| Example | Structure | IUPAC Name | ¹H NMR ppm (δ) | MS (M + H) |
|---|---|---|---|---|
| 138 | 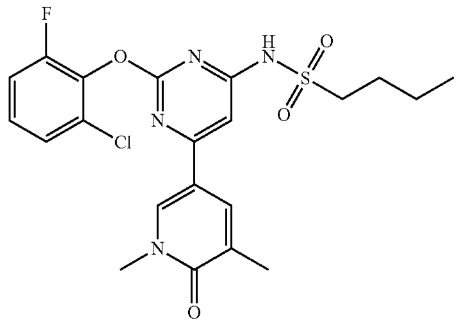 [SMILES: CCCCS(=O)(=O)Nc1cc(-c2cc(C)c(=O)n(C)c2)nc(Oc2c(F)cccc2Cl)n1] | Butane-1-sulfonic acid [2-(2-chloro-6-fluoro-phenoxy)-6-(1,5-dimethyl-6-oxo-1,6-dihydro-pyridin-3-yl)-pyrimidin-4-yl]-amide | (CDCl₃, 300 MHz) 8.25 (d, J = 2.1 Hz, 1H), 7.71 (s, 1H), 7.41 (br, 1H), 7.32-7.29 (m, 1H), 7.25-7.16 (m, 2H), 7.04 (s, 1H), 3.64 (s, 3H), 3.23-3.18 (m, 2H), 2.23 (s, 3H), 1.79-1.74 (m, 2H), 1.46-1.38 (m, 2H), 0.94 (t, J = 7.2 Hz, 3H) | 481 |
| 139 | 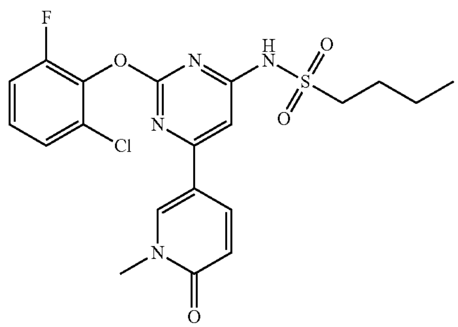 [SMILES: CCCCS(=O)(=O)Nc1cc(-c2ccc(=O)n(C)c2)nc(Oc2c(F)cccc2Cl)n1] | Butane-1-sulfonic acid [2-(2-chloro-6-fluoro-phenoxy)-6-(1-methyl-6-oxo-1,6-dihydro-pyridin-3-yl)-pyrimidin-4-yl]-amide | (CD₃OD, 400 MHz) 8.56 (d, J = 2.4 Hz, 1H), 8.09 (dd, J = 9.6 Hz, 2.4 Hz, 1H), 7.38-7.26 (m, 3H), 6.90 (s, 1H), 6.62 (d, J = 9.6 Hz, 1H), 3.66 (s, 3H), 3.12 (t, J = 8.0 Hz, 2H), 1.63-1.58 (m, 2H), 1.38-1.33 (m, 2H), 0.90 (t, J = 7.2 Hz, 3H) | 467 |
| 140 | 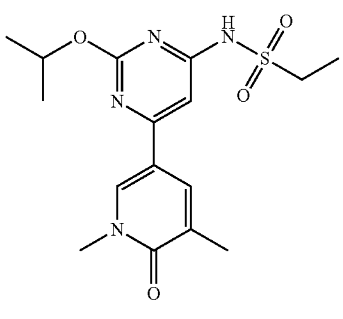 [SMILES: CCS(=O)(=O)Nc1cc(-c2cc(C)c(=O)n(C)c2)nc(OC(C)C)n1] | Ethanesulfonic acid [6-(1,5-dimethyl-6-oxo-1,6-dihydro-pyridin-3-yl)-2-isopropoxy-pyrimidin-4-yl]-amide | (CDCl₃, 300 MHz) 8.23 (d, J = 2.1 Hz, 1H), 7.74 (s, 1H), 6.88 (s, 1H), 5.33-5.29 (m, 1H), 3.67 (s, 3H), 3.43-3.36 (m, 2H), 2.24 (s, 3H), 1.48-1.39 (m, 9H) | 367 |
| 141 | 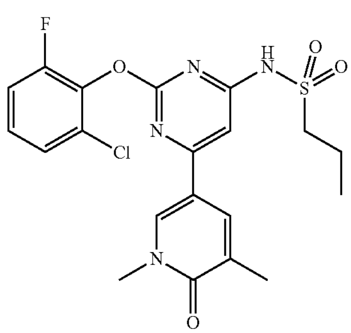 [SMILES: CCCS(=O)(=O)Nc1cc(-c2cc(C)c(=O)n(C)c2)nc(Oc2c(F)cccc2Cl)n1] | Propane-1-sulfonic acid [2-(2-chloro-6-fluoro-phenoxy)-6-(1,5-dimethyl-6-oxo-1,6-dihydro-pyridin-3-yl)-pyrimidin-4-yl]-amide | (CD₃OD, 300 MHz) 8.44 (d, J = 1.8 Hz, 1H), 7.93 (s, 1H), 7.41-7.28 (m, 3H), 6.88 (s, 1H), 3.67 (s, 3H), 3.12-3.07 (m, 2H), 2.19 (s, 3H), 1.71-1.63 (m, 2H), 0.97 (t, J = 7.2 Hz, 3H) | 467 |

TABLE 12-continued

| Example | Structure | IUPAC Name | ¹H NMR ppm (δ) | MS (M + H) |
|---|---|---|---|---|
| 142 | 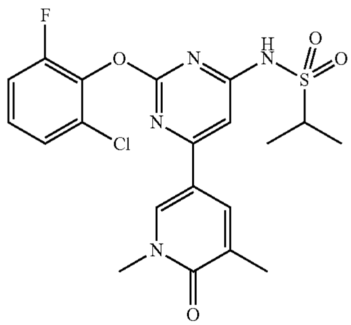 [SMILES: Cc1cc(-c2cc(NS(=O)(=O)C(C)C)nc(Oc3c(F)cccc3Cl)n2)cn(C)c1=O] | Propane-2-sulfonic acid [2-(2-chloro-6-fluoro-phenoxy)-6-(1,5-dimethyl-6-oxo-1,6-dihydro-pyridin-3-yl)-pyrimidin-4-yl]-amide | (CD₃OD, 300 MHz) 8.41 (d, J = 2.8 Hz, 1H), 7.96 (s, 1H), 7.39-7.36 (m, 1H), 7.32-7.26 (m, 2H), 6.89 (s, 1H), 3.65 (s, 3H), 3.39-3.36 (m, 1H), 2.18 (s, 3H), 1.20 (d, J = 6.8 Hz, 6H) | 467 |
| 143 | 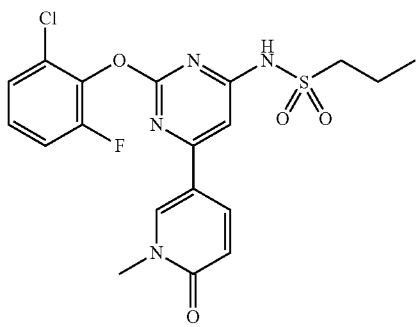 [SMILES: CCCS(=O)(=O)Nc1cc(-c2ccc(=O)n(C)c2)nc(Oc2c(F)cccc2Cl)n1] | Propane-1-sulfonic acid [2-(2-chloro-6-fluoro-phenoxy)-6-(1-methyl-6-oxo-1,6-dihydro-pyridin-3-yl)-pyrimidin-4-yl]-amdie | (CD₃OD, 400 MHz) 8.55 (d, J = 2.4 Hz, 1H), 8.09 (dd, J = 9.6 Hz, 2.4 Hz 1H), 7.39-7.27 (m, 3H), 6.89 (s, 1H), 6.62 (d, J = 9.6 Hz, 1H), 3.66 (s, 3H), 3.11-3.07 (m, 2H), 1.69-1.63 (m, 2H), 0.96 (t, J = 7.2 Hz, 3H) | 453 |
| 144 | 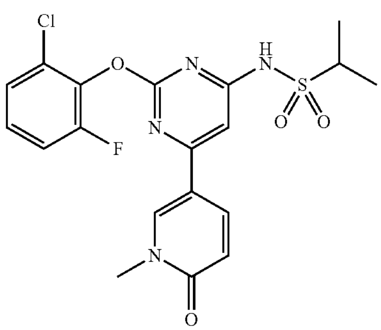 [SMILES: CC(C)S(=O)(=O)Nc1cc(-c2ccc(=O)n(C)c2)nc(Oc2c(F)cccc2Cl)n1] | Propane-2-sulfonic acid [2-(2-chloro-6-fluoro-phenoxy)-6-(1-methyl-6-oxo-1,6-dihydro-pyridin-3-yl)-pyrimidin-4-yl]-amide | (CDCl₃, 400 MHz) 8.33 (s, 1H), 7.81 (d, J = 9.6 Hz, 1H), 7.43-7.29 (m, 2H), 7.25-7.12 (m, 3H), 6.64 (d, J = 9.2 Hz, 1H), 3.62 (s, 3H), 3.44-3.41 (m, 1H), 1.39 (d, J = 6.8 Hz, 6H) | 453 |
| 145 | 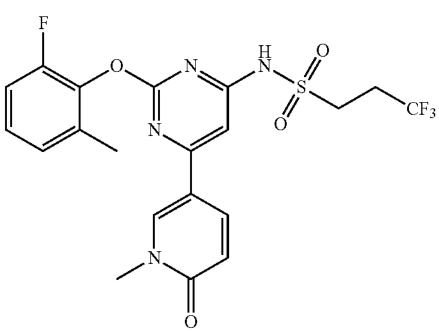 [SMILES: Cc1cccc(F)c1Oc1nc(NS(=O)(=O)CCC(F)(F)F)cc(-c2ccc(=O)n(C)c2)n1] | 3,3,3-Trifluoro-propane-1-sulfonic acid [2-(2-fluoro-6-methyl-phenoxy)-6-(1-methyl-6-oxo-1,6-dihydro-pyridin-3-yl)-pyrimidin-4-yl]-amide | (CDCl₃, 300 MHz) 8.45 (s, 1H), 7.82-7.79 (d, J = 6.9 Hz, 1H), 7.18-7.14 (m, 1H), 7.11-7.05 (m, 2H), 6.84 (s, 1H), 6.69 (d, J = 9.6 Hz, 1H), 3.66 (s, 3H), 3.35-3.30 (m, 2H), 2.57-2.45 (m, 2H), 2.27 (s, 3H) | 488 |

TABLE 12-continued

| Example | Structure | IUPAC Name | ¹H NMR ppm (δ) | MS (M + H) |
|---|---|---|---|---|
| 146 | 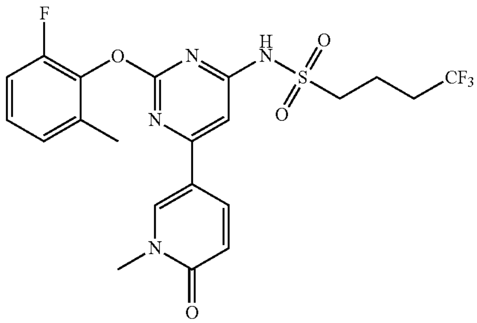 | 4,4,4-Trifluoro-butane-1-sulfonic acid [2-(2-fluoro-6-methyl-phenoxy)-6-(1-methyl-6-oxo-1,6-dihydro-pyridin-3-yl)-pyrimidin-4-yl]-amide | (CDCl₃, 300 MHz) 8.42 (s, 1H), 7.83 (d, J = 7.2 Hz, 1H), 7.18-7.14 (m, 1H), 7.10-7.04 (m, 2H), 6.88 (s, 1H), 6.68 (d, J = 9.6 Hz, 1H), 3.66 (s, 3H), 3.23-3.18 (t, J = 7.8 Hz, 2H), 2.21 (s, 3H), 2.20-2.02 (m, 2H), 2.01-2.00 (m, 2H) | 501 |
| 147 | 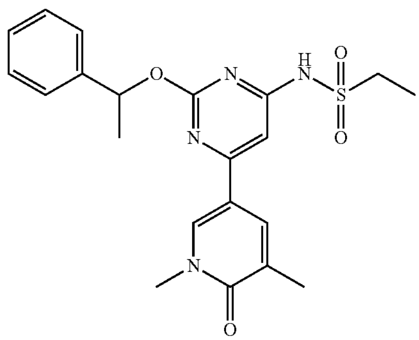 [SMILES: CCS(=O)(=O)Nc1cc(-c2cc(C)c(=O)n(C)c2)nc(OC(C)c2ccccc2)n1] | Ethanesulfonic acid [6-(1,5-dimethyl-6-oxo-1,6-dihydro-pyridin-3-yl)-2-(1-phenyl-ethoxy)-pyrimidin-4-yl]-amide | (CDCl₃, 400 MHz) 8.10 (d, J = 1.6 Hz, 1H), 7.66 (s, 1H), 7.43 (d, J = 7.2 Hz, 2H), 7.35 (t, J = 7.4 Hz, 2H), 7.29-7.26 (m, 1H), 6.83 (s, 1H), 6.05 (q, J = 6.7 Hz, 1H), 3.64 (s, 3H), 3.22 (q, J = 7.5 Hz, 2H), 2.21 (s, 3H), 1.71 (d, J = 6.8 Hz, 3H), 1.33 (t, J = 7.4 Hz, 3H) | 429 |
| 148 | 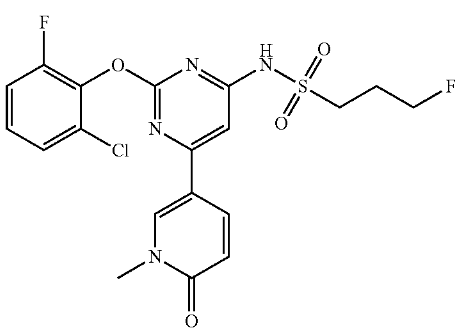 [SMILES: Cn1cc(-c2cc(NS(=O)(=O)CCCF)nc(Oc3c(F)cccc3Cl)n2)ccc1=O] | N-(2-(2-chloro-6-fluorophenoxy)-6-(1-methyl-6-oxo-1,6-dihydropyridin-3yl)pyrimidin-4-yl)-3-fluoropropane-1-sulfonamide | (DMSO-d₆, 400 MHz) 11.5 (s, 1H), 8.59 (d, J = 2.4 HZ, 1H), 7.88 (dd, J = 9.6 Hz, 2.8 Hz, 1H), 7.49-7.37 (m ,3H), 6.91 (s, 1H), 6.52 (d, J = 9.6 Hz, 1H), 4.48 (t, J = 6.0 Hz, 1H), 4.37 (t, J = 6.0 Hz, 1H), 3.55 (s, 3H), 3.23-3.19 (m, 2H), 1.95-1.85 (m, 2H) | 471 |
| 149 | 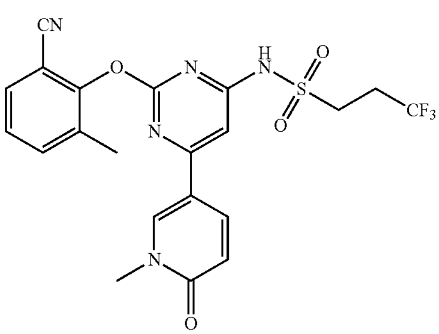 [SMILES: Cc1cccc(C#N)c1Oc1nc(NS(=O)(=O)CCC(F)(F)F)cc(-c2ccc(=O)n(C)c2)n1] | N-(2-(2-cyano-6-methylphenoxy)-6-(1-methyl-6-oxo-1,6-dihydropyridin-3-yl)pyrimidin-4-yl)-3,3,3-trifluoropropane-1-sulfonamide | (CD₃OD, 400 MHz) 8.61 (d, J = 2.4 Hz, 1H), 8.11 (dd, J = 9.6 Hz, 2.4 Hz, 1H), 7.65-7.62 (m, 2H), 7.39-7.35 (m, 1H), 6.88 (s, 1H), 6.62 (d, J = 9.2 Hz, 1H), 3.65 (s, 3H), 3.26-3.22 (m, 2H), 2.53-2.46 (m, 2H), 2.21 (s, 3H) | 494 |

TABLE 12-continued

| Example | Structure | IUPAC Name | ¹H NMR ppm (δ) | MS (M + H) |
|---|---|---|---|---|
| 150 | 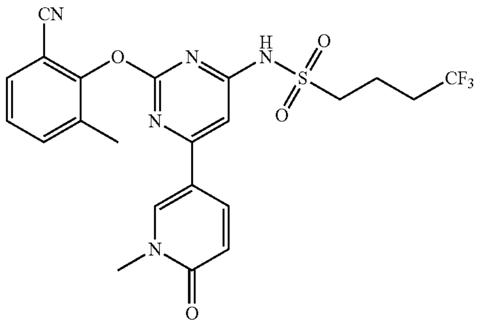 [SMILES: Cc1cccc(C#N)c1Oc1nc(NS(=O)(=O)CCCC(F)(F)F)cc(-c2ccc(=O)n(C)c2)n1] | N-(2-(2-cyano-6-methylphenoxy)-6-(1-methyl-6-oxo-1,6-dihdyropyridin-3-yl)pyrimidin-4-yl)-4,4,4-trifluorobutane-1-sulfonamide | (CD₃OD, 400 MHz) 8.57 (d, J = 2.8 Hz, 1H), 8.10 (dd, J = 9.6 Hz, 2.8 Hz, 1H), 7.67-7.65 (m, 2H), 7.39-7.35 (m, 1H), 6.91 (s, 1H), 6.62 (d, J = 9.2 Hz, 1H), 3.65 (s, 3H), 3.16 (t, J = 7.6 Hz, 2H), 2.25-2.18 (m, 5H), 1.89-1.83 (m, 2H) | 508 |
| 151 | 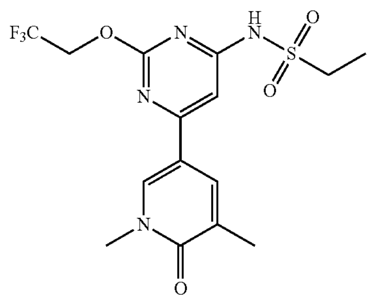 | N-(6-(1,5-dimehtyl-6-oxo-1,6-dihydropyridin-3-yl)-2-(2,2,2-trifluoroethoxy)pyrimidin-4-yl)ethanesulfonamide | (CD₃OD, 400 MHz) 8.46 (d, J = 2.4 Hz, 1H), 7.98 (s, 1H), 6.90 (s, 1H), 4.97-4.91 (m, 2H), 3.66 (s, 3H), 3.57-3.52 (m, 2H), 2.18 (s, 3H), 1.38-1.34 (t, J = 7.6 Hz, 3H) | 407 |
| 152 | | N-(6-(1,5-dimethyl-6-oxo-1,6-dihydropyridin-3-yl)-2-isobutoxypyrimidin-4-yl)propane-2-sulfonamide | (CDCl₃, 400 MHz) 8.21 (d, J = 2.0 Hz, 1H), 7.74 (s, 1H), 7.00 (s, 1H), 4.15 (d, J = 6.8 Hz, 2H), 3.67 (s, 3H), 3.53-5.50 (m, 1H), 2.23 (s, 3H), 2.18-2.11 (m, 1H), 1.47 (d, J = 6.8 Hz, 6H), 1.05 (d, J = 6.4 Hz, 6H) | 395 |

Example 153: Ethanesulfonic acid [4-(1,5-dimethyl-6-oxo-1,6-dihydro-pyridin-3-yl)-6-(2,6-dimethyl-phenoxy)-[1,3,5]triazin-2-yl]-amide Step 1: 2,4-Dichloro-6-(2,6-dimethyl-phenoxy)-[1,3,5]triazine

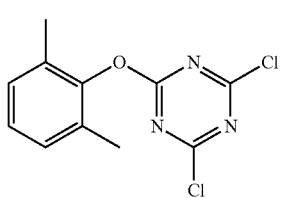 [SMILES: Cc1cccc(C)c1Oc1nc(Cl)nc(Cl)n1]

To a solution of 2,4,6-trichloro-[1,3,5]triazine (2.0 g, 11 mmol) and 2,6-dimethyl-phenol (1.3 g, 11 mmol) and tetra(n-butyl)ammonium hydrogen sulfate (36 mg, 0.11 mmol) in toluene (45 mL) was added slowly a solution of NaOH (435 mg, 11 mmol) in H₂O (4.0 mL) at 0° C. The mixture was allowed to stir at 0° C. for 2 h, and then warmed to RT overnight. Et₂O (50 mL) was added and the organics washed with water (80 mL), HCl (80 mL, 10%, w/w), brine (50 mL) and dried over Na₂SO₄. The organics were concentrated in vacuum and the residue was triturated in PE (15 mL). The solids were filtered and dried to give 2.0 g (67%) of the title compound as a white solid. ¹H NMR (300 MHz, CDCl₃) δ 7.16-7.11 (m, 3H), 2.15 (s, 6H). LCMS (M+H)⁺ 270.

Step 2: 5-[4-Chloro-6-(2,6-dimethyl-phenoxy)-[1,3,5]triazin-2-yl]-1,3-dimethyl-1H-pyridin-2-one

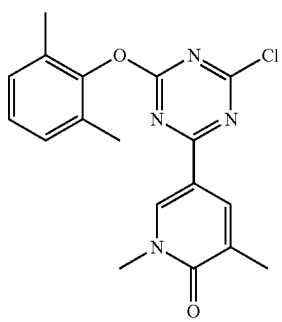 [SMILES: Cc1cccc(C)c1Oc1nc(Cl)nc(-c2cc(C)c(=O)n(C)c2)n1]

A mixture of 2,4-dichloro-6-(2,6-dimethyl-phenoxy)-[1,3,5]triazine (500 mg, 1.9 mmol), 1,3-dimethyl-5-(4,4,5,5-tetramethyl-[1,3,2]dioxaborolan-2-yl)-1H-pyridin-2-one (309 mg, 1.2 mmol), Pd(PPh₃)₄ (72 mg, 0.06 mmol) and Na₂CO₃ (2.0 mL, 2.0 mol/L) in dioxane (20 mL) was placed in a sealed tube, purged with N₂, sealed and heated to 75° C. for 2 h. The mixture was cooled to room temperature, poured into NH₄Cl solution (50 mL) and extracted with DCM (50 mL*2). The combined organic layer was washed with brine (50 mL), dried over Na₂SO₄ and concentrated in vacuum. The residue was purified by silica gel column chromatography (PE/EtOAc, 5:1) to give the title compound 225 mg (52%) as a white solid. $^1$H NMR (400 MHz, CDCl₃) δ 8.51 (d, J=2.4 Hz, 1H), 8.02 (s, 1H), 7.14-7.13 (m, 3H), 3.63 (s, 3H), 2.17 (s, 3H), 2.15 (s, 6H). LCMS (M+H)⁺ 357.

Step 3: Ethanesulfonic acid [4-(1,5-dimethyl-6-oxo-1,6-dihydro-pyridin-3-yl)-6-(2,6-dimethyl-phenoxy)-[1,3,5]triazin-2-yl]-amide

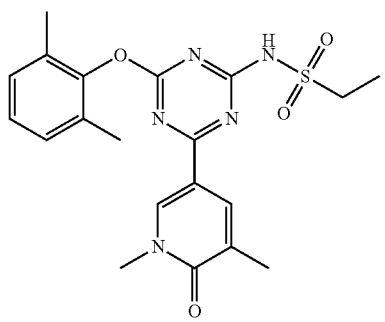 [SMILES: CCS(=O)(=O)Nc1nc(Oc2c(C)cccc2C)nc(-c2cc(C)c(=O)n(C)c2)n1]

A mixture of 5-[4-chloro-6-(2,6-dimethyl-phenoxy)-[1,3,5]triazin-2-yl]-1,3-dimethyl-1H-pyridin-2-one (50 mg, 0.14 mmol), ethanesulfonic acid amide (23 mg, 0.21 mmol), Pd₂(dba)₃ (6 mg, 0.007 mmol), XPhos (10 mg, 0.02 mmol) and Cs₂CO₃ (64 mg, 0.20 mmol) in dioxane (3 mL) was placed in a sealed tube, purged with N₂, sealed and heated to 95° C. for 6 h. The mixture was cooled to room temperature, poured into NH₄Cl solution (40 mL) and the solution was adjusted pH to 5 with HCl (2 mol/L). The solution was extracted with DCM (45 mL*2). The combined organic layers was washed with brine (50 mL), dried over Na₂SO₄ and concentrated in vacuum. The residue was slurried in MeOH (3 mL) for 5 min. The solids were filtered, washed with Et₂O (5 mL*3) and dried to give 23 mg (38%) of the title compound 0.05 mmol) as a white solid. $^1$H NMR (400 MHz, DMSO-d₆) δ 11.8 (s, 1H), 8.66 (d, J=2.4 Hz, 1H), 8.02 (s, 1H), 7.17-7.11 (m, 3H), 3.58 (s, 3H), 3.14-3.09 (m, 2H), 2.08 (s, 9H), 1.04 (t, J=7.2 Hz, 3H). LCMS (M+H)⁺ 430

Examples 154-155 (Table 13) were prepared using the appropriate sulfonamide in a similar multi-step manner as Example 153.

Example 156: N-(6-(1,5-dimethyl-6-oxo-1,6-dihydropyridin-3-yl)-2-phenylpyrimidin-4-yl)propane-1-sulfonamide Step 1: 5-(6-chloro-2-phenylpyrimidin-4-yl)-1,3-dimethylpyridin-2(1H)-one

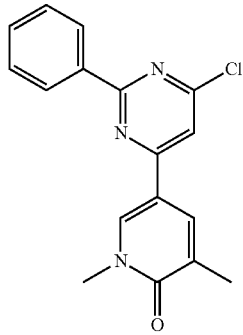 [SMILES: Cc1cc(-c2cc(Cl)nc(-c3ccccc3)n2)cn(C)c1=O]

A mixture of 1,3-dimethyl-5-(4,4,5,5-tetramethyl-1,3,2-dioxaborolan-2-yl)pyridin-2(1H)-one (249 mg, 1 mmol), 4,6-dichloro-2-phenylpyrimidine (171 mg, 1.0 mmol), Pd(PPh₃)₄ (116 mg, 0.1 mmol), aqueous sodium carbonate (2.0 M, 1 mL, 2 mmol) in dioxane (5 mL) was stirred and heated at 100° C. for 2 h. The reaction mixture was diluted with water and extracted with EtOAc (3×). The extracts were combined, washed with brine, dried (Na₂SO₄) and concentrated. The residue was purified by flash column chromatography (EA:Hex, 0-80%) to provide the 173 mg (67%) of the desired product as an off-white solid. $^1$H NMR (400 MHz, DMSO-d₆) δ ppm 2.13 (s, 3H) 3.61 (s, 3H) 7.51-7.66 (m, 4H) 8.01 (s, 1H) 8.29 (s, 1H) 8.49 (dd, J=7.83, 1.77 Hz, 2H) 8.87 (d, J=2.27 Hz, 1H). LCMS (M+H)⁺ 312.

TABLE 13

| Example | Structure | IUPAC Name | $^1$H NMR ppm (δ) | MS (M + H) |
|---|---|---|---|---|
| 154 | | Propane-1-sulfonic acid [4-(1,5-dimethyl-6-oxo-1,6-dihydro-pyridin-3-yl)-6-(2,6-dimethyl-phenoxy)-[1,3,5]triazin-2-yl]-amide | (CDCl₃, 300 MHz) 8.55 (d, J = 2.1 Hz, 1H), 8.12 (s, 1H), 7.13 (s, 3H), 3.65 (s, 3H), 3.18-3.12 (m, 2H), 2.21 (s, 3H), 2.14 (s, 6H), 1.76-1.69 (m, 2H), 0.94 (t, J = 7.2 Hz, 3H) | 444 |
| 155 | | Propane-2-sulfonic acid [4-(1,5-dimethyl-6-oxo-1,6-dihydro-pyridin-3-yl)-6-(2,6-dimethyl-phenoxy)-[1,3,5]triazin-2-yl]-amide | (CDCl₃, 300 MHz) 8.54 (d, J = 2.1 Hz, 1H), 8.12 (d, J = 2.4 Hz, 1H), 7.13 (s, 3H), 3.67 (s, 3H), 3.51-3.50 (m, 1H), 2.22 (s, 3H), 2.17 (s, 6H), 1.27 (d, J = 6.9 Hz, 6H) | 444 |

Step 2: N-(6-(1,5-dimethyl-6-oxo-1,6-dihydropyridin-3-yl)-2-phenylpyrimidin-4-yl) propane-1-sulfonamide

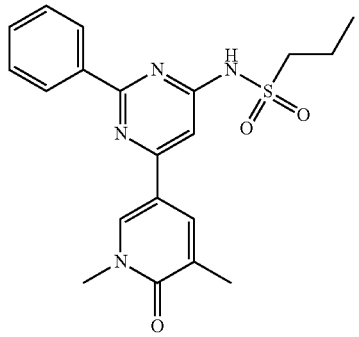 [SMILES: CCCS(=O)(=O)Nc1cc(-c2cc(C)c(=O)n(C)c2)nc(-c2ccccc2)n1]

A mixture of 5-(6-chloro-2-phenylpyrimidin-4-yl)-1,3-dimethylpyridin-2(1H)-one (51 mg, 0.2 mmol), propane-1-sulfonamide (37 mg, 0.3 mmol), Pd(dba)$_3$ (18 mg, 0.02 mmol), Xphos (9 mg, 0.2 mmol), CsCO$_3$ (130 mg, 0.4 mmol) in dioxane (3 mL) was stirred and heated at 90° C. for 16 hr. The reaction mixture was diluted with water and extracted with EtOAc (3×). The extracts were combined, washed with brine, dried (Na$_2$SO$_4$) and concentrated. The residue was purified by flash column chromatography (EA:Hex, 0-100%) to provide the 16 mg (23%) of the desired product as an off-white solid. $^1$H NMR (400 MHz, DMSO-d$_6$) δ ppm 0.99 (t, J=7.45 Hz, 3H) 1.78 (sxt, J=7.38 Hz, 2H) 2.14 (s, 3H) 3.32 (s, 3H) 3.62 (s, 3H) 3.63-3.69 (m, 2H) 7.06 (s, 1H) 7.51-7.59 (m, 3H) 7.99 (s, 1H) 8.41-8.52 (m, 2H) 8.64 (d, J=2.27 Hz, 1H) 11.26 (br. s., 1H).

Example 157: Butane-1-sulfonic acid [2-(2-chloro-6-methyl-phenoxy)-6-(5-methyl-6-oxo-1,6-dihydropyridin-3-yl)-pyrimidin-4-yl]-amide

Step 1: 4,6-Dichloro-2-(2-chloro-6-methyl-phenoxy)-pyrimidine

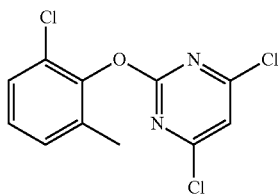 [SMILES: Cc1cccc(Cl)c1Oc1nc(Cl)cc(Cl)n1]

To a mixture of 2-chloro-6-methyl-phenol (3.0 g, 21 mmol) in dry THF (50 mL) was added NaH (0.84 g, 21 mmol) at −50° C. under N$_2$. The reaction contents were stirred at −50° C. over 30 min. 4,6-Dichloro-2-methanesulfonyl-pyrimidine (4.8 g, 21 mmol) was added. The reaction mixture was stirred at −50° C. over 30 hr. It was quenched with water (50 mL) and concentrated. The residue was treated with DCM (50 mL) and washed with brine (20 mL). The organic phase was dried over Na$_2$SO$_4$, filtered and concentrated under reduced pressure. The residue was purified by column chromatography on silica gel PE/E EtOAc (50:1) to give the title compound (3.2 g, 11 mmol) as a white solid in 52% yield. $^1$H NMR (300 MHz, CDCl$_3$) δ 7.33 (dd, J=7.2 Hz, 2.4 Hz, 1H), 7.18 (m, 3H), 2.23 (s, 3H). LCMS (M+H)$^+$ 289.

Step 2: 4-Chloro-2-(2-chloro-6-methyl-phenoxy)-6-(6-methoxy-5-methyl-pyridin-3-yl)-pyrimidine A mixture of 4,6-dichloro-2-(2-chloro-6-methyl-phenoxy)-pyrimidine (1.0 g, 3.4 mmol), 2-methoxy-3-methyl-5-boronic acid pyridine (580 mg, 3.4 mmol) and Pd(dppf)Cl$_2$ (250 mg, 0.34 mmol) in dioxane (10 mL) and K$_3$PO$_4$ solution (2.3 mL, 8.6 mmol, 3.75 mol/L) was placed in a seal tube. The mixture was degassed by bubbling N$_2$ for 3 min. The tube was sealed and heated to 75° C. for 2 hr. After cooling to room temperature, the reaction mixture was filtered through a short plug of celite. The filtrate was washed with brine, dried over Na$_2$SO$_4$, filtered and concentrated under vacuum. The resulting residue was purified by silica gel column chromatography PE/EA (1:1) to give the title (325 mg, 0.86 mmol) as a white solid in 62% yield. LCMS (M+H)$^+$ 376.

Step 3: Butane-1-sulfonic acid [2-(2-chloro-6-methyl-phenoxy)-6-(6-methoxy-5-methyl-pyridin-3-yl)-pyrimidin-4-yl]-amide

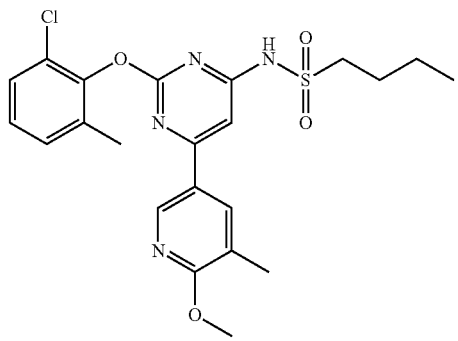 [SMILES: CCCCS(=O)(=O)Nc1cc(-c2cnc(OC)c(C)c2)nc(Oc2c(C)cccc2Cl)n1]

A suspension of 4-chloro-2-(2-chloro-6-methyl-phenoxy)-6-(6-methoxy-5-methyl-pyridin-3-yl)-pyrimidine (200 mg, 0.53 mmol), butane-1-sulfonamide (183 mg, 1.3 mmol), $Pd_2(dba)_3$ (24 mg, 0.026 mmol), X-Phos (38 mg, 0.079 mmol) and $Cs_2CO_3$ (225 mg, 0.69 mmol) in dioxane (5 mL) was degassed by bubbling nitrogen through for about 5 min. The capped vial was stirred at 90° C. for 3 hours. After cooling to room temperature, the reaction mixture was filtered through a short plug of celite. The celite plug was washed with EtOAc (10 mL) and water (10 mL). After the two layers separated, the aqueous one was extracted with EtOAc (20 mL). The combined organic layers were washed with brine, dried over $Na_2SO_4$, filtered and concentrated under reduced pressure to give the title compound (230 mg, crude) that was used in the following step without further purification. LCMS (M+H)+ 477.

Step 4: Butane-1-sulfonic acid [2-(2-chloro-6-methyl-phenoxy)-6-(5-methyl-6-oxo-1,6-dihydro-pyridin-3-yl)-pyrimidin-4-yl]-amide

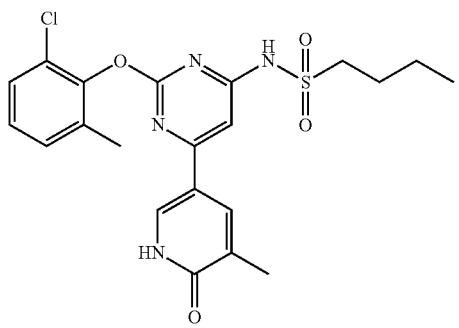 [SMILES: CCCCS(=O)(=O)Nc1cc(-c2c[nH]c(=O)c(C)c2)nc(Oc2c(C)cccc2Cl)n1]

A mixture of butane-1-sulfonic acid [2-(2-chloro-6-methyl-phenoxy)-6-(6-methoxy-5-methyl-pyridin-3-yl)-pyrimidin-4-yl]-amide (220 mg, crude) in aq. HBr (40%, 10 mL) was heated at 80° C. for 4 hr. After cooling to room temp, the mixture was extracted with DCM (10 mL*2). The pH of the aqueous layer was adjusted to 6 with aq. $NaHCO_3$ followed by extraction with DCM (20 mL*2). The combined organic layers were washed with brine (20 mL), dried over $Na_2SO_4$, filtered and concentrated under vacuum to give the title compound as an off-white solid in 28% yield. $^1$H NMR (400 MHz, $CD_3OD$) δ 8.14 (s, 1H), 8.02 (s, 1H), 7.33 (d, J=7.6 Hz, 1H), 7.26 (d, J=7.2 Hz, 1H), 7.19-7.15 (m, 1H), 6.81 (s, 1H), 3.03-2.99 (m, 2H), 2.21 (s, 3H), 2.17 (s, 3H), 1.57-1.53 (m, 2H), 1.34-1.28 (m, 2H), 0.88 (t, J=7.2 Hz, 3H). LCMS (M+H)+ 463.

Example 158: Propane-2-sulfonic acid [2-(2-chloro-6-methyl-phenoxy)-6-(5-methyl-6-oxo-1,6-dihydro-pyridin-3-yl)-pyrimidin-4-yl]-amide

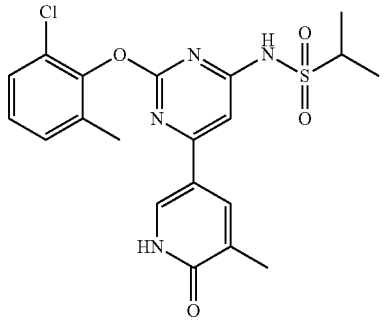 [SMILES: Cc1cccc(Cl)c1Oc1nc(NS(=O)(=O)C(C)C)cc(-c2c[nH]c(=O)c(C)c2)n1]

The title compound was prepared in a manner similar to Example 157 by substituting propane-2-sulfonamide for butane-1-sulfonamide in step 3. $^1$H NMR ($CD_3OD$, 400 MHz) δ 8.15 (s, 1H), 8.03 (s, 1H), 7.34 (dd, J=8.0, 0.8 Hz, 1H), 7.26 (d, J=6.8 Hz, 1H), 7.20-7.16 (m, 1H), 6.84 (s, 1H), 3.26-3.23 (m, 1H), 2.21 (s, 3H), 2.17 (s, 3H), 1.14 (d, J=6.4 Hz, 6H). LCMS (M+H)+ 449.

Examples 159-165 (Table 14) were prepared from 4,6-dichloro-2-methanesulfonyl-5-methyl-pyrimidine (synthesis shown below) and the appropriate sulfonamides and pyridin-2-ones in a similar multi-step manner as Example 1.

4,6-dichloro-2-methanesulfonyl-5-methyl-pyrimidine

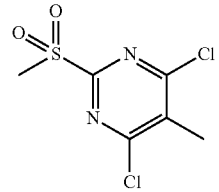

To a mixture of 4,6-dichloro-2-methylsulfanyl-pyrimidine (3.5 g, 17 mmol) in DCM (25 mL) was added mCPBA (9.0 g, 50 mmol) slowly at 0° C. The resulting mixture was stirred at room temperature for two hours. The mixture was quenched with water (5 mL) and extracted with DCM (20 mL×3). The combined organic layers were washed with saturated $NaHCO_3$ solution (10 mL×3), dried over $Na_2SO_4$, filtered and concentrated under reduced pressure to give the crude product. The residue was purified by silica gel column chromatography (PE/EtOAc=3/1) to afford the title compound (3.3 g, 14 mmol) as a white solid in 80% yield. $^1$H NMR (400 MHz, $CDCl_3$): δ 3.36 (s, 3H), 2.59 (s, 3H).

TABLE 14

| Example | Structure | IUPAC Name | ¹H NMR ppm (δ) | MS (M + H) |
|---|---|---|---|---|
| 159 | | Ethane-2-sulfonic acid [6-(1,5-dimethyl-6-oxo-1,6-dihydro-pyridin-3-yl)-2-(2-fluoro-6-methyl-phenoxy)-5-methyl-pyrimidin-4-yl]-amide | (CD$_3$OD, 400 MHz) δ 7.91 (d, J = 2.4 Hz, 1H), 7.68 (d, J = 1.2 Hz, 1H), 7.19-7.07 (m, 3H), 3.65 (s, 3H), 2.92-2.87 (m, 2H), 2.22 (s, 3H), 2.20 (s, 3H), 2.18 (s, 3H), 1.06 (t, J = 7.2 Hz, 3H) | 447 |
| 160 | | Ethanesulfonic acid [6-(1,5-dimethyl-6-oxo-1,6-dihydro-pyridin-3-yl)-2-(2,6-dimethyl-phenoxy)-5-methyl-pyrimidin-4-yl]-amide | (CDCl$_3$, 400 MHz) δ 7.72 (s, 1H), 7.47 (s, 1H), 7.12-7.07 (m 3H), 3.64 (s 3H), 2.83-2.81 (m, 2H), 2.22 (s, 3H), 2.20 (s, 3H), 2.165 (s, 6H), 1.11 (t, J = 7.6 Hz, 3H) | 443 |
| 161 | | Propane-1-sulfonic acid [6-(1,5-dimethyl-6-oxo-1,6-dihydro-pyridin-3-yl)-2-(2-fluoro-6-methyl-phenoxy)-5-methyl-pyrimidin-4-yl]-amide | (CD$_3$OD, 400 MHz) δ 7.90 (d, J = 2.8 Hz, 1H), 7.66 (d, J = 1.2 Hz, 1H), 7.19-7.07 (m, 3H), 3.65 (s, 3H), 2.86-2.82 (m, 2H), 2.22 (s, 3H), 2.18 (s, 6H), 1.58-1.52 (m, 2H), 0.95 (q, J = 7.6 Hz, 3H) | 461 |
| 162 | | Propane-2-sulfonic acid [6-(1,5-dimethyl-6-oxo-1,6-dihydro-pyridin-3-yl)-2-(2-fluoro-6-methyl-phenoxy)-5-methyl-pyrimidin-4-yl]-amide | (CD$_3$OD, 400 MHz) δ 7.74 (d, J = 2.8 Hz, 1H), 7.60 (d, J = 1.2 Hz, 1H), 7.13-6.98 (m, 3H), 3.64 (s, 3H), 3.09-3.02 (m, 1H), 2.22 (s, 3H), 2.18 (s, 3H), 2.07 (s, 3H), 0.96 (d, J = 6.8 Hz, 6H) | 461 |
| 163 | | Propane-2-sulfonic acid [6-(1,5-dimethyl-6-oxo-1,6-dihydro-pyridin-3-yl)-2-(2,6-dimethyl-phenoxy)-5-methyl-pyrimidin-4-yl]-amide | (CDCl$_3$, 400 MHz) δ 7.73 (s, 1H), 7.48 (s, 1H), 7.12-7.08 (m, 3H), 3.64 (s, 3H), 2.96-2.80 (m, 1H), 2.22 (s, 3H), 2.20 (s, 3H), 2.165 (s, 6H), 1.08 (d, J = 6.8 Hz, 3H) | 457 |
| 164 | | Propane-1-sulfonic acid [6-(1,5-dimethyl-6-oxo-1,6-dihydro-pyridin-3-yl)-2-(2,6-dimethyl-phenoxy)-5-methyl-pyrimidin-4-yl]-amide | (CDCl$_3$, 400 MHz) δ 7.72 (s, 1H), 7.47 (s, 1H), 7.12-7.06 (m, 3H), 3.65 (s, 3H), 2.81-2.77 (m, 2H), 2.22 (s, 3H), 2.18 (s, 3H), 2.18 (s, 6H), 0.84 (t, J = 7.2 Hz, 3H) | 457 |
| 165 | | Propane-2-sulfonic acid [2-(2,4-difluoro-phenoxy)-6-(1,5-dimethyl-6-oxo-1,6-dihydro-pyridin-3-yl)-5-methyl-pyrimidin-4-yl]-amide | (CDCl$_3$, 400 MHz) δ 7.66 (s, 1H), 7.43 (s, 1H), 7.31-7.29 (m, 1H), 6.99-6.94 (m, 2H), 3.62 (s, 3H), 3.49 (m, 1H), 2.21 (s, 3H), 2.20 (s, 3H), 1.27 (d, J = 8.0 Hz, 6H) | 465 |

Examples 166-170 (Table 15) were prepared from the appropriate phenols, pyridin-2-ones and halogenated alkyl sulfonamides in a similar multi-step manner as Example 1. The 1-fluoro-propane-1-sulfonic acid amide and the 1,1-difluoro-propane-1-sulfonic acid amide were prepared as shown below.

1-Fluoro-propane-1-sulfonic acid amide

Step 1: Propane-1-sulfonic acid bis-(2,4-dimethoxy-benzyl)-amide

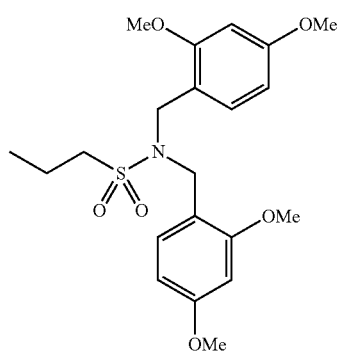 [SMILES: CCCS(=O)(=O)N(Cc1ccc(OC)cc1OC)Cc1ccc(OC)cc1OC]

To a cooled solution of 1-propanesulfonyl chloride (7.4 g, 51.7 mmol) in THF (60 mL) was added a solution of bis-(2,4-dimethoxy-benzyl)-amine (15 g, 47.3 mmol) and triethylamine (5.7 g, 56.4 mmol) in THF (120 mL) over 1 hr. The reaction mixture was removed from the ice bath, stirred overnight and filtered. The solids were washed with EtOAc (40 mL×3) and the filtrates concentrated to dryness. The residue was purified by silica gel column chromatography (PE:EtOAc, 4:1) to give the title compound (12 g, 28.3 mmol) as a white solid in 60% yield. $^1$H NMR (300 MHz, CDCl$_3$): δ 7.22 (d, J=8.1 Hz, 2H), 6.48-6.43 (m, 4H), 4.38 (s, 4H), 3.82 (s, 6H), 3.77 (s, 6H), 2.84-2.79 (m, 2H), 1.79-1.71 (m, 2H), 0.94 (t, J=7.4 Hz, 3H)

Step 2: 1-Fluoro-propane-1-sulfonic acid bis-(2,4-dimethoxy-benzyl)-amide

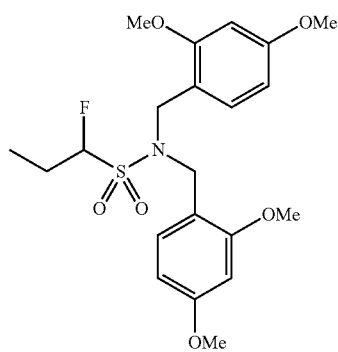 [SMILES: CCC(F)S(=O)(=O)N(Cc1ccc(OC)cc1OC)Cc1ccc(OC)cc1OC]

To a solution of propane-1-sulfonic acid bis-(2,4-dimethoxy-benzyl)-amide (8.0 g, 18.9 mmol) in THF (500 mL) was added n-BuLi (21.5 mL, 53.7 mmol, 2.5 mol/L) at −65° C. under N$_2$. The mixture was stirred at −65° C. for 40 min and a solution of NFSi (15 g, 47.6 mmol) in THF (100 mL) was added dropwise. The mixture was stirred for an additional 2 hr at the same temperature. The reaction mixture was quenched with NH$_4$Cl solution and extracted with EtOAc (500 mL×2). The combined organic layers were washed with brine (600 mL), dried over Na$_2$SO$_4$, filtered and concentrated under reduced pressure. The residue was purified by silica gel column chromatography (PE/DCM, 5:1) to give the title compound (3.9 g, 8.8 mmol) as a colorless oil in 46% yield. $^1$H NMR (300 MHz, CDCl$_3$): δ 7.22 (d, J=8.1 Hz, 2H), 6.48-6.39 (m, 4H), 4.78 (ddd, J=48.3 Hz, 8.7 Hz, 3.9 Hz, 1H), 4.54 (d, J=15.6 Hz, 2H), 4.33 (d, J=15.6 Hz, 2H), 3.81 (s, 6H), 3.75 (s, 6H), 2.11-1.98 (m, 2H), 1.08 (t, J=7.5 Hz, 3H).

Step 3: 1-Fluoro-propane-1-sulfonic acid amide

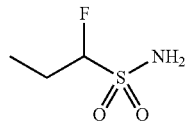

TFA (10 mL) was added to a solution of 1-fluoro-propane-1-sulfonic acid bis-(2,4-dimethoxy-benzyl)-amide (500 mg, 1.1 mmol) in DCM (25 mL) at room temp. The reaction mixture was stirred for 2 hr. The mixture was concentrated and the residue was treated with ether (5 mL), stirred for 5 min and filtered. The filtrate was concentrated to give the crude product as a pinky oil which was used in the next step without further purification. $^1$H NMR (300 MHz, CDCl$_3$): δ 5.10 (ddd, J=48.0 Hz, 9.0 Hz, 3.6 Hz, 1H), 4.78 (br, 2H), 2.14-2.02 (m, 2H), 1.18 (t, J=7.5 Hz, 3H).

1,1-Difluoro-propane-1-sulfonic acid amide

Step 1: 1,1-Difluoro-propane-1-sulfonic acid bis-(2,4-dimethoxy-benzyl)-amide

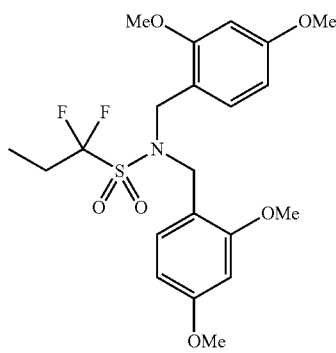 [SMILES: CCC(F)(F)S(=O)(=O)N(Cc1ccc(OC)cc1OC)Cc1ccc(OC)cc1OC]

To a solution of 1-fluoro-propane-1-sulfonic acid bis-(2,4-dimethoxy-benzyl)-amide (1.0 g, 2.27 mmol) in THF (100 mL) was added n-BuLi (2.1 mL, 5.3 mmol, 2.5 mol/L) at −65° C. under N$_2$. The mixture was stirred at −65° C. for 20 min. A solution of NFSi (1.4 g, 4.44 mmol) in THF (20 mL) was added dropwise. The reaction mixture was stirred for another 3 hours at the same temperature. It was then quenched with NH₄Cl solution and extracted with EtOAc (100 mL*2). The combined organic layers were washed with brine (60 mL), dried over Na₂SO₄, filtered and concentrated under reduced pressure. The residue was purified by silica gel column chromatography (PE/DCM, 50:1) to give the crude product which was purified by preparative TLC (PE/DCM 1:1) to afford the title compound (450 mg, 0.98 mmol) as a colorless oil in 43% yield. ¹H NMR (400 MHz, CDCl₃): δ 7.16 (d, J=8.4 Hz, 2H), 6.38 (dd, J=8.4 Hz, 2.4 Hz, 2H), 6.28 (d, J=2.0 Hz, 2H), 4.48 (s, 4H), 3.77 (s, 6H), 3.63 (s, 6H), 2.36-2.25 (m, 2H), 1.16 (t, J=7.5 Hz, 3H).

Step 2: 1,1-Difluoro-propane-1-sulfonic acid amide

TFA (3 mL) was added to a solution of 1,1-difluoro-propane-1-sulfonic acid bis-(2,4-dimethoxy-benzyl)-amide (150 mg, 0.33 mmol) in DCM (15 mL) at room temperature. The reaction mixture was stirred for 2 hr and concentrated under reduced pressure. The residue was treated with ether (5 mL), stirred for 5 min and filtered. The filtrate was concentrated to afford the crude product as a pinky oil which was used in the next step without further purification.

TABLE 15

| Example | Structure | IUPAC Name | ¹H NMR ppm (δ) | MS (M + H) |
|---|---|---|---|---|
| 166 | | 1,1-Difluoro-propane-1-sulfonic acid [2-(2-fluoro-6-methyl-phenoxy)-6-(1-methyl-6-oxo-1,6-dihydro-pyridin-3-yl)-pyrimidin-4-yl]-amide | (CD₃OD, 400 MHz) 8.27 (s, 1H), 7.97 (dd, J = 9.2 Hz, 2.8 Hz, 1H), 7.22 (s, 1H), 7.12-6.99 (m, 3H), 6.57 (d, J = 9.2 Hz, 1H), 3.59 (s, 3H), 2.28-217 (m, 5H), 1.06 (t, J = 7.2 Hz, 3H) | 469 |
| 167 | | 1,1-Difluoro-propane-1-sulfonic acid [6-(1,5-dimethyl-6-oxo-1,6-dihydro-pyridin-3-yl)-2-(2-fluoro-6-methyl-phenoxy)-pyrimidin-4-yl]-amide | (CD₃OD, 400 MHz) 8.27 (d, J = 2.0 Hz, 1H), 7.86 (s, 1H), 7.31 (s, 1H), 7.20-7.14 (m, 1H), 7.11-7.04 (m, 2H), 3.62 (s, 3H), 2.32-217 (m, 5H), 2.15 (s, 3H), 1.11 (t, J = 7.2 Hz, 3H) | 483 |
| 168 | | 1-Fluoro-propane-1-sulfonic acid [2-(2-fluoro-6-methyl-phenoxy)-6-(1-methyl-6-oxo-1,6-dihydro-pyridin-3-yl)-pyrimidin-4-yl]-amide | (CD₃OD, 400 MHz) 8.44 (d, J = 2.4 HZ, 1H), 8.09 (dd, J = 9.2 Hz, 2.4 Hz, 1H), 7.16-7.03 (m, 3H), 6.68 (s, 1H), 6.61 (d, J = 9.2 Hz, 1H), 4.95 (ddd, J = 48.8 Hz, 8.8 Hz, 3.6 Hz, 1H), 3.65 (s, 3H), 2.23 (s, 3H), 1.83-1.75 (m, 2H), 0.92 (t, J = 7.6 Hz, 3H) | 451 |
| 169 | | 1-Fluoro-propane-1-sulfonic acid [6-(1,5-dimethyl-6-oxo-1,6-dihydro-pyridin-3-yl)-2-(2-fluoro-6-methyl-phenoxy)-pyrimidin-4-yl]-amide | (CD₃OD, 400 MHz) 8.43 (d, J = 2.0 HZ, 1H), 7.98 (s, 1H), 7.21-7.07 (m, 3H), 6.89 (s, 1H), 5.01 (ddd, J = 48.4 Hz, 8.8 Hz, 4.4 Hz, 1H), 3.66 (s, 3H), 2.22 (s, 3H), 2.18 (s, 3H), 1.89-1.79 (m, 2H), 0.98 (t, J = 7.6 Hz, 3H) | 465 |
| 170 | | 1,1-Difluoro-propane-1-sulfonic acid [2-(2-chloro-6-methyl-phenoxy)-6-(1-methyl-6-oxo-1,6-dihydro-pyridin-3-yl)-pyrimidin-4-yl]-amide | (CD₃OD, 400 MHz) 8.29 (d, J = 2.4 Hz, 1H), 7.97 (dd, J = 9.2 Hz, 2.4 Hz, 1H), 7.29 (d, J = 8.0 Hz, 1H), 7.22-7.20 (m, 2H), 7.12 (t, J = 8.0 Hz, 1H), 6.57 (d, J = 10.0 Hz, 1H), 3.60 (s, 3H), 2.26-2.15 (m, 5H), 1.06 (t, J = 7.6 Hz, 3H) | 485 |

Examples 171-182 (Table 16) were prepared from the appropriate phenols, pyridin-2-ones and sulfonamides in a similar multi-step manner as Example 153.

TABLE 16

| Example | Structure | IUPAC Name | $^1$H NMR ppm ($\delta$) | MS (M + H) |
|---|---|---|---|---|
| 171 | | Ethanesulfonic acid [4-(1,5-dimethyl-6-oxo-1,6-dihydro-pyridin-3-yl)-6-(2-fluoro-6-methyl-phenoxy)-[1,3,5]triazin-2-yl]-amide | (DMSO-d$_6$, 400 MHz) $\delta$ 11.97 (br, 1H), 8.64 (d, J = 2.0 Hz, 1H), 7.99 (s, 1H), 7.27-7.18 (m, 3H), 3.57 (s, 3H), 3.29-3.24 (m, 2H), 2.19 (s, 3H), 2.07 (s, 3H), 1.11 (q, J = 7.2 Hz, 3H) | 434 |
| 172 | | Propane-2-sulfonic acid [4-(1,5-dimethyl-6-oxo-1,6-dihydro-pyridin-3-yl)-6-(2-fluoro-6-methyl-phenoxy)-[1,3,5]triazin-2-yl]-amide | (DMSO-d$_6$, 400 MHz) $\delta$ 11.89 (br, 1H), 8.65 (d, J = 1.6 Hz, 1H), 8.01 (d, J = 1.2 Hz, 1H), 7.27-7.18 (m, 3H), 3.57 (s, 3H), 3.49-3.43 (m, 1H), 2.18 (s, 3H), 2.07 (s, 3H), 1.13 (d, J = 7.2 Hz, 6H) | 448 |
| 173 | 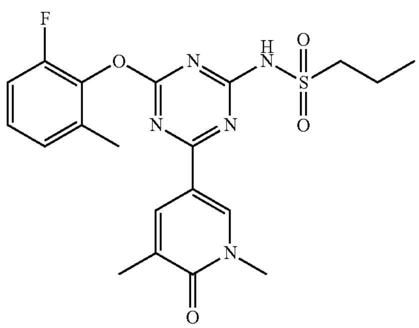 [SMILES: CCCS(=O)(=O)Nc1nc(Oc2c(C)cccc2F)nc(-c2cc(C)c(=O)n(C)c2)n1] | Propane-1-sulfonic acid [4-(1,5-dimethyl-6-oxo-1,6-dihydro-pyridin-3-yl)-6-(2-fluoro-6-methyl-phenoxy)-[1,3,5]triazin-2-yl]-amide | (DMSO-d$_6$, 400 MHz) $\delta$ 11.99 (br, 1H), 8.66 (d, J = 2.4 Hz, 1H), 8.02 (s, 1H), 7.27-7.18 (m, 3H), 3.58 (s, 3H), 3.17-3.13 (m, 2H), 2.19 (s, 3H), 2.08 (s, 3H), 1.58-1.52 (m, 2H), 0.87 (q, J = 7.6 Hz, 3H) | 448 |
| 174 | 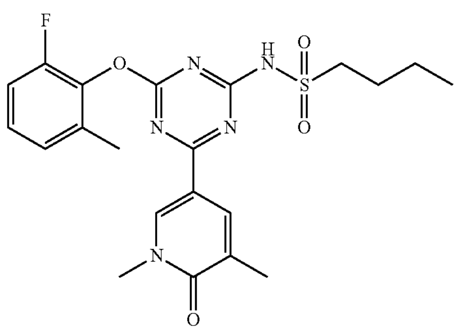 [SMILES: CCCCS(=O)(=O)Nc1nc(Oc2c(C)cccc2F)nc(-c2cc(C)c(=O)n(C)c2)n1] | Butane-1-sulfonic acid [4-(1,5-dimethyl-6-oxo-1,6-dihydro-pyridin-3-yl)-6-(2-fluoro-6-methyl-phenoxy)-[1,3,5]triazin-2-]-amide | (CD$_3$OD, 400 MHz) $\delta$ 8.70 (d, J = 2.0 Hz, 1H), 8.21 (s, 1H), 7.24-7.07 (m, 3H), 3.66 (s, 3H), 3.31-3.24 (m, 2H), 2.23 (s, 3H), 2.16 (s, 3H), 1.68-1.61 (m, 2H), 1.39-1.33 (m, 2H), 0.91-0.86 (m, 3H) | 462 |
| 175 | 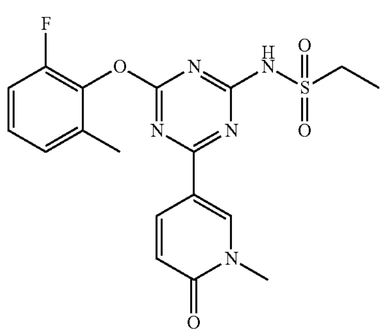 [SMILES: CCS(=O)(=O)Nc1nc(Oc2c(C)cccc2F)nc(-c2ccc(=O)n(C)c2)n1] | Ethanesulfonic acid [4-(2-fluoro-6-methyl-phenxoy)-6-(1-methyl-6-oxo-1,6-dihydro-pyridin-3-yl)-[1,3,5]triazin-2-yl]-amide | (CD$_3$OD, 400 MHz) $\delta$ 8.80 (d, J = 2.4 Hz, 1H), 8.32 (dd, J = 9.2 Hz, 2.0 Hz, 1H), 7.24-7.07 (m, 3H), 6.58 (d, J = 9.2 Hz, 1H), 3.65 (s, 3H), 3.31-3.28 (m, 2H), 2.23 (s, 3H), 1.23 (q, J = 7.6 Hz, 3H) | 420 |

TABLE 16-continued

| Example | Structure | IUPAC Name | ¹H NMR ppm (δ) | MS (M + H) |
|---|---|---|---|---|
| 176 | 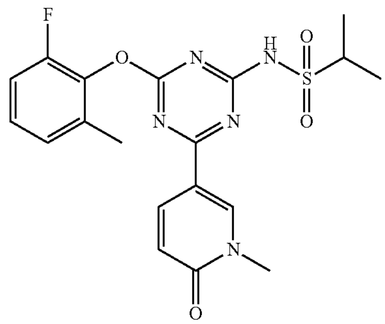 [SMILES: Cc1cccc(F)c1Oc1nc(NS(=O)(=O)C(C)C)nc(-c2ccc(=O)n(C)c2)n1] | Propane-2-sulfonic acid [4-(2-fluoro-6-methyl-phenoxy)-6-(1-methyl-6-oxo-1,6-dihydro-pyridin-3-yl)-[1,3,5]triazin-2-yl]-amide | (CD₃OD, 400 MHz) δ 8.82 (d, J = 2.4 Hz, 1H), 8.33 (dd, J = 9.6 Hz, 2.4 Hz, 1H), 7.24-7.07 (m, 3H), 6.58 (d, J = 9.6 Hz, 1H), 3.66 (s, 3H), 3.63-3.56 (m, 1H), 2.23 (s, 3H), 1.24 (d, J= 6.8 Hz, 6H) | 434 |
| 177 | 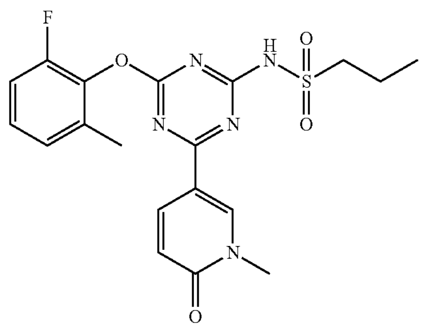 [SMILES: CCCS(=O)(=O)Nc1nc(Oc2c(C)cccc2F)nc(-c2ccc(=O)n(C)c2)n1] | Propane-1-sulfonic acid [4-(2-fluoro-6-methyl-phenoxy)-6-(1-methyl-6-oxo-1,6-dihydro-pyridin-3-yl)-[1,3,5]triazin-2-yl]-amide | (CD₃OD, 400 MHz) δ 8.83 (d, J = 2.4 Hz, 1H), 8.34 (dd, J = 9.6 Hz, 2.4 Hz, 1H), 7.24-7.07 (m, 3H), 6.59 (d, J = 9.2 Hz, 1H), 3.66 (s, 3H), 3.25-3.21 (m, 2H), 2.23 (s, 3H), 1.74-1.65 (m, 2H), 0.96 (q, J = 7.2 Hz, 3H) | 434 |
| 178 | 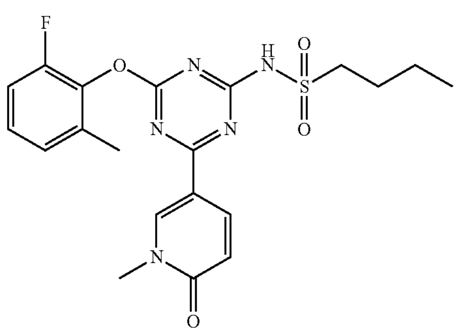 [SMILES: CCCCS(=O)(=O)Nc1nc(Oc2c(C)cccc2F)nc(-c2ccc(=O)n(C)c2)n1] | Butane-1-sulfonic acid [4-(2-fluoro-6-methyl-phenoxy)-6-(1-methyl-6-oxo-1,6-dihydro-pyridin-3-yl)-[1,3,5]triazin-2-yl]-amide | (CD₃OD, 400 MHz) δ 8.83 (d, J = 2.4 Hz, 1H), 8.34 (dd, J = 9.6 Hz, 2.4 Hz, 1H), 7.24-7.07 (m, 3H), 6.59 (d, J = 5.6 Hz, 1H), 3.66 (s, 3H), 3.29-3.24 (m, 2H), 2.23 (s, 3H), 1.68-1.60 (m, 2H), 1.39-1.33 (m, 2H), 0.89 (q, J = 7.6 Hz, 3H) | 448 |
| 179 | 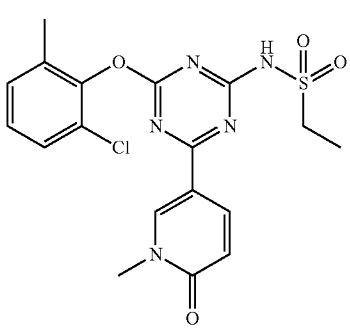 [SMILES: CCS(=O)(=O)Nc1nc(Oc2c(C)cccc2Cl)nc(-c2ccc(=O)n(C)c2)n1] | Ethanesulfonic acid [4-(2-chloro-6-methyl-phenxoy)-6-(1-methyl-6-oxo-1,6-dihydro-pyridin-3-yl)-[1,3,5]triazin-2-yl]-amide | (CD₃OD, 400 MHz) δ 8.82 (s, 1H), 8.34 (dd, J = 2.8 Hz, 9.6 Hz, 1H), 7.37 (d, J = 8.4 Hz, 1H), 7.29 (d, J = 7.2 Hz, 1H), 7.20 (t, J = 7.6 Hz, 1H), 6.60 (d, J = 9.6 Hz, 1H), 3.66 (s, 3H), 3.26-3.20 (m, 2H), 2.22 (s, 3H), 1.22 (t, J = 7.2 Hz, 3H) | 436 |

TABLE 16-continued

| Example | Structure | IUPAC Name | ¹H NMR ppm (δ) | MS (M + H) |
|---|---|---|---|---|
| 180 | 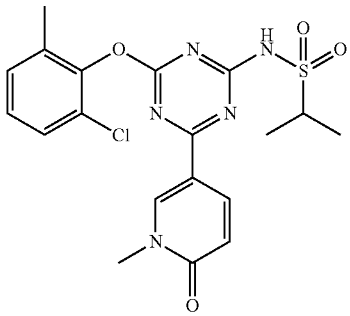 [SMILES: Cc1cccc(Cl)c1Oc1nc(NS(=O)(=O)C(C)C)nc(-c2ccc(=O)n(C)c2)n1] | Propane-2-sulfonic acid [4-(2-chloro-6-methyl-phenoxy)-6-(1-methyl-6-oxo-1,6-dihydro-pyridin-3-yl)-[1,3,5]triazin-2-yl]-amide | (CD₃OD, 400 MHz) 8.85 (d, J = 2.4 Hz, 1H), 8.35 (dd, J = 2.4 Hz, 9.2 Hz, 1H), 7.37 (d, J = 7.6 Hz, 1H), 7.29 (d, J = 7.2 Hz, 1H), 7.20 (t, J = 7.6 Hz, 1H), 6.60 (d, J = 9.2 Hz, 1H), 3.66 (s, 3H), 3.52-3.50 (m, 1H), 2.22 (s, 3H), 1.24 (d, J = 6.8 Hz, 6H) | 450 |
| 181 | 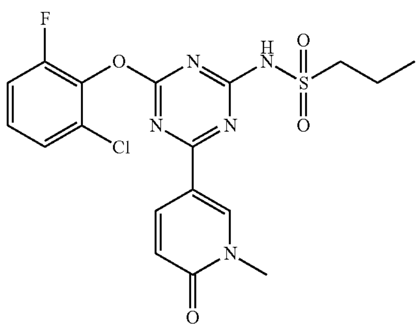 | Propane-1-sulfonic acid [4-(2-chloro-6-fluoro-phenoxy)-6-(1-methyl-6-oxo-1,6-dihydro-pyridin-3-yl)-[1,3,5]triazin-2-yl]-amide | (CDCl₃, 400 MHz) δ 8.64 (d, J = 2.4 Hz, 1H), 8.18 (dd, J = 9.6 Hz, 2.8 Hz, 1H), 7.64 (br, 1H), 7.32-7.15 (m, 3H), 6.63 (d, J = 10.0 Hz, 1H), 3.64 (s, 3H), 3.38-3.34 (m, 2H), 1.88-1.80 (m, 2H), 1.03 (q, J = 7.6 Hz, 3H) | 454 |
| 182 | 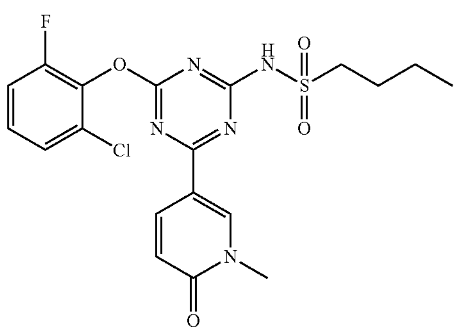 [SMILES: CCCCS(=O)(=O)Nc1nc(Oc2c(F)cccc2Cl)nc(-c2ccc(=O)n(C)c2)n1] | Butane-1-sulfonic acid [4-(2-chloro-6-fluoro-phenoxy)-6-(1-methyl-6-oxo-1,6-dihydro-pyridin-3-yl)-[1,3,5]triazin-2-yl]-amide | (CDCl₃, 400 MHz) δ 8.63 (d, J = 2.4 Hz, 1H), 8.28 (dd, J = 9.6 Hz, 2.4 Hz, 1H), 7.49 (br, 1H), 7.32-7.15 (m, 3H), 6.64 (d, J = 9.6 Hz, 1H), 3.65 (s, 3H), 3.41-3.37 (m, 2H), 1.81-1.74 (m, 2H), 1.47-1.38 (m, 2H), 0.93 (q, J = 7.2 Hz, 3H) | 468 |
| 183 | 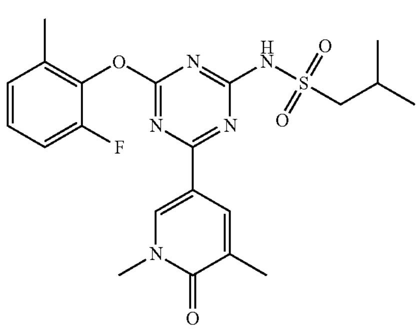 [SMILES: Cc1cccc(F)c1Oc1nc(NS(=O)(=O)CC(C)C)nc(-c2cc(C)c(=O)n(C)c2)n1] | 2-Methyl-propane-1-sulfonic acid [4-(1,5-dimethyl-6-oxo-1,6-dihydro-pyridin-3-yl)-6-(2-fluoro-6-methyl-phenoxy)-[1,3,5]triazin-2-yl]-amide | (CD₃OD, 400 MHz) 8.60 (s, 1H), 8.19 (s, 1H), 7.18-7.12 (m, 1H), 7.11-7.10 (m, 2H), 3.65 (s, 3H), 3.08-3.07 (m, 2H), 2.23 (s, 3H), 2.16 (s, 3H), 2.15-2.00 (m, 1H), 0.97 (d, J = 1.6 Hz, 3H), 0.98 (d, J = 1.6 Hz, 3H). | 462 |

TABLE 16-continued

| Example | Structure | IUPAC Name | ¹H NMR ppm (δ) | MS (M + H) |
|---|---|---|---|---|
| 184 | 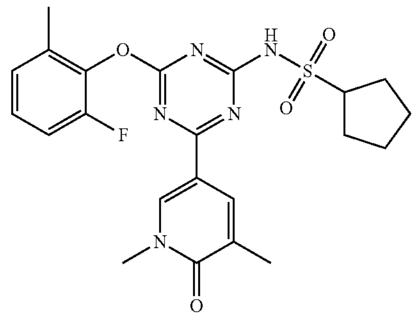 [SMILES: Cc1cccc(F)c1Oc1nc(NS(=O)(=O)C2CCCC2)nc(-c2cc(C)c(=O)n(C)c2)n1] | Cyclopentanesulfonic acid [4-(1,5-dimethyl-6-oxo-1,6-dihydro-pyridin-3-yl)-6-(2-fluoro-6-methyl-phenoxy)-[1,3,5]triazin-2-yl]-amide | (CD₃OD, 400 MHz) 8.65 (s, 1H), 8.25 (s, 1H), 7.19-7.17 (m, 1H), 7.11-7.06 (m, 2H), 3.77-.375 (m, 1H), 3.67 (s, 3H), 2.25 (s, 3H), 2.12 (s, 3H), 1.95-1.87 (m, 2H), 1.71-1.66 (m, 4H), 1.53-1.49 (m, 2H). | 474 |
| 185 | 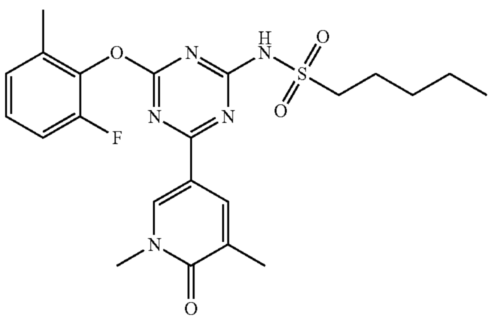 [SMILES: CCCCCS(=O)(=O)Nc1nc(Oc2c(C)cccc2F)nc(-c2cc(C)c(=O)n(C)c2)n1] | Pentane-1-sulfonic acid [4-(1,5-dimethyl-6-oxo-1,6-dihydro-pyridin-3-yl)-6-(2-fluoro-6-methyl-phenoxy)-[1,3,5]triazin-2-yl]-amide | (CD₃OD, 400 MHz) 8.70 (s, 1H), 8.21 (s, 1H), 7.23-7.21 (m, 1H), 7.14-7.01 (m, 2H), 3.66 (s, 3H), 3.25-3.24 (m, 2H), 2.34 (s, 3H), 2.17 (s, 3H), 1.70-1.66 (m, 2H), 1.31-1.30 (m, 4H), 0.90 (t, J = 6.8 Hz, 3H). | 476 |
| 186 | 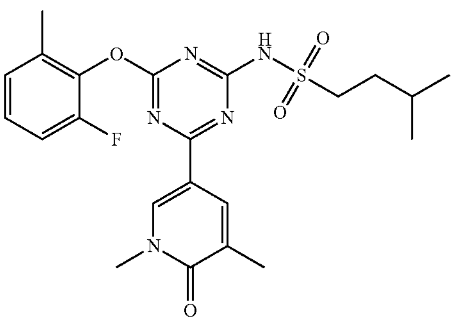 [SMILES: Cc1cccc(F)c1Oc1nc(NS(=O)(=O)CCC(C)C)nc(-c2cc(C)c(=O)n(C)c2)n1] | 3-Methyl-butane-1-sulfonic acid [4-(1,5-dimethyl-6-oxo-1,6-dihydro-pyridin-3-yl)-6-(2-fluoro-6-methyl-phenoxy)-[1,3,5]triazin-2-yl]-amide | (CDCl₃, 400 MHz) 8.51 (s, 1H), 8.07 (s, 1H), 7.19-7.15 (m, 1H), 7.08-7.03 (m ,2H), 3.65 (s, 3H), 3.35-3.34 (m, 2H), 2.26 (s, 3H), 2.20 (s, 3H), 1.60-1.54 (m, 3H), 0.90 (d, J = 6.4 Hz, 6H). | 476 |
| 187 | 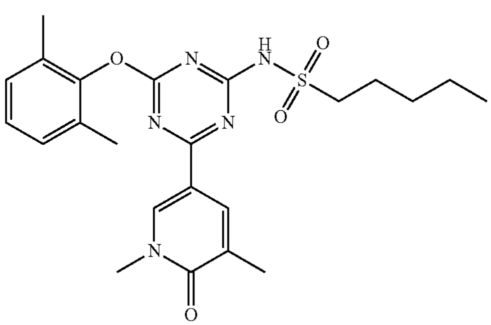 [SMILES: CCCCCS(=O)(=O)Nc1nc(Oc2c(C)cccc2C)nc(-c2cc(C)c(=O)n(C)c2)n1] | Butane-1-sulfonic acid [4-(1,5-dimethyl-6-oxo-1,6-dihydro-pyridin-3-yl)-6-(2,6-dimethyl-phenxoy)-[1,3,5]triazin-2-yl]-amide | (CD₃OD, 400 MHz) 8.64 (d, J = 2.4 Hz, 1H), 8.26 (s, 1H), 7.11-7.06 (m, 3H), 3.67 (s, 3H), 2.97-2.93 (m, 2H), 2.18 (s, 3H), 2.16 (s, 6H), 1.57-1.53 (m, 2H), 1.30-1.25 (m, 2H), 0.87 (t, J = 7.2 Hz, 3H). | 458 |
| 188 | | Butane-1-sulfonic acid [4-(2-chloro-6-methyl-phenoxy)-6-(1,5-dimethyl-6-oxo-1,6-dihydro-pyridin-3-yl)-[1,3,5]triazin-2-yl]-amide | (CD₃OD, 400 MHz) 8.64 (s, 1H), 8.24 (s, 1H), 7.32 (d, J = 8.4 Hz, 1H), 7.24 (d, J = 7.2 Hz, 1H), 7.18-7.16 (m, 1H), 3.66 (s, 3H), 3.05-3.00 (m, 2H), 2.23 (s, 3H), 2.17 (s, 3H), 1.60-1.56 (m, 2H), 1.35-1.29 (m, 2H), 0.88 (t, J = 7.2 Hz, 3H). | 478 |
| 189 | | Butane-1-sulfonic acid [4-(2,6-difluoro-phenoxy)-6-(1,5-dimethyl-6-oxo-1,6-dihydro-pyridin-3-yl)- | (CD₃OD, 400 MHz) 8.62 (d, J = 2.4 Hz, 1H), 8.21-8.20 (m, 1H), 7.32-7.26 (m, 1H), 7.11 (t, J = 8 Hz, | 466 |

TABLE 16-continued

| Example | Structure | IUPAC Name | $^1$H NMR ppm (δ) | MS (M + H) |
|---|---|---|---|---|
| | | [1,3,5]triazin-2-yl]-amide | 2H), 3.65 (s, 3H), 3.16-3.12 (m, 2H), 2.16 (s, 3H), 1.67-1.61 (m, 2H), 1.40-1.34 (m, 2H), 0.90 (t, J = 7.2 Hz, 3H). | |
| 190 | | Butane-1-sulfonic acid [4-(2-chloro-6-fluoro-phenoxy)-6-(1,5-dimethyl-6-oxo-1,6-dihydro-pyridin-3-yl)-[1,3,5]triazin-2-yl]-amide | (CD$_3$OD, 400 MHz) 8.63 (s, 1H), 8.21 (s, 1H), 7.34-7.24 (m, 3H), 3.65 (s, 3H), 3.15-3.09 (m, 2H), 2.16 (s, 3H), 1.65-1.62 (m, 2H), 1.40-1.36 (m, 2H), 0.90 (t, J = 7.2 Hz, 3H). | 482 |

Examples 191-199 (Table 17) were prepared from the appropriate phenols, pyridin-2-ones and sulfonamides in a similar multi-step manner as Example 156.

TABLE 17

| Example | Structure | IUPAC Name | $^1$H NMR ppm (δ) | MS (M + H) |
|---|---|---|---|---|
| 191 | | Ethanesulfonic acid [6-(1,5-dimethyl-6-oxo-1,6-dihydro-pyridin-3-yl)-2-phenyl-pyrimidin-4-yl]-amide | (CDCl$_3$, 400 MHz) δ 8.40-8.39 (m, 3H), 7.92 (s, 1H), 7.53-7.51 (m, 3H), 7.05 (s, 1H), 3.71 (s, 3H), 3.59-3.54 (m, 2H), 2.25 (s, 3H), 1.96-1.90 (m, 2H), 1.44 (t, J = 7.6 Hz, 3H) | 385 |
| 192 | | Ethanesulfonic acid [6-(1,5-dimethyl-6-oxo-1,6-dihydro-pyridin-3-yl)-2-o-tolyl-pyrimidin-4-yl]-amide | (CDCl$_3$, 400 MHz) δ 8.33 (s, 1H), 7.80-7.71 (m, 2H), 7.44-7.32 (m, 3H), 7.10 (s, 1H), 3.67 (s, 3H), 3.35 (m, 2H), 2.59 (s, 3H), 2.25 (s, 3H), 1.44 (m, 3H) | 399 |
| 193 | 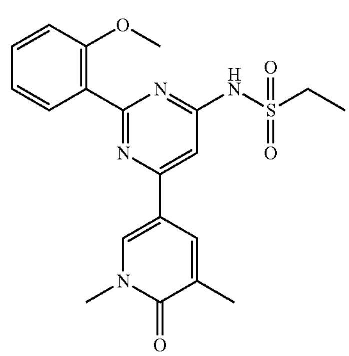 [SMILES: CCS(=O)(=O)Nc1cc(-c2cc(C)c(=O)n(C)c2)nc(-c2ccccc2OC)n1] | Ethanesulfonic acid [6-(1,5-dimethyl-6-oxo-1,6-dihydro-pyridin-3-yl)-2-(2-methoxy-phenyl)-pyrimidin-4-yl]-amide | (CDCl$_3$, 400 MHz) δ 8.54 (d, J = 6.8 Hz, 1H), 8.33 (s, 1H), 7.73 (s, 1H), 7.59 (m, 1H), 7.18 (m, 1H), 7.09 (d, J = 8 Hz, 1H), 6.76 (s, 1H), 4.13 (s, 3H), 3.71 (s, 3H), 3.17 (m, 2H), 2.24 (s, 3H), 1.45 (m, 3H) | 415 |
| 194 | 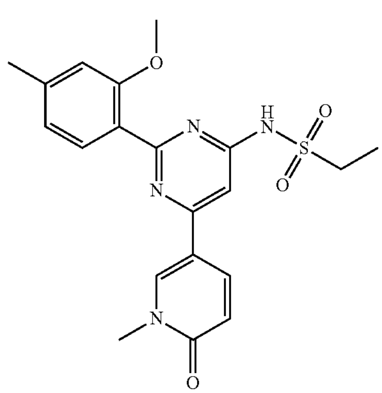 [SMILES: CCS(=O)(=O)Nc1cc(-c2ccc(=O)n(C)c2)nc(-c2ccc(C)cc2OC)n1] | Ethanesulfonic acid [2-(2-methoxy-4-methyl-phenyl)-6-(1-methyl-6-oxo-1,6-dihydro-pyridin-3-yl)-pyrimidin-4-yl]-amide | (CDCl$_3$, 300 MHz) 8.46-8.41 (m, 2H), 7.96 (d, J = 9.3 Hz, 1H), 7.00 (d, J = 7.2 Hz, 1H), 6.92 (s, 1H), 6.79-6.75 (m, 2H), 4.13 (s, 3H), 3.75 (s, 3H), 3.23-3.16 (m, 2H), 2.48 (s, 3H), 1.46 (t, J = 7.2 Hz, 3H). | 415 |

TABLE 17-continued

| Example | Structure | IUPAC Name | ¹H NMR ppm (δ) | MS (M + H) |
|---|---|---|---|---|
| 195 | 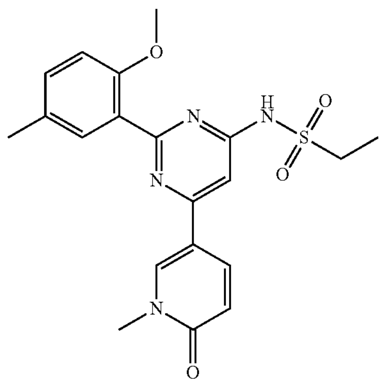 [SMILES: CCS(=O)(=O)Nc1cc(-c2ccc(=O)n(C)c2)nc(-c2cc(C)ccc2OC)n1] | Ethanesulfonic acid [2-(2-methoxy-5-methyl-phenyl)-6-(1-methyl-6-oxo-1,6-dihydro-pyridin-3-yl)-pyrimidin-4-yl]-amide | (CD$_3$OD, 400 MHz) 8.68 (s, 1H), 8.23-8.19 (m, 2H), 7.41 (d, J = 9.2 Hz, 1H), 7.11 (d, J = 8.4 Hz, 1H), 6.98 (s, 1H), 6.65 (d, J = 9.6 Hz, 1H), 4.00 (s, 3H), 3.70 (s, 3H), 3.27-3.24 (m, 2H), 2.39 (s, 3H), 1.38 (t, J = 7.2 Hz, 3H). | 415 |
| 196 | 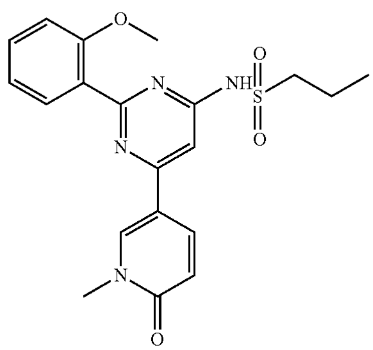 | Propane-1-sulfonic acid [2-(2-methoxy-phenyl)-6-(1-methyl-6-oxo-1,6-dihydro-pyridin-3-yl)-pyrimidin-4-yl]-amide | (DMSO-d6, 400 MHz) 8.64 (d, J = 2.4 Hz, 1H), 8.10-8.06 (m, 1H), 7.53-7.52 (m, 2H), 7.24-7.21 (m, 1H), 7.14-7.07 (m, 2H), 6.54 (d, J = 9.2 Hz, 1H), 3.86 (s, 3H), 3.59 (s, 3H), 3.46-36 (m, 2H), 1.78-1.72 (m, 2H), 1.00 (t, J = 7.6 Hz, 3H). | 415 |
| 197 | 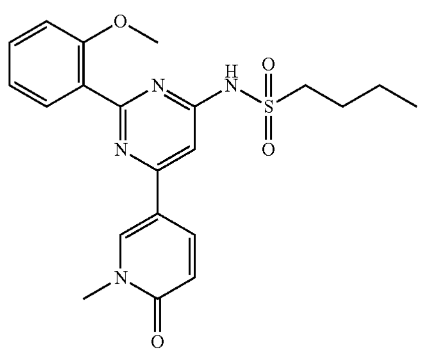 [SMILES: CCCCS(=O)(=O)Nc1cc(-c2ccc(=O)n(C)c2)nc(-c2ccccc2OC)n1] | Butane-1-sulfonic acid [2-(2-methoxy-phenyl)-6-(1-methyl-6-oxo-1,6-dihydro-pyridin-3-yl)-pyrimidin-4-yl]-amide | (CD$_3$COCD$_3$, 400 MHz) 8.64 (d, J = 2.8 Hz, 1H), 8.40 (br, 1H), 8.02 (dd, J = 9.6 Hz, 2.8 Hz, 1H), 7.50 (t, J = 8.0 Hz, 1H), 7.17 (d, J = 8.4 Hz, 1H), 7.04 (d, J = 7.67 Hz, 1H), 6.77 (s, 1H), 6.38 (d, J = 9.6 Hz, 1H), 3.97 (s, 3H), 3.52 (s, 3H), 3.08-3.02 (m, 2H), 1.73-1.65 (m, 2H), 1.39-1.30 (m, 2H), 0.79 (t, J = 7.2 Hz, 3H). | 429 |
| 198 | | Ethanesulfonic acid [2-(2-cyano-phenyl)-6-(1-methyl-6-oxo-1,6-dihydro-pyridin-3-yl)-pyrimidin-4-yl]-amide | (DMSO-d$_6$, 400 MHz) 11.4 (br, 1H), 8.91 (d, J = 2.4 Hz, 1H), 8.41 (d, J = 7.6 Hz, 1H), 8.15 (dd, J = 9.6 Hz, 2.4 Hz, 1H), 8.03 (d, J = 6.8 Hz, 1H), 7.91 (t, J = 8.8 Hz, 1H), 7.75 (t, J = 7.6 Hz, 1H), 7.16 (s, 1H), 6.56 (d, J = 10 Hz, 1H), 3.65 (q, J = 7.2 Hz, 2H), 3.55 (s, 3H), 1.28 (t, J = 7.2 Hz, 3H). | 396 |
| 199 | | Ethanesulfonic acid [2-(2-methoxy-phenyl)-6-(1-methyl-6-oxo-1,6-dihydro-pyridin-3-yl)-pyrimidin-4-yl]-amide | (CDCl$_3$ + CD$_3$OD, 400 MHz) 8.64 (d, J = 2.4 Hz, 1H), 8.54 (d, J = 2.4 Hz, 1H), 8.13 (dd, J = 9.6 Hz, 2.4 Hz, 1H), 7.67-7.63 (m, | 401 |

TABLE 17-continued

| Example | Structure | IUPAC Name | $^1$H NMR ppm (δ) | MS (M + H) |
|---|---|---|---|---|
| | | | 1H), 7.24-7.20 (m, 2H), 6.95 (s, 1H), 6.70 (d, J = 9.6 Hz, 1H), 4.13 (s, 3H), 3.74 (s, 3H), 3.20 (q, J = 7.2 Hz, 2H), 1.44 (t, J = 7.2 Hz, 3H). | |

Examples 200-201 (Table 18) were prepared in a similar multi-step manner as Example 153 by substituting isopropanol for 2,6-dimethylphenol and using the appropriate sulfonamides.

TABLE 18

| Example | Structure | IUPAC Name | $^1$H NMR ppm (δ) | MS (M + H) |
|---|---|---|---|---|
| 200 | | Ethanesulfonic acid [4-isopropoxy-6-(1-methyl-6-oxo-1,6-dihydro-pyridin-3-yl)-[1,3,5]triazin-2-yl]-amide | (CD$_3$OD, 400 MHz) δ 8.78 (d, J = 2.4 Hz, 1H), 8.35 (dd, J = 9.6 Hz, 2.4 Hz, 1H), 6.58 (d, J = 9.6 Hz, 1H), 5.42-5.38 (m, 1H), 4.84 (s, 3H), 3.66-3.60 (m, 2H), 1.41-1.36 (m, 9H) | 354 |
| 201 | | Propane-1-sulfonic acid [4-isopropoxy-6-(1-methyl-6-oxo-1,6-dihydro-pyridin-3-yl)-[1,3,5]triazin-2-yl]-amide | (CD$_3$OD, 400 MHz) δ 8.78 (d, J = 2.4 Hz, 1H), 8.36 (d, J = 9.6 Hz, 2.4 Hz, 1H), 6.58 (d, J = 9.2 Hz, 1H), 5.42-5.36 (m, 1H), 3.66 (s, 3H), 3.62-3.58 (m, 2H), 1.90-1.85 (m, 2H), 1.41 (d, J = 6.4 Hz, 6H), 1.08 (q, J = 7.2 Hz, 3H) | 368 |

Examples 202-228 (Table 19) were prepared from the appropriate phenols, pyridin-2-ones and chiral sulfonamides in a similar multi-step manner as Example 1. (S)-Butane-2-sulfonamide and analogs were prepared as shown below by using the appropriate alcohol.

Step 1: (2S)-2-sec-Butyl sulfanyl-pyrimidine

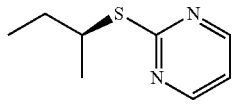

A dry flask containing a stir bar was charged with triphenylphosphine (4.68 g, 17.85 mmol) and purged with nitrogen. The triphenylphosphine was dissolved in toluene (17 mL) and the resulting solution cooled to 0° C. in an ice-water bath. Diethyl diazene-1,2-dicarboxylate (3.1 g, 17.85 mmol) as a 40% w/w toluene solution was added dropwise over 10 min. After 10 min of additional stirring, a solution of (R)-butan-2-ol (880 mg, 11.9 mmol) in toluene (8 mL) was added dropwise over 10 min. Ten minutes after addition of the alcohol, pyrimidine-2-thiol (1.6 g, 14.28 mmol) was added as a solid. The resulting yellow suspension was stirred for 2 hr at 0° C. and gradually warmed to room temp overnight. The mixture was filtered through a fitted funnel and the precipitate washed with toluene (10 mL). The filtrate was concentrated under reduced pressure to afford a residue which was purified by silica gel column chromatography (PE:EtOAc=2:1) to afford (2S)-2-sec-butylsulfanyl-pyrimidine (2.4 g, 98%) as a red oil. $^1$H NMR (CDCl$_3$, 300 MHz) δ 8.52 (d, J=4.8 Hz, 2H), 6.94 (t, J=5.1 Hz, 1H), 3.87-3.80 (m, 1H), 1.82-1.62 (m, 2H), 1.45 (d, J=6.9 Hz, 3H), 1.08 (t, J=7.2 Hz, 3H).

Step 2: (2S)-2-(Butane-2-sulfonyl)-pyrimidine

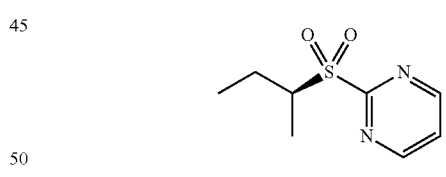

A mixture of (2S)-2-sec-butylsulfanyl-pyrimidine (2 g, 11.8 mmol) in DCM (20 mL) was cooled to 0° C. MCPBA (6.3 g, 35.4 mmol) was added slowly. The mixture was stirred at room temp for 3 hr. It was then poured over water (10 mL) and extracted with EtOAc (10 mL×2). The combined organic layers were washed with aqueous saturated NaHCO$_3$ (10 mL×3). The organic layer was dried over Na$_2$SO$_4$, filtered and concentrated under reduced pressure to give the crude product which was purified by silica gel column chromatography (PE:EtOAc=2:1) to afford 2-(Butane-2-sulfonyl)-pyrimidine (1.74 g, 73%) as a yellow oil. $^1$H NMR (CDCl$_3$, 300 MHz) δ 9.00 (d, J=4.8 Hz, 2H), 7.59 (t, J=4.5 Hz, 1H), 3.78-3.71 (m, 1H), 2.10-2.01 (m, 1H), 1.75-1.65 (m, 1H), 1.42 (d, J=7.2 Hz, 3H), 1.06 (t, J=7.2 Hz, 3H).

Step 3: (2S)-butane-2-sulfonamide

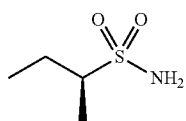

To a solution of (2S)-2-(butane-2-sulfonyl)-pyrimidine (1.74 g, 8.7 mmol) in MeOH (17.4 mL) at room temperature in a water bath was added dropwise a sodium methoxide solution in methanol (2 mL, 8.7 mmol, 25% wt). The mixture was stirred at room temp for 15 min and then concentrated under reduced pressure. The residue was treated with diethylether (43.5 mL). The resulting precipitate was filtered and dried under a stream of nitrogen to afford sodium (2S)-butane-2-sulfinate (1.2 g, 8.26 mmol) as a white power. A solution of hydroxylamine-o-sulfonic acid (0.98 g, 8.7 mmol) in water (4.35 mmol) was added dropwise over 5 min to a stirring solution of sodium acetate (709 mg, 8.7 mmol) and sodium (2S)-butane-2-sulfinate (1.2 g, 8.26 mmol) in water (4.35 mmol) at ambient temp. The mixture was allowed to stir until the sulfinate was no longer detected by LCMS. The reaction was neutralized with solid sodium bicarbonate and extracted exhaustively with ethyl acetate. The organic layers were combined, dried over anhydrous magnesium sulfate, filtered and concentrated under reduced pressure to afford (2S)-butane-2-sulfonamide (557 mg, 81%) as a colorless oil. $^1$H NMR (CD$_3$OD, 400 MHz) 1.86-1.79 (m, 2H), 1.31-1.27 (m, 1H) 1.08 (d, J=6.8 Hz, 3H), 0.98 (t, J=7.6 Hz, 3H).

TABLE 19

| Example | Structure | IUPAC Name | $^1$H NMR ppm (δ) | MS (M + H) |
|---|---|---|---|---|
| 202 | | (S)-N-(2-(2-fluoro-6-methylphenoxy)-6-(1-methyl-6-oxo-1,6-dihydropyridin-3-yl)pyrimidin-4-yl)butane-2-sulfonamide | (CD$_3$OD 400 MHz) 8.56 (d, J = 2.4 Hz, 1H), 8.11 (dd, J = 2.8, 9.6 Hz, 1H), 7.19-7.05 (m, 3H), 6.85 (s, 1H), 6.64 (d, J = 9.6 Hz, 1H), 3.66 (s, 3H), 3.11-3.08 (m, 1 H), 2.22 (s, 3H), 1.82-1.76 (m, 1 H), 1.48-31.34 (m, 1 H), 1.15 (d, J = 6.8 Hz, 3H), 0.88 (t, J = 7.2 Hz, 3H) | 447 |
| 203 | 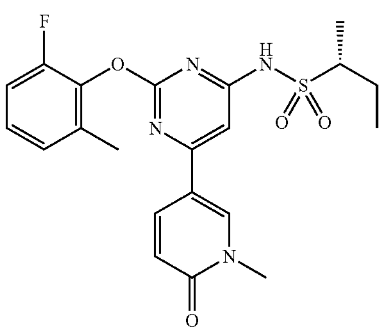 [SMILES: CC[C@@H](C)S(=O)(=O)Nc1cc(-c2ccc(=O)n(C)c2)nc(Oc2c(C)cccc2F)n1] | (R)-N-(2-(2-fluoro-6-methylphenoxy)-6-(1-methyl-6-oxo-1,6-dihydropyridin-3-yl)pyrimidin-4-yl)butane-2-sulfonamide | (CDCl$_3$, 400 MHz) 8.34 (d, J = 2.4 Hz, 1H), 7.80 (dd, J = 9.6 Hz, 2.8 Hz, 1H), 7.16-7.11 (m, 1H), 7.07-6.99 (m, 3H), 6.64 (d, J = 9.6 Hz, 1H), 3.63 (s, 3H), 3.15-3.10 (m, 1H), 2.25 (s, 3H), 1.97-1.93 (m, 1H), 1.58-1.53 (m, 1H), 1.30 (d, J = 6.8 Hz, 3H), 0.96 (t, J = 7.2 Hz, 3H) | 447 |
| 204 | 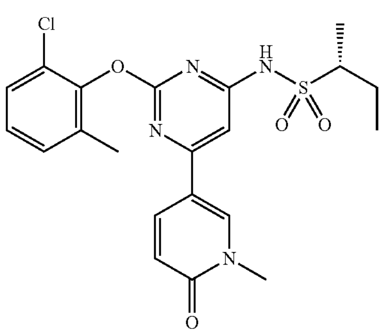 | Butane-(2R)-sulfonic acid [2-(2-chloro-6-methyl-phenoxy)-6-(1-methyl-6-oxo-1,6-dihydro-pyridin-3-yl)-pyrimidin-4-yl]-amide | (CDCl$_3$, 300 MHz) 8.40 (s, 1H), 7.82 (d, J = 9.3 Hz, 1H), 7.32 (d, J = 7.2 Hz, 1H), 7.23-7.15 (m, 2H), 6.98 (s, 1H), 6.65 (d, J = 10.2 Hz, 1H), 3.65 (s, 3H), 3.12-3.08 (m ,1H), 2.25 (s, 3H), 1.98-1.91 (m, 1H), 1.66-1.51 (m, 1H), 1.30 (d, J = 6.6 Hz, 3H), 0.97 (t, J = 7.5 Hz, 3H) | 463 |

TABLE 19-continued

| Example | Structure | IUPAC Name | ¹H NMR ppm (δ) | MS (M + H) |
|---|---|---|---|---|
| 205 | 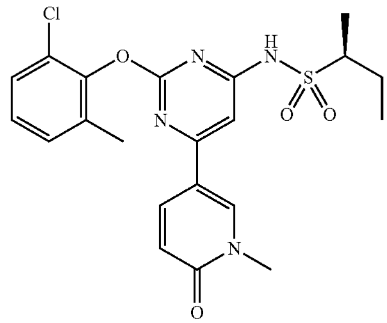 [SMILES: CC[C@H](C)S(=O)(=O)Nc1cc(-c2ccc(=O)n(C)c2)nc(Oc2c(C)cccc2Cl)n1] | Butane-(2S)-sulfonic acid [2-(2-chloro-6-mehtyl-phenoxy)-6-(1-methyl-6-oxo-1,6-dihydro-pyridin-3-yl)-pyrimidin-4-yl]-amide | (CDCl$_3$, 300 MHz) 8.41 (s, 1H), 7.83-7.80 (m, 1H), 7.34-7.30 (m, 1H), 7.23-7.12 (m, 2H), 6.98 (s, 1H), 6.65 (d, J = 10.2 Hz, 1H), 3.65 (s, 3H), 3.13-3.08 (m, 1H), 2.25 (s, 3H), 1.98-1.91 (m, 1H), 1.66-1.50 (m, 1H), 1.32 (d, J = 6.6 Hz, 3H), 0.97 (t, J = 7.5 Hz, 3H) | 463 |
| 206 | 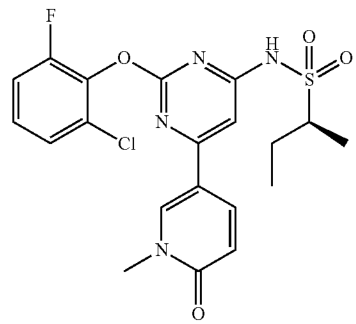 [SMILES: CC[C@H](C)S(=O)(=O)Nc1cc(-c2ccc(=O)n(C)c2)nc(Oc2c(F)cccc2Cl)n1] | Butane-(2S)-sulfonic acid [2-(2-chloro-6-fluoro-phenoxy)-6-(1-methyl-6-oxo-1,6-dihydro-pyridin-3-yl)-pyrimidin-4-yl]-amide | (CDCl$_3$, 400 MHz) 8.34 (s, 1H), 7.79 (dd, J = 2.8 Hz, 9.6 Hz, 1H), 7.34-7.26 (m, 1H), 7.23-7.04 (m, 2H), 7.09 (s, 1 H), 6.64 (d, J = 9.6 Hz, 1H), 3.62 (s, 3 H), 3.20-3.15 (m, 1 H), 2.04-1.98 (m, 1 H), 1.65-1.59 (m, 1 H), 1.36 (d, J = 6.8 Hz, 3H), 1.02 (t, J = 7.6 Hz, 3H) | 467 |
| 207 | 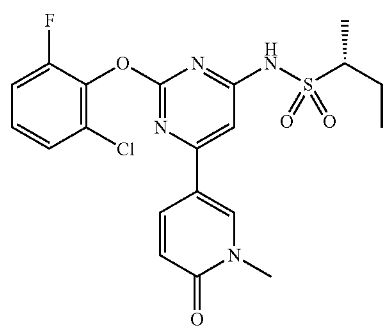 | Butane-(2R)-sulfonic acid [2-(2-chloro-6-fluoro-phenoxy)-6-(1-methyl-6-oxo-1,6-dihydro-pyridin-3-yl)-pyrimidin-4-yl]-amide | (CDCl$_3$, 300 MHz) 8.36 (s, 1H), 7.82 (d, J = 9.3 Hz, 1H), 7.33-7.29 (m, 1H), 7.25-7.13 (m, 2H), 7.11 (s, 1H), 6.66 (d, J = 9.3 Hz, 1H), 3.64 (s, 3H), 3.20-3.17 (m, 1H), 2.03-2.01 (m, 1H), 1.63-1.59 (m, 1H), 1.36 (d, J = 6.9 Hz, 3H), 1.01 (t, J = 7.5 Hz, 3H) | 467 |
| 208 | 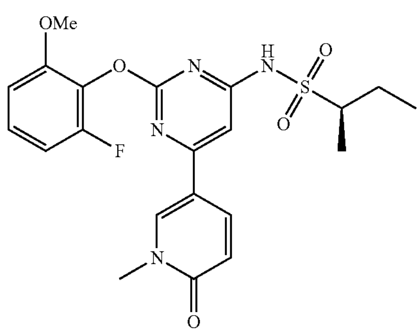 [SMILES: CC[C@@H](C)S(=O)(=O)Nc1cc(-c2ccc(=O)n(C)c2)nc(Oc2c(F)cccc2OC)n1] | Butane-(2R)-sulfonic acid [2-(2-fluoro-6-methoxy-phenoxy)-6-(1-methyl-6-oxo-1,6-dihydro-pyridin-3-yl)-pyrimidin-4-yl]-amide | (DMSO-d$_6$, 400 MHz) 11.2 (s, 1H), 8.58 (d, J = 2.8 Hz, 1H), 7.90 (dd, J = 10.0 Hz, 1H), 7.30-7.24 (m, 1H), 7.03-6.94 (m, 2H), 6.83 (s, 1H), 6.52 (d, J = 9.6 Hz, 1H), 3.75 (s, 3H), 3.55 (s, 3H), 3.03-3.00 (m, 1H), 1.68-1.63 (m, 1H), 1.38-1.30 (m, 1H), 1.05 (d, J = 6.8 Hz, 3H), 0.81 (t, J = 7.6 Hz, 3H) | 463 |

TABLE 19-continued

| Example | Structure | IUPAC Name | ¹H NMR ppm (δ) | MS (M + H) |
|---|---|---|---|---|
| 209 | 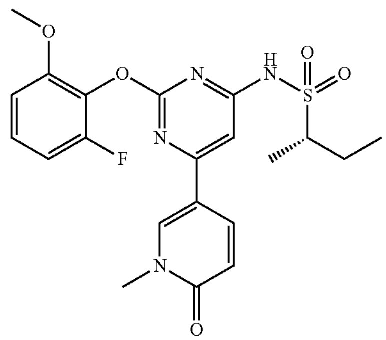 [SMILES: CC[C@H](C)S(=O)(=O)Nc1cc(-c2ccc(=O)n(C)c2)nc(Oc2c(F)cccc2OC)n1] | Butane-(2S)-sulfonic acid [2-(2-fluoro-6-methoxy-phenoxy)-6-(1-methyl-6-oxo-1,6-dihydro-pyridin-3-yl)-pyrimidin-4-yl]-amide | (DMSO-d₆, 400 MHz) 11.27 (s, 1H), 8.58 (d, J = 2.4 Hz, 1H), 7.92 (dd, J = 2.8, 9.6 Hz, 1H), 7.30-7.25 (m, 1H), 7.04-6.95 (m, 2H), 6.83 (s, 1H), 6.54 (d, J = 9.6 Hz, 1H), 3.75 (s, 3H), 3.5 (s, 3H), 3.04-3.00 (m, 1H), 1.68-1.63 (m, 1H), 1.38-1.30 (m, 1H), 1.06 (d, J = 6.4 Hz, 3H), 0.82 (t, J = 7.6 Hz, 3H) | 463 |
| 210 | 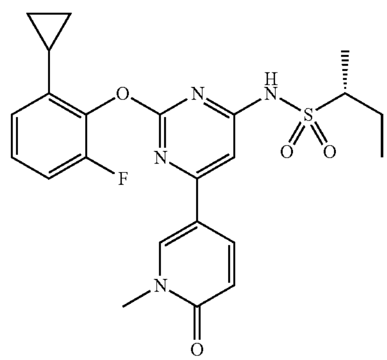 [SMILES: CC[C@@H](C)S(=O)(=O)Nc1cc(-c2ccc(=O)n(C)c2)nc(Oc2c(F)cccc2C2CC2)n1] | Butane-(2R)-sulfonic acid [2-(2-cyclopropyl-6-fluoro-phenoxy)-6-(1-methyl-6-oxo-1,6-dihydro-pyridin-3-yl)-pyrimidin-4-yl]-amide | (CD₃OD, 400 MHz) 8.54 (s, 1H), 8.10 (d, J = 8.8 Hz, 1H), 7.18-7.16 (m, 1H), 7.06-7.03 (m, 1H), 6.85-6.82 (m, 2H), 6.12 (d, J = 9.2 Hz, 1H), 3.66 (s, 3H), 3.15-3.10 (m, 1H), 1.99-1.96 (m, 1H), 1.79-1.77 (m, 1H), 1.45-1.41 (m, 1H), 1.14-1.12 (m, 3H), 0.89-0.84 (m, 5H), 0.68-0.65 (m, 2H) | 473 |
| 211 | 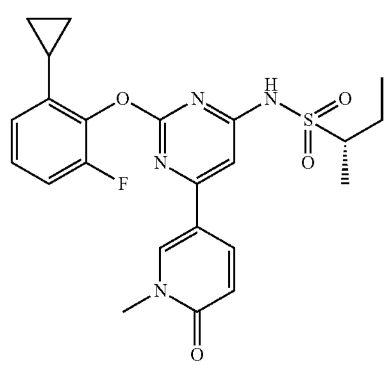 [SMILES: CC[C@H](C)S(=O)(=O)Nc1cc(-c2ccc(=O)n(C)c2)nc(Oc2c(F)cccc2C2CC2)n1] | Butane-(2S)-sulfonic acid [2-(2-cylcopropyl-6-methyl-phenoxy)-6-(1-methyl-6-oxo-1,6-dihydro-pyridin-3-yl)-pyrimidin-4-yl]-amide | (CDCl₃, 400 MHz) 8.35 (s, 1 H), 7.82 (d, J = 7.2 Hz, 1 H), 7.54 (br, 1 H), 7.16-7.13 (m, 1 H), 7.03-6.97 (m, 2 H), 6.75 (d, J = 8.0 Hz, 1 H), 6.64 (d, J = 9.6 Hz, 1H), 3.62 (s, 3H), 3.18-3.13 (m, 1 H), 2.04-1.95 (m, 2 H), 1.56-1.54 (m, 1 H), 1.32 (d, J = 6.8 Hz, 3 H), 0.99 (t, J = 7.2 Hz, 3 H), 0.91-0.87 (m, 2 H), 0.69-0.65 (m, 2 H). | 469 |
| 212 | 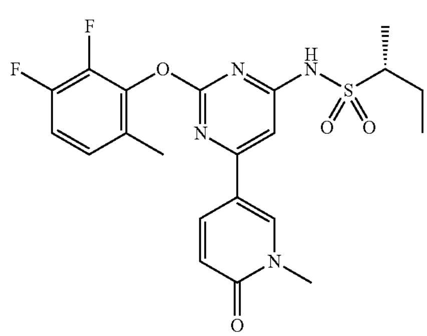 [SMILES: CC[C@@H](C)S(=O)(=O)Nc1cc(-c2ccc(=O)n(C)c2)nc(Oc2c(C)ccc(F)c2F)n1] | (2R)-Butane-2-sulfonic acid [2-(2,3-difluoro-6-methyl-phenoxy)-6-(1-methyl-6-oxo-1,6-dihydro-pyridin-3-yl)-pyrimidin-4-yl]-amide | (CD₃OD, 400 MHz) 8.55 (d, J = 2.8 Hz, 1H), 8.10 (dd, J = 9.2 Hz, 2.8 Hz, 1H), 7.13-7.10 (m, 2H), 6.85 (s, 2H), 6.63 (d, J = 9.6 Hz, 1H), 3.66 (s, 3H), 3.13-3.08 (m, 1H), 2.18 (s, 3H), 1.84-1.78 (m, 1H), 1.49-1.41 (m, 1H), 1.17 (d, J = 7.2 Hz, 3H), 0.89 (t, J = 7.6 Hz, 3H). | 465 |

TABLE 19-continued

| Example | Structure | IUPAC Name | ¹H NMR ppm (δ) | MS (M + H) |
|---|---|---|---|---|
| 213 | 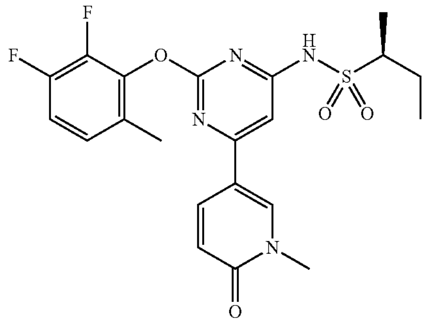 [SMILES: CC[C@H](C)S(=O)(=O)Nc1cc(-c2ccc(=O)n(C)c2)nc(Oc2c(C)ccc(F)c2F)n1] | (2S)-Butane-2-sulfonic acid [2-(2,3-difluoro-6-methyl-phenoxy)-6-(1-methyl-6-oxo-1,6-dihydro-pyridin-3-yl)-pyrimidin-4-yl]-amide | (CD$_3$OD, 400 MHz) 8.56 (d, J = 2.4 Hz, 1H), 8.10 (dd, J = 9.2 Hz, 2.8 Hz, 1H), 7.13-7.10 (m, 2H), 6.86 (s, 2H), 6.63 (d, J = 10.0 Hz, 1H), 3.66 (s, 3H), 3.14-3.08 (m, 1H), 2.18 (s, 3H), 1.84-1.78 (m, 1H), 1.49-1.42 (m, 1H), 1.17 (d, J = 7.2 Hz, 3H), 0.89 (t, J = 7.6 Hz, 3H). | 465 |
| 214 | 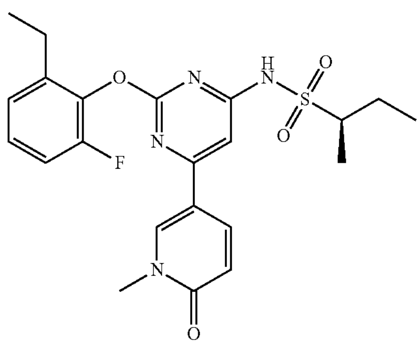 [SMILES: CCc1cccc(F)c1Oc1nc(NS(=O)(=O)[C@H](C)CC)cc(-c2ccc(=O)n(C)c2)n1] | (2R)-Butane-2-sulfonic acid [2-(2-ethyl-6-fluoro-phenoxy)-6-(1-methyl-6-oxo-1,6-dihydro-pyridin-3-yl)-pyrimidin-4-yl]-amide | (CDCl$_3$, 400 MHz) 8.39 (s, 1H), 7.86 (s, 1H), 7.18-7.15 (m, 1H), 7.09-6.99 (m, 3H), 6.71 (s, 1H), 3.65 (s, 3H), 3.14-3.13 (m, 1H), 2.64 (q, J = 7.2 Hz, 2H), 1.96-1.94 (m, 1H), 1.56-1.54 (m, 1H), 1.30 (d, J = 6.0 Hz, 3H), 1.18 (t, J = 7.2 Hz, 3H), 0.96 (t, J = 7.2 Hz, 3H). | 461 |
| 215 | 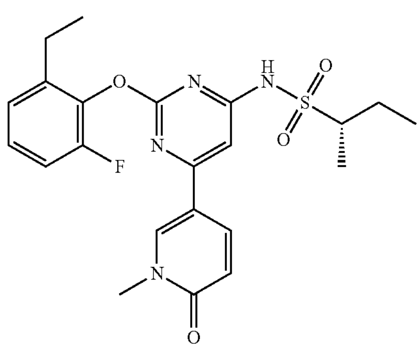 [SMILES: CCc1cccc(F)c1Oc1nc(NS(=O)(=O)[C@@H](C)CC)cc(-c2ccc(=O)n(C)c2)n1] | (2S)-Butane-2-sulfonic acid [2-(2-ethyl-6-fluoro-phenoxy)-6-(1-methyl-6-oxo-1,6-dihydro-pyridin-3-yl)-pyrimidin-4-yl]-amide | (CDCl$_3$, 400 MHz) 8.34 (s, 1H), 7.82 (d, J = 9.6 Hz, 1H), 7.40 (s, 1H), 7.26-7.19 (m, 1H), 7.18-7.17 (m, 1H), 7.10-7.00 (m, 2H), 6.64 (d, J = 9.2 Hz, 1H), 3.62 (s, 3H), 3.15-3.14 (m, 1H), 2.67 (q, J = 7.6 Hz, 2H), 1.964-1.62 (m, 2H), 1.64 (br, 1H), 1.33 (d, J = 6.8 H, 3H), 1.30 (t, J = 7.2 Hz, 3H), 0.98 (t, J = 7.6 Hz, 3H). | 461 |
| 216 | 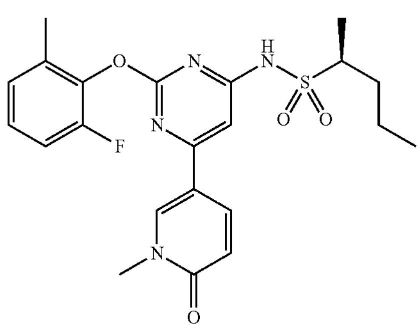 [SMILES: CCC[C@H](C)S(=O)(=O)Nc1cc(-c2ccc(=O)n(C)c2)nc(Oc2c(C)cccc2F)n1] | (2S)-Pentane-2-sulfonic acid [2-(2-fluoro-6-methyl-phenoxy)-6-(1-methyl-6-oxo-1,6-dihydro-pyridin-3-yl)-pyrimidin-4-yl]-amide | (CD$_3$OD, 400 MHz) 8.52 (d, J = 2.4 Hz, 1H), 8.09 (dd, J = 2.8 Hz, 9.2 Hz, 1H), 7.20-7.03 (m, 3H), 6.83 (s, 1H), 6.62 (d, J = 9.6 Hz, 1H), 3.66 (s, 3H), 3.22-3.17 (m, 1H), 2.22 (s, 3H), 1.72-1.69 (m, 1H), 1.43-1.33 (m, 2H), 1.21-1.17 (m, 1H), 1.14 (d, J = 6.8 Hz, 3H), 0.87 (t, J = 7.2 Hz, 3H) | 461 |

| Example | Structure | IUPAC Name | $^1$H NMR ppm (δ) | MS (M + H) |
|---|---|---|---|---|
| 217 | 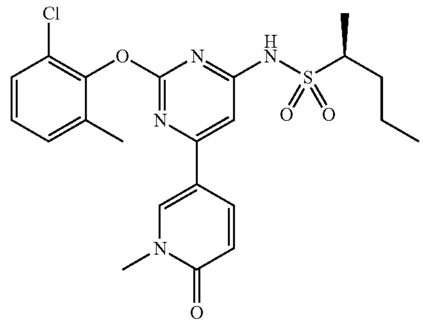 | (2S)-Pentane-2-sulfonic acid [2-(2-chloro-6-methyl-phenoxy)-6-(1-methyl-6-oxo-1,6-dihydro-pyridin-3-yl)-pyrimidin-4-yl]-amide | (CD$_3$OD, 400 MHz) 8.56 (d, J = 2.4 Hz, 1H), 8.12-8.09 (dd, J = 2.8 Hz, 9.6 Hz, 1H), 7.33 (d, J = 8.0 Hz, 1H), 7.26 (d, J = 6.8 Hz, 1H), 7.18 (t, J = 8.0 Hz, 1H), 6.83 (s, 1H), 6.63 (d, J = 9.6 Hz, 1H), 3.67 (s, 3H), 3.15-3.12 (m, 1H), 2.21 (s, 3H), 1.68-1.66 (m, 1H), 1.40-1.33 (m, 2H), 1.22-1.19 (m, 1H), 1.12 (d, J = 6.8 Hz, 3H), 0.87 (t, J = 7.6 Hz, 3H) | 477 |
| 218 | 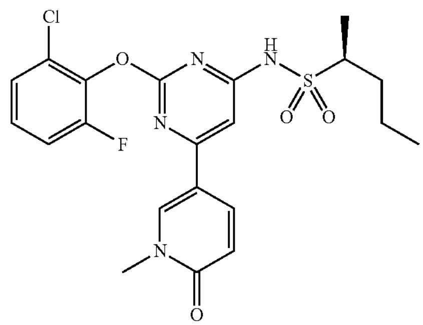 [SMILES: CCC[C@H](C)S(=O)(=O)Nc1cc(-c2ccc(=O)n(C)c2)nc(Oc2c(F)cccc2Cl)n1] | (2S)-Pentane-2-sulfonic acid [2-(2-chloro-6-fluoro-phenoxy)-6-(1-methyl-6-oxo-1,6-dihydro-pyridin-3-yl)-pyrimidin-4-yl]-amide | (CD$_3$OD, 400 MHz) 8.54 (d, J = 2.4 Hz, 1H), 8.09 (dd, J = 2.4 Hz, 9.6 Hz, 1H), 7.38-7.24 (m, 3H), 6.90 (s, 1H), 6.62 (d, J = 9.6 Hz, 1H), 3.66 (s, 3H), 3.29-3.25 (m, 1H), 1.74-1.73 (m, 1H), 1.46-1.39 (m, 2H), 1.27-1.23 (m, 1H), 1.19 (d, J = 6.8 Hz, 3H), 0.89 (t, J = 7.2 Hz, 3H) | 481 |
| 219 | 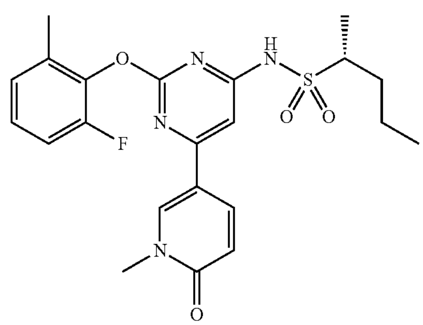 [SMILES: CCC[C@@H](C)S(=O)(=O)Nc1cc(-c2ccc(=O)n(C)c2)nc(Oc2c(C)cccc2F)n1] | (2R)-Pentane-2-sulfonic acid [2-(2-fluoro-6-methyl-phenoxy)-6-(1-methyl-6-oxo-1,6-dihydro-pyridin-3-yl)-pyrimidin-4-yl]-amide | (CD$_3$OD, 400 MHz) 8.54 (d, J = 2.4 Hz, 1H), 8.09 (dd, J = 2.8 Hz, 9.2 Hz, 1H), 7.20-7.04 (m, 3H), 6.85 (s, 1H), 6.62 (d, J = 9.2 Hz, 1H), 3.66 (s, 3H), 3.22-3.17 (m, 1H), 2.22 (s, 3H), 1.72-1.69 (m, 1H), 1.43-1.35 (m, 2H), 1.21-1.14 (m, 4H), 0.87 (t, J = 7.2 Hz, 3H) | 461 |
| 220 | 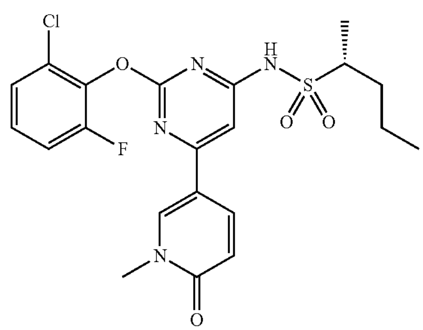 | (2R)-Pentane-2-sulfonic acid [2-(2-chloro-6-fluoro-phenoxy)-6-(1-methyl-6-oxo-1,6-dihydro-pyridin-3-yl)-pyrimidin-4-yl]-amide | (CD$_3$OD, 400 MHz) 8.54 (d, J = 2.4 Hz, 1H), 8.10-8.07 (dd, J = 2.4 Hz, 9.6 Hz, 1H), 7.37-7.26 (m, 3H), 6.90 (s, 1H), 6.62 (d, J = 9.6 Hz, 1H), 3.66 (s, 3H), 3.29-3.25 (m, 1H), 1.74-1.72 (m, 1H), 1.44-1.38 (m, 2H), 1.26-1.23 (m, 1H), 1.18 (d, J = 6.8 Hz, 3H), 0.89 (t, J = 7.2 Hz, 3H) | 481 |

TABLE 19-continued

| Example | Structure | IUPAC Name | ¹H NMR ppm (δ) | MS (M + H) |
|---|---|---|---|---|
| 221 | 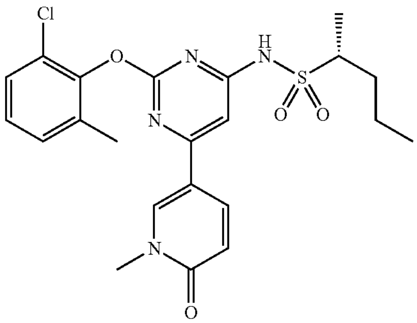 [SMILES: CCC[C@@H](C)S(=O)(=O)Nc1cc(-c2ccc(=O)n(C)c2)nc(Oc2c(C)cccc2Cl)n1] | (2R)-Pentane-2-sulfonic acid [2-(2-chloro-6-methyl-phenoxy)-6-(1-methyl-6-oxo-1,6-dihydro-pyridin-3-yl)-pyrimidin-4-yl]-amide | (CD$_3$OD, 400 MHz) 8.56 (d, J = 2.4 Hz, 1H), 8.12-8.09 (dd, J = 2.8 Hz, 9.6 Hz, 1H), 7.33 (d, J = 8.0 Hz, 1H), 7.26 (d, J = 6.8 Hz, 1H), 7.18 (t, J = 8.0 Hz, 1H), 6.84 (s, 1H), 6.63 (d, J = 9.6 Hz, 1H), 3.67 (s, 3H), 3.16-3.11 (m, 1H), 2.21 (s, 3H), 1.72-1.63 (m, 1H), 1.43-1.31 (m, 2H), 1.23-1.17 (m, 1H), 1.12 (d, J = 6.8 Hz, 3H), 0.87 (t, J = 7.6 Hz, 3H) | 477 |
| 222 | 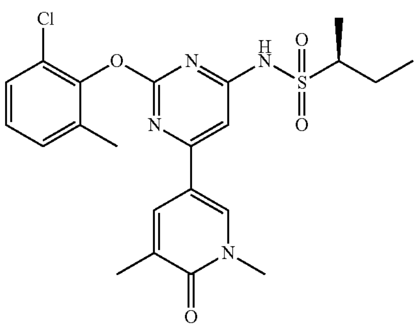 [SMILES: CC[C@H](C)S(=O)(=O)Nc1cc(-c2cc(C)c(=O)n(C)c2)nc(Oc2c(C)cccc2Cl)n1] | (S)-N-(2-(2-chloro-6-methylphenoxy)-6-(1,5-dimethyl-6-oxo-1,6-dihydropyridin-3-yl)pyrimidin-4-yl)butane-2-sulfonamide | (DMSO-d6, 400 MHz) 8.46 (s, 1H), 7.84 (s, 1H), 7.40 (d, J = 8.0 Hz, 1H), 7.31 (d, J = 8.0 Hz, 1H), 7.21 (t, J = 6.0 Hz, 1H) 6.81 (s, 1H), 3.57 (s, 3H), 2.88-2.83 (m, 1H), 2.14 (s, 3H), 2.10 (s, 3H), 1.61-1.59 (m, 1H), 1.30-1.24 (m, 1H), 0.99-0.97 (d, J= 8.0 Hz, 3H), 0.80-0.76 (t, J = 6.0 Hz, 3H), | 477 |
| 223 | 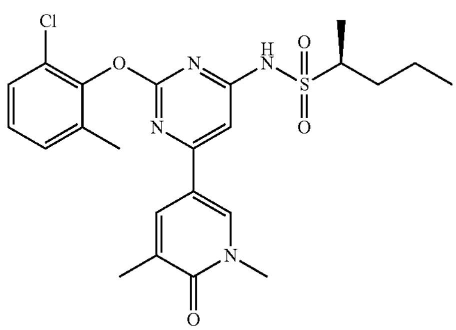 [SMILES: CCC[C@H](C)S(=O)(=O)Nc1cc(-c2cc(C)c(=O)n(C)c2)nc(Oc2c(C)cccc2Cl)n1] | (S)-N-(2-(2-chloro-6-methylphenoxy)-6-(1,5-dimethyl-6-oxo-1,6-dihydropyridin-3-yl)pyrimidin-4-yl)pentane-2-sulfonamide | (CDCl$_3$, 400 MHz) 8.23 (s, 1H), 7.70 (s, 1H), 7.29 (d, J = 8.0 Hz, 1H), 7.19 (d, J = 8.0 Hz, 1H), 7.12 (t, J = 8 Hz, 1H), 6.99. 1 (s, 1H), 3.62 (s, 3H), 3.20-3.15 (m, 1H), 2.24 (s, 3H), 2.21 (s, 3H), 1.88-1.82 (m, 1H), 1.63-1.60 (m, 2H), 1.29 (d, J = 8.0 Hz, 4H), 0.90 (t, J = 8.0 Hz, 3H) | 491 |
| 224 | 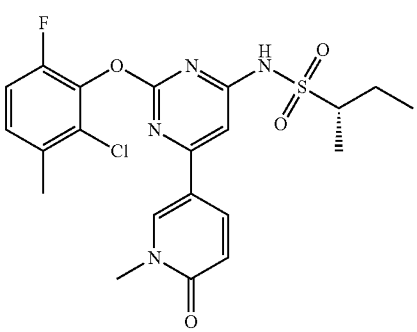 [SMILES: CC[C@H](C)S(=O)(=O)Nc1cc(-c2ccc(=O)n(C)c2)nc(Oc2c(F)ccc(C)c2Cl)n1] | (2S)-Butane-2-sulfonic acid [2-(2-chloro-6-fluoro-3-methyl-phenoxy)-6-(1-methyl-6-oxo-1,6-dihydro-pyridin-3-yl)-pyrimidin-4 yl]-amide | (CD$_3$OD, 400 MHz) 8.56 (d, J = 2.4 Hz, 1H), 8.09 (dd, J = 2.4 Hz, 9.6 Hz, 1H), 7.28-7.24 (m, 1H), 7.18-7.14 (m, 1H), 6.88 (s, 1H), 6.63 (d, J = 8.4 Hz, 1H), 3.66 (s, 3H), 3.31-3.30 (m, 1H), 2.40 (s, 3H), 1.84-1.78 (m, 1H), 1.50-1.42 (m, 1H), 1.16 (d, J = 6.8 Hz, 3H), 0.90 (t, J= 7.6 Hz, 3H) | 481 |

TABLE 19-continued

| Example | Structure | IUPAC Name | ¹H NMR ppm (δ) | MS (M + H) |
|---|---|---|---|---|
| 225 | (structure) | (S)-N-(2-(2,6-difluoro-3-methylphenoxy)-6-(1-methyl-6-oxo-1,6-dihydropyridin-3-yl)pyrimidin-4-yl)butane-2-sulfonamide | (DMSO-d6, 400 MHz) 8.56 (s, 1H), 7.89 (d, J = 8.0 Hz, 1H), 7.29-7.16 (m, 2H), 6.88 (s, 1H), 6.52 (d, J = 8.0 Hz, 1H), 3.55 (s, 3H), 3.04-3.02 (m, 1H), 2.25 (s, 3H), 1.73-1.66 (m, 1H), 1.40-1.33 (m, 1H), 1.08 (d, J = 8.0 Hz, 3H), 0.82 (t, J = 6.0 Hz, 3H) | 465 |
| 226 | (structure) | (S)-Butane-2-sulfonic acid [2-(6-chloro-2-fluoro-3-methyl-phenoxy)-6-(1-methyl-6-oxo-1,6-dihydro-pyridin-3-yl)-pyrimidin-4-yl]-amide | (CD₃OD, 400 MHz) 8.58 (d, J = 2.8 Hz, 1H), 8.11 (dd, J = 9.6 Hz, 2.8 Hz, 1H), 7.26-7.17 (m, 2H), 6.88 (s, 1H), 6.64 (d, J = 9.6 Hz, 1H), 3.67 (s, 3H), 3.15-3.10 (m, 1H), 2.31 (d, J = 2.0 Hz, 3H), 1.84-1.78 (m, 1H), 1.50-1.43 (m, 1H), 1.17 (d, J = 6.8 Hz, 3H), 0.91 (t, J = 7.2 Hz, 3H). | 481 |
| 227 | | (2S)-Pentane-2-sulfonic acid [2-(6-chloro-2-fluoro-3-methyl-phenoxy)-6-(1-methyl-6-oxo-1,6-dihydro-pyridin-3-yl)-pyrimidin-4-yl]-amide | (CD₃OD, 400 MHz) 8.56 (s, 1H), 8.09 (d, J = 8.0 Hz, 1H), 7.24-7.18 (m, 2H), 6.87 (s, 1H), 6.64 (d, J = 8.0 Hz, 1H), 3.66 (s, 3H), 3.30-3.18 (m, 1H), 2.30 (s, 3H), 1.76-1.67 (m, 1H), 1.46-1.34 (m, 2H), 1.25-1.19 (m, 1H), 1.16 (d, J = 8.0 Hz, 3H), 0.88 (t, J = 6.0 Hz, 3H) | 495 |
| 228 | | (2S)-Pentane-2-sulfonic acid [2-(2-chloro-6-fluoro-3-methyl-phenoxy)-6-(1-methyl-6-oxo-1,6-dihydro-pyridin-3-yl)-pyrimidin-4-yl]-amide | (CD₃OD, 400 MHz) 8.56 (d, J = 2.8 Hz, 1H), 8.10 (dd, J = 2.4 Hz, 9.2 Hz, 1H), 7.28-7.25 (m, 1H), 7.19-7.14 (m, 1H), 6.90 (s, 1H), 6.64 (d, J = 9.2 Hz, 1H), 3.66 (s, 3H), 3.24-3.21 (m, 1H), 2.40 (s, 3H), 1.73-1.72 (m, 1H), 1.45-1.38 (m, 2H), 1.23-1.20 (m, 1H), 1.17 (d, J = 7.2 Hz, 3H), 0.88 (t, J = 7.2 Hz, 3H) | 495 |
| 229 | | (S)-N-(2-(2,6-difluorophenoxy)-6-(1-methyl-6-oxo-1,6-dihydropyridin-3-yl)pyrimidin-4-yl)butane-2-sulfonamide | (400 MHz, DMSO-d₆) δ ppm 11.29-11.49 (br s, 1 H), 8.54-8.62 (m, 1 H), 7.85-7.94 (m, 1 H), 7.25-7.44 (m, 3 H), 6.89 (s, 1 H), 6.48-6.57 (m, 1 H), 3.55 (s, 3 H), 3.01-3.13 (m, 1 H), 1.62-1.77 (m, 1 H), 1.29-1.45 (m, 1 H), 1.05-1.13 (m, 3 H), 0.78-0.88 (m, 3 H) | 451 |
| 230 | | (R)-N-(2-(2,6-difluorophenoxy)-6-(1-methyl-6-oxo-1,6-dihydropyridin-3-yl)pyrimidin-4-yl)butane-2-sulfonamide | (400 MHz, DMSO-d₆) δ ppm 11.18-11.73 (br s, 1 H), 8.52-8.60 (m, 1 H), 7.85-7.93 (m, 1 H), 7.24-7.43 (m, 3 H), 6.85 (s, 1 H), 6.47-6.57 (m, 1 H), 3.55 (s, 3 H), 2.97-3.11 (m, 1 H), 1.62-1.76 (m, 1 | 451 |

TABLE 19-continued

| Example | Structure | IUPAC Name | $^1$H NMR ppm (δ) | MS (M + H) |
|---|---|---|---|---|
| | | | H), 1.27-1.41 (m, 1 H), 1.02-1.11 (m, 3 H), 0.78-0.87 (m, 3 H) | |

Examples 231-269 (Table 20) were prepared from the appropriate phenols, pyridin-2-ones and sulfonamides in a similar multi-step manner as Example 1.

TABLE 20

| Example | Structure | IUPAC Name | $^1$H NMR ppm (δ) | MS (M + H) |
|---|---|---|---|---|
| 231 | 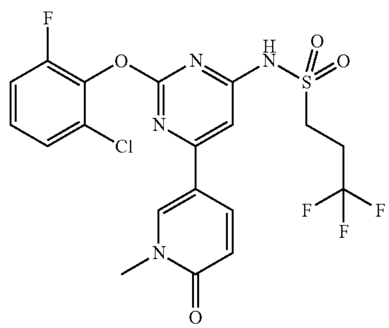 [SMILES: Cn1cc(-c2cc(NS(=O)(=O)CCC(F)(F)F)nc(Oc3c(F)cccc3Cl)n2)ccc1=O] | 3,3,3-Trifluoro-propane-1-sulfonic acid [2-(2-chloro-6-fluoro-phenoxy)-6-(1-methyl-6-oxo-1,6-dihydro-pyridin-3-yl)-pyrimidin-4-yl]-amide | (CD$_3$OD, 400 MHz) 8.56 (d, J = 2.8 HZ, 1H), 8.10 (dd, J = 9.6 Hz, 2.8 Hz, 1H), 7.37-7.22 (m, 3H), 6.89 (s, 1H), 6.61 (d, J = 9.6 Hz, 1H), 3.65 (s, 3H), 3.39-3.35 (m, 2H), 2.57-2.51 (m, 2H) | 507 |
| 232 | 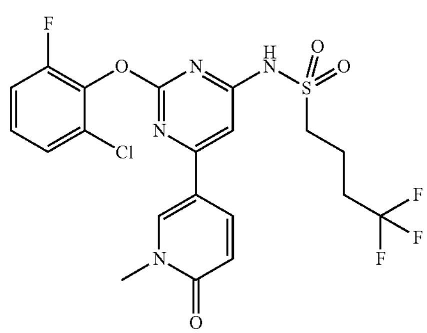 [SMILES: Cn1cc(-c2cc(NS(=O)(=O)CCCC(F)(F)F)nc(Oc3c(F)cccc3Cl)n2)ccc1=O] | 4,4,4-Trifluoro-butane-1-sulfonic acid [2-(2-chloro-6-fluoro-phenoxy)-6-(1-methyl-6-oxo-1,6-dihydro-pyridin-3-yl)-pyrimidin-4-yl]-amide | (CD$_3$OD, 400 MHz) 8.55 (d, J = 2.4 HZ, 1H), 8.08 (dd, J = 9.6 Hz, 2.4 Hz, 1H), 7.39-7.38 (m, 1H), 7.34-7.25 (m, 2H), 6.92 (s, 1H), 6.61 (d, J = 9.6 Hz, 1H), 3.65 (s, 3H), 3.25 (t, J = 7.6 Hz, 2H), 2.29-2.222 (m, 2H), 1.93-1.85 (m, 2H) | 521 |
| 233 | 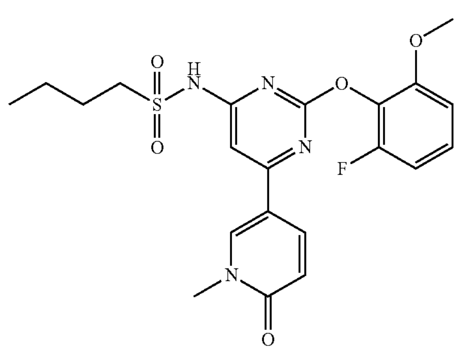 [SMILES: CCCCS(=O)(=O)Nc1cc(-c2ccc(=O)n(C)c2)nc(Oc2c(F)cccc2OC)n1] | Butane-1-sulfonic acid [2-(2-fluoro-6-methoxy-phenoxy)-6-(1-methyl-6-oxo-1,6-dihydro-pyridin-3-yl)-pyrimidin-4-yl]-amide | (CD$_3$OD, 400 MHz) 8.53 (d, J = 2.4 Hz, 1h), 8.09 (dd, J = 2.0 Hz, 9.2 Hz, 1H), 7.25-7.23 (m, 1H), 6.95 (d, J = 8.4 Hz, 1H), 6.88-6.83 (m, 2H), 6.62 (d, J = 9.2 Hz, 1H), 3.80 (s, 3H), 3.66 (s, 3H), 3.07 (t, J = 7.8 Hz, 2H), 1.62-1.54 (m, 2H), 1.35-1.29 (m, 2H), 0.,88 (t, J = 7.2 Hz, 3H) | 463 |

TABLE 20-continued

| Example | Structure | IUPAC Name | $^1$H NMR ppm (δ) | MS (M + H) |
|---|---|---|---|---|
| 234 | 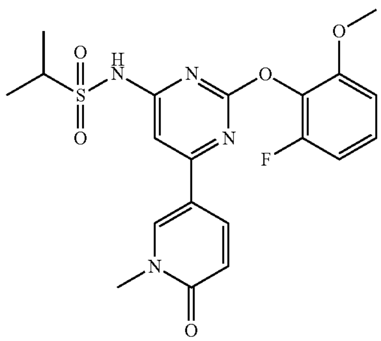 [SMILES: COc1cccc(F)c1Oc1nc(NS(=O)(=O)C(C)C)cc(-c2ccc(=O)n(C)c2)n1] | Propane-2-sulfonic acid [2-(2-fluoro-6-methoxy-phenoxy)-6-(1-methyl-6-oxo-1,6-dihydro-pyridin-3-yl)-pyrimidin-4-yl]-amide | (CD$_3$OD, 400 MHz) 8.46 (d, J = 2.4 Hz, 1H), 8.08 (dd, J = 2.8, 9.6 Hz, 1H), 7.25-7.19 (m, 1H), 6.93 (d, J = 8.8 Hz, 1H), 6.86-6.82 (m, 1H), 6.70 (s, 1H), 6.61 (d, J = 9.6 Hz, 1H), 3.80 (s, 3H), 3.65 (s, 3H), 3.29-3.25 (m, 1H), 1.11 (d, J = 6.4 Hz, 6H) | 449 |
| 235 | 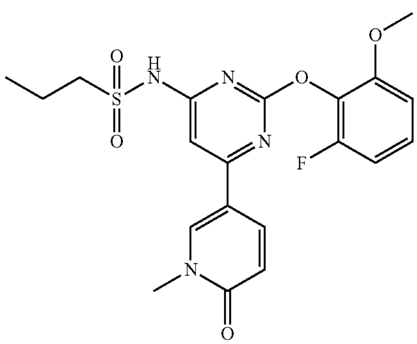 [SMILES: CCCS(=O)(=O)Nc1cc(-c2ccc(=O)n(C)c2)nc(Oc2c(F)cccc2OC)n1] | Propane-1-sulfonic acid [2-(2-fluoro-6-methoxy-phenoxy)-6-(1-methyl-6-oxo-1,6-dihydro-pyridin-3-yl)-pyrimidin-4-yl]-amide | (CD$_3$OD, 400 MHz) 8.53 (d, J = 2.4 Hz, 1H), 8.09 (dd, J = 2.4 Hz, 9.6 Hz, 1H), 7.27-7.21 (m, 1H), 6.96 (d, J = 8.4 Hz, 1H), 6.88-6.83 (m, 2H), 6.62 (d, J = 9.2 Hz, 1H), 3.81 (s, 3H), 3.66 (s, 3H), 3.06-3.03 (m, 2H), 1.66-1.60 (m, 2H), 0.93 (t, J = 7.6 Hz, 3H) | 449 |
| 236 | 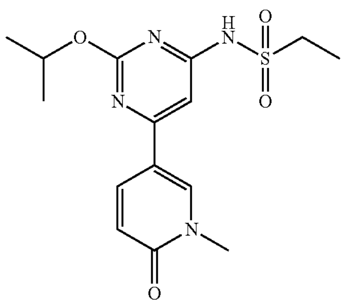 [SMILES: CCS(=O)(=O)Nc1cc(-c2ccc(=O)n(C)c2)nc(OC(C)C)n1] | Ethanesulfonic acid [2-isopropoxy-6-(1-methyl-6-oxo-1,6-dihydro-pyridin-3-yl)-pyrimidin-4-yl]-amide | (CD$_3$OD, 400 MHz) 8.50 (d, J = 2.8 Hz, 1H), 8.10 (dd, J = 9.6 Hz, 2.8 Hz, 1H), 6.80 (s, 1H), 6.62 (d, J = 10.0 Hz, 1H), 5.34-5.28 (m, 1H), 3.65 (s, 3H), 3.56-3.51 (m, 2H), 1.40-1.35 (m, 9H) | 353 |
| 237 | 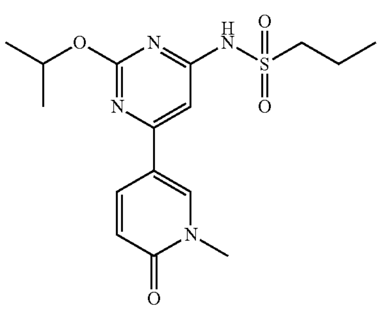 [SMILES: CCCS(=O)(=O)Nc1cc(-c2ccc(=O)n(C)c2)nc(OC(C)C)n1] | Propane-1-sulfonic acid [2-isopropoxy-6-(1-methyl-6-oxo-1,6-dihydro-pyridin-3-yl)-pyrimidin-4-yl]-amide | (CD$_3$OD, 400 MHz) 8.50 (d, J = 2.4 Hz, 1H), 8.09 (d, J = 9.6 Hz, 2.8 Hz, 1H), 6.79 (s, 1H), 6.61 (d, J = 9.6 Hz, 1H), 5.35-5.28 (m, 1H), 3.65 (s, 3h), 3.53-3.49 (m, 2H), 1.91-1.82 (m, 2H), 1.40 (d, J = 6.0 Hz, 6H), 1.07 (q, J = 7.2 Hz, 3H) | 367 |

TABLE 20-continued

| Example | Structure | IUPAC Name | ¹H NMR ppm (δ) | MS (M + H) |
|---|---|---|---|---|
| 238 | 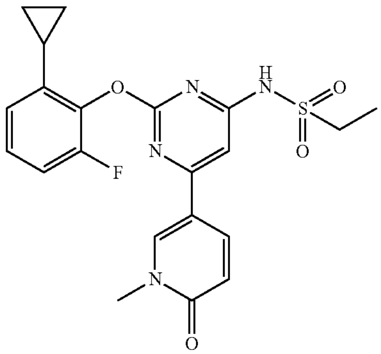 [SMILES: CCS(=O)(=O)Nc1cc(-c2ccc(=O)n(C)c2)nc(Oc2c(F)cccc2C2CC2)n1] | Ethanesulfonic acid [2-(2-cyclopropyl-6-fluoro-phenoxy)-6-(1-methyl-6-oxo-1,6-dihydro-pyridin-3-yl)-pyrimidin-4-yl]-amide | (CD₃OD, 400 MHz) 8.51 (d, J = 2.4 Hz, 1H), 8.09 (dd, J = 2.4 Hz, 9.2 Hz, 1H), 7.18-7.14 (m, 1H), 7.06-7.01 (m, 1H), 6.83-6.81 (m, 2H), 6.62 (d, J = 9.2 Hz, 1H), 3.65 (s, 3H), 3.06-3.00 (m, 2H), 2.01-1.97 (m, 1H), 1.13 (t, J = 7.2 Hz, 3H), 0.88-0.83 (m, 2H), 0.70-0.66 (m, 2H) | 445 |
| 239 | 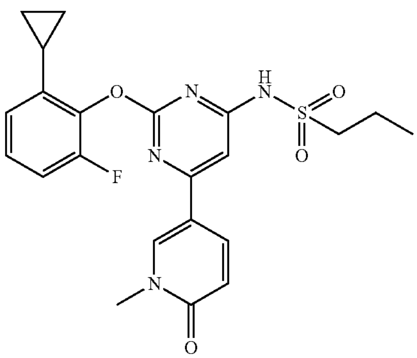 [SMILES: CCCS(=O)(=O)Nc1cc(-c2ccc(=O)n(C)c2)nc(Oc2c(F)cccc2C2CC2)n1] | Propane-1-sulfonic acid [2-(2-cyclopropyl-6-fluoro-phenoxy)-6-(1-methyl-6-oxo-1,6-dihydro-pyridin-3-yl)-pyrimidin-4-yl]-amide | (CD₃OD, 400 MHz) 8.56 (d, J = 2.8 Hz, 1H), 8.10 (dd, J = 2.4 Hz, 9.6 Hz, 1H), 7.21-7.16 (m, 1H), 7.07-7.02 (m, 1H), 6.86-6.84 (m, 2H), 6.63 (d, J = 9.2 Hz, 1H), 3.66 (s, 3H), 3.07-3.03 (m, 2H), 2.00-1.96 (m, 1H), 1.66-1.60 (m, 2H), 0.93 (t, J = 7.2 Hz, 3H), 0.88-0.83 (m, 2H), 0.71-0.67 (m, 2H) | 459 |
| 240 | 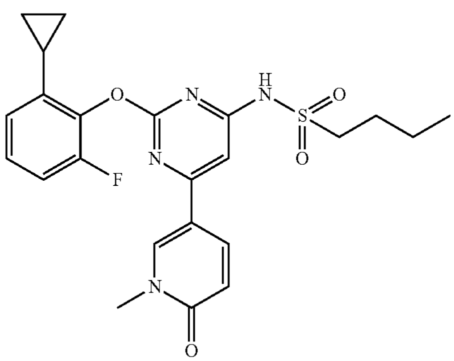 [SMILES: CCCCS(=O)(=O)Nc1cc(-c2ccc(=O)n(C)c2)nc(Oc2c(F)cccc2C2CC2)n1] | Butane-1-sulfonic acid [2-(2-cyclopropyl-6-fluoro-phenoxy)-6-(1-methyl-6-oxo-1,6-dihydro-pyridin-3-yl)-pyrimidin-4-yl]-amide | (CD₃OD, 400 MHz) 8.56 (d, J = 2.8 Hz, 1H), 8.10 (dd, J = 2.8 Hz, 9.6 Hz, 1H), 7.21-7.16 (m, 1H), 7.06-7.02 (m, 1H), 6.86-6.84 (m, 2H), 6.63 (d, J = 9.6 Hz, 1H), 3.66 (s, 3H), 3.10-3.06 (m, 2H), 2.00-1.96 (m, 1H), 1.62-1.54 (m, 2H), 1.35-1.29 (m, 2H), 0.90-0.83 (m, 5H), 0.70-0.66 (m, 2H) | 473 |
| 241 | 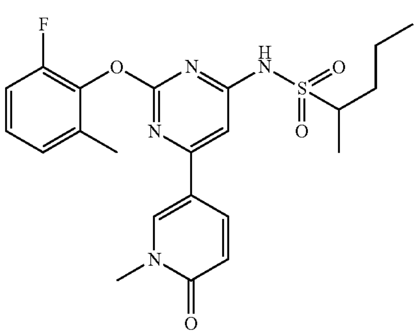 [SMILES: CCCC(C)S(=O)(=O)Nc1cc(-c2ccc(=O)n(C)c2)nc(Oc2c(C)cccc2F)n1] | Pentane-2-sulfonic acid [2-(2-fluoro-6-methyl-phenoxy)-6-(1-methyl-6-oxo-1,6-dihydro-pyridin-3-yl)-pyrimidin-4-yl]-amide | (CD₃OD, 400 MHz), 8.55 (d, J = 2.4 Hz, 1H), 8.09 (dd, J = 9.6 Hz, 2.4 Hz, 1H), 7.28-7.04 (m, 3H), 6.86 (s, 1H), 6.65 (d, J = 9.6 Hz, 1H), 3.66 (s, 3H), 3.28-3.17 (m, 1H), 2.22 (s, 3H), 1.73-1.66 (m, 1H), 1.43-1.33 (m, 2H), 1.21-1.08 (m, 4H), 0.82 (t, J = 7.2 Hz, 3H). | 461 |

TABLE 20-continued

| Example | Structure | IUPAC Name | ¹H NMR ppm (δ) | MS (M + H) |
|---|---|---|---|---|
| 242 | 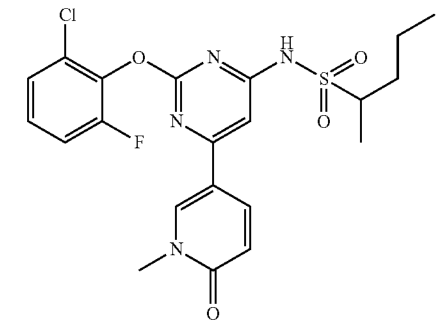 | Pentane-2-sulfonic acid [2-(2-chloro-6-fluoro-phenoxy)-6-(1-methyl-6-oxo-1,6-dihydro-pyridin-3-yl)-pyrimidin-4-yl]-amide | (CD$_3$OD, 400 MHz) 8.55 (s, 1H), 8.10 (d, J = 9.6 Hz, 1H), 7.38-7.24 (m, 3H), 6.94 (s, 1H), 6.62 (d, J = 9.6 Hz, 1H), 3.62 (s, 3H), 3.26-3.24 (m, 1H), 1.76-1.71 (m, 1H), 1.49-1.38 (m, 2H), 1.28-1.11 (m, 1H), 1.20 (d, J = 7.2 Hz, 3H), 0.89 (t, J = 7.2 Hz, 3H). | 481 |
| 243 | 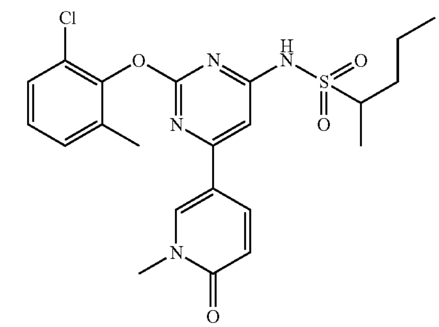 | Pentane-2-sulfonic acid [2-(2-chloro-6-methyl-pphenoxy)-6-(1-methyl-6-oxo-1,6-dihydro-pyridin-3-yl)-pyrimidin-4-yl]-amide | (DMSO-d$_6$, 400 MHz), 11.25 (br, 1H), 8.61 (s, 1H), 7.92 (d, J = 9.6 Hz, 1H), 7.41 (d, J = 7.2 Hz, 1H), 7.33 (d, J = 7.6 Hz, 1H), 7.22 (t, J = 7.6 Hz, 1H), 6.83 (s, 1H), 6.54 (d, J = 9.6 Hz, 1H), 3.55 (s, 3H), 3.01-2.96 (m, 1H), 2.14 (s, 3H), 1.56-1.51 (m, 1H), 1.30-1.22 (m, 2H), 1.11-1.08 (m, 1H), 1.01 (d, J = 7.2 Hz, 3H), 0.83-0.79 (t, J = 7.2 Hz, 3H). | 477 |
| 244 | 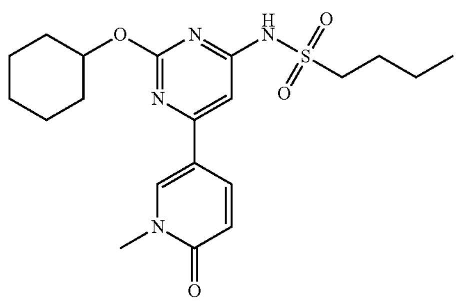 [SMILES: CCCCS(=O)(=O)Nc1cc(-c2ccc(=O)n(C)c2)nc(OC2CCCCC2)n1] | Butane-1-sulfonic acid [2-cyclohexyloxy-6-(1-methyl-6-oxo-1,6-dihydro-pyridin-3-yl)-pyrimidin-4-yl]-amide | (CD$_3$OD, 400 MHz) 8.48 (d, J = 2.8 Hz, 1H), 8.08 (dd, J = 2.4 Hz, 9.2 Hz 1H), 6.76 (s, 1H), 6.62 (d, J = 9.2 Hz, 1H), 5.03-5.02 (m, 1H), 3.66 (s, 3H), 3.56-3.52 (m, 2H), 2.09-2.06 (m, 2H), 1.86-1.78 (m, 4H), 1.63-1.44 (m, 8H), 0.95 (t, J= 7.2 Hz, 3H) | 421 |
| 245 | 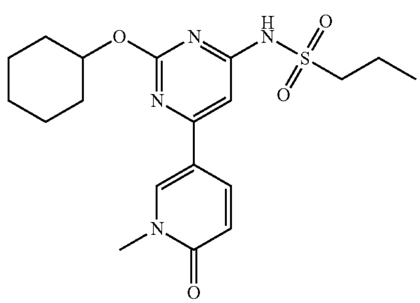 [SMILES: CCCS(=O)(=O)Nc1cc(-c2ccc(=O)n(C)c2)nc(OC2CCCCC2)n1] | Propane-1-sulfonic acid [2-cylcohexyloxy-6-(1-methyl-6-oxo-1,6-dihydro-pyridin-3-yl)-pyrimidin-4-yl]-amide | (CD$_3$OD, 400 MHz) 8.47 (d, J = 2.4 Hz, 1H), 8.08 (dd, J = 2.4 Hz, 9.6 Hz, 1H), 6.74 (s, 1H), 6.62 (d, J = 9.2 Hz, 1H), 5.03-5.02 (m, 1H), 3.65 (s, 3H), 3.52-3.49 (m, 2H), 2.10-2.06 (m, 2H), 1.90-1.82 (m, 4H), 1.63-1.09 (m, 6H), 1.07 (t, J = 7.6 Hz, 3H) | 407 |
| 246 | 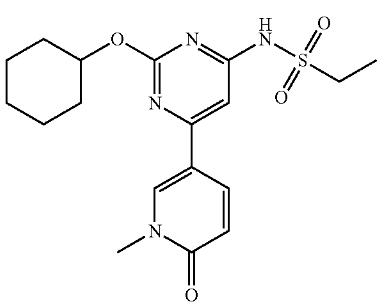 [SMILES: CCS(=O)(=O)Nc1cc(-c2ccc(=O)n(C)c2)nc(OC2CCCCC2)n1] | Ethanesulfonic acid [2-cylcohexyloxy-6-(1-methyl-6-oxo-1,6-dihydro-pyridin-3-yl)-pyrimidin-4-yl]-amide | (CD$_3$OD, 400 MHz) 8.49 (s, 1H), 8.08 (d, J = 9.2 Hz, 1H), 6.79 (s, 1H), 6.62 (d, J = 9.2 Hz, 1H), 503-5.02 (m, 1H), 3.66 (s, 3H), 3.57-3.52 (m, 2H), 2.08-2.06 (m, 2H), 1.85-1.82 (m, 2H), 1.63-1.36 (m, 9H) | 393 |

TABLE 20-continued

| Example | Structure | IUPAC Name | ¹H NMR ppm (δ) | MS (M + H) |
|---|---|---|---|---|
| 247 | 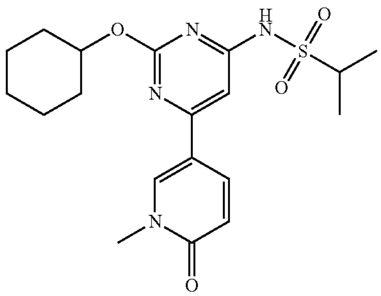 [SMILES: CC(C)S(=O)(=O)Nc1cc(-c2ccc(=O)n(C)c2)nc(OC2CCCCC2)n1] | Propane-2-sulfonic acid [2-cylcohexyloxy-6-(1-methyl-6-oxo-1,6-dihydro-pyridin-3-yl)-pyrimidin-4-yl]-amide | (CD₃OD, 400 MHz) 8.49 (s, 1H), 8.08 (d, J = 9.2 Hz, 1H), 6.83 (s, 1H), 6.62 (d, J = 9.6 Hz, 1H), 5.04-4.99 (m, 1H), 3.91-3.89 (m, 1H), 3.66 (s, 3H), 2.10-2.06 (m, 2H), 1.86-1.81 (m, 2H), 1.65-1.36 (m, 12H) | 407 |
| 248 | 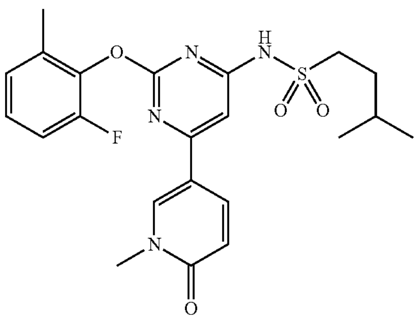 [SMILES: Cc1cccc(F)c1Oc1nc(NS(=O)(=O)CCC(C)C)cc(-c2ccc(=O)n(C)c2)n1] | 3-Methyl-butane-1-sulfonic acid [2-(2-fluoro-6-methyl-phenoxy)-6-(1-methyl-6-oxo-1,6-dihydro-pyridin-3-yl)-pyrimidin-4-yl]-amide | (CD₃OD, 400 MHz) 8.53-8.51 (m, 1H), 8.10-8.07 (m, 1H), 7.18-7.03 (m, 3H), 6.85 (s, 1H), 6.62 (d, J = 9.6 Hz, 1H), 3.65 (s, 3H), 3.09-3.04 (m, 2H), 2.22 (s, 3H) 1.55-1.45 (m, 3H), 0.88-0.84 (m, 6H) | 461 |
| 249 | 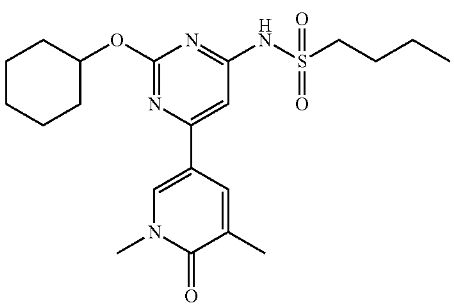 [SMILES: CCCCS(=O)(=O)Nc1cc(-c2cc(C)c(=O)n(C)c2)nc(OC2CCCCC2)n1] | Butane-1-sulfonic acid [2-cyclohexyloxy-6-(1,5-dimethyl-6-oxo-1,6-dihydro-pyridin-3-yl)-pyrimidin-4-yl]-amide | (CDCl₃, 400 MHz) 8.25 (s, 1H), 7.73 (s, 1H), 6.90 (s, 1H), 5.04-5.02 (m, 1H), 3.67 (s, 3H), 3.37-3.36 (m, 2H), 2.23 (s, 3H), 2.11-2.04 (m, 2H), 1.87-1.84 (m, 4H), 1.64-1.61 (m, 2H), 1.51-1.31 (m, 6H), 0.95 (t, J = 7.2 Hz, 3H). | 435 |
| 250 | 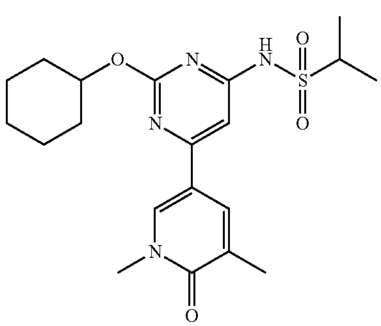 [SMILES: Cc1cc(-c2cc(NS(=O)(=O)C(C)C)nc(OC3CCCCC3)n2)cn(C)c1=O] | Propane-2-sulfonic acid [2-cyclohexyloxy-6-(1,5-dimethyl-6-oxo-1,6-dihydro-pyridin-3-yl)-pyrimidin-4-yl]-amide | (CDCl₃ + CD₃OD, 400 MHz) 8.30 (d, J = 2.4 Hz, 1H), 7.92-7.91 (m, 1H), 6.81 (s, 1H), 5.03-4.98 (m, 1H), 3.88-3.86 (m, 1H), 3.38 (s, 3H), 2.21 (s, 3H), 2.11-2.08 (m, 2H), 1.89-1.85 (m, 2H), 1.65-1.56 (m, 2H), 1.49-1.35 (m, 10H). | 421 |
| 251 | 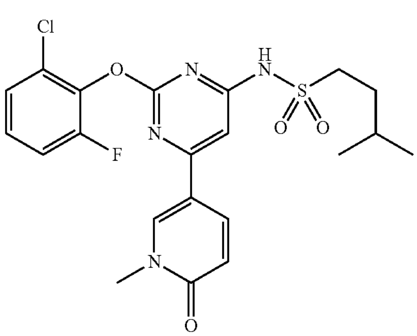 [SMILES: CC(C)CCS(=O)(=O)Nc1cc(-c2ccc(=O)n(C)c2)nc(Oc2c(F)cccc2Cl)n1] | 3-Mehtyl-butane-1-sulfonic acid [2-(2-chloro-6-fluoro-phenoxy)-6-(1-methyl-6-oxo-1,6-dihydro-pyridin-3-yl)-pyrimidin-4-yl]-amide | (CD₃OD, 400 MHz) 8.52 (d, J = 2.4 Hz, 1H), 8.08 (dd, J = 9.6 Hz, 2.4 Hz, 1H), 7.39-7.22 (m, 3H), 6.87 (s, 1H), 6.61 (d, J = 9.6 Hz, 1H), 3.65 (s, 3H), 3.16-3.09 (m, 2H), 1.59-1.48 (m, 3H), 0.87 (d, J = 6.4 Hz, 6H) | 481 |

TABLE 20-continued

| Example | Structure | IUPAC Name | $^1$H NMR ppm (δ) | MS (M + H) |
|---|---|---|---|---|
| 252 | 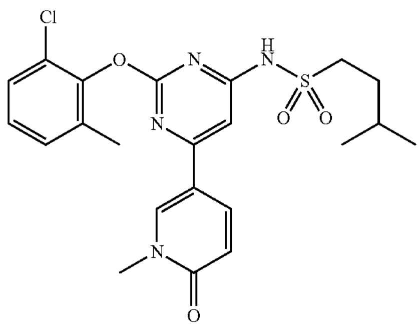 [SMILES: Cc1cccc(Cl)c1Oc1nc(NS(=O)(=O)CCC(C)C)cc(-c2ccc(=O)n(C)c2)n1] | 3-Methyl-butane-1-sulfonic acid [2-(2-chloro-6-methyl-phenoxy)-6-(1-methyl-6-oxo-1,6-dihydro-pyridin-3-yl)-pyrimidin-4-yl]-amide | (CD$_3$OD, 400 MHz) 8.53 (d, J = 2.4 Hz, 1H), 8.08 (dd, J = 9.6 Hz, 2.4 Hz, 1H), 7.31 (d, J = 6.4 Hz, 1H), 7.25 (d, J = 7.6 Hz, 1H), 7.16 (t, J = 7.6 Hz, 1H0, 6.81 (s, 1H), 6.61 (d, J = 9.6 Hz, 1H), 3.65 (s, 3H), 3.04-2.95 (m, 2H), 2.20 (s, 3H), 1.53-1.42 (m, 3H), 0.84 (d, J = 6.4 Hz, 6H) | 477 |
| 253 | 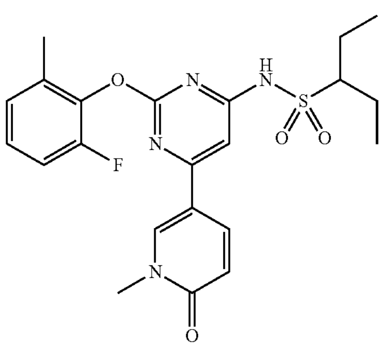 [SMILES: CCC(CC)S(=O)(=O)Nc1cc(-c2ccc(=O)n(C)c2)nc(Oc2c(C)cccc2F)n1] | Pentane-3-sulfonic acid [2-(2-fluoro-6-methyl-pphenoxy)-6-(1-methyl-6-oxo-1,6-dihydro-pyridin-3-yl)-pyrimidin-4-yl]-amide | (CD$_3$OD, 400 MHz) 8.56 (d, J = 2.4 Hz, 1H), 8.10 (dd, J = 9.6, 2.4 Hz, 1H), 7.22-7.03 (m, 3H), 6.83 (s, 1H), 6.63 (d, J = 9.6 Hz, 1H, 3.67 (s, 3H), 3.06-2.97 (m, 1H), 2.23 (s, 3H), 1.78-1.67 (m, 2H), 1.62-1.57 (m, 2H), 0.89 (t, J = 7.5 Hz, 6H) | 461 |
| 254 | 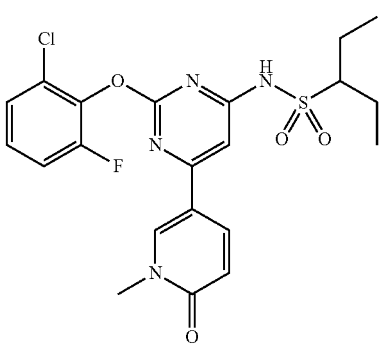 | Pentane-3-sulfonic acid [2-(2-chloro-6-fluoro-phenoxy)-6-(1-methyl-6-oxo-1,6-dihydro-pyridin-3-yl)-pyrimidin-4-yl]-amide | (CD$_3$OD, 400 MHz) 8.55 (d, J = 2.4 Hz, 1H), 8.09 (dd, J = 9.6 Hz, 2.4 Hz, 1H), 7.38-7.24 (m, 3H), 6.85 (s, 1H), 6.63 (d, J = 9.6 Hz, 1H), 3.66 (s, 3H), 3.09-3.07 (m, 1H), 1.82-1.71 (m, 2H), 1.67-1.60 (m, 2H), 0.92 (t, J = 7.6 Hz, 6H) | 481 |
| 255 | 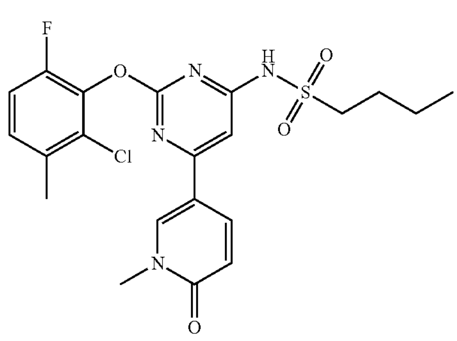 [SMILES: CCCCS(=O)(=O)Nc1cc(-c2ccc(=O)n(C)c2)nc(Oc2c(F)ccc(C)c2Cl)n1] | Butane-1-sulfonic acid [2-(2-chloro-6-fluoro-3-methyl-phenoxy)-6-(1-methyl-6-oxo-1,6-dihydro-pyridin-3-yl)-pyrimidin-4-yl]-amide | (CD$_3$OD, 400 MHz) 8.54 (s, 1H), 8.08 (dd, J = 2.4 Hz,, 9.6 Hz, 1H), 7.27-7.24 (m, 1H), 7.18-7.13 (m, 1H), 6.87 (s, 1H), 6.62 (d, J = 9.6 Hz, 1H), 3.66 (s, 3H), 3.11-3.07 (m, 2H), 2.39 (s, 3H), 1.61-1.57 (m, 2H), 1.36-1.30 (m, 2H), 0.89 (t, J = 7.2 Hz, 3H) | 481 |

TABLE 20-continued

| Example | Structure | IUPAC Name | ¹H NMR ppm (δ) | MS (M + H) |
|---|---|---|---|---|
| 256 | 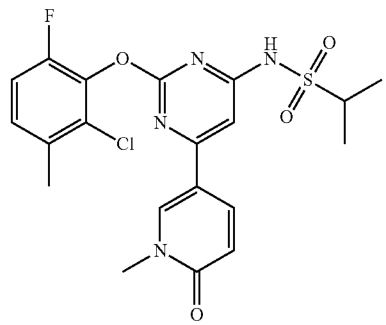 [SMILES: Cc1ccc(F)c(Oc2nc(NS(=O)(=O)C(C)C)cc(-c3ccc(=O)n(C)c3)n2)c1Cl] | Propane-2-sulfonic acid [2-(2-chloro-6-fluoro-3-methyl-phenoxy)-6-(1-methyl-6-oxo-1,6-dihydro-pyridin-3-yl)-pyrimidin-4-yl]-amide | (CD₃OD, 400 MHz) 8.55 (d, J = 2.4 Hz, 1H), 8.09 (dd, J = 2.4 Hz, 9.2 Hz, 1H), 7.28-7.24 (m, 1H), 7.19-7.14 (m, 1H), 6.91 (s, 1H), 6.62 (d, J = 9.6 Hz, 1H), 3.66 (s, 3H), 3.36-3.30 (m, 1H), 2.40 (s, 3H), 1.19 (d, J = 6.8 Hz, 6H) | 467 |
| 257 | 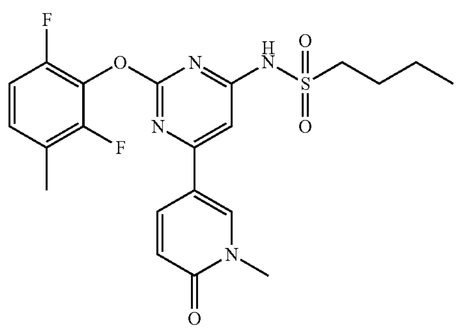 [SMILES: CCCCS(=O)(=O)Nc1cc(-c2ccc(=O)n(C)c2)nc(Oc2c(F)ccc(C)c2F)n1] | Butane-1-sulfonic acid [2-(2,6-difluoro-3-methyl-phenoxy)-6-(1-methyl-6-oxo-1,6-dihydro-pyridin-3-yl)-pyrimidin-4-yl]-amide | (DMSO-d6, 400 MHz) 8.56 (s, 1H), 7.88 (d, J = 8.0 Hz, 1H), 7.26-7.20 (m, 1H), 7.19-7.15 (m, 1H), 6.86 (s, 1H), 6.51 (d, J = 8.0 Hz, 1H), 3.57 (s, 3H), 3.07 (t, J = 6.0 Hz, 2H), 2.25 (s, 3H), 1.50-1.44 (m, 2H), 1.27-1.21 (m, 2H), 0.81 (t, J = 6.0 Hz, 3H) | 465 |
| 258 | 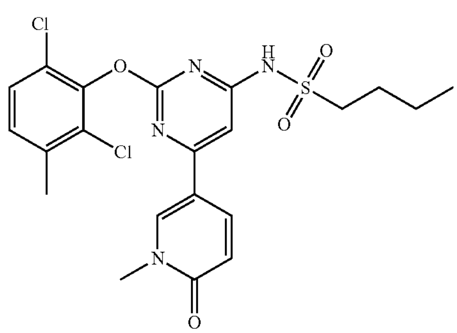 | Butane-1-sulfonic acid [2-(6-chloro-2-fluoro-3-methyl-phenoxy)-6-(1-methyl-6-oxo-1,6-dihydro-pyridin-3-yl)-pyrimidin-4-yl]-amide | (CD₃OD, 400 MHz) 8.56 (d, J = 2.4 Hz, 1H), 8.09 (dd, J = 9.6 Hz, 2.4 Hz, 1H), 7.25-7.15 (m, 2H), 6.87 (s, 1H), 6.62 (d, J = 10.0 Hz, 1H) 3.66 (s, 3H), 3.10-3.06 (m, 2H), 2.30 (d, J = 2.0 Hz, 3H), 1.63-1.55 (m, 2H), 1.36-1.31 (m, 2H), 0.89 (t, J = 7.2 Hz, 3H). | 481 |
| 259 | 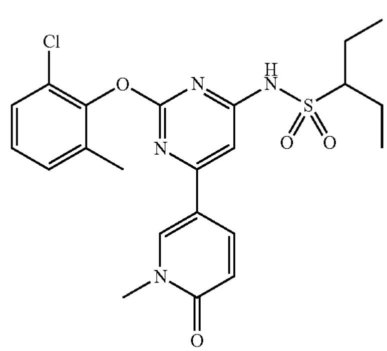 [SMILES: CCC(CC)S(=O)(=O)Nc1cc(-c2ccc(=O)n(C)c2)nc(Oc2c(C)cccc2Cl)n1] | Pentane-3-sulfonic acid [2-(2-chloro-6-methyl-phenoxy)-6-(1-methyl-6-oxo-1,6-dihydro-pyridin-3-yl)-pyrimidin-4-yl]-amide | (CD₃OD, 400 MHz) 8.58 (d, J = 2.4 Hz, 1H), 8.11 (dd, J = 9.6 Hz, 2.4 Hz, 1H), 7.34 (d, H = 8.0 Hz, 1H), 7.27 (d, J = 6.8 Hz, 1H), 7.18 (t, J = 7.6 Hz, 1H), 6.80 (s, 1H), 6.64 (d, J = 9.6 Hz, 1H), 3.67 (s, 3H), 3.02-2.92 (m, 1H), 2.22 (s, 3H), 1.75-1.66 (m, 2H), 1.66-1.55 (m, 2H), 0.89 (t, J = 7.6 Hz, 6H) | 477 |

TABLE 20-continued

| Example | Structure | IUPAC Name | ¹H NMR ppm (δ) | MS (M + H) |
|---|---|---|---|---|
| 260 | 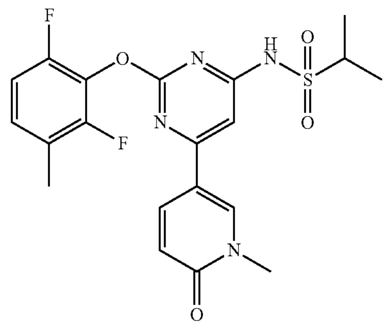 [SMILES: Cc1ccc(F)c(Oc2nc(NS(=O)(=O)C(C)C)cc(-c3ccc(=O)n(C)c3)n2)c1F] | Propane-2-sulfonic acid [2-(2,6-difluoro-3-methyl-phenoxy)-6-(1-methyl-6-oxo-1,6-dihydro-pyridin-3-yl)-pyrimidin-4-yl]-amide | (DMSO-d6, 400 MHz) 8.53 (s, 1H), 7.89 (d, J = 8.0 Hz, 1H), 7.27-7.17 (m, 2H), 6.82 (s, 1H), 6.49 (d, J = 8.0 Hz, 1H), 3.55 (s, 3H), 3.26-3.22 (m, 1H), 2.25 (s, 3H), 1.08 (d, J = 4.0 Hz, 6H) | 451 |
| 261 | 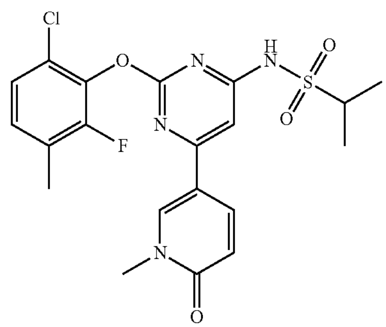 | Propane-2-sulfonic acid [2-(6-chloro-2-fluoro-3-methyl-phenoxy)-6-(1-methyl-6-oxo-1,6-dihydro-pyridin-3-yl)-pyrimidin-4-yl]-amide | (CD₃OD, 400 MHz) 8.54 (d, J = 2.4 Hz, 1H), 8.08 (dd, J = 9.6 Hz, 2.4 Hz, 1H), 7.24-7.16 (m, 2H), 6.89 (s, 1H), 6.61 (d, J = 9.2 Hz, 1H), 3.65 (s, 3H), 3.35-3.31 (m, 1H), 2.30 (s, 3H), 1.18 (d, J = 6.8 Hz, 6H). | 467 |
| 262 | 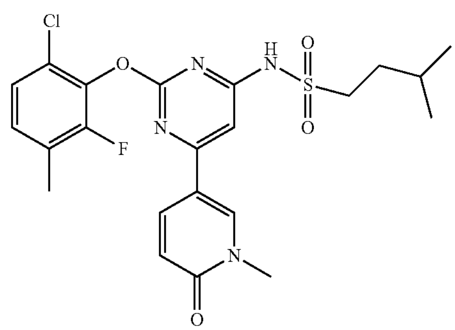 [SMILES: Cc1ccc(Cl)c(Oc2nc(NS(=O)(=O)CCC(C)C)cc(-c3ccc(=O)n(C)c3)n2)c1F] | 3-Methyl-butane-1-sulfonic acid [2-(6-chloro-2-fluoro-3-methyl-phenoxy)-6-(1-methyl-6-oxo-1,6-dihydro-pyridin-3-yl)-pyrimidin-4-yl]-amide | (CD₃OD, 400 MHz) 8.56 (s, 1H), 8.09 (d, J = 8.0 Hz, 1H), 7.21-7.18 (m, 2H), 6.87 (s, 1H), 6.64 (d, J = 8.0 Hz, 1H), 3.66 (s, 3H), 3.10 (t, J = 7.2 Hz, 2H), 2.30 (s, 3H), 1.53-1.48 (m, 3H), 0.85 (d, J = 4.0 Hz, 6H) | 495 |
| 263 | 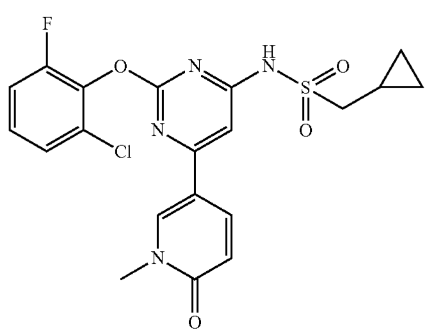 [SMILES: Cn1cc(-c2cc(NS(=O)(=O)CC3CC3)nc(Oc3c(F)cccc3Cl)n2)ccc1=O] | N-[2-(2-Chloro-6-fluoro-phenoxy)-6-(1-methyl-6-oxo-1,6-dihydro-pyridin-3-yl)-pyrimidin-4-yl]-C-cyclopropyl-methanesulfonamide | (CD₃OD, 400 MHz) 8.55 (d, J = 2.4 Hz, 1H), 8.09 (dd, J = 9.6 Hz, 2.4 Hz, 1H), 7.38-7.24 (m, 3H), 6.93 (s, 1H), 6.62 (d, J = 9.6 Hz, 1H), 3.66 (s, 3H), 3.03 (d, J = 7.2 Hz, 2H), 1.01-0.97 (m, 1H), 0.63-0.51 (m, 2H), 0.23-0.13 (m, 2H) | 465 |

TABLE 20-continued

| Example | Structure | IUPAC Name | ¹H NMR ppm (δ) | MS (M + H) |
|---|---|---|---|---|
| 264 | 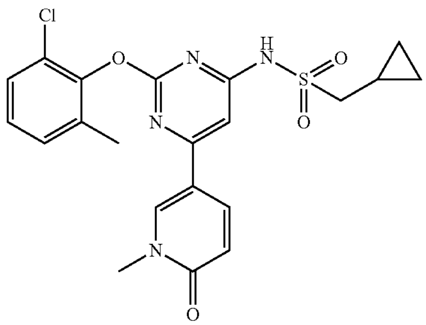 | N-[2-(2-Chloro-6-methyl-phenoxy)-6-(1-methyl-6-moxo-1,6-dihydro-pyridin-3-yl)-pyrimidin-4-yl]-C-cyclopropyl-methanesulfonamide | (CD₃OD, 400 MHz) 8.62 (d, J = 2.4 Hz, 1H), 8.15 (dd, J = 9.6 Hz, 2.4 Hz, 1H), 7.38 (d, J = 8.0 Hz, 1H), 7.31 (d, J = 7.6 Hz, 1H), 7.22 (t, J = 7.6 Hz, 1H), 6.90 (s, 1H), 6.67 (d, J = 9.6 Hz, 1H), 3.71 (s, 3H), 2.93 (d, J = 7.2 Hz, 2H), 2.25 (s, 3H), 1.01-0.96 (m, 1H), 0.63-0.52 (m, 2H), 0.18-0.13 (m, 2H) | 461 |
| 265 | 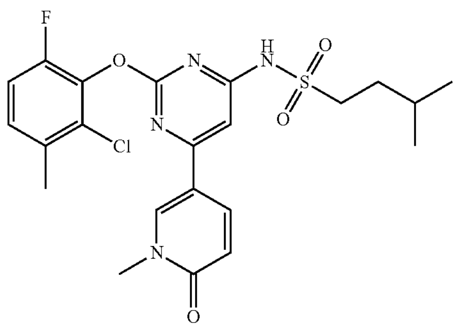 [SMILES: Cc1ccc(F)c(Oc2nc(NS(=O)(=O)CCC(C)C)cc(-c3ccc(=O)n(C)c3)n2)c1Cl] | 3-Methyl-butane-1-sulfonic acid [2-(2-chloro-6-fluoro-3-methyl-phenoxy)-6-(1-methyl-6-oxo-1,6-dihydro-pyridin-3-yl)-pyrimidin-4-yl]-amide | (CD₃OD, 400 MHz) 8.52 (m, 1H), 8.07 (dd, J = 2.4 Hz, 9.2 Hz, 1H), 7.25 (s, 1H), 7.16-7.14 (m, 1H), 6.85 (d, J = 10.0 Hz, 1H), 6.62 (d, J = 9.2 Hz, 1H), 3.65 (s, 3H), 3.12-3.08 (m, 2H), 2.39 (s, 3H), 1.52-1.48 (m, 3H), 0.85 (d, J = 6.4 Hz, 6H) | 495 |
| 266 | 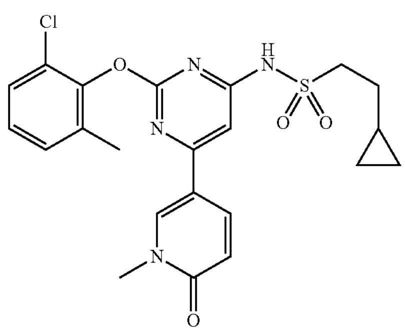 [SMILES: Cc1cccc(Cl)c1Oc1nc(NS(=O)(=O)CCC2CC2)cc(-c2ccc(=O)n(C)c2)n1] | 2-Cyclopropyl-ethanesulfonic acid [2-(2-chloro-6-methyl-phenoxy)-6-(1-methyl-6-oxo-1,6-dihydro-pyridin-3-yl)-pyrimidin-4-yl]-amide | (CD₃OD, 400 MHz) 8.56 (d, J = 2.4 Hz, 1H), 8.10-8.07 (m, 1H), 7.34 (d, J = 7.6 Hz, 1H), 7.26 (d, J = 7.6 Hz, 1H), 7.18 (t, J = 7.6 Hz, 1H), 6.83 (s, 1H), 6.62 (d, J = 9.6 Hz, 1H), 3.66 (s, 3H), 3.12-3.05 (m, 2H), 2.22 (s, 3H), 1.50-1.44 (m, 2H), 0.69-0.61 (m, 1H), 0.46-0.41 (m, 2H), 0.03-0.01 (m, 2H) | |
| 267 | 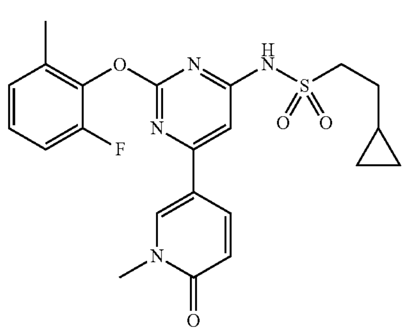 [SMILES: Cc1cccc(F)c1Oc1nc(NS(=O)(=O)CCC2CC2)cc(-c2ccc(=O)n(C)c2)n1] | 2-Cyclopropyl-ethanesulfonic acid [2-(2-fluoro-6-methyl-phenoxy)-6-(1-methyl-6-oxo-1,6-dihydro-pyridin-3-yl)-pyrimidin-4-yl]-amide | (CD₃OD, 400 MHz) 8.53 (d, J = 2.8 Hz, 1H), 8.10-8.07 (m, 1H), 7.21-7.05 (m, 3H), 6.84 (s, 1H), 6.62 (d, J = 9.6 Hz, 1H), 3.66 (s, 3H), 3.17-3.14 (m, 2H), 2.24 (s, 3H), 1.52-1.47 (m, 2H), 0.69-0.64 (m, 1H), 0.46-0.41 (m, 2H), 0.03-0.01 (m, 2H) | 458 |

TABLE 20-continued

| Example | Structure | IUPAC Name | ¹H NMR ppm (δ) | MS (M + H) |
|---|---|---|---|---|
| 268 | 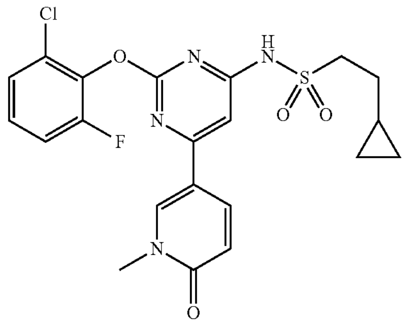 [SMILES: Cn1cc(-c2cc(NS(=O)(=O)CCC3CC3)nc(Oc3c(F)cccc3Cl)n2)ccc1=O] | 2-Cyclopropyl-ethanesulfonic acid [2-(2-chloro-6-fluoro-phenoxy)-6-(1-methyl-6-oxo-1,6-dihydro-pyridin-3-yl)-pyrimidin-4-yl]-amide | (CD$_3$OD, 400 MHz) 8.52 (d, J = 2.4 Hz, 1H), 8.09-8.06 (m, 1H), 7.39-7.24 (m, 3H), 6.87 (s, 1H), 6.61 (d, J = 9.6 Hz, 1H), 3.65 (s, 3H), 3.23-3.19 (m, 2H), 1.55-1.50 (m, 2H), 0.71-0.69 (m, 1H), 0.47-0.43 (m, 2H), 0.05-0.03 (m, 2H) | |
| 269 | | 1-Cyclopropyl-N-[2-(2-fluoro-6-methyl-phenoxy)-6-(1-methyl-6-oxo-1,6-dihydro-pyridin-3-yl)-pyrimidin-4-yl]-methanesulfonamide | (CD$_3$OD, 400 MHz) 8.55 (d, J = 2.4 Hz, 1H), 8.10 (dd, J = 9.6 Hz, 2.4 Hz, 1H), 7.18-7.04 (m, 3H), 6.87 (s, 1H), 6.62 (d, J = 9.6 Hz, 1H), 3.66 (s, 3H), 2.95 (d, J = 7.2 Hz, 2H), 2.22 (s, 3H), 0.97-0.94 (m, 1H), 0.57-0.52 (m, 2H), 0.15-0.11 (m, 2H) | 461 |

Example 270: 5-(6-amino-2-(2,4-difluorophenoxy) pyrimidin-4-yl)-1,3-dimethy-1pyridin-2(1H)-one Step 1: 5-(6-chloro-2-(2,4-difluorophenoxy)pyrimidin-4-yl)-1,3-dimethylpyridin-2(1H)-one

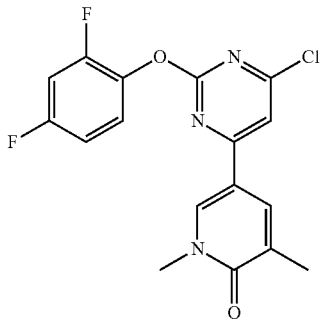 [SMILES: Cc1cc(-c2cc(Cl)nc(Oc3ccc(F)cc3F)n2)cn(C)c1=O]

The title compound was prepared in a manner similar to Example 1 by substituting 2,4-difluorophenol for 2,5-dichlorophenol in Step 1. LCMS (M+H)⁺ 364.

Step 2: 5-(6-amino-2-(2,4-difluorophenoxy)pyrimidin-4-yl)-1,3-dimethylpyridin-2(1H)-one

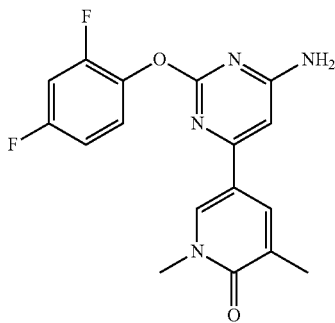 [SMILES: Cc1cc(-c2cc(N)nc(Oc3ccc(F)cc3F)n2)cn(C)c1=O]

A solution of the title compound of Step 1 (50 mg, 0.14 mmol) in DMSO (1 mL) was treated with ammonium hydroxide (300 The mixture was heated to 60° C. by microwave irradiation for 12 hr. The mixture was diluted with MeOH and filtered; the resulting filtrate was purified by prep-HPLC to afford the title compound (18 mg, 38%) as a white solid. ¹H NMR (400 MHz, DMSO-d$_6$) δ ppm 8.19-8.26 (m, 1H), 7.71-7.77 (m, 1H), 7.35-7.46 (m, 2H), 7.08-7.16 (m, 1H), 7.02 (s, 2H), 6.46 (s, 1H), 3.51 (s, 3H), 2.05 (s, 3H). LCMS (M+H)⁺ 345

Example 271: 5-(2-(2,4-difluorophenoxy)-6-(phenethylamino)pyrimidin-4-yl)-1,3-dimethylpyridin-2(1H)-one

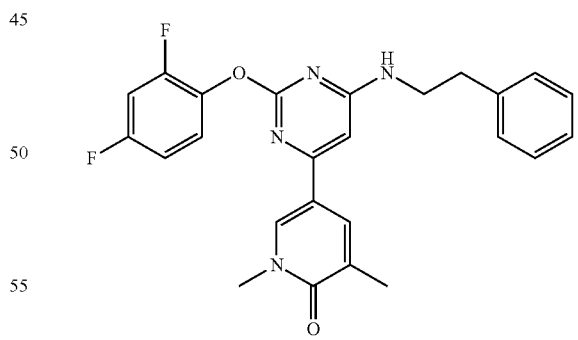

A 0.2 M solution of the title compound from Step 1 in Example 270 (58 mg, 0.16 mmol) in 1-butanol was treated with Hunig's base (69 μL, 0.4 mmol) and phenylethylamine (30 μL, 0.24 mmol). The mixture was heated to 100° C. for 3 h. After cooling to RT, the mixture was filtered. The filtrate was purified by prep-HPLC to afford the title compound (28 mg, 42%) as a tan solid. ¹H NMR (400 MHz, DMSO-d$_6$) δ ppm 8.19-8.37 (m, 1H), 7.72-7.80 (m, 1H), 7.35-7.50 (m, 2H), 7.09-7.33 (m, 5H), 6.93-7.00 (m, 1H), 6.39-6.63 (m, 1H), 3.50-3.55 (m, 3H), 3.24-3.30 (m, 2H), 2.56-2.74 (m, 2H), 2.04-2.11 (m, 3H). LCMS (M+H)+ 449.

Examples 272-323 (Table 21) were prepared from 2,4-difluorophenol or 2-fluoro-6-methylphenol, the appropriate amine and either 1,3-dimethyl-5-(4,4,5,5-tetramethyl-[1,3,2]dioxa-borolan-2-yl)-1H-pyridin-2-one or 1-methyl-5-(4,4,5,5-tetramethyl-1,3,2-dioxaborolan-2-yl)-pyridin-2(1H)-one in a similar manner as Example 271.

TABLE 21

| Example | Structure | IUPAC Name | $^1$H NMR ppm (δ) | MS (M + H) |
|---|---|---|---|---|
| 272 | | 5-(6-(benzylamino)-2-(2,4-difluorophenoxy)pyrimidin-4-yl)-1,3-dimethylpyridin-2(1H)-one | (400 MHz, DMSO-d$_6$) δ ppm 8.20-8.30 (m, 1 H), 8.07-8.20 (m, 1 H), 7.68-7.82 (m, 1 H), 6.98-7.54 (m, 8 H), 6.51-6.65 (m, 1 H), 4.19-4.44 (m, 2 H), 3.51 (s, 3 H), 2.05 (s, 3 H) | 435 |
| 273 | | 5-(2-(2,4-difluorophenoxy)-6-(ethylamino)pyrimidin-4-yl)-1,3-dimethylpyridin-2(1H)-one | (400 MHz, DMSO-d$_6$) δ ppm 8.20-8.48 (m, 1 H), 7.53-7.98 (m, 2 H), 7.34-7.48 (m, 2 H), 7.08-7.18 (m, 1 H), 6.38-6.61 (m, 2 H), 3.50 (s, 3 H), 3.06-3.25 (m, 2 H), 0.89-1.18 (m, 3 H) | 359 |
| 274 | 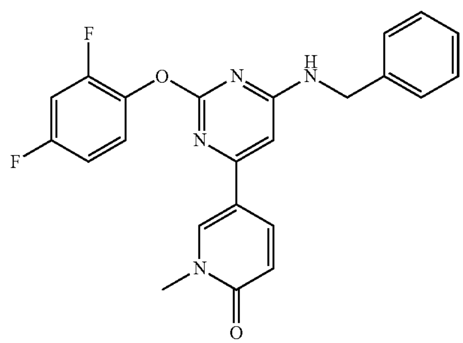 | 5-(6-(benzylamino)-2-(2,4-difluorophenoxy)pyrimidin-4-yl)-1-methylpyridin-2(1H)-one | (400 MHz, DMSO-d$_6$) δ ppm 8.32-8.44 (m, 1 H), 8.10-8.25 (m, 1 H), 7.76-7.92 (m, 1 H), 7.07-7.45 (m, 8 H), 6.50-6.63 (m, 1 H), 6.41-6.49 (m, 1 H), 4.23-4.46 (m, 2 H), 3.49 (s, 3 H) | 421 |
| 275 | 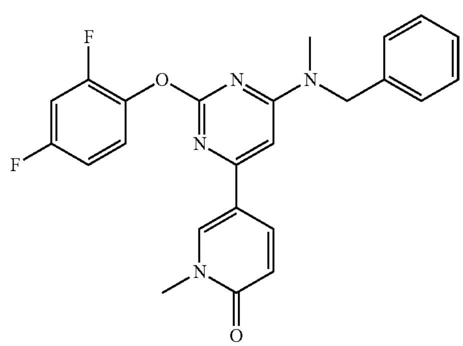 | 5-(6-(benzyl(methyl)amino)-2-(2,4-difluorophenoxy)pyrimidin-4-yl)-1-methylpyridin-2(1H)-one | (400 MHz, DMSO-d$_6$) δ ppm 8.49-8.59 (m, 1 H), 7.98-8.11 (m, 1 H), 7.01-7.47 (m, 9 H), 6.42-6.51 (m, 1 H), 4.64 (s, 2 H), 3.50 (s, 3 H), 3.04 (s, 3 H) | 435 |
| 276 | 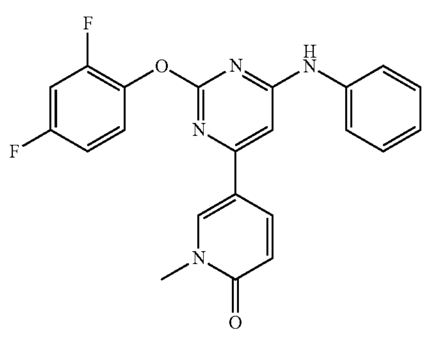 [SMILES: Cn1cc(-c2cc(Nc3ccccc3)nc(Oc3ccc(F)cc3F)n2)ccc1=O] | 5-(2-(2,4-difluorophenoxy)-6-(phenylamino)pyrimidin-4-yl)-1-methylpyridin-2(1H)-one | (400 MHz, DMSO-d$_6$) δ ppm 9.78-9.85 (m, 1 H), 8.44-8.52 (m, 1 H), 7.83-7.94 (m, 1 H), 7.42-7.57 (m, 2 H), 7.31-7.38 (m, 2 H), 7.09-7.25 (m, 3 H), 6.92-7.00 (m, 1 H), 6.75 (s, 1 H), 6.48-6.56 (m, 1 H), 3.54 (s, 3 H) | 407 |

TABLE 21-continued

| Example | Structure | IUPAC Name | ¹H NMR ppm (δ) | MS (M + H) |
|---|---|---|---|---|
| 277 | 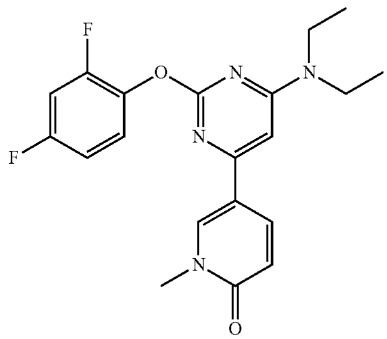 [SMILES: CCN(CC)c1cc(-c2ccc(=O)n(C)c2)nc(Oc2ccc(F)cc2F)n1] | 5-(6-(diethylamino)-2-(2,4-difluorophenoxy)pyrimidin-4-yl)-1-methylpyridin-2(1H)-one | (400 MHz, DMSO-d₆) δ ppm 8.49-8.55 (m, 1 H), 8.03-8.11 (m, 1 H), 7.35-7.46 (m, 2 H), 7.07-7.18 (m, 1 H), 6.73 (s, 1 H), 6.42-6.49 (m, 1 H), 3.49-3.57 (m, 3 H), 3.35-3.48 (m, 4 H), 0.80-1.23 (m, 6H) | 387 |
| 278 | 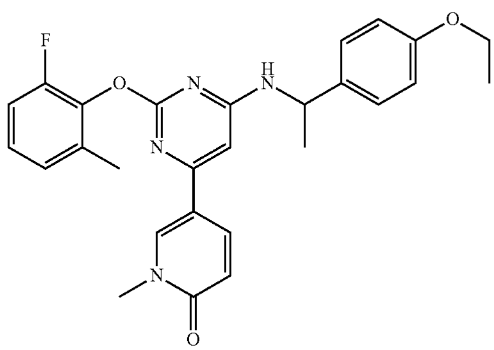 [SMILES: CCOc1ccc(C(C)Nc2cc(-c3ccc(=O)n(C)c3)nc(Oc3c(C)cccc3F)n2)cc1] | 5-(6-((1-(4-ethoxyphenyl)ethyl)amino)-2-(2-fluoro-6-methylphenoxy)pyrimidin-4-yl)-1-methylpyridin-2(1H)-one | (400 MHz, DMSO-d₆) δ ppm 8.35-8.43 (m, 1 H), 8.03-8.15 (m, 1 H), 7.74-7.87 (m, 1 H), 7.01-7.28 (m, 5 H), 6.81-6.90 (m, 1 H), 6.39-6.53 (m, 2 H), 4.50-4.69 (m, 1 H), 3.50 (s, 3 H), 2.52-2.58 (m, 2 H), 1.97 (s, 3 H), 1.24-1.40 (m, 3 H), 1.09-1.18 (m, 3 H) | 475 |
| 279 | 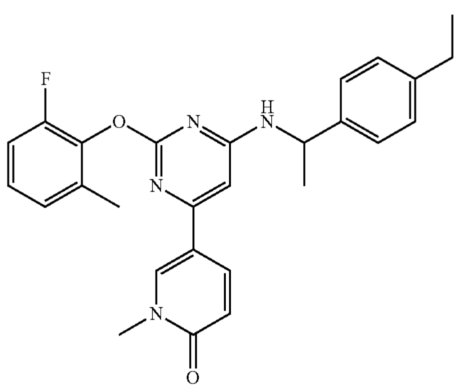 [SMILES: CCc1ccc(C(C)Nc2cc(-c3ccc(=O)n(C)c3)nc(Oc3c(C)cccc3F)n2)cc1] | 5-(6-((1-(4-ethylphenyl)ethyl)amino)-2-(2-fluoro-6-methylphenoxy)pyrimidin-4-yl)-1-methylpyridin-2(1H)-one | (400 MHz, DMSO-d₆) δ ppm 8.32-8.42 (m, 1 H) 7.97-8.12 (m, 1 H), 7.74-7.85 (m, 1 H), 7.09-7.26 (m, 3 H), 6.68-6.93 (m, 4 H), 6.40-6.52 (m, 2 H), 4.49-4.67 (m, 1 H), 3.91-4.03 (m, 2 H), 3.50 (s, 3 H), 1.95-2.06 (m, 3 H), 1.22-1.37 (m, 6 H) | 459 |
| 280 | 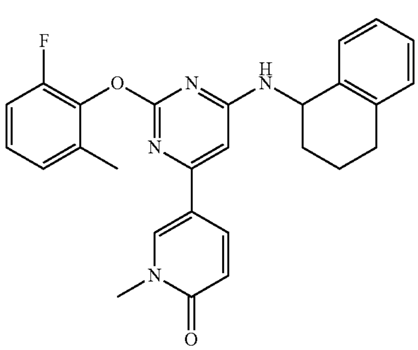 [SMILES: Cc1cccc(F)c1Oc1nc(NC2CCCc3ccccc32)cc(-c2ccc(=O)n(C)c2)n1] | 5-(2-(2-fluoro-6-methylphenoxy)-6-((1,2,3,4-tetrahydronaphthalen-1-yl)amino)pyrimidin-4-yl)-1-methylpyridin-2(1H)-one | (400 MHz, DMSO-d₆) δ ppm 8.26-8.38 (m, 1 H), 7.95-8.06 (m, 1 H), 7.65-7.83 (m, 1 H), 7.05-7.21 (m, 7 H), 6.39-6.59 (m, 2 H), 4.85-5.00 (m, 1 H), 3.49 (s, 3 H), 2.59-2.79 (m, 2 H), 2.12-2.22 (m, 3 H), 1.54-1.90 (m, 4 H) | 457 |

TABLE 21-continued

| Example | Structure | IUPAC Name | ¹H NMR ppm (δ) | MS (M + H) |
|---|---|---|---|---|
| 281 | 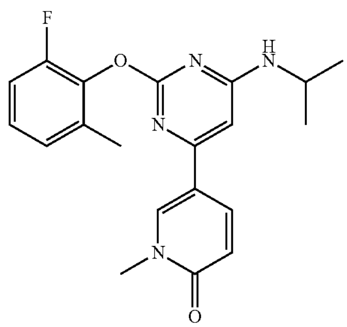 [SMILES: Cc1cccc(F)c1Oc1nc(NC(C)C)cc(-c2ccc(=O)n(C)c2)n1] | 5-(2-(2-fluoro-6-methylphenoxy)-6-(isopropylamino)pyrimidin-4-yl)-1-methylpyridin-2(1H)-one | (400 MHz, DMSO-d$_6$) δ ppm 8.21-8.45 (m, 1 H), 7.65-7.87 (m, 1 H), 7.36-7.57 (m, 1 H), 7.11-7.18 (m, 3 H), 6.38-6.51 (m, 2 H), 3.63-3.82 (m, 1 H), 3.50 (s, 3 H), 2.16 (s, 3 H), 0.97-1.10 (m, 6 H) | 369 |
| 282 | 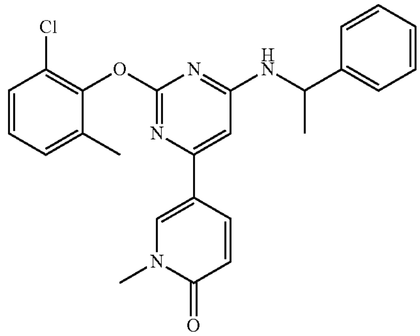 [SMILES: Cc1cccc(Cl)c1Oc1nc(NC(C)c2ccccc2)cc(-c2ccc(=O)n(C)c2)n1] | 5-(2-(2-chloro-6-methylphenoxy)-6-((1-phenylethyl)amino)pyrimidin-4-yl)-1-methylpyridin-2(1H)-one | (400 MHz, DMSO-d$_6$) δ ppm 8.37-8.43 (m, 1 H), 8.04-8.21 (m, 1 H), 7.75-7.89 (m, 1 H), 7.36-7.44 (m, 1 H), 7.13-7.33 (m, 4 H), 6.85-6.97 (m, 1 H), 6.41-6.55 (m, 2 H), 4.47-4.69 (m, 1 H), 3.50 (s, 3 H), 1.84-2.01 (m, 3 H), 1.35 (s, 3 H) | 447 |
| 283 | 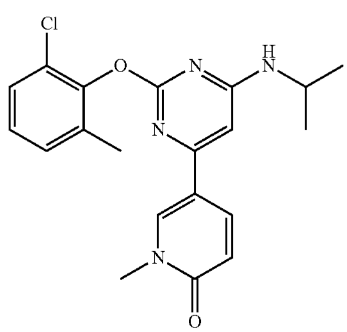 [SMILES: Cc1cccc(Cl)c1Oc1nc(NC(C)C)cc(-c2ccc(=O)n(C)c2)n1] | 5-(2-(2-chloro-6-methylphenoxy)-6-(isopropylamino)pyrimidin-4-yl)-1-methylpyridin-2(1H)-one | (400 MHz, DMSO-d$_6$) δ ppm 8.29-8.45 (m, 1 H), 7.70-7.87 (m, 1 H), 7.40-7.55 (m, 1 H), 7.35-7.40 (m, 1 H), 7.24-7.31 (m, 1 H), 7.13-7.22 (m, 1 H), 6.40-6.55 (m, 2 H), 3.60-3.75 (m, 1 H), 3.51 (s, 3 H), 2.14 (s, 3 H), 0.89-1.11 (m, 6 H) | 385 |
| 284 | 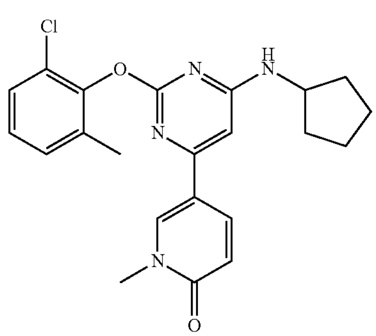 | 5-(2-(2-chloro-6-methylphenoxy)-6-(cyclopentylamino)pyrimidin-4-yl)-1-methylpyridin-2(1H)-one | (400 MHz, DMSO-d$_6$) δ ppm 8.24-8.45 (m, 1 H), 7.68-7.85 (m, 1 H), 7.52-7.67 (m, 1 H), 7.34-7.40 (m, 1 H), 7.25-7.30 (m, 1 H), 7.11-7.21 (m, 1 H), 6.34-6.56 (m, 2 H), 3.66-3.84 (m, 1 H), 3.51 (s, 3 H), 2.14 (s, 3 H), 1.23-1.84 (m, 8 H) | 411 |

TABLE 21-continued

| Example | Structure | IUPAC Name | ¹H NMR ppm (δ) | MS (M + H) |
|---|---|---|---|---|
| 285 | 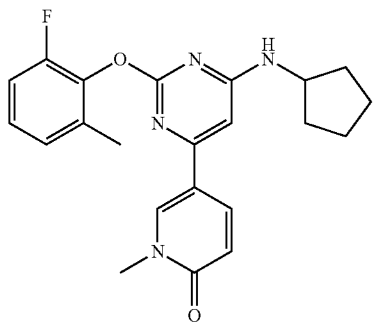 [SMILES: Cc1cccc(F)c1Oc1nc(NC2CCCC2)cc(-c2ccc(=O)n(C)c2)n1] | 5-(6-(cyclopentylamino)-2-(2-fluoro-6-methylphenoxy)pyrimidin-4-yl)-1-methylpyridin-2(1H)-one | (400 MHz, DMSO-d₆) δ ppm 8.24-8.44 (m, 1 H), 7.50-7.89 (m, 2 H), 7.07-7.22 (m, 3 H), 6.37-6.56 (m, 2 H), 3.72-3.91 (m, 1 H), 3.50 (s, 3 H), 2.16 (s, 3 H), 1.23-1.86 (m, 8 H) | 395 |
| 286 | 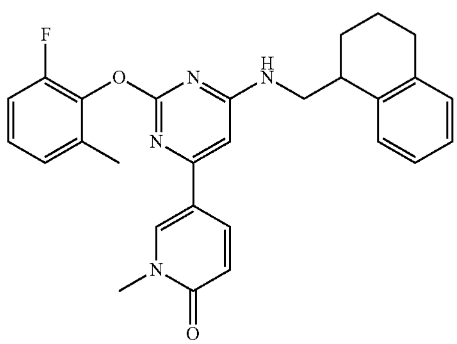 [SMILES: Cc1cccc(F)c1Oc1nc(NCC2CCCc3ccccc32)cc(-c2ccc(=O)n(C)c2)n1] | 5-(2-(2-fluoro-6-methylphenoxy)-6-(((1,2,3,4-tetrahydronaphthalen-1-yl)methyl)amino)pyrimidin-4-yl)-1-methylpyridin-2(1H)-one | (400 MHz, DMSO-d₆) δ ppm 8.44-8.54 (m, 1 H), 7.84-8.05 (m, 2 H), 6.96-7.26 (m, 6 H), 6.38-6.59 (m, 3 H), 3.50-3.57 (m, 3 H), 3.28-3.48 (m, 2 H), 2.91-3.07 (m, 1 H), 2.62-2.80 (m, 2 H), 2.13-2.24 (m, 4 H), 1.50-1.77 (m, 4 H) | 471 |
| 287 | 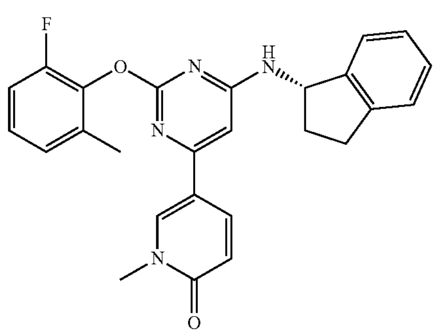 [SMILES: Cc1cccc(F)c1Oc1nc(N[C@H]2CCc3ccccc32)cc(-c2ccc(=O)n(C)c2)n1] | (S)-5-(6-((2,3-dihydro-1H-inden-1-yl)amino)-2-(2-fluoro-6-methylphenoxy)pyrimidin-4-yl)-1-methylpyridin-2(1H)-one | (400 MHz, DMSO-d₆) δ ppm 8.32-8.40 (m, 1 H), 8.00-8.11 (m, 1 H), 7.73-7.85 (m, 1 H), 7.09-7.25 (m, 7 H), 6.42-6.56 (m, 2 H), 5.11-5.26 (m, 1 H), 3.50 (s, 3 H), 2.65-3.01 (m, 2 H), 2.23-2.39 (m, 1 H), 2.18 (s, 3 H), 1.71-1.95 (m, 1 H) | 443 |
| 288 | 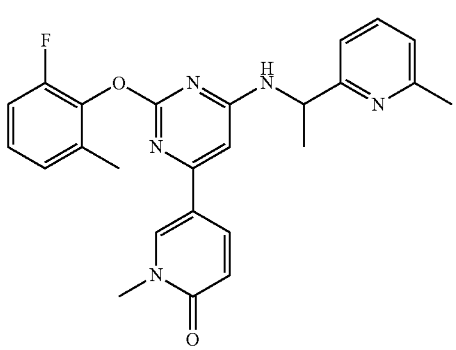 [SMILES: Cc1cccc(C(C)Nc2cc(-c3ccc(=O)n(C)c3)nc(Oc3c(C)cccc3F)n2)n1] | 5-(2-(2-fluoro-6-methylphenoxy)-6-((1-(6-methylpyridin-2-yl)ethyl)amino)pyrimidin-4-yl)-1-methylpyridin-2(1H)-one | (400 MHz, DMSO-d₆) δ ppm 8.33-8.43 (m, 1 H), 8.05-8.14 (m, 1 H), 7.74-7.86 (m, 1 H), 7.44-7.57 (m, 1 H), 7.03-7.23 (m, 5 H), 6.42-6.58 (m, 2 H), 4.58-4.75 (m, 1 H), 3.50 (s, 3 H), 2.43 (s, 3 H), 1.98 (s, 3 H), 1.25-1.42 (m, 3 H) | 446 |

TABLE 21-continued

| Example | Structure | IUPAC Name | ¹H NMR ppm (δ) | MS (M + H) |
|---|---|---|---|---|
| 289 | 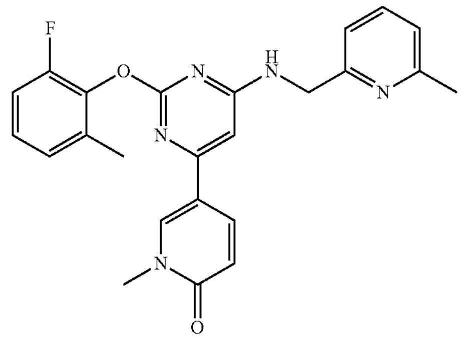 [SMILES: Cc1cccc(CNc2cc(-c3ccc(=O)n(C)c3)nc(Oc3c(C)cccc3F)n2)n1] | 5-(2-(2-fluoro-6-methylphenoxy)-6-(((6-methylpyridin-2-yl)methyl)amino)pyrimidin-4-yl)-1-methylpyridin-2(1H)-one | (400 MHz, DMSO-d₆) δ ppm 8.34-8.47 (m, 1 H), 8.21-8.33 (m, 1 H), 7.78-7.93 (m, 1 H), 7.47-7.61 (m, 1 H), 7.05-7.20 (m, 4 H), 6.59-6.70 (m, 2 H), 6.41-6.51 (m, 1 H), 4.19-4.36 (m, 2 H), 3.50 (s, 3 H), 2.43 (s, 3 H), 2.05 (s, 3 H) | 432 |
| 290 | 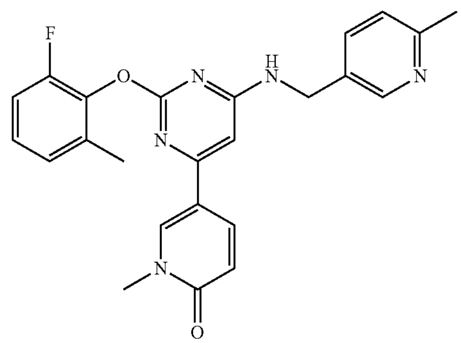 [SMILES: Cc1ccc(CNc2cc(-c3ccc(=O)n(C)c3)nc(Oc3c(C)cccc3F)n2)cn1] | 5-(2-(2-fluoro-6-methylphenoxy)-6-(((6-methylpyridin-3-yl)methyl)amino)pyrimidin-4-yl)-1-methylpyridin-2(1H)-one | (400 MHz, DMSO-d₆) δ ppm 8.35-8.45 (m, 1 H), 8.11-8.24 (m, 1 H), 7.97-8.09 (m, 1 H), 7.77-7.88 (m, 1 H), 7.07-7.23 (m, 5 H), 6.43-6.57 (m, 2 H), 3.51 (s, 3 H), 2.41 (s, 3H), 1.98 (s, 2H), 1.27-1.43 (m, 3H) | 432 |
| 291 | 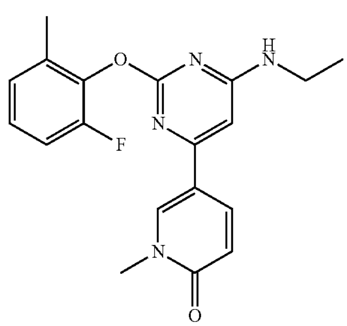 [SMILES: CCNc1cc(-c2ccc(=O)n(C)c2)nc(Oc2c(C)cccc2F)n1] | 5-[6-Ethylamino-2-(2-fluoro-6-methyl-phenoxy)-pyrimidin-4-yl]-1-methyl-1H-pyridin-2-one | (CD₃OD, 400 MHz) 8.27 (s, 1H), 7.97 (s, 1H), 7.16-7.01 (m, 3H), 6.56 (d, J = 9.6 Hz, 1H), 6.44 (s, 1H), 3.59 (s, 3H), 3.22-3.21 (m, 2H), 2.22 (s, 3H), 1.07-1.09 (m, 3H). | 355 |
| 292 | 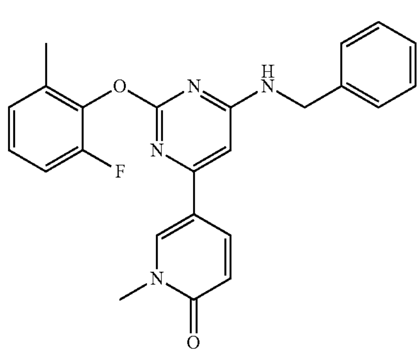 [SMILES: Cc1cccc(F)c1Oc1nc(NCc2ccccc2)cc(-c2ccc(=O)n(C)c2)n1] | 5-[6-Benzylamino-2-(2-fluoro-6-methyl-phenoxy)-pyrimidin-4-yl]-1-methyl-1H-pyridin-2-one | (CD₃OD, 400 MHz) 8.21 (s, 1H), 7.69-7.67 (m, 1H), 7.31-7.30 (m, 3H), 7.20-7.16 (m, 2H), 7.09-6.96 (m, 3H), 6.57 (d, J = 7.2 Hz, 1H), 6.21 (s, 1H), 5.39 (br, 1H), 4.43 (d, J = 5.2 Hz, 2H), 3.56 (s, 3H), 2.23 (s, 3H). | 417 |

TABLE 21-continued

| Example | Structure | IUPAC Name | ¹H NMR ppm (δ) | MS (M + H) |
|---|---|---|---|---|
| 293 | 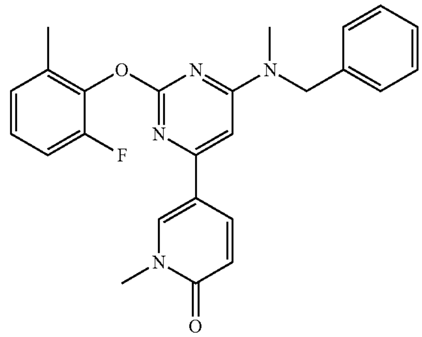 [SMILES: Cc1cccc(F)c1Oc1nc(-c2ccc(=O)n(C)c2)cc(N(C)Cc2ccccc2)n1] | 5-[6-(Benzyl-methyl-amino)-2-(2-fluoro-6-methyl-phenoxy)-pyrimidin-4-yl]-1-methyl-1H-pyridin-2-one | (CD₃OD, 400 MHz) 8.43 (s, 1H), 8.10 (d, J = 4.4 Hz, 1H), 7.23-7.20 (m, 3H), 7.12-6.97 (m, 5H), 6.67 (s, 1H), 6.58 (d, J = 9.6 Hz, 1H), 4.58 (s, 2H), 3.62 (s, 3H), 3.05 (s, 3H), 2.16 (s, 3H). | 431 |
| 294 | 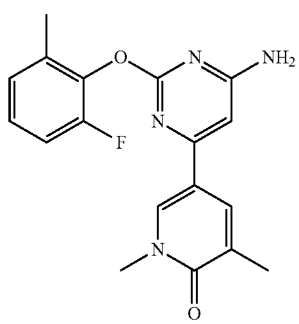 [SMILES: Cc1cccc(F)c1Oc1nc(N)cc(-c2cc(C)c(=O)n(C)c2)n1] | 5-[6-Amino-2-(2-fluoro-6-methyl-phenoxy)-pyrimidin-4-yl]-1,3-dimethyl-1H-pyridin-2-one | (CDCl₃, 400 MHz) 8.07 (s, 1H), 7.63 (s, 1H), 7.04-7.03 (m, 1H), 7.02-7.00 (m, 2H), 6.33 (s, 1H), 4.92 (br, 2H), 3.58 (s, 3H), 2.67 (s, 3H), 2.19 (s, 3H) | 341 |
| 295 | 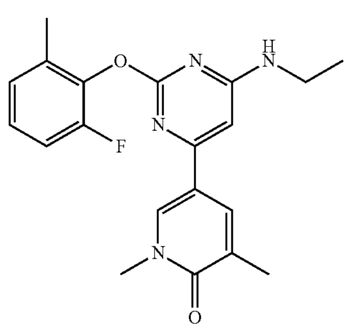 [SMILES: CCNc1cc(-c2cc(C)c(=O)n(C)c2)nc(Oc2c(C)cccc2F)n1] | 5-[6-Ethylamino-2-(2-fluoro-6-methyl-phenoxy)-pyrimidin-4-yl]-1,3-dimethyl-1H-pyridin-2-one | (CDCl₃, 400 MHz) 8.08 (d, J = 2.0 Hz, 1H), 7.64 (s, 1H), 7.09-6.99 (m, 3H), 6.19 (s, 1H), 4.94 (br. 1H), 3.57 (s, 3H), 3.33-3.27 (m, 2H), 2.26 (s, 3H), 2.20 (s, 3H), 1.21 (t, J = 7.2 Hz, 3H). | 369 |
| 296 | 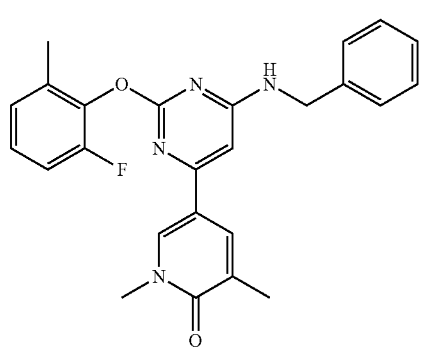 [SMILES: Cc1cccc(F)c1Oc1nc(NCc2ccccc2)cc(-c2cc(C)c(=O)n(C)c2)n1] | 5-[6-Benzylamino-2-(2-fluoro-6-methyl-phenoxy)-pyrimidin-4-yl]-1,3-dimethyl-1H-pyridin-2-one | (CDCl₃, 400 MHz) 8.09 (d, J = 2.4 Hz, 1H), 7.50 (s, 1H), 7.32-7.26 (m, 3H), 7.23-7.20 (m, 2H), 7.09-7.02 (m, 1H), 7.01-6.98 (m, 2H), 6.22 (s, 1H), 5.26 (br, 1H), 4.43 (d, J = 5.6 Hz, 2H), 3.57 (s, 3H), 2.24 (s, 3H), 2.18 (s, 3H). | 431 |

TABLE 21-continued

| Example | Structure | IUPAC Name | $^1$H NMR ppm (δ) | MS (M + H) |
|---|---|---|---|---|
| 297 | 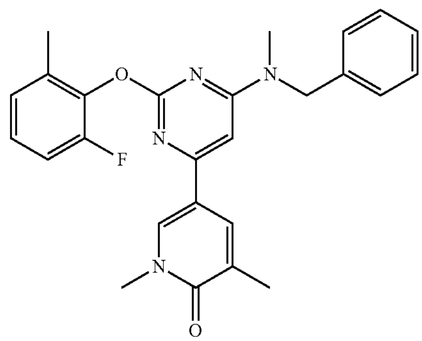 [SMILES: Cc1cccc(F)c1Oc1nc(-c2cc(C)c(=O)n(C)c2)cc(N(C)Cc2ccccc2)n1] | 5-[6-(Benzyl-methyl-amino)-2-(2-fluoro-6-methyl-phenoxy)-pyrimidin-4-yl]-1,3-dimethyl-1H-pyridin-2-one | (CDCl$_3$, 400 MHz) 8.17 (s, 1H), 7.65 (s, 1H), 7.32-7.26 (m, 3H), 7.06-6.94 (m, 5H), 6.30 (s, 1H), 4.55 (s, 2H), 3.60 (s, 3H), 3.04 (s, 3H), 2.22 (s, 3H), 2.20 (s, 3H) | 445 |
| 298 | 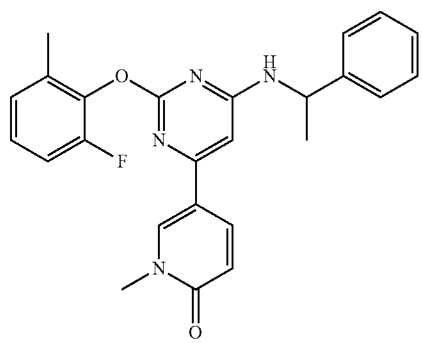 [SMILES: Cc1cccc(F)c1Oc1nc(NC(C)c2ccccc2)cc(-c2ccc(=O)n(C)c2)n1] | 5-[2-(2-Fluoro-6-methyl-phenoxy)-6-(1-phenyl-ethylamino)-pyrimidin-4-yl]-1-methyl-1H-pyridin-2-one | (CDCl$_3$, 400 MHz) 8.19 (s, 1H), 7.59 (s, 1 H) 7.57-7.31 (m, 1H), 7.17-7.10 (m, 2H), 7.08-7.01 (m, 3H), 6.56 (d, J = 9.2 Hz, 1H), 6.01 (s, 1H), 5.34 (m, 1H), 4.73 (br, 1H), 3.55 (s, 3H), 2.18 (s, 3H), 1.51 (d, J = 6.8 Hz, 3H). | 431 |
| 299 | 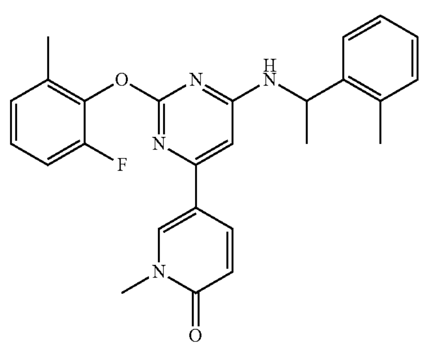 [SMILES: Cc1ccccc1C(C)Nc1cc(-c2ccc(=O)n(C)c2)nc(Oc2c(C)cccc2F)n1] | 5-[2-(2-Fluoro-6-methyl-phenoxy)-6-(1-o-tolyl-ethylamino)-pyrimidin-4-yl]-1-methyl-1H-pyridin-2-one | (CDCl$_3$, 400 MHz) 8.24 (s, 1H), 7.27 (s, 1H), 7.24 (m, 1H), 7.14-7.06 (m, 4H), 6.99-6.58 (m, 2H), 6.55 (d, J = 9.6 Hz, 1H), 6.06 (s, 1H), 5.22 (s, 1H), 4.94 (m, H), 3.57 (s, 3H), 2.18 (s, 6H), 1.42 (d, J = 6.4 Hz, 3H). | 445 |
| 300 | 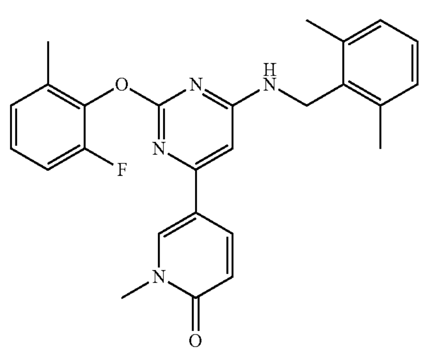 [SMILES: Cc1cccc(C)c1CNc1cc(-c2ccc(=O)n(C)c2)nc(Oc2c(C)cccc2F)n1] | 5-[6-(2,6-Dimethyl-benzylamino)-2-(2-fluoro-6-methyl-phenoxy)-pyrimidin-4-yl]-1-methyl-1H-pyridin-2-one | (CDCl$_3$, 400 MHz) 8.23 (s, 1H), 7.76 (s, 1H), 7.15-6.97 (m, 6H), 6.60 (d, J = 9.6 Hz, 1H), 6.23 (s, 1H), 4.73 (s, 1H), 4.45 (s, 2H), 3.78 (s, 3H), 2.41 (s, 6H), 2.33 (s, 3H). | 445 |

TABLE 21-continued

| Example | Structure | IUPAC Name | ¹H NMR ppm (δ) | MS (M + H) |
|---|---|---|---|---|
| 301 | 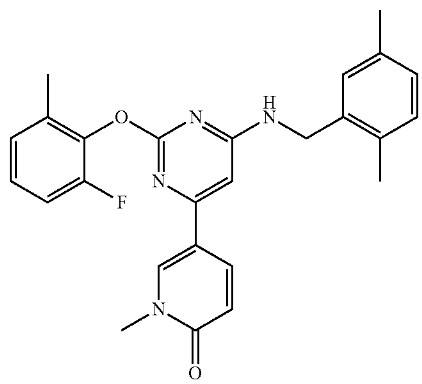 [SMILES: Cc1ccc(C)c(CNc2cc(-c3ccc(=O)n(C)c3)nc(Oc3c(C)cccc3F)n2)c1] | 5-[6-(2,5-Dimethyl-benzylamino)-2-(2-fluoro-6-methyl-phenoxy)-pyrimidin-4-yl]-1-methyl-1H-pyridin-2-one | (CD₃OD, 400 MHz) 8.33 (d, J = 2.8 Hz, 1H), 7.99 (dd, J = 7.2 Hz, 2.8 Hz, 1H), 7.15-7.13 (m, 1H), 7.06-6.94 (m, 5H), 6.59 (d, J = 7.2 Hz, 1H), 6.52 (s, 1H), 4.31 (s, 2H), 3.62 (s, 3H), 2.25 (s, 3H), 2.15 (s, 3H), 2.12 (m, 3H). | 445 |
| 302 | 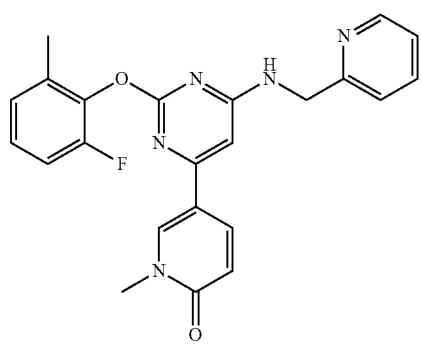 [SMILES: Cc1cccc(F)c1Oc1nc(NCc2ccccn2)cc(-c2ccc(=O)n(C)c2)n1] | 5-{2-(2-Fluoro-6-methyl-phenoxy)-6-[(pyridin-2-ylmethyl)-amino]-pyrimidin-4-yl}-1-methyl-1H-pyridin-2-one | (CDCl₃, 400 MHz) 8.53 (d, J = 4.0 Hz, 1H), 8.17 (d, J = 2.4 Hz, 1H), 7.71 (dd, J = 9.6 Hz, 2.4 Hz, 1H), 7.65-7.61 (m, 1H), 7.21-7.18 (m, 1H), 7.13-7.07 (m, 2H), 7.04-6.97 (m, 2H), 6.57 (d, J = 9.6 Hz, 1H), 6.33 (s, 1H), 6.28-6.26 (m, 1H), 4.56 (d, J = 5.2 Hz, 2H), 3.56 (s, 3H), 2.24 (s, 3H). | 418 |
| 303 | 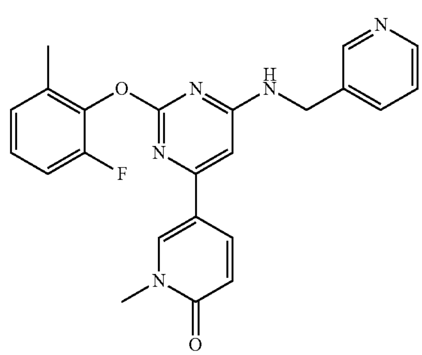 [SMILES: Cc1cccc(F)c1Oc1nc(NCc2cccnc2)cc(-c2ccc(=O)n(C)c2)n1] | 5-{2-(2-Fluoro-6-methyl-phenoxy)-6-[(pyridin-3-ylmethyl)-amino]-pyrimidin-4-yl}-1-methyl-1H-pyridin-2-one | (CDCl₃, 400 MHz) 8.51 (dd, J = 4.8 Hz, 1.6 Hz, 1H), 8.40 (s, 1H), 8.26 (d, J = 2.8 Hz, 1H), 7.69 (dd, J = 9.6 Hz, 2.8 Hz, 1H), 7.43-7.41 (m, 1H), 7.21-7.18 (m, 1H), 7.13-7.01 (m, 1H), 7.99-6.96 (m, 2H), 6.57 (d, J = 9.6 Hz, 1H), 6.25 (s, 1H), 5.48-5.46 (m, 1H), 4.43 (d, J = 5.6 Hz, 2H), 3.57 (s, 3H), 2.20 (s, 3H). | 418 |
| 304 | 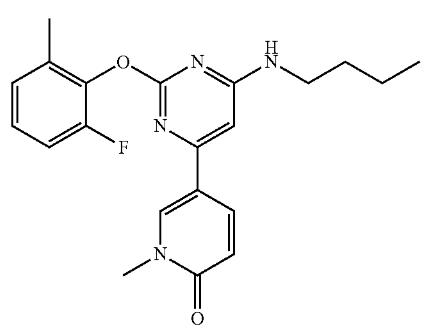 [SMILES: CCCCNc1cc(-c2ccc(=O)n(C)c2)nc(Oc2c(C)cccc2F)n1] | 5-[6-Butylamino-2-(2-fluoro-6-methyl-phenoxy)-pyrimidin-4-yl]-1-methyl-1H-pyridin-2-one | (CD₃OD, 400 MHz) 8.31-8.29 (m, 1H), 7.99-7.97 (m, 1H), 7.14-6.99 (m, 3H), 6.59-6.56 (m, 1H), 6.43 (s, 1H), 3.60 (s, 3H), 3.20-3.15 (m, 2H), 2.22 (s, 3H), 1.44-1.40 (m, 2H), 1.25-1.22 (m, 2H), 0.88-0.82 (m, 3H) | 383 |

TABLE 21-continued

| Example | Structure | IUPAC Name | $^1$H NMR ppm (δ) | MS (M + H) |
|---|---|---|---|---|
| 305 | 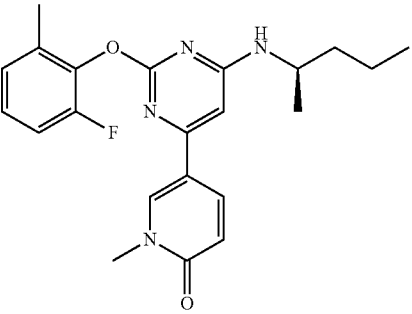 [SMILES: CCC[C@@H](C)Nc1cc(-c2ccc(=O)n(C)c2)nc(Oc2c(C)cccc2F)n1] | (R)-5-[2-(2-Fluoro-6-methyl-phenoxy)-6-(1-methyl-butylamino)-pyrimidin-4-yl]-1-methyl-1H-pyridin-2-one | (CD$_3$OD, 400 MHz) 8.32 (s, 1H), 7.99-7.97 (m, 1H), 7.16-7.01 (m, 3H), 6.59 (d, J = 9.6 Hz, 1H), 6.41 (s, 1H), 3.77-3.72 (m, 1H), 3.63 (s, 3H), 2.23 (s, 3H), 1.45-1.19 (m, 4H), 1.06-1.05 (m, 3H), 0.85-0.79 (m, 3H) | 397 |
| 306 | 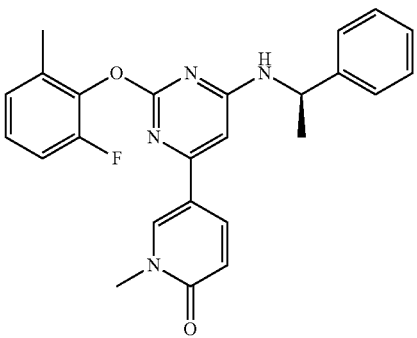 [SMILES: Cc1cccc(F)c1Oc1nc(N[C@H](C)c2ccccc2)cc(-c2ccc(=O)n(C)c2)n1] | (R)-5-[2-(2-Fluoro-6-methyl-phenoxy)-6-(1-phenyl-ethylamino)-pyrimidin-4-yl]-1-methyl-1H-pyridin-2-one | (CDCl$_3$, 400 MHz) 8.17 (d, J = 6.4 Hz, 1H), 7.60-7.56 (m, 1H), 7.36-7.29 (m, 2H), 7.25-7.23 (m, 1H), 7.13-7.08 (m, 3H), 7.03-6.98 (m, 2H), 6.54 (d, J = 9.6 Hz, 1H), 6.09 (s, 1H), 5.34 (br, 1H), 4.76-4.71 (m, 1H), 3.55 (s, 3H), 2.20 (m, 3H), 1.50-1.47 (m, 3H). | 431 |
| 307 | 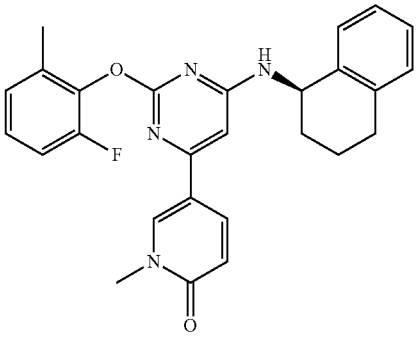 | (R)-5-[2-(2-Fluoro-6-methyl-phenoxy)-6-(1,2,3,4-tetrahydro-naphthalen-1-ylamino)-pyrimidin-4-yl]-1-methyl-1H-pyridin-2-one | (CD$_3$OD, 400 MHz) 8.31 (s, 1H), 7.97 (d, J = 8.4 Hz, 1H), 7.15-7.00 (m, 7H), 6.57 (d, J = 9.6 Hz, 1H), 6.46 (s, 1H), 4.96-4.93 (m, 1H), 3.61 (s, 3H), 2.79-2.67 (m, 2H), 2.23 (s, 3H), 1.85-1.66 (m, 4H). | 457 |
| 308 | 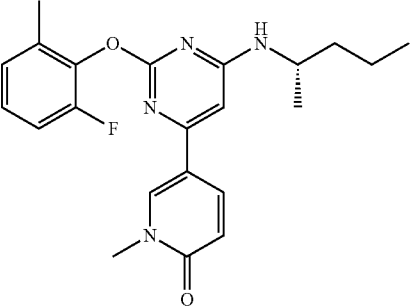 [SMILES: CCC[C@H](C)Nc1cc(-c2ccc(=O)n(C)c2)nc(Oc2c(C)cccc2F)n1] | (S)-5-[2-(2-Fluoro-6-methyl-phenoxy)-6-(1,2,3,4-tetrahydro-naphthalen-1-ylamino)-pyrimidin-4-yl]-1-methyl-1H-pyridin-2-one | (CD$_3$OD, 400 MHz) 8.31 (s, 1H), 7.97 (d, J = 8.4 Hz, 1H), 7.16-7.00 (m, 3H), 6.58 (d, J = 8.8 Hz, 1H), 6.40 (s, 1H), 3.76-3.72 (m, 1H), 3.61 (s, 3H), 2.22 (s, 3H), 1.44-1.42 (m, 1H), 1.28-1.22 (m, 3H), 1.04 (s, 3H), 0.82 (s, 3H). | 397 |

TABLE 21-continued

| Example | Structure | IUPAC Name | $^1$H NMR ppm (δ) | MS (M + H) |
|---|---|---|---|---|
| 309 | 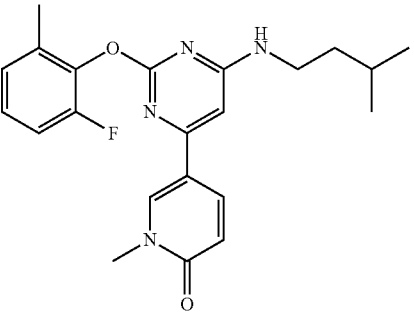 [SMILES: Cc1cccc(F)c1Oc1nc(NCCC(C)C)cc(-c2ccc(=O)n(C)c2)n1] | 5-[2-(2-Fluoro-6-methyl-phenoxy)-6-(3-methyl-butylamino)-pyrimidin-4-yl]-1-methyl-1H-pyridin-2-one | (CD$_3$OD, 400 MHz) 8.31 (s, 1H), 7.97 (d, J = 8.4 Hz, 1H), 7.14-7.00 (m, 3H), 6.58 (d, J = 9.6 Hz, 1H), 6.43 (s, 1H), 3.62 (s, 3H), 3.17-3.16 (m, 2H), 2.22 (s, 3H), 1.53-1.45 (m, 1H), 1.33-1.30 (m, 2H), 0.82 (m, 6H). | 397 |
| 310 | 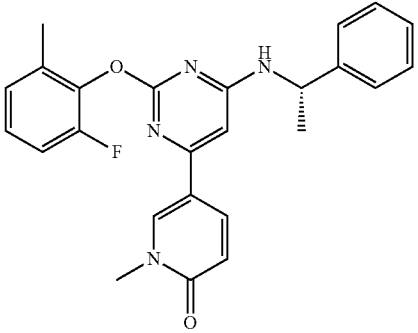 [SMILES: Cc1cccc(F)c1Oc1nc(N[C@@H](C)c2ccccc2)cc(-c2ccc(=O)n(C)c2)n1] | (S)-5-[2-(2-Fluoro-6-methyl-phenoxy)-6-(1-phenyl-ethylamino)-pyrimidin-4-yl]-1-methyl-1H-pyridin-2-one | (CD$_3$OD, 400 MHz) 8.33 (s, 1H), 7.99-7.97 (m, 1H), 7.24-6.96 (m, 8H), 6.60 (d, J = 9.2 Hz, 1H), 6.47 (s, 1H), 4.75-4.72 (m, 1H), 3.64 (s, 3H), 2.06-1.98 (m, 3H), 1.42-1.39 (m, 3H). | 431 |
| 311 | 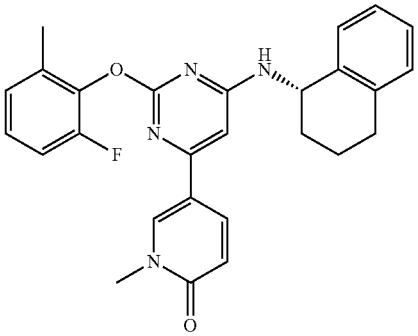 [SMILES: Cc1cccc(F)c1Oc1nc(N[C@H]2CCCc3ccccc32)cc(-c2ccc(=O)n(C)c2)n1] | (S)-5-[2-(2-Fluoro-6-methyl-phenoxy)-6-(1,2,3,4-tetrahydro-naphthalen-1-ylamino)-pyrimidin-4-yl]-1-methyl-1H-pyridin-2-one | (CD$_3$OD, 400 MHz) 8.31 (s, 1H), 7.99-7.96 (m, 1H), 7.15-7.00 (m, 7H), 6.58 (d, J = 9.6 Hz, 1H), 6.46 (m, 1H), 4.97-4.94 (m, 1H), 3.61 (s, 3H), 2.77-2.69 (m, 2H), 2.23 (s, 3H), 1.87-1.68 (m, 4H). | 457 |
| 312 | 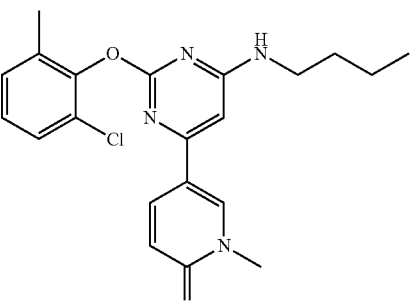 | 5-[6-Butylamino-2-(2-chloro-6-methyl-phenoxy)-pyrimidin-4-yl]-1-methyl-1H-pyridin-2-one | (CD$_3$OD, 400 MHz) 8.30 (s, 1H), 7.98 (d, J = 8.0 Hz, 1H), 7.30 (d, J = 8.0 Hz, 1H), 7.22 (d, J = 8.0 Hz, 1H), 7.12 (t, J = 8.0 Hz, 1H), 6.58 (d, J = 8.0 Hz, 1H), 6.43 (s, 1H), 3.61 (s, 3H), 3.12 (m, 2H), 2.20 (s, 3H), 1.40-1.38 (m, 2H), 1.23-1.21 (m, 2H), 0.85 (s, 3H). | 399 |

TABLE 21-continued

| Example | Structure | IUPAC Name | ¹H NMR ppm (δ) | MS (M + H) |
|---|---|---|---|---|
| 313 | 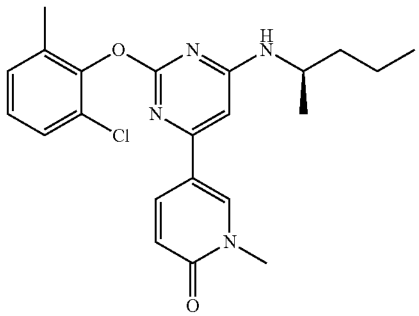 [SMILES: CCC[C@@H](C)Nc1cc(-c2ccc(=O)n(C)c2)nc(Oc2c(C)cccc2Cl)n1] | (R)-5-[2-(2-Chloro-6-methyl-phenoxy)-6-(1-methyl-butylamino)-pyrimidin-4-yl]-1-methyl-1H-pyridin-2-one | (CD₃OD, 400 MHz) 8.33 (s, 1H), 7.99 (d, J = 8.0 Hz, 1H), 7.32 (d, J = 8.0 Hz, 1H), 7.23 (d, J = 8.0 Hz, 1H), 7.14 (t, J = 8.0 Hz, 1H), 6.60 (d, J = 8.0 Hz, 1H), 6.41 (s, 1H), 3.72-3.70 (m, 1H), 3.64 (s, 3H), 2.22 (s, 3H), 1.31-1.20 (m, 4H), 1.05 (s, 3H), 0.83 (s, 3H). | 413 |
| 314 | 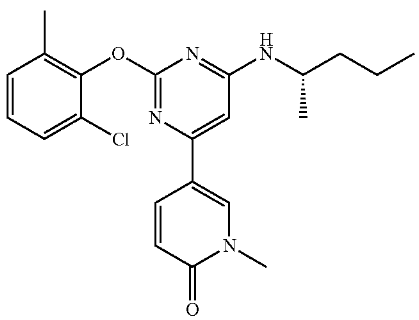 [SMILES: CCC[C@H](C)Nc1cc(-c2ccc(=O)n(C)c2)nc(Oc2c(C)cccc2Cl)n1] | (S)-5-[2-(2-Chloro-6-methyl-phenoxy)-6-(1-methyl-butylamino)-pyrimidin-4-yl]-1-methyl-1H-pyridin-2-one | (CD₃OD, 400 MHz) 8.32 (s, 1H), 7.98 (d, J = 8.0 Hz, 1H), 7.31 (d, J = 8.0 Hz, 1H), 7.22 (d, J = 8.0 Hz, 1H), 7.14 (t, J = 8.0 Hz, 1H), 6.59 (d, J = 8.0 Hz, 1H), 6.40 (s, 1H), 3.70-3.68 (m, 1H), 3.62 (s, 3H), 2.20 (s, 3H), 1.41-1.40 (m, 2H), 1.29-1.25 (m, 2H), 1.18 (s, 3H), 0.88 (s, 3H). | 413 |
| 315 | 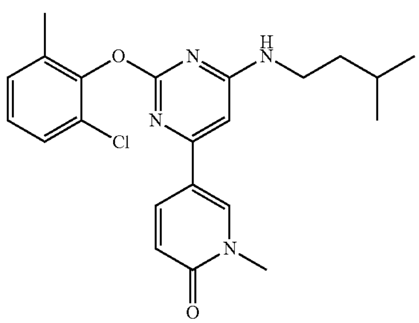 [SMILES: Cc1cccc(Cl)c1Oc1nc(NCCC(C)C)cc(-c2ccc(=O)n(C)c2)n1] | 5-[2-(2-Chloro-6-methyl-phenoxy)-6-(3-methyl-butylamino)-pyrimidin-4-yl]-1-methyl-1H-pyridin-2-one | (CD₃OD, 400 MHz) 8.34 (s, 1H), 7.98 (d, J = 8.0 Hz, 1H), 7.33 (d, J = 8.0 Hz, 1H), 7.22 (d, J = 8.0 Hz, 1H), 7.14 (t, J = 8.0 Hz, 1H), 6.60 (d, J = 8.0 Hz, 1H), 6.44 (s, 1H), 3.64 (s, 3H), 3.15 (s, 2H), 2.23 (s, 3H), 1.49-1.27 (m, 3H), 0.80 (m, 6H). | 413 |
| 316 | 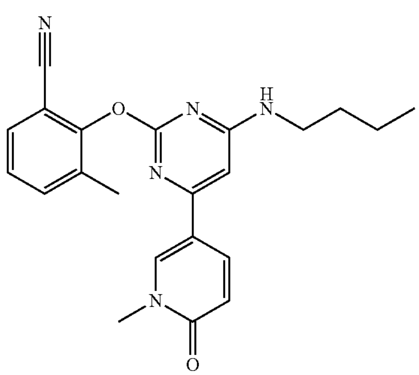 [SMILES: CCCCNc1cc(-c2ccc(=O)n(C)c2)nc(Oc2c(C)cccc2C#N)n1] | 2-[4-Butylamino-6-(1-methyl-6-oxo-1,6-dihydro-pyridin-3-yl)-pyrimidin-2-yloxy]-3-methyl-benzonitrile | (CD₃OD, 400 MHz) 8.32 (s, 1H), 8.00-7.96 (m, 1H), 7.62-7.60 (m, 2H), 7.35-7.31 (m, 1H), 6.59 (d, J = 9.2 Hz, 1H), 6.47 (s, 1H), 3.62 (s, 3H), 3.15-3.10 (m, 2H), 2.22 (s, 3H), 1.45-1.36 (m, 2H), 1.25-1.19 (m, 2H), 0.89-0.82 (m, 3H). | 390 |

TABLE 21-continued

| Example | Structure | IUPAC Name | ¹H NMR ppm (δ) | MS (M + H) |
|---|---|---|---|---|
| 317 | 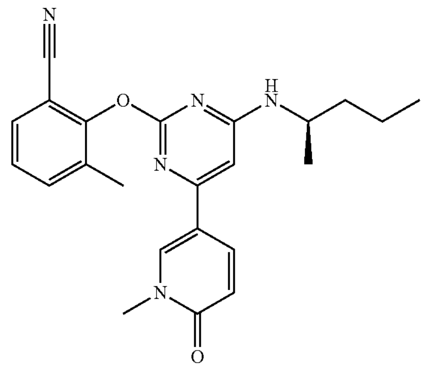 [SMILES: CCC[C@@H](C)Nc1cc(-c2ccc(=O)n(C)c2)nc(Oc2c(C)cccc2C#N)n1] | (R)-3-Methyl-2-[4-(1-methyl-butylamino)-6-(1-methyl-6-oxo-1,6-dihydro-pyridin-3-yl)-pyrimidin-2-yloxy]-benzonitrile | (CD₃OD, 400 MHz) 8.33 (s, 1H), 7.99-7.97 (m, 1H), 7.62-7.60 (m, 2H), 7.32 (t, J = 7.6 Hz, 1H), 6.59 (d, J = 9.2 Hz, 1H), 6.45-6.42 (m, 1H), 3.73-3.68 (m, 1H), 3.63 (s, 3H), 2.22 (s, 3H), 1.45-1.34 (m, 2H), 1.27-1.14 (m, 2H), 1.10-1.01 (m, 3H), 0.90-0.78 (m, 3H). | 404 |
| 318 | 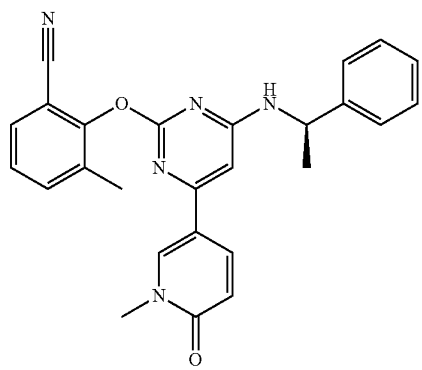 [SMILES: Cc1cccc(C#N)c1Oc1nc(N[C@H](C)c2ccccc2)cc(-c2ccc(=O)n(C)c2)n1] | (R)-3-Methyl-2-[4-(1-methyl-6-oxo-1,6-dihydro-pyridin-3-yl)-6-(1-phenyl-ethylamino)-pyrimidin-2-yloxy]-benzonitrile | (CD₃OD, 400 MHz) 8.36 (s, 1H), 8.01-7.98 (m, 1H), 7.60-7.55 (m, 2H), 7.37-7.33 (m, 1H), 7.24-7.16 (m, 3H), 6.94-6.89 (m, 2H), 6.60 (d, J = 9.6 Hz, 1H), 6.52-6.51 (m, 1H), 4.66-4.62 (m, 1H), 3.63 (s, 3H), 1.97-1.89 (m, 3H), 1.39-1.36 (m, 3H). | 438 |
| 319 | 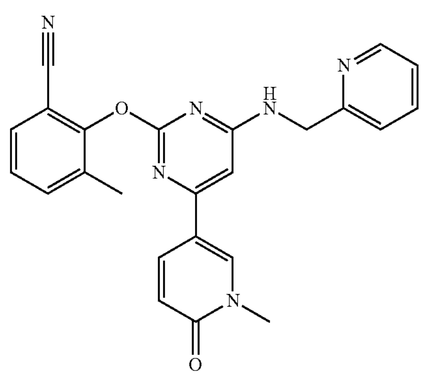 [SMILES: Cc1cccc(C#N)c1Oc1nc(NCc2ccccn2)cc(-c2ccc(=O)n(C)c2)n1] | 3-Methyl-2-{4-(1-methyl-6-oxo-1,6-dihydro-pyridin-3-yl)-6-[(pyridin-2-ylmethyl)-amino]-pyrimidin-2-yloxy}-benzonitrile | (CD₃OD, 400 MHz) 8.40 (s, 2H), 8.02 (d, J = 7.2 Hz, 1H), 7.68 (s, 1H), 7.50 (d, J = 10.0 Hz, 2H), 7.27 (d, J = 7.2 Hz, 2H), 6.99 (s, 1H), 6.60 (t, J = 6.0 Hz, 2H), 4.40 (s, 2H), 3.63 (s, 3H), 2.02 (s, 3H). | 425 |
| 320 | 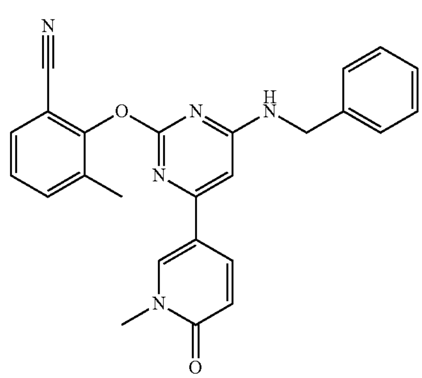 [SMILES: Cc1cccc(C#N)c1Oc1nc(NCc2ccccc2)cc(-c2ccc(=O)n(C)c2)n1] | 2-[4-Benzylamino-6-(1-methyl-6-oxo-1,6-dihydro-pyridin-3-yl)-pyrimidin-2-yloxy]-3-methyl-benzonitrile | (CD₃OD, 400 MHz) 8.35 (s, 1H), 7.99 (d, J = 10.0 Hz, 1H), 7.60-7.58 (m, 2H), 7.35-7.31 (m, 1H), 7.21-7.18 (m, 3H), 7.01-6.98 (m, 2H), 6.68 (d, J = 9.2 Hz, 1H), 6.53 (s, 1H), 4.27 (s, 2H), 3.62 (s, 3H), 2.09 (s, 3H). | 424 |

TABLE 21-continued

| Example | Structure | IUPAC Name | ¹H NMR ppm (δ) | MS (M + H) |
|---------|-----------|------------|----------------|------------|
| 321 | 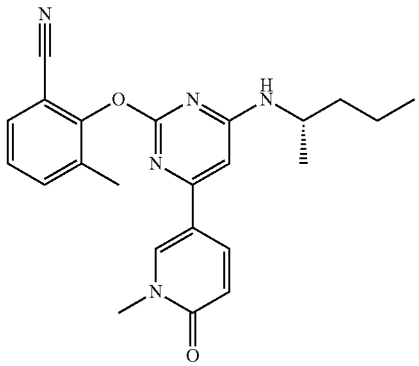 [SMILES: CCC[C@H](C)Nc1cc(-c2ccc(=O)n(C)c2)nc(Oc2c(C)cccc2C#N)n1] | (S)-3-Methyl-2-[4-(1-methyl-butylamino)-6-(1-methyl-6-oxo-1,6-dihydro-pyridin-3-yl)-pyrimidin-2-yloxy]-benzonitrile | (CD₃OD, 400 MHz) 8.33 (s, 1H), 7.99-7.97 (m, 1H), 7.62-7.60 (m, 2H), 7.32 (t, J = 7.6 Hz, 1H), 6.59 (d, J = 9.2 Hz, 1H), 6.44 (br, 1H), 3.73-3.68 (m, 1H), 3.63 (s, 3H), 2.22 (s, 3H), 1.45-1.40 (m, 1H), 1.38-1.29 (m, 1H), 1.25-1.15 (m, 2H), 1.09-1.05 (m, 3H), 0.88-0.82 (m, 3H). | 404 |
| 322 | 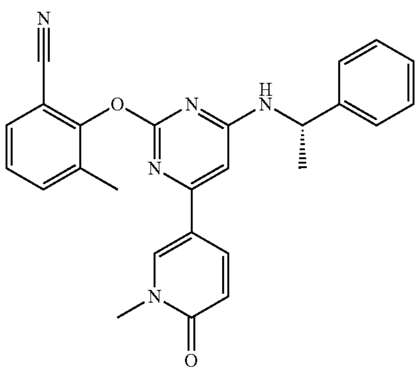 [SMILES: Cc1cccc(C#N)c1Oc1nc(N[C@@H](C)c2ccccc2)cc(-c2ccc(=O)n(C)c2)n1] | (S)-3-Methyl-2-[4-(1-methyl-6-oxo-1,6-dihydro-pyridin-3-yl)-6-(1-phenyl-ethylamino)-pyrimidin-2-yloxy]-benzonitrile | (CD₃OD, 400 MHz) 8.36 (s, 1H), 8.01-7.97 (m, 1H), 7.60-7.54 (m, 2H), 7.35 (t, J = 8.0 Hz, 1H), 7.20-7.15 (m, 3H), 6.95-6.89 (m, 2H), 6.60 (d, J = 9.6 Hz, 1H), 6.53-6.51 (m, 1H), 4.66-4.62 (m, 1H), 3.63 (s, 3H), 1.96-1.89 (m, 3H), 1.41-1.34 (m, 3H). | 438 |
| 323 | 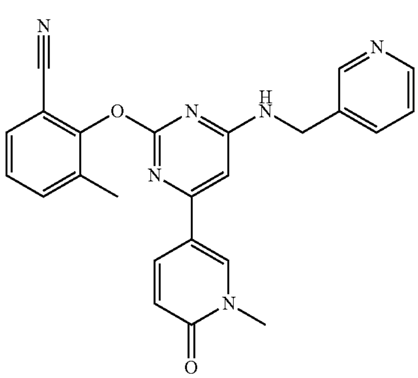 [SMILES: Cc1cccc(C#N)c1Oc1nc(NCc2cccnc2)cc(-c2ccc(=O)n(C)c2)n1] | 3-Methyl-2-{4-(1-methyl-6-oxo-1,6-dihydro-pyridin-3-yl)-6-[(pyridin-3-ylmethyl)-amino]-pyrimidin-2-yloxy}-benzonitrile | (CD₃OD, 400 MHz) 8.40 (s, 2H), 78.14 (s, 1H), 8.02 (d, J = 7.2 Hz, 1H), 7.58 (d, J = 10.0 Hz, 2H), 7.33 (s, 1H), 7.31 (t, J = 10.0 Hz, 2H), 6.59 (d, J = 7.2 Hz, 2H), 4.40 (s, 2H), 3.63 (s, 3H), 2.02 (s, 3H). | 425 |

Example 324: 5-(6-Benzylamino-2-methoxy-pyrimidin-4-yl)-1-methyl-1H-pyridin-2-one

Step 1: 5-(6-Chloro-2-methoxy-pyrimidin-4-yl)-1-methyl-1H-pyridin-2-one

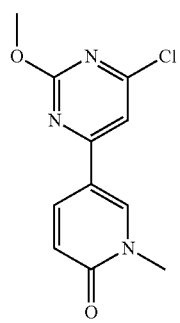 [SMILES: COc1nc(Cl)cc(-c2ccc(=O)n(C)c2)n1]

To a solution of 4,6-dichloro-2-methoxypyrimidine (986 mg, 5.5 mmol) and 1-methyl-5-(4,4,5,5-tetramethyl-[1,3,2]dioxaborolan-2-yl)-1H-pyridin-2-one (1.0 g, 4.3 mmol) in 1,4-dioxane (15 mL) was added Pd(dppf)$_2$Cl$_2$ (312 mg, 0.43 mmol) and K$_3$PO$_4$ (2.7 mL, 11 mmol, 4.0 mol/L). The mixture was stirred at 75° C. under N$_2$ for 3 h. The mixture was cooled to room temp, diluted with saturated NH$_4$Cl solution (50 mL) and extracted with DCM (50 mL×2). The combined organic layers were dried over Na$_2$SO$_4$, filtered and concentrated under reduced pressure. The residue was purified by silica gel column chromatography (PE/EtOAc, 1:1) to afford the title compound (590 mg, 2.4 mmol) as a white solid. $^1$H NMR (400 MHz, CDCl$_3$): δ 8.41 (d, J=2.4 Hz, 1H), 7.88 (dd, J=9.6 Hz, 2.8 Hz, 1H), 7.13 (s, 1H), 6.65 (d, J=10 Hz, 1H), 4.07 (s, 3H), 3.66 (s, 1H). LCMS (M+H)$^+$ 252

Step 2: 5-(6-Benzylamino-2-methoxy-pyrimidin-4-yl)-1-methyl-1H-pyridin-2-one

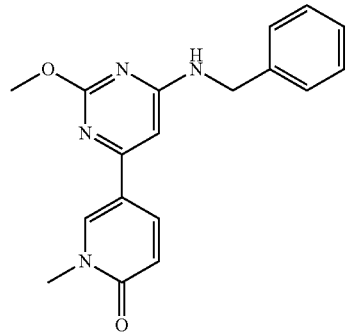 [SMILES: COc1nc(NCc2ccccc2)cc(-c2ccc(=O)n(C)c2)n1]

A solution of the title compounds from Step 1, benzylamine (0.2 mL) and Et$_3$N (0.2 mL) in n-butanol (6 mL) was heated to 95° C. for 5 h. The mixture was cooled down, diluted with H$_2$O (30 mL) and extracted with DCM (40 mL×3). The combined organic layers were concentrated under reduced pressure. The residue was purified by preparative TLC (DCM/MeOH=15:1) to afford the title compound (51 mg, 80%) as a white solid. $^1$H NMR (400 MHz, CD$_3$OD) δ 8.38 (s, 1H), 8.02 (d, J=9.6 Hz, 1H), 7.37-7.29 (m, 4H), 7.26-7.24 (m, 1H), 6.58 (d, J=9.6 Hz, 1H), 6.42 (s, 1H), 4.60 (s, 2H), 3.93 (s, 3H), 3.63 (s, 3H). LCMS (M+H)$^+$ 323.

Examples 325-331 (Table 22) were prepared from the appropriate amine in a similar multi-step manner as Example 324.

TABLE 22

| Example | Structure | IUPAC Name | $^1$H NMR ppm (δ) | MS (M + H) |
|---|---|---|---|---|
| 325 | 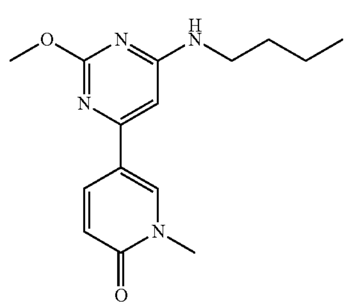 [SMILES: CCCCNc1cc(-c2ccc(=O)n(C)c2)nc(OC)n1] | 5-(6-Butylamino-2-methoxy-pyrimidin-4-yl)-1-methyl-1H-pyridin-2-one | (CD$_3$OD, 400 MHz) 8.38 (s, 1H), 8.03 (s, 1H), 6.59 (d, J = 8.0 Hz, 1H), 6.37 (s, 1H), 3.95 (s, 3H), 3.64 (s, 3H), 3.38 (m, 2H), 1.62-1.57 (m, 2H), 1.46-1.40 (m, 2H), 0.97 (t, J = 8.0 Hz, 3H). | 289 |
| 326 | 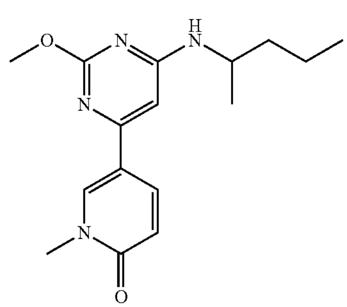 [SMILES: CCCC(C)Nc1cc(-c2ccc(=O)n(C)c2)nc(OC)n1] | 5-[2-Methoxy-6-(1-methyl-butylamino)-pyrimidin-4-yl]-1-methyl-1H-pyridin-2-one | (CD$_3$OD, 400 MHz) 8.37 (s, 1H), 8.02 (d, J = 7.6 Hz, 1H), 6.59 (d, J = 9.6 Hz, 1H), 6.35 (s, 1H), 4.21-4.13 (m, 1H), 3.94 (s, 3H), 3.64 (s, 3H), 1.55-1.49 (m, 2H), 1.48-1.39 (m, 2H), 1.19 (d, J = 6.4 Hz, 3H), 0.94 (t, J = 6.8 Hz, 3H). | 303 |

TABLE 22-continued

| Example | Structure | IUPAC Name | $^1$H NMR ppm (δ) | MS (M + H) |
|---|---|---|---|---|
| 327 | 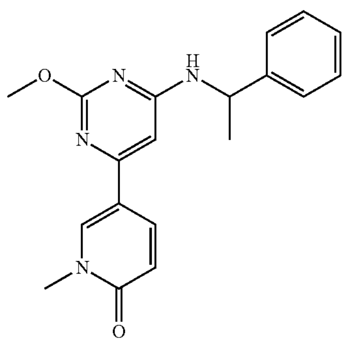 [SMILES: COc1nc(NC(C)c2ccccc2)cc(-c2ccc(=O)n(C)c2)n1] | 5-[2-Methoxy-6-(1-phenyl-ethylamino)-pyrimidin-4-yl]-1-methyl-1H-pyridin-2-one | (CD$_3$OD, 400 MHz) 8.33 (d, J = 2.8 Hz, 1H), 7.97 (d, J = 9.2 Hz, 1H), 7.38 (s, 1H), 7.37 (s, 1H), 7.31 (t, J = 7.6 Hz, 2H), 7.22-7.19 (m, 1H), 6.57 (d, J = 9.2 Hz, 1H), 6.37-6.15 (m, 1H), 5.23-5.09 (m, 1H), 3.95 (s, 3H), 3.62 (s, 3H), 1.53 (d, J = 7.2 Hz, 3H). | 337 |
| 328 | 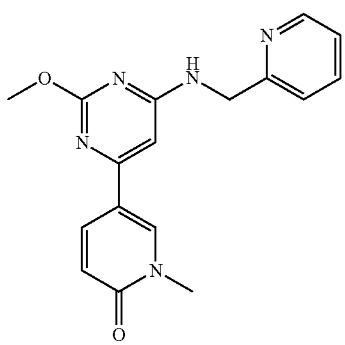 [SMILES: COc1nc(NCc2ccccn2)cc(-c2ccc(=O)n(C)c2)n1] | 5-{2-Methoxy-6-[(pyridin-2-ylmethyl)-amino]-pyrimidin-4-yl}-1-methyl-1H-pyridin-2-one | (CD$_3$OD, 400 MHz) 8.50 (s, 1H), 8.38 (s, 1H), 8.03 (d, J = 8.0 Hz, 1H), 7.79 (t, J = 6.0 Hz, 1H), 7.42 (d, J = 8.0 Hz, 1H), 7.30 (t, J = 6.0 Hz, 1H), 6.58 (d, J = 8.0 Hz, 1H), 6.50 (s, 1H), 4.71 (s, 2H), 3.86 (s, 3H), 3.63 (s, 3H). | 324 |
| 329 | | 5-(2-Methoxy-6-phenethylamino-pyrimidin-4-yl)-1-methyl-1H-pyridin-2-one | (CDCl$_3$, 400 MHz) 8.31 (d, J = 2.4 Hz, 1H), 7.77 (dd, J = 9.6 Hz, 2.4 Hz, 1H), 7.35-7.31 (m, 2H), 7.26-7.21 (m, 3H), 6.59 (d, J = 9.2 Hz, 1H), 6.09 (s, H), 4.94 (br, 1H), 3.96 (s, 3H), 3.70-3.68 (m, 2H), 3.62 (s, 3H), 2.96-2.93 (m, 2H). | |
| 330 | | 5-{2-Methoxy-6-[(pyridin-3-ylmethyl)-amino]-pyrimidin-4-yl}-1-methyl-1H-pyridin-2-one | (CD$_3$OD, 400 MHz) 8.57 (s, 1H), 8.43 (d, J = 7.2 Hz, 1H), 8.38 (s, 1H), 8.01 (d, J = 7.2 Hz, 1H), 7.85 (t, J = 6.0 Hz, 1H), 7.42 (d, J = 8.0 Hz, 1H), 6.57 (d, J = 8.0 Hz, 1H), 6.44 (s, 1H), 4.66 (s, 2H), 3.91 (s, 3H), 3.62 (s, 3H). | 324 |
| 331 | | 5-{2-Methoxy-6-[(1,2,3,4-tetrahydro-naphthalen-1-ylmethyl)-amino]-pyrimidin-4-yl}-1-methyl-1H-pyridin-2-one | (CD$_3$OD, 400 MHz) 8.37 (s, 1H), 8.02 (d, J = 7.2 Hz, 1H), 7.27-7.25 (m, 1H), 7.09-7.06 (m, 3H), 6.58 (d, J = 7.2 Hz, 1H), 6.39 (s, 1H), 3.98 (s, 3H), 3.64-3.63 (m, 1H), 3.52 (s, 3H), 3.51-3.49 (m, 1H), 3.15-3.12 (m, 1H), 2.79-2.74 (m, 2H), 1.92-1.87 (m, 3H), 1.76-1.74 (m, 1H). | 377 |

Example 332: 5-[6-Amino-2-(2-fluoro-6-methyl-phenoxy)-pyrimidin-4-yl]-1-methyl-1H-pyridin-2-one

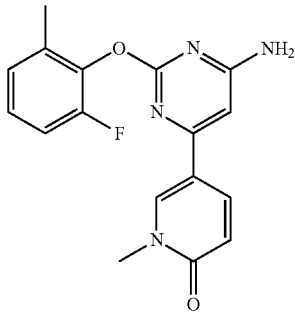 [SMILES: Cc1cccc(F)c1Oc1nc(N)cc(-c2ccc(=O)n(C)c2)n1]

A solution of 5-[6-chloro-2-(2-fluoro-6-methyl-phenoxy)-pyrimidin-4-yl]-1-methyl-1H-pyridin-2-one (150 mg, 0.43 mmol) and $NH_3 \cdot H_2O$ (15 mL) in n-BuOH (10 mL) was heated to 75° C. for 2 days. The mixture was diluted with $H_2O$ (50 mL) and extracted with DCM (40 mL×3). The combined organic layer was concentrated under reduced pressure. The residue was purified by preparative HPLC to give the title compound (65 mg, 0.19 mmol) as a white solid in 44% yield. $^1$H NMR (400 MHz, DMSO-$d_6$) δ 8.37 (d, J=2.8 Hz, 1H), 7.81 (dd, J=9.6 Hz, 2.8 Hz, 1H), 7.16-7.11 (m, 3H), 7.02 (br, 2H), 6.46-6.44 (m, 2H), 3.50 (s, 3H), 2.15 (s, 3H). LCMS (M+H)$^+$ 327.

Examples 333-334 (Table 23) were prepared from the appropriate chloropyrimidine in a similar manner as Example 332.

Example 335: 6-(1,5-dimethyl-6-oxo(3-hydropyridyl))-2-(2,6-dimethylphenoxy)pyrimidine-4-carbonitrile

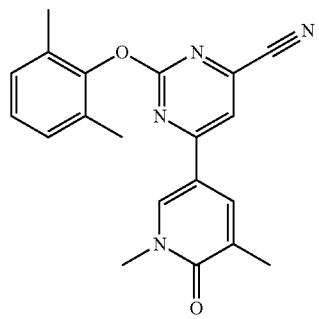

NaCN (17 mg, 0.35 mmol) and DABCO (2.5 mg, 0.02 mmol) were dissolved in $H_2O$ (1.2 mL) and cooled to 0° C. To this solution was slowly added 5-(6-chloro-2-(2,6-dimethyl-phenoxy)pyrimidin-4-yl)-1,3-dimethylpyridin-2(1H)-one (80 mg. 0.23 mmol) in DMSO (4 mL) and the reaction mixture was stirred at 30° C. overnight. The reaction mixture was extracted with DCM and the organics were concentrated under reduced pressure. Ether (3 mL) was added and the resulting solid precipitate was filtered and dried to give the title compound as a white solid (78 mg, 80% yield). $^1$H NMR (400 MHz, CDCl$_3$) δ 8.23 (d, J=2.4 Hz, 1H), 7.72 (s, 1H), 7.47 (s, 1H), 7.13-7.11 (m, 3H), 3.63 (s, 3H), 2.22 (s, 3H), 2.14 (s, 6H). LCMS (M+H) 347

TABLE 23

| Example | Structure | IUPAC Name | $^1$H NMR ppm (δ) | MS (M + H) |
|---|---|---|---|---|
| 333 | | 5-[6-Amino-2-(2-chloro-6-methyl-phenoxy)-pyrimidin-4-yl]-1-methyl-1H-pyridin-2-one | (CDCl$_3$, 400 MHz) 8.17 (d, J = 2.0 Hz, 1H), 7.73 (dd, J = 9.6, 2.4 Hz, 1H), 7.30-7.26 (m, 1H), 7.18-7.16 (m, 1H), 7.12-7.10 (m, 1H), 6.60 (d, J = 9.6 Hz, 1H), 6.30 (s, 1H), 4.99 (br, 2H), 3.58 (s, 3H), 2.24 (s, 3H). | 343 |
| 334 | | 5-[6-Amino-2-(2-chloro-6-methyl-phenoxy)-pyrimidin-4-yl]-1,3-dimethyl-1H-pyridin-2-one | (CDCl$_3$, 400 MHz) 8.03 (s, 1H), 7.62 (s, 1H), 7.32-7.29 (m, 1H), 7.20-7.10 (m, 2H), 6.48 (s, 1H), 5.73 (br, 2H), 3.56 (s, 3H), 2.27 (s, 3H), 2.22 (s, 3H) | 357 |

Example 336: Propane-1-sulfonic acid [5-(1,5-dimethyl-6-oxo-1,6-dihydro-pyridin-3-yl)-2-methyl-2H-pyrazol-3-yl]-amide

Step 1: 5-(5-Amino-1-methyl-1H-pyrazol-3-yl)-1,3-dimethyl-1H-pyridin-2-one

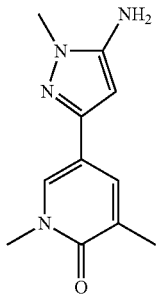

To a mixture of 5-bromo-2-methyl-2H-pyrazol-3-ylamine (200 mg, 1.14 mmol) in dioxane (6 mL) was added 1,3-dimethyl-5-(4,4,5,5-tetramethyl-[1,3,2]dioxaborolan-2-yl)-1H-pyridin-2-one (226 mg, 0.91 mmol), Pd(dppf)Cl$_2$ (83 mg, 0.11 mmol) and K$_3$PO$_4$/H$_2$O (481 mg, 2.27 mmol, 2 mL) under N$_2$. The reaction was stirred at 75° C. for 5 hours. The reaction mixture was concentrated under reduced pressure and the residue was dissolved in DCM (20 mL). The organics were washed with brine (10 mL), dried over Na$_2$SO$_4$, filtered, and purified by preparative TLC (EA/MeOH=30/1) to give the title compound (110 mg, 55%) as a brown solid. LCMS (M+H) 219.

Step 2: Propane-1-sulfonic acid [5-(1,5-dimethyl-6-oxo-1,6-dihydro-pyridin-3-yl)-2-methyl-2H-pyrazol-3-yl]-amide

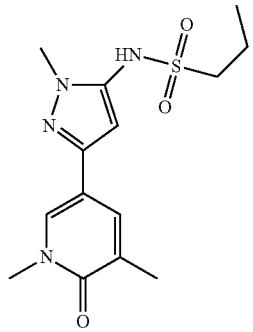 [SMILES: CCCS(=O)(=O)Nc1cc(-c2cc(C)c(=O)n(C)c2)nn1C]

To a mixture of the title compound from Step 1 (110 mg, 0.50 mmol) in pyridine (5 mL) was added propane-1-sulfonyl chloride (72 mg, 0.50 mmol) under N$_2$ and the reaction mixture was stirred at 50° C. for 10 h. The mixture was concentrated under reduced pressure and the residue was purified by preparative HPLC to afford the title compound (20 mg, 12%) as an off-white solid. $^1$H NMR (CDCl$_3$, 400 MHz) δ 7.66 (s, 1H), 7.65 (s, 1H), 6.27 (s, 1H), 3.87 (s, 3H), 3.62 (s, 3H), 3.17-3.13 (m, 2H), 2.18 (s, 3H), 1.96-1.90 (m, 2H), 1.10 (t, J=8.0 Hz, 3H). LCMS (M+H) 325

Examples 337-342 (Table 24) were prepared from 2-ethyl-6-fluoro-phenol or 2,6-difluorophenol, the appropriate sulfonamide and 1-methyl-5-(4,4,5,5-tetramethyl-1,3,2-dioxaborolan-2-yl)pyridin-2(1H)-one in a similar multi-step manner as Example 1.

TABLE 24

| Example | Structure | IUPAC Name | $^1$H NMR ppm (δ) | MS (M + H) |
|---|---|---|---|---|
| 337 | | N-(2-(2-ethyl-6-fluorophenoxy)-6-(1-methyl-6-oxo-1,6-dihydropyridin-3-yl)pyrimidin-4-yl)butane-1-sulfonamide | (400 MHz, DMSO-d$_6$) δ ppm 11.23-11.39 (br s, 1 H), 8.54-8.61 (m, 1 H), 7.85-7.92 (m, 1 H), 7.14-7.31 (m, 3 H), 6.81-6.87 (m, 1 H), 6.47-6.56 (m, 1 H), 3.52-3.59 (m, 3 H), 2.97-3.05 (m, 2 H), 2.54-2.59 (m, 2 H), 1.38-1.51 (m, 2 H), 1.17-1.29 (m, 2 H), 1.02-1.16 (m, 3 H), 0.76-0.88 (m, 3 H) | 461 |
| 338 | | N-(2-(2-ethyl-6-fluorophenoxy)-6-(1-methyl-6-oxo-1,6-dihydropyridin-3-yl)pyrimidin-4-yl)butane-2-sulfonamide | (400 MHz, DMSO-d$_6$) δ ppm 11.08-11.45 (br s, 1 H), 8.55-8.64 (m, 1 H), 7.86-7.95 (m, 1 H), 7.14-7.30 (m, 3 H), 6.83 (s, 1 H), 6.49-6.56 (m, 1 H), 3.56 (s, 3 H), 2.90-3.04 (m, 1 H), 2.52-2.59 (m, 2 H), 1.59-1.71 (m, 1 H), 1.26-1.41 (m, 1 H), 1.06-1.13 (m, 3 H), 0.99-1.05 (m, 3 H), 0.75-0.82 (m, 3 H) | 461 |
| 339 | | N-(2-(2-ethyl-6-fluorophenoxy)-6-(1-methyl-6-oxo-1,6-dihydropyridin-3-yl)pyrimidin-4-yl)propane-1-sulfonamide | (400 MHz, DMSO-d$_6$) δ ppm 11.18-11.51 (br s, 1 H), 8.55-8.60 (m, 1 H), 7.87-7.93 (m, 1 H), 7.16-7.29 (m, 3 H), 6.80-6.85 (m, 1 H), 6.48-6.54 (m, 1 H), 3.52-3.58 (m, 3 H), 2.92-2.99 (m, 2 H), 2.52-2.59 (m, 2 H), 1.42-1.54 (m, 2 H), 1.07-1.13 (m, 3 H), 0.79-0.86 (m, 3 H) | 447 |

TABLE 24-continued

| Example | Structure | IUPAC Name | ¹H NMR ppm (δ) | MS (M + H) |
|---------|-----------|------------|----------------|------------|
| 340 | | N-(2-(2,6-difluorophenoxy)-6-(1-methyl-6-oxo-1,6-dihydropyridin-3-yl)pyrimidin-4-yl)propane-2-sulfonamide | (400 MHz, DMSO-$d_6$) δ ppm 11.34-11.49 (br s, 1 H), 8.52-8.60 (m, 1 H), 7.84-7.93 (m, 1 H), 7.27-7.46 (m, 3 H), 6.91 (s, 1 H), 6.47-6.57 (m, 1 H), 3.54 (s, 3 H), 3.26-3.31 (m, 1 H), 1.09-1.16 (m, 6 H) | 437 |
| 341 | | N-(2-(2,6-difluorophenoxy)-6-(1-methyl-6-oxo-1,6-dihydropyridin-3-yl)pyrimidin-4-yl)propane-1-sulfonamide | (400 MHz, DMSO-$d_6$) δ ppm 11.36-11.60 (br s, 1 H), 8.54-8.60 (m, 1 H), 7.86-7.93 (m, 1 H), 7.26-7.45 (m, 3 H), 6.88 (s, 1 H), 6.48-6.55 (m, 1 H), 3.55 (s, 3 H), 3.02-3.13 (m, 2 H), 1.47-1.60 (m, 2 H), 0.82-0.91 (m, 3 H) | 437 |
| 342 | | N-(2-(2,6-difluorophenoxy)-6-(1-methyl-6-oxo-1,6-dihydropyridin-3-yl)pyrimidin-4-yl)butane-1-sulfonamide | (400 MHz, DMSO-$d_6$) δ ppm 10.96-12.11 (br s, 1 H), 8.54-8.59 (m, 1 H), 7.85-7.92 (m, 1 H), 7.25-7.44 (m, 3 H), 6.89 (s, 1 H), 6.49-6.55 (m, 1 H), 3.54 (s, 3 H), 3.04-3.16 (m, 2 H), 1.44-1.54 (m, 2 H), 1.21-1.32 (m, 2 H), 0.79-0.85 (m, 3 H) | 451 |

Example 343: N-(2-(2,4-difluoro-6-methylphenoxy)-6-(1-methyl-6-oxo-1,6-dihydropyridin-3-yl)pyrimidin-4-yl)butane-1-sulfonamide Step 1: 2,4-difluoro-6-(hydroxymethyl)phenol

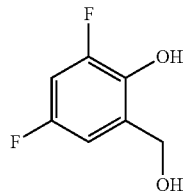

Pd/C (1 g) was added to a solution of 3,5-difluoro-2-hydroxybenzaldehyde (2.08 g, 13.2 mmol) in ethyl acetate (40 mL) and acetic acid (10 mL). The mixture was stirred at RT under H₂. After 14 h the reaction mixture was filtered and concentrated under reduced pressure to afford the title compound (1.56 g, 74%) as a colorless clear oil. LCMS (M−H)⁻ 159.

Step 2: 2,4-difluoro-6-methylphenol

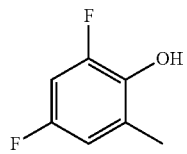

A 0.15 M solution of 2,4-difluoro-6-(hydroxymethyl)phenol (700 mg, 4.4 mmol) in THF (29 mL) under N₂ was treated with Et₂N (735 µL, 5.3 mmol). After cooling to 0° C., the mixture was treated with ethyl chloroformate (1.05 mL, 11 mmol). After stirring for 2 h, the ice bath was removed and the reaction was allowed to warm to RT for 30 min. After the mixture was filtered, the filtrate was concentrated under reduced pressure. The resulting residue was dissolved in THF (8.7 mL) and was added slowly to a solution of NaBH₄ in water (4 mL) stirred at 0° C. After stirring for 1 h, the mixture was treated with 1N HCl (aq) until pH~4. The mixture was diluted with water and extracted with EtOAc. The combined organic layers were dried over Na₂SO₄, filtered and concentrated under reduced pressure. The residue was purified by silica gel column chromatography eluting with a gradient of EtOAc [0 to 60%] in hexanes. The fractions were collected and concentrated under reduced pressure to afford the title compound (590 mg, 93%) as a colorless clear oil. LCMS (M−H)⁻ 143.

Step 3: N-(2-(2,4-difluoro-6-methylphenoxy)-6-(1-methyl-6-oxo-1,6-dihydropyridin-3-yl)pyrimidin-4-yl)butane-1-sulfonamide

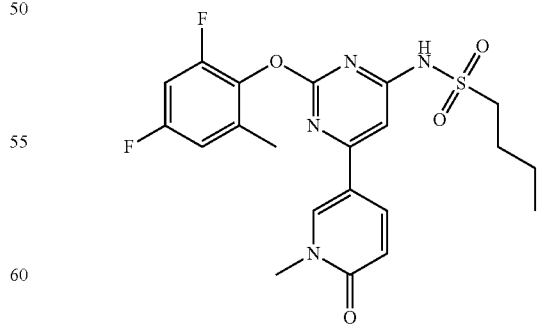

The title compound was prepared in a manner similar to Example 1 by substituting 2,4-difluoro-6-methylphenol for 2,5-dichlorophenol in Step 1, 1-methyl-5-(4,4,5,5-tetramethyl-1,3,2-dioxaborolan-2-yl)pyridin-2(1H)-one for 1,3- dimethyl-5-(4,4,5,5-tetramethyl-[1,3,2]diox-aborolan-2-yl)-1H-pyridin-2-one in Step 2 and butane-1-sulfonamide for propane-2-sulfonamide in Step 3. $^1$H NMR (400 MHz, DMSO-d$_6$) δ ppm 11.37 (br s, 1H), 8.58 (m, 1H), 7.90 (m, 1H), 7.27 (m, 1H), 7.12 (m, 1H), 6.84 (s, 1H), 6.53-6.51 (m, 1H), 3.55 (s, 3H), 3.03-3.08 (m, 2H), 2.17 (s, 3H), 1.43-1.51 (m, 2H), 1.24 (m, 2H), 0.82 (m, 3H). LCMS (M+H)$^+$ 465.

Examples 344-351 (Table 25) were prepared from the appropriate phenol, sulfonamide and 1-methyl-5-(4,4,5,5-tetramethyl-1,3,2-dioxaborolan-2-yl)pyridin-2(1H)-one in a similar manner as Example 1. 2,3-Difluoro-6-methylphenol and 3,6-difluoro-2-methylphenol (Examples 347-351) were made in a similar manner as 2,4-difluoro-6-methylphenol in Example 343.

TABLE 25

| Example | Structure | IUPAC Name | $^1$H NMR ppm (δ) | MS (M + H) |
|---|---|---|---|---|
| 344 | 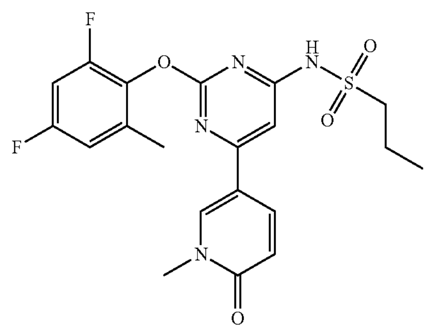 | N-(2-(2,4-difluoro-6-methylphenoxy)-6-(1-methyl-6-oxo-1,6-dihydropyridin-3-yl)pyrimidin-4-yl)propane-1-sulfonamide | (400 MHz, DMSO-d$_6$) δ ppm 11.22-11.55 (br s, 1 H), 8.53-8.60 (m, 1 H), 7.87-7.94 (m, 1 H), 7.21-7.33 (m, 1 H), 7.07-7.16 (m, 1 H), 6.79-6.86 (m, 1 H), 6.47-6.57 (m, 1 H), 3.52 (s, 3 H), 2.96-3.07 (m, 2 H), 2.17 (s, 3 H), 1.42-1.58 (m, 2 H), 0.78-0.90 (m, 3 H) | 451 |
| 345 | 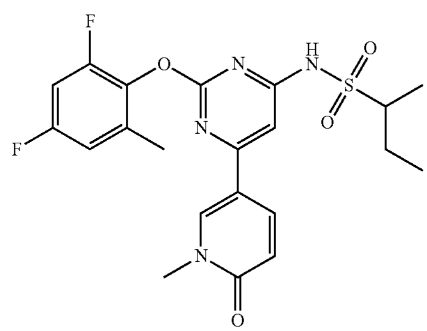 [SMILES: CCC(C)S(=O)(=O)Nc1cc(-c2ccc(=O)n(C)c2)nc(Oc2c(C)cc(F)cc2F)n1] | N-(2-(2,4-difluoro-6-methylphenoxy)-6-(1-methyl-6-oxo-1,6-dihydropyridin-3-yl)pyrimidin-4-yl)butane-2-sulfonamide | (400 MHz, DMSO-d$_6$) δ ppm 11.22-11.46 (br s, 1 H), 8.58-8.62 (m, 1 H), 7.88-7.95 (m, 1 H), 7.25-7.33 (m, 1 H), 7.10-7.16 (m, 1 H), 6.84 (s, 1 H), 6.50-6.56 (m, 1 H), 3.57 (s, 3 H), 2.92-3.02 (m, 1 H), 2.17 (s, 3 H), 1.61-1.76 (m, 1 H), 1.27-1.42 (m, 1 H), 1.04-1.10 (m, 3 H), 0.78-0.86 (m, 3 H) | 465 |
| 346 | 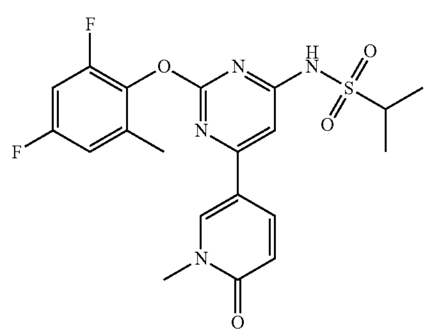 [SMILES: Cc1cc(F)cc(F)c1Oc1nc(NS(=O)(=O)C(C)C)cc(-c2ccc(=O)n(C)c2)n1] | N-(2-(2,4-difluoro-6-methylphenoxy)-6-(1-methyl-6-oxo-1,6-dihydropyridin-3-yl)pyrimidin-4-yl)propane-2-sulfonamide | 400 MHz, DMSO-d$_6$) δ ppm 11.25-11.41 (br s, 1 H), 8.55-8.63 (m, 1 H), 7.86-7.95 (m, 1 H), 7.25-7.36 (m, 1 H), 7.08-7.18 (m, 1 H), 6.82-6.90 (m, 1 H), 6.47-6.58 (m, 1 H), 3.50-3.62 (m, 3 H), 3.18-3.29 (m, 1 H), 2.11-2.20 (m, 3 H), 1.08-1.14 (m, 6 H) | 451 |
| 347 | 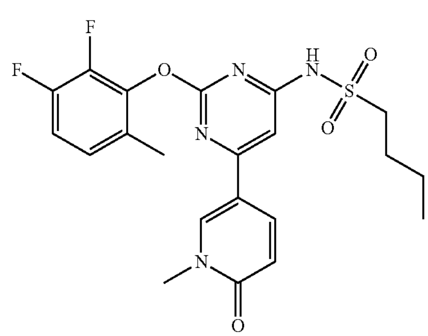 [SMILES: CCCCS(=O)(=O)Nc1cc(-c2ccc(=O)n(C)c2)nc(Oc2c(C)ccc(F)c2F)n1] | N-(2-(2,3-difluoro-6-methylphenoxy)-6-(1-methyl-6-oxo-1,6-dihydropyridin-3-yl)pyrimidin-4-yl)butane-1-sulfonamide | (400 MHz, DMSO-d$_6$) δ ppm 11.28-11.53 (br s, 1 H), 8.56-8.66 (m, 1 H), 7.86-7.95 (m, 1 H), 7.26-7.37 (m, 1 H), 7.13-7.25 (m, 1 H), 6.86 (s, 1 H), 6.48-6.58 (m, 1 H), 3.56 (s, 3 H), 2.96-3.05 (m, 2 H), 2.13 (s, 3H), 1.38-1.52 (m, 2 H), 1.13-1.29 (m, 2 H), 0.75-0.87 (m, 3 H) | 465 |

TABLE 25-continued

| Example | Structure | IUPAC Name | $^1$H NMR ppm (δ) | MS (M + H) |
|---|---|---|---|---|
| 348 | 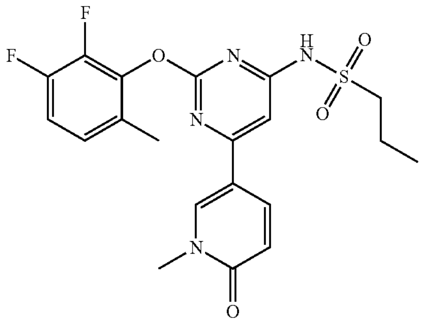 [SMILES: CCCS(=O)(=O)Nc1cc(-c2ccc(=O)n(C)c2)nc(Oc2c(C)ccc(F)c2F)n1] | N-(2-(2,3-difluoro-6-methylphenoxy)-6-(1-methyl-6-oxo-1,6-dihydropyridin-3-yl)pyrimidin-4-yl)propane-1-sulfonamide | (400 MHz, DMSO-d$_6$) δ ppm 11.33-11.54 (br s, 1 H), 8.56-8.63 (m, 1 H), 7.86-7.97 (m, 1 H), 7.27-7.37 (m, 1 H), 7.14-7.24 (m, 1 H), 6.82-6.90 (m, 1 H), 6.47-6.59 (m, 1 H), 3.56 (s, 3 H), 2.94-3.04 (m, 2 H), 2.14 (s, 3 H), 1.42-1.58 (m, 2 H), 0.77-0.89 (m, 3 H) | 451 |
| 349 | 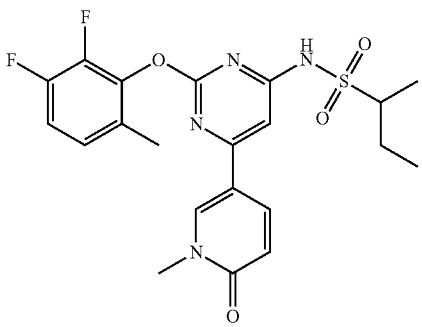 [SMILES: CCC(C)S(=O)(=O)Nc1cc(-c2ccc(=O)n(C)c2)nc(Oc2c(C)ccc(F)c2F)n1] | N-(2-(2,3-difluoro-6-methylphenoxy)-6-(1-methyl-6-oxo-1,6-dihydropyridin-3-yl)pyrimidin-4-yl)butane-2-sulfonamide | 400 MHz, DMSO-d$_6$) δ ppm 11.18-11.53 (br s, 1 H), 8.57-8.65 (m, 1 H), 7.86-7.98 (m, 1 H), 7.25-7.38 (m, 1 H), 7.13-7.25 (m, 1 H), 6.85 (s, 1 H), 6.45-6.57 (m, 1 H), 3.56 (s, 3 H), 2.87-2.99 (m, 1H), 2.13 (s, 3 H), 1.59-1.73 (m, 1 H), 1.25-1.40 (m, 1 H), 1.01-1.09 (m, 3 H), 0.75-0.84 (m, 3 H) | 465 |
| 350 | 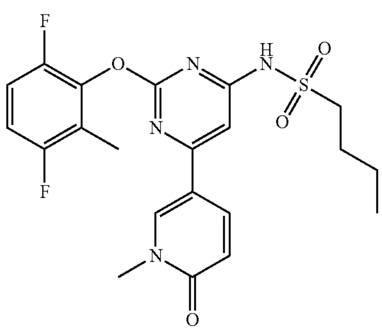 [SMILES: CCCCS(=O)(=O)Nc1cc(-c2ccc(=O)n(C)c2)nc(Oc2c(F)ccc(F)c2C)n1] | N-(2-(3,6-difluoro-2-methylphenoxy)-6-(1-methyl-6-oxo-1,6-dihydropyridin-3-yl)pyrimidin-4-yl)butane-1-sulfonamide | (400 MHz, DMSO-d$_6$) δ ppm 11.30-11.54 (br s, 1 H), 8.55-8.63 (m, 1 H), 7.86-7.95 (m, 1 H), 7.13-7.34 (m, 2 H), 6.84 (s, 1 H), 6.48-6.57 (m, 1 H), 3.56 (s, 3 H), 2.97-3.06 (m, 2 H), 2.04-2.11 (m, 3 H), 1.40-1.52 (m, 2 H), 1.15-1.29 (m, 2 H), 0.76-0.86 (m, 3 H) | 465 |
| 351 | 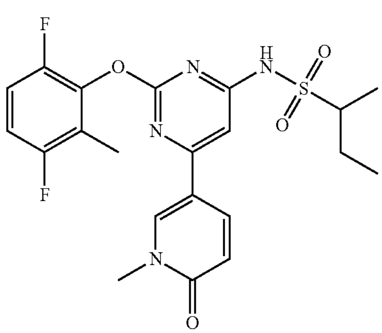 [SMILES: CCC(C)S(=O)(=O)Nc1cc(-c2ccc(=O)n(C)c2)nc(Oc2c(F)ccc(F)c2C)n1] | N-(2-(3,6-difluoro-2-methylphenoxy)-6-(1-methyl-6-oxo-1,6-dihydropyridin-3-yl)pyrimidin-4-yl)butane-2-sulfonamide | (400 MHz, DMSO-d$_6$) δ ppm 11.24-11.46 (br s, 1 H), 8.58-8.65 (m, 1 H), 7.87-7.96 (m, 1 H), 7.16-7.34 (m, 2 H), 6.85 (s, 1 H), 6.49-6.56 (m, 1 H), 3.56 (s, 3 H), 2.90-3.00 (m, 1 H), 2.05-2.09 (m, 3 H), 1.59-1.74 (m, 1 H), 1.26-1.40 (m, 1 H), 1.03-1.08 (m, 3 H), 0.77-0.84 (m, 3 H) | 465 |

Example 352: N-(5-fluoro-2-(2-fluoro-6-methylphenoxy)-6-(1-methyl-6-oxo-1,6-dihydropyridin-3-yl)pyrimidin-4-yl)butane-1-sulfonamide

Step 1: 5-(2,6-dichloro-5-fluoropyrimidin-4-yl)-1-methylpyridin-2(1H)-one

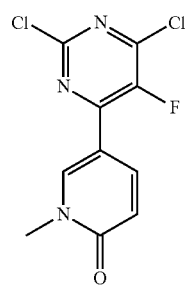 [SMILES: Cn1cc(-c2nc(Cl)nc(Cl)c2F)ccc1=O]

A mixture of 2,4,6-trichloro-5-fluoropyrimidine (736 mg, 3.7 mmol), 1-methyl-5-(4,4,5,5-tetramethyl-1,3,2-dioxaborolan-2-yl)pyridin-2(1H)-one (860 mg, 3.7 mmol), Pd(PPh$_3$)$_4$ (295 mg, 0.26 mmol), K$_3$PO$_4$ (0.92 mL, 2 mol/L, aq) in dioxane (24 mL) was bubbled with N$_2$ for 5 min. The mixture was stirred at 80° C. for 4 h. After the mixture was diluted with water, it was extracted with EtOAc; the combined organic layers were washed with brine, dried over Na$_2$SO$_4$, filtered and concentrated under reduced pressure. The resulting residue was purified by silica gel column chromatography eluting with a gradient of EtOAc [0 to 80%] in DCM. The fractions were collected and concentrated under reduced pressure to afford the title compound (190 mg, 19%) as a white solid. LCMS (M+H)$^+$ 275.

Step 2: 5-(6-chloro-5-fluoro-2-(2-fluoro-6-methylphenoxy)pyrimidin-4-yl)-1-methylpyridin-2(1H)-one and 5-(2-chloro-5-fluoro-6-(2-fluoro-6-methylphenoxy)pyrimidin-4-yl)-1-methylpyridin-2(1H)-one

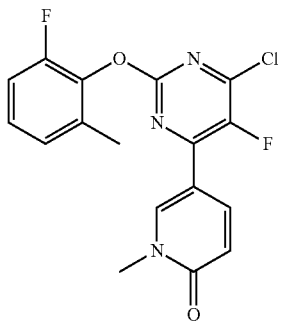

-continued

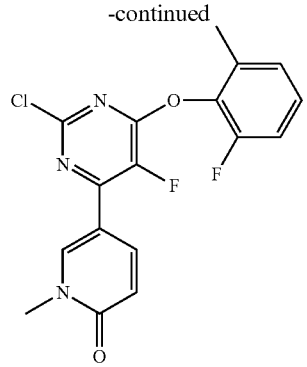

A mixture of 2-fluoro-6-methylphenol (65 mg, 0.5 mmol) and 5-(2,6-dichloro-5-fluoropyrimidin-4-yl)-1-methylpyridin-2(1H)-one (140 mg, 0.5 mmol) in DMF (1.3 mL) and THF (1.3 mL) was treated with K$_2$CO$_3$ (69 mg, 0.5 mmol). The mixture was stirred at rt for 12 h. The resulting suspension was diluted with water and extracted with EtOAc. The combined organic layers were washed with 1N NaOH, water, brine, dried over MgSO$_4$, and concentrated under reduced pressure. The crude solid was purified by silica gel column chromatography using a gradient of EtOAc (0 to 50%) in DCM to afford an unseparated mixture of regioisomeric title compounds (100 mg, 96% combined) as an off-white solid. LCMS (M+H)$^+$ 364.

Step 3: N-(5-fluoro-2-(2-fluoro-6-methylphenoxy)-6-(1-methyl-6-oxo-1,6-dihydropyridin-3-yl)pyrimidin-4-yl)butane-1-sulfonamide

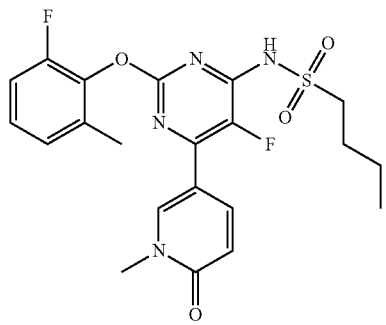 [SMILES: CCCCS(=O)(=O)Nc1nc(Oc2c(C)cccc2F)nc(-c2ccc(=O)n(C)c2)c1F]

A mixture of the title compounds from Step 2 (100 mg, 0.28 mmol) was treated with butane-1-sulfonamide (76 mg, 0.56 mmol), Pd$_2$(dba)$_3$ (12 mg, 5%), X-Phos (20 mg, 15%) and Cs$_2$CO$_3$ (127 mg, 0.39 mmol). The mixture was diluted with 1,4 dioxane (1.9 mL), purged with nitrogen for 5 min, sealed and heated to 90° C. for 2 h. After the cooled mixture was filtered, the filtrate was purified directly by prep-HPLC. Both regioisomers were isolated. The title compound (6 mg) was obtained as a white solid. $^1$H NMR (400 MHz, DMSO-d6) δ 11.44 (br s, 1H), 8.54-8.64 (m, 1H), 7.86-7.97 (m, 1H), 7.22-7.36 (m, 1H), 7.11-7.22 (m, 1H), 6.73-6.83 (m, 1H), 6.47-6.55 (m, 1H), 3.52-3.58 (m, 3H), 2.85-2.97 (m, 2H), 2.13 (s, 3H), 1.29-1.53 (m, 2H), 1.16-1.28 (m, 2H), 0.75-0.83 (m, 3H). LCMS (M+H)$^+$ 465.

Examples 353-355 (Table 26) were prepared from tetrahydro-2H-pyran-4-ol or 2-propanol, the appropriate sulfonamide and 1-methyl-5-(4,4,5,5-tetramethyl-1,3,2-dioxaborolan-2-yl)pyridin-2(1H)-one in a similar multi-step manner as Example 1.

TABLE 26

| Example | Structure | IUPAC Name | ¹H NMR ppm (δ) | MS (M + H) |
|---|---|---|---|---|
| 353 | 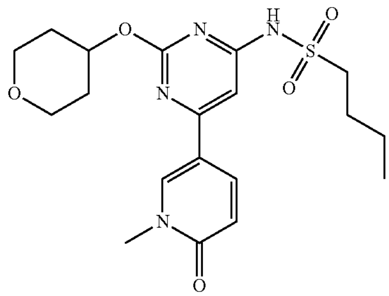 [SMILES: CCCCS(=O)(=O)Nc1cc(-c2ccc(=O)n(C)c2)nc(OC2CCOCC2)n1] | N-(6-(1-methyl-6-oxo-1,6-dihydropyridin-3-yl)-2-((tetrahydro-2H-pyran-4-yl)oxy)pyrimidin-4-yl)butane-1-sulfonamide | (400 MHz, DMSO-$d_6$) δ ppm 11.00-11.52 (br s, 1 H), 8.50-8.61 (m, 1 H), 7.87-7.99 (m, 1 H), 6.75 (s, 1 H), 6.45-6.57 (m, 1 H), 5.03-5.15 (m, 1 H), 3.83-3.94 (m, 2 H), 3.55-3.57 (m, 3 H), 3.44-3.55 (m, 4 H), 2.02-2.11 (m, 2 H), 1.60-1.75 (m, 4 H), 1.34-1.47 (m, 2 H), 0.83-0.91 (m, 3 H) | 423 |
| 354 | 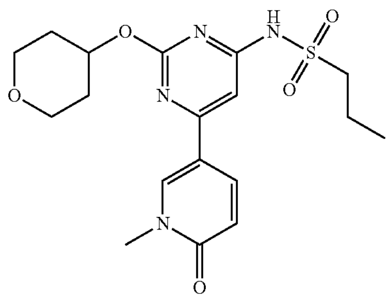 [SMILES: CCCS(=O)(=O)Nc1cc(-c2ccc(=O)n(C)c2)nc(OC2CCOCC2)n1] | N-(6-(1-methyl-6-oxo-1,6-dihydropyridin-3-yl)-2-((tetrahydro-2H-pyran-4-yl)oxy)pyrimidin-4-yl)propane-1-sulfonamide | (400 MHz, DMSO-$d_6$) δ ppm 11.06-11.39 (br s, 1 H), 8.50-8.57 (m, 1 H), 7.89-7.99 (m, 1 H), 6.76 (s, 1 H), 6.46-6.56 (m, 1 H), 5.04-5.14 (m, 1 H), 3.83-3.94 (m, 2 H), 3.55-3.57 (m, 3 H), 3.45-3.55 (m, 4 H), 2.02-2.13 (m, 2 H), 1.60-1.79 (m, 4 H), 0.93-1.05 (m, 3 H) | 409 |
| 355 | 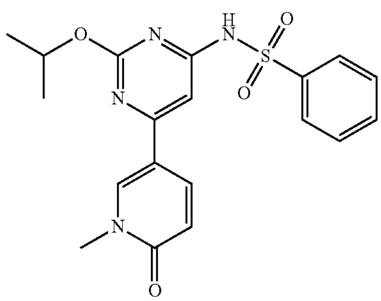 [SMILES: CC(C)Oc1nc(NS(=O)(=O)c2ccccc2)cc(-c2ccc(=O)n(C)c2)n1] | N-(2-isopropoxy-6-(1-methyl-6-oxo-1,6-dihydropyridin-3-yl)pyrimidin-4-yl)benzenesulfonamide | (400 MHz, CDCl₃) δ 8.29 (d, J = 2.0 Hz, 1H), 7.99-7.97 (m, 2H), 7.83-7.80 (m, 1H), 7.62-7.51 (m, 3H), 6.93 (s, 1H), 6.66 (d, J = 9.5 Hz, 1H), 5.23-5.20 (m, 1H), 3.63 (s, 3H), 1.36 (s, 3H), 1.34 (s, 3H) | 401 |

Example 356: 5-(10,10-dioxido-2,4-dioxa-10-thia-11-aza-1 (2,4)-pyrimidina-3(1,3)-benzenacyclounde-caphan-6-en-16-yl)-1-methylpyridin-2(1H)-one Step 1: 4,6-Dichloro-2-(3-methoxymethoxy-phenoxy)-pyrimidine

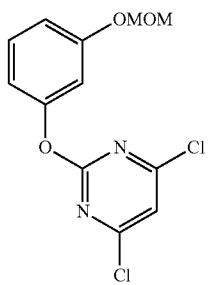

NaH (60% dispersion in oil, 960 mg, 24 mmol) was added to a solution of 3-methoxy-methoxy-phenol (3.1 g, 20 mmol) in THF (100 mL) at −60° C. under $N_2$. After stirring for 1 hr, 4,6-Dichloro-2-methanesulfonyl-pyrimidine (5.5 g, 24 mmol) was added to the mixture. After stirring and additional 2 h at −60° C., the mixture was allowed to warm to RT and stir overnight. The resulting suspension was treated with water and extracted with DCM. The combined organic layers were dried over $Na_2SO_4$, filtered and concentrated under reduced pressure. The resulting residue was purified by silica gel column chromatography eluting with PE/EtOAc (20:1) to give the title compound (5.3 g, 90%) as a white oil. ¹H NMR (300 MHz, CDCl₃) δ ppm 7.34 (m, 1H), 7.13 (s, 1H), 6.96 (m, 1H), 6.91 (s, 1H), 6.85 (m, 1H), 5.19 (s, 2H), 3.50 (s, 3H). LCMS (M+H)⁺ 301.

Step 2: 5-(6-chloro-2-(3-(methoxymethoxy)phenoxy)pyrimidin-4-yl)-1-methylpyridin-2(1H)-one

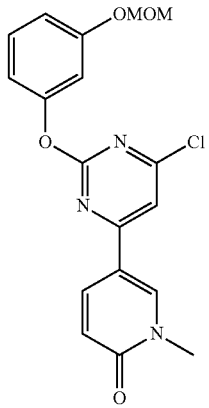

A mixture of the title compound of Step 1 (3.0 g, 10 mmol), 1-methyl-5-(4,4,5,5-tetra-methyl-[1,3,2]dioxaborolan-2-yl)-1H-pyridin-2-one (2.3 g, 10 mmol), Pd(dppf)Cl$_2$ (732 mg, 1.0 mmol) and 3.75 M K$_3$PO$_4$ (6.6 mL, 25 mmol) in 1,4-dioxane (40 mL) was heated to 75° C. for 4 hr under N$_2$. After the mixture was cooled to room temp, it was poured into H$_2$O and was extracted with EtOAc. The combined organic layers were dried over Na$_2$SO$_4$, filtered and concentrated under reduced pressure. The resulting residue was purified by silica gel column chromatography eluting with PE/EtOAc (1:3) to give the title compound (1.8 g, 49%) as a yellow solid. $^1$H NMR (300 MHz, CDCl$_3$) δ ppm 8.33 (s, 1H), 7.85 (m, 1H), 7.34 (m, 1H), 7.22 (s, 1H), 6.98-6.96 (m, 2H), 6.88 (m, 1H), 6.67 (m, 1H), 5.20 (s, 2H), 3.63 (s, 3H), 3.50 (s, 3H). LCMS (M+H)$^+$ 374.

Step 3: N-(2-(3-(methoxymethoxy)phenoxy)-6-(1-methyl-6-oxo-1,6-dihydropyridin-3-yl) pyrimidin-4-yl)but-3-ene-1-sulfonamide

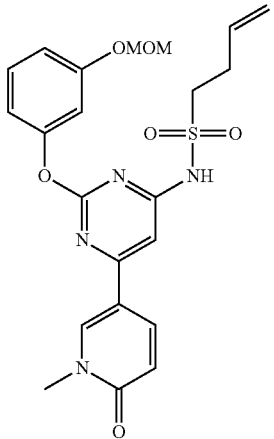

A mixture of the title compound (594 mg, 1.6 mmol) of Step 2, but-3-ene-1-sulfonamide (300 mg, 2.2 mmol), Pd$_2$(dba)$_3$ (73 mg, 0.08 mmol), X-Phos (115 mg, 0.24 mmol) and Cs$_2$CO$_3$ (1.0 g, 3.1 mmol) was diluted with 1,4-dioxane (15 mL). After purging with N$_2$, the mixture was stirred for 5 hr at 90° C. The mixture was diluted with H$_2$O, adjusted to pH 4 with 2N HCl, and extracted with DCM. The combined organic layers were dried over Na$_2$SO$_4$, filtered and concentrated under reduced pressure. The residue was purified by silica gel column chromatography eluting with DCM/MeOH (20:1) to give the title compound (600 g, 80%) as a yellow solid. $^1$H NMR (400 MHz, DMSO-d$_6$) δ ppm 11.4 (br s, 1H), 8.55 (m, 1H), 7.91 (m, 1H), 7.33 (m, 1H), 6.92-6.85 (m, 4H), 6.52 (m, 1H), 5.71-5.63 (m, 1H), 5.19 (s, 2H), 5.05-4.98 (m, 2H), 3.54 (s, 3H), 3.38 (s, 3H), 3.30-3.26 (m, 2H), 2.33-2.27 (m, 2H). LCMS (M+H)$^+$ 473

Step 4: N-(2-(3-hydroxyphenoxy)-6-(1-methyl-6-oxo-1,6-dihydropyridin-3-yl)pyrimidin-4-yl)but-3-ene-1-sulfonamide

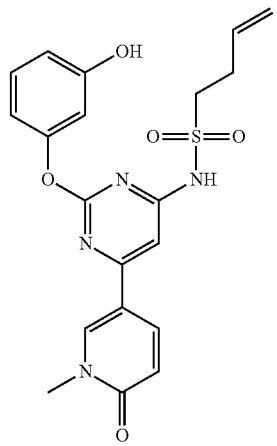 [SMILES: C=CCCS(=O)(=O)Nc1cc(-c2ccc(=O)n(C)c2)nc(Oc2cccc(O)c2)n1]

TFA (5 mL) was added to a solution of the title compound (600 mg, 1.3 mmol) of Step 3 in DCM (15 mL) at room temperature. After the mixture was stirred overnight, the mixture was concentrated. The resulting residue was purified by silica gel column chromatography eluting with DCM/MeOH (20:1) to give the title compound (450 mg, 83%) as a yellow solid. $^1$H NMR (400 MHz, DMSO-d$_6$) δ ppm 11.4 (br s, 1H), 9.67 (br s, 1H), 8.54 (s, 1H), 7.89 (m, 1H), 7.19 (m, 1H), 6.84 (s, 1H), 6.66-6.57 (m, 3H), 6.51 (m, 1H), 5.75-5.64 (m, 1H), 5.08-4.99 (m, 2H), 3.54 (s, 3H), 3.33-3.27 (m, 2H), 2.32-2.28 (m, 2H). LCMS (M+H)$^+$ 429

Step 5: N-(2-(3-(allyloxy)phenoxy)-6-(1-methyl-6-oxo-1,6-dihydropyridin-3-yl)pyrimidin-4-yl)but-3-ene-1-sulfonamide

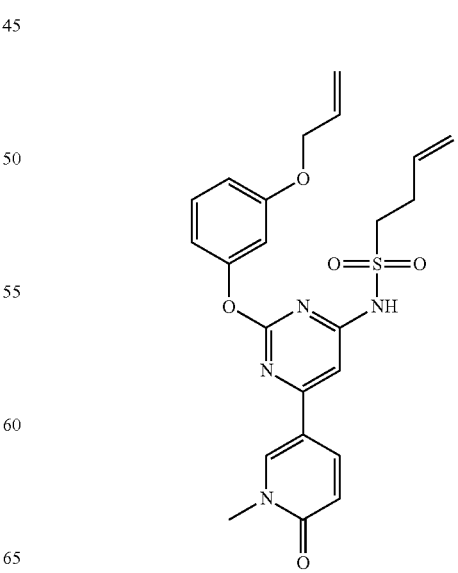

NaH (60% dispersion in oil, 51 mg, 1.3 mmol) was added to a solution of the title compound (250 mg, 0.58 mmol) of Step 4 stirred in DMF (15 mL) at 0° C. After 30 min, 3-bromoprop-1-ene (141 mg, 1.2 mmol) was added to the resulting mixture. After the ice bath was removed, the mixture was stirred at RT overnight. The mixture was diluted with H₂O, adjusted to pH 4 with 2N HCl, and extracted with DCM. The combined organic layers were dried over Na₂SO₄, filtered and concentrated under reduced pressure. The residue was purified by silica gel column chromatography eluting with DCM/MeOH (20:1) to give the title compound (150 mg, 54%) as a white solid. $^1$H NMR (400 MHz, DMSO-$d_6$) δ ppm 11.4 (br s, 1H), 8.56 (m, 1H), 7.91 (m, 1H), 7.31 (m, 1H), 6.86-6.84 (m, 3H), 6.79 (m, 1H), 6.52 (m, 1H), 6.07-6.00 (m, 1H), 5.70-5.63 (m, 1H), 5.41-5.37 (m, 1H), 5.27-5.24 (m, 1H), 5.05-4.98 (m, 2H), 4.56 (m, 2H), 3.55 (s, 3H), 3.28-3.24 (m, 2H), 2.32-2.28 (m, 2H). LCMS (M+H)$^+$ 469.

Step 6: 5-(10,10-dioxido-2,4-dioxa-10-thia-11-aza-1(2,4)-pyrimidina-3(1,3)-benzenacycloundecaphan-6-en-1$^6$-yl)-1-methylpyridin-2(1H)-one

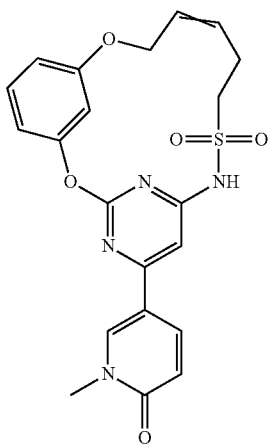 [SMILES: Cn1cc(-c2cc3nc(n2)Oc2cccc(c2)OCC=CCCS(=O)(=O)N3)ccc1=O]

A solution of the title compound (200 mg, 0.43 mmol) of Step 5 in toluene (80 mL) was bubbled with N₂ for 1 hr at room temp. After Grubbs Catalyst™ 2nd Generation (36 mg, 0.04 mmol) was added, the mixture was evacuated and filled with N₂ three times. The reaction mixture was heated to 95° C. for 12 hr. After the mixture was cooled to room temp, Grubbs Catalyst™ 2nd Generation (36 mg, 0.04 mmol) was added and mixture was heated to 95° C. for 6 hr. After the mixture was cooled to room temp, Grubbs Catalyst™ 2nd Generation (36 mg, 0.04 mmol) was added and mixture was heated to 95° C. for 12 hr. After the mixture was cooled to room temp, the mixture was filtered and the filtrate was concentrated under reduced pressure. The resulting residue was purified by silica gel column chromatography eluting with DCM/MeOH (20:1) to give the title product (11 mg, 6%) as yellow solid. $^1$H NMR (400 MHz, DMSO-$d_6$) δ ppm 11.3-11.2 (br s, 1H), 8.68 (s, 1H), 7.99 (s, 1H), 7.30-6.54 (m, 6H), 5.70-5.63 (m, 2H), 4.68-4.59 (m, 2H), 3.63 (s, 3H), 3.52-3.25 (m, 2H), 2.43-2.29 (m, 2H). LCMS (M+H)$^+$ 441

Example 357: 5-(10,10-dioxido-2,4-dioxa-10-thia-11-aza-1(2,4)-pyrimidina-3(1,3)-benzenacycloundecaphane-1$^6$-yl)-1-methylpyridin-2(1H)-one

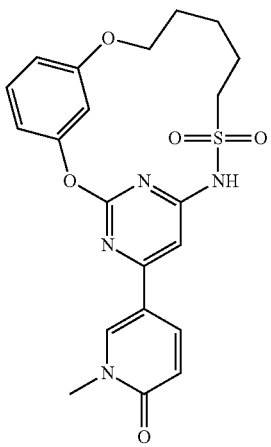 [SMILES: Cn1cc(-c2cc3nc(n2)Oc2cccc(c2)OCCCCCS(=O)(=O)N3)ccc1=O]

A solution of the title compound from Step 6 of Example 356 (5 mg, 0.01 mmol) in MeOH (5 mL) was treated with 10% Pd/C (2 mg). After the mixture was stirred under H₂ for 20 min, the reaction was deemed complete by LCMS. The mixture was filtered and the filtrate was concentrated under reduced pressure. The residue was purified by prep-TLC (DCM:MeOH=20:1) to give the title compound (4 mg, 80%) as a white solid. $^1$H NMR (400 MHz, CDCl₃+CD₃OD) δ ppm 11.4-11.2 (br s, 1H), 8.56 (m, 1H), 8.08 (m, 1H), 7.36 (m, 1H), 6.90-6.84 (m, 3H), 6.75 (s, 1H), 6.67 (m, 1H), 4.28-4.25 (m, 2H), 3.70 (s, 3H), 3.19-3.15 (m, 2H), 1.81-1.69 (m, 4H), 1.61-1.57 (m, 2H). LCMS (M+H)$^+$ 443.

Example 358: 5-(11,11-dioxido-2,4-dioxa-11-thia-12-aza-1(2,4)-pyrimidina-3(1,3)-benzenacyclododecaphan-7-en-1$^6$-yl)-1-methylpyridin-2(1H)-one Step 1: N-(2-(3-(but-3-en-1-yloxy)phenoxy)-6-(1-methyl-6-oxo-1,6-dihydropyridin-3-yl)pyrimidin-4-yl)but-3-ene-1-sulfonamide

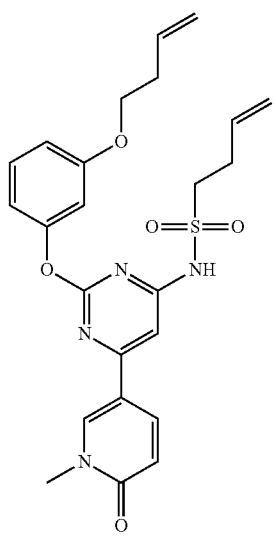 [SMILES: C=CCCOc1cccc(Oc2nc(NS(=O)(=O)CCC=C)cc(-c3ccc(=O)n(C)c3)n2)c1]

Sodium tert-butoxide (403 mg, 4.2 mmol) was added to a solution of the title compound from Step 4 of Example 356 (600 mg, 1.4 mmol) in DMF (10 mL). After the mixture was stirred at room temperature for 30 min, it was treated with 4-bromobut-1-ene (392 mg, 2.9 mmol) and stirred at room temp overnight. An additional portion of 4-bromobut-1-ene (392 mg, 2.9 mmol) was added to the mixture and was stirred at for 7 hr. A third portion of 4-bromobut-1-ene (208 mg, 1.5 mmol) was added and stirred at room temperature for 48 h. The mixture was treated with $H_2O$ and extracted with DCM. The combined organic layers were dried over $Na_2SO_4$, filtered and concentrated under reduced pressure. The residue was purified by silica gel column chromatography eluting with DCM/MeOH (20:1) to give the title compound (320 mg, 47%) as a yellow solid. $^1$H NMR (400 MHz, DMSO-$d_6$) δ ppm 11.4 (br s, 1H), 8.56 (m, 1H), 7.92 (m, 1H), 7.31 (m, 1H), 6.84-6.77 (m, 4H), 6.52 (m, 1H), 5.91-5.84 (m, 1H), 5.70-5.64 (m, 1H), 5.18-4.99 (m, 4H), 4.03 (m, 2H), 3.55 (s, 3H), 3.26 (m, 2H), 2.48-2.45 (m, 2H), 2.34-2.29 (m, 2H). LCMS (M+H)$^+$ 483.

Step 2: 5-(11,11-dioxido-2,4-dioxa-11-thia-12-aza-1(2,4)-pyrimidina-3(1,3)-benzenacyclododecaphan-7-en-1$^6$-yl)-1-methylpyridin-2(1H)-one

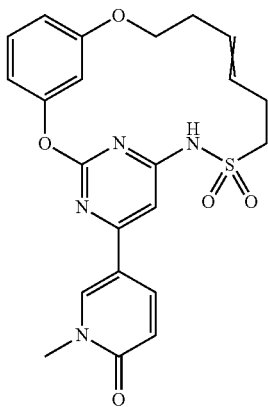 [SMILES: Cn1cc(-c2cc3nc(n2)Oc2cccc(c2)OCCC=CCCS(=O)(=O)N3)ccc1=O]

A solution of the title compound (320 mg, 0.7 mmol) of Step 1 in toluene (130 mL) was bubbled with $N_2$ for 1 hr at room temp. After Grubbs Catalyst™ 2nd Generation (112 mg, 0.1 mmol) was added, the mixture purged with $N_2$ for an additional 1 hr. The reaction mixture was heated to 90° C. for 12 hr. After the mixture was cooled to RT, Grubbs Catalyst™ 2nd Generation (112 mg, 0.1 mmol) was added and mixture was heated to 90° C. for 12 hr. After cooling to RT, the mixture was concentrated under reduced pressure. The residue was purified by silica gel column chromatography eluting with DCM/MeOH (30:1) to give a red solid. The solid was triturated with MeOH (3 mL) and filtered. The filter cake was collected and dried to give the title compound (32 mg, 10%) as red solid. $^1$H NMR (400 MHz, DMSO-$d_6$) δ ppm 11.3 (br s, 1H), 8.65 (s, 1H), 7.98 (m, 1H), 7.29 (m, 1H), 6.84-6.73 (m, 3H), 6.65 (m, 1H), 6.55 (m, 1H), 5.45-5.39 (m, 1H), 5.31-5.26 (m, 1H), 4.28 (s, 2H), 3.58 (s, 3H), 2.91-2.87 (m, 2H), 2.34-2.29 (m, 2H), 2.09-2.07 (, 2H). LCMS (M+H)$^+$ 455.

Example 359: 5-(11,11-dioxido-2,4-dioxa-11-thia-12-aza-1(2,4)-pyrimidina-3(1,3)-benzenacyclododecaphane-1$^6$-yl)-1-methylpyridin-2(1H)-one

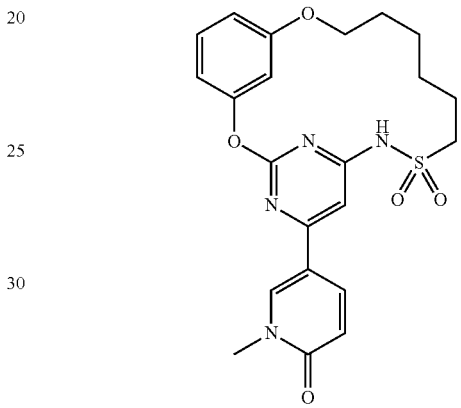

A solution of the title compound from Step 2 of Example 358 (30 mg, 0.07 mmol) in MeOH (12 mL) was treated with 10% Pd/C (7 mg). After the mixture was stirred under $H_2$ for 4.5 hr, the mixture was filtered and the filtrate was concentrated under reduced pressure. The residue was purified by preparative HPLC to give the title compound (10 mg, 33%) as a white solid. $^1$H NMR (400 MHz, DMSO-$d_6$) δ ppm 11.2 (br s, 1H), 8.64 (m, 1H), 7.97 (m, 1H), 7.34 (m, 1H), 6.87-6.85 (m, 2H), 6.80 (s, 1H), 6.74-6.72 (m, 1H), 6.55 (m, 1H), 4.25-4.23 (m, 2H), 3.58 (s, 3H), 2.98-2.94 (m, 2H), 1.62-1.54 (m, 4H), 1.45-1.42 (m, 2H), 1.34-1.27 (m, 2H). LCMS (M+H)$^+$ 457.

Examples 360-361 (Table 27) were prepared from an appropriate phenol in a similar multi-step manner as Examples 356 and 358.

TABLE 27

| Example | Structure | IUPAC Name | $^1$H NMR ppm (δ) | MS (M + H) |
|---|---|---|---|---|
| 360 | | 5-(36-chloro-10,10-dioxido-2,4-dioxa-10-thia-11-aza-1(2,4)-pyrimidina-3(1,3)-benzenacycloundecaphan-6-en-1$^6$-yl)-1-methylpyridin-2(1H)-one | (400 MHz, DMSO-$d_6$) δ ppm 8.62 (s, 1H), 8.02-8.00 (m, 1H), 7.39 (m, 1H), 7.17 (br s, 1H), 6.79-6.66 (m, 3H), 6.52-6.48 (m, 1H), 5.68-5.41 (m, 2H), 4.63-4.56 (m, 2H), 3.56 (s, 3H), 3.15-2.67 (m, 2H), 2.33-2.25 (m, 2H) | 475 |
| 361 | | 5-(36-chloro-11,11-dioxido-2,4-dioxa-11-thia-12-aza-1(2,4)-pyrimidina-3(1,3)-benzenacyclododecaphan- | (400 MHz, DMSO-$d_6$) δ ppm 11.33 (br s, 1H), 8.65 (m, 1H), 7.96 (m, 1H), 7.42 (m, 1H), 7.14 (m, 1H), 6.84 (m, 1H), 6.75 (s, 1H), 6.55 (m, 1H), | 489 |

TABLE 27-continued

| Example | Structure | IUPAC Name | $^1$H NMR ppm (δ) | MS (M + H) |
|---|---|---|---|---|
| | | 6-en-1⁶-yl)-1-methylpyridin-2(1H)-one | 5.60-5.56 (m, 1H), 5.41-5.37 (m, 1H), 4.67 (m, 2H), 3.58 (s, 3H), 2.88-2.84 (m, 2H), 2.09-2.08 (m, 2H), 1.59-1.50 (m, 2H) | |
| 362 | | 5-(36-fluoro-11,11-dioxido-2,4-dioxa-11-thia-12-aza-1(2,4)-pyrimidina-3(1,3)-benzenacyclododecaphan-6-en-1⁶-yl)-1-methylpyridin-2(1H)-one | (400 MHz, DMSO-d₆) δ ppm 11.33 (br s, 1H), 8.65 (m, 1H), 7.96 (m, 1H), 7.42 (m, 1H), 7.14 (m, 1H), 6.84 (m, 1H), 6.75 (s, 1H), 6.55 (m, 1H), 5.60-5.56 (m, 1H), 5.41-5.37 (m, 1H), 4.67 (m, 2H), 3.58 (s, 3H), 2.88-2.84 (m, 2H), 2.09-2.08 (m, 2H), 1.59-1.50 (m, 2H) | 473 |

II. Biological Evaluation

Example 1a: In Vitro Enzyme Inhibition Assay—CREBBP Inhibition

Determination of the $IC_{50}$ for the CREBBP inhibitors disclosed herein was performed as follows: CREBBP was cloned and expressed in *E. Coli* as His-tag protein and purified by Nickel affinity and gel-filtration chromatography. The protein was further characterized as a single band with the correct molecular weight by SDS-PAGE. CREBBP binding and inhibition was assessed by monitoring the interaction of biotinylated H4-tetraacetyl peptide (AnaSpec, H4K5/8/12/16(Ac), biotin-labeled) with the target using the AlphaScreen technology (Perkin Elmer). In a 384-well ProxiPlate CREBBP (50 nM final) was combined with peptide (20 nM final) in 50 mM HEPES (pH 7.3), 10 mM NaCl, 0.25 mM TCEP, 0.1% (w/v) BSA, and 0.005% (w/v) Brij-35 either in the presence of DMSO (final 0.4% DMSO) or compound dilution series in DMSO. After 20-minute incubation at room temperature, Alpha streptavidin donor beads and Nickel Chelate acceptor beads were added to a final concentration of 5 μg/mL. After two hours of equilibration, plates were read on an Envision instrument and the $IC_{50}$ was calculated using a four parameter non-linear curve fit.

The ability of the compounds disclosed herein to inhibit CBP activity was quantified and the respective $IC_{50}$ value was determined. The $IC_{50}$ values of various compounds disclosed herein is provided in Table 28.

Example 1b: In Vitro Enzyme Inhibition Assay—BRD4 Inhibition

Inhibition of BRD4 was determined as previously described in U.S. Pat. No. 9,034,900.

TABLE 28

| Chemical Synthesis Example | Name | $IC_{50}$ CREBBP (μM) |
|---|---|---|
| 1 | Propane-2-sulfonic acid [2-(2,5-dichloro-phenoxy)-6-(1,5-dimethyl-6-oxo-1,6-dihydro-pyridin-3-yl)-pyrimidin-4-yl]-amide | A |
| 2 | Propane-2-sulfonic acid [6-(1,5-dimethyl-6-oxo-1,6-dihydro-pyridin-3-yl)-2-(2,5-dimethyl-phenoxy)-pyrimidin-4-yl]-amide | A |
| 3 | Propane-2-sulfonic acid [2-(2-chloro-6-methyl-phenoxy)-6-(1,5-dimethyl-6-oxo-1,6-dihydro-pyridin-3-yl)-pyrimidin-4-yl]-amide | A |
| 4 | Propane-2-sulfonic acid [6-(1,5-dimethyl-6-oxo-1,6-dihydro-pyridin-3-yl)-2-(2-methoxy-5-methyl-phenoxy)-pyrimidin-4-yl]-amide | A |
| 5 | Propane-2-sulfonic acid [2-(2-chloro-5-methyl-phenoxy)-6-(1,5-dimethyl-6-oxo-1,6-dihydro-pyridin-3-yl)-pyrimidin-4-yl]-amide | A |
| 6 | Propane-2-sulfonic acid [2-(5-chloro-2-methyl-phenoxy)-6-(1,5-dimethyl-6-oxo-1,6-dihydro-pyridin-3-yl)-pyrimidin-4-yl]-amide | A |
| 7 | Propane-2-sulfonic acid [2-(5-cyano-2-methyl-phenoxy)-6-(1,5-dimethyl-6-oxo-1,6-dihydro-pyridin-3-yl)-pyrimidin-4-yl]-amide | A |
| 8 | Propane-2-sulfonic acid [6-(1,5-dimethyl-6-oxo-1,6-dihydro-pyridin-3-yl)-2-(2-methoxy-6-methyl-phenoxy)-pyrimidin-4-yl]-amide | A |
| 9 | Propane-2-sulfonic acid [2-(5-cyano-2-methoxy-phenoxy)-6-(1,5-dimethyl-6-oxo-1,6-dihydro-pyridin-3-yl)-pyrimidin-4-yl]-amide | A |
| 10 | Butane-1-sulfonic acid [2-(5-cyano-2-methoxy-phenoxy)-6-(1,5-dimethyl-6-oxo-1,6-dihydro-pyridin-3-yl)-pyrimidin-4-yl]-amide | A |
| 11 | Propane-2-sulfonic acid [2-(2-cyano-6-methoxy-phenoxy)-6-(1,5-dimethyl-6-oxo-1,6-dihydro-pyridin-3-yl)-pyrimidin-4-yl]-amide | A |
| 12 | Butane-1-sulfonic acid [2-(2-cyano-6-methoxy-phenoxy)-6-(1,5-dimethyl-6-oxo-1,6-dihydro-pyridin-3-yl)-pyrimidin-4-yl]-amide | A |
| 13 | Butane-1-sulfonic acid [2-(2,5-dichloro-phenoxy)-6-(1,5-dimethyl-6-oxo-1,6-dihydro-pyridin-3-yl)-pyrimidin-4-yl]-amide | A |
| 14 | Butane-1-sulfonic acid [2-(2-chloro-6-methyl-phenoxy)-6-(1,5-dimethyl-6-oxo-1,6-dihydro-pyridin-3-yl)-pyrimidin-4-yl]-amide | A |

TABLE 28-continued

| Chemical Synthesis Example | Name | IC$_{50}$ CREBBP (μM) |
|---|---|---|
| 15 | Butane-1-sulfonic acid [2-(2-chloro-5-methyl-phenoxy)-6-(1,5-dimethyl-6-oxo-1,6-dihydro-pyridin-3-yl)-pyrimidin-4-yl]-amide | A |
| 16 | Butane-1-sulfonic acid [2-(2-chloro-phenoxy)-6-(1,5-dimethyl-6-oxo-1,6-dihydro-pyridin-3-yl)-pyrimidin-4-yl]-amide | A |
| 17 | Propane-2-sulfonic acid [2-(2,6-difluoro-phenoxy)-6-(1,5-dimethyl-6-oxo-1,6-dihydro-pyridin-3-yl)-pyrimidin-4-yl]-amide | A |
| 18 | Butane-1-sulfonic acid [2-(2,6-difluoro-phenoxy)-6-(1,5-dimethyl-6-oxo-1,6-dihydro-pyridin-3-yl)-pyrimidin-4-yl]-amide | A |
| 19 | Butane-1-sulfonic acid [6-(1,5-dimethyl-6-oxo-1,6-dihydro-pyridin-3-yl)-2-(2-fluoro-6-methyl-phenoxy)-pyrimidin-4-yl]-amide | A |
| 20 | Propane-1-sulfonic acid [2-(2,6-difluoro-phenoxy)-6-(1,5-dimethyl-6-oxo-1,6-dihydro-pyridin-3-yl)-pyrimidin-4-yl]-amide | A |
| 21 | Propane-1-sulfonic acid [6-(1,5-dimethyl-6-oxo-1,6-dihydro-pyridin-3-yl)-2-(2-fluoro-6-methyl-phenoxy)-pyrimidin-4-yl]-amide | A |
| 22 | Butane-1-sulfonic acid [2-(2-cyano-6-methyl-phenoxy)-6-(1,5-dimethyl-6-oxo-1,6-dihydro-pyridin-3-yl)-pyrimidin-4-yl]-amide | A |
| 23 | Propane-1-sulfonic acid [2-(2-cyano-6-methyl-phenoxy)-6-(1,5-dimethyl-6-oxo-1,6-dihydro-pyridin-3-yl)-pyrimidin-4-yl]-amide | A |
| 24 | Propane-2-sulfonic acid [2-(2-cyano-6-methyl-phenoxy)-6-(1,5-dimethyl-6-oxo-1,6-dihydro-pyridin-3-yl)-pyrimidin-4-yl]-amide | A |
| 25 | N-[2-(2,4-Dichloro-6-methyl-phenoxy)-6-(1,5-dimethyl-6-oxo-1,6-dihydro-pyridin-3-yl)-pyrimidin-4-yl]-methanesulfonamide | A |
| 26 | Ethanesulfonic acid [2-(2,4-dichloro-6-methyl-phenoxy)-6-(1,5-dimethyl-6-oxo-1,6-dihydro-pyridin-3-yl)-pyrimidin-4-yl]-amide | A |
| 27 | Propane-1-sulfonic acid [2-(2,4-dichloro-6-methyl-phenoxy)-6-(1,5-dimethyl-6-oxo-1,6-dihydro-pyridin-3-yl)-pyrimidin-4-yl]-amide | A |
| 28 | Butane-1-sulfonic acid [2-(2,4-dichloro-6-methyl-phenoxy)-6-(1,5-dimethyl-6-oxo-1,6-dihydro-pyridin-3-yl)-pyrimidin-4-yl]-amide | A |
| 29 | N-[2-(2,4-Dichloro-6-methyl-phenoxy)-6-(1-methyl-6-oxo-1,6-dihydro-pyridin-3-yl)-pyrimidin-4-yl]-methanesulfonamide | A |
| 30 | Ethanesulfonic acid [2-(2,4-dichloro-6-methyl-phenoxy)-6-(1-methyl-6-oxo-1,6-dihydro-pyridin-3-yl)-pyrimidin-4-yl]-amide | A |
| 31 | Propane-1-sulfonic acid [2-(2,4-dichloro-6-methyl-phenoxy)-6-(1-methyl-6-oxo-1,6-dihydro-pyridin-3-yl)-pyrimidin-4-yl]-amide | A |
| 32 | Butane-1-sulfonic acid [2-(2,4-dichloro-6-methyl-phenoxy)-6-(1-methyl-6-oxo-1,6-dihydro-pyridin-3-yl)-pyrimidin-4-yl]-amide | A |
| 33 | Propane-2-sulfonic acid [2-(2,4-dichloro-6-methyl-phenoxy)-6-(1,5-dimethyl-6-oxo-1,6-dihydro-pyridin-3-yl)-pyrimidin-4-yl]-amide | A |
| 34 | Propane-2-sulfonic acid [2-(2,4-dichloro-6-methyl-phenoxy)-6-(1-methyl-6-oxo-1,6-dihydro-pyridin-3-yl)-pyrimidin-4-yl]-amide | A |
| 35 | Butane-1-sulfonic acid [2-(2-cyano-5-methoxy-phenoxy)-6-(1,5-dimethyl-6-oxo-1,6-dihydro-pyridin-3-yl)-pyrimidin-4-yl]-amide | A |
| 36 | Butane-1-sulfonic acid [2-(2-cyano-5-methyl-phenoxy)-6-(1,5-dimethyl-6-oxo-1,6-dihydro-pyridin-3-yl)-pyrimidin-4-yl]-amide | A |
| 37 | Butane-1-sulfonic acid [2-(2-cyano-phenoxy)-6-(1,5-dimethyl-6-oxo-1,6-dihydro-pyridin-3-yl)-pyrimidin-4-yl]-amide | A |
| 38 | Butane-1-sulfonic acid [2-(2-chloro-5-isopropyl-phenoxy)-6-(1,5-dimethyl-6-oxo-1,6-dihydro-pyridin-3-yl)-pyrimidin-4-yl]-amide | A |
| 39 | Propane-1-sulfonic acid [2-(2-chloro-5-isopropyl-phenoxy)-6-(1,5-dimethyl-6-oxo-1,6-dihydro-pyridin-3-yl)-pyrimidin-4-yl]-amide | A |
| 40 | Propane-2-sulfonic acid [2-(2-chloro-5-isopropyl-phenoxy)-6-(1,5-dimethyl-6-oxo-1,6-dihydro-pyridin-3-yl)-pyrimidin-4-yl]-amide | A |
| 41 | Butane-1-sulfonic acid [2-(2-chloro-6-ethyl-phenoxy)-6-(1,5-dimethyl-6-oxo-1,6-dihydro-pyridin-3-yl)-pyrimidin-4-yl]-amide | A |
| 42 | Propane-1-sulfonic acid [2-(2-chloro-6-ethyl-phenoxy)-6-(1,5-dimethyl-6-oxo-1,6-dihydro-pyridin-3-yl)-pyrimidin-4-yl]-amide | A |
| 43 | Propane-2-sulfonic acid [2-(2-chloro-6-ethyl-phenoxy)-6-(1,5-dimethyl-6-oxo-1,6-dihydro-pyridin-3-yl)-pyrimidin-4-yl]-amide | A |
| 44 | Propane-2-sulfonic acid [2-(2,4-difluoro-phenoxy)-6-(1-ethyl-5-methyl-6-oxo-1,6-dihydro-pyridin-3-yl)-pyrimidin-4-yl]-amide | A |
| 45 | Propane-2-sulfonic acid [2-(2,4-difluoro-phenoxy)-6-(5-methyl-6-oxo-1-propyl-1,6-dihydro-pyridin-3-yl)-pyrimidin-4-yl]-amide | B |
| 46 | Propane-2-sulfonic acid [6-(1-butyl-5-methyl-6-oxo-1,6-dihydro-pyridin-3-yl)-2-(2,4-difluoro-phenoxy)-pyrimidin-4-yl]-amide | C |
| 47 | Propane-2-sulfonic acid [2-(2,4-difluoro-phenoxy)-6-(1-isopropyl-5-methyl-6-oxo-1,6-dihydro-pyridin-3-yl)-pyrimidin-4-yl]-amide | B |
| 48 | Propane-2-sulfonic acid [2-(2,4-difluoro-phenoxy)-6-(1-isobutyl-5-methyl-6-oxo-1,6-dihydro-pyridin-3-yl)-pyrimidin-4-yl]-amide | C |
| 49 | Propane-2-sulfonic acid [6-(1-cyclopropylmethyl-5-methyl-6-oxo-1,6-dihydro-pyridin-3-yl)-2-(2,4-difluoro-phenoxy)-pyrimidin-4-yl]-amide | A |
| 50 | Propane-2-sulfonic acid [6-(1-cyclobutylmethyl-5-methyl-6-oxo-1,6-dihydro-pyridin-3-yl)-2-(2,4-difluoro-phenoxy)-pyrimidin-4-yl]-amide | C |

TABLE 28-continued

| Chemical Synthesis Example | Name | IC$_{50}$ CREBBP (µM) |
|---|---|---|
| 51 | Acetic acid 2-{5-[2-(2,4-difluoro-phenoxy)-6-(propane-2-sulfonylamino)-pyrimidin-4-yl]-3-methyl-2-oxo-2H-pyridin-1-yl}-ethyl ester | B |
| 52 | Propane-2-sulfonic acid {2-(2,4-difluoro-phenoxy)-6-[5-methyl-6-oxo-1-(2,2,2-trifluoro-ethyl)-1,6-dihydro-pyridin-3-yl]-pyrimidin-4-yl}-amide | B |
| 53 | Propane-2-sulfonic acid {2-(2,4-difluoro-phenoxy)-6-[1-(2-methoxy-ethyl)-5-methyl-6-oxo-1,6-dihydro-pyridin-3-yl]-pyrimidin-4-yl}-amide | B |
| 54 | Propane-1-sulfonic acid [6-(1-cyclopropyl-5-methyl-6-oxo-1,6-dihydro-pyridin-3-yl)-2-(2,6-dimethyl-phenoxy)-pyrimidin-4-yl]-amide | B |
| 55 | Propane-1-sulfonic acid [2-(2,6-dimethyl-phenoxy)-6-(5-methyl-1-oxetan-3-yl-6-oxo-1,6-dihydro-pyridin-3-yl)-pyrimidin-4-yl]-amide | B |
| 56 | Butane-1-sulfonic acid [2-(1,5-dimethyl-6-oxo-1,6-dihydro-pyridin-3-yl)-6-(2,6-dimethyl-phenoxy)-pyrimidin-4-yl]-amide | A |
| 57 | Propane-2-sulfonic acid [6-(1,5-dimethyl-6-oxo-1,6-dihydro-pyridin-3-yl)-2-(1-methyl-1H-indol-7-yloxy)-pyrimidin-4-yl]-amide | A |
| 58 | N-(6-(1,5-dimethyl-6-oxo-1,6-dihydropyridin-3-yl)-2-((2-methylbenzofuran-4-yl)oxy)pyrimidin-4-yl)propane-2-sulfonamide | A |
| 59 | N-(2-(benzofuran-4-yloxy)-6-(1,5-dimethyl-6-oxo-1,6-dihydropyridin-3-yl)pyrimidin-4-yl)propane-2-sulfonamide | A |
| 60 | Propane-1-sulfonic acid [6-(2,4-dichloro-6-methyl-phenoxy)-2-(1,5-dimethyl-6-oxo-1,6-dihydro-pyridin-3-yl)-pyrimidin-4-yl]-amide | A |
| 61 | N-(2-(2,4-difluorophenoxy)-6-(1,5-dimethyl-6-oxo-1,6-dihydropyridin-3-yl)pyrimidin-4-yl)methanesulfonamide | A |
| 62 | N-(2-(2,4-difluorophenoxy)-6-(1,5-dimethyl-6-oxo-1,6-dihydropyridin-3-yl)pyrimidin-4-yl)propane-2-sulfonamide | A |
| 63 | N-(2-(2,4-difluorophenoxy)-6-(1,5-dimethyl-6-oxo-1,6-dihydropyridin-3-yl)pyrimidin-4-yl)cyclopropanesulfonamide | A |
| 64 | N-(2-(2,4-difluorophenoxy)-6-(1,5-dimethyl-6-oxo-1,6-dihydropyridin-3-yl)pyrimidin-4-yl)butane-1-sulfonamide | A |
| 65 | N-(2-(2,4-difluorophenoxy)-6-(1,5-dimethyl-6-oxo-1,6-dihydropyridin-3-yl)pyrimidin-4-yl)-2-methylpropane-2-sulfonamide | A |
| 66 | N-(2-(2,4-difluorophenoxy)-6-(1,5-dimethyl-6-oxo-1,6-dihydropyridin-3-yl)pyrimidin-4-yl)cyclopentanesulfonamide | A |
| 67 | N-(6-(1,5-dimethyl-6-oxo-1,6-dihydropyridin-3-yl)-2-(4-fluoro-2-methylphenoxy)pyrimidin-4-yl)propane-2-sulfonamide | A |
| 68 | N-(2-(3-chloro-4-methoxyphenoxy)-6-(1,5-dimethyl-6-oxo-1,6-dihydropyridin-3-yl)pyrimidin-4-yl)propane-2-sulfonamide | A |
| 69 | N-(6-(1,5-dimethyl-6-oxo 1,6-dihydropyridin-3-yl)-2-phenoxypyrimidin-4-yl)propane-2-sulfonamide | A |
| 70 | N-(6-(1,5-dimethyl-6-oxo-1,6-dihydropyridin-3-yl)-2-(4-fluorophenoxy)pyrimidin-4-yl)propane-2-sulfonamide | A |
| 71 | N-(6-(1,5-dimethyl-6-oxo-1,6-dihydropyridin-3-yl)-2-(2,6-dimethylphenoxy)pyrimidin-4-yl)propane-2-sulfonamide | A |
| 72 | N-(6-(1,5-dimethyl-6-oxo-1,6-dihydropyridin-3-yl)-2-(2,6-dimethylphenoxy)pyrimidin-4-yl)butane-1-sulfonamide | A |
| 73 | N-(2-(2,4-difluorophenoxy)-6-(1,5-dimethyl-6-oxo-1,6-dihydropyridin-3-yl)pyrimidin-4-yl)-N-methylpropane-2-sulfonamide | A |
| 74 | N-(6-(1,5-dimethyl-6-oxo-1,6-dihydropyridin-3-yl)-2-((1-methyl-1H-pyrazol-4-yl)oxy)pyrimidin-4-yl)butane-1-sulfonamide | A |
| 75 | N-(6-(1,5-dimethyl-6-oxo-1,6-dihydropyridin-3-yl)-2-((1-methyl-1H-indol-4-yl)oxy)pyrimidin-4-yl)butane-1-sulfonamide | A |
| 76 | N-(6-(1,5-dimethyl-6-oxo-1,6-dihydropyridin-3-yl)-2-((1-methyl-1H-indol-4-yl)oxy)pyrimidin-4-yl)propane-2-sulfonamide | A |
| 77 | N-(2-(2,4-difluorophenoxy)-6-(1,5-dimethyl-6-oxo-1,6-dihydropyridin-3-yl)pyrimidin-4-yl)-3-methylbutanamide | B |
| 78 | N-(6-(1,5-dimethyl-6-oxo-1,6-dihydropyridin-3-yl)-2-(2,6-dimethylphenoxy)pyrimidin-4-yl)-2-methoxyethane-1-sulfonamide | A |
| 79 | N-(2-(2,4-difluorophenoxy)-6-(1,5-dimethyl-6-oxo-1,6-dihydropyridin-3-yl)pyrimidin-4-yl)pentanamide | A |
| 80 | N-(6-(1,5-dimethyl-6-oxo-1,6-dihydropyridin-3-yl)-2-(2,6-dimethylphenoxy)pyrimidin-4-yl)propane-1-sulfonamide | A |
| 81 | N-(6-(1,5-dimethyl-6-oxo-1,6-dihydropyridin-3-yl)-2-(2,6-dimethylphenoxy)pyrimidin-4-yl)-3-fluoropropane-1-sulfonamide | A |
| 82 | 1-cyclopropyl-N-(6-(1,5-dimethyl-6-oxo-1,6-dihydropyridin-3-yl)-2-(2,6-dimethylphenoxy)pyrimidin-4-yl)methanesulfonamide | A |
| 83 | N-(6-(1,5-dimethyl-6-oxo-1,6-dihydropyridin-3-yl)-2-(2,6-dimethylphenoxy)pyrimidin-4-yl)-2-methylpropane-1-sulfonamide | A |
| 84 | N-(6-(1,5-dimethyl-6-oxo-1,6-dihydropyridin-3-yl)-2-(2,6-dimethylphenoxy)pyrimidin-4-yl)butane-2-sulfonamide | A |
| 85 | N-(6-(1,5-dimethyl-6-oxo-1,6-dihydropyridin-3-yl)-2-(2,6-dimethylphenoxy)pyrimidin-4-yl)-2-methoxypropane-1-sulfonamide | A |
| 86 | N-(2-(2,6-dimethylphenoxy)-6-(5-fluoro-1-methyl-6-oxo-1,6-dihydropyridin-3-yl)pyrimidin-4-yl)butane-1-sulfonamide | A |

TABLE 28-continued

| Chemical Synthesis Example | Name | IC₅₀ CREBBP (µM) |
|---|---|---|
| 87 | N-(6-(5-chloro-1-methyl-6-oxo-1,6-dihydropyridin-3-yl)-2-(2,6-dimethylphenoxy)pyrimidin-4-yl)butane-1-sulfonamide | A |
| 88 | N-(6-(1,5-dimethyl-6-oxo-1,6-dihydropyridin-3-yl)-2-((1,3,5-trimethyl-1H-pyrazol-4-yl)oxy)pyrimidin-4-yl)butane-1-sulfonamide | A |
| 89 | N-(6-(1,4-dimethyl-6-oxo-1,6-dihydropyridin-3-yl)-2-(2,6-dimethylphenoxy)pyrimidin-4-yl)butane-1-sulfonamide | A |
| 90 | N-(6-(2,4-difluorophenoxy)-1',5'-dimethyl-6'-oxo-1',6'-dihydro-[2,3'-bipyridin]-4-yl)propane-2-sulfonamide | A |
| 91 | N-(2-((2,4-difluorophenyl)amino)-6-(1,5-dimethyl-6-oxo-1,6-dihydropyridin-3-yl)pyrimidin-4-yl)propane-2-sulfonamide | A |
| 92 | N-(6'-(2,6-dimethylphenoxy)-1,5-dimethyl-6-oxo-1,6-dihydro-[3,4'-bipyridin]-2'-yl)propane-1-sulfonamide | A |
| 93 | Propane-2-sulfonic acid [2-(2,4-difluoro-benzyl)-6-(1,5-dimethyl-6-oxo-1,6-dihydro-pyridin-3-yl)-pyrimidin-4-yl]-amide | B |
| 94 | Ethanesulfonic acid [2-(2,4-difluoro-benzyl)-6-(1,5-dimethyl-6-oxo-1,6-dihydro-pyridin-3-yl)-pyrimidin-4-yl]-amide | A |
| 95 | 5-[2-(2,4-Difluoro-phenoxy)-6-(propane-2-sulfonylmethyl)-pyrimidin-4-yl]-1,3-dimethyl-1H-pyridin-2-one | A |
| 96 | 5-[2-(2,4-Difluoro-phenoxy)-6-ethanesulfonylmethyl-pyrimidin-4-yl]-1,3-dimethyl-1H-pyridin-2-one | A |
| 97 | Butane-1-sulfonic acid [2-(2,6-dimethyl-phenoxy)-6-(2-methyl-1-oxo-1,2-dihydro-isoquinolin-4-yl)-pyrimidin-4-yl]-amide | B |
| 98 | Butane-1-sulfonic acid [2-(2-chloro-4-fluoro-6-methyl-phenoxy)-6-(1,5-dimethyl-6-oxo-1,6-dihydro-pyridin-3-yl)-pyrimidin-4-yl]-amide | A |
| 99 | Propane-1-sulfonic acid [2-(2-chloro-4-fluoro-6-methyl-phenoxy)-6-(1,5-dimethyl-6-oxo-1,6-dihydro-pyridin-3-yl)-pyrimidin-4-yl]-amide | A |
| 100 | Propane-2-sulfonic acid [2-(2-chloro-4-fluoro-6-methyl-phenoxy)-6-(1,5-dimethyl-6-oxo-1,6-dihydro-pyridin-3-yl)-pyrimidin-4-yl]-amide | A |
| 101 | Propane-1-sulfonic acid [2-(2-chloro-6-methyl-phenoxy)-6-(1,5-dimethyl-6-oxo-1,6-dihydro-pyridin-3-yl)-pyrimidin-4-yl]-amide | A |
| 102 | Butane-1-sulfonic acid [2-(2-chloro-6-methyl-phenoxy)-6-(1-methyl-6-oxo-1,6-dihydro-pyridin-3-yl)-pyrimidin-4-yl]-amide | A |
| 103 | Propane-1-sulfonic acid [2-(2-chloro-6-methyl-phenoxy)-6-(1-methyl-6-oxo-1,6-dihydro-pyridin-3-yl)-pyrimidin-4-yl]-amide | A |
| 104 | Propane-2-sulfonic acid [2-(2-chloro-6-methyl-phenoxy)-6-(1-methyl-6-oxo-1,6-dihydro-pyridin-3-yl)-pyrimidin-4-yl]-amide | A |
| 105 | Propane-2-sulfonic acid [2-(2-chloro-6-methyl-phenoxy)-6-(1-methyl-6-oxo-1,6-dihydro-pyridin-3-yl)-pyrimidin-4-yl]-amide | A |
| 106 | N-(2-(2,6-dimethylphenoxy)-6-(5-methoxy-1-methyl-6-oxo-1,6-dihydropyridin-3-yl)pyrimidin-4-yl)butane-1-sulfonamide | A |
| 107 | Propane-1-sulfonic acid [6-(2-chloro-6-methyl-phenoxy)-2-(1,5-dimethyl-6-oxo-1,6-dihydro-pyridin-3-yl)-pyrimidin-4-yl]-amide | A |
| 108 | Butane-1-sulfonic acid [2-(2-cyano-6-methyl-phenoxy)-6-(1-methyl-6-oxo-1,6-dihydro-pyridin-3-yl)-pyrimidin-4-yl]-amide | A |
| 109 | Propane-1-sulfonic acid [2-(2-cyano-6-methyl-phenoxy)-6-(1-methyl-6-oxo-1,6-dihydro-pyridin-3-yl)-pyrimidin-4-yl]-amide | A |
| 110 | Propane-2-sulfonic acid [2-(2-cyano-6-methyl-phenoxy)-6-(1-methyl-6-oxo-1,6-dihydro-pyridin-3-yl)-pyrimidin-4-yl]-amide | A |
| 111 | Propane-1-sulfonic acid [6-(1,5-dimethyl-6-oxo-1,6-dihydro-pyridin-3-yl)-2-(3-methyl-pyridin-4-yloxy)-pyrimidin-4-yl]-amide | B |
| 112 | Propane-1-sulfonic acid [6-(1,5-dimethyl-6-oxo-1,6-dihydro-pyridin-3-yl)-2-(4-methyl-pyridin-3-yloxy)-pyrimidin-4-yl]-amide | A |
| 113 | Butane-1-sulfonic acid [2-(2-fluoro-6-methyl-phenoxy)-6-(1-methyl-6-oxo-1,6-dihydro-pyridin-3-yl)-pyrimidin-4-yl]-amide | A |
| 114 | Butane-1-sulfonic acid [6-(5-chloro-1-methyl-6-oxo-1,6-dihydro-pyridin-3-yl)-2-(2-cyano-6-methyl-phenoxy)-pyrimidin-4-yl]-amide | A |
| 115 | 3-Fluoro-propane-1-sulfonic acid [2-(2-cyano-6-methyl-phenoxy)-6-(1,5-dimethyl-6-oxo-1,6-dihydro-pyridin-3-yl)-pyrimidin-4-yl]-amide | A |
| 116 | Ethanesulfonic acid [2-(2-fluoro-6-methyl-phenoxy)-6-(1-methyl-6-oxo-1,6-dihydro-pyridin-3-yl)-pyrimidin-4-yl]-amide | A |
| 117 | Propane-2-sulfonic acid [6-(5-chloro-1-methyl-6-oxo-1,6-dihydro-pyridin-3-yl)-2-(2-fluoro-6-methyl-phenoxy)-pyrimidin-4-yl]-amide | A |
| 118 | Propane-2-sulfonic acid [6-(5-chloro-1-methyl-6-oxo-1,6-dihydro-pyridin-3-yl)-2-(2-chloro-6-methyl-phenoxy)-pyrimidin-4-yl]-amide | A |
| 119 | Propane-2-sulfonic acid [2-(2-fluoro-6-methyl-phenoxy)-6-(1-methyl-6-oxo-1,6-dihydro-pyridin-3-yl)-pyrimidin-4-yl]-amide | A |
| 120 | Propane-1-sulfonic acid [2-(2-fluoro-6-methyl-phenoxy)-6-(1-methyl-6-oxo-1,6-dihydro-pyridin-3-yl)-pyrimidin-4-yl]-amide | A |
| 121 | Butane-1-sulfonic acid [6-(5-chloro-1-methyl-6-oxo-1,6-dihydro-pyridin-3-yl)-2-(2-chloro-6-methyl-phenoxy)-pyrimidin-4-yl]-amide | A |
| 122 | Butane-1-sulfonic acid [6-(5-chloro-1-methyl-6-oxo-1,6-dihydro-pyridin-3-yl)-2-(2-fluoro-6-methyl-phenoxy)-pyrimidin-4-yl]-amide | A |
| 123 | 3-Fluoro-propane-1-sulfonic acid [2-(2-cyano-6-methyl-phenoxy)-6-(1-methyl-6-oxo-1,6-dihydro-pyridin-3-yl)-pyrimidin-4-yl]-amide | A |
| 124 | Butane-1-sulfonic acid [6-(1-methyl-6-oxo-1,6-dihydro-pyridin-3-yl)-2-(1,3,5-trimethyl-1H-pyrazol-4-yloxy)-pyrimidin-4-yl]-amide | A |

TABLE 28-continued

| Chemical Synthesis Example | Name | IC$_{50}$ CREBBP (μM) |
|---|---|---|
| 125 | Propane-2-sulfonic acid [6-(1-methyl-6-oxo-1,6-dihydro-pyridin-3-yl)-2-(1,3,5-trimethyl-1H-pyrazol-4-yloxy)-pyrimidin-4-yl]-amide | A |
| 126 | Propane-1-sulfonic acid [6-(1-methyl-6-oxo-1,6-dihydro-pyridin-3-yl)-2-(1,3,5-trimethyl-1H-pyrazol-4-yloxy)-pyrimidin-4-yl]-amide | A |
| 127 | Propane-2-sulfonic acid [6-(1,5-dimethyl-6-oxo-1,6-dihydro-pyridin-3-yl)-2-(1-ethyl-3,5-dimethyl-1H-pyrazol-4-yloxy)-pyrimidin-4-yl]-amide | A |
| 128 | Butane-1-sulfonic acid [6-(1,5-dimethyl-6-oxo-1,6-dihydro-pyridin-3-yl)-2-(1-ethyl-3,5-dimethyl-1H-pyrazol-4-yloxy)-pyrimidin-4-yl]-amide | A |
| 129 | Propane-1-sulfonic acid [6-(2-cyano-6-methyl-phenoxy)-2-(1,5-dimethyl-6-oxo-1,6-dihydro-pyridin-3-yl)-pyrimidin-4-yl]-amide | A |
| 130 | Propane-1-sulfonic acid [6-(2-cyano-6-methoxy-phenoxy)-2-(1,5-dimethyl-6-oxo-1,6-dihydro-pyridin-3-yl)-pyrimidin-4-yl]-amide | A |
| 131 | Ethanesulfonic acid [2-cyclopentyloxy-6-(1,5-dimethyl-6-oxo-1,6-dihydro-pyridin-3-yl)-pyrimidin-4-yl]-amide | A |
| 132 | 5-[2-(2,4-Difluoro-phenoxy)-6-methanesulfonyl-pyrimidin-4-yl]-1,3-dimethyl-1H-pyridin-2-one | A |
| 133 | 5-[2-(2-Chloro-6-methyl-phenoxy)-6-methanesulfonyl-pyrimidin-4-yl]-1,3-dimethyl-1H-pyridin-2-one | A |
| 134 | 5-[2-(2,4-Difluoro-phenoxy)-6-(propane-2-sulfonyl)-pyrimidin-4-yl]-1,3-dimethyl-1H-pyridin-2-one | A |
| 135 | 5-[2-(2-Chloro-6-methyl-phenoxy)-6-(propane-2-sulfonyl)-pyrimidin-4-yl]-1,3-dimethyl-1H-pyridin-2-one | A |
| 136 | 3-Fluoro-propane-1-sulfonic acid [2-(2-fluoro-6-methyl-phenoxy)-6-(1-methyl-6-oxo-1,6-dihydro-pyridin-3-yl)-pyrimidin-4-yl]-amide | A |
| 137 | Butane-2-sulfonic acid [2-(2-fluoro-6-methyl-phenoxy)-6-(1-methyl-6-oxo-1,6-dihydro-pyridin-3-yl)-pyrimidin-4-yl]-amide | A |
| 138 | Butane-1-sulfonic acid [2-(2-chloro-6-fluoro-phenoxy)-6-(1,5-dimethyl-6-oxo-1,6-dihydro-pyridin-3-yl)-pyrimidin-4-yl]-amide | A |
| 139 | Butane-1-sulfonic acid [2-(2-chloro-6-fluoro-phenoxy)-6-(1-methyl-6-oxo-1,6-dihydro-pyridin-3-yl)-pyrimidin-4-yl]-amide | A |
| 140 | Ethanesulfonic acid [6-(1,5-dimethyl-6-oxo-1,6-dihydro-pyridin-3-yl)-2-isopropoxy-pyrimidin-4-yl]-amide | A |
| 141 | Propane-1-sulfonic acid [2-(2-chloro-6-fluoro-phenoxy)-6-(1,5-dimethyl-6-oxo-1,6-dihydro-pyridin-3-yl)-pyrimidin-4-yl]-amide | A |
| 142 | Propane-2-sulfonic acid [2-(2-chloro-6-fluoro-phenoxy)-6-(1,5-dimethyl-6-oxo-1,6-dihydro-pyridin-3-yl)-pyrimidin-4-yl]-amide | A |
| 143 | Propane-1-sulfonic acid [2-(2-chloro-6-fluoro-phenoxy)-6-(1-methyl-6-oxo-1,6-dihydro-pyridin-3-yl)-pyrimidin-4-yl]-amide | A |
| 144 | Propane-2-sulfonic acid [2-(2-chloro-6-fluoro-phenoxy)-6-(1-methyl-6-oxo-1,6-dihydro-pyridin-3-yl)-pyrimidin-4-yl]-amide | A |
| 145 | 3,3,3-Trifluoro-propane-1-sulfonic acid [2-(2-fluoro-6-methyl-phenoxy)-6-(1-methyl-6-oxo-1,6-dihydro-pyridin-3-yl)-pyrimidin-4-yl]-amide | A |
| 146 | 4,4,4-Trifluoro-butane-1-sulfonic acid [2-(2-fluoro-6-methyl-phenoxy)-6-(1-methyl-6-oxo-1,6-dihydro-pyridin-3-yl)-pyrimidin-4-yl]-amide | A |
| 147 | Ethane sulfonic acid [6-(1,5-dimethyl-6-oxo-1,6-dihydro-pyridin-3-yl)-2-(1-phenyl-ethoxy)-pyrimidin-4-yl]-amide | A |
| 148 | N-(2-(2-chloro-6-fluorophenoxy)-6-(1-methyl-6-oxo-1,6-dihydropyridin-3-yl)pyrimidin-4-yl)-3-fluoropropane-1-sulfonamide | A |
| 149 | N-(2-(2-cyano-6-methylphenoxy)-6-(1-methyl-6-oxo-1,6-dihydropyridin-3-yl)pyrimidin-4-yl)-3,3,3-trifluoropropane-1-sulfonamide | A |
| 150 | N-(2-(2-cyano-6-methylphenoxy)-6-(1-methyl-6-oxo-1,6-dihydropyridin-3-yl)pyrimidin-4-yl)-4,4,4-trifluorobutane-1-sulfonamide | A |
| 151 | N-(6-(1,5-dimethyl-6-oxo-1,6-dihydropyridin-3-yl)-2-(2,2,2-trifluoroethoxy)pyrimidin-4-yl)ethanesulfonamide | A |
| 152 | N-(6-(1,5-dimethyl-6-oxo-1,6-dihydropyridin-3-yl)-2-isobutoxypyrimidin-4-yl)propane-2-sulfonamide | A |
| 153 | Ethane sulfonic acid [4-(1,5-dimethyl-6-oxo-1,6-dihydro-pyridin-3-yl)-6-(2,6-dimethyl-phenoxy)-[1,3,5]triazin-2-yl]-amide | A |
| 154 | Propane-1-sulfonic acid [4-(1,5-dimethyl-6-oxo-1,6-dihydro-pyridin-3-yl)-6-(2,6-dimethyl-phenoxy)-[1,3,5]triazin-2-yl]-amide | A |
| 155 | Propane-2-sulfonic acid [4-(1,5-dimethyl-6-oxo-1,6-dihydro-pyridin-3-yl)-6-(2,6-dimethyl-phenoxy)-[1,3,5]triazin-2-yl]-amide | A |
| 156 | N-(6-(1,5-dimethyl-6-oxo-1,6-dihydropyridin-3-yl)-2-phenylpyrimidin-4-yl)propane-1-sulfonamide | B |
| 157 | Butane-1-sulfonic acid [2-(2-chloro-6-methyl-phenoxy)-6-(5-methyl-6-oxo-1,6-dihydro-pyridin-3-yl)-pyrimidin-4-yl]-amide | A |
| 158 | Propane-2-sulfonic acid [2-(2-chloro-6-methyl-phenoxy)-6-(5-methyl-6-oxo-1,6-dihydro-pyridin-3-yl)-pyrimidin-4-yl]-amide | A |
| 159 | Ethane-2-sulfonic acid [6-(1,5-dimethyl-6-oxo-1,6-dihydro-pyridin-3-yl)-2-(2-fluoro-6-methyl-phenoxy)-5-methyl-pyrimidin-4-yl]-amide | A |

TABLE 28-continued

| Chemical Synthesis Example | Name | IC$_{50}$ CREBBP (μM) |
|---|---|---|
| 160 | Ethanesulfonic acid [6-(1,5-dimethyl-6-oxo-1,6-dihydro-pyridin-3-yl)-2-(2,6-dimethyl-phenoxy)-5-methyl-pyrimidin-4-yl]-amide | A |
| 161 | Propane-1-sulfonic acid [6-(1,5-dimethyl-6-oxo-1,6-dihydro-pyridin-3-yl)-2-(2-fluoro-6-methyl-phenoxy)-5-methyl-pyrimidin-4-yl]-amide | A |
| 162 | Propane-2-sulfonic acid [6-(1,5-dimethyl-6-oxo-1,6-dihydro-pyridin-3-yl)-2-(2-fluoro-6-methyl-phenoxy)-5-methyl-pyrimidin-4-yl]-amide | A |
| 163 | Propane-2-sulfonic acid [6-(1,5-dimethyl-6-oxo-1,6-dihydro-pyridin-3-yl)-2-(2,6-dimethyl-phenoxy)-5-methyl-pyrimidin-4-yl]-amide | A |
| 164 | Propane-1-sulfonic acid [6-(1,5-dimethyl-6-oxo-1,6-dihydro-pyridin-3-yl)-2-(2,6-dimethyl-phenoxy)-5-methyl-pyrimidin-4-yl]-amide | A |
| 165 | Propane-2-sulfonic acid [2-(2,4-difluoro-phenoxy)-6-(1,5-dimethyl-6-oxo-1,6-dihydro-pyridin-3-yl)-5-methyl-pyrimidin-4-yl]-amide | A |
| 166 | 1,1-Difluoro-propane-1-sulfonic acid [2-(2-fluoro-6-methyl-phenoxy)-6-(1-methyl-6-oxo-1,6-dihydro-pyridin-3-yl)-pyrimidin-4-yl]-amide | A |
| 167 | 1,1-Difluoro-propane-1-sulfonic acid [6-(1,5-dimethyl-6-oxo-1,6-dihydro-pyridin-3-yl)-2-(2-fluoro-6-methyl-phenoxy)-pyrimidin-4-yl]-amide | A |
| 168 | 1-Fluoro-propane-1-sulfonic acid [2-(2-fluoro-6-methyl-phenoxy)-6-(1-methyl-6-oxo-1,6-dihydro-pyridin-3-yl)-pyrimidin-4-yl]-amide | A |
| 169 | 1-Fluoro-propane-1-sulfonic acid [6-(1,5-dimethyl-6-oxo-1,6-dihydro-pyridin-3-yl)-2-(2-fluoro-6-methyl-phenoxy)-pyrimidin-4-yl]-amide | A |
| 170 | 1,1-Difluoro-propane-1-sulfonic acid [2-(2-chloro-6-methyl-phenoxy)-6-(1-methyl-6-oxo-1,6-dihydro-pyridin-3-yl)-pyrimidin-4-yl]-amide | A |
| 171 | Ethanesulfonic acid [4-(1,5-dimethyl-6-oxo-1,6-dihydro-pyridin-3-yl)-6-(2-fluoro-6-methyl-phenoxy)-[1,3,5]triazin-2-yl]-amide | A |
| 172 | Propane-2-sulfonic acid [4-(1,5-dimethyl-6-oxo-1,6-dihydro-pyridin-3-yl)-6-(2-fluoro-6-methyl-phenoxy)-[1,3,5]triazin-2-yl]-amide | A |
| 173 | Propane-1-sulfonic acid [4-(1,5-dimethyl-6-oxo-1,6-dihydro-pyridin-3-yl)-6-(2-fluoro-6-methyl-phenoxy)-[1,3,5]triazin-2-yl]-amide | A |
| 174 | Butane-1-sulfonic acid [4-(1,5-dimethyl-6-oxo-1,6-dihydro-pyridin-3-yl)-6-(2-fluoro-6-methyl-phenoxy)-[1,3,5]triazin-2-yl]-amide | A |
| 175 | Ethanesulfonic acid [4-(2-fluoro-6-methyl-phenoxy)-6-(1-methyl-6-oxo-1,6-dihydro-pyridin-3-yl)-[1,3,5]triazin-2-yl]-amide | A |
| 176 | Propane-2-sulfonic acid [4-(2-fluoro-6-methyl-phenoxy)-6-(1-methyl-6-oxo-1,6-dihydro-pyridin-3-yl)-[1,3,5]triazin-2-yl]-amide | A |
| 177 | Propane-1-sulfonic acid [4-(2-fluoro-6-methyl-phenoxy)-6-(1-methyl-6-oxo-1,6-dihydro-pyridin-3-yl)-[1,3,5]triazin-2-yl]-amide | A |
| 178 | Butane-1-sulfonic acid [4-(2-fluoro-6-methyl-phenoxy)-6-(1-methyl-6-oxo-1,6-dihydro-pyridin-3-yl)-[1,3,5]triazin-2-yl]-amide | A |
| 179 | Ethanesulfonic acid [4-(2-chloro-6-methyl-phenoxy)-6-(1-methyl-6-oxo-1,6-dihydro-pyridin-3-yl)-[1,3,5]triazin-2-yl]-amide | A |
| 180 | Propane-2-sulfonic acid [4-(2-chloro-6-methyl-phenoxy)-6-(1-methyl-6-oxo-1,6-dihydro-pyridin-3-yl)-[1,3,5]triazin-2-yl]-amide | A |
| 181 | Propane-1-sulfonic acid [4-(2-chloro-6-fluoro-phenoxy)-6-(1-methyl-6-oxo-1,6-dihydro-pyridin-3-yl)-[1,3,5]triazin-2-yl]-amide | A |
| 182 | Butane-1-sulfonic acid [4-(2-chloro-6-fluoro-phenoxy)-6-(1-methyl-6-oxo-1,6-dihydro-pyridin-3-yl)-[1,3,5]triazin-2-yl]-amide | A |
| 183 | 2-Methyl-propane-1-sulfonic acid [4-(1,5-dimethyl-6-oxo-1,6-dihydro-pyridin-3-yl)-6-(2-fluoro-6-methyl-phenoxy)-[1,3,5]triazin-2-yl]-amide | A |
| 184 | Cyclopentanesulfonic acid [4-(1,5-dimethyl-6-oxo-1,6-dihydro-pyridin-3-yl)-6-(2-fluoro-6-methyl-phenoxy)-[1,3,5]triazin-2-yl]-amide | A |
| 185 | Pentane-1-sulfonic acid [4-(1,5-dimethyl-6-oxo-1,6-dihydro-pyridin-3-yl)-6-(2-fluoro-6-methyl-phenoxy)-[1,3,5]triazin-2-yl]-amide | A |
| 186 | 3-Methyl-butane-1-sulfonic acid [4-(1,5-dimethyl-6-oxo-1,6-dihydro-pyridin-3-yl)-6-(2-fluoro-6-methyl-phenoxy)-[1,3,5]triazin-2-yl]-amide | A |
| 187 | Butane-1-sulfonic acid [4-(1,5-dimethyl-6-oxo-1,6-dihydro-pyridin-3-yl)-6-(2,6-dimethyl-phenoxy)-[1,3,5]triazin-2-yl]-amide | A |
| 188 | Butane-1-sulfonic acid [4-(2-chloro-6-methyl-phenoxy)-6-(1,5-dimethyl-6-oxo-1,6-dihydro-pyridin-3-yl)-[1,3,5]triazin-2-yl]-amide | A |
| 189 | Butane-1-sulfonic acid [4-(2,6-difluoro-phenoxy)-6-(1,5-dimethyl-6-oxo-1,6-dihydro-pyridin-3-yl)-[1,3,5]triazin-2-yl]-amide | A |
| 190 | Butane-1-sulfonic acid [4-(2-chloro-6-fluoro-phenoxy)-6-(1,5-dimethyl-6-oxo-1,6-dihydro-pyridin-3-yl)-[1,3,5]triazin-2-yl]-amide | A |
| 191 | Ethanesulfonic acid [6-(1,5-dimethyl-6-oxo-1,6-dihydro-pyridin-3-yl)-2-phenyl-pyrimidin-4-yl]-amide | B |
| 192 | Ethanesulfonic acid [6-(1,5-dimethyl-6-oxo-1,6-dihydro-pyridin-3-yl)-2-o-tolyl-pyrimidin-4-yl]-amide | A |
| 193 | Ethanesulfonic acid [6-(1,5-dimethyl-6-oxo-1,6-dihydro-pyridin-3-yl)-2-(2-methoxy-phenyl)-pyrimidin-4-yl]-amide | A |

TABLE 28-continued

| Chemical Synthesis Example | Name | IC$_{50}$ CREBBP (μM) |
|---|---|---|
| 194 | Ethanesulfonic acid [2-(2-methoxy-4-methyl-phenyl)-6-(1-methyl-6-oxo-1,6-dihydro-pyridin-3-yl)-pyrimidin-4-yl]-amide | B |
| 195 | Ethanesulfonic acid [2-(2-methoxy-5-methyl-phenyl)-6-(1-methyl-6-oxo-1,6-dihydro-pyridin-3-yl)-pyrimidin-4-yl]-amide | B |
| 196 | Propane-1-sulfonic acid [2-(2-methoxy-phenyl)-6-(1-methyl-6-oxo-1,6-dihydro-pyridin-3-yl)-pyrimidin-4-yl]-amide | B |
| 197 | Butane-1-sulfonic acid [2-(2-methoxy-phenyl)-6-(1-methyl-6-oxo-1,6-dihydro-pyridin-3-yl)-pyrimidin-4-yl]-amide | A |
| 198 | Ethanesulfonic acid [2-(2-cyano-phenyl)-6-(1-methyl-6-oxo-1,6-dihydro-pyridin-3-yl)-pyrimidin-4-yl]-amide | A |
| 199 | Ethanesulfonic acid [2-(2-methoxy-phenyl)-6-(1-methyl-6-oxo-1,6-dihydro-pyridin-3-yl)-pyrimidin-4-yl]-amide | B |
| 200 | Ethanesulfonic acid [4-isopropoxy-6-(1-methyl-6-oxo-1,6-dihydro-pyridin-3-yl)-[1,3,5]triazin-2-yl]-amide | B |
| 201 | Propane-1-sulfonic acid [4-isopropoxy-6-(1-methyl-6-oxo-1,6-dihydro-pyridin-3-yl)-[1,3,5]triazin-2-yl]-amide | B |
| 202 | (S)—N-(2-(2-fluoro-6-methylphenoxy)-6-(1-methyl-6-oxo-1,6-dihydropyridin-3-yl)pyrimidin-4-yl)butane-2-sulfonamide | A |
| 203 | (R)—N-(2-(2-fluoro-6-methylphenoxy)-6-(1-methyl-6-oxo-1,6-dihydropyridin-3-yl)pyrimidin-4-yl)butane-2-sulfonamide | A |
| 204 | Butane-(2R)-sulfonic acid [2-(2-chloro-6-methyl-phenoxy)-6-(1-methyl-6-oxo-1,6-dihydro-pyridin-3-yl)-pyrimidin-4-yl]-amide | A |
| 205 | Butane-(2S)-sulfonic acid [2-(2-chloro-6-methyl-phenoxy)-6-(1-methyl-6-oxo-1,6-dihydro-pyridin-3-yl)-pyrimidin-4-yl]-amide | A |
| 206 | Butane-(2S)-sulfonic acid [2-(2-chloro-6-fluoro-phenoxy)-6-(1-methyl-6-oxo-1,6-dihydro-pyridin-3-yl)-pyrimidin-4-yl]-amide | A |
| 207 | Butane-(2R)-sulfonic acid [2-(2-chloro-6-fluoro-phenoxy)-6-(1-methyl-6-oxo-1,6-dihydro-pyridin-3-yl)-pyrimidin-4-yl]-amide | A |
| 208 | Butane-(2R)-sulfonic acid [2-(2-fluoro-6-methoxy-phenoxy)-6-(1-methyl-6-oxo-1,6-dihydro-pyridin-3-yl)-pyrimidin-4-yl]-amide | A |
| 209 | Butane-(2S)-sulfonic acid [2-(2-fluoro-6-methoxy-phenoxy)-6-(1-methyl-6-oxo-1,6-dihydro-pyridin-3-yl)-pyrimidin-4-yl]-amide | A |
| 210 | Butane-(2R)-sulfonic acid [2-(2-cyclopropyl-6-fluoro-phenoxy)-6-(1-methyl-6-oxo-1,6-dihydro-pyridin-3-yl)-pyrimidin-4-yl]-amide | A |
| 211 | Butane-(2S)-sulfonic acid [2-(2-cyclopropyl-6-methyl-phenoxy)-6-(1-methyl-6-oxo-1,6-dihydro-pyridin-3-yl)-pyrimidin-4-yl]-amide | A |
| 212 | (2R)-Butane-2-sulfonic acid [2-(2,3-difluoro-6-methyl-phenoxy)-6-(1-methyl-6-oxo-1,6-dihydro-pyridin-3-yl)-pyrimidin-4-yl]-amide | A |
| 213 | (2S)-Butane-2-sulfonic acid [2-(2,3-difluoro-6-methyl-phenoxy)-6-(1-methyl-6-oxo-1,6-dihydro-pyridin-3-yl)-pyrimidin-4-yl]-amide | A |
| 214 | (2R)-Butane-2-sulfonic acid [2-(2-ethyl-6-fluoro-phenoxy)-6-(1-methyl-6-oxo-1,6-dihydro-pyridin-3-yl)-pyrimidin-4-yl]-amide | A |
| 215 | (2S)-Butane-2-sulfonic acid [2-(2-ethyl-6-fluoro-phenoxy)-6-(1-methyl-6-oxo-1,6-dihydro-pyridin-3-yl)-pyrimidin-4-yl]-amide | A |
| 216 | (2S)-Pentane-2-sulfonic acid [2-(2-fluoro-6-methyl-phenoxy)-6-(1-methyl-6-oxo-1,6-dihydro-pyridin-3-yl)-pyrimidin-4-yl]-amide | A |
| 217 | (2S)-Pentane-2-sulfonic acid [2-(2-chloro-6-methyl-phenoxy)-6-(1-methyl-6-oxo-1,6-dihydro-pyridin-3-yl)-pyrimidin-4-yl]-amide | A |
| 218 | (2S)-Pentane-2-sulfonic acid [2-(2-chloro-6-fluoro-phenoxy)-6-(1-methyl-6-oxo-1,6-dihydro-pyridin-3-yl)-pyrimidin-4-yl]-amide | A |
| 219 | (2R)-Pentane-2-sulfonic acid [2-(2-fluoro-6-methyl-phenoxy)-6-(1-methyl-6-oxo-1,6-dihydro-pyridin-3-yl)-pyrimidin-4-yl]-amide | A |
| 220 | (2R)-Pentane-2-sulfonic acid [2-(2-chloro-6-fluoro-phenoxy)-6-(1-methyl-6-oxo-1,6-dihydro-pyridin-3-yl)-pyrimidin-4-yl]-amide | A |
| 221 | (2R)-Pentane-2-sulfonic acid [2-(2-chloro-6-methyl-phenoxy)-6-(1-methyl-6-oxo-1,6-dihydro-pyridin-3-yl)-pyrimidin-4-yl]-amide | A |
| 222 | (S)—N-(2-(2-chloro-6-methylphenoxy)-6-(1,5-dimethyl-6-oxo-1,6-dihydropyridin-3-yl)pyrimidin-4-yl)butane-2-sulfonamide | A |
| 223 | (S)—N-(2-(2-chloro-6-methylphenoxy)-6-(1,5-dimethyl-6-oxo-1,6-dihydropyridin-3-yl)pyrimidin-4-yl)pentane-2-sulfonamide | A |
| 224 | (2S)-Butane-2-sulfonic acid [2-(2-chloro-6-fluoro-3-methyl-phenoxy)-6-(1-methyl-6-oxo-1,6-dihydro-pyridin-3-yl)-pyrimidin-4-yl]-amide | A |
| 225 | (S)—N-(2-(2,6-difluoro-3-methylphenoxy)-6-(1-methyl-6-oxo-1,6-dihydropyridin-3-yl)pyrimidin-4-yl)butane-2-sulfonamide | A |
| 226 | (S)-Butane-2-sulfonic acid [2-(6-chloro-2-fluoro-3-methyl-phenoxy)-6-(1-methyl-6-oxo-1,6-dihydro-pyridin-3-yl)-pyrimidin-4-yl]-amide | A |
| 227 | (2S)-Pentane-2-sulfonic acid [2-(6-chloro-2-fluoro-3-methyl-phenoxy)-6-(1-methyl-6-oxo-1,6-dihydro-pyridin-3-yl)-pyrimidin-4-yl]-amide | A |
| 228 | (2S)-Pentane-2-sulfonic acid [2-(2-chloro-6-fluoro-3-methyl-phenoxy)-6-(1-methyl-6-oxo-1,6-dihydro-pyridin-3-yl)-pyrimidin-4-yl]-amide | A |
| 229 | (S)—N-(2-(2,6-difluorophenoxy)-6-(1-methyl-6-oxo-1,6-dihydropyridin-3-yl)pyrimidin-4-yl)butane-2-sulfonamide | A |

TABLE 28-continued

| Chemical Synthesis Example | Name | IC$_{50}$ CREBBP (μM) |
|---|---|---|
| 230 | (R)—N-(2-(2,6-difluorophenoxy)-6-(1-methyl-6-oxo-1,6-dihydropyridin-3-yl)pyrimidin-4-yl)butane-2-sulfonamide | A |
| 231 | 3,3,3-Trifluoro-propane-1-sulfonic acid [2-(2-chloro-6-fluoro-phenoxy)-6-(1-methyl-6-oxo-1,6-dihydro-pyridin-3-yl)-pyrimidin-4-yl]-amide | A |
| 232 | 4,4,4-Trifluoro-butane-1-sulfonic acid [2-(2-chloro-6-fluoro-phenoxy)-6-(1-methyl-6-oxo-1,6-dihydro-pyridin-3-yl)-pyrimidin-4-yl]-amide | A |
| 233 | Butane-1-sulfonic acid [2-(2-fluoro-6-methoxy-phenoxy)-6-(1-methyl-6-oxo-1,6-dihydro-pyridin-3-yl)-pyrimidin-4-yl]-amide | A |
| 234 | Propane-2-sulfonic acid [2-(2-fluoro-6-methoxy-phenoxy)-6-(1-methyl-6-oxo-1,6-dihydro-pyridin-3-yl)-pyrimidin-4-yl]-amide | A |
| 235 | Propane-1-sulfonic acid [2-(2-fluoro-6-methoxy-phenoxy)-6-(1-methyl-6-oxo-1,6-dihydro-pyridin-3-yl)-pyrimidin-4-yl]-amide | A |
| 236 | Ethanesulfonic acid [2-isopropoxy-6-(1-methyl-6-oxo-1,6-dihydro-pyridin-3-yl)-pyrimidin-4-yl]-amide | A |
| 237 | Propane-1-sulfonic acid [2-isopropoxy-6-(1-methyl-6-oxo-1,6-dihydro-pyridin-3-yl)-pyrimidin-4-yl]-amide | A |
| 238 | Ethanesulfonic acid [2-(2-cyclopropyl-6-fluoro-phenoxy)-6-(1-methyl-6-oxo-1,6-dihydro-pyridin-3-yl)-pyrimidin-4-yl]-amide | A |
| 239 | Propane-1-sulfonic acid [2-(2-cyclopropyl-6-fluoro-phenoxy)-6-(1-methyl-6-oxo-1,6-dihydro-pyridin-3-yl)-pyrimidin-4-yl]-amide | A |
| 240 | Butane-1-sulfonic acid [2-(2-cyclopropyl-6-fluoro-phenoxy)-6-(1-methyl-6-oxo-1,6-dihydro-pyridin-3-yl)-pyrimidin-4-yl]-amide | A |
| 241 | Pentane-2-sulfonic acid [2-(2-fluoro-6-methyl-phenoxy)-6-(1-methyl-6-oxo-1,6-dihydro-pyridin-3-yl)-pyrimidin-4-yl]-amide | A |
| 242 | Pentane-2-sulfonic acid [2-(2-chloro-6-fluoro-phenoxy)-6-(1-methyl-6-oxo-1,6-dihydro-pyridin-3-yl)-pyrimidin-4-yl]-amide | A |
| 243 | Pentane-2-sulfonic acid [2-(2-chloro-6-methyl-phenoxy)-6-(1-methyl-6-oxo-1,6-dihydro-pyridin-3-yl)-pyrimidin-4-yl]-amide | A |
| 244 | Butane-1-sulfonic acid [2-cyclohexyloxy-6-(1-methyl-6-oxo-1,6-dihydro-pyridin-3-yl)-pyrimidin-4-yl]-amide | A |
| 245 | Propane-1-sulfonic acid [2-cyclohexyloxy-6-(1-methyl-6-oxo-1,6-dihydro-pyridin-3-yl)-pyrimidin-4-yl]-amide | A |
| 246 | Ethanesulfonic acid [2-cyclohexyloxy-6-(1-methyl-6-oxo-1,6-dihydro-pyridin-3-yl)-pyrimidin-4-yl]-amide | A |
| 247 | Propane-2-sulfonic acid [2-cyclohexyloxy-6-(1-methyl-6-oxo-1,6-dihydro-pyridin-3-yl)-pyrimidin-4-yl]-amide | A |
| 248 | 3-Methyl-butane-1-sulfonic acid [2-(2-fluoro-6-methyl-phenoxy)-6-(1-methyl-6-oxo-1,6-dihydro-pyridin-3-yl)-pyrimidin-4-yl]-amide | A |
| 249 | Butane-1-sulfonic acid [2-cyclohexyloxy-6-(1,5-dimethyl-6-oxo-1,6-dihydro-pyridin-3-yl)-pyrimidin-4-yl]-amide | A |
| 250 | Propane-2-sulfonic acid [2-cyclohexyloxy-6-(1,5-dimethyl-6-oxo-1,6-dihydro-pyridin-3-yl)-pyrimidin-4-yl]-amide | A |
| 251 | 3-Methyl-butane-1-sulfonic acid [2-(2-chloro-6-fluoro-phenoxy)-6-(1-methyl-6-oxo-1,6-dihydro-pyridin-3-yl)-pyrimidin-4-yl]-amide | A |
| 252 | 3-Methyl-butane-1-sulfonic acid [2-(2-chloro-6-methyl-phenoxy)-6-(1-methyl-6-oxo-1,6-dihydro-pyridin-3-yl)-pyrimidin-4-yl]-amide | A |
| 253 | Pentane-3-sulfonic acid [2-(2-fluoro-6-methyl-phenoxy)-6-(1-methyl-6-oxo-1,6-dihydro-pyridin-3-yl)-pyrimidin-4-yl]-amide | A |
| 254 | Pentane-3-sulfonic acid [2-(2-chloro-6-fluoro-phenoxy)-6-(1-methyl-6-oxo-1,6-dihydro-pyridin-3-yl)-pyrimidin-4-yl]-amide | A |
| 255 | Butane-1-sulfonic acid [2-(2-chloro-6-fluoro-3-methyl-phenoxy)-6-(1-methyl-6-oxo-1,6-dihydro-pyridin-3-yl)-pyrimidin-4-yl]-amide | A |
| 256 | Propane-2-sulfonic acid [2-(2-chloro-6-fluoro-3-methyl-phenoxy)-6-(1-methyl-6-oxo-1,6-dihydro-pyridin-3-yl)-pyrimidin-4-yl]-amide | A |
| 257 | Butane-1-sulfonic acid [2-(2,6-difluoro-3-methyl-phenoxy)-6-(1-methyl-6-oxo-1,6-dihydro-pyridin-3-yl)-pyrimidin-4-yl]-amide | A |
| 258 | Butane-1-sulfonic acid [2-(6-chloro-2-fluoro-3-methyl-phenoxy)-6-(1-methyl-6-oxo-1,6-dihydro-pyridin-3-yl)-pyrimidin-4-yl]-amide | A |
| 259 | Pentane-3-sulfonic acid [2-(2-chloro-6-methyl-phenoxy)-6-(1-methyl-6-oxo-1,6-dihydro-pyridin-3-yl)-pyrimidin-4-yl]-amide | A |
| 260 | Propane-2-sulfonic acid [2-(2,6-difluoro-3-methyl-phenoxy)-6-(1-methyl-6-oxo-1,6-dihydro-pyridin-3-yl)-pyrimidin-4-yl]-amide | A |
| 261 | Propane-2-sulfonic acid [2-(6-chloro-2-fluoro-3-methyl-phenoxy)-6-(1-methyl-6-oxo-1,6-dihydro-pyridin-3-yl)-pyrimidin-4-yl]-amide | A |
| 262 | 3-Methyl-butane-1-sulfonic acid [2-(6-chloro-2-fluoro-3-methyl-phenoxy)-6-(1-methyl-6-oxo-1,6-dihydro-pyridin-3-yl)-pyrimidin-4-yl]-amide | A |
| 263 | N-[2-(2-Chloro-6-fluoro-phenoxy)-6-(1-methyl-6-oxo-1,6-dihydro-pyridin-3-yl)-pyrimidin-4-yl]-C-cyclopropyl-methanesulfonamide | A |
| 264 | N-[2-(2-Chloro-6-methyl-phenoxy)-6-(1-methyl-6-oxo-1,6-dihydro-pyridin-3-yl)-pyrimidin-4-yl]-C-cyclopropyl-methanesulfonamide | A |
| 265 | 3-Methyl-butane-1-sulfonic acid [2-(2-chloro-6-fluoro-3-methyl-phenoxy)-6-(1-methyl-6-oxo-1,6-dihydro-pyridin-3-yl)-pyrimidin-4-yl]-amide | A |

TABLE 28-continued

| Chemical Synthesis Example | Name | IC$_{50}$ CREBBP (μM) |
|---|---|---|
| 266 | 2-Cyclopropyl-ethanesulfonic acid [2-(2-chloro-6-methyl-phenoxy)-6-(1-methyl-6-oxo-1,6-dihydro-pyridin-3-yl)-pyrimidin-4-yl]-amide | A |
| 267 | 2-Cyclopropyl-ethanesulfonic acid [2-(2-fluoro-6-methyl-phenoxy)-6-(1-methyl-6-oxo-1,6-dihydro-pyridin-3-yl)-pyrimidin-4-yl]-amide | A |
| 268 | 2-Cyclopropyl-ethanesulfonic acid [2-(2-chloro-6-fluoro-phenoxy)-6-(1-methyl-6-oxo-1,6-dihydro-pyridin-3-yl)-pyrimidin-4-yl]-amide | A |
| 269 | 1-Cyclopropyl-N-[2-(2-fluoro-6-methyl-phenoxy)-6-(1-methyl-6-oxo-1,6-dihydro-pyridin-3-yl)-pyrimidin-4-yl]-methanesulfonamide | A |
| 270 | 5-(6-amino-2-(2,4-difluorophenoxy)pyrimidin-4-yl)-1,3-dimethylpyridin-2(1H)-one | A |
| 271 | 5-(2-(2,4-difluorophenoxy)-6-(phenethylamino)pyrimidin-4-yl)-1,3-dimethylpyridin-2(1H)-one | A |
| 272 | 5-(6-(benzylamino)-2-(2,4-difluorophenoxy)pyrimidin-4-yl)-1,3-dimethylpyridin-2(1H)-one | A |
| 273 | 5-(2-(2,4-difluorophenoxy)-6-(ethylamino)pyrimidin-4-yl)-1,3-dimethylpyridin-2(1H)-one | A |
| 274 | 5-(6-(benzylamino)-2-(2,4-difluorophenoxy)pyrimidin-4-yl)-1-methylpyridin-2(1H)-one | A |
| 275 | 5-(6-(benzyl(methyl)amino)-2-(2,4-difluorophenoxy)pyrimidin-4-yl)-1-methylpyridin-2(1H)-one | A |
| 276 | 5-(2-(2,4-difluorophenoxy)-6-(phenylamino)pyrimidin-4-yl)-1-methylpyridin-2(1H)-one | A |
| 277 | 5-(6-(diethylamino)-2-(2,4-difluorophenoxy)pyrimidin-4-yl)-1-methylpyridin-2(1H)-one | A |
| 278 | 5-(6-((1-(4-ethoxyphenyl)ethyl)amino)-2-(2-fluoro-6-methylphenoxy)pyrimidin-4-yl)-1-methylpyridin-2(1H)-one | A |
| 279 | 5-(6-((1-(4-ethylphenyl)ethyl)amino)-2-(2-fluoro-6-methylphenoxy)pyrimidin-4-yl)-1-methylpyridin-2(1H)-one | A |
| 280 | 5-(2-(2-fluoro-6-methylphenoxy)-6-((1,2,3,4-tetrahydronaphthalen-1-yl)amino)pyrimidin-4-yl)-1-methylpyridin-2(1H)-one | A |
| 281 | 5-(2-(2-fluoro-6-methylphenoxy)-6-(isopropylamino)pyrimidin-4-yl)-1-methylpyridin-2(1H)-one | A |
| 282 | 5-(2-(2-chloro-6-methylphenoxy)-6-((1-phenylethyl)amino)pyrimidin-4-yl)-1-methylpyridin-2(1H)-one | A |
| 283 | 5-(2-(2-chloro-6-methylphenoxy)-6-(isopropylamino)pyrimidin-4-yl)-1-methylpyridin-2(1H)-one | A |
| 284 | 5-(2-(2-chloro-6-methylphenoxy)-6-(cyclopentylamino)pyrimidin-4-yl)-1-methylpyridin-2(1H)-one | A |
| 285 | 5-(6-(cyclopentylamino)-2-(2-fluoro-6-methylphenoxy)pyrimidin-4-yl)-1-methylpyridin-2(1H)-one | A |
| 286 | 5-(2-(2-fluoro-6-methylphenoxy)-6-(((1,2,3,4-tetrahydronaphthalen-1-yl)methyl)amino)pyrimidin-4-yl)-1-methylpyridin-2(1H)-one | A |
| 287 | (S)-5-(6-((2,3-dihydro-1H-inden-1-yl)amino)-2-(2-fluoro-6-methylphenoxy)pyrimidin-4-yl)-1-methylpyridin-2(1H)-one | A |
| 288 | 5-(2-(2-fluoro-6-methylphenoxy)-6-((1-(6-methylpyridin-2-yl)ethyl)amino)pyrimidin-4-yl)-1-methylpyridin-2(1H)-one | A |
| 289 | 5-(2-(2-fluoro-6-methylphenoxy)-6-(((6-methylpyridin-2-yl)methyl)amino)pyrimidin-4-yl)-1-methylpyridin-2(1H)-one | A |
| 290 | 5-(2-(2-fluoro-6-methylphenoxy)-6-(((6-methylpyridin-3-yl)methyl)amino)pyrimidin-4-yl)-1-methylpyridin-2(1H)-one | A |
| 291 | 5-[6-Ethylamino-2-(2-fluoro-6-methyl-phenoxy)-pyrimidin-4-yl]-1-methyl-1H-pyridin-2-one | A |
| 292 | 5-[6-Benzylamino-2-(2-fluoro-6-methyl-phenoxy)-pyrimidin-4-yl]-1-methyl-1H-pyridin-2-one | A |
| 293 | 5-[6-(Benzyl-methyl-amino)-2-(2-fluoro-6-methyl-phenoxy)-pyrimidin-4-yl]-1-methyl-1H-pyridin-2-one | A |
| 294 | 5-[6-Amino-2-(2-fluoro-6-methyl-phenoxy)-pyrimidin-4-yl]-1,3-dimethyl-1H-pyridin-2-one | A |
| 295 | 5-[6-Ethylamino-2-(2-fluoro-6-methyl-phenoxy)-pyrimidin-4-yl]-1,3-dimethyl-1H-pyridin-2-one | A |
| 296 | 5-[6-Benzylamino-2-(2-fluoro-6-methyl-phenoxy)-pyrimidin-4-yl]-1,3-dimethyl-1H-pyridin-2-one | A |
| 297 | 5-[6-(Benzyl-methyl-amino)-2-(2-fluoro-6-methyl-phenoxy)-pyrimidin-4-yl]-1,3-dimethyl-1H-pyridin-2-one | A |
| 298 | 5-[2-(2-Fluoro-6-methyl-phenoxy)-6-(1-phenyl-ethylamino)-pyrimidin-4-yl]-1-methyl-1H-pyridin-2-one | A |
| 299 | 5-[2-(2-Fluoro-6-methyl-phenoxy)-6-(1-o-tolyl-ethylamino)-pyrimidin-4-yl]-1-methyl-1H-pyridin-2-one | A |
| 300 | 5-[6-(2,6-Dimethyl-benzylamino)-2-(2-fluoro-6-methyl-phenoxy)-pyrimidin-4-yl]-1-methyl-1H-pyridin-2-one | A |
| 301 | 5-[6-(2,5-Dimethyl-benzylamino)-2-(2-fluoro-6-methyl-phenoxy)-pyrimidin-4-yl]-1-methyl-1H-pyridin-2-one | A |
| 302 | 5-{2-(2-Fluoro-6-methyl-phenoxy)-6-[(pyridin-2-ylmethyl)-amino]-pyrimidin-4-yl}-1-methyl-1H-pyridin-2-one | A |
| 303 | 5-{2-(2-Fluoro-6-methyl-phenoxy)-6-[(pyridin-3-ylmethyl)-amino]-pyrimidin-4-yl}-1-methyl-1H-pyridin-2-one | A |

TABLE 28-continued

| Chemical Synthesis Example | Name | IC$_{50}$ CREBBP (μM) |
|---|---|---|
| 304 | 5-[6-Butylamino-2-(2-fluoro-6-methyl-phenoxy)-pyrimidin-4-yl]-1-methyl-1H-pyridin-2-one | A |
| 305 | (R)-5-[2-(2-Fluoro-6-methyl-phenoxy)-6-(1-methyl-butylamino)-pyrimidin-4-yl]-1-methyl-1H-pyridin-2-one | A |
| 306 | (R)-5-[2-(2-Fluoro-6-methyl-phenoxy)-6-(1-phenyl-ethylamino)-pyrimidin-4-yl]-1-methyl-1H-pyridin-2-one | A |
| 307 | (R)-5-[2-(2-Fluoro-6-methyl-phenoxy)-6-(1,2,3,4-tetrahydro-naphthalen-1-ylamino)-pyrimidin-4-yl]-1-methyl-1H-pyridin-2-one | A |
| 308 | (S)-5-[2-(2-Fluoro-6-methyl-phenoxy)-6-(1,2,3,4-tetrahydro-naphthalen-1-ylamino)-pyrimidin-4-yl]-1-methyl-1H-pyridin-2-one | A |
| 309 | 5-[2-(2-Fluoro-6-methyl-phenoxy)-6-(3-methyl-butylamino)-pyrimidin-4-yl]-1-methyl-1H-pyridin-2-one | A |
| 310 | (S)-5-[2-(2-Fluoro-6-methyl-phenoxy)-6-(1-phenyl-ethylamino)-pyrimidin-4-yl]-1-methyl-1H-pyridin-2-one | A |
| 311 | (S)-5-[2-(2-Fluoro-6-methyl-phenoxy)-6-(1,2,3,4-tetrahydro-naphthalen-1-ylamino)-pyrimidin-4-yl]-1-methyl-1H-pyridin-2-one | A |
| 312 | 5-[6-Butylamino-2-(2-chloro-6-methyl-phenoxy)-pyrimidin-4-yl]-1-methyl-1H-pyridin-2-one | A |
| 313 | (R)-5-[2-(2-Chloro-6-methyl-phenoxy)-6-(1-methyl-butylamino)-pyrimidin-4-yl]-1-methyl-1H-pyridin-2-one | A |
| 314 | (S)-5-[2-(2-Chloro-6-methyl-phenoxy)-6-(1-methyl-butylamino)-pyrimidin-4-yl]-1-methyl-1H-pyridin-2-one | A |
| 315 | 5-[2-(2-Chloro-6-methyl-phenoxy)-6-(3-methyl-butylamino)-pyrimidin-4-yl]-1-methyl-1H-pyridin-2-one | A |
| 316 | 2-[4-Butylamino-6-(1-methyl-6-oxo-1,6-dihydro-pyridin-3-yl)-pyrimidin-2-yloxy]-3-methyl-benzonitrile | A |
| 317 | (R)-3-Methyl-2-[4-(1-methyl-butylamino)-6-(1-methyl-6-oxo-1,6-dihydro-pyridin-3-yl)-pyrimidin-2-yloxy]-benzonitrile | A |
| 318 | (R)-3-Methyl-2-[4-(1-methyl-6-oxo-1,6-dihydro-pyridin-3-yl)-6-(1-phenyl-ethylamino)-pyrimidin-2-yloxy]-benzonitrile | A |
| 319 | 3-Methyl-2-{4-(1-methyl-6-oxo-1,6-dihydro-pyridin-3-yl)-6-[(pyridin-2-ylmethyl)-amino]-pyrimidin-2-yloxy}-benzonitrile | A |
| 320 | 2-[4-Benzylamino-6-(1-methyl-6-oxo-1,6-dihydro-pyridin-3-yl)-pyrimidin-2-yloxy]-3-methyl-benzonitrile | A |
| 321 | (S)-3-Methyl-2-[4-(1-methyl-butylamino)-6-(1-methyl-6-oxo-1,6-dihydro-pyridin-3-yl)-pyrimidin-2-yloxy]-benzonitrile | A |
| 322 | (S)-3-Methyl-2-[4-(1-methyl-6-oxo-1,6-dihydro-pyridin-3-yl)-6-(1-phenyl-ethylamino)-pyrimidin-2-yloxy]-benzonitrile | A |
| 323 | 3-Methyl-2-{4-(1-methyl-6-oxo-1,6-dihydro-pyridin-3-yl)-6-[(pyridin-3-ylmethyl)-amino]-pyrimidin-2-yloxy}-benzonitrile | A |
| 324 | 5-(6-Benzylamino-2-methoxy-pyrimidin-4-yl)-1-methyl-1H-pyridin-2-one | A |
| 325 | 5-(6-Butylamino-2-methoxy-pyrimidin-4-yl)-1-methyl-1H-pyridin-2-one | B |
| 326 | 5-[2-Methoxy-6-(1-methyl-butylamino)-pyrimidin-4-yl]-1-methyl-1H-pyridin-2-one | B |
| 327 | 5-[2-Methoxy-6-(1-phenyl-ethylamino)-pyrimidin-4-yl]-1-methyl-1H-pyridin-2-one | A |
| 328 | 5-{2-Methoxy-6-[(pyridin-2-ylmethyl)-amino]-pyrimidin-4-yl}-1-methyl-1H-pyridin-2-one | A |
| 329 | 5-(2-Methoxy-6-phenethylamino-pyrimidin-4-yl)-1-methyl-1H-pyridin-2-one | A |
| 330 | 5-{2-Methoxy-6-[(pyridin-3-ylmethyl)-amino]-pyrimidin-4-yl}-1-methyl-1H-pyridin-2-one | A |
| 331 | 5-{2-Methoxy-6-[(1,2,3,4-tetrahydro-naphthalen-1-ylmethyl)-amino]-pyrimidin-4-yl}-1-methyl-1H-pyridin-2-one | A |
| 332 | 5-[6-Amino-2-(2-fluoro-6-methyl-phenoxy)-pyrimidin-4-yl]-1-methyl-1H-pyridin-2-one | A |
| 333 | 5-[6-Amino-2-(2-chloro-6-methyl-phenoxy)-pyrimidin-4-yl]-1-methyl-1H-pyridin-2-one | A |
| 334 | 5-[6-Amino-2-(2-chloro-6-methyl-phenoxy)-pyrimidin-4-yl]-1,3-dimethyl-1H-pyridin-2-one | A |
| 335 | 6-(1,5-dimethyl-6-oxo(3-hydroxypyridyl))-2-(2,6-dimethylphenoxy)pyrimidine-4-carbonitrile | A |
| 336 | Propane-1-sulfonic acid [5-(1,5-dimethyl-6-oxo-1,6-dihydro-pyridin-3-yl)-2-methyl-2H-pyrazol-3-yl]-amide | B |
| 337 | N-(2-(2-ethyl-6-fluorophenoxy)-6-(1-methyl-6-oxo-1,6-dihydropyridin-3-yl)pyrimidin-4-yl)butane-1-sulfonamide | A |
| 338 | N-(2-(2-ethyl-6-fluorophenoxy)-6-(1-methyl-6-oxo-1,6-dihydropyridin-3-yl)pyrimidin-4-yl)butane-2-sulfonamide | A |
| 339 | N-(2-(2-ethyl-6-fluorophenoxy)-6-(1-methyl-6-oxo-1,6-dihydropyridin-3-yl)pyrimidin-4-yl)propane-1-sulfonamide | A |
| 340 | N-(2-(2,6-difluorophenoxy)-6-(1-methyl-6-oxo-1,6-dihydropyridin-3-yl)pyrimidin-4-yl)propane-2-sulfonamide | A |
| 341 | N-(2-(2,6-difluorophenoxy)-6-(1-methyl-6-oxo-1,6-dihydropyridin-3-yl)pyrimidin-4-yl)propane-1-sulfonamide | A |

TABLE 28-continued

| Chemical Synthesis Example | Name | IC$_{50}$ CREBBP (μM) |
|---|---|---|
| 342 | N-(2-(2,6-difluorophenoxy)-6-(1-methyl-6-oxo-1,6-dihydropyridin-3-yl)pyrimidin-4-yl)butane-1-sulfonamide | A |
| 343 | N-(2-(2,4-difluoro-6-methylphenoxy)-6-(1-methyl-6-oxo-1,6-dihydropyridin-3-yl)pyrimidin-4-yl)butane-1-sulfonamide | A |
| 344 | N-(2-(2,4-difluoro-6-methylphenoxy)-6-(1-methyl-6-oxo-1,6-dihydropyridin-3-yl)pyrimidin-4-yl)propane-1-sulfonamide | A |
| 345 | N-(2-(2,4-difluoro-6-methylphenoxy)-6-(1-methyl-6-oxo-1,6-dihydropyridin-3-yl)pyrimidin-4-yl)butane-2-sulfonamide | A |
| 346 | N-(2-(2,4-difluoro-6-methylphenoxy)-6-(1-methyl-6-oxo-1,6-dihydropyridin-3-yl)pyrimidin-4-yl)propane-2-sulfonamide | A |
| 347 | N-(2-(2,3-difluoro-6-methylphenoxy)-6-(1-methyl-6-oxo-1,6-dihydropyridin-3-yl)pyrimidin-4-yl)butane-1-sulfonamide | A |
| 348 | N-(2-(2,3-difluoro-6-methylphenoxy)-6-(1-methyl-6-oxo-1,6-dihydropyridin-3-yl)pyrimidin-4-yl)propane-1-sulfonamide | A |
| 349 | N-(2-(2,3-difluoro-6-methylphenoxy)-6-(1-methyl-6-oxo-1,6-dihydropyridin-3-yl)pyrimidin-4-yl)butane-2-sulfonamide | A |
| 350 | N-(2-(3,6-difluoro-2-methylphenoxy)-6-(1-methyl-6-oxo-1,6-dihydropyridin-3-yl)pyrimidin-4-yl)butane-1-sulfonamide | A |
| 351 | N-(2-(3,6-difluoro-2-methylphenoxy)-6-(1-methyl-6-oxo-1,6-dihydropyridin-3-yl)pyrimidin-4-yl)butane-2-sulfonamide | A |
| 352 | N-(5-fluoro-2-(2-fluoro-6-methylphenoxy)-6-(1-methyl-6-oxo-1,6-dihydropyridin-3-yl)pyrimidin-4-yl)butane-1-sulfonamide | A |
| 353 | N-(6-(1-methyl-6-oxo-1,6-dihydropyridin-3-yl)-2-((tetrahydro-2H-pyran-4-yl)oxy)pyrimidin-4-yl)butane-1-sulfonamide | A |
| 354 | N-(6-(1-methyl-6-oxo-1,6-dihydropyridin-3-yl)-2-((tetrahydro-2H-pyran-4-yl)oxy)pyrimidin-4-yl)propane-1-sulfonamide | A |
| 355 | N-(2-isopropoxy-6-(1-methyl-6-oxo-1,6-dihydropyridin-3-yl)pyrimidin-4-yl)benzenesulfonamide | A |
| 356 | 5-(10,10-dioxido-2,4-dioxa-10-thia-11-aza-1(2,4)-pyrimidina-3(1,3)-benzenacycloundecaphan-6-en-1$^6$-yl)-1-methylpyridin-2(1H)-one | A |
| 357 | 5-(10,10-dioxido-2,4-dioxa-10-thia-11-aza-1(2,4)-pyrimidina-3(1,3)-benzenacycloundecaphane-1$^6$-yl)-1-methylpyridin-2(1H)-one | A |
| 358 | 5-(11,11-dioxido-2,4-dioxa-11-thia-12-aza-1(2,4)-pyrimidina-3(1,3)-benzenacyclododecaphan-7-en-1$^6$-yl)-1-methylpyridin-2(1H)-one | A |
| 359 | 5-(11,11-dioxido-2,4-dioxa-11-thia-12-aza-1(2,4)-pyrimidina-3(1,3)-benzenacyclododecaphane-1$^6$-yl)-1-methylpyridin-2(1H)-one | A |
| 360 | 5-(36-chloro-10,10-dioxido-2,4-dioxa-10-thia-11-aza-1(2,4)-pyrimidina-3(1,3)-benzenacycloundecaphan-6-en-1$^6$-yl)-1-methylpyridin-2(1H)-one | A |
| 361 | 5-(36-chloro-11,11-dioxido-2,4-dioxa-11-thia-12-aza-1(2,4)-pyrimidina-3(1,3)-benzenacyclododecaphan-6-en-1$^6$-yl)-1-methylpyridin-2(1H)-one | A |
| 362 | 5-(36-fluoro-11,11-dioxido-2,4-dioxa-11-thia-12-aza-1(2,4)-pyrimidina-3(1,3)-benzenacyclododecaphan-6-en-1$^6$-yl)-1-methylpyridin-2(1H)-one | A |

IC$_{50}$ data are designated within the following ranges:
A: ≤0.5 μM;
B: >0.5 μM to ≤5.0 μM;
C: >5.0 μM The IC$_{50}$ values for inhibition of CREBBP and BRD4 by various compounds disclosed herein and known in the art are provided in Table 29.

TABLE 29

| Chemical Synthesis Example | Structure | Name | IC$_{50}$ BRD4 BD1 (μM) | IC$_{50}$ CREBBP (μM) |
|---|---|---|---|---|
| 3 | | Propane-2-sulfonic acid [2-(2-chloro-6-methyl-phenoxy)-6-(1,5-dimethyl-6-oxo-1,6-dihydro-pyridin-3-yl)-pyrimidin-4-yl]-amide | B | A |
| 11 | | Propane-2-sulfonic acid [2-(2-cyano-6-methoxy-phenoxy)-6-(1,5-dimethyl-6-oxo-1,6-dihydro-pyridin-3-yl)-pyrimidin-4-yl]-amide | C | A |
| 14 | | Butane-1-sulfonic acid [2-(2-chloro-6-methyl-phenoxy)-6-(1,5-dimethyl-6-oxo-1,6- | B | A |

TABLE 29-continued

| Chemical Synthesis Example | Structure | Name | IC$_{50}$ BRD4 BD1 (μM) | IC$_{50}$ CREBBP (μM) |
|---|---|---|---|---|
| 33 | | dihydro-pyridin-3-yl)-pyrimidin-4-yl]-amide Propane-2-sulfonic acid [2-(2,4-dichloro-6-methyl-phenoxy)-6-(1,5-dimethyl-6-oxo-1,6-dihydro-pyridin-3-yl)-pyrimidin-4-yl]-amide | C | A |
| 41 | 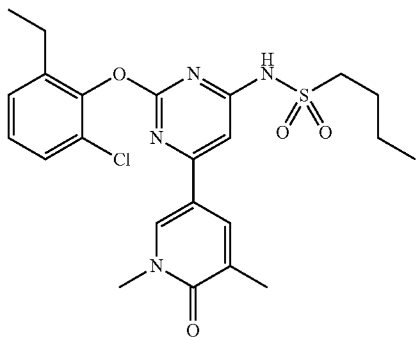 [SMILES: CCCCS(=O)(=O)Nc1cc(-c2cc(C)c(=O)n(C)c2)nc(Oc2c(Cl)cccc2CC)n1] | Butane-1-sulfonic acid [2-(2-chloro-6-ethyl-phenoxy)-6-(1,5-dimethyl-6-oxo-1,6-dihydro-pyridin-3-yl)-pyrimidin-4-yl]-amide | C | A |
| 66 | 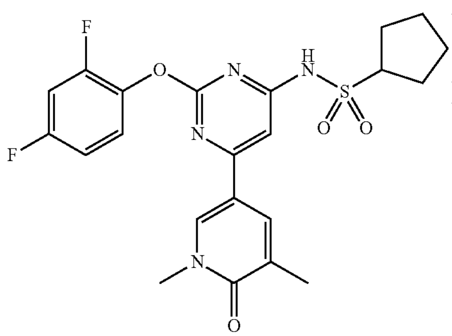 | N-(2-(2,4-difluorophenoxy)-6-(1,5-dimethyl-6-oxo-1,6-dihydropyridin-3-yl)pyrimidin-4-yl)cyclopentane-sulfonamide | B | A |
| 72 | 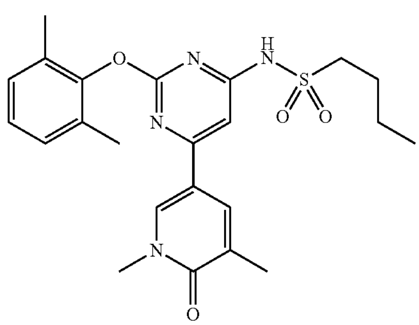 [SMILES: CCCCS(=O)(=O)Nc1cc(-c2cc(C)c(=O)n(C)c2)nc(Oc2c(C)cccc2C)n1] | N-(6-(1,5-dimethyl-6-oxo-1,6-dihydropyridin-3-yl)-2-(2,6-dimethylphenoxy)pyrimidin-4-yl)butane-1-sulfonamide | C | A |
| 87 | 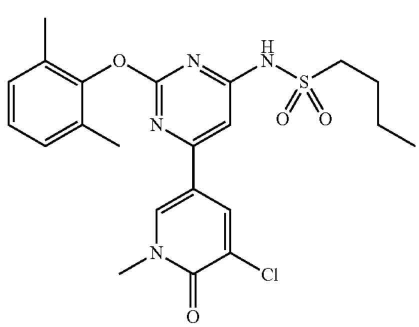 [SMILES: CCCCS(=O)(=O)Nc1cc(-c2cc(Cl)c(=O)n(C)c2)nc(Oc2c(C)cccc2C)n1] | N-(6-(5-chloro-1-methyl-6-oxo-1,6-dihydropyridin-3-yl)-2-(2,6-dimethylphenoxy)pyrimidin-4-yl)butane-1-sulfonamide | C | A |

TABLE 29-continued

| Chemical Synthesis Example | Structure | Name | IC$_{50}$ BRD4 BD1 (μM) | IC$_{50}$ CREBBP (μM) |
|---|---|---|---|---|
| 113 | 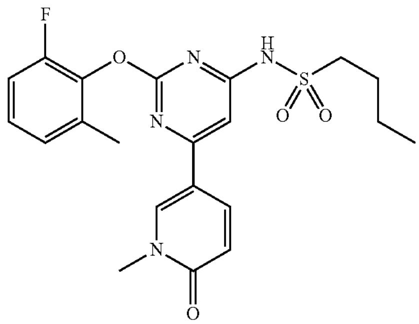 [SMILES: CCCCS(=O)(=O)Nc1cc(-c2ccc(=O)n(C)c2)nc(Oc2c(C)cccc2F)n1] | Butane-1-sulfonic acid [2-(2-fluoro-6-methyl-phenoxy)-6-(1-methyl-6-oxo-1,6-dihydro-pyridin-3-yl)-pyrimidin-4-yl]-amide | C | A |
| | | N-(5-(2,4-difluorophenoxy)-4-(1,5-dimethyl-6-oxo-1,6-dihydropyridin-3-yl)-pyrimidin-2-yl)ethanesulfonamide | A | C |
| | | N-(5-(2,4-difluorophenoxy)-4-(1,5-dimethyl-6-oxo-1,6-dihydropyridin-3-yl)-pyrimidin-2-yl)methanesulfonamide | A | C |
| | | N-(4-(1-(cyclopropylmethyl)-5-methyl-6-oxo-1,6-dihydropyridin-3-yl)-5-(2,4-difluorophenoxy)pyrimidin-2-yl)ethanesulfonamide | A | C |
| JQ-1 | | tert-butyl (S)-2-(4-(4-chlorophenyl)-2,3,9-trimethyl-6H-thieno[3,2-f][1,2,4]triazolo[4,3-a][1,4]diazepin-6-yl)acetate | A | C |

IC$_{50}$ data are designated within the following ranges:
A: ≤0.5 μM;
B: >0.5 μM to ≤5.0 μM;
C: >5.0 μM

Example 2: In Vitro Cell-based Assay

Th17 Differentiation—IL-17A Secretion Assay: 100K CD4+ cells per well are plated in a 96 well plate in 1× Th17 differentiation cocktail (0.05 μg/ml IL6, 0.02 μg/ml IL23, 10 μg/ml anti-IFNγ, 10 μg/ml anti-IL4, 0.01 μg/ml IL1β, 0.003 μg/ml TGFβ and 1 bead/cell anti-CD3/CD28) for a total volume of 100 μL/well. The plates are cultured for 96 hr at 37° C. in 5% CO$_2$. Differentiated Th17 cells are pooled, washed and suspended in complete media. 100K Th17 cells per well are plated in a 96 well plate in the presence of IL-23 at a final concentration of 25 ng/mL. Appropriate concentrations of CBP inhibitors are added to the cells for a total volume of 100 μL/well. DMSO and media controls are included. Plates are cultured for 96 h at 37° C. in 5% CO$_2$. IL-17A levels in the supernatants are determined by using manufacturer's protocol (Meso Scale Discovery # K151ATB-2). Secreted IL-17A levels are interpolated from a standard curve and plotted by % DMSO control.

Example 3: In Vitro Cell-based Assay

Effect on Treg Differentiation and Immune Checkpoints Assay: 100K naïve CD4+ cells per well were plated in a 96 well plate and appropriate concentrations of CBP inhibitors were added to the cells. DMSO and media controls were included. Cells were incubated for 1 hr at 37° C. in 5% CO2 and Treg differentiation cocktail (final concentrations: 0.010 μg/ml TGFβ, 10 U/ml IL2 and 1:1 bead:cell ratio of anti-CD3/CD28) was added for a total volume of 100 μL/well. Plates were cultured for 96 hr at 37° C. in 5% CO₂. Tregs were stained for CD4 (562424; BD Biosciences), CTLA4 (563931; BD Biosciences), CD25 (562660; BD Biosciences), LAG-3 (11-2239-42; eBioscience), PD-1 (17-9969-42; eBioscience), Tim3 (25-3109-42; eBioscience) and FOXP3 (560046; BD Biosciences). For FOXP3 and CTLA4 intracellular staining cells were fixed and permeabilized using BD Cytofix/Cytoperm solution (554722; BD Biosciences). Markers were quantified on iQue Screener PLUS flow cytometry analyzer (IntelliCyt) and data were analyzed using FCS Express 5 Software (DeNovo Software).

III. Preparation of Pharmaceutical Dosage Forms

Example 1: Oral Tablet

A tablet is prepared by mixing 48% by weight of a compound of Formula (I), or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

The invention claimed is:
1. A compound, or pharmaceutically acceptable salt thereof, having the structure of Formula (I):

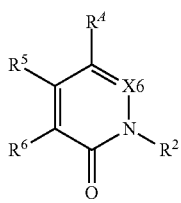

Formula (I)

wherein,
R² is hydrogen, alkyl, aryl, aralkyl, cycloalkyl, cycloalkylalkyl, heterocyclyl, heterocyclylalkyl, heteroaryl, or heteroarylalkyl;
X6 is C—H, C—F, C—Cl, C—Br, or N;
R⁵ is hydrogen, halogen, —CN, alkyl, cycloalkyl, or alkoxy;
R⁶ is hydrogen, halogen, —CN, alkyl, cycloalkyl, cycloalkylalkyl, —OR²², or —N(R²²)₂;
R⁴ is

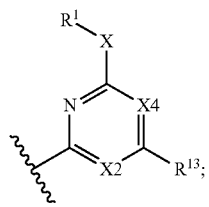

R¹³ is Y—Z;
Y is selected from a bond, —CH₂—, or CH(C₁-C₄alkyl)-;
Z is selected from —SO₂R²¹, —N(R²²)SO₂R²¹, —SO₂N(R²²)₂, —N(R²²)SO₂N(R²²)₂, —CON(R²²)₂, —N(R²²)CO₂R²¹, —N(R²²)CON(R²²)₂, —N(R²²)COR²¹, —COR²¹, —OC(O)N(R²²)₂, —OSO₂N(R²²)₂, —OSO₂R²¹, —N(R²²)SO₃R²¹, N(R²²)₂, or —CN;
X2 is N, or C—R¹²; wherein R¹² is hydrogen, halogen, —CN, alkyl, cycloalkyl, or alkoxy;
X4 is N, or C—R¹⁴; wherein R¹⁴ is hydrogen, halogen, —CN, alkyl, cycloalkyl, or alkoxy;
X is a bond, —O—, —S—, —N(R⁷)—, —CH₂—, —CF(H)—, —CF₂—, or —CH(C₁-C₅alkyl)-;
R⁷ is H or C₁-C₆ alkyl;
R¹ is alkyl, aryl, aralkyl, cycloalkyl, cycloalkylalkyl, heterocyclyl, heterocyclylalkyl, heteroaryl, or heteroarylalkyl;
each R²¹ is independently selected from alkyl, cycloalkyl, cycloalkylalkyl, aryl, aralkyl, heterocyclyl, heterocyclylalkyl, heteroaryl, or heteroarylalkyl;
each R²² is independently selected from hydrogen, alkyl, cycloalkyl, cycloalkylalkyl, aryl, aralkyl, heterocyclyl, heterocyclylalkyl, heteroaryl, or heteroarylalkyl; and
provided that the compound of Formula (I) is not N-[2-(2,4-difluorophenoxy)-6-(1,5-dimethyl-6-oxopyridin-3-yl)pyrimidin-4-yl]ethanesulfonamide.

2. The compound of claim 1, or pharmaceutically acceptable salt thereof, wherein R² is alkyl, aryl, aralkyl, cycloalkyl, cycloalkylalkyl, heterocyclyl, heterocyclylalkyl, heteroaryl, or heteroarylalkyl.

3. The compound of claim 1, or pharmaceutically acceptable salt thereof, wherein R² is alkyl, cycloalkyl, cycloalkylalkyl, or heterocyclyl.

4. The compound of claim 3, or pharmaceutically acceptable salt thereof, wherein R² is alkyl.

5. The compound of claim 1, or pharmaceutically acceptable salt thereof, wherein X6 is C—H or N.

6. The compound of claim 1, or pharmaceutically acceptable salt thereof, wherein R⁵ is hydrogen or alkyl.

7. The compound of claim 1, or pharmaceutically acceptable salt thereof, wherein R⁵ is hydrogen.

8. The compound of claim 1, or pharmaceutically acceptable salt thereof, wherein R⁶ is hydrogen, halogen, alkyl, or —OR²²; and R²² is alkyl.

9. The compound of claim 1, or pharmaceutically acceptable salt thereof, wherein R⁶ is hydrogen, halogen, or alkyl.

10. The compound of claim 1, or pharmaceutically acceptable salt thereof, wherein R⁶ is hydrogen or methyl.

11. The compound of claim 1, or pharmaceutically acceptable salt thereof, wherein Y is selected from a bond or —CH₂—.

12. The compound of claim 1, or pharmaceutically acceptable salt thereof, wherein Y is a bond.

13. The compound of claim 1, or pharmaceutically acceptable salt thereof, wherein Z is selected from —SO₂R²¹, —N(R²²)SO₂R²¹, —SO₂N(R²²)₂, —N(R²²)SO₂N(R²²)₂, —CON(R²²)₂, —N(R²²)CO₂R²¹, —N(R²²)CON(R²²)₂, —N(R²²)COR²¹, —COR^M, —OC(O)N(R²²)₂, —OSO₂N(R²²)₂, or —N(R²²)SO₃R²¹.

14. The compound of claim 1, or pharmaceutically acceptable salt thereof, wherein Z is selected from —SO₂R²¹, —N(R²²)SO₂R²¹, or —N(R²²)COR²¹.

15. The compound of claim 1, or pharmaceutically acceptable salt thereof, wherein Z is —N($R^{22}$)$SO_2R^{21}$; $R^{21}$ is alkyl, cycloalkyl, or cycloalkylalkyl; and $R^{22}$ is hydrogen or alkyl.

16. The compound of claim 1, or pharmaceutically acceptable salt thereof, wherein Z is —$SO_2R^{21}$ and $R^{21}$ is alkyl.

17. The compound of claim 1, or pharmaceutically acceptable salt thereof, wherein Z is —N($R^{22}$)$COR^{21}$; $R^{21}$ is alkyl, cycloalkyl, or cycloalkylalkyl; and $R^{22}$ is hydrogen or alkyl.

18. The compound of claim 1, or pharmaceutically acceptable salt thereof, wherein X2 is N and X4 is C—H.

19. The compound of claim 1, or pharmaceutically acceptable salt thereof, wherein X4 is N and X2 is C—H.

20. The compound of claim 1, or pharmaceutically acceptable salt thereof, wherein X2 is N and X4 is N.

21. The compound of claim 1, or pharmaceutically acceptable salt thereof, wherein X is —O— or —$CH_2$—.

22. The compound of claim 1, or pharmaceutically acceptable salt thereof, wherein X is —O—.

23. The compound of claim 1, or pharmaceutically acceptable salt thereof, wherein $R^1$ is alkyl, aryl, cycloalkyl, heterocyclyl, heteroaryl, or heteroarylalkyl.

24. The compound of claim 1, or pharmaceutically acceptable salt thereof, wherein $R^1$ is alkyl, aryl, or heteroaryl.

25. A pharmaceutical composition comprising the compound of claim 1, or a pharmaceutically acceptable salt thereof, and a pharmaceutically acceptable excipient.

26. The compound of claim 1, or pharmaceutically acceptable salt thereof, having the structure of Formula (Ia):

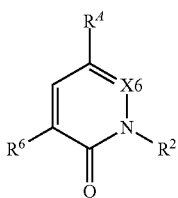

Formula (Ia)

wherein,
$R^2$ is alkyl, aryl, aralkyl, cycloalkyl, cycloalkylalkyl, heterocyclyl, heterocyclylalkyl, heteroaryl, or heteroarylalkyl;
X6 is C—H or N;
$R^6$ is hydrogen, halogen, or $C_1$-$C_3$ alkyl;
$R^4$ is

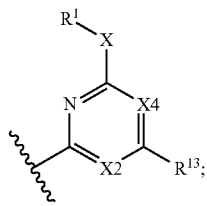

$R^{13}$ is —Y—Z;
Y is selected from a bond, —$CH_2$—, or —CH($C_1$-$C_4$alkyl)-;
Z is selected from —$SO_2R^{21}$, —N($R^{22}$)$SO_2R^{21}$, —$SO_2$N($R^{22}$)$_2$, —N($R^{22}$)$SO_2$N($R^{22}$)$_2$, —CON($R^{22}$)$_2$, —N($R^{22}$)$CO_2R^{21}$, —N($R^{22}$)CON($R^{22}$)$_2$, —N($R^{22}$)$COR^{21}$, —$COR^{21}$, —OC(O)N($R^{22}$)$_2$, —$OSO_2$N($R^{22}$)$_2$, or —N($R^{22}$)$SO_3R^{21}$;
X2 is N or C—H;
X4 is N or C—$R^{14}$, wherein $R^{14}$ is hydrogen, halogen, —CN, alkyl, cycloalkyl, or alkoxy;
X is a bond, —O—, —N($R^7$)—, or —CH($C_1$-$C_5$alkyl)-;
$R^7$ is H or $C_1$-$C_6$ alkyl;
$R^1$ is alkyl, aryl, aralkyl, cycloalkyl, cycloalkylalkyl, heterocyclyl, heterocyclylalkyl, heteroaryl, or heteroarylalkyl;
each $R^{21}$ is independently selected from alkyl, cycloalkyl, cycloalkylalkyl, aryl, aralkyl, heterocyclyl, heterocyclylalkyl, heteroaryl, or heteroarylalkyl;
each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl; and
provided that the compound of Formula (Ia) is not N-[2-(2,4-difluorophenoxy)-6-(1,5-dimethyl-6-oxopyridin-3-yl)pyrimidin-4-yl]ethanesulfonamide.

27. A pharmaceutical composition comprising the compound of claim 26, or a pharmaceutically acceptable salt thereof, and a pharmaceutically acceptable excipient.

28. A compound, or a pharmaceutically acceptable salt thereof, chosen from:
Butane-1-sulfonic acid [2-(2-chloro-6-methyl-phenoxy)-6-(1,5-dimethyl-6-oxo-1,6-dihydro-pyridin-3-yl)-pyrimidin-4-yl]-amide;
Propane-2-sulfonic acid [2-(2,4-dichloro-6-methyl-phenoxy)-6-(1,5-dimethyl-6-oxo-1,6-dihydro-pyridin-3-yl)-pyrimidin-4-yl]-amide;
Butane-1-sulfonic acid [2-(2-fluoro-6-methyl-phenoxy)-6-(1-methyl-6-oxo-1,6-dihydro-pyridin-3-yl)-pyrimidin-4-yl]-amide;
(S)—N-(2-(2-fluoro-6-methylphenoxy)-6-(1-methyl-6-oxo-1,6-dihydropyridin-3-yl)pyrimidin-4-yl)butane-2-sulfonamide;
(R)—N-(2-(2-fluoro-6-methylphenoxy)-6-(1-methyl-6-oxo-1,6-dihydropyridin-3-yl)pyrimidin-4-yl)butane-2-sulfonamide;
3,3,3-Trifluoro-propane-1-sulfonic acid [2-(2-fluoro-6-methyl-phenoxy)-6-(1-methyl-6-oxo-1,6-dihydro-pyridin-3-yl)-pyrimidin-4-yl]-amide; or
4,4,4-Trifluoro-butane-1-sulfonic acid [2-(2-fluoro-6-methyl-phenoxy)-6-(1-methyl-6-oxo-1,6-dihydro-pyridin-3-yl)-pyrimidin-4-yl]-amide.

29. A pharmaceutical composition comprising a compound of claim 28, or a pharmaceutically acceptable salt thereof, and a pharmaceutically acceptable excipient.

\* \* \* \* \*